US010358473B2

(12) United States Patent
Baeuerle et al.

(10) Patent No.: US 10,358,473 B2
(45) Date of Patent: *Jul. 23, 2019

(54) COMPOSITIONS AND METHODS FOR TCR REPROGRAMMING USING FUSION PROTEINS

(71) Applicant: TCR2 Therapeutics Inc., Cambridge, MA (US)

(72) Inventors: Patrick Baeuerle, Cambridge, MA (US); Gregory Sieczkiewicz, Cambridge, MA (US); Robert Hofmeister, Scituate, MA (US)

(73) Assignee: TCR2 THERAPEUTICS INC., Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/965,738

(22) Filed: Apr. 27, 2018

(65) Prior Publication Data

US 2018/0244747 A1 Aug. 30, 2018

Related U.S. Application Data

(63) Continuation of application No. 15/419,398, filed on Jan. 30, 2017, which is a continuation of application No. PCT/US2016/033146, filed on May 18, 2016.

(60) Provisional application No. 62/163,342, filed on May 18, 2015.

(51) Int. Cl.

| | |
|---|---|
| ***C07K 14/725*** | (2006.01) |
| ***C07K 14/705*** | (2006.01) |
| ***C07K 16/28*** | (2006.01) |
| ***A61K 39/00*** | (2006.01) |
| ***C07K 16/30*** | (2006.01) |
| ***C12N 5/0783*** | (2010.01) |
| ***C07K 16/40*** | (2006.01) |

(52) U.S. Cl.

CPC ...... *C07K 14/7051* (2013.01); *A61K 39/0011* (2013.01); *C07K 14/70578* (2013.01); *C07K 16/2803* (2013.01); *C07K 16/2878* (2013.01); *C07K 16/30* (2013.01); *C07K 16/40* (2013.01); *C12N 5/0636* (2013.01); *A61K 2039/505* (2013.01); *A61K 2039/5158* (2013.01); *C07K 2317/24* (2013.01); *C07K 2317/56* (2013.01); *C07K 2317/622* (2013.01); *C07K 2317/73* (2013.01); *C07K 2319/00* (2013.01); *C07K 2319/02* (2013.01); *C07K 2319/03* (2013.01); *C07K 2319/10* (2013.01); *C12N 2510/00* (2013.01)

(58) Field of Classification Search

None

See application file for complete search history.

(56) References Cited

U.S. PATENT DOCUMENTS

| | | | |
|---|---|---|---|
| 4,816,567 | A | 3/1989 | Cabilly et al. |
| 5,199,942 | A | 4/1993 | Gillis |
| 5,225,539 | A | 7/1993 | Winter |
| 5,350,674 | A | 9/1994 | Boenisch et al. |
| 5,399,346 | A | 3/1995 | Anderson et al. |
| 5,530,101 | A | 6/1996 | Queen et al. |
| 5,565,332 | A | 10/1996 | Hoogenboom et al. |
| 5,580,859 | A | 12/1996 | Felgner et al. |
| 5,585,089 | A | 12/1996 | Queen et al. |
| 5,585,362 | A | 12/1996 | Wilson et al. |
| 5,589,466 | A | 12/1996 | Felgner et al. |
| 5,766,886 | A | 6/1998 | Studnicka et al. |
| 5,858,358 | A | 1/1999 | June et al. |
| 5,883,223 | A | 3/1999 | Gray |
| 6,120,766 | A | 9/2000 | Hale et al. |
| 6,326,193 | B1 | 12/2001 | Liu et al. |
| 6,331,415 | B1 | 12/2001 | Cabilly et al. |
| 6,352,694 | B1 | 3/2002 | June et al. |
| 6,407,213 | B1 | 6/2002 | Carter et al. |
| 6,534,055 | B1 | 3/2003 | June et al. |
| 6,548,640 | B1 | 4/2003 | Winter |
| 6,692,964 | B1 | 2/2004 | June et al. |
| 6,797,514 | B2 | 9/2004 | Berenson et al. |
| 6,867,041 | B2 | 3/2005 | Berenson et al. |
| 6,887,466 | B2 | 5/2005 | June et al. |
| 6,905,680 | B2 | 6/2005 | June et al. |
| 6,905,681 | B1 | 6/2005 | June et al. |
| 6,905,874 | B2 | 6/2005 | Berenson et al. |
| 7,067,318 | B2 | 6/2006 | June et al. |
| 7,081,518 | B1 | 7/2006 | Pastan et al. |
| 7,144,575 | B2 | 12/2006 | June et al. |
| 7,172,869 | B2 | 2/2007 | June et al. |
| 7,175,843 | B2 | 2/2007 | June et al. |
| 7,232,566 | B2 | 6/2007 | June et al. |

(Continued)

FOREIGN PATENT DOCUMENTS

| | | | |
|---|---|---|---|
| EP | 0239400 | A2 | 9/1987 |
| EP | 0519596 | A1 | 12/1992 |

(Continued)

OTHER PUBLICATIONS

Bridgeman et al. (Current Gene Therapy. 2010, 10, 77-90). (Year: 2010).*

(Continued)

*Primary Examiner* — Zachary S Skelding

(74) *Attorney, Agent, or Firm* — Wilson Sonsini Goodrich & Rosati

(57) ABSTRACT

Provided herein are T-cell receptor (TCR) fusion proteins (TFPs), T-cells engineered to express one or more TFPs, and methods of use thereof for the treatment of diseases, including cancer.

30 Claims, 29 Drawing Sheets

Specification includes a Sequence Listing.

(56) References Cited

U.S. PATENT DOCUMENTS 7,572,631 B2 8/2009 Berenson et al.
7,695,936 B2 4/2010 Carter et al.
7,741,465 B1 6/2010 Eshhar et al.
8,206,710 B2 6/2012 Ebel et al.
8,389,282 B2 3/2013 Sadelain et al.
8,697,359 B1 4/2014 Zhang
8,911,732 B2 12/2014 Dennis et al.
9,023,351 B2 5/2015 Kahnert et al.
9,062,127 B2 6/2015 Voss et al.
9,102,736 B2 8/2015 Hofmeister et al.
9,115,197 B2 8/2015 Ebel et al.
9,181,527 B2 11/2015 Sentman
9,220,728 B2 12/2015 Sadelain et al.
9,272,002 B2 3/2016 Powell, Jr. et al.
9,365,641 B2 6/2016 June et al.
9,393,257 B2 7/2016 Osborn et al.
9,422,351 B2 8/2016 Scholler et al.
9,447,194 B2 9/2016 Jensen et al.
9,464,140 B2 10/2016 June et al.
10,093,900 B2 10/2018 Jantz et al.
2004/0266390 A1 12/2004 Faucher et al.
2005/0042664 A1 2/2005 Wu et al.
2005/0048617 A1 3/2005 Wu et al.
2005/0100543 A1 5/2005 Hansen et al.
2005/0175606 A1 8/2005 Huang et al.
2006/0121005 A1 6/2006 Berenson et al.
2007/0014794 A1 1/2007 Carter et al.
2008/0294058 A1 11/2008 Shklarski
2009/0047211 A1 2/2009 Pastan et al.
2009/0322513 A1 12/2009 Hwang et al.
2011/0189141 A1 8/2011 Kieback et al.
2013/0066283 A1 3/2013 Alster et al.
2013/0266551 A1 10/2013 Campana et al.
2013/0280220 A1 10/2013 Ahmed et al.
2013/0315884 A1 11/2013 Galetto et al.
2013/0323214 A1 12/2013 Gottschalk et al.
2013/0323247 A1 12/2013 Zugmaier et al.
2014/0004132 A1 1/2014 Brenner et al.
2014/0050708 A1 2/2014 Powell et al.
2014/0099340 A1 4/2014 June et al.
2014/0227237 A1 8/2014 June et al.
2014/0271635 A1 9/2014 Brogdon et al.
2014/0286973 A1 9/2014 Powell, Jr. et al.
2014/0301993 A1 10/2014 Powell, Jr. et al.
2014/0308259 A1 10/2014 Scholler et al.
2014/0322212 A1 10/2014 Brogdon et al.
2014/0322216 A1 10/2014 Kaplan
2014/0370045 A1 12/2014 June et al.
2015/0031624 A1 1/2015 Feldman et al.
2015/0051266 A1 2/2015 Kochenderfer
2015/0093822 A1 4/2015 June et al.
2015/0190428 A1 7/2015 June et al.
2015/0203817 A1 7/2015 Galetto et al.
2015/0238631 A1 8/2015 Kim et al.
2015/0252110 A1 9/2015 Hansen et al.
2015/0284475 A1 10/2015 Zhou et al.
2015/0297640 A1 10/2015 Cooper et al.
2015/0306141 A1 10/2015 Jensen et al.
2015/0307564 A1 10/2015 Young et al.
2015/0322169 A1 11/2015 June et al.
2015/0329640 A1 11/2015 Finer
2015/0342993 A1 12/2015 Kloss et al.
2015/0344573 A1 12/2015 Chang et al.
2015/0344844 A1 12/2015 Better et al.
2015/0368360 A1 12/2015 Liang et al.
2015/0376287 A1 12/2015 Vu et al.
2015/0376296 A1 12/2015 Fedorov et al.
2016/0008398 A1 1/2016 Sadelain et al.
2016/0009813 A1 1/2016 Themeli et al.
2016/0015749 A1 1/2016 Gottschalk et al.
2016/0030479 A1 2/2016 Abbot et al.
2016/0039903 A1 2/2016 Ring et al.
2016/0040127 A1 2/2016 Leventhal et al.
2016/0045551 A1 2/2016 Brentjens et al.
2016/0046678 A1 2/2016 Roschke et al.
2016/0046724 A1* 2/2016 Brogdon ................ A61K 35/12 424/134.1
2016/0052990 A1 2/2016 Ring et al.
2016/0120906 A1 5/2016 Galetto et al.
2016/0122782 A1 5/2016 Crisman et al.
2016/0144026 A1 5/2016 Lutteropp et al.
2016/0145354 A1 5/2016 Bacac et al.
2016/0158359 A1 6/2016 Gilbert
2016/0176973 A1 6/2016 Kufer et al.
2016/0184362 A1 6/2016 Duchateau et al.
2016/0185861 A1 6/2016 Bedoya et al.
2016/0185862 A1 6/2016 Wu et al.
2016/0186165 A1 6/2016 Dose et al.
2016/0194375 A1 7/2016 Kitchen et al.
2016/0206656 A1 7/2016 Gilbert
2016/0207989 A1 7/2016 Short
2016/0215051 A1 7/2016 Sharma et al.
2016/0228547 A1 8/2016 Wagner et al.
2016/0235787 A1 8/2016 June et al.
2016/0237139 A1 8/2016 Pulé et al.
2016/0237407 A1 8/2016 Wagner et al.
2016/0256488 A1 9/2016 Wu
2016/0257762 A1 9/2016 Kwon et al.
2016/0264665 A1 9/2016 Lim et al.
2016/0272999 A1 9/2016 Duchateau et al.
2016/0289343 A1 10/2016 Wu
2016/0296633 A1 10/2016 Goldenberg et al.
2016/0340406 A1* 11/2016 Zhao ................. C07K 14/7051
2017/0166622 A1 6/2017 Baeuerle et al.

FOREIGN PATENT DOCUMENTS

EP 0592106 A1 4/1994
EP 0638119 A1 2/1995
EP 1075517 B1 7/2006
EP 2258719 A1 12/2010
EP 2258720 A1 12/2010
EP 2894164 A1 7/2015
EP 2342227 B1 10/2015
EP 2632954 B1 11/2015
EP 2953974 A1 12/2015
EP 2970472 A1 1/2016
EP 2982692 A1 2/2016
EP 2982696 A2 2/2016
EP 2361936 B1 4/2016
EP 3006459 A1 4/2016
EP 3018145 A1 5/2016
EP 3019622 A2 5/2016
EP 3023437 A1 5/2016
EP 2686417 B1 6/2016
EP 2982694 B1 6/2016
EP 3025719 A1 6/2016
EP 3029067 A1 6/2016
EP 3029068 A1 6/2016
EP 3057991 A1 8/2016
EP 3057994 A1 8/2016
EP 2370467 B1 9/2016
EP 3087101 A1 11/2016
FR 901228 A 7/1945
KR 20090092900 A 9/2009
WO WO-9109967 A1 7/1991
WO WO-9317105 A1 9/1993
WO WO-0129058 A1 4/2001
WO WO-0196584 A2 12/2001
WO WO-2006020258 A2 2/2006
WO WO-2007024715 A2 3/2007
WO WO-2010052014 A1 5/2010
WO WO-2010104949 A2 * 9/2010
WO WO-2012138475 A1 10/2012
WO WO-2013040557 A2 3/2013
WO WO-2013063419 A2 5/2013
WO WO-2013072415 A1 * 5/2013
WO WO-2013126712 A1 8/2013
WO WO-2013154760 A1 * 10/2013
WO WO-2013176916 A1 11/2013
WO WO-2014153270 A1 9/2014
WO WO-2014184143 A1 11/2014
WO WO-2014190273 A1 11/2014
WO WO-2015092024 A2 6/2015

(56) References Cited

FOREIGN PATENT DOCUMENTS

| | | | |
|---|---|---|---|
| WO | WO-2015095895 | A1 | 6/2015 |
| WO | WO-2015107075 | A1 | 7/2015 |
| WO | WO-2015112800 | A1 | 7/2015 |
| WO | WO-2015112830 | A1 | 7/2015 |
| WO | WO-2015121454 | A1 | 8/2015 |
| WO | WO-2015123642 | A1 | 8/2015 |
| WO | WO-2015124715 | A1 | 8/2015 |
| WO | WO-2015142661 | A1 | 9/2015 |
| WO | WO-2015142675 | A2 | 9/2015 |
| WO | WO-2015158671 | A1 | 10/2015 |
| WO | WO-2015164745 | A1 | 10/2015 |
| WO | WO-2015168613 | A2 | 11/2015 |
| WO | WO-2015179801 | A1 | 11/2015 |
| WO | WO-2015188141 | A2 | 12/2015 |
| WO | WO-2016011210 | A2 | 1/2016 |
| WO | WO-2016014789 | A2 | 1/2016 |
| WO | WO-2016019969 | A1 | 2/2016 |
| WO | WO-2016025454 | A2 | 2/2016 |
| WO | WO-2016030691 | A1 | 3/2016 |
| WO | WO-2016036678 | A1 | 3/2016 |
| WO | WO-2016040441 | A1 | 3/2016 |
| WO | WO-2016044853 | A1 | 3/2016 |
| WO | WO-2016054520 | A2 | 4/2016 |
| WO | WO-2016055551 | A1 | 4/2016 |
| WO | WO-2016070061 | A1 | 5/2016 |
| WO | WO-2016073381 | A1 | 5/2016 |
| WO | WO-2016079081 | A1 | 5/2016 |
| WO | WO-2016087245 | A1 | 6/2016 |
| WO | WO-2016090034 | A2 | 6/2016 |
| WO | WO-2016090312 | A1 | 6/2016 |
| WO | WO-2016090320 | A1 | 6/2016 |
| WO | WO-2016090327 | A2 | 6/2016 |
| WO | WO-2016097231 | A2 | 6/2016 |
| WO | WO-2016115274 | A1 | 7/2016 |
| WO | WO-2016115482 | A1 | 7/2016 |
| WO | WO-2016116601 | A1 | 7/2016 |
| WO | WO-2016123675 | A1 | 8/2016 |
| WO | WO-2016126608 | A1 | 8/2016 |
| WO | WO-2016127043 | A1 | 8/2016 |
| WO | WO-2016127257 | A1 | 8/2016 |
| WO | WO-2016132366 | A1 | 8/2016 |
| WO | WO-2016151315 | A1 | 9/2016 |
| WO | WO-2016161415 | A2 | 10/2016 |
| WO | WO-2016187349 | A1 | 11/2016 |
| WO | WO-2016203048 | A1 | 12/2016 |
| WO | WO-2017112741 | A1 | 6/2017 |
| WO | WO-2017173256 | A1 | 10/2017 |
| WO | WO-2018026953 | A1 | 2/2018 |
| WO | WO-2018067993 | A1 | 4/2018 |
| WO | WO-2018098365 | A2 | 5/2018 |
| WO | WO-2018119298 | A1 | 6/2018 |
| WO | WO-2018232020 | A1 | 12/2018 |

OTHER PUBLICATIONS

Zhao et al. (J Immunol 2009; 183:5563-5574) (Year: 2009).*
Bridgeman et al. (Immunology. Jan. 2012;135(1):9-18). (Year: 2012).*
Merry et al. (JBC, vol. 278, No. 29, pp. 27119-27128, 2003). (Year: 2003).*
Hombach et al. (J Immunol 2007; 178:4650-4657). (Year: 2007).*
James et al. (J Immunol 2008; 180:7028-7038). (Year: 2008).*
Wang et al., J Exp Med. Mar. 14, 2011;208(3):577-92. (Year: 2011).*
Wegener et al., Cell, vol. 68, pp. 83-95, 1992. (Year: 1992).*
Griffin et al., Clin Exp Immunol. Sep. 2011;165(3):285-91 (Year: 2011) (Year: 2011).*
Desnnyter et al., Nat Struct Biol. Sep. 1996;3(9):803-11 (Year: 1996) (Year: 1996).*
Punt et al., J Exp Med. Aug. 1, 1994;180(2):587-93 (Year: 1994) (Year: 1994).*
Vernneire et al., PLoS Biol 12(12): e1002011. (Year: 2014).*
NP_000724, human T-cell surface glycoprotein CD3 epsilon chain precursor, NCBI, pp. 1-4, May 4, 2019. (Year: 2019).*
NP_000064, human T-cell surface glycoprotein CD3 gamma chain precursor, NCBI, pp. 1-4, May 4, 2019. (Year: 2019).*
Abate-Daga et al. CAR models: next-generation CAR modifications for enhanced T-cell function. Mol Ther Oncolytics 3:16014 (2016).
Acuto et al. Tailoring T-cell receptor signals by proximal negative feedback mechanisms. Nat Rev Immunol 8(9):699-712 (2008).
Agata et al. Expression of the PD-1 antigen on the surface of stimulated mouse T and B lymphocytes. Int Immunol 8:765-775 (1996).
Ager et al. Homing to solid cancers: a vascular checkpoint in adoptive cell therapy using CAR T-cells. Biochemical Society transactions. 44(2):377-385 (2016).
Almasbak et al. CAR T Cell Therapy: A Game Changer in Cancer Treatment. Journal of Immunology Research. 2016:1-10 (2016).
Al-Rawi et al. Interleukin-7 (IL-7) and IL-7 receptor (IL-7R) signalling complex in human solid tumours. Hist Histopathol 18:911-923 (2003).
Altschul, et al. Basic local alignment search tool. Journal of Molecular Biology 215.3 (1990): 403-410.
Altschul et al. Gapped BLAST and PSI-BLAST: a new generation of protein database search programs. Nucleic Acids Res 25:3389-3402 (1977).
Ankri et al. Human T cells engineered to express a programmed death 1/28 costimulatory retargeting molecule display enhanced antitumor activity. J Immunol 191:4121-4129 (2013).
Baca et al. Antibody humanization using monovalent phage display. J Biol Chem 272(16):10678-10684 (1997).
Baeuerle. Abstract No. A058. TRuC-T Cells Targeting CD19 or Mesothelin Demonstrate Superior Antitumor Activity in Preclinical Models Compared to CAR-T Cells (Poster session). Third CRI-CIMT-EATI-AACR International Cancer Immunotherapy Conference. URL:https://static1.squarespace.com/static/56dee71e555986fb3ae583e2/t/59adO8b1b8a79b086c865d6c/1504512189107/CIMT_Abstracts_170904.pdf (1 pg.) (2017) [retrieved on Jan. 9, 2018].
Baeuerle et al. A Novel T Cell Therapy Engaging the Complete T Cell Receptor. (45 pgs) (2016).
Barretina et al. The Cancer Cell Line Encyclopedia enables predictive modelling of anticancer drug sensitivity. Nature 483:603-607 (2012).
Barrett et al. Treatment of advanced leukemia in mice with mRNA engineered T cells. Hum Gene Ther 22:1575-1586 (2011).
Batlevi et al. Novel immunotherapies in lymphoid malignancies. Nat Rev Clin Oncol 13(1):25-40 (2016).
Batzer et al. Enhanced evolutionary PCR using oligonucleotides with inosine at the 3'-terminus. Nucleic Acid Res 19:5081 (1991).
Bezverbnaya et al. Tumor-targeting domains for chimeric antigen receptor T cells. Immunotherapy 9(1):33-46 (2017).
Billadeau et al. ITAMs versus ITIMs: striking a balance during cell regulation. J Clin Invest 109:161-168 (2002).
Bird et al. Single-chain antigen-binding proteins. Science 242(4877):423-426 (1988).
Blank et al. Interaction of PD-L1 on tumor cells with PD-1 on tumor-specific T cells as a mechanism of immune evasion: implications for tumor immunotherapy. Cancer Immunol Immunother 54:307-314 (2005).
Bonifant et al. Toxicity and management in CAR T-cell Therapy. Mol Ther Oncolytics 3:16011 (2016).
Brentjens et al. Genetically targeted T cells eradicate systemic acute lymphoblastic leukemia xenograft. Clin Cancer Res13:5426-5435 (2007).
Brentjens. Novel cellular therapies for leukemia: CAR-modified T cells targeted to the CD19 antigen. Hematology Am Soc Hematol Educ Program 2012:143-151 (2012).
Bridgeman et al. Building better chimeric antigen receptors for adoptive T cell therapy. Current Gene Therapy 10:77-90 (2010).
Bridgeman et al. Structural and biophysical determinants of αβ T-cell antigen recognition. Immunology 135(1):9-18 (2012).
Brudno et al. Allogeneic T cells that express an anti-CD19 chimeric antigen receptor induce remissions of B-cell malignancies that progress after allogeneic hematopoietic stem-cell transplantation without causing graft-versus-host disease. J Clin Oncol 34(10):1112-1121 (2016).

(56) References Cited

OTHER PUBLICATIONS

Budde et al. Combining a CD20 chimeric antigen receptor and an inducible caspase 9 suicide switch to improve the efficacy and safety of T cell adoptive immunotherapy for lymphoma. PLoS One 8(12):e82742 (2013).
Caldas et al. Design and synthesis of germline-based hemi-humanized single-chain Fv against the CD18 surface antigen. Protein Eng 13(5):353-360 (2000).
Call et al. The organizing principle in the formation of the T cell receptor-CD3 complex. Cell 111(7):967-979 (2002).
Carpenter et al. B-cell maturation antigen is a promising target for adoptive T-cell therapy of multiple myeloma. Clin Cancer Res 19(8):2048-2060 (2013).
Cartellieri et al. Switching CAR T cells on and off: a novel modular platform for retargeting of T cells to AML blasts. Blood Cancer J 6(8):e458 (2016).
Carter et al. Humanization of an anti-p185HER2 antibody for human cancer therapy. PNAS USA 89(10):4285-4289 (1992).
Carter et al. PD-1: PD-L inhibitory pathway affects both CD4(+) and CD8(+) T cells and is overcome by IL-2. Eur J Immunol 32:634-643 (2002).
Chan et al. Chimeric antigen receptor-redirected CD45RA-negative T cells have potent antileukemia and pathogen memory response without graft-versus-host activity. Leukemia 29:387-395 (2015).
Chen et al. Novel anti-CD3 chimeric antigen receptor targeting of aggressive T cell malignancies. Oncotarget 7(35):56219-56232 (2016).
Chen et al. Oncology Meets Immunology: The Cancer-Immunity Cycle. Immunity 39(1):1-10 (2013).
Chhabra et al. TCR-Engineered, Customized, Antitumor T Cells for Cancer Immunotherapy: Advantages and Limitations. Scientific World Journal 11:121-129 (2011).
Chmielewski et al. Of CARs and TRUCKs: Chimeric antigen receptor (CAR) T cells engineered with an inducible cytokine to modulate the tumor stroma, Immunological Reviews 257(1):83-90 (2014).
Chothia et al. Canonical structures for the hypervariable regions of immunoglobulins. J Mol Biol. 196(4):901-917 (1987).
Cieri et al. Adoptive immunotherapy with genetically modified lymphocytes in allogeneic stem cell transplantation. Immun Rev 257(1):165-180 (2014).
Cieri et al. IL-7 and IL-15 instruct the generation of human memory stem T cells from naive precursors. Blood 121(4):573-584 (2013).
Cooper. Adoptive transfer of T cells genetically modified using the Sleeping Beauty system. Adoptive Transfer Session. 24th iSBTc Annual Meeting (30 pgs) (Oct. 31, 2009).
Co-pending U.S. Appl. No. 15/888,897, filed Feb. 5, 2018.
Co-pending U.S. Appl. No. 15/965,739, filed Apr. 27, 2018.
Cougot et al. 'Cap-tabolism'. Trends in Biochem Sci 29:436-444 (2001).
Couto et al. Anti-BA46 monoclonal antibody Mc3: humanization using a novel positional consensus and in vivo and in vitro characterization. Cancer Res 55(8):1717-1722 (1995).
Couto et al. Designing human consensus antibodies with minimal positional templates. Cancer Res 55(23 Supp):5973s-5977s (1995).
D'Argouges. Combination of rituximab with blinatumomab (MT103/MEDI-538), a T cell-engaging CD19-/CD3-bispecific antibody, for highly efficient lysis of human B lymphoma cells. Leukemia Res 33:465-473 (2009).
Davila. Efficacy and toxicity management of 19-28z CAR T cell therapy in B cell acute lymphoblastic leukemia. Sci Transl Med 6(224):224ra25 (2014).
Davila et al. How do CARs work? Early insights from recent clinical studies targeting CD19. Oncoimmunology 1(9):1577-1583 (2012).
Desmyter et al. Crystal structure of a camel single-domain VH antibody fragment in complex with lysozyme. Nat Struct Biol 3(9):803-811 (1996).
Dong et al. B7-H1 pathway and its role in the evasion of tumor immunity. J Mol Med 81:281-287 (2003).
Dopfer et al. The CD3 conformational change in the Gamma Delta T cell receptor is not triggered by antigens but can be enforced to enhance tumor killing. Cell Reports 7(5):1704-1715 (2014).
Elango et al. Optimized transfection of mRNA transcribed from a d(A/T)100 tail-containing vector. Biochim Biophys Res Commun 330:958-966 (2005).
Eshhar et al. Chimeric T cell receptor which incorporates the anti-tumour specificity of a monoclonal antibody with the cytolytic activity of T cells: a model system for immunotherapeutical approach. Br J Cancer 62:27-29 (1990).
Fang et al. Immunotherapy for advanced melanoma. J Invest Derm 128(11):2596-2605 (2008).
Finney et al. Activation of resting human primary T cells with chimeric receptors: costimulation from CD28, inducible costimulator, CD134, and CD137 in series with signals from the TCR zeta chain. J Immunol 172:104-113 (2004).
Finney et al. Chimeric Receptors Providing Both Primary and Costimulatory Signaling in T Cells from a Single Gene Product. J Immunol 161:2791-2797 (1998).
Fraietta et al. Ibrutinib enhances chimeric antigen receptor T-cell engraftment and efficacy in leukemia. Blood 127(9):1117-1127 (2016).
Freeman et al. Engagement of the PD-1 immunoinhibitory receptor by a novel B7 family member leads to negative regulation of lymphocyte activation. J Exp Med 192:1027-1034 (2000).
Frigault et al. Chimeric antigen receptor-modified T cells strike back. Int Immunol 28(7):355-363 (2016).
Gabrilovich et al. Myeloid-derived-suppressor cells as regulators of the immune system Nat Rev Immunol 9(3):162-174 (2009).
Garfall. Chimeric Antigen Receptor T Cells against CD19 for Multiple Myeloma. N Engl J Med 373(11):1040-1047 (2015).
Gargett et al. Different cytokine and stimulation conditions influence the expansion and immune phenotype of third-generation chimeric antigen receptor T cells specific for tumor antigen GD2. Cytotherapy 17(4):487-495 (2015).
Garland et al. The use of Teflon cell culture bags to expand functionally active CD8+ cytotoxic T lymphocytes. J Immunol Meth 227(1-2):53-63 (1999).
Gattinoni et al. Paths to stemness: building the ultimate antitumour T cell. Nature Reviews Cancer 12(10):671-684 (2012).
Ghosh et al. Donor CD19 Car T cells exert potent graft-versus-lymphoma activity with diminished graft-versus-host activity. Nature Medicine 23:242-249 (2017).
Gorochov et al. Functional assembly of chimeric T-cell receptor chains. Int J Cancer Supp 7:53-57 (1992).
Govers et al. TCRs Genetically Linked to CD28 and CD3ε Do Not Mispair with Endogenous TCR Chains and Mediate Enhanced T Cell Persistence and Anti-Melanoma Activity. J Immunol 193:5315-5326 (2014).
Griffin et al. Antibody fragments as tools in crystallography. Clin Exp Immunol 165(3):285-291 (2011).
Gross et al. Generation of effector T cells expressing chimeric T cell receptor with antibody type-specificity. Transplant Proc. 21(1 Pt 1):127-130 (1989).
Grupp et al. Chimeric antigen receptor-modified T cells for acute lymphoid leukemia. NEJM 368:1509-1518 (2013).
Guest et al. The role of extracellular spacer regions in the optimal design of chimeric immune receptors: evaluation of four different scFvs and antigens. J Immunother 28(3):203-211 (2005).
Haanen et al. Selective expansion of cross-reactive CD8(+) memory T cells by viral variants. J Exp Med 190(9):1319-1328 (1999).
Hatzoglou et al. TNF receptor family member BCMA (B cell maturation) associates with TNF receptor-associated factor (TRAF) 1, TRAF2, and TRAF3 and activates NF-kappa B, elk-1, c-Jun N-terminal kinase, and p38 mitogen-activated protein kinase. Immunology 165(3):1322-1330 (2000).
Hollinger et al. "Diabodies": Small bivalent and bispeific antibody fragments. PNAS USA 90:6444 6448 (1993).
Holzinger et al. The growing world of CAR T cell trials: a systematic review, Cancer Immunology. Immunotherapy 65(12):1433-1450 (2016).

(56) References Cited

OTHER PUBLICATIONS

Hombach et al. T cell activation by antibody-like immunoreceptors: the position of the binding epitope within the target molecule determines the efficiency of activation of redirected T cells. J Immunol 178:4650-4657 (2007).
Huang et al. Driving an improved CAR for cancer immunotherapy. J Clin Invest 126(8):2795-2798 (2016).
Huston et al. Protein engineering of antibody binding sites: recovery of specific activity in an anti-digoxin single-chain Fv analogue produced in *Escherichia coli*. PNAS USA 85(16):5879-5883 (1988).
Iwahori et al. Engager T cells: a new class of antigen-specific T cells that redirect bystander T cells. Mol Ther 23(1):171-178 (2015).
Izumoto et al. Phase II clinical trial of Wilms tumor 1 peptide vaccination for patients with recurrent glioblastoma multiforme. J Neurosurg 108:963-971 (2008).
Jackson et al. Driving CAR T-cells forward. Nat Rev Clin Oncol 13(6):370-383 (2016).
Jacoby. CD19 CAR immune pressure induces B-precursor acute lymphoblastic leukaemia lineage switch exposing inherent leukaemic plasticity. Nat Commun 7:12320 (2016).
Jacoby et al. Murine models of acute leukemia: important tools in current pediatric leukemia research. Front Oncol 4:95 (2014).
James et al. Antigen sensitivity of CD22-specific chimeric TCR is modulated by target epitope distance from the cell membrane. J Immunol 180:7028-7038 (2008).
Jena et al. Chimeric antigen receptor (CAR)-specific monoclonal antibody to detect CD19-specific T cells in clinical trials. PLoS One. 8(3):e57838 (2013).
Jin et al. Safe engineering of CAR T cells for adoptive cell therapy of cancer using long-term episomal gene transfer. EMBO Mol Med 8(7):702-711 (2016).
John et al. Anti-PD-1 antibody therapy potently enhances the eradication of established tumors by gene-modified T cells. Clin Cancer Res 19(20):5636-5646 (2013).
Jones et al. Replacing the complementarity-determining regions in a human antibody with those from a mouse. Nature 321:522-525 (1986).
Jonnalagadda et al. Chimeric Antigen Receptors With Mutated IgG4 Fc Spacer Avoid Fc Receptor Binding and Improve T Cell Persistence and Antitumor Efficacy. Mol Ther 23(4):757-768 (2015).
June et al. Engineering lymphocyte subsets: tools, trials and tribulations. Nat Rev Immunol 9.10:704-716 (2009).
Kabat et al. Sequences of Proteins of Immunological Interest. NIH Pub. No. 91-3242. Public Health Service, National Institutes of Health. 1:647-669 (1991).
Kaiser. Towards a commercial process for the manufacture of genetically modified T cells for therapy. Cancer Gene Thera 22(2):72-78 (2015).
Kalos et al. T cells with chimeric antigen receptors have potent antitumor effects and can establish memory in patients with advanced leukemia. Sci Transl Med 3(95):95ra73 (2011).
Karlsson et al. Evaluation of Intracellular Signaling Downstream Chimeric Antigen Receptors. PLoS One 10(12):e0144787 (2015).
Kawalekar et al. Distinct Signaling of Coreceptors Regulates Specific Metabolism Pathways and Impacts Memory Development in CAR T Cells. Immunity 44(2):380-390 (2016).
Kebriaei et al. Phase I trials using Sleeping Beauty to generate CD19-specific CAR T cells. J Clin Invest 126(9):3363-3376 (2016).
Kershaw et al. Gene-engineered T cells for cancer therapy. Nat Rev Cancer 13(8):525-541 (2013).
Klebanoff et al. Memory T cell-driven differentiation of naive cells impairs adoptive immunotherapy. J Clin Invest 126(1):318-334 (2016).
Klebanoff et al. Prospects for gene-engineered T cell immunotherapy for solid cancers. Nat Med 22(1):26-36 (2016).
Knies et al. An optimized single chain TCR scaffold relying on the assembly with the native CD3-complex prevents residual mispairing with endogenous TCRs in human T-cells. Oncotarget 7(16):21199-211221 (2016).
Kochenderfer et al. B-cell depletion and remissions of malignancy along with cytokine-associated toxicity in a clinical trial of anti-CD19 chimeric-antigen-receptor-transduced T cells. Blood 119(12):2709-2720 (2012).
Kochenderfer et al. Construction and Pre-clinical Evaluation of an Anti-CD19 Chimeric Antigen Receptor. Immunotherapy 32(7):689-702 (2010).
Kojima et al. Molecular cloning and expression of megakaryocyte potentiating factor cDNA. J Biol Chem 270:21984-21990 (1995).
Konishi et al. B7-H1 expression on non-small cell lung cancer cells and its relationship with tumor-infiltrating lymphocytes and their PD-1 expression. Clin Cancer Res 10:5094-5100 (2004).
Kowolik et al. CD28 costimulation provided through a CD19-specific chimeric antigen receptor enhances in vivo persistence and antitumor efficacy of adoptively transferred T cells. Cancer Res 66(22):10995-11004 (2006).
Krenciute et al. Characterization and Functional Analysis of scFv-based Chimeric Antigen Receptors to Redirect T Cells to IL13Rα2-positive Glioma. Mol Ther 24(2):354-363 (2016).
Kunert et al. TCR-engineered T cells meet new challenges to treat solid tumors: Choice of antigen, T cell fitness, and sensitization of tumor milieu. Front Immun 4:363 (2013).
Kunkele et al. Functional Tuning of CARs Reveals Signaling Threshold above Which CD8+ CTL Antitumor Potency Is Attenuated due to Cell Fas-FasL-Dependent AICD. Cancer Immunol Res 3(4):368-379 (2015).
Laabi et al. A new gene, BCM, on chromosome 16 is fused to the interleukin 2 gene by a t(4;16)(q26;p13) translocation in a malignant T cell lymphoma. EMBO 11(11):3897-3904 (1992).
Laabi et al. The BCMA gene, preferentially expressed during B lymphoid maturation, is bidirectionally transcribed. Nucleic Acids Res 22(7):1147-1154 (1994).
Langer. Comparative Evaluation of Peripheral Blood T Cells and Resultant Engineered Anti-CD19 CAR T-Cell Products From Patients With Relapsed / Refractory Non-Hodgkin Lymphoma (NHL). Abstract 2305 AACR Apr. 16-20, 2016 (1 pg.).
Lanier. NKG2D Receptor and Its Ligands in Host Defense. Cancer Immunol Res. 3(6):575-582 (2015).
Lanitis et al. Chimeric antigen receptor T Cells with dissociated signaling domains exhibit focused antitumor activity with reduced potential for toxicity in vivo. Cancer Immunol Res 1(1):45-53 (2013).
Lanzavecchia et al. The use of hybrid hybridomas to target human cytotoxic T lymphocytes. Eur J Immunol. 17(1):105-111 (1987).
Latchman et al. PD-L2 is a second ligand for PD-1 and inhibits T cell activation. Nat Immunol 2:261-268 (2001).
Lee et al. Current concepts in the diagnosis and management of cytokine release syndrome. Blood 124(2):188-196 (2014).
Lee et al. T cells expressing CD19 chimeric antigen receptors for acute lymphoblastic leukaemia in children and young adults: a phase 1 dose-escalation trial. The Lancet 385(9967):517-528 (2014).
Lee. Solid-state target CAR-T, 'TRUC platform' (KR). Biol.co.kr Retrieved from the Internet: URL:http://www.biospectator.com/view/news_print.php?varAtcId=4037 (7 pgs.) (2017) [retrieved on Jan. 9, 2018] (Machine translation).
Li et al. Adoptive immunotherapy using T lymphocytes redirected to glypican-3 for the treatment of lung squamous cell carcinoma. Oncotarget 7(3):2496-2507 (2015).
Lipowska-Bhalla et al. Targeted immunotherapy of cancer with CAR T cells: Achievements and challenges. Cancer Immunol Immuno 61(7):953-962 (2012).
Liu et al. A Chimeric Switch-Receptor Targeting PD1 Augments the Efficacy of Second-Generation CAR T Cells in Advanced Solid Tumors. Cancer Res 76(6):1578-1590 (2016).
Long et al. 4-1BB Costimulation Ameliorates T Cell Exhaustion Induced by Tonic Signaling of Chimeric Antigen Receptors. Nat Med 21(6):581-590 (2015).
Ma et al. Recognition of mesothelin by the therapeutic antibody MORAb-009: structural and mechanistic insights. J Biol Chem 287:33123-33131(2012).
Ma et al. Versatile strategy for controlling the specificity and activity of engineered T cells. PNAS 113(4):E450-E458 (2016).

(56) References Cited

OTHER PUBLICATIONS

Maher et al. Human T-lymphocyte cytotoxicity and proliferation directed by a single chimeric TCRzeta /CD28 receptor. Nat Biotech 20(1):70-75 (2002).
Mahmoud et al. Enforced CD19 expression leads to growth inhibition and reduced tumorigenicity. Blood 94(10):3551-3558 (1999).
Maude et al. CD19-targeted chimeric antigen receptor T-cell therapy for acute lymphoblastic leukemia. Blood 125(26):4017-4024 (2015).
Maus et al. Adoptive immunotherapy for cancer of viruses. Annual Review of Immunology 32:189-225 (2014).
Maus et al. Ex vivo expansion of polyclonal and antigen-specific cytotoxic T lymphocytes by artificial APCs expressing ligands for the T-cell receptor, CD28 and 4-1BB. Nature Biotech 20(2):143-148 (2002).
Maus et al. Making Better Chimeric Antigen Receptors for Adoptive T-cell Therapy. Clin Cancer Res 22(8):1875-1884 (2016).
Maus et al. Zoom zoom: Racing CARs for multiple myeloma. Clin Cancer Res 19(8):1917-1919 (2013).
Merry et al. O-glycan sialylation and the structure of the stalk-like region of the T cell co-receptor CD8. J Biol Chem 278(29):27119-27128 (2003).
Miller et al. CD19-Targeted CAR T Cells: A New Tool in the Fight against B Cell Malignancies. Oncol Res Treat 38(12):683-690 (2015).
Milone et al. Chimeric receptors containing CD137 signal transduction domains mediate enhanced survival of T cells and increased antileukemic efficacy in vivo. Mol Ther 17(8):1453-1464 (2009).
Minguet et al. A permissive geometry model for TCR-CD3 activation. Trends in Biochemical Sciences 33(2):51-57 (2008).
Minguet et al. Full Activation of the T Cell Receptor Requires Both Clustering and Conformational Changes at CD3. Immunity 26(1):43-54 (2007).
Moon et al. Expression of a functional CCR2 receptor enhances tumor localization and tumor eradication by retargeted human T cells expressing a mesothelin-specific chimeric antibody receptor. Clin Cancer Res 17(14):4719-4730 (2011).
Morea et al. Antibody modeling: implications for engineering and design. Methods 20(3):267-279 (2000).
Morton et al. Establishment of human tumor xenografts in immunodeficient mice. Nat Procol 2:247 (2007).
Moynihan et al. Eradication of large established tumors in mice by combination immunotherapy that engages innate and adaptive immune responses. Nat Med 12(22):1402-1410 (2016).
Mumtaz et al. Design of liposomes for circumventing the reticuloendothelial cells. Glycobiology 5:505-510 (1991).
Nacheva et al. Preventing nondesired RNA-primed RNA extension catalyzed by T7 RNA polymerase. Eur J Biochem 270:1458-1465 (2003).
Needleman et al. A general method applicable to the search for similarities in the amino acid sequence of two proteins. J. Mol. Biol. 48:443-453 (1970).
Nicholson et al. Construction and characterisation of a functional CD19 specific single chain Fv fragment for immunotherapy of B lineage leukaemia and lymphoma. Mol Immun 34(16-17):1157-1165 (1997).
Nishikawa et al. Nonviral vectors in the new millennium: delivery barriers in gene transfer. Human Gene Therapy. 12:861-870 (2001).
Nolan et al. Bypassing immunization: optimized design of "designer T cells" against carcinoembryonic antigen (CEA)-expressing tumors, and lack of suppression by soluble CEA. Clin Cancer Res 5:3928-3941 (1999).
Oden et al. Potent anti-tumor response by targeting B cell maturation antigen (BCMA) in a mouse model of multiple myeloma. Mole Oncol 9(7):1348-1358 (2015).
Ohtsuka et al. An alternative approach to deoxyoligonucleotides as hybridization probes by insertion of Deoxyinosine at Ambiguous Codon Positions. J Biol Chem 260:2605-2608 (1985).
Onda et al. Megakaryocyte potentiation factor cleaved from mesothelin precursor is a useful tumor marker in the serum of patients with mesothelioma. Clin Cancer Res. 12:4225-4231 (2006).
Padlan. A possible procedure for reducing the immunogenicity of antibody variable domains while preserving their ligand-binding properties. Mol Immunol 28(4-5):489-498 (1991).
Park et al. Adoptive Immunotherapy for B-cell Malignancies with Autologous Chimeric Antigen Receptor Modified Tumor Targeted T Cells. Disc Med 9(47)277-288 (2010).
Patel et al. Engineering an APRIL-specific B Cell Maturation Antigen. J Bio Chem 279(16):16727-16735 (2004).
Patel et al. PDL-1 Expression as a Predictive Biomarker in cancer Immunotherapy. Mol Cancer Ther 14(4):847-856 (2015).
PCT/US2016/033146 International Preliminary Report on Patentability dated Nov. 30, 2017.
PCT/US2016/033146 International Search Report and Written Opinion dated Oct. 20, 2016.
PCT/US2017/045159 International Search Report and Written Opinion dated Nov. 3, 2017.
PCT/US2017/055628 International Search Report and Written Opinion dated Jan. 24, 2018.
PCT/US2017/068002 International Search Report and Written Opinion dated Apr. 12, 2018.
Pearson, et al. Improved Tools for Biological Sequence Comparison. Proc. Nat'l Acad. Sci. USA. 85 (1988): 2444-48.
Pedersen et al. Comparison of surface accessible residues in human and murine immunoglobulin Fv domains. Implication for humanization of murine antibodies. J Mol Biol 235(3):959-973 (1994).
Philip et al. A highly compact epitope-based marker suicide gene for safer and easier adoptive T-cell gene therapy. Blood 124:1277-1287 (2014).
Porter et al. Chimeric antigen receptor T cells persist and induce sustained remissions in relapsed refractory chronic lymphocytic leukemia. Sci Trans Med 7(303):303ra319 (2015).
Porter et al. Chimeric antigen receptor-modified T cells in chronic lymphoid leukemia. NEJM 365:725-733 (2011).
Porter et al. Pilot study of redirected autologous t cells engineered to contain anti-CD19 attached to TCRZ and 4-1BB signaling domains in patients with chemotherapy resistant or refractory CD19+ leukemia and lymphoma. NCT02374333. Available at https://www.clinicaltrials.gov/ct2/show/NCT02374333?term=13BT022 (3 pgs.) (2016).
Presta. Antibody Engineering. Curr Op Struct Biol 2:593-596 (1992).
Presta et al. Humanization of an antibody directed against IgE. J Immunol 151:2623-2632 (1993).
Pule et al. A chimeric T cell antigen receptor that augments cytokine release and supports clonal expansion of primary human T cells. Mol Ther 12(5):933-941 (2005).
Punt et al. Stoichiometry of the T cell antigen receptor (TCR) complex: each TCR/CD3 complex contains one TCR alpha, one TCR beta, and two CD3 epsilon chains. J Exp Med 180(2):587-593 (1994).
Riechmann et al. Reshaping human antibodies for therapy. Nature, 332.6162 (1988): 323-7.
Rodgers et al. Switch-mediated activation and retargeting of CAR-T cells for B-cell malignancies. PNAS USA 113(4):E459-E468 (2016).
Roguska et al. A comparison of two murine monoclonal antibodies humanized by CDR-grafting and variable domain resurfacing. Protein Eng 9(10):895-904 (1996).
Roguska et al. Humanization of murine monoclonal antibodies through variable domain resurfacing. PNAS 91:969-973 (1994).
Rosenberg. Cell transfer immunotherapy for metastatic solid cancer—what clinicians need to know. Nat Rev Clin Oncol 8(10):577-585 (2011).
Rosenberg et al. Use of tumor-infiltrating lymphocytes and interleukin-2 in the immunotherapy of patients with metastatic melanoma. A preliminary report. NEJM 319:1676 (1988).
Rossolini et al. Use of deoxyinosine-containing primers vs degenerate primers for polymerase chain reaction based on ambiguous sequence information. Mol Cell Probes 8(2):91-98 (1994).
Rump et al. Binding of ovarian cancer antigen CA125/MUC16 to mesothelin mediates cell adhesion. J Biol Chem 279:9190-9198 (2004).

(56) References Cited

OTHER PUBLICATIONS

Rushworth et al. Universal Artificial Antigen Presenting Cells to Selectively Propagate T Cells Expressing Chimeric Antigen Receptor Independent of Specificity. J Immunother 37(4):204-213 (2014).
Sadelain. CAR therapy: The CD19 paradigm. J Clin Invest 135(9):3392-3400 (2015).
Sadelain et al. Tales of Antigen Evasion from CAR Therapy. Cancer Immunol Res 4(6):473 (2016).
Sadelain et al. The Basic Principles of Chimeric Antigen Receptor Design. Cancer Discov 3(4):388-398 (2013).
Sakemura et al. A Tet-On Inducible System for Controlling CD19-Chimeric Antigen Receptor Expression upon Drug Administration. Cancer Immunol Res 4(8):658-668 (2016).
Sandhu. A rapid procedure for the humanization of monoclonal antibodies. Gene 150(2):409-410 (1994).
Schenborn et al. A novel transcription property of SP6 and T7 RNA polymerases: dependence on template structure. Nuc Acids Res 13:6223-6236 (1985).
Shin et al. Positive conversion of negative signaling of CTLA4 potentiates antitumor efficacy of adoptive T-cell therapy in murine tumor models. Blood 119(24):5678-5687 (2012).
Simon et al. PD-1 expression conditions T cell avidity within an antigen-specific repertoire. Oncoimmunology 5(1):e1104448 (2015).
Sims et al. A humanized CD18 antibody can block function without cell destruction. J Immunol., 151 (1993): 2296-2308.
Smith, et al. Comparison of Biosequences. Advances in Applied Mathematics. 1981;2: 482-489.
Sommers et al. Function of CD3c-mediated Signals in T Cell Development. J Exper Med 192(6):913-920 (2000).
Song et al. CD27 costimulation augments the survival and antitumor activity of redirected human T cells in vivo. Blood 119(3):696-706 (2012).
Song et al. In Vivo Persistence, Tumor Localization, and Antitumor Activity of CAR-Engineered T Cells Is Enhanced by Costimulatory Signaling through CD137 (4-1BB). Cancer Res 71(13):4617-4627 (2011).
Spear et al. Collaboration of chimeric antigen receptor (CAR)-expressing T cells and host T cells for optimal elimination of established ovarian tumors. Oncoimmunology 2(4):e23564 (2013).
Srivastava et al. Engineering CAR-T cells: Design concepts. Trends Immunol 36(8):494-502 (2015).
Stepinski et al. Synthesis and properties of mRNAs containing the novel ‘anti-reverse’ cap analogs 7-methyl(3'0-methyl)GpppG and 7-methyl(e'-deoxy)GpppG. RNA 7:1486-1495 (2001).
Stone et al. A novel T cell receptor single-chain signaling complex mediates antigen-specific T cell activity and tumor control. Cancer Immunol Immunother 63(11):1163-1176 (2014).
Studnicka et al. Human-engineered monoclonal antibodies retain full specific binding activity by preserving non-CDR complementarity-modulating residues. Pro Eng 7(6):805-814 (1994).
Sun et al. The quest for spatio-temporal control of CAR T cells. Cell Res 25(12):1281-1282 (2015).
Tan et al. “Superhumanized” antibodies: reduction of immunogenic potential by complementarity-determining region grafting with human germline sequences: application to an anti-CD28. J Immunol 169:1119-1125 (2002).
TCR2 Therapeutics Presents Positive Solid Tumor Data for its Novel TRuC™ Engineered T Cell Therapies at the World Preclinical Congress. PRNewswire. Available at http://www.prnewswire.com/news-releases/tcr2-therapeutics-presents-positive-solid-tumor-data-for-its-novel-truc-engineered-t-cell-therapies-at-the-world-preclinical-congress-300472629.html (Jun. 13, 2017) (2 pgs.).
Teachey. Identification of Predictive Biomarkers for Cytokine Release Syndrome after Chimeric Antigen Receptor T cell Therapy for Acute Lymphoblastic Leukemia. Cancer Disc 6(6):664-679 (2016).
Ten Berg et al. Selective expansion of a peripheral blood CD8+ memory T cell subset expressing both granzyme B and L-selectin during primary viral infection in renal allograft recipients. Transplant Proc 30(8):3975-3977 (1998).
Themeli et al. Generation of tumor-targeted human T lymphocytes from induced pluripotent stem cells for cancer therapy. Nat Biotech 31:928-933 (2013).
Themeli et al. New cell sources for T cell engineering and adoptive immunotherapy. Cell Stem Cell 16(4):357-366 (2015).
Thokala et al. Redirecting Specificity of T cells Using the Sleeping Beauty System to Express Chimeric Antigen Receptors by Mix-and-Matching of VLand VHDomains Targeting CD123+ Tumors. PLoS One 11(8):e0159477 (2016).
Torikai et al. A foundation for universal T-cell based immunotherapy: T cells engineered to express a CD19-specific chimeric-antigen-receptor and eliminate expression of endogenous TCR. Blood 119(24):5697-5705 (2012).
Torikai et al. Translational Implications for Off-the-shelf Immune Cells Expressing Chimeric Antigen Receptors. Mol Ther 24(7):1178-1186 (2016).
Tran et al. Cancer Immunotherapy Based on Mutation-Specific CD4+ T Cells in a Patient with Epithelial Cancer. Science 9:641-645 (2014).
Tsai et al. Producer T cells: Using genetically engineered T cells as vehicles to generate and deliver therapeutics to tumors. Oncoimmunol 5(5):e1122158 (2016).
Tumaini et al. Simplified process for the production of anti-CD19-CAR engineered T cells. Cytotherapy 15(11):1406-1415 (2014).
Turtle et al. CD19 CAR-T cells of defined CD4+:CD8+ composition in adult B cell ALL patients. J Clin Invest 126(6):2123-2138 (2016).
Ui-Tei et al. Sensitive assay of RNA interference in *Drosophila* and Chinese hamster cultured cells using firefly luciferase gene as target. FEBS Letters 479: 79-82 (2000).
U.S. Appl. No. 15/419,398 1st Action Interview dated Jul. 3, 2017.
U.S. Appl. No. 15/419,398 Office Action dated Mar. 7, 2018.
U.S. Appl. No. 15/419,398 Office Action dated Nov. 9, 2017.
Valton et al. A Multidrug-resistant Engineered CAR T Cell for Allogeneic Combination Immunotherapy. Mol Ther 23(9):1507-1518 (2015).
Van Der Stegen et al. The pharmacology of second-generation chimeric antigen receptors. Nat Rev Drug Discov 14(7):499-509 (2015).
Velasquez. T cells expressing CD19-specific Engager Molecules for the Immunotherapy of CD19-positive Malignancies. Sci Rep 6:27130 (2016).
Verhoeyen et al. Reshaping human antibodies: grafting an antilysozyme activity. Science 239:1534-1536 (1988).
Wang et al. Generation of Potent T-cell Immunotherapy for Cancer Using DAP12-Based, Multichain, Chimeric Immunoreceptors. Cancer Immunol Res 3(7):815-826 (2015).
Wang et al. Manufacture of tumor- and virus-specific T lymphocytes for adoptive cell therapies. Cancer Gene Therapy 22(2):85-94 (2015).
Wang et al. VISTA, a novel mouse Ig superfamily ligand that negatively regulates T cell responses. J Exp Med 208(3):577-592 (2011).
Watanabe et al. Fine-tuning the CAR spacer improves T-cell potency. Oncoimmunology. 5(2):e1253656 (2016).
Wegener et al. The T cell receptor/CD3 complex is composed of at least two autonomous transduction modules. Cell 68:83-95 (1992).
Wilkie et al. Selective Expansion of Chimeric Antigen Receptor-targeted T-cells with Potent Effector Function using Interleukin-4. J Biol Chem 285(33):25538-25544 (2010).
Wu et al. Protein design of IgG/TCR chimeras for the co-expression of Fab-like moieties within bispecific antibodies. MABS 7(2):364-376 (2015).
Wucherpfennig et al. Structural Biology of the T-cell Receptor: Insights into Receptor Assembly, Ligand Recognition, and Initiation of Signaling. Cold Spring Harb Perspect Biol 2(4):a005140 (2010).
Yun et al. Targeting of T Lymphocytes to Melanoma Cells Through Chimeric Anti-GD3 Immunoglobulin T-Cell Receptors. Neoplasia 2(5):449-459 (2000).
Zah et al. T cells expressing CD19/CD20 bi-specific chimeric antigen receptors prevent antigen escape by malignant B cells. Cancer Immunol Res 4(6)498-509 (2016).

(56) References Cited

OTHER PUBLICATIONS

Zhang et al. 4-1BB is superior to CD28 costimulation for generating CD8+ cytotoxic lymphocytes for adoptive immunotherapy. J Immunol 179:4910-4918 (2007).
Zhao et al. A herceptin-based chimeric antigen receptor with modified signaling domains leads to enhanced survival of transduced T lymphocytes and antitumor activity. J Immunol 183:5563-5574 (2009).
Zhao et al. Structural Design of Engineered Costimulation Determines Tumor Rejection Kinetics and Persistence of Car T cells. Cancer Cell 28(4):415-428 (2015).
Zhou et al. Exclusive Transduction of Human CD4+ T Cells upon Systemic Delivery of CD4-Targeted Lentiviral Vectors. J Immunol 195:2493-2501 (2015).
Brocker et al. Redirecting the complete T cell receptor/CD3 signaling machinery towards native antigen via modified T cell receptor. Eur J. Immunol 26:1770-1774 (1996).
Brocker et al. Signals through T cell receptor-zeta chain alone are insufficient to prime resting T lymphocytes. J Med Chem 181:1653-1659 (1995).
Brocker. Chimeric Fv-zeta or Fv-epsilon receptors are not sufficient to induce activation or cytokine production in peripheral T cells. Blood 96(5):1999-2001 (2000).
Mosquera et al. In vitro and in vivo characterization of a novel antibody-like single-chain TCR human IgG1 fusion protein. J Immunol 174(7):4381-4388 (2005).
Sommermeyer et al. Designer T cells by T cell receptor replacement. Eur J Immunol 36(11):3052-3059 (2006).
Barrett et al. Eradication of established CD19-positive leukemia using a single injection of chimeric immunoreceptor modified lentiviral-transduced T cells in a xenograft NOG mouse model. Journal of Immunotherapy 32(9):941 (2009).
Co-pending U.S. Appl. No. 16/222,846, filed Dec. 17, 2018.
Sander et al. CRISPR-Cas systems for editing, regulating and targeting genomes. Nat. Biotechnol 32:347-355 (2014).
Adusumilli et al. 342: A Phase 1 Clinical Trial of Malignant Pleural Disease Treated with Regionally Delivered Autologous Mesothelin-Targeted CAR T Cells: Safety and Efficacy—A Preliminary Report. Mol Therapy 26(551):158-159 (2018).
Adusumilli et al. Regional delivery of mesothelin-targeted CAR T cell therapy generates potent and long-lasting CD4-dependent tumor immunity. Sci Transl Med 6(261):261ra151 (2014) (w/Supplementary Data).
Angelo et al. Antitumor Activity Associated with Prolonged Persistence of Adoptively Transferred NY-ESO-1c259 T cells in Synovial Sarcoma. Cancer Disov 8(8):944-957 (2018).
Beatty et al. Activity of Mesothelin-specific Chimeric Antigen Receptor T cells Against Pancreatic Carcinoma Metastases in a Phase 1 Trial. Gastroenterology 5085(18)30323-30328 (accepted manuscript).
Beatty et al. Mesothelin-Specific Chimeric Antigen Receptor mRNA-Engineered T Cells Induce Antitumor Activity in Solid Malignancies. Cancer Immunol 3(2):217 (2015).
Beatty et al. Mesothelin-specific Chimeric Antigen Receptor mRNA-Engineered T cells Induce Anti-Tumor Activity in Solid Malignancies. Cancer Immunol Res 2(2):112-120 (2014).
Buck et al. Mitochondrial Dynamics Controls T Cell Fate through Metabolic Programming. Cell 166:63-76 (2016).
Carpenito et al. Control of large, established tumor xenografts with genetically retargeted human T cells containing CD28 and CD137 domains. PNAS USA 106(9):3360-3365 (2009).
Chu et al. Targeting+ CD20 Aggressive B-cell Non-Hodgkin Lymphoma by Anti-CD20 CAR mRNA-Modified Expanded Natural Killer Cells In Vitro and in NSG Mice. Cancer Immunol Res 3(4):333-344 (2015).
Cristaudo et al. Clinical significance of serum mesothelin in patients with mesothelioma and lung cancer. Clin. Cancer Res. 13:5076-5081 (2007).
Dotti et al. Design and Development of Therapies using Chimeric Antigen Receptor-Expressing T cells. Immunol Rev. 257(1):35 pgs (2014).
Eshhar et al., Design of cytotoxic T lymphocytes with antibody-type specificity against tumor cells using chimeric PCR. Journal of Cellular Biochemistry, A.R. Liss, Suppl. 14B: 70 (1990).
Feng et al. A novel human monoclonal antibody that binds with high affinity to mesothelin-expressing cells and kills them by antibody-dependent cell-mediated cytotoxicity. Mol Cancer Ther 8(5):1113-1118.
Garrido et al. The urgent need to recover MHC class I in cancers for effective immunotherapy. Current Opinion in Immunology 39:44-51 (2016).
Guedan et al. ICOS-based chimeric antigen receptors program bipolar TH17/TH1 cells. Blood 124(7):1070-1080 (2014).
Guy et al. Distinct T cell receptor signaling pathways drive proliferation and cytokine production in T cells. Nat Immunol 14(3):262-270 (2013).
Hassan et al. Major Cancer Regressions in Mesothelioma After Treatment with an Anti-Mesothelin Immunotoxin and Immune Suppression. Sci Transl Med 5:208ra147 (2013).
Hassan et al. Mesothelin: a new target for immunotherapy. Clin Cancer Res 10:3937-3942 (2004).
Hicklin et al. HLA class I antigen downregulation in human cancers: T-cell immunotherapy revives and old story. Mol Med Today 5(4):178-186 (1999).
Ho et al. Mesothelin expression in human lung cancer. Clin Cancer Res 13:1571-1575 (2007).
Hudecek et al. The Nonsignaling Extracellular Spacer Domain of Chimeric Antigen Receptors Is Decisive for In Vivo Antitumor Activity. Cancer Immunol Res 3(2):125-135 (2015).
Hwan et al. Universal Chimeric Antigen Receptors for Multiplexed and Logical Control of T Cell Responses. Cell 173(6):1426-1438.e11 (2018).
Hwu et al., the genetic modification of T cells for cancer therapy: an overview of laboratory and clinical trials. Cancer Detect Prev. 18(1):43-50 (1994).
Illei et al. Mesothelin Expression in Advanced Gastroesophageal Cancer Represents a Novel Target for Immunotherapy. Appl Immunohistochem Mol Morphol 24(4):246-252 (2016).
Institute for Clinical and Economic review (ICER). Chimeric Antigen Receptor T-Cell Therapy for B-Cell Cancers: Effectiveness and Value. Final Evidence Report dated Mar. 23, 2018 (185 pgs).
Jamnani et al. T cells expressing VHH-directed oligoclonal chimeric HER2 antigen receptors: towards tumor-directed oligoclonal T cell therapy. Biochim Biophys Acta 1840(1):378-386 (2014).
Johnson et al. Rational development and characterization of humanized anti-EGFR variant III chimeric antigen receptor T cells for glioblastoma. Immunotherapy 7(275):275ra22 (2015).
June et al. Chimeric Antigen Receptor Therapy. N Engl J Med 379:64-73 (2018).
June et al. Is autoimmunity the Achilles' heel of cancer immunotherapy? Nat Med 23(5):540-547 (2017).
Junghans. The challenges of solid tumor for designer CAR-T therapies: a 25-year perspective. Cancer Gene Ther 24(3):89-99 (2017).
Kachala et al. Mesothelin Overexpression Is a Marker of Tumor Aggressiveness and Is Associated with Reduced Recurrence-Free and Overall Survival in Early-Stage Lung Adenocarcinoma. Clin Cancer Res 20(4):1020-1028 (2013).
Kawalekar et al. Supplemental Information. Distinct Signaling of Coreceptors Regulates Specific Metabolism Pathways and Impacts Memory Development in CAR T Cells. Immunity 44(2):380-390 (2016).
Kuhns et al. TCR Signaling Emerges from the Sum of Many Parts. Front. Immunol. 3:159 (2012).
Lanitis et al. Redirected Antitumor Activity of Primary Human Lymphocytes Transduced With a Fully Human Anti-mesothelin Chimeric Receptor. Mol Ther 20(3):633-643 (2012).
Leone et al. MHC Class I Antigen Processing and Presenting Machinery: Organization, Function, and Defects in Tumor Cells. J Natl Cancer Inst 105:1172-1187 (2013).

(56) References Cited

OTHER PUBLICATIONS

Li et al. Enhanced Cancer Immunotherapy by Chimeric Antigen Receptor-Modified T Cells Engineered to Secrete Checkpoint Inhibitors. Clin Cancer Res 23(22):6982-6992 (2017).
Liu et al. Affinity-Tuned ErbB2 or EGFR Chimeric Antigen Receptor T Cells Exhibit an Increased Therapeutic Index against Tumors in Mice. Cancer Res 75(17):3596-3607 (2015).
Liu et al. Improved anti-leukemia activities of adoptively transferred T cells expressing bispecific T-cell engager in mice. Blood Cancer J 6:e430 (2016).
Liu et al. Supplemental Information. A Chimeric Switch-Receptor Targeting PD1 Augments the Efficacy of Second-Generation CAR T Cells in Advanced Solid Tumors. Cancer Res 76(6):1578-1590 (2016).
Lu et al. Treatment of Patients With Metastatic Cancer Using a Major Histocompatibility Complex Class II-Restricted T-Cell Receptor Targeting the Cancer Germline Antigen MAGE-A3. J Clin Oncol 35(29):3322-3329.
Maus et al. T Cells Expressing Chimeric Antigen Receptors Can Cause Anaphylaxis in Humans. Cancer Immunol Res. 1:26-31 (2013).
Menk et al. 4-1BB costimulation induces T cell mitochondrial function and biogenesis enabling cancer immunotherapeutic responses. J Exp Med 215(4):1091-1100 (2018).
Morello et al. Mesothelin-Targeted CARs: Driving T Cells to Solid Tumors. Cancer Discov 6(2):133-146 (2016).
Newick et al. Chimeric antigen receptor T-cell therapy for solid tumors. Molecular Therapy—Oncolytics 3:16006 (2016).
O'Hare et al. Mesothelin as a target for chimeric antigen receptor-modified T cells as anticancer therapy. Immunotherapy 8(4):449-460 (2016).
Onda et al. New Monoclonal Antibodies to Mesothelin Useful for Immunohistochemistry, Fluorescence-Activated Cell Sorting, Western Blotting, and ELISA. Clin Cancer Res 11(16):5840-5846 (2005).
Pastan et al. Discovery of Mesothelin and Exploiting It as a Target for Immunotherapy. Cancer Res 74(11):2907-2912 (2014).
PCT/US2017/063137 International Search Report and Written Opinion dated Jun. 14, 2018.
PCT/US2018/037387 International Search Report and Written Opinion dated Sep. 17, 2018.
Posey et al. Engineered CAR T Cells Targeting the Cancer-Associated Tn-Glycoform of theMembraneMucinMUC1 Control Adenocarcinoma. Immunity 44:1444-1454 (2016).
Rivadeneira et al. Antitumor T cell reconditioning: improving metabolic fitness for optimal cancer immunotherapy. Clin Cancer Res 24(11):2473-2481 (2018).
Rosenberg et al. Adoptive cell transfer as personalized immunotherapy for human cancer. Science 348(6230):62-68 (2015).
Roybal et al. Precision Tumor Recognition by T Cells With Combinatorial Antigen-Sensing Circuits. Cell 164:1-10 (2016).
Ruella et al. Smart CARS: optimized development of a chimeric antigen receptor (CAR) T cell targeting epidermal growth factor receptor variant III (EGFRvIII) for glioblastoma. Ann Transl Med 4(1):13 (2016).
Sadelain et al. Therapeutic T cell engineering. Nature 545:423-431 (2017).
Sapede et al. Aberrant splicing and protease involvement in mesothelin release from epithelioid mesothelioma cells. Cancer Sci 99(3):590-594 (2008).
Servais et al. An In Vivo Platform for Tumor Biomarker Assessment. PloS One 6(10):e26772.
Sharpe et al. Genetically modified T cells in cancer therapy: opportunities and challenges. Dis Model Mech 8(4):337-350 (2015).
Stromnes et al. T Cells Engineered against a Native Antigen Can Surmount Immunologic and Physical Barriers to Treat Pancreatic Ductal Adenocarcinoma. Cancer Cell 28:638-652 (2015).
Tang et al. A human single-domain antibody elicits potent antitumor activity by targeting an epitope in mesothelin close to the cancer cell surface. Mol. Cancer Thera 12(4):416-426 (2013).
Tanyi et al. Possible Compartmental Cytokine Release Syndrome in a Patient With Recurrent Ovarian Cancer After Treatment With Mesothelin-targeted CAR-T Cells. J Immunother 40(3):104-107 (2017).
Tchou et al. Safety and efficacy of intratumoral injections of chimeric antigen receptor (CAR) T cells in metastatic breast cancer. Cancer Immunol Res 5(12):1152-1161 (2017).
U.S. Appl. No. 15/965,739 Preinterview First Action dated Nov. 15, 2018.
Weekes et al. Phase I Study of DMOT4039A, an Antibody-Drug Conjugate Targeting Mesothelin, in Patients with Unresectable Pancreatic or Platinum-Resistant Ovarian Cancer. Mol Cancer Ther 15(3):439-447 (2016).
Whittington et al. Accounting for All Costs in the Total Cost of Chimeric Antigen Receptor T-Cell Immunotherapy. JAMA Oncol. Published online Oct. 11, 2018 (1 pg.).
Xu et al. The basics of CAR T design and challenges in immunotherapy of solid tumors—Ovarian cancer as a model. Hum Vaccin Immunother 13(7):1548-1555 (2017).
Zhang et al. New High Affinity Monoclonal Antibodies Recognize Non-Overlapping Epitopes on Mesothelin for Monitoring and Treating Mesothelioma. Sci Rep 5:9928 (2015).
Zhang et al. Phase I Escalating-Dose Trial of CAR-T Therapy Targeting CEA+ Metastatic Colorectal Cancers. Mol Ther 25:1248-1258 (2017).
Zhao et al. Multiple injections of electroporated autologous T cells expressing a chimeric antigen receptor mediate regression of human disseminated tumor. Cancer Res 70(22):9053-9061 w/Supplemental Information (2010).

* cited by examiner

SEQUENCE LISTING

```
<160> NUMBER OF SEQ ID NOS: 74

<210> SEQ ID NO 1
<211> LENGTH: 556
<212> TYPE: PRT
```

```
<213> ORGANISM: Homo sapiens

<400> SEQUENCE: 1

Met Pro Pro Pro Arg Leu Leu Phe Phe Leu Leu Phe Leu Thr Pro Met
1               5                   10                  15

Glu Val Arg Pro Glu Glu Pro Leu Val Val Lys Val Glu Glu Gly Asp
            20                  25                  30

Asn Ala Val Leu Gln Cys Leu Lys Gly Thr Ser Asp Gly Pro Thr Gln
        35                  40                  45

Gln Leu Thr Trp Ser Arg Glu Ser Pro Leu Lys Pro Phe Leu Lys Leu
    50                  55                  60

Ser Leu Gly Leu Pro Gly Leu Gly Ile His Met Arg Pro Leu Ala Ile
65                  70                  75                  80

Trp Leu Phe Ile Phe Asn Val Ser Gln Gln Met Gly Gly Phe Tyr Leu
                85                  90                  95

Cys Gln Pro Gly Pro Pro Ser Glu Lys Ala Trp Gln Pro Gly Trp Thr
            100                 105                 110

Val Asn Val Glu Gly Ser Gly Glu Leu Phe Arg Trp Asn Val Ser Asp
        115                 120                 125

Leu Gly Gly Leu Gly Cys Gly Leu Lys Asn Arg Ser Ser Glu Gly Pro
    130                 135                 140

Ser Ser Pro Ser Gly Lys Leu Met Ser Pro Lys Leu Tyr Val Trp Ala
145                 150                 155                 160

Lys Asp Arg Pro Glu Ile Trp Glu Gly Glu Pro Pro Cys Leu Pro Pro
                165                 170                 175

Arg Asp Ser Leu Asn Gln Ser Leu Ser Gln Asp Leu Thr Met Ala Pro
            180                 185                 190

Gly Ser Thr Leu Trp Leu Ser Cys Gly Val Pro Pro Asp Ser Val Ser
        195                 200                 205

Arg Gly Pro Leu Ser Trp Thr His Val His Pro Lys Gly Pro Lys Ser
    210                 215                 220

Leu Leu Ser Leu Glu Leu Lys Asp Asp Arg Pro Ala Arg Asp Met Trp
225                 230                 235                 240

Val Met Glu Thr Gly Leu Leu Leu Pro Arg Ala Thr Ala Gln Asp Ala
                245                 250                 255

Gly Lys Tyr Tyr Cys His Arg Gly Asn Leu Thr Met Ser Phe His Leu
            260                 265                 270

Glu Ile Thr Ala Arg Pro Val Leu Trp His Trp Leu Leu Arg Thr Gly
        275                 280                 285

Gly Trp Lys Val Ser Ala Val Thr Leu Ala Tyr Leu Ile Phe Cys Leu
    290                 295                 300

Cys Ser Leu Val Gly Ile Leu His Leu Gln Arg Ala Leu Val Leu Arg
305                 310                 315                 320

Arg Lys Arg Lys Arg Met Thr Asp Pro Thr Arg Arg Phe Phe Lys Val
                325                 330                 335

Thr Pro Pro Pro Gly Ser Gly Pro Gln Asn Gln Tyr Gly Asn Val Leu
            340                 345                 350

Ser Leu Pro Thr Pro Thr Ser Gly Leu Gly Arg Ala Gln Arg Trp Ala
        355                 360                 365

Ala Gly Leu Gly Gly Thr Ala Pro Ser Tyr Gly Asn Pro Ser Ser Asp
    370                 375                 380

Val Gln Ala Asp Gly Ala Leu Gly Ser Arg Ser Pro Pro Gly Val Gly
385                 390                 395                 400
```

```
Pro Glu Glu Glu Glu Gly Glu Gly Tyr Glu Glu Pro Asp Ser Glu Glu
                405                 410                 415

Asp Ser Glu Phe Tyr Glu Asn Asp Ser Asn Leu Gly Gln Asp Gln Leu
            420                 425                 430

Ser Gln Asp Gly Ser Gly Tyr Glu Asn Pro Glu Asp Glu Pro Leu Gly
        435                 440                 445

Pro Glu Asp Glu Asp Ser Phe Ser Asn Ala Glu Ser Tyr Glu Asn Glu
    450                 455                 460

Asp Glu Glu Leu Thr Gln Pro Val Ala Arg Thr Met Asp Phe Leu Ser
465                 470                 475                 480

Pro His Gly Ser Ala Trp Asp Pro Ser Arg Glu Ala Thr Ser Leu Gly
                485                 490                 495

Ser Gln Ser Tyr Glu Asp Met Arg Gly Ile Leu Tyr Ala Ala Pro Gln
            500                 505                 510

Leu Arg Ser Ile Arg Gly Gln Pro Gly Pro Asn His Glu Glu Asp Ala
        515                 520                 525

Asp Ser Tyr Glu Asn Met Asp Asn Pro Asp Gly Pro Asp Pro Ala Trp
    530                 535                 540

Gly Gly Gly Gly Arg Met Gly Thr Trp Ser Thr Arg
545                 550                 555


<210> SEQ ID NO 2
<211> LENGTH: 184
<212> TYPE: PRT
<213> ORGANISM: Homo sapiens

<400> SEQUENCE: 2

Met Leu Gln Met Ala Gly Gln Cys Ser Gln Asn Glu Tyr Phe Asp Ser
1               5                   10                  15

Leu Leu His Ala Cys Ile Pro Cys Gln Leu Arg Cys Ser Ser Asn Thr
            20                  25                  30

Pro Pro Leu Thr Cys Gln Arg Tyr Cys Asn Ala Ser Val Thr Asn Ser
        35                  40                  45

Val Lys Gly Thr Asn Ala Ile Leu Trp Thr Cys Leu Gly Leu Ser Leu
    50                  55                  60

Ile Ile Ser Leu Ala Val Phe Val Leu Met Phe Leu Leu Arg Lys Ile
65                  70                  75                  80

Asn Ser Glu Pro Leu Lys Asp Glu Phe Lys Asn Thr Gly Ser Gly Leu
                85                  90                  95

Leu Gly Met Ala Asn Ile Asp Leu Glu Lys Ser Arg Thr Gly Asp Glu
            100                 105                 110

Ile Ile Leu Pro Arg Gly Leu Glu Tyr Thr Val Glu Glu Cys Thr Cys
        115                 120                 125

Glu Asp Cys Ile Lys Ser Lys Pro Lys Val Asp Ser Asp His Cys Phe
    130                 135                 140

Pro Leu Pro Ala Met Glu Glu Gly Ala Thr Ile Leu Val Thr Thr Lys
145                 150                 155                 160

Thr Asn Asp Tyr Cys Lys Ser Leu Pro Ala Ala Leu Ser Ala Thr Glu
                165                 170                 175

Ile Glu Lys Ser Ile Ser Ala Arg
            180


<210> SEQ ID NO 3
<211> LENGTH: 10
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 3

Gly Gly Gly Gly Ser Gly Gly Gly Gly Ser
1               5                   10


<210> SEQ ID NO 4
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4

ggtggcggag gttctggagg tggaggttcc                                        30


<210> SEQ ID NO 5
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Ala Ala Ala Gly Gly Gly Gly Ser Gly Gly Gly Gly Ser Gly Gly Gly
1               5                   10                  15

Gly Ser Leu Glu
            20


<210> SEQ ID NO 6
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Ala Ala Ala Ile Glu Val Met Tyr Pro Pro Pro Tyr Leu Gly Gly Gly
1               5                   10                  15

Gly Ser Gly Gly Gly Gly Ser Gly Gly Gly Gly Ser Leu Glu
            20                  25                  30


<210> SEQ ID NO 7
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Gly Gly Gly Gly Ser Gly Gly Gly Gly Ser Gly Gly Gly Gly Ser Leu
1               5                   10                  15

Glu


<210> SEQ ID NO 8
<211> LENGTH: 8147
<212> TYPE: DNA
<213> ORGANISM: Artificial Sequence
<220> FEATURE:
<223> OTHER INFORMATION: Description of Artificial Sequence: Synthetic
```

polynucleotide

<400> SEQUENCE: 8

```
acgcgtgtag tcttatgcaa tactcttgta gtcttgcaac atggtaacga tgagttagca     60
acatgcctta caaggagaga aaaagcaccg tgcatgccga ttggtggaag taaggtggta    120
cgatcgtgcc ttattaggaa ggcaacagac gggtctgaca tggattggac gaaccactga    180
attgccgcat tgcagagata ttgtatttaa gtgcctagct cgatacataa acgggtctct    240
ctggttagac cagatctgag cctgggagct ctctggctaa ctagggaacc cactgcttaa    300
gcctcaataa agcttgcctt gagtgcttca agtagtgtgt gcccgtctgt tgtgtgactc    360
tggtaactag agatccctca gaccctttta gtcagtgtgg aaaatctcta gcagtggcgc    420
ccgaacaggg acctgaaagc gaaagggaaa ccagagctct ctcgacgcag gactcggctt    480
gctgaagcgc gcacggcaag aggcgagggg cggcgactgg tgagtacgcc aaaaattttg    540
actagcggag gctagaagga gagagatggg tgcgagagcg tcagtattaa gcgggggaga    600
attagatcgc gatgggaaaa aattcggtta aggccagggg gaaagaaaaa atataaatta    660
aaacatatag tatgggcaag cagggagcta gaacgattcg cagttaatcc tggcctgtta    720
gaaacatcag aaggctgtag acaaatactg ggacagctac aaccatccct tcagacagga    780
tcagaagaac ttagatcatt atataataca gtagcaaccc tctattgtgt gcatcaaagg    840
atagagataa aagacaccaa ggaagcttta gacaagatag aggaagagca aaacaaaagt    900
aagaccaccg cacagcaagc ggccactgat cttcagacct ggaggaggag atatgaggga    960
caattggaga agtgaattat ataaatataa agtagtaaaa attgaaccat taggagtagc   1020
acccaccaag gcaaagagaa gagtggtgca gagagaaaaa agagcagtgg gaataggagc   1080
tttgttcctt gggttcttgg gagcagcagg aagcactatg ggcgcagcgt caatgacgct   1140
gacggtacag gccagacaat tattgtctgg tatagtgcag cagcagaaca atttgctgag   1200
ggctattgag gcgcaacagc atctgttgca actcacagtc tggggcatca agcagctcca   1260
ggcaagaatc ctggctgtgg aaagatacct aaaggatcaa cagctcctgg ggatttgggg   1320
ttgctctgga aaactcattt gcaccactgc tgtgccttgg aatgctagtt ggagtaataa   1380
atctctggaa cagatttgga atcacacgac ctggatggag tgggacagag aaattaacaa   1440
ttacacaagc ttaatacact ccttaattga agaatcgcaa aaccagcaag aaaagaatga   1500
acaagaatta ttggaattag ataaatgggc aagtttgtgg aattggttta acataacaaa   1560
ttggctgtgg tatataaaat tattcataat gatagtagga ggcttggtag gtttaagaat   1620
agtttttgct gtactttcta tagtgaatag agttaggcag ggatattcac cattatcgtt   1680
tcagacccac ctcccaaccc cgaggggacc cgacaggccc gaaggaatag aagaagaagg   1740
tggagagaga gacagagaca gatccattcg attagtgaac ggatctcgac ggtatcggtt   1800
aacttttaaa agaaaagggg ggattggggg gtacagtgca ggggaaagaa tagtagacat   1860
aatagcaaca gacatacaaa ctaaagaatt acaaaaacaa attacaaaat tcaaaatttt   1920
atcgatacta gtattatgcc cagtacatga ccttatggga ctttcctact tggcagtaca   1980
tctacgtatt agtcatcgct attaccatgg tgatgcggtt ttggcagtac atcaatgggc   2040
gtggatagcg gtttgactca cggggatttc caagtctcca ccccattgac gtcaatggga   2100
gtttgttttg gcaccaaaat caacgggact ttccaaaatg tcgtaacaac tccgccccat   2160
tgacgcaaat gggcggtagg cgtgtacggt gggaggttta tataagcaga gctcgtttag   2220
tgaaccgtca gatcgcctgg agacgccatc cacgctgttt tgacctccat agaagattct   2280
```

```
agagctagcg ccgccaccat gctccagatg gctggccagt gcagccagaa cgagtacttc   2340
gacagcctgc tgcacgcctg catcccttgc cagctgcggt gcagcagcaa caccccaccc   2400
ctgacctgcc agcggtactg caacgccagc gtgaccaaca gcgtgaaggg caccaacgcc   2460
atcctgtgga cctgcctggg cctgagcctg atcatcagcc tggccgtgtt cgtgctgatg   2520
ttcctgctgc ggaagatcaa cagcgagccc ctgaaggacg agttcaagaa caccggcagc   2580
ggcctgctgg gcatggccaa catcgacctg gaaaagagcc ggaccggcga cgagatcatc   2640
ctgcccagag gcctggagta caccgtggaa gagtgtacct gcgaggactg catcaagagc   2700
aagcccaagg tggacagcga ccactgcttc cctctgcccg ccatggaaga gggcgccacc   2760
atcctggtga caacaaagac caacgactac tgcaagagcc tgcctgccgc cctgagcgcc   2820
accgagatcg agaagtccat cagcgccaga tgaggatccg cggccgcaag gatctgcgat   2880
cgctccggtg cccgtcagtg ggcagagcgc acatcgccca cagtccccga gaagttgggg   2940
ggaggggtcg gcaattgaac gggtgcctag agaaggtggc gcggggtaaa ctgggaaagt   3000
gatgtcgtgt actggctccg cctttttccc gagggtgggg gagaaccgta tataagtgca   3060
gtagtcgccg tgaacgttct ttttcgcaac gggtttgccg ccagaacaca gctgaagctt   3120
cgaggggctc gcatctctcc ttcacgcgcc cgccgcccta cctgaggccg ccatccacgc   3180
cggttgagtc gcgttctgcc gcctcccgcc tgtggtgcct cctgaactgc gtccgccgtc   3240
taggtaagtt taaagctcag gtcgagaccg ggcctttgtc cggcgctccc ttggagccta   3300
cctagactca gccggctctc cacgctttgc ctgaccctgc ttgctcaact ctacgtcttt   3360
gtttcgtttt ctgttctgcg ccgttacaga tccaagctgt gaccggcgcc tacgtcgaga   3420
tgattgaaca agatggattg cacgcaggtt ctccggccgc ttgggtggag aggctattcg   3480
gctatgactg ggcacaacag acaatcggct gctctgatgc cgccgtgttc cggctgtcag   3540
cgcaggggcg cccggttctt tttgtcaaga ccgacctgtc cggtgccctg aatgaactgc   3600
aggacgaggc agcgcggcta tcgtggctgg ccgcgacggg cgttccttgc gcagctgtgc   3660
tcgacgttgt cactgaagcg ggaagggact ggctgctatt gggcgaagtg ccggggcagg   3720
atctcctgtc atctcacctt gctcctgccg agaaagtatc catcatggct gatgcaatgc   3780
ggcggctgca tacgcttgat ccggctacct gcccattcga ccaccaagcg aaacatcgca   3840
tcgagcgagc acgtactcgg atggaagccg gtcttgtcga tcaggatgat ctggacgaag   3900
agcatcaggg gctcgcgcca gccgaactgt tcgccaggct caaggcgcgc atgcccgacg   3960
gcgaggatct cgtcgtgacc catggcgatg cctgcttgcc gaatatcatg gtggaaaatg   4020
gccgcttttc tggattcatc gactgtggcc ggctgggtgt ggcggaccgc tatcaggaca   4080
tagcgttggc tacccgtgat attgctgaag agcttggcgg cgaatgggct gaccgcttcc   4140
tcgtgcttta cggtatcgcc gctcccgatt cgcagcgcat cgccttctat cgccttcttg   4200
acgagttctt ctgactcgac aatcaacctc tggattacaa aatttgtgaa agattgactg   4260
gtattcttaa ctatgttgct ccttttacgc tatgtggata cgctgcttta atgcctttgt   4320
atcatgctat tgcttcccgt atggctttca ttttctcctc cttgtataaa tcctggttgc   4380
tgtctcttta tgaggagttg tggcccgttg tcaggcaacg tggcgtggtg tgcactgtgt   4440
ttgctgacgc aacccccact ggttggggca ttgccaccac ctgtcagctc ctttccggga   4500
ctttcgcttt ccccctccct attgccacgg cggaactcat cgccgcctgc cttgcccgct   4560
gctggacagg ggctcggctg ttgggcactg acaattccgt ggtgttgtcg ggaaatcat    4620
```

```
cgtcctttcc ttggctgctc gcctgtgttg ccacctggat tctgcgcggg acgtccttct   4680
gctacgtccc ttcggccctc aatccagcgg accttccttc ccgcggcctg ctgccggctc   4740
tgcggcctct tccgcgtctt cgccttcgcc ctcagacgag tcggatctcc ctttgggccg   4800
cctccccgcc tggtaccttt aagaccaatg acttacaagg cagctgtaga tcttagccac   4860
tttttaaaag aaaagggggg actggaaggg ctaattcact cccaacgaag ataagatctg   4920
ctttttgctt gtactgggtc tctctggtta gaccagatct gagcctggga gctctctggc   4980
taactaggga acccactgct taagcctcaa taaagcttgc cttgagtgct tcaagtagtg   5040
tgtgcccgtc tgttgtgtga ctctggtaac tagagatccc tcagaccctt ttagtcagtg   5100
tggaaaatct ctagcagtag tagttcatgt catcttatta ttcagtattt ataacttgca   5160
aagaaatgaa tatcagagag tgagaggaac ttgtttattg cagcttataa tggttacaaa   5220
taaagcaata gcatcacaaa tttcacaaat aaagcatttt tttcactgca ttctagttgt   5280
ggtttgtcca aactcatcaa tgtatcttat catgtctggc tctagctatc ccgcccctaa   5340
ctccgcccat cccgccccta actccgccca gttccgccca ttctccgccc catggctgac   5400
taattttttt tatttatgca gaggccgagg ccgcctcggc ctctgagcta ttccagaagt   5460
agtgaggagg cttttttgga ggcctagact tttgcagaga cggcccaaat tcgtaatcat   5520
ggtcatagct gtttcctgtg tgaaattgtt atccgctcac aattccacac aacatacgag   5580
ccggaagcat aaagtgtaaa gcctggggtg cctaatgagt gagctaactc acattaattg   5640
cgttgcgctc actgcccgct ttccagtcgg gaaacctgtc gtgccagctg cattaatgaa   5700
tcggccaacg cgcggggaga ggcggtttgc gtattgggcg ctcttccgct tcctcgctca   5760
ctgactcgct gcgctcggtc gttcggctgc ggcgagcggt atcagctcac tcaaaggcgg   5820
taatacggtt atccacagaa tcaggggata acgcaggaaa gaacatgtga gcaaaaggcc   5880
agcaaaaggc caggaaccgt aaaaaggccg cgttgctggc gtttttccat aggctccgcc   5940
cccctgacga gcatcacaaa aatcgacgct caagtcagag gtggcgaaac ccgacaggac   6000
tataaagata ccaggcgttt ccccctggaa gctccctcgt gcgctctcct gttccgaccc   6060
tgccgcttac cggatacctg tccgcctttc tcccttcggg aagcgtggcg ctttctcata   6120
gctcacgctg taggtatctc agttcggtgt aggtcgttcg ctccaagctg ggctgtgtgc   6180
acgaaccccc cgttcagccc gaccgctgcg ccttatccgg taactatcgt cttgagtcca   6240
acccggtaag acacgactta tcgccactgg cagcagccac tggtaacagg attagcagag   6300
cgaggtatgt aggcggtgct acagagttct tgaagtggtg gcctaactac ggctacacta   6360
gaaggacagt atttggtatc tgcgctctgc tgaagccagt taccttcgga aaaagagttg   6420
gtagctcttg atccggcaaa caaaccaccg ctggtagcgg tggttttttt gtttgcaagc   6480
agcagattac gcgcagaaaa aaaggatctc aagaagatcc tttgatcttt tctacggggt   6540
ctgacgctca gtggaacgaa aactcacgtt aagggatttt ggtcatgaga ttatcaaaaa   6600
ggatcttcac ctagatcctt ttaaattaaa aatgaagttt taaatcaatc taaagtatat   6660
atgagtaaac ttggtctgac agttaccaat gcttaatcag tgaggcacct atctcagcga   6720
tctgtctatt tcgttcatcc atagttgcct gactccccgt cgtgtagata actacgatac   6780
gggagggctt accatctggc cccagtgctg caatgatacc gcgagaccca cgctcaccgg   6840
ctccagattt atcagcaata aaccagccag ccggaagggc cgagcgcaga agtggtcctg   6900
caactttatc cgcctccatc cagtctatta attgttgccg ggaagctaga gtaagtagtt   6960
cgccagttaa tagtttgcgc aacgttgttg ccattgctac aggcatcgtg gtgtcacgct   7020
```

```
cgtcgtttgg tatggcttca ttcagctccg gttcccaacg atcaaggcga gttacatgat   7080
cccccatgtt gtgcaaaaaa gcggttagct ccttcggtcc tccgatcgtt gtcagaagta   7140
agttggccgc agtgttatca ctcatggtta tggcagcact gcataattct cttactgtca   7200
tgccatccgt aagatgcttt tctgtgactg gtgagtactc aaccaagtca ttctgagaat   7260
agtgtatgcg gcgaccgagt tgctcttgcc cggcgtcaat acgggataat accgcgccac   7320
atagcagaac tttaaaagtg ctcatcattg gaaaacgttc ttcggggcga aaactctcaa   7380
ggatcttacc gctgttgaga tccagttcga tgtaacccac tcgtgcaccc aactgatctt   7440
cagcatcttt tactttcacc agcgtttctg ggtgagcaaa aacaggaagg caaaatgccg   7500
caaaaaaggg aataagggcg acacggaaat gttgaatact catactcttc ctttttcaat   7560
attattgaag catttatcag ggttattgtc tcatgagcgg atacatattt gaatgtattt   7620
agaaaaataa acaaataggg gttccgcgca catttccccg aaaagtgcca cctgacgtct   7680
aagaaaccat tattatcatg acattaacct ataaaaatag gcgtatcacg aggccctttc   7740
gtctcgcgcg tttcggtgat gacggtgaaa acctctgaca catgcagctc ccggagacgg   7800
tcacagcttg tctgtaagcg gatgccggga gcagacaagc ccgtcagggc gcgtcagcgg   7860
gtgttggcgg gtgtcggggc tggcttaact atgcggcatc agagcagatt gtactgagag   7920
tgcaccatat gcggtgtgaa ataccgcaca gatgcgtaag gagaaaatac cgcatcaggc   7980
gccattcgcc attcaggctg cgcaactgtt gggaagggcg atcggtgcgg gcctcttcgc   8040
tattacgcca gctggcgaaa gggggatgtg ctgcaaggcg attaagttgg gtaacgccag   8100
ggttttccca gtcacgacgt tgtaaaacga cggccagtgc caagctg                 8147
```

<210> SEQ ID NO 9
<211> LENGTH: 8846
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 9

```
acgcgtgtag tcttatgcaa tactcttgta gtcttgcaac atggtaacga tgagttagca     60
acatgcctta caaggagaga aaaagcaccg tgcatgccga ttggtggaag taaggtggta    120
cgatcgtgcc ttattaggaa ggcaacagac gggtctgaca tggattggac gaaccactga    180
attgccgcat tgcagagata ttgtatttaa gtgcctagct cgatacaata aacgggtctc    240
tctggttaga ccagatctga gcctgggagc tctctggcta actagggaac ccactgctta    300
agcctcaata aagcttgcct tgagtgcttc aagtagtgtg tgcccgtctg ttgtgtgact    360
ctggtaacta gagatccctc agaccctttt agtcagtgtg gaaaatctct agcagtggcg    420
cccgaacagg gacctgaaag cgaaagggaa accagagctc tctcgacgca ggactcggct    480
tgctgaagcg cgcacggcaa gaggcgaggg gcggcgactg gtgagtacgc caaaaatttt    540
gactagcgga ggctagaagg agagagatgg gtgcgagagc gtcagtatta agcgggggag    600
aattagatcg cgatgggaaa aaattcggtt aaggccaggg ggaaagaaaa aatataaatt    660
aaaacatata gtatgggcaa gcagggagct agaacgattc gcagttaatc ctggcctgtt    720
agaaacatca gaaggctgta gacaaatact gggacagcta caaccatccc ttcagacagg    780
atcagaagaa cttagatcat tatataatac agtagcaacc ctctattgtg tgcatcaaag    840
gatagagata aaagacacca aggaagcttt agacaagata gaggaagagc aaaacaaaag    900
```

```
taagaccacc gcacagcaag cggccactga tcttcagacc tggaggagga gatatgaggg    960
acaattggag aagtgaatta tataaatata aagtagtaaa aattgaacca ttaggagtag   1020
cacccaccaa ggcaaagaga agagtggtgc agagagaaaa aagagcagtg ggaataggag   1080
ctttgttcct tgggttcttg ggagcagcag gaagcactat gggcgcagcc tcaatgacgc   1140
tgacggtaca ggccagacaa ttattgtctg gtatagtgca gcagcagaac aatttgctga   1200
gggctattga ggcgcaacag catctgttgc aactcacagt ctggggcatc aagcagctcc   1260
aggcaagaat cctggctgtg gaaagatacc taaaggatca acagctcctg gggatttggg   1320
gttgctctgg aaaactcatt tgcaccactg ctgtgccttg gaatgctagt tggagtaata   1380
aatctctgga acagattgga atcacacgac ctggatggag tgggacagag aaattaacaa   1440
ttacacaagc ttaatacact ccttaattga agaatcgcaa aaccagcaag aaaagaatga   1500
acaagaatta ttggaattag ataaatgggc aagtttgtgg aattggttta acataacaaa   1560
ttggctgtgg tatataaaat tattcataat gatagtagga ggcttggtag gtttaagaat   1620
agtttttgct gtactttcta tagtgaatag agttaggcag ggatattcac cattatcgtt   1680
tcagacccac ctcccaaccc cgaggggacc cgacaggccc gaaggaatag aagaagaagg   1740
tggagagaga gacagagaca gatccattcg attagtgaac ggatctcgac ggtatcggtt   1800
aacttttaaa agaaaagggg ggattggggg gtacagtgca ggggaaagaa tagtagacat   1860
aatagcaaca gacatacaaa ctaaagaatt acaaaaacaa attacaaaat tcaaaatttt   1920
atcgatacta gtattatgcc cagtacatga ccttatggga ctttcctact tggcagtaca   1980
tctacgtatt agtcatcgct attaccatgg tgatgcggtt ttggcagtac atcaatgggc   2040
gtggatagcg gtttgactca cggggatttc caagtctcca ccccattgac gtcaatggga   2100
gtttgttttg gcaccaaaat caacgggact ttccaaaatg tcgtaacaac tccgccccat   2160
tgacgcaaat gggcggtagg cgtgtacggt gggaggttta tataagcaga gctcgtttag   2220
tgaaccgtca gatcgcctgg agacgccatc cacgctgttt tgacctccat agaagattct   2280
agagccgcca ccatgcttct cctggtgaca agccttctgc tctgtgagtt accacaccca   2340
gcattcctcc tgatcccaga catccagatg acacagacta catcctccct gtctgcctct   2400
ctgggagaca gagtcaccat cagttgcagg gcaagtcagg acattagtaa atatttaaat   2460
tggtatcagc agaaaccaga tggaactgtt aaactcctga tctaccatac atcaagatta   2520
cactcaggag tcccatcaag gttcagtggc agtgggtctg gaacagatta ttctctcacc   2580
attagcaacc tggagcaaga agatattgcc acttactttt gccaacaggg taatacgctt   2640
ccgtacacgt tcggaggggg gactaagttg gaaataacag gctccacctc tggatccggc   2700
aagcccggat ctggcgaggg atccaccaag ggcgaggtga aactgcagga gtcaggacct   2760
ggcctggtgg cgccctcaca gagcctgtcc gtcacatgca ctgtctcagg ggtctcatta   2820
cccgactatg gtgtaagctg gattcgccag cctccacgaa agggtctgga gtggctggga   2880
gtaatatggg gtagtgaaac cacatactat aattcagctc tcaaatccag actgaccatc   2940
atcaaggaca actccaagag ccaagttttc ttaaaaatga acagtctgca aactgatgac   3000
acagccattt actactgtgc caaacattat tactacggtg gtagctatgc tatggactac   3060
tggggtcaag gaacctcagt caccgtctcc tcagcggccg caattgaagt tatgtatcct   3120
cctccttacc tagacaatga gaagagcaat ggaaccatta tccatgtgaa agggaaacac   3180
ctttgtccaa gtcccctatt tcccggacct tctaagccct tttgggtgct ggtggtggtt   3240
```

```
gggggagtcc tggcttgcta tagcttgcta gtaacagtgg cctttattat tttctgggtg   3300
aggagtaaga ggagcaggct cctgcacagt gactacatga acatgactcc ccgccgcccc   3360
gggcccaccc gcaagcatta ccagccctat gccccaccac gcgacttcgc agcctatcgc   3420
tccagagtga agttcagcag gagcgcagac gcccccgcgt accagcaggg ccagaaccag   3480
ctctataacg agctcaatct aggacgaaga gaggagtacg atgttttgga caagagacgt   3540
ggccgggacc ctgagatggg gggaaagccg agaaggaaga accctcagga aggcctgtac   3600
aatgaactgc agaaagataa gatggcggag gcctacagtg agattgggat gaaaggcgag   3660
cgccggaggg gcaaggggca cgatggcctt taccagggtc tcagtacagc caccaaggac   3720
acctacgacg cccttcacat gcaggccctg ccccctcgct aagaattcgg atccgcggcc   3780
gcgaaggatc tgcgatcgct ccggtgcccg tcagtgggca gagcgcacat cgcccacagt   3840
ccccgagaag ttggggggag gggtcggcaa ttgaacgggt gcctagagaa ggtggcgcgg   3900
ggtaaactgg gaaagtgatg tcgtgtactg gctccgcctt tttcccgagg gtgggggaga   3960
accgtatata agtgcagtag tcgccgtgaa cgttcttttt cgcaacgggt ttgccgccag   4020
aacacagctg aagcttcgag gggctcgcat ctctccttca cgcgcccgcc gccctacctg   4080
aggccgccat ccacgccggt tgagtcgcgt tctgccgcct cccgcctgtg gtgcctcctg   4140
aactgcgtcc gccgtctagg taagtttaaa gctcaggtcg agaccgggcc tttgtccggc   4200
gctcccttgg agcctaccta gactcagccg gctctccacg ctttgcctga ccctgcttgc   4260
tcaactctac gtctttgttt cgttttctgt tctgcgccgt tacagatcca agctgtgacc   4320
ggcgcctacg ctagatgacc gagtacaagc ccacggtgcg cctcgccacc cgcgacgacg   4380
tccccagggc cgtacgcacc ctcgccgccg cgttcgccga ctaccccgcc acgcgccaca   4440
ccgtcgatcc ggaccgccac atcgagcggg tcaccgagct gcaagaactc ttcctcacgc   4500
gcgtcgggct cgacatcggc aaggtgtggg tcgcggacga cggcgccgcg gtggcggtct   4560
ggaccacgcc ggagagcgtc gaagcggggg cggtgttcgc cgagatcggc ccgcgcatgg   4620
ccgagttgag cggttcccgg ctggccgcgc agcaacagat ggaaggcctc ctggcgccgc   4680
accggcccaa ggagcccgcg tggttcctgg ccaccgtcgg cgtctcgccc gaccaccagg   4740
gcaagggtct gggcagcgcc gtcgtgctcc ccggagtgga ggcggccgag cgcgccgggg   4800
tgcccgcctt cctggagacc tccgcgcccc gcaacctccc cttctacgag cggctcggct   4860
tcaccgtcac cgccgacgtc gaggtgcccg aaggaccgcg cacctggtgc atgacccgca   4920
agcccggtgc ctgagtcgac aatcaacctc tggattacaa aatttgtgaa agattgactg   4980
gtattcttaa ctatgttgct ccttttacgc tatgtggata cgctgcttta atgcctttgt   5040
atcatgctat tgcttcccgt atggctttca ttttctcctc cttgtataaa tcctggttgc   5100
tgtctcttta tgaggagttg tggcccgttg tcaggcaacg tggcgtggtg tgcactgtgt   5160
ttgctgacgc aacccccact ggttggggca ttgccaccac ctgtcagctc ctttccggga   5220
ctttcgcttt ccccctccct attgccacgg cggaactcat cgccgcctgc cttgcccgct   5280
gctggacagg ggctcggctg ttgggcactg acaattccgt ggtgttgtcg gggaaatcat   5340
cgtcctttcc ttggctgctc gcctgtgttg ccacctggat tctgcgcggg acgtccttct   5400
gctacgtccc ttcggccctc aatccagcgg accttccttc ccgcggcctg ctgccggctc   5460
tgcggcctct tccgcgtctt cgccttcgcc ctcagacgag tcggatctcc ctttgggccg   5520
cctccccgcc tggtaccttt aagaccaatg acttacaagg cagctgtaga tcttagccac   5580
tttttaaaag aaaagggggg actggaaggg ctaattcact cccaacgaaa ataagatctg   5640
```

```
cttttttgctt gtactgggtc tctctggtta gaccagatct gagcctggga gctctctggc   5700
taactaggga acccactgct taagcctcaa taaagcttgc cttgagtgct tcaagtagtg   5760
tgtgcccgtc tgttgtgtga ctctggtaac tagagatccc tcagaccctt ttagtcagtg   5820
tggaaaatct ctagcagtag tagttcatgt catcttatta ttcagtattt ataacttgca   5880
aagaaatgaa tatcagagag tgagaggaac ttgtttattg cagcttataa tggttacaaa   5940
taaagcaata gcatcacaaa tttcacaaat aaagcatttt tttcactgca ttctagttgt   6000
ggtttgtcca aactcatcaa tgtatcttat catgtctggc tctagctatc ccgcccctaa   6060
ctccgcccag ttccgcccat tctccgcccc atggctgact aatttttttt atttatgcag   6120
aggccgaggc cgcctcggcc tctgagctat tccagaagta gtgaggaggc ttttttggag   6180
gcctagactt ttgcagagac ggcccaaatt cgtaatcatg gtcatagctg tttcctgtgt   6240
gaaattgtta tccgctcaca attccacaca acatacgagc cggaagcata aagtgtaaag   6300
cctggggtgc ctaatgagtg agctaactca cattaattgc gttgcgctca ctgcccgctt   6360
tccagtcggg aaacctgtcg tgccagctgc attaatgaat cggccaacgc gcggggagag   6420
gcggtttgcg tattgggcgc tcttccgctt cctcgctcac tgactcgctg cgctcggtcg   6480
ttcggctgcg gcgagcggta tcagctcact caaaggcggt aatacggtta tccacagaat   6540
caggggataa cgcaggaaag aacatgtgag caaaaggcca gcaaaaggcc aggaaccgta   6600
aaaaggccgc gttgctggcg tttttccata ggctccgccc ccctgacgag catcacaaaa   6660
atcgacgctc aagtcagagg tggcgaaacc cgacaggact ataaagatac caggcgtttc   6720
cccctggaag ctccctcgtg cgctctcctg ttccgaccct gccgcttacc ggatacctgt   6780
ccgcctttct cccttcggga agcgtggcgc tttctcatag ctcacgctgt aggtatctca   6840
gttcggtgta ggtcgttcgc tccaagctgg gctgtgtgca cgaacccccc gttcagcccg   6900
accgctgcgc cttatccggt aactatcgtc ttgagtccaa cccggtaaga cacgacttat   6960
cgccactggc agcagccact ggtaacagga ttagcagagc gaggtatgta ggcggtgcta   7020
cagagttctt gaagtggtgg cctaactacg gctacactag aaggacagta tttggtatct   7080
gcgctctgct gaagccagtt accttcggaa aaagagttgg tagctcttga tccggcaaac   7140
aaaccaccgc tggtagcggt ggtttttttg tttgcaagca gcagattacg cgcagaaaaa   7200
aaggatctca agaagatcct ttgatctttt ctacggggtc tgacgctcag tggaacgaaa   7260
actcacgtta agggattttg gtcatgagat tatcaaaaag gatcttcacc tagatccttt   7320
taaattaaaa atgaagtttt aaatcaatct aaagtatata tgagtaaact tggtctgaca   7380
gttaccaatg cttaatcagt gaggcaccta tctcagcgat ctgtctattt cgttcatcca   7440
tagttgcctg actccccgtc gtgtagataa ctacgatacg ggagggctta ccatctggcc   7500
ccagtgctgc aatgataccg cgagacccac gctcaccggc tccagattta tcagcaataa   7560
accagccagc cggaagggcc gagcgcagaa gtggtcctgc aactttatcc gcctccatcc   7620
agtctattaa ttgttgccgg gaagctagag taagtagttc gccagttaat agtttgcgca   7680
acgttgttgc cattgctaca ggcatcgtgg tgtcacgctc gtcgtttggt atggcttcat   7740
tcagctccgg ttcccaacga tcaaggcgag ttacatgatc ccccatgttg tgcaaaaaag   7800
cggttagctc cttcggtcct ccgatcgttg tcagaagtaa gttggccgca gtgttatcac   7860
tcatggttat ggcagcactg cataattctc ttactgtcat gccatccgta agatgctttt   7920
ctgtgactgg tgagtactca accaagtcat tctgagaata gtgtatgcgg cgaccgagtt   7980
```

```
gctcttgccc ggcgtcaata cgggataata ccgcgccaca tagcagaact ttaaaagtgc   8040

tcatcattgg aaaacgttct tcggggcgaa aactctcaag gatcttaccg ctgttgagat   8100

ccagttcgat gtaacccact cgtgcaccca actgatcttc agcatctttt actttcacca   8160

gcgtttctgg gtgagcaaaa acaggaaggc aaaatgccgc aaaaaaggga ataagggcga   8220

cacggaaatg ttgaatactc atactcttcc tttttcaata ttattgaagc atttatcagg   8280

gttattgtct catgagcgga tacatatttg aatgtattta gaaaaataaa caaatagggg   8340

ttccgcgcac atttccccga aaagtgccac ctgacgtcta agaaaccatt attatcatga   8400

cattaaccta taaaaatagg cgtatcacga ggccctttcg tctcgcgcgt ttcggtgatg   8460

acggtgaaaa cctctgacac atgcagctcc cggagacggt cacagcttgt ctgtaagcgg   8520

atgccgggag cagacaagcc cgtcagggcg cgtcagcggg tgttggcggg tgtcggggct   8580

ggcttaacta tgcggcatca gagcagattg tactgagagt gcaccatatg cggtgtgaaa   8640

taccgcacag atgcgtaagg agaaaatacc gcatcaggcg ccattcgcca ttcaggctgc   8700

gcaactgttg ggaagggcga tcggtgcggg cctcttcgct attacgccag ctggcgaaag   8760

ggggatgtgc tgcaaggcga ttaagttggg taacgccagg gttttcccag tcacgacgtt   8820

gtaaaacgac ggccagtgcc aagctg                                        8846
```

```
<210> SEQ ID NO 10
<211> LENGTH: 8717
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 10
```

```
acgcgtgtag tcttatgcaa tactcttgta gtcttgcaac atggtaacga tgagttagca     60

acatgcctta caaggagaga aaaagcaccg tgcatgccga ttggtggaag taaggtggta    120

cgatcgtgcc ttattaggaa ggcaacagac gggtctgaca tggattggac gaaccactga    180

attgccgcat tgcagagata ttgtatttaa gtgcctagct cgatacaata aacgggtctc    240

tctggttaga ccagatctga gcctgggagc tctctggcta actagggaac ccactgctta    300

agcctcaata aagcttgcct tgagtgcttc aagtagtgtg tgcccgtctg ttgtgtgact    360

ctggtaacta gagatccctc agaccctttt agtcagtgtg gaaaatctct agcagtggcg    420

cccgaacagg gacctgaaag cgaaagggaa accagagctc tctcgacgca ggactcggct    480

tgctgaagcg cgcacggcaa gaggcgaggg gcggcgactg gtgagtacgc caaaaatttt    540

gactagcgga ggctagaagg agagagatgg gtgcgagagc gtcagtatta agcgggggag    600

aattagatcg cgatgggaaa aaattcggtt aaggccaggg ggaaagaaaa aatataaatt    660

aaaacatata gtatgggcaa gcagggagct agaacgattc gcagttaatc ctggcctgtt    720

agaaacatca gaaggctgta gacaaatact gggacagcta caaccatccc ttcagacagg    780

atcagaagaa cttagatcat tatataatac agtagcaacc ctctattgtg tgcatcaaag    840

gatagagata aaagacacca aggaagcttt agacaagata gaggaagagc aaaacaaaag    900

taagaccacc gcacagcaag cggccactga tcttcagacc tggaggagga gatatgaggg    960

acaattggag aagtgaatta tataaatata aagtagtaaa aattgaacca ttaggagtag   1020

cacccaccaa ggcaaagaga agagtggtgc agagagaaaa aagagcagtg ggaataggag   1080

ctttgttcct tgggttcttg ggagcagcag gaagcactat gggcgcagcg tcaatgacgc   1140
```

```
tgacggtaca ggccagacaa ttattgtctg gtatagtgca gcagcagaac aatttgctga   1200
gggctattga ggcgcaacag catctgttgc aactcacagt ctggggcatc aagcagctcc   1260
aggcaagaat cctggctgtg gaaagatacc taaaggatca acagctcctg gggatttggg   1320
gttgctctgg aaaactcatt tgcaccactg ctgtgccttg gaatgctagt tggagtaata   1380
aatctctgga acagatttgg aatcacacga cctggatgga gtgggacaga gaaattaaca   1440
attacacaag cttaatacac tccttaattg aagaatcgca aaaccagcaa gaaaagaatg   1500
aacaagaatt attggaatta gataaatggg caagtttgtg gaattggttt aacataacaa   1560
attggctgtg gtatataaaa ttattcataa tgatagtagg aggcttggta ggtttaagaa   1620
tagtttttgc tgtactttct atagtgaata gagttaggca gggatattca ccattatcgt   1680
ttcagaccca cctcccaacc ccgaggggac ccgacaggcc cgaaggaata gaagaagaag   1740
gtggagagag agacagagac agatccattc gattagtgaa cggatctcga cggtatcggt   1800
taacttttaa aagaaaaggg gggattgggg ggtacagtgc aggggaaaga atagtagaca   1860
taatagcaac agacatacaa actaaagaat tacaaaaaca aattacaaaa ttcaaaattt   1920
tatcgatact agtggatctg cgatcgctcc ggtgcccgtc agtgggcaga gcgcacatcg   1980
cccacagtcc ccgagaagtt ggggggaggg gtcggcaatt gaacgggtgc ctagagaagg   2040
tggcgcgggg taaactggga aagtgatgtc gtgtactggc tccgcctttt tcccgagggt   2100
gggggagaac cgtatataag tgcagtagtc gccgtgaacg ttcttttcg caacgggttt    2160
gccgccagaa cacagctgaa gcttcgaggg gctcgcatct ctccttcacg cgcccgccgc   2220
cctacctgag gccgccatcc acgccggttg agtcgcgttc tgccgcctcc cgcctgtggt   2280
gcctcctgaa ctgcgtccgc cgtctaggta agtttaaagc tcaggtcgag accgggcctt   2340
tgtccggcgc tcccttggag cctacctaga ctcagccggc tctccacgct ttgcctgacc   2400
ctgcttgctc aactctacgt ctttgtttcg ttttctgttc tgcgccgtta cagatccaag   2460
ctgtgaccgg cgcctactct agagccgcca ccatggccct gcctgtgaca gctctgctgc   2520
tgcctctggc cctgctgctc catgccgcca gacccgatat ccagatgacc cagaccacca   2580
gcagcctgag cgccagcctg ggcgatagag tgaccatcag ctgccgggcc agccaggaca   2640
tcagcaagta cctgaactgg tatcagcaga aacccgacgg caccgtgaag ctgctgatct   2700
accacaccag cagactgcac agcggcgtgc ccagcagatt ttctggcagc ggctccggca   2760
ccgactacag cctgaccatc tccaacctgg aacaggaaga tatcgctacc tacttctgtc   2820
agcaaggcaa caccctgccc tacaccttcg gcggaggcac caagctggaa atcacaggcg   2880
gcggaggatc tggcggaggt ggaagtggcg gaggcggcag cgaagtgaaa ctgcaggaaa   2940
gcggccctgg cctggtggcc ccttctcagt ctctgtccgt gacctgtacc gtgtccggcg   3000
tgtccctgcc cgattatggc gtgtcctgga tccggcagcc tcccagaaag ggcctggaat   3060
ggctgggcgt gatctggggc agcgagacaa cctactacaa cagcgccctg aagtcccggc   3120
tgaccatcat caaggacaac tccaagagcc aggtgttcct gaagatgaac agcctgcaga   3180
ccgacgacac cgccatctac tactgcgcca agcactacta ctacggcggc agctacgcca   3240
tggactactg gggccagggc accagcgtga ccgtgtctag cacaaccacc cctgccccta   3300
gacctcccac cccagcccca acaattgcca gccagcctct gtctctgcgg cccgaagctt   3360
gtagacctgc tgccggcgga gccgtgcaca ccagaggact ggatttcgcc tgcgacatct   3420
acatctgggc ccctctggcc ggcacatgtg gcgtgctgct cctcagcctg gtcatcaccc   3480
tgtactgcaa gcggggcaga aagaaactgc tctacatctt caagcagccc ttcatgcggc   3540
```

```
ccgtgcagac cacacaggaa gaggacggct gctcctgcag attccccgag gaagaagaag   3600
gcggctgcga gctgagagtg aagttcagca gatccgccga cgcccctgcc taccagcagg   3660
gacagaacca gctgtacaac gagctgaacc tgggcagacg ggaagagtac gacgtgctgg   3720
acaagcggag aggcagagat cccgagatgg gcggcaagcc cagacggaag aatccccagg   3780
aaggcctgta taacgaactg cagaaagaca agatggccga ggcctacagc gagatcggaa   3840
tgaagggcga gcggagaaga ggcaagggcc acgatggcct gtaccagggc ctgagcaccg   3900
ccaccaagga cacctacgat gccctgcaca tgcaggccct gccacccaga gaattcgaag   3960
gatccgcggc cgctgagggc agaggaagtc ttctaacatg cggtgacgtg gaggagaatc   4020
ccggcccttc cggaatggag agcgacgaga gcggcctgcc cgccatggag atcgagtgcc   4080
gcatcaccgg caccctgaac ggcgtggagt tcgagctggt gggcggcgga gagggcaccc   4140
ccaagcaggg ccgcatgacc aacaagatga agagcaccaa aggcgccctg accttcagcc   4200
cctacctgct gagccacgtg atgggctacg gcttctacca cttcggcacc taccccagcg   4260
gctacgagaa ccccttcctg cacgccatca acaacggcgg ctacaccaac acccgcatcg   4320
agaagtacga ggacggcggc gtgctgcacg tgagcttcag ctaccgctac gaggccggcc   4380
gcgtgatcgg cgacttcaag gtggtgggca ccggcttccc cgaggacagc gtgatcttca   4440
ccgacaagat catccgcagc aacgccaccg tggagcacct gcaccccatg ggcgataacg   4500
tgctggtggg cagcttcgcc cgcaccttca gcctgcgcga cggcggctac tacagcttcg   4560
tggtggacag ccacatgcac ttcaagagcg ccatccaccc cagcatcctg cagaacgggg   4620
gccccatgtt cgccttccgc cgcgtggagg agctgcacag caacaccgag ctgggcatcg   4680
tggagtacca gcacgccttc aagaccccca tcgccttcgc cagatcccgc gctcagtcgt   4740
ccaattctgc cgtggacggc accgccggac ccggctccac cggatctcgc tagagctgaa   4800
tctaagtcga caatcaacct ctggattaca aaatttgtga aagattgact ggtattctta   4860
actatgttgc tccttttacg ctatgtggat acgctgcttt aatgcctttg tatcatgcta   4920
ttgcttcccg tatggctttc attttctcct ccttgtataa atcctggttg ctgtctcttt   4980
atgaggagtt gtggcccgtt gtcaggcaac gtggcgtggt gtgcactgtg tttgctgacg   5040
caacccccac tggttggggc attgccacca cctgtcagct cctttccggg actttcgctt   5100
tccccctccc tattgccacg gcggaactca tcgccgcctg ccttgcccgc tgctggacag   5160
gggctcggct gttgggcact gacaattccg tggtgttgtc ggggaaatca tcgtcctttc   5220
cttggctgct cgcctgtgtt gccacctgga ttctgcgcgg gacgtccttc tgctacgtcc   5280
cttcggccct caatccagcg gaccttcctt cccgcggcct gctgccggct ctgcggcctc   5340
ttccgcgtct tcgccttcgc cctcagacga gtcggatctc cctttgggcc gcctccccgc   5400
ctggtacctt taagaccaat gacttacaag gcagctgtag atcttagcca ctttttaaaa   5460
gaaaaggggg gactggaagg gctaattcac tcccaacgaa aataagatct gctttttgct   5520
tgtactgggt ctctctggtt agaccagatc tgagcctggg agctctctgg ctaactaggg   5580
aacccactgc ttaagcctca ataaagcttg ccttgagtgc ttcaagtagt gtgtgcccgt   5640
ctgttgtgtg actctggtaa ctagagatcc ctcagaccct tttagtcagt gtggaaaatc   5700
tctagcagta gtagttcatg tcatcttatt attcagtatt tataacttgc aaagaaatga   5760
atatcagaga gtgagaggaa cttgtttatt gcagcttata atggttacaa ataaagcaat   5820
agcatcacaa atttcacaaa taaagcattt ttttcactgc attctagttg tggtttgtcc   5880
```

```
aaactcatca atgtatctta tcatgtctgg ctctagctat cccgccccta actccgccca   5940
gttccgccca ttctccgccc catggctgac taattttttt tatttatgca gaggccgagg   6000
ccgcctcggc ctctgagcta ttccagaagt agtgaggagg cttttttgga ggcctagact   6060
tttgcagaga cggcccaaat tcgtaatcat ggtcatagct gtttcctgtg tgaaattgtt   6120
atccgctcac aattccacac aacatacgag ccggaagcat aaagtgtaaa gcctggggtg   6180
cctaatgagt gagctaactc acattaattg cgttgcgctc actgcccgct ttccagtcgg   6240
gaaacctgtc gtgccagctg cattaatgaa tcggccaacg cgcggggaga ggcggtttgc   6300
gtattgggcg ctcttccgct tcctcgctca ctgactcgct gcgctcggtc gttcggctgc   6360
ggcgagcggt atcagctcac tcaaaggcgg taatacggtt atccacagaa tcaggggata   6420
acgcaggaaa gaacatgtga gcaaaaggcc agcaaaaggc caggaaccgt aaaaaggccg   6480
cgttgctggc gtttttccat aggctccgcc cccctgacga gcatcacaaa aatcgacgct   6540
caagtcagag gtggcgaaac ccgacaggac tataaagata ccaggcgttt ccccctggaa   6600
gctccctcgt gcgctctcct gttccgaccc tgccgcttac cggatacctg tccgcctttc   6660
tcccttcggg aagcgtggcg ctttctcata gctcacgctg taggtatctc agttcggtgt   6720
aggtcgttcg ctccaagctg ggctgtgtgc acgaaccccc cgttcagccc gaccgctgcg   6780
ccttatccgg taactatcgt cttgagtcca acccggtaag acacgactta tcgccactgg   6840
cagcagccac tggtaacagg attagcagag cgaggtatgt aggcggtgct acagagttct   6900
tgaagtggtg gcctaactac ggctacacta gaaggacagt atttggtatc tgcgctctgc   6960
tgaagccagt taccttcgga aaaagagttg gtagctcttg atccggcaaa caaaccaccg   7020
ctggtagcgg tggttttttt gtttgcaagc agcagattac gcgcagaaaa aaaggatctc   7080
aagaagatcc tttgatcttt tctacggggt ctgacgctca gtggaacgaa aactcacgtt   7140
aagggatttt ggtcatgaga ttatcaaaaa ggatcttcac ctagatcctt ttaaattaaa   7200
aatgaagttt taaatcaatc taaagtatat atgagtaaac ttggtctgac agttaccaat   7260
gcttaatcag tgaggcacct atctcagcga tctgtctatt tcgttcatcc atagttgcct   7320
gactccccgt cgtgtagata actacgatac gggagggctt accatctggc cccagtgctg   7380
caatgatacc gcgagaccca cgctcaccgg ctccagattt atcagcaata aaccagccag   7440
ccggaagggc cgagcgcaga agtggtcctg caactttatc cgcctccatc cagtctatta   7500
attgttgccg ggaagctaga gtaagtagtt cgccagttaa tagtttgcgc aacgttgttg   7560
ccattgctac aggcatcgtg gtgtcacgct cgtcgtttgg tatggcttca ttcagctccg   7620
gttcccaacg atcaaggcga gttacatgat cccccatgtt gtgcaaaaaa gcggttagct   7680
ccttcggtcc tccgatcgtt gtcagaagta agttggccgc agtgttatca ctcatggtta   7740
tggcagcact gcataattct cttactgtca tgccatccgt aagatgcttt tctgtgactg   7800
gtgagtactc aaccaagtca ttctgagaat agtgtatgcg gcgaccgagt tgctcttgcc   7860
cggcgtcaat acgggataat accgcgccac atagcagaac tttaaaagtg ctcatcattg   7920
gaaaacgttc ttcggggcga aaactctcaa ggatcttacc gctgttgaga tccagttcga   7980
tgtaacccac tcgtgcaccc aactgatctt cagcatcttt tactttcacc agcgtttctg   8040
ggtgagcaaa aacaggaagg caaaatgccg caaaaaaggg aataagggcg acacggaaat   8100
gttgaatact catactcttc ctttttcaat attattgaag catttatcag ggttattgtc   8160
tcatgagcgg atacatattt gaatgtattt agaaaaataa acaaataggg gttccgcgca   8220
catttccccg aaaagtgcca cctgacgtct aagaaaccat tattatcatg acattaacct   8280
```

```
ataaaaatag gcgtatcacg aggccctttc gtctcgcgcg tttcggtgat gacggtgaaa   8340

acctctgaca catgcagctc ccggagacgg tcacagcttg tctgtaagcg gatgccggga   8400

gcagacaagc ccgtcagggc gcgtcagcgg gtgttggcgg gtgtcggggc tggcttaact   8460

atgcggcatc agagcagatt gtactgagag tgcaccatat gcggtgtgaa ataccgcaca   8520

gatgcgtaag gagaaaatac cgcatcaggc gccattcgcc attcaggctg cgcaactgtt   8580

gggaagggcg atcggtgcgg gcctcttcgc tattacgcca gctggcgaaa gggggatgtg   8640

ctgcaaggcg attaagttgg gtaacgccag ggttttccca gtcacgacgt tgtaaaacga   8700

cggccagtgc caagctg                                                  8717
```

```
<210> SEQ ID NO 11
<211> LENGTH: 9046
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 11

acgcgtgtag tcttatgcaa tactcttgta gtcttgcaac atggtaacga tgagttagca     60

acatgcctta caaggagaga aaaagcaccg tgcatgccga ttggtggaag taaggtggta    120

cgatcgtgcc ttattaggaa ggcaacagac gggtctgaca tggattggac gaaccactga    180

attgccgcat tgcagagata ttgtatttaa gtgcctagct cgatacaata aacgggtctc    240

tctggttaga ccagatctga gcctgggagc tctctggcta actagggaac ccactgctta    300

agcctcaata aagcttgcct tgagtgcttc aagtagtgtg tgcccgtctg ttgtgtgact    360

ctggtaacta gagatccctc agaccctttt agtcagtgtg gaaaatctct agcagtggcg    420

cccgaacagg gacctgaaag cgaaagggaa accagagctc tctcgacgca ggactcggct    480

tgctgaagcg cgcacggcaa gaggcgaggg gcggcgactg gtgagtacgc caaaaatttt    540

gactagcgga ggctagaagg agagagatgg gtgcgagagc gtcagtatta agcgggggag    600

aattagatcg cgatgggaaa aaattcggtt aaggccaggg ggaaagaaaa aatataaatt    660

aaaacatata gtatgggcaa gcagggagct agaacgattc gcagttaatc ctggcctgtt    720

agaaacatca gaaggctgta gacaaatact gggacagcta caaccatccc ttcagacagg    780

atcagaagaa cttagatcat tatataatac agtagcaacc ctctattgtg tgcatcaaag    840

gatagagata aaagacacca aggaagcttt agacaagata gaggaagagc aaaacaaaag    900

taagaccacc gcacagcaag cggccactga tcttcagacc tggaggagga gatatgaggg    960

acaattggag aagtgaatta tataaatata aagtagtaaa aattgaacca ttaggagtag   1020

cacccaccaa ggcaaagaga agagtggtgc agagagaaaa aagagcagtg ggaataggag   1080

ctttgttcct tgggttcttg ggagcagcag gaagcactat gggcgcagcc tcaatgacgc   1140

tgacggtaca ggccagacaa ttattgtctg gtatagtgca gcagcagaac aatttgctga   1200

gggctattga ggcgcaacag catctgttgc aactcacagt ctggggcatc aagcagctcc   1260

aggcaagaat cctggctgtg gaaagatacc taaaggatca acagctcctg gggatttggg   1320

gttgctctgg aaaactcatt tgcaccactg ctgtgccttg gaatgctagt tggagtaata   1380

aatctctgga acagattgga atcacacgac ctggatggag tgggacagag aaattaacaa   1440

ttacacaagc ttaatacact ccttaattga agaatcgcaa aaccagcaag aaaagaatga   1500

acaagaatta ttggaattag ataaatgggc aagtttgtgg aattggttta acataacaaa   1560
```

```
ttggctgtgg tatataaaat tattcataat gatagtagga ggcttggtag gtttaagaat   1620
agtttttgct gtactttcta tagtgaatag agttaggcag ggatattcac cattatcgtt   1680
tcagacccac ctcccaaccc cgaggggacc cgacaggccc gaaggaatag aagaagaagg   1740
tggagagaga gacagagaca gatccattcg attagtgaac ggatctcgac ggtatcggtt   1800
aacttttaaa agaaaagggg ggattggggg gtacagtgca ggggaaagaa tagtagacat   1860
aatagcaaca gacatacaaa ctaaagaatt acaaaaacaa attacaaaat tcaaaatttt   1920
atcgatacta gtattatgcc cagtacatga ccttatggga ctttcctact tggcagtaca   1980
tctacgtatt agtcatcgct attaccatgg tgatgcggtt ttggcagtac atcaatgggc   2040
gtggatagcg gtttgactca cggggatttc caagtctcca ccccattgac gtcaatggga   2100
gtttgttttg gcaccaaaat caacgggact ttccaaaatg tcgtaacaac tccgccccat   2160
tgacgcaaat gggcggtagg cgtgtacggt gggaggttta tataagcaga gctcgtttag   2220
tgaaccgtca gatcgcctgg agacgccatc cacgctgttt tgacctccat agaagattct   2280
agagccgcca ccatgcttct cctggtgaca agccttctgc tctgtgagtt accacaccca   2340
gcattcctcc tgatcccaga catccagatg acacagacta catcctccct gtctgcctct   2400
ctgggagaca gagtcaccat cagttgcagg gcaagtcagg acattagtaa atatttaaat   2460
tggtatcagc agaaaccaga tggaactgtt aaactcctga tctaccatac atcaagatta   2520
cactcaggag tcccatcaag gttcagtggc agtgggtctg gaacagatta ttctctcacc   2580
attagcaacc tggagcaaga agatattgcc acttactttt gccaacaggg taatacgctt   2640
ccgtacacgt tcggaggggg gactaagttg gaaataacag gctccacctc tggatccggc   2700
aagcccggat ctggcgaggg atccaccaag ggcgaggtga aactgcagga gtcaggacct   2760
ggcctggtgg cgccctcaca gagcctgtcc gtcacatgca ctgtctcagg ggtctcatta   2820
cccgactatg gtgtaagctg gattcgccag cctccacgaa agggtctgga gtggctggga   2880
gtaatatggg gtagtgaaac cacatactat aattcagctc tcaaatccag actgaccatc   2940
atcaaggaca actccaagag ccaagttttc ttaaaaatga acagtctgca aactgatgac   3000
acagccattt actactgtgc caaacattat tactacggtg gtagctatgc tatggactac   3060
tggggtcaag gaacctcagt caccgtctcc tcagcggccg caattgaagt tatgtatcct   3120
cctccttacc taggtggcgg cggttctggt ggcggcggtt ctggtggcgg cggttctctc   3180
gaggtgaatg gagagaatgt ggagcagcat ccttcaaccc tgagtgtcca ggagggagac   3240
agcgctgtta tcaagtgtac ttattcagac agtgcctcaa actacttccc ttggtataag   3300
caagaacttg gaaaaagacc tcagcttatt atagacattc gttcaaatgt gggcgaaaag   3360
aaagaccaac gaattgctgt tacattgaac aagacagcca aacatttctc cctgcacatc   3420
acagagaccc aacctgaaga ctcggctgtc tacttctgtg cagcaagtag gaaggactct   3480
gggggttacc agaaagttac ctttggaact ggaacaaagc tccaagtcat cccaaatatc   3540
cagaaccctg accctgccgt gtaccagctg agagactcta aatccagtga caagtctgtc   3600
tgcctattca ccgattttga ttctcaaaca aatgtgtcac aaagtaagga ttctgatgtg   3660
tatatcacag acaaaactgt gctagacatg aggtctatgg acttcaagag caacagtgct   3720
gtggcctgga gcaacaaatc tgactttgca tgtgcaaacg ccttcaacaa cagcattatt   3780
ccagaagaca ccttcttccc cagcccagaa agttcctgtg atgtcaagct ggtcgagaaa   3840
agctttgaaa cagatacgaa cctaaacttt caaaacctgt cagtgattgg gttccgaatc   3900
```

-continued

```
ctcctcctga aagtggccgg gtttaatctg ctcatgacgc tgcggctgtg gtccagctga   3960
taagaattcg atccgcggcc gcgaaggatc tgcgatcgct ccggtgcccg tcagtgggca   4020
gagcgcacat cgcccacagt ccccgagaag ttgggggggag gggtcggcaa ttgaacgggt   4080
gcctagagaa ggtggcgcgg ggtaaactgg gaaagtgatg tcgtgtactg gctccgcctt   4140
tttcccgagg gtgggggaga accgtatata agtgcagtag tcgccgtgaa cgttcttttt   4200
cgcaacgggt ttgccgccag aacacagctg aagcttcgag gggctcgcat ctctccttca   4260
cgcgcccgcc gccctacctg aggccgccat ccacgccggt tgagtcgcgt tctgccgcct   4320
cccgcctgtg gtgcctcctg aactgcgtcc gccgtctagg taagtttaaa gctcaggtcg   4380
agaccgggcc tttgtccggc gctcccttgg agcctaccta gactcagccg gctctccacg   4440
ctttgcctga ccctgcttgc tcaactctac gtctttgttt cgttttctgt tctgcgccgt   4500
tacagatcca agctgtgacc ggcgcctacg ctagatgacc gagtacaagc ccacggtgcg   4560
cctcgccacc cgcgacgacg tccccagggc cgtacgcacc ctcgccgccg cgttcgccga   4620
ctaccccgcc acgcgccaca ccgtcgatcc ggaccgccac atcgagcggg tcaccgagct   4680
gcaagaactc ttcctcacgc gcgtcgggct cgacatcggc aaggtgtggg tcgcggacga   4740
cggcgccgcg gtggcggtct ggaccacgcc ggagagcgtc gaagcggggg cggtgttcgc   4800
cgagatcggc ccgcgcatgg ccgagttgag cggttcccgg ctggccgcgc agcaacagat   4860
ggaaggcctc ctggcgccgc accggcccaa ggagcccgcg tggttcctgg ccaccgtcgg   4920
cgtctcgccc gaccaccagg gcaagggtct gggcagcgcc gtcgtgctcc ccggagtgga   4980
ggcggccgag cgcgccgggg tgcccgcctt cctggagacc tccgcgcccc gcaacctccc   5040
cttctacgag cggctcggct tcaccgtcac cgccgacgtc gaggtgcccg aaggaccgcg   5100
cacctggtgc atgacccgca agcccggtgc ctgagtcgac aatcaacctc tggattacaa   5160
aatttgtgaa agattgactg gtattcttaa ctatgttgct ccttttacgc tatgtggata   5220
cgctgcttta atgcctttgt atcatgctat tgcttcccgt atggctttca ttttctcctc   5280
cttgtataaa tcctggttgc tgtctcttta tgaggagttg tggcccgttg tcaggcaacg   5340
tggcgtggtg tgcactgtgt ttgctgacgc aacccccact ggttggggca ttgccaccac   5400
ctgtcagctc ctttccggga ctttcgcttt ccccctccct attgccacgg cggaactcat   5460
cgccgcctgc cttgcccgct gctggacagg ggctcggctg ttgggcactg acaattccgt   5520
ggtgttgtcg gggaaatcat cgtcctttcc ttggctgctc gcctgtgttg ccacctggat   5580
tctgcgcggg acgtccttct gctacgtccc ttcggccctc aatccagcgg accttccttc   5640
ccgcggcctg ctgccggctc tgcggcctct tccgcgtctt cgccttcgcc ctcagacgag   5700
tcggatctcc ctttgggccg cctccccgcc tggtaccttt aagaccaatg acttacaagg   5760
cagctgtaga tcttagccac tttttaaaag aaaagggggg actggaaggg ctaattcact   5820
cccaacgaaa ataagatctg ctttttgctt gtactgggtc tctctggtta gaccagatct   5880
gagcctggga gctctctggc taactaggga acccactgct taagcctcaa taaagcttgc   5940
cttgagtgct tcaagtagtg tgtgcccgtc tgttgtgtga ctctggtaac tagagatccc   6000
tcagaccctt ttagtcagtg tggaaaatct ctagcagtag tagttcatgt catcttatta   6060
ttcagtattt ataacttgca aagaaatgaa tatcagagag tgagaggaac ttgtttattg   6120
cagcttataa tggttacaaa taaagcaata gcatcacaaa tttcacaaat aaagcatttt   6180
tttcactgca ttctagttgt ggtttgtcca aactcatcaa tgtatcttat catgtctggc   6240
tctagctatc ccgcccctaa ctccgcccag ttccgcccat tctccgcccc atggctgact   6300
```

```
aatttttttt atttatgcag aggccgaggc cgcctcggcc tctgagctat tccagaagta   6360
gtgaggaggc ttttttggag gcctagactt ttgcagagac ggcccaaatt cgtaatcatg   6420
gtcatagctg tttcctgtgt gaaattgtta tccgctcaca attccacaca acatacgagc   6480
cggaagcata aagtgtaaag cctggggtgc ctaatgagtg agctaactca cattaattgc   6540
gttgcgctca ctgcccgctt tccagtcggg aaacctgtcg tgccagctgc attaatgaat   6600
cggccaacgc gcggggagag gcggtttgcg tattgggcgc tcttccgctt cctcgctcac   6660
tgactcgctg cgctcggtcg ttcggctgcg gcgagcggta tcagctcact caaaggcggt   6720
aatacggtta tccacagaat caggggataa cgcaggaaag aacatgtgag caaaaggcca   6780
gcaaaaggcc aggaaccgta aaaaggccgc gttgctggcg tttttccata ggctccgccc   6840
ccctgacgag catcacaaaa atcgacgctc aagtcagagg tggcgaaacc cgacaggact   6900
ataaagatac caggcgtttc cccctggaag ctccctcgtg cgctctcctg ttccgaccct   6960
gccgcttacc ggatacctgt ccgcctttct cccttcggga agcgtggcgc tttctcatag   7020
ctcacgctgt aggtatctca gttcggtgta ggtcgttcgc tccaagctgg gctgtgtgca   7080
cgaacccccc gttcagcccg accgctgcgc cttatccggt aactatcgtc ttgagtccaa   7140
cccggtaaga cacgacttat cgccactggc agcagccact ggtaacagga ttagcagagc   7200
gaggtatgta ggcggtgcta cagagttctt gaagtggtgg cctaactacg gctacactag   7260
aaggacagta tttggtatct gcgctctgct gaagccagtt accttcggaa aaagagttgg   7320
tagctcttga tccggcaaac aaaccaccgc tggtagcggt ggtttttttg tttgcaagca   7380
gcagattacg cgcagaaaaa aaggatctca agaagatcct ttgatctttt ctacggggtc   7440
tgacgctcag tggaacgaaa actcacgtta agggattttg gtcatgagat tatcaaaaag   7500
gatcttcacc tagatccttt taaattaaaa atgaagtttt aaatcaatct aaagtatata   7560
tgagtaaact tggtctgaca gttaccaatg cttaatcagt gaggcaccta tctcagcgat   7620
ctgtctattt cgttcatcca tagttgcctg actccccgtc gtgtagataa ctacgatacg   7680
ggagggctta ccatctggcc ccagtgctgc aatgataccg cgagacccac gctcaccggc   7740
tccagattta tcagcaataa accagccagc cggaagggcc gagcgcagaa gtggtcctgc   7800
aactttatcc gcctccatcc agtctattaa ttgttgccgg gaagctagag taagtagttc   7860
gccagttaat agtttgcgca acgttgttgc cattgctaca ggcatcgtgg tgtcacgctc   7920
gtcgtttggt atggcttcat tcagctccgg ttcccaacga tcaaggcgag ttacatgatc   7980
ccccatgttg tgcaaaaaag cggttagctc cttcggtcct ccgatcgttg tcagaagtaa   8040
gttggccgca gtgttatcac tcatggttat ggcagcactg cataattctc ttactgtcat   8100
gccatccgta agatgctttt ctgtgactgg tgagtactca accaagtcat tctgagaata   8160
gtgtatgcgg cgaccgagtt gctcttgccc ggcgtcaata cgggataata ccgcgccaca   8220
tagcagaact ttaaaagtgc tcatcattgg aaaacgttct tcggggcgaa aactctcaag   8280
gatcttaccg ctgttgagat ccagttcgat gtaacccact cgtgcaccca actgatcttc   8340
agcatctttt actttcacca gcgtttctgg gtgagcaaaa acaggaaggc aaaatgccgc   8400
aaaaaaggga ataagggcga cacggaaatg ttgaatactc atactcttcc tttttcaata   8460
ttattgaagc atttatcagg gttattgtct catgagcgga tacatatttg aatgtattta   8520
gaaaaataaa caaatagggg ttccgcgcac atttccccga aaagtgccac ctgacgtcta   8580
agaaaccatt attatcatga cattaaccta taaaaatagg cgtatcacga ggccctttcg   8640
```

```
tctcgcgcgt ttcggtgatg acggtgaaaa cctctgacac atgcagctcc cggagacggt   8700

cacagcttgt ctgtaagcgg atgccgggag cagacaagcc cgtcagggcg cgtcagcggg   8760

tgttggcggg tgtcggggct ggcttaacta tgcggcatca gagcagattg tactgagagt   8820

gcaccatatg cggtgtgaaa taccgcacag atgcgtaagg agaaaatacc gcatcaggcg   8880

ccattcgcca ttcaggctgc gcaactgttg ggaagggcga tcggtgcggg cctcttcgct   8940

attacgccag ctggcgaaag ggggatgtgc tgcaaggcga ttaagttggg taacgccagg   9000

gttttcccag tcacgacgtt gtaaaacgac ggccagtgcc aagctg                  9046
```

<210> SEQ ID NO 12
<211> LENGTH: 8698
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 12

```
acgcgtgtag tcttatgcaa tactcttgta gtcttgcaac atggtaacga tgagttagca     60

acatgcctta caaggagaga aaaagcaccg tgcatgccga ttggtggaag taaggtggta    120

cgatcgtgcc ttattaggaa ggcaacagac gggtctgaca tggattggac gaaccactga    180

attgccgcat tgcagagata ttgtatttaa gtgcctagct cgatacaata aacgggtctc    240

tctggttaga ccagatctga gcctgggagc tctctggcta actagggaac ccactgctta    300

agcctcaata aagcttgcct tgagtgcttc aagtagtgtg tgcccgtctg ttgtgtgact    360

ctggtaacta gagatccctc agaccctttt agtcagtgtg gaaaatctct agcagtggcg    420

cccgaacagg gacctgaaag cgaaagggaa accagagctc tctcgacgca ggactcggct    480

tgctgaagcg cgcacggcaa gaggcgaggg gcggcgactg gtgagtacgc caaaaatttt    540

gactagcgga ggctagaagg agagagatgg gtgcgagagc gtcagtatta agcgggggag    600

aattagatcg cgatgggaaa aaattcggtt aaggccaggg ggaaagaaaa aatataaatt    660

aaaacatata gtatgggcaa gcagggagct agaacgattc gcagttaatc ctggcctgtt    720

agaaacatca gaaggctgta gacaaatact gggacagcta caaccatccc ttcagacagg    780

atcagaagaa cttagatcat tatataatac agtagcaacc ctctattgtg tgcatcaaag    840

gatagagata aaagacacca aggaagcttt agacaagata gaggaagagc aaaacaaaag    900

taagaccacc gcacagcaag cggccactga tcttcagacc tggaggagga gatatgaggg    960

acaattggag aagtgaatta tataaatata aagtagtaaa aattgaacca ttaggagtag   1020

cacccaccaa ggcaaagaga agagtggtgc agagagaaaa aagagcagtg ggaataggag   1080

ctttgttcct tgggttcttg ggagcagcag gaagcactat gggcgcagcc tcaatgacgc   1140

tgacggtaca ggccagacaa ttattgtctg gtatagtgca gcagcagaac aatttgctga   1200

gggctattga ggcgcaacag catctgttgc aactcacagt ctggggcatc aagcagctcc   1260

aggcaagaat cctggctgtg gaaagatacc taaaggatca acagctcctg gggatttggg   1320

gttgctctgg aaaactcatt tgcaccactg ctgtgccttg gaatgctagt tggagtaata   1380

aatctctgga acagattgga atcacacgac ctggatggag tgggacagag aaattaacaa   1440

ttacacaagc ttaatacact ccttaattga agaatcgcaa aaccagcaag aaaagaatga   1500

acaagaatta ttggaattag ataaatgggc aagtttgtgg aattggttta acataacaaa   1560

ttggctgtgg tatataaaat tattcataat gatagtagga ggcttggtag gtttaagaat   1620
```

```
agtttttgct gtactttcta tagtgaatag agttaggcag ggatattcac cattatcgtt   1680
tcagacccac ctcccaaccc cgaggggacc cgacaggccc gaaggaatag aagaagaagg   1740
tggagagaga gacagagaca gatccattcg attagtgaac ggatctcgac ggtatcggtt   1800
aacttttaaa agaaaagggg ggattggggg gtacagtgca ggggaaagaa tagtagacat   1860
aatagcaaca gacatacaaa ctaaagaatt acaaaaacaa attacaaaat tcaaaatttt   1920
atcgatacta gtattatgcc cagtacatga ccttatggga ctttcctact tggcagtaca   1980
tctacgtatt agtcatcgct attaccatgg tgatgcggtt ttggcagtac atcaatgggc   2040
gtggatagcg gtttgactca cggggatttc caagtctcca ccccattgac gtcaatggga   2100
gtttgttttg gcaccaaaat caacgggact ttccaaaatg tcgtaacaac tccgccccat   2160
tgacgcaaat gggcggtagg cgtgtacggt gggaggttta tataagcaga gctcgtttag   2220
tgaaccgtca gatcgcctgg agacgccatc cacgctgttt tgacctccat agaagattct   2280
agagccgcca ccatgcttct cctggtgaca agccttctgc tctgtgagtt accacaccca   2340
gcattcctcc tgatcccaga catccagatg acacagacta catcctccct gtctgcctct   2400
ctgggagaca gagtcaccat cagttgcagg gcaagtcagg acattagtaa atatttaaat   2460
tggtatcagc agaaaccaga tggaactgtt aaactcctga tctaccatac atcaagatta   2520
cactcaggag tcccatcaag gttcagtggc agtgggtctg gaacagatta ttctctcacc   2580
attagcaacc tggagcaaga agatattgcc acttactttt gccaacaggg taatacgctt   2640
ccgtacacgt tcggaggggg gactaagttg gaaataacag gctccacctc tggatccggc   2700
aagcccggat ctggcgaggg atccaccaag ggcgaggtga aactgcagga gtcaggacct   2760
ggcctggtgg cgccctcaca gagcctgtcc gtcacatgca ctgtctcagg ggtctcatta   2820
cccgactatg gtgtaagctg gattcgccag cctccacgaa agggtctgga gtggctggga   2880
gtaatatggg gtagtgaaac cacatactat aattcagctc tcaaatccag actgaccatc   2940
atcaaggaca actccaagag ccaagttttc ttaaaaatga acagtctgca aactgatgac   3000
acagccattt actactgtgc caaacattat tactacggtg gtagctatgc tatggactac   3060
tggggtcaag gaacctcagt caccgtctcc tcagcggccg caattgaagt tatgtatcct   3120
cctccttacc taggtggcgg cggttctggt ggcggcggtt ctggtggcgg cggttctctc   3180
gagccaaata tccagaaccc tgaccctgcc gtgtaccagc tgagagactc taaatccagt   3240
gacaagtctg tctgcctatt caccgatttt gattctcaaa caaatgtgtc acaaagtaag   3300
gattctgatg tgtatatcac agacaaaact gtgctagaca tgaggtctat ggacttcaag   3360
agcaacagtg ctgtggcctg gagcaacaaa tctgactttg catgtgcaaa cgccttcaac   3420
aacagcatta ttccagaaga caccttcttc cccagcccag aaagttcctg tgatgtcaag   3480
ctggtcgaga aaagctttga aacagatacg aacctaaact ttcaaaacct gtcagtgatt   3540
gggttccgaa tcctcctcct gaaagtggcc gggtttaatc tgctcatgac gctgcggctg   3600
tggtccagct gataagaatt cgatccgcgg ccgcgaagga tctgcgatcg ctccggtgcc   3660
cgtcagtggg cagagcgcac atcgcccaca gtccccgaga agttgggggg aggggtcggc   3720
aattgaacgg gtgcctagag aaggtggcgc ggggtaaact gggaaagtga tgtcgtgtac   3780
tggctccgcc tttttcccga gggtggggga gaaccgtata taagtgcagt agtcgccgtg   3840
aacgttcttt ttcgcaacgg gtttgccgcc agaacacagc tgaagcttcg aggggctcgc   3900
atctctcctt cacgcgcccg ccgccctacc tgaggccgcc atccacgccg gttgagtcgc   3960
gttctgccgc ctcccgcctg tggtgcctcc tgaactgcgt ccgccgtcta ggtaagttta   4020
```

aagctcaggt cgagaccggg cctttgtccg gcgctccctt ggagcctacc tagactcagc 4080
cggctctcca cgctttgcct gaccctgctt gctcaactct acgtctttgt ttcgttttct 4140
gttctgcgcc gttacagatc caagctgtga ccggcgccta cgctagatga ccgagtacaa 4200
gcccacggtg cgcctcgcca cccgcgacga cgtccccagg gccgtacgca ccctcgccgc 4260
cgcgttcgcc gactaccccg ccacgcgcca caccgtcgat ccggaccgcc acatcgagcg 4320
ggtcaccgag ctgcaagaac tcttcctcac gcgcgtcggg ctcgacatcg gcaaggtgtg 4380
ggtcgcggac gacggcgccg cggtggcggt ctggaccacg ccggagagcg tcgaagcggg 4440
ggcggtgttc gccgagatcg gcccgcgcat ggccgagttg agcggttccc ggctggccgc 4500
gcagcaacag atggaaggcc tcctggcgcc gcaccggccc aaggagcccg cgtggttcct 4560
ggccaccgtc ggcgtctcgc ccgaccacca gggcaagggt ctgggcagcg ccgtcgtgct 4620
ccccggagtg gaggcggccg agcgcgccgg ggtgcccgcc ttcctggaga cctccgcgcc 4680
ccgcaacctc cccttctacg agcggctcgg cttcaccgtc accgccgacg tcgaggtgcc 4740
cgaaggaccg cgcacctggt gcatgacccg caagcccggt gcctgagtcg acaatcaacc 4800
tctggattac aaaatttgtg aaagattgac tggtattctt aactatgttg ctccttttac 4860
gctatgtgga tacgctgctt taatgccttt gtatcatgct attgcttccc gtatggcttt 4920
cattttctcc tccttgtata aatcctggtt gctgtctctt tatgaggagt tgtggcccgt 4980
tgtcaggcaa cgtggcgtgg tgtgcactgt gtttgctgac gcaaccccca ctggttgggg 5040
cattgccacc acctgtcagc tcctttccgg gactttcgct ttccccctcc ctattgccac 5100
ggcggaactc atcgccgcct gccttgcccg ctgctggaca ggggctcggc tgttgggcac 5160
tgacaattcc gtggtgttgt cggggaaatc atcgtccttt ccttggctgc tcgcctgtgt 5220
tgccacctgg attctgcgcg ggacgtcctt ctgctacgtc ccttcggccc tcaatccagc 5280
ggaccttcct tcccgcggcc tgctgccggc tctgcggcct cttccgcgtc ttcgccttcg 5340
ccctcagacg agtcggatct ccctttgggc cgcctccccg cctggtacct ttaagaccaa 5400
tgacttacaa ggcagctgta gatcttagcc actttttaaa agaaaagggg ggactggaag 5460
ggctaattca ctcccaacga aaataagatc tgctttttgc ttgtactggg tctctctggt 5520
tagaccagat ctgagcctgg gagctctctg gctaactagg gaacccactg cttaagcctc 5580
aataaagctt gccttgagtg cttcaagtag tgtgtgcccg tctgttgtgt gactctggta 5640
actagagatc cctcagaccc ttttagtcag tgtggaaaat ctctagcagt agtagttcat 5700
gtcatcttat tattcagtat ttataacttg caaagaaatg aatatcagag agtgagagga 5760
acttgtttat tgcagcttat aatggttaca aataaagcaa tagcatcaca aatttcacaa 5820
ataaagcatt tttttcactg cattctagtt gtggtttgtc caaactcatc aatgtatctt 5880
atcatgtctg gctctagcta tcccgcccct aactccgccc agttccgccc attctccgcc 5940
ccatggctga ctaatttttt ttatttatgc agaggccgag gccgcctcgg cctctgagct 6000
attccagaag tagtgaggag gcttttttgg aggcctagac ttttgcagag acggcccaaa 6060
ttcgtaatca tggtcatagc tgtttcctgt gtgaaattgt tatccgctca caattccaca 6120
caacatacga gccggaagca taaagtgtaa agcctggggt gcctaatgag tgagctaact 6180
cacattaatt gcgttgcgct cactgcccgc tttccagtcg ggaaacctgt cgtgccagct 6240
gcattaatga atcggccaac gcgcggggag aggcggtttg cgtattgggc gctcttccgc 6300
ttcctcgctc actgactcgc tgcgctcggt cgttcggctg cggcgagcgg tatcagctca 6360

```
ctcaaaggcg gtaatacggt tatccacaga atcaggggat aacgcaggaa agaacatgtg   6420
agcaaaaggc cagcaaaagg ccaggaaccg taaaaaggcc gcgttgctgg cgtttttcca   6480
taggctccgc ccccctgacg agcatcacaa aaatcgacgc tcaagtcaga ggtggcgaaa   6540
cccgacagga ctataaagat accaggcgtt tccccctgga agctccctcg tgcgctctcc   6600
tgttccgacc ctgccgctta ccggatacct gtccgccttt ctcccttcgg gaagcgtggc   6660
gctttctcat agctcacgct gtaggtatct cagttcggtg taggtcgttc gctccaagct   6720
gggctgtgtg cacgaacccc ccgttcagcc cgaccgctgc gccttatccg gtaactatcg   6780
tcttgagtcc aacccggtaa gacacgactt atcgccactg gcagcagcca ctggtaacag   6840
gattagcaga gcgaggtatg taggcggtgc tacagagttc ttgaagtggt ggcctaacta   6900
cggctacact agaaggacag tatttggtat ctgcgctctg ctgaagccag ttaccttcgg   6960
aaaaagagtt ggtagctctt gatccggcaa acaaaccacc gctggtagcg gtggtttttt   7020
tgtttgcaag cagcagatta cgcgcagaaa aaaaggatct caagaagatc ctttgatctt   7080
ttctacgggg tctgacgctc agtggaacga aaactcacgt taagggattt tggtcatgag   7140
attatcaaaa aggatcttca cctagatcct tttaaattaa aaatgaagtt ttaaatcaat   7200
ctaaagtata tatgagtaaa cttggtctga cagttaccaa tgcttaatca gtgaggcacc   7260
tatctcagcg atctgtctat ttcgttcatc catagttgcc tgactccccg tcgtgtagat   7320
aactacgata cgggagggct taccatctgg ccccagtgct gcaatgatac cgcgagaccc   7380
acgctcaccg gctccagatt tatcagcaat aaaccagcca gccggaaggg ccgagcgcag   7440
aagtggtcct gcaactttat ccgcctccat ccagtctatt aattgttgcc gggaagctag   7500
agtaagtagt tcgccagtta atagtttgcg caacgttgtt gccattgcta caggcatcgt   7560
ggtgtcacgc tcgtcgtttg gtatggcttc attcagctcc ggttcccaac gatcaaggcg   7620
agttacatga tcccccatgt tgtgcaaaaa agcggttagc tccttcggtc ctccgatcgt   7680
tgtcagaagt aagttggccg cagtgttatc actcatggtt atggcagcac tgcataattc   7740
tcttactgtc atgccatccg taagatgctt ttctgtgact ggtgagtact caaccaagtc   7800
attctgagaa tagtgtatgc ggcgaccgag ttgctcttgc ccggcgtcaa tacgggataa   7860
taccgcgcca catagcagaa ctttaaaagt gctcatcatt ggaaaacgtt cttcggggcg   7920
aaaactctca aggatcttac cgctgttgag atccagttcg atgtaaccca ctcgtgcacc   7980
caactgatct tcagcatctt ttactttcac cagcgtttct gggtgagcaa aaacaggaag   8040
gcaaaatgcc gcaaaaaagg gaataagggc gacacggaaa tgttgaatac tcatactctt   8100
cctttttcaa tattattgaa gcatttatca gggttattgt ctcatgagcg gatacatatt   8160
tgaatgtatt tagaaaaata aacaaatagg ggttccgcgc acatttcccc gaaaagtgcc   8220
acctgacgtc taagaaacca ttattatcat gacattaacc tataaaaata ggcgtatcac   8280
gaggcccttt cgtctcgcgc gtttcggtga tgacggtgaa aacctctgac acatgcagct   8340
cccggagacg gtcacagctt gtctgtaagc ggatgccggg agcagacaag cccgtcaggg   8400
cgcgtcagcg ggtgttggcg ggtgtcgggg ctggcttaac tatgcggcat cagagcagat   8460
tgtactgaga gtgcaccata tgcggtgtga aataccgcac agatgcgtaa ggagaaaata   8520
ccgcatcagg cgccattcgc cattcaggct gcgcaactgt tgggaagggc gatcggtgcg   8580
ggcctcttcg ctattacgcc agctggcgaa agggggatgt gctgcaaggc gattaagttg   8640
ggtaacgcca gggttttccc agtcacgacg ttgtaaaacg acggccagtg ccaagctg     8698
```

<210> SEQ ID NO 13
<211> LENGTH: 9163
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 13

```
acgcgtgtag tcttatgcaa tactcttgta gtcttgcaac atggtaacga tgagttagca     60
acatgcctta caaggagaga aaaagcaccg tgcatgccga ttggtggaag taaggtggta    120
cgatcgtgcc ttattaggaa ggcaacagac gggtctgaca tggattggac gaaccactga    180
attgccgcat tgcagagata ttgtatttaa gtgcctagct cgatacaata aacgggtctc    240
tctggttaga ccagatctga gcctgggagc tctctggcta actagggaac ccactgctta    300
agcctcaata aagcttgcct tgagtgcttc aagtagtgtg tgcccgtctg ttgtgtgact    360
ctggtaacta gagatccctc agaccctttt agtcagtgtg gaaaatctct agcagtggcg    420
cccgaacagg gacctgaaag cgaaagggaa accagagctc tctcgacgca ggactcggct    480
tgctgaagcg cgcacggcaa gaggcgaggg gcggcgactg gtgagtacgc caaaaatttt    540
gactagcgga ggctagaagg agagagatgg gtgcgagagc gtcagtatta agcgggggag    600
aattagatcg cgatgggaaa aaattcggtt aaggccaggg ggaaagaaaa aatataaatt    660
aaaacatata gtatgggcaa gcagggagct agaacgattc gcagttaatc ctggcctgtt    720
agaaacatca gaaggctgta gacaaatact gggacagcta caaccatccc ttcagacagg    780
atcagaagaa cttagatcat tatataatac agtagcaacc ctctattgtg tgcatcaaag    840
gatagagata aaagacacca aggaagcttt agacaagata gaggaagagc aaaacaaaag    900
taagaccacc gcacagcaag cggccactga tcttcagacc tggaggagga gatatgaggg    960
acaattggag aagtgaatta tataaatata aagtagtaaa aattgaacca ttaggagtag   1020
cacccaccaa ggcaaagaga agagtggtgc agagagaaaa aagagcagtg ggaataggag   1080
ctttgttcct tgggttcttg ggagcagcag gaagcactat gggcgcagcc tcaatgacgc   1140
tgacggtaca ggccagacaa ttattgtctg gtatagtgca gcagcagaac aatttgctga   1200
gggctattga ggcgcaacag catctgttgc aactcacagt ctggggcatc aagcagctcc   1260
aggcaagaat cctggctgtg gaaagatacc taaaggatca acagctcctg gggatttggg   1320
gttgctctgg aaaactcatt tgcaccactg ctgtgccttg gaatgctagt tggagtaata   1380
aatctctgga acagattgga atcacacgac ctggatggag tgggacagag aaattaacaa   1440
ttacacaagc ttaatacact ccttaattga agaatcgcaa aaccagcaag aaaagaatga   1500
acaagaatta ttggaattag ataaatgggc aagtttgtgg aattggttta acataacaaa   1560
ttggctgtgg tatataaaat tattcataat gatagtagga ggcttggtag gtttaagaat   1620
agtttttgct gtactttcta tagtgaatag agttaggcag ggatattcac cattatcgtt   1680
tcagacccac ctcccaaccc cgaggggacc cgacaggccc gaaggaatag aagaagaagg   1740
tggagagaga gacagagaca gatccattcg attagtgaac ggatctcgac ggtatcggtt   1800
aacttttaaa agaaaagggg ggattggggg gtacagtgca ggggaaagaa tagtagacat   1860
aatagcaaca gacatacaaa ctaaagaatt acaaaaacaa attacaaaat tcaaaatttt   1920
atcgatacta gtattatgcc cagtacatga ccttatggga ctttcctact tggcagtaca   1980
tctacgtatt agtcatcgct attaccatgg tgatgcggtt ttggcagtac atcaatgggc   2040
gtggatagcg gtttgactca cggggatttc caagtctcca ccccattgac gtcaatggga   2100
```

-continued

```
gtttgttttg gcaccaaaat caacgggact ttccaaaatg tcgtaacaac tccgccccat   2160
tgacgcaaat gggcggtagg cgtgtacggt gggaggttta tataagcaga gctcgtttag   2220
tgaaccgtca gatcgcctgg agacgccatc cacgctgttt tgacctccat agaagattct   2280
agagccgcca ccatgcttct cctggtgaca agccttctgc tctgtgagtt accacaccca   2340
gcattcctcc tgatcccaga catccagatg acacagacta catcctccct gtctgcctct   2400
ctgggagaca gagtcaccat cagttgcagg gcaagtcagg acattagtaa atatttaaat   2460
tggtatcagc agaaaccaga tggaactgtt aaactcctga tctaccatac atcaagatta   2520
cactcaggag tcccatcaag gttcagtggc agtgggtctg gaacagatta ttctctcacc   2580
attagcaacc tggagcaaga agatattgcc acttactttt gccaacaggg taatacgctt   2640
ccgtacacgt tcggaggggg gactaagttg gaaataacag gctccacctc tggatccggc   2700
aagcccggat ctggcgaggg atccaccaag ggcgaggtga aactgcagga gtcaggacct   2760
ggcctggtgg cgccctcaca gagcctgtcc gtcacatgca ctgtctcagg ggtctcatta   2820
cccgactatg gtgtaagctg gattcgccag cctccacgaa agggtctgga gtggctggga   2880
gtaatatggg gtagtgaaac cacatactat aattcagctc tcaaatccag actgaccatc   2940
atcaaggaca actccaagag ccaagttttc ttaaaaatga acagtctgca aactgatgac   3000
acagccattt actactgtgc caaacattat tactacggtg gtagctatgc tatggactac   3060
tggggtcaag gaacctcagt caccgtctcc tcagcggccg caattgaagt tatgtatcct   3120
cctccttacc taggtggcgg cggttctggt ggcggcggtt ctggtggcgg cggttctctc   3180
gagctgggag caggcccagt ggattctgga gtcacacaaa ccccaaagca cctgatcaca   3240
gcaactggac agcgagtgac gctgagatgc tcccctaggt ctggagacct ctctgtgtca   3300
tggtaccaac agagcctgga ccagggcctc cagttcctca ttcagtatta taatggagaa   3360
gagagagcaa aaggaaacat tcttgaacga ttctccgcac aacagttccc tgacttgcac   3420
tctgaactaa acctgagctc tctggagctg ggggactcag ctttgtattt ctgtgccagc   3480
agcccccgga caggcctgaa cactgaagct ttctttggac aaggcaccag actcacagtt   3540
gtagaggacc tgaacaaggt gttcccaccc gaggtcgctg tgtttgagcc atcagaagca   3600
gagatctccc acacccaaaa ggccacactg gtgtgcctgg ccacaggctt cttccccgac   3660
cacgtggagc tgagctggtg ggtgaatggg aaggaggtgc acagtggggt cagcacggac   3720
ccgcagcccc tcaaggagca gcccgccctc aatgactcca gatactgcct gagcagccgc   3780
ctgagggtct cggccacctt ctggcagaac ccccgcaacc acttccgctg tcaagtccag   3840
ttctacgggc tctcggagaa tgacgagtgg acccaggata gggccaaacc cgtcacccag   3900
atcgtcagcg ccgaggcctg gggtagagca gactgtggct ttacctcggt gtcctaccag   3960
caaggggtcc tgtctgccac catcctctat gagatcctgc tagggaaggc caccctgtat   4020
gctgtgctgg tcagcgccct tgtgttgatg gccatggtca agagaaagga tttctgataa   4080
gaattcgatc cgcggccgcg aaggatctgc gatcgctccg gtgcccgtca gtgggcagag   4140
cgcacatcgc ccacagtccc cgagaagttg gggggagggg tcggcaattg aacgggtgcc   4200
tagagaaggt ggcgcggggt aaactgggaa agtgatgtcg tgtactggct ccgccttttt   4260
cccgagggtg ggggagaacc gtatataagt gcagtagtcg ccgtgaacgt tctttttcgc   4320
aacgggtttg ccgccagaac acagctgaag cttcgagggg ctcgcatctc tccttcacgc   4380
gcccgccgcc ctacctgagg ccgccatcca cgccggttga gtcgcgttct gccgcctccc   4440
```

```
gcctgtggtg cctcctgaac tgcgtccgcc gtctaggtaa gtttaaagct caggtcgaga   4500
ccgggccttt gtccggcgct cccttggagc ctacctagac tcagccggct ctccacgctt   4560
tgcctgaccc tgcttgctca actctacgtc tttgtttcgt ttctgttct gcgccgttac   4620
agatccaagc tgtgaccggc gcctacgcta gatgaccgag tacaagccca cggtgcgcct   4680
cgccacccgc gacgacgtcc ccagggccgt acgcaccctc gccgccgcgt tcgccgacta   4740
ccccgccacg cgccacaccg tcgatccgga ccgccacatc gagcgggtca ccgagctgca   4800
agaactcttc ctcacgcgcg tcgggctcga catcggcaag gtgtgggtcg cggacgacgg   4860
cgccgcggtg gcggtctgga ccacgccgga gagcgtcgaa gcgggggcgg tgttcgccga   4920
gatcggcccg cgcatggccg agttgagcgg ttcccggctg gccgcgcagc aacagatgga   4980
aggcctcctg gcgccgcacc ggcccaagga gcccgcgtgg ttcctggcca ccgtcggcgt   5040
ctcgcccgac caccagggca agggtctggg cagcgccgtc gtgctccccg gagtggaggc   5100
ggccgagcgc gccggggtgc ccgccttcct ggagacctcc gcgccccgca acctcccctt   5160
ctacgagcgg ctcggcttca ccgtcaccgc cgacgtcgag gtgcccgaag gaccgcgcac   5220
ctggtgcatg acccgcaagc ccggtgcctg agtcgacaat caacctctgg attacaaaat   5280
ttgtgaaaga ttgactggta ttcttaacta tgttgctcct tttacgctat gtggatacgc   5340
tgctttaatg cctttgtatc atgctattgc ttcccgtatg gctttcattt tctcctcctt   5400
gtataaatcc tggttgctgt ctctttatga ggagttgtgg cccgttgtca ggcaacgtgg   5460
cgtggtgtgc actgtgtttg ctgacgcaac ccccactggt tggggcattg ccaccacctg   5520
tcagctcctt tccgggactt tcgctttccc cctccctatt gccacggcgg aactcatcgc   5580
cgcctgcctt gcccgctgct ggacaggggc tcggctgttg ggcactgaca attccgtggt   5640
gttgtcgggg aaatcatcgt cctttccttg gctgctcgcc tgtgttgcca cctggattct   5700
gcgcgggacg tccttctgct acgtcccttc ggccctcaat ccagcggacc ttccttcccg   5760
cggcctgctg ccggctctgc ggcctcttcc gcgtcttcgc cttcgccctc agacgagtcg   5820
gatctccctt tgggccgcct ccccgcctgg tacctttaag accaatgact tacaaggcag   5880
ctgtagatct tagccacttt ttaaaagaaa aggggggact ggaagggcta attcactccc   5940
aacgaaaata agatctgctt tttgcttgta ctgggtctct ctggttagac cagatctgag   6000
cctgggagct ctctggctaa ctagggaacc cactgcttaa gcctcaataa agcttgcctt   6060
gagtgcttca agtagtgtgt gcccgtctgt tgtgtgactc tggtaactag agatccctca   6120
gaccctttta gtcagtgtgg aaaatctcta gcagtagtag ttcatgtcat cttattattc   6180
agtatttata acttgcaaag aaatgaatat cagagagtga gaggaacttg tttattgcag   6240
cttataatgg ttacaaataa agcaatagca tcacaaattt cacaaataaa gcattttttt   6300
cactgcattc tagttgtggt ttgtccaaac tcatcaatgt atcttatcat gtctggctct   6360
agctatcccg cccctaactc cgcccagttc cgcccattct ccgccccatg gctgactaat   6420
ttttttatt tatgcagagg ccgaggccgc ctcggcctct gagctattcc agaagtagtg   6480
aggaggcttt tttggaggcc tagacttttg cagagacggc ccaaattcgt aatcatggtc   6540
atagctgttt cctgtgtgaa attgttatcc gctcacaatt ccacacaaca tacgagccgg   6600
aagcataaag tgtaaagcct ggggtgccta atgagtgagc taactcacat taattgcgtt   6660
gcgctcactg cccgctttcc agtcgggaaa cctgtcgtgc cagctgcatt aatgaatcgg   6720
ccaacgcgcg gggagaggcg gtttgcgtat tgggcgctct tccgcttcct cgctcactga   6780
ctcgctgcgc tcggtcgttc ggctgcggcg agcggtatca gctcactcaa aggcggtaat   6840
```

```
acggttatcc acagaatcag gggataacgc aggaaagaac atgtgagcaa aaggccagca   6900
aaaggccagg aaccgtaaaa aggccgcgtt gctggcgttt ttccataggc tccgcccccc   6960
tgacgagcat cacaaaaatc gacgctcaag tcagaggtgg cgaaacccga caggactata   7020
aagataccag gcgtttcccc ctggaagctc cctcgtgcgc tctcctgttc cgaccctgcc   7080
gcttaccgga tacctgtccg cctttctccc ttcgggaagc gtggcgcttt ctcatagctc   7140
acgctgtagg tatctcagtt cggtgtaggt cgttcgctcc aagctgggct gtgtgcacga   7200
accccccgtt cagcccgacc gctgcgcctt atccggtaac tatcgtcttg agtccaaccc   7260
ggtaagacac gacttatcgc cactggcagc agccactggt aacaggatta gcagagcgag   7320
gtatgtaggc ggtgctacag agttcttgaa gtggtggcct aactacggct acactagaag   7380
gacagtattt ggtatctgcg ctctgctgaa gccagttacc ttcggaaaaa gagttggtag   7440
ctcttgatcc ggcaaacaaa ccaccgctgg tagcggtggt ttttttgttt gcaagcagca   7500
gattacgcgc agaaaaaaag gatctcaaga agatcctttg atcttttcta cggggtctga   7560
cgctcagtgg aacgaaaact cacgttaagg gattttggtc atgagattat caaaaaggat   7620
cttcacctag atccttttaa attaaaaatg aagttttaaa tcaatctaaa gtatatatga   7680
gtaaacttgg tctgacagtt accaatgctt aatcagtgag gcacctatct cagcgatctg   7740
tctatttcgt tcatccatag ttgcctgact ccccgtcgtg tagataacta cgatacggga   7800
gggcttacca tctggcccca gtgctgcaat gataccgcga gacccacgct caccggctcc   7860
agatttatca gcaataaacc agccagccgg aagggccgag cgcagaagtg gtcctgcaac   7920
tttatccgcc tccatccagt ctattaattg ttgccgggaa gctagagtaa gtagttcgcc   7980
agttaatagt ttgcgcaacg ttgttgccat tgctacaggc atcgtggtgt cacgctcgtc   8040
gtttggtatg gcttcattca gctccggttc ccaacgatca aggcgagtta catgatcccc   8100
catgttgtgc aaaaaagcgg ttagctcctt cggtcctccg atcgttgtca gaagtaagtt   8160
ggccgcagtg ttatcactca tggttatggc agcactgcat aattctctta ctgtcatgcc   8220
atccgtaaga tgcttttctg tgactggtga gtactcaacc aagtcattct gagaatagtg   8280
tatgcggcga ccgagttgct cttgcccggc gtcaatacgg gataataccg cgccacatag   8340
cagaacttta aaagtgctca tcattggaaa acgttcttcg gggcgaaaac tctcaaggat   8400
cttaccgctg ttgagatcca gttcgatgta acccactcgt gcacccaact gatcttcagc   8460
atcttttact ttcaccagcg tttctgggtg agcaaaaaca ggaaggcaaa atgccgcaaa   8520
aaagggaata agggcgacac ggaaatgttg aatactcata ctcttccttt ttcaatatta   8580
ttgaagcatt tatcagggtt attgtctcat gagcggatac atatttgaat gtatttagaa   8640
aaataaacaa ataggggttc cgcgcacatt tccccgaaaa gtgccacctg acgtctaaga   8700
aaccattatt atcatgacat taacctataa aaataggcgt atcacgaggc cctttcgtct   8760
cgcgcgtttc ggtgatgacg gtgaaaacct ctgacacatg cagctcccgg agacggtcac   8820
agcttgtctg taagcggatg ccgggagcag acaagcccgt cagggcgcgt cagcgggtgt   8880
tggcgggtgt cggggctggc ttaactatgc ggcatcagag cagattgtac tgagagtgca   8940
ccatatgcgg tgtgaaatac cgcacagatg cgtaaggaga aaataccgca tcaggcgcca   9000
ttcgccattc aggctgcgca actgttggga agggcgatcg gtgcgggcct cttcgctatt   9060
acgccagctg gcgaaagggg gatgtgctgc aaggcgatta agttgggtaa cgccagggtt   9120
ttcccagtca cgacgttgta aaacgacggc cagtgccaag ctg                      9163
```

<210> SEQ ID NO 14
<211> LENGTH: 8803
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 14
acgcgtgtag tcttatgcaa tactcttgta gtcttgcaac atggtaacga tgagttagca 60
acatgcctta caaggagaga aaaagcaccg tgcatgccga ttggtggaag taaggtggta 120
cgatcgtgcc ttattaggaa ggcaacagac gggtctgaca tggattggac gaaccactga 180
attgccgcat tgcagagata ttgtatttaa gtgcctagct cgatacaata aacgggtctc 240
tctggttaga ccagatctga gcctgggagc tctctggcta actagggaac ccactgctta 300
agcctcaata aagcttgcct tgagtgcttc aagtagtgtg tgcccgtctg ttgtgtgact 360
ctggtaacta gagatccctc agaccctttt agtcagtgtg gaaaatctct agcagtggcg 420
cccgaacagg gacctgaaag cgaaagggaa accagagctc tctcgacgca ggactcggct 480
tgctgaagcg cgcacggcaa gaggcgaggg gcggcgactg gtgagtacgc caaaaatttt 540
gactagcgga ggctagaagg agagagatgg gtgcgagagc gtcagtatta agcgggggag 600
aattagatcg cgatgggaaa aaattcggtt aaggccaggg ggaaagaaaa aatataaatt 660
aaaacatata gtatgggcaa gcagggagct agaacgattc gcagttaatc ctggcctgtt 720
agaaacatca gaaggctgta gacaaatact gggacagcta caaccatccc ttcagacagg 780
atcagaagaa cttagatcat tatataatac agtagcaacc ctctattgtg tgcatcaaag 840
gatagagata aaagacacca aggaagcttt agacaagata gaggaagagc aaaacaaaag 900
taagaccacc gcacagcaag cggccactga tcttcagacc tggaggagga gatatgaggg 960
acaattggag aagtgaatta tataaatata aagtagtaaa aattgaacca ttaggagtag 1020
cacccaccaa ggcaaagaga agagtggtgc agagagaaaa aagagcagtg ggaataggag 1080
ctttgttcct tgggttcttg ggagcagcag gaagcactat gggcgcagcc tcaatgacgc 1140
tgacggtaca ggccagacaa ttattgtctg gtatagtgca gcagcagaac aatttgctga 1200
gggctattga ggcgcaacag catctgttgc aactcacagt ctggggcatc aagcagctcc 1260
aggcaagaat cctggctgtg gaaagatacc taaaggatca acagctcctg gggatttggg 1320
gttgctctgg aaaactcatt tgcaccactg ctgtgccttg gaatgctagt tggagtaata 1380
aatctctgga acagattgga atcacacgac ctggatggag tgggacagag aaattaacaa 1440
ttacacaagc ttaatacact ccttaattga agaatcgcaa aaccagcaag aaaagaatga 1500
acaagaatta ttggaattag ataaatgggc aagtttgtgg aattggttta acataacaaa 1560
ttggctgtgg tatataaaat tattcataat gatagtagga ggcttggtag gtttaagaat 1620
agtttttgct gtactttcta tagtgaatag agttaggcag ggatattcac cattatcgtt 1680
tcagacccac ctcccaaccc cgaggggacc cgacaggccc gaaggaatag aagaagaagg 1740
tggagagaga gacagagaca gatccattcg attagtgaac ggatctcgac ggtatcggtt 1800
aacttttaaa agaaaagggg ggattggggg gtacagtgca ggggaaagaa tagtagacat 1860
aatagcaaca gacatacaaa ctaaagaatt acaaaaacaa attacaaaat tcaaaatttt 1920
atcgatacta gtattatgcc cagtacatga ccttatggga ctttcctact tggcagtaca 1980
tctacgtatt agtcatcgct attaccatgg tgatgcggtt ttggcagtac atcaatgggc 2040

```
gtggatagcg gtttgactca cggggatttc caagtctcca ccccattgac gtcaatggga   2100
gtttgttttg gcaccaaaat caacgggact ttccaaaatg tcgtaacaac tccgccccat   2160
tgacgcaaat gggcggtagg cgtgtacggt gggaggttta tataagcaga gctcgtttag   2220
tgaaccgtca gatcgcctgg agacgccatc cacgctgttt tgacctccat agaagattct   2280
agagccgcca ccatgcttct cctggtgaca agccttctgc tctgtgagtt accacaccca   2340
gcattcctcc tgatcccaga catccagatg acacagacta catcctccct gtctgcctct   2400
ctgggagaca gagtcaccat cagttgcagg gcaagtcagg acattagtaa atatttaaat   2460
tggtatcagc agaaaccaga tggaactgtt aaactcctga tctaccatac atcaagatta   2520
cactcaggag tcccatcaag gttcagtggc agtgggtctg gaacagatta ttctctcacc   2580
attagcaacc tggagcaaga agatattgcc acttactttt gccaacaggg taatacgctt   2640
ccgtacacgt tcggaggggg gactaagttg gaaataacag gctccacctc tggatccggc   2700
aagcccggat ctggcgaggg atccaccaag ggcgaggtga aactgcagga gtcaggacct   2760
ggcctggtgg cgccctcaca gagcctgtcc gtcacatgca ctgtctcagg ggtctcatta   2820
cccgactatg gtgtaagctg gattcgccag cctccacgaa agggtctgga gtggctggga   2880
gtaatatggg gtagtgaaac cacatactat aattcagctc tcaaatccag actgaccatc   2940
atcaaggaca actccaagag ccaagttttc ttaaaaatga acagtctgca aactgatgac   3000
acagccattt actactgtgc caaacattat tactacggtg gtagctatgc tatggactac   3060
tggggtcaag gaacctcagt caccgtctcc tcagcggccg caattgaagt tatgtatcct   3120
cctccttacc taggtggcgg cggttctggt ggcggcggtt ctggtggcgg cggttctctc   3180
gaggaggacc tgaacaaggt gttcccaccc gaggtcgctg tgtttgagcc atcagaagca   3240
gagatctccc acacccaaaa ggccacactg gtgtgcctgg ccacaggctt cttccccgac   3300
cacgtggagc tgagctggtg ggtgaatggg aaggaggtgc acagtggggt cagcacagac   3360
ccgcagcccc tcaaggagca gcccgccctc aatgactcca gatactgcct gagcagccgc   3420
ctgagggtct cggccacctt ctggcagaac ccccgcaacc acttccgctg tcaagtccag   3480
ttctacgggc tctcggagaa tgacgagtgg acccaggata gggccaaacc cgtcacccag   3540
atcgtcagcg ccgaggcctg gggtagagca gactgtggct ttacctcggt gtcctaccag   3600
caaggggtcc tgtctgccac catcctctat gagatcctgc tagggaaggc caccctgtat   3660
gctgtgctgg tcagcgccct tgtgttgatg gccatggtca agagaaagga tttctgataa   3720
gaattcgatc cgcggccgcg aaggatctgc gatcgctccg gtgcccgtca gtgggcagag   3780
cgcacatcgc ccacagtccc cgagaagttg gggggagggg tcggcaattg aacgggtgcc   3840
tagagaaggt ggcgcggggt aaactgggaa agtgatgtcg tgtactggct ccgccttttt   3900
cccgagggtg ggggagaacc gtatataagt gcagtagtcg ccgtgaacgt tctttttcgc   3960
aacgggtttg ccgccagaac acagctgaag cttcgagggg ctcgcatctc tccttcacgc   4020
gcccgccgcc ctacctgagg ccgccatcca cgccggttga gtcgcgttct gccgcctccc   4080
gcctgtggtg cctcctgaac tgcgtccgcc gtctaggtaa gtttaaagct caggtcgaga   4140
ccgggccttt gtccggcgct cccttggagc ctacctagac tcagccggct ctccacgctt   4200
tgcctgaccc tgcttgctca actctacgtc tttgtttcgt ttctgttctg gcgccgttac   4260
agatccaagc tgtgaccggc gcctacgcta gatgaccgag tacaagccca cggtgcgcct   4320
cgccacccgc gacgacgtcc ccagggccgt acgcaccctc gccgccgcgt tcgccgacta   4380
ccccgccacg cgccacaccg tcgatccgga ccgccacatc gagcgggtca ccgagctgca   4440
```

```
agaactcttc ctcacgcgcg tcgggctcga catcggcaag gtgtgggtcg cggacgacgg   4500
cgccgcggtg gcggtctgga ccacgccgga gagcgtcgaa gcgggggcgg tgttcgccga   4560
gatcggcccg cgcatggccg agttgagcgg ttcccggctg gccgcgcagc aacagatgga   4620
aggcctcctg gcgccgcacc ggcccaagga gcccgcgtgg ttcctggcca ccgtcggcgt   4680
ctcgcccgac caccagggca agggtctggg cagcgccgtc gtgctccccg gagtggaggc   4740
ggccgagcgc gccggggtgc ccgccttcct ggagacctcc gcgccccgca acctcccctt   4800
ctacgagcgg ctcggcttca ccgtcaccgc cgacgtcgag gtgcccgaag gaccgcgcac   4860
ctggtgcatg acccgcaagc ccggtgcctg agtcgacaat caacctctgg attacaaaat   4920
ttgtgaaaga ttgactggta ttcttaacta tgttgctcct tttacgctat gtggatacgc   4980
tgctttaatg cctttgtatc atgctattgc ttcccgtatg gctttcattt tctcctcctt   5040
gtataaatcc tggttgctgt ctctttatga ggagttgtgg cccgttgtca ggcaacgtgg   5100
cgtggtgtgc actgtgtttg ctgacgcaac ccccactggt tggggcattg ccaccacctg   5160
tcagctcctt tccgggactt tcgctttccc cctccctatt gccacggcgg aactcatcgc   5220
cgcctgcctt gcccgctgct ggacaggggc tcggctgttg ggcactgaca attccgtggt   5280
gttgtcgggg aaatcatcgt cctttccttg gctgctcgcc tgtgttgcca cctggattct   5340
gcgcgggacg tccttctgct acgtcccttc ggccctcaat ccagcggacc ttccttcccg   5400
cggcctgctg ccggctctgc ggcctcttcc gcgtcttcgc cttcgccctc agacgagtcg   5460
gatctccctt tgggccgcct ccccgcctgg tacctttaag accaatgact tacaaggcag   5520
ctgtagatct tagccacttt ttaaaagaaa aggggggact ggaagggcta attcactccc   5580
aacgaaaata agatctgctt tttgcttgta ctgggtctct ctggttagac cagatctgag   5640
cctgggagct ctctggctaa ctagggaacc cactgcttaa gcctcaataa agcttgcctt   5700
gagtgcttca agtagtgtgt gcccgtctgt tgtgtgactc tggtaactag agatccctca   5760
gaccctttta gtcagtgtgg aaaatctcta gcagtagtag ttcatgtcat cttattattc   5820
agtatttata acttgcaaag aaatgaatat cagagagtga gaggaacttg tttattgcag   5880
cttataatgg ttacaaataa agcaatagca tcacaaattt cacaaataaa gcattttttt   5940
cactgcattc tagttgtggt ttgtccaaac tcatcaatgt atcttatcat gtctggctct   6000
agctatcccg cccctaactc cgcccagttc cgcccattct ccgccccatg gctgactaat   6060
ttttttttatt tatgcagagg ccgaggccgc ctcggcctct gagctattcc agaagtagtg   6120
aggaggcttt tttggaggcc tagacttttg cagagacggc ccaaattcgt aatcatggtc   6180
atagctgttt cctgtgtgaa attgttatcc gctcacaatt ccacacaaca tacgagccgg   6240
aagcataaag tgtaaagcct ggggtgccta atgagtgagc taactcacat taattgcgtt   6300
gcgctcactg cccgctttcc agtcgggaaa cctgtcgtgc cagctgcatt aatgaatcgg   6360
ccaacgcgcg gggagaggcg gtttgcgtat tgggcgctct tccgcttcct cgctcactga   6420
ctcgctgcgc tcggtcgttc ggctgcggcg agcggtatca gctcactcaa aggcggtaat   6480
acggttatcc acagaatcag gggataacgc aggaaagaac atgtgagcaa aaggccagca   6540
aaaggccagg aaccgtaaaa aggccgcgtt gctggcgttt ttccataggc tccgcccccc   6600
tgacgagcat cacaaaaatc gacgctcaag tcagaggtgg cgaaacccga caggactata   6660
aagataccag gcgtttcccc ctggaagctc cctcgtgcgc tctcctgttc cgaccctgcc   6720
gcttaccgga tacctgtccg cctttctccc ttcgggaagc gtggcgcttt ctcatagctc   6780
```

```
acgctgtagg tatctcagtt cggtgtaggt cgttcgctcc aagctgggct gtgtgcacga   6840

accccccgtt cagcccgacc gctgcgcctt atccggtaac tatcgtcttg agtccaaccc   6900

ggtaagacac gacttatcgc cactggcagc agccactggt aacaggatta gcagagcgag   6960

gtatgtaggc ggtgctacag agttcttgaa gtggtggcct aactacggct acactagaag   7020

gacagtattt ggtatctgcg ctctgctgaa gccagttacc ttcggaaaaa gagttggtag   7080

ctcttgatcc ggcaaacaaa ccaccgctgg tagcggtggt ttttttgttt gcaagcagca   7140

gattacgcgc agaaaaaaag gatctcaaga agatcctttg atcttttcta cggggtctga   7200

cgctcagtgg aacgaaaact cacgttaagg gattttggtc atgagattat caaaaaggat   7260

cttcacctag atccttttaa attaaaaatg aagttttaaa tcaatctaaa gtatatatga   7320

gtaaacttgg tctgacagtt accaatgctt aatcagtgag gcacctatct cagcgatctg   7380

tctatttcgt tcatccatag ttgcctgact ccccgtcgtg tagataacta cgatacggga   7440

gggcttacca tctggcccca gtgctgcaat gataccgcga gacccacgct caccggctcc   7500

agatttatca gcaataaacc agccagccgg aagggccgag cgcagaagtg gtcctgcaac   7560

tttatccgcc tccatccagt ctattaattg ttgccgggaa gctagagtaa gtagttcgcc   7620

agttaatagt ttgcgcaacg ttgttgccat tgctacaggc atcgtggtgt cacgctcgtc   7680

gtttggtatg gcttcattca gctccggttc ccaacgatca aggcgagtta catgatcccc   7740

catgttgtgc aaaaaagcgg ttagctcctt cggtcctccg atcgttgtca gaagtaagtt   7800

ggccgcagtg ttatcactca tggttatggc agcactgcat aattctctta ctgtcatgcc   7860

atccgtaaga tgcttttctg tgactggtga gtactcaacc aagtcattct gagaatagtg   7920

tatgcggcga ccgagttgct cttgcccggc gtcaatacgg gataataccg cgccacatag   7980

cagaacttta aaagtgctca tcattggaaa acgttcttcg gggcgaaaac tctcaaggat   8040

cttaccgctg ttgagatcca gttcgatgta acccactcgt gcacccaact gatcttcagc   8100

atcttttact ttcaccagcg tttctgggtg agcaaaaaca ggaaggcaaa atgccgcaaa   8160

aaagggaata agggcgacac ggaaatgttg aatactcata ctcttccttt ttcaatatta   8220

ttgaagcatt tatcagggtt attgtctcat gagcggatac atatttgaat gtatttagaa   8280

aaataaacaa ataggggttc cgcgcacatt tccccgaaaa gtgccacctg acgtctaaga   8340

aaccattatt atcatgacat taacctataa aaataggcgt atcacgaggc cctttcgtct   8400

cgcgcgtttc ggtgatgacg gtgaaaacct ctgacacatg cagctcccgg agacggtcac   8460

agcttgtctg taagcggatg ccgggagcag acaagcccgt cagggcgcgt cagcgggtgt   8520

tggcgggtgt cggggctggc ttaactatgc ggcatcagag cagattgtac tgagagtgca   8580

ccatatgcgg tgtgaaatac cgcacagatg cgtaaggaga aaataccgca tcaggcgcca   8640

ttcgccattc aggctgcgca actgttggga agggcgatcg gtgcgggcct cttcgctatt   8700

acgccagctg gcgaaagggg gatgtgctgc aaggcgatta agttgggtaa cgccagggtt   8760

ttcccagtca cgacgttgta aaacgacggc cagtgccaag ctg                     8803
```

```
<210> SEQ ID NO 15
<211> LENGTH: 8752
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 15
```

```
acgcgtgtag tcttatgcaa tactcttgta gtcttgcaac atggtaacga tgagttagca     60
acatgcctta caaggagaga aaaagcaccg tgcatgccga ttggtggaag taaggtggta    120
cgatcgtgcc ttattaggaa ggcaacagac gggtctgaca tggattggac gaaccactga    180
attgccgcat tgcagagata ttgtatttaa gtgcctagct cgatacaata aacgggtctc    240
tctggttaga ccagatctga gcctgggagc tctctggcta actagggaac ccactgctta    300
agcctcaata aagcttgcct tgagtgcttc aagtagtgtg tgcccgtctg ttgtgtgact    360
ctggtaacta gagatccctc agaccctttt agtcagtgtg gaaaatctct agcagtggcg    420
cccgaacagg gacctgaaag cgaaagggaa accagagctc tctcgacgca ggactcggct    480
tgctgaagcg cgcacggcaa gaggcgaggg gcggcgactg gtgagtacgc caaaaatttt    540
gactagcgga ggctagaagg agagagatgg gtgcgagagc gtcagtatta agcgggggag    600
aattagatcg cgatgggaaa aaattcggtt aaggccaggg ggaaagaaaa aatataaatt    660
aaaacatata gtatgggcaa gcagggagct agaacgattc gcagttaatc ctggcctgtt    720
agaaacatca gaaggctgta gacaaatact gggacagcta caaccatccc ttcagacagg    780
atcagaagaa cttagatcat tatataatac agtagcaacc ctctattgtg tgcatcaaag    840
gatagagata aaagacacca aggaagcttt agacaagata gaggaagagc aaaacaaaag    900
taagaccacc gcacagcaag cggccactga tcttcagacc tggaggagga gatatgaggg    960
acaattggag aagtgaatta tataaatata aagtagtaaa aattgaacca ttaggagtag   1020
cacccaccaa ggcaaagaga agagtggtgc agagagaaaa aagagcagtg ggaataggag   1080
ctttgttcct tgggttcttg ggagcagcag gaagcactat gggcgcagcc tcaatgacgc   1140
tgacggtaca ggccagacaa ttattgtctg gtatagtgca gcagcagaac aatttgctga   1200
gggctattga ggcgcaacag catctgttgc aactcacagt ctggggcatc aagcagctcc   1260
aggcaagaat cctggctgtg gaaagatacc taaaggatca acagctcctg gggatttggg   1320
gttgctctgg aaaactcatt tgcaccactg ctgtgccttg gaatgctagt tggagtaata   1380
aatctctgga acagattgga atcacacgac ctggatggag tgggacagag aaattaacaa   1440
ttacacaagc ttaatacact ccttaattga agaatcgcaa aaccagcaag aaaagaatga   1500
acaagaatta ttggaattag ataaatgggc aagtttgtgg aattggttta acataacaaa   1560
ttggctgtgg tatataaaat tattcataat gatagtagga ggcttggtag gtttaagaat   1620
agtttttgct gtactttcta tagtgaatag agttaggcag ggatattcac cattatcgtt   1680
tcagacccac ctcccaaccc cgaggggacc cgacaggccc gaaggaatag aagaagaagg   1740
tggagagaga gacagagaca gatccattcg attagtgaac ggatctcgac ggtatcggtt   1800
aacttttaaa agaaaagggg ggattggggg gtacagtgca ggggaaagaa tagtagacat   1860
aatagcaaca gacatacaaa ctaaagaatt acaaaaacaa attacaaaat tcaaaatttt   1920
atcgatacta gtattatgcc cagtacatga ccttatggga ctttcctact tggcagtaca   1980
tctacgtatt agtcatcgct attaccatgg tgatgcggtt ttggcagtac atcaatgggc   2040
gtggatagcg gtttgactca cggggatttc caagtctcca ccccattgac gtcaatggga   2100
gtttgttttg gcaccaaaat caacgggact ttccaaaatg tcgtaacaac tccgccccat   2160
tgacgcaaat gggcggtagg cgtgtacggt gggaggttta tataagcaga gctcgtttag   2220
tgaaccgtca gatcgcctgg agacgccatc cacgctgttt tgacctccat agaagattct   2280
agagccgcca ccatgcttct cctggtgaca agccttctgc tctgtgagtt accacaccca   2340
gcattcctcc tgatcccaga catccagatg acacagacta catcctccct gtctgcctct   2400
```

ctgggagaca gagtcaccat cagttgcagg gcaagtcagg acattagtaa atatttaaat 2460
tggtatcagc agaaaccaga tggaactgtt aaactcctga tctaccatac atcaagatta 2520
cactcaggag tcccatcaag gttcagtggc agtgggtctg gaacagatta ttctctcacc 2580
attagcaacc tggagcaaga agatattgcc acttactttt gccaacaggg taatacgctt 2640
ccgtacacgt tcggaggggg gactaagttg gaaataacag gctccacctc tggatccggc 2700
aagcccggat ctggcgaggg atccaccaag ggcgaggtga aactgcagga gtcaggacct 2760
ggcctggtgg cgccctcaca gagcctgtcc gtcacatgca ctgtctcagg ggtctcatta 2820
cccgactatg gtgtaagctg gattcgccag cctccacgaa agggtctgga gtggctggga 2880
gtaatatggg gtagtgaaac cacatactat aattcagctc tcaaatccag actgaccatc 2940
atcaaggaca actccaagag ccaagttttc ttaaaaatga acagtctgca aactgatgac 3000
acagccattt actactgtgc caaacattat tactacggtg gtagctatgc tatggactac 3060
tggggtcaag gaacctcagt caccgtctcc tcagcggccg caattgaagt tatgtatcct 3120
cctccttacc taggtggcgg cggttctggt ggcggcggtt ctggtggcgg cggttctctc 3180
gagcagtcaa tcaaaggaaa ccacttggtt aaggtgtatg actatcaaga agatggttcg 3240
gtacttctga cttgtgatgc agaagccaaa aatatcacat ggtttaaaga tgggaagatg 3300
atcggcttcc taactgaaga taaaaaaaaa tggaatctgg gaagtaatgc caaggaccca 3360
cgagggatgt atcagtgtaa aggatcacag aacaagtcaa aaccactcca agtgtattac 3420
agaatgtgtc agaactgcat tgaactaaat gcagccacca tatctggctt tctctttgct 3480
gaaatcgtca gcattttcgt ccttgctgtt ggggtctact tcattgctgg acaggatgga 3540
gttcgccagt cgagagcttc agacaagcag actctgttgc ccaatgacca gctctaccag 3600
cccctcaagg atcgagaaga tgaccagtac agccaccttc aaggaaacca gttgaggagg 3660
aattgataag aattcgatcc gcggccgcga aggatctgcg atcgctccgg tgcccgtcag 3720
tgggcagagc gcacatcgcc cacagtcccc gagaagttgg ggggaggggt cggcaattga 3780
acgggtgcct agagaaggtg gcgcggggta aactgggaaa gtgatgtcgt gtactggctc 3840
cgcctttttc ccgagggtgg gggagaaccg tatataagtg cagtagtcgc cgtgaacgtt 3900
ctttttcgca acgggtttgc cgccagaaca cagctgaagc ttcgaggggc tcgcatctct 3960
ccttcacgcg cccgccgccc tacctgaggc cgccatccac gccggttgag tcgcgttctg 4020
ccgcctcccg cctgtggtgc ctcctgaact gcgtccgccg tctaggtaag tttaaagctc 4080
aggtcgagac cgggcctttg tccggcgctc ccttggagcc tacctagact cagccggctc 4140
tccacgcttt gcctgaccct gcttgctcaa ctctacgtct ttgtttcgtt ttctgttctg 4200
cgccgttaca gatccaagct gtgaccggcg cctacgctag atgaccgagt acaagcccac 4260
ggtgcgcctc gccacccgcg acgacgtccc cagggccgta cgcaccctcg ccgccgcgtt 4320
cgccgactac cccgccacgc gccacaccgt cgatccggac cgccacatcg agcgggtcac 4380
cgagctgcaa gaactcttcc tcacgcgcgt cgggctcgac atcggcaagg tgtgggtcgc 4440
ggacgacggc gccgcggtgg cggtctggac cacgccggag agcgtcgaag cgggggcggt 4500
gttcgccgag atcggcccgc gcatggccga gttgagcggt tcccggctgg ccgcgcagca 4560
acagatggaa ggcctcctgg cgccgcaccg gcccaaggag cccgcgtggt tcctggccac 4620
cgtcggcgtc tcgcccgacc accagggcaa gggtctgggc agcgccgtcg tgctccccgg 4680
agtggaggcg gccgagcgcg ccggggtgcc cgccttcctg gagacctccg cgccccgcaa 4740

-continued

```
cctccccttc tacgagcggc tcggcttcac cgtcaccgcc gacgtcgagg tgcccgaagg   4800
accgcgcacc tggtgcatga cccgcaagcc cggtgcctga gtcgacaatc aacctctgga   4860
ttacaaaatt tgtgaaagat tgactggtat tcttaactat gttgctcctt ttacgctatg   4920
tggatacgct gctttaatgc ctttgtatca tgctattgct tcccgtatgg ctttcatttt   4980
ctcctccttg tataaatcct ggttgctgtc tctttatgag gagttgtggc ccgttgtcag   5040
gcaacgtggc gtggtgtgca ctgtgtttgc tgacgcaacc cccactggtt ggggcattgc   5100
caccacctgt cagctccttt ccgggacttt cgctttcccc ctccctattg ccacggcgga   5160
actcatcgcc gcctgccttg cccgctgctg gacaggggct cggctgttgg gcactgacaa   5220
ttccgtggtg ttgtcgggga aatcatcgtc ctttccttgg ctgctcgcct gtgttgccac   5280
ctggattctg cgcgggacgt ccttctgcta cgtcccttcg gccctcaatc cagcggacct   5340
tccttcccgc ggcctgctgc cggctctgcg gcctcttccg cgtcttcgcc ttcgccctca   5400
gacgagtcgg atctcccttt gggccgcctc cccgcctggt acctttaaga ccaatgactt   5460
acaaggcagc tgtagatctt agccactttt taaaagaaaa ggggggactg gaagggctaa   5520
ttcactccca acgaaaataa gatctgcttt ttgcttgtac tgggtctctc tggttagacc   5580
agatctgagc ctgggagctc tctggctaac tagggaaccc actgcttaag cctcaataaa   5640
gcttgccttg agtgcttcaa gtagtgtgtg cccgtctgtt gtgtgactct ggtaactaga   5700
gatccctcag acccttttag tcagtgtgga aaatctctag cagtagtagt tcatgtcatc   5760
ttattattca gtatttataa cttgcaaaga aatgaatatc agagagtgag aggaacttgt   5820
ttattgcagc ttataatggt tacaaataaa gcaatagcat cacaaatttc acaaataaag   5880
catttttttc actgcattct agttgtggtt tgtccaaact catcaatgta tcttatcatg   5940
tctggctcta gctatcccgc ccctaactcc gcccagttcc gcccattctc cgccccatgg   6000
ctgactaatt ttttttattt atgcagaggc cgaggccgcc tcggcctctg agctattcca   6060
gaagtagtga ggaggctttt ttggaggcct agacttttgc agagacggcc caaattcgta   6120
atcatggtca tagctgtttc ctgtgtgaaa ttgttatccg ctcacaattc cacacaacat   6180
acgagccgga agcataaagt gtaaagcctg gggtgcctaa tgagtgagct aactcacatt   6240
aattgcgttg cgctcactgc ccgctttcca gtcgggaaac ctgtcgtgcc agctgcatta   6300
atgaatcggc caacgcgcgg ggagaggcgg tttgcgtatt gggcgctctt ccgcttcctc   6360
gctcactgac tcgctgcgct cggtcgttcg gctgcggcga gcggtatcag ctcactcaaa   6420
ggcggtaata cggttatcca cagaatcagg ggataacgca ggaaagaaca tgtgagcaaa   6480
aggccagcaa aaggccagga accgtaaaaa ggccgcgttg ctggcgtttt tccataggct   6540
ccgcccccct gacgagcatc acaaaaatcg acgctcaagt cagaggtggc gaaacccgac   6600
aggactataa agataccagg cgtttccccc tggaagctcc ctcgtgcgct ctcctgttcc   6660
gaccctgccg cttaccggat acctgtccgc ctttctccct tcgggaagcg tggcgctttc   6720
tcatagctca cgctgtaggt atctcagttc ggtgtaggtc gttcgctcca agctgggctg   6780
tgtgcacgaa ccccccgttc agcccgaccg ctgcgcctta tccggtaact atcgtcttga   6840
gtccaacccg gtaagacacg acttatcgcc actggcagca gccactggta acaggattag   6900
cagagcgagg tatgtaggcg gtgctacaga gttcttgaag tggtggccta actacggcta   6960
cactagaagg acagtatttg gtatctgcgc tctgctgaag ccagttacct tcggaaaaag   7020
agttggtagc tcttgatccg gcaaacaaac caccgctggt agcggtggtt tttttgtttg   7080
caagcagcag attacgcgca gaaaaaaagg atctcaagaa gatcctttga tcttttctac   7140
```

```
ggggtctgac gctcagtgga acgaaaactc acgttaaggg attttggtca tgagattatc   7200
aaaaaggatc ttcacctaga tccttttaaa ttaaaaatga agttttaaat caatctaaag   7260
tatatatgag taaacttggt ctgacagtta ccaatgctta atcagtgagg cacctatctc   7320
agcgatctgt ctatttcgtt catccatagt tgcctgactc cccgtcgtgt agataactac   7380
gatacgggag ggcttaccat ctggccccag tgctgcaatg ataccgcgag acccacgctc   7440
accggctcca gatttatcag caataaacca gccagccgga agggccgagc gcagaagtgg   7500
tcctgcaact ttatccgcct ccatccagtc tattaattgt tgccgggaag ctagagtaag   7560
tagttcgcca gttaatagtt tgcgcaacgt tgttgccatt gctacaggca tcgtggtgtc   7620
acgctcgtcg tttggtatgg cttcattcag ctccggttcc caacgatcaa ggcgagttac   7680
atgatccccc atgttgtgca aaaaagcggt tagctccttc ggtcctccga tcgttgtcag   7740
aagtaagttg gccgcagtgt tatcactcat ggttatggca gcactgcata attctcttac   7800
tgtcatgcca tccgtaagat gcttttctgt gactggtgag tactcaacca agtcattctg   7860
agaatagtgt atgcggcgac cgagttgctc ttgcccggcg tcaatacggg ataataccgc   7920
gccacatagc agaactttaa aagtgctcat cattggaaaa cgttcttcgg ggcgaaaact   7980
ctcaaggatc ttaccgctgt tgagatccag ttcgatgtaa cccactcgtg cacccaactg   8040
atcttcagca tcttttactt tcaccagcgt ttctgggtga gcaaaaacag gaaggcaaaa   8100
tgccgcaaaa aagggaataa gggcgacacg gaaatgttga atactcatac tcttcctttt   8160
tcaatattat tgaagcattt atcagggtta ttgtctcatg agcggataca tatttgaatg   8220
tatttagaaa aataaacaaa taggggttcc gcgcacattt ccccgaaaag tgccacctga   8280
cgtctaagaa accattatta tcatgacatt aacctataaa aataggcgta tcacgaggcc   8340
ctttcgtctc gcgcgtttcg gtgatgacgg tgaaaacctc tgacacatgc agctcccgga   8400
gacggtcaca gcttgtctgt aagcggatgc cgggagcaga caagcccgtc agggcgcgtc   8460
agcgggtgtt ggcgggtgtc ggggctggct taactatgcg gcatcagagc agattgtact   8520
gagagtgcac catatgcggt gtgaaatacc gcacagatgc gtaaggagaa aataccgcat   8580
caggcgccat tcgccattca ggctgcgcaa ctgttgggaa gggcgatcgg tgcgggcctc   8640
ttcgctatta cgccagctgg cgaaaggggg atgtgctgca aggcgattaa gttgggtaac   8700
gccagggttt tcccagtcac gacgttgtaa aacgacggcc agtgccaagc tg           8752
```

<210> SEQ ID NO 16
<211> LENGTH: 8722
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 16

```
acgcgtgtag tcttatgcaa tactcttgta gtcttgcaac atggtaacga tgagttagca     60
acatgcctta caaggagaga aaaagcaccg tgcatgccga ttggtggaag taaggtggta    120
cgatcgtgcc ttattaggaa ggcaacagac gggtctgaca tggattggac gaaccactga    180
attgccgcat tgcagagata ttgtatttaa gtgcctagct cgatacaata aacgggtctc    240
tctggttaga ccagatctga gcctgggagc tctctggcta actagggaac ccactgctta    300
agcctcaata aagcttgcct tgagtgcttc aagtagtgtg tgcccgtctg ttgtgtgact    360
ctggtaacta gagatccctc agaccctttt agtcagtgtg gaaaatctct agcagtggcg    420
```

```
cccgaacagg gacctgaaag cgaaagggaa accagagctc tctcgacgca ggactcggct    480
tgctgaagcg cgcacggcaa gaggcgaggg gcggcgactg gtgagtacgc caaaaatttt    540
gactagcgga ggctagaagg agagagatgg gtgcgagagc gtcagtatta agcgggggag    600
aattagatcg cgatgggaaa aaattcggtt aaggccaggg ggaaagaaaa aatataaatt    660
aaaacatata gtatgggcaa gcagggagct agaacgattc gcagttaatc ctggcctgtt    720
agaaacatca gaaggctgta gacaaatact gggacagcta caaccatccc ttcagacagg    780
atcagaagaa cttagatcat tatataatac agtagcaacc ctctattgtg tgcatcaaag    840
gatagagata aaagacacca aggaagcttt agacaagata gaggaagagc aaaacaaaag    900
taagaccacc gcacagcaag cggccactga tcttcagacc tggaggagga gatatgaggg    960
acaattggag aagtgaatta tataaatata aagtagtaaa aattgaacca ttaggagtag   1020
cacccaccaa ggcaaagaga agagtggtgc agagagaaaa aagagcagtg ggaataggag   1080
ctttgttcct tgggttcttg ggagcagcag gaagcactat gggcgcagcc tcaatgacgc   1140
tgacggtaca ggccagacaa ttattgtctg gtatagtgca gcagcagaac aatttgctga   1200
gggctattga ggcgcaacag catctgttgc aactcacagt ctggggcatc aagcagctcc   1260
aggcaagaat cctggctgtg gaaagatacc taaaggatca acagctcctg gggatttggg   1320
gttgctctgg aaaactcatt tgcaccactg ctgtgccttg gaatgctagt tggagtaata   1380
aatctctgga acagattgga atcacacgac ctggatggag tgggacagag aaattaacaa   1440
ttacacaagc ttaatacact ccttaattga agaatcgcaa aaccagcaag aaaagaatga   1500
acaagaatta ttggaattag ataaatgggc aagtttgtgg aattggttta acataacaaa   1560
ttggctgtgg tatataaaat tattcataat gatagtagga ggcttggtag gtttaagaat   1620
agtttttgct gtactttcta tagtgaatag agttaggcag ggatattcac cattatcgtt   1680
tcagacccac ctcccaaccc cgaggggacc cgacaggccc gaaggaatag aagaagaagg   1740
tggagagaga gacagagaca gatccattcg attagtgaac ggatctcgac ggtatcggtt   1800
aacttttaaa agaaaagggg ggattggggg gtacagtgca ggggaaagaa tagtagacat   1860
aatagcaaca gacatacaaa ctaaagaatt acaaaaacaa attacaaaat tcaaaatttt   1920
atcgatacta gtattatgcc cagtacatga ccttatggga ctttcctact tggcagtaca   1980
tctacgtatt agtcatcgct attaccatgg tgatgcggtt ttggcagtac atcaatgggc   2040
gtggatagcg gtttgactca cggggatttc caagtctcca ccccattgac gtcaatggga   2100
gtttgttttg gcaccaaaat caacgggact ttccaaaatg tcgtaacaac tccgccccat   2160
tgacgcaaat gggcggtagg cgtgtacggt gggaggttta tataagcaga gctcgtttag   2220
tgaaccgtca gatcgcctgg agacgccatc cacgctgttt tgacctccat agaagattct   2280
agagccgcca ccatgcttct cctggtgaca agccttctgc tctgtgagtt accacaccca   2340
gcattcctcc tgatcccaga catccagatg acacagacta catcctccct gtctgcctct   2400
ctgggagaca gagtcaccat cagttgcagg gcaagtcagg acattagtaa atatttaaat   2460
tggtatcagc agaaaccaga tggaactgtt aaactcctga tctaccatac atcaagatta   2520
cactcaggag tcccatcaag gttcagtggc agtgggtctg gaacagatta ttctctcacc   2580
attagcaacc tggagcaaga agatattgcc acttactttt gccaacaggg taatacgctt   2640
ccgtacacgt tcggaggggg gactaagttg gaaataacag gctccacctc tggatccggc   2700
aagcccggat ctggcgaggg atccaccaag ggcgaggtga aactgcagga gtcaggacct   2760
```

```
ggcctggtgg cgccctcaca gagcctgtcc gtcacatgca ctgtctcagg ggtctcatta   2820
cccgactatg gtgtaagctg gattcgccag cctccacgaa agggtctgga gtggctggga   2880
gtaatatggg gtagtgaaac cacatactat aattcagctc tcaaatccag actgaccatc   2940
atcaaggaca actccaagag ccaagttttc ttaaaaatga acagtctgca aactgatgac   3000
acagccattt actactgtgc caaacattat tactacggtg gtagctatgc tatggactac   3060
tggggtcaag gaacctcagt caccgtctcc tcagcggccg caattgaagt tatgtatcct   3120
cctccttacc taggtggcgg cggttctggt ggcggcggtt ctggtggcgg cggttctctc   3180
gagttcaaga tacctataga ggaacttgag gacagagtgt ttgtgaattg caataccagc   3240
atcacatggg tagagggaac ggtgggaaca ctgctctcag acattacaag actggacctg   3300
ggaaaacgca tcctggaccc acgaggaata tataggtgta atgggacaga tatatacaag   3360
gacaaagaat ctaccgtgca agttcattat cgaatgtgcc agagctgtgt ggagctggat   3420
ccagccaccg tggctggcat cattgtcact gatgtcattg ccactctgct ccttgctttg   3480
ggagtcttct gctttgctgg acatgagact ggaaggctgt ctggggctgc cgacacacaa   3540
gctctgttga ggaatgacca ggtctatcag cccctccgag atcgagatga tgctcagtac   3600
agccaccttg gaggaaactg ggctcggaac aagtgataag aattcgatcc gcggccgcga   3660
aggatctgcg atcgctccgg tgcccgtcag tgggcagagc gcacatcgcc cacagtcccc   3720
gagaagttgg ggggaggggt cggcaattga acgggtgcct agagaaggtg gcgcggggta   3780
aactgggaaa gtgatgtcgt gtactggctc cgcctttttc ccgagggtgg gggagaaccg   3840
tatataagtg cagtagtcgc cgtgaacgtt ctttttcgca acgggtttgc cgccagaaca   3900
cagctgaagc ttcgaggggc tcgcatctct ccttcacgcg cccgccgccc tacctgaggc   3960
cgccatccac gccggttgag tcgcgttctg ccgcctcccg cctgtggtgc ctcctgaact   4020
gcgtccgccg tctaggtaag tttaaagctc aggtcgagac cgggcctttg tccggcgctc   4080
ccttggagcc tacctagact cagccggctc tccacgcttt gcctgaccct gcttgctcaa   4140
ctctacgtct ttgtttcgtt ttctgttctg cgccgttaca gatccaagct gtgaccggcg   4200
cctacgctag atgaccgagt acaagcccac ggtgcgcctc gccacccgcg acgacgtccc   4260
cagggccgta cgcaccctcg ccgccgcgtt cgccgactac cccgccacgc gccacaccgt   4320
cgatccggac cgccacatcg agcgggtcac cgagctgcaa gaactcttcc tcacgcgcgt   4380
cgggctcgac atcggcaagg tgtgggtcgc ggacgacggc gccgcggtgg cggtctggac   4440
cacgccggag agcgtcgaag cgggggcggt gttcgccgag atcggcccgc gcatggccga   4500
gttgagcggt tcccggctgg ccgcgcagca acagatggaa ggcctcctgg cgccgcaccg   4560
gcccaaggag cccgcgtggt tcctggccac cgtcggcgtc tcgcccgacc accagggcaa   4620
gggtctgggc agcgccgtcg tgctccccgg agtggaggcg gccgagcgcg ccggggtgcc   4680
cgccttcctg gagacctccg cgccccgcaa cctccccttc tacgagcggc tcggcttcac   4740
cgtcaccgcc gacgtcgagg tgcccgaagg accgcgcacc tggtgcatga cccgcaagcc   4800
cggtgcctga gtcgacaatc aacctctgga ttacaaaatt tgtgaaagat tgactggtat   4860
tcttaactat gttgctcctt ttacgctatg tggatacgct gctttaatgc ctttgtatca   4920
tgctattgct tcccgtatgg ctttcatttt ctcctccttg tataaatcct ggttgctgtc   4980
tctttatgag gagttgtggc ccgttgtcag gcaacgtggc gtggtgtgca ctgtgtttgc   5040
tgacgcaacc cccactggtt ggggcattgc caccacctgt cagctccttt ccgggacttt   5100
cgctttcccc ctccctattg ccacggcgga actcatcgcc gcctgccttg cccgctgctg   5160
```

```
gacaggggct cggctgttgg gcactgacaa ttccgtggtg ttgtcgggga aatcatcgtc   5220
ctttccttgg ctgctcgcct gtgttgccac ctggattctg cgcgggacgt ccttctgcta   5280
cgtcccttcg gccctcaatc cagcggacct tccttcccgc ggcctgctgc cggctctgcg   5340
gcctcttccg cgtcttcgcc ttcgccctca gacgagtcgg atctcccttt gggccgcctc   5400
cccgcctggt acctttaaga ccaatgactt acaaggcagc tgtagatctt agccactttt   5460
taaaagaaaa ggggggactg gaagggctaa ttcactccca acgaaaataa gatctgcttt   5520
ttgcttgtac tgggtctctc tggttagacc agatctgagc ctgggagctc tctggctaac   5580
tagggaaccc actgcttaag cctcaataaa gcttgccttg agtgcttcaa gtagtgtgtg   5640
cccgtctgtt gtgtgactct ggtaactaga gatccctcag acccttttag tcagtgtgga   5700
aaatctctag cagtagtagt tcatgtcatc ttattattca gtatttataa cttgcaaaga   5760
aatgaatatc agagagtgag aggaacttgt ttattgcagc ttataatggt tacaaataaa   5820
gcaatagcat cacaaatttc acaaataaag cattttttc actgcattct agttgtggtt   5880
tgtccaaact catcaatgta tcttatcatg tctggctcta gctatcccgc ccctaactcc   5940
gcccagttcc gcccattctc cgccccatgg ctgactaatt ttttttattt atgcagaggc   6000
cgaggccgcc tcggcctctg agctattcca gaagtagtga ggaggctttt ttggaggcct   6060
agacttttgc agagacggcc caaattcgta atcatggtca tagctgtttc ctgtgtgaaa   6120
ttgttatccg ctcacaattc cacacaacat acgagccgga agcataaagt gtaaagcctg   6180
gggtgcctaa tgagtgagct aactcacatt aattgcgttg cgctcactgc ccgctttcca   6240
gtcgggaaac ctgtcgtgcc agctgcatta atgaatcggc caacgcgcgg ggagaggcgg   6300
tttgcgtatt gggcgctctt ccgcttcctc gctcactgac tcgctgcgct cggtcgttcg   6360
gctgcggcga gcggtatcag ctcactcaaa ggcggtaata cggttatcca cagaatcagg   6420
ggataacgca ggaaagaaca tgtgagcaaa aggccagcaa aaggccagga accgtaaaaa   6480
ggccgcgttg ctggcgtttt tccataggct ccgcccccct gacgagcatc acaaaaatcg   6540
acgctcaagt cagaggtggc gaaacccgac aggactataa agataccagg cgtttccccc   6600
tggaagctcc ctcgtgcgct ctcctgttcc gaccctgccg cttaccggat acctgtccgc   6660
ctttctccct tcgggaagcg tggcgctttc tcatagctca cgctgtaggt atctcagttc   6720
ggtgtaggtc gttcgctcca agctgggctg tgtgcacgaa ccccccgttc agcccgaccg   6780
ctgcgcctta tccggtaact atcgtcttga gtccaacccg gtaagacacg acttatcgcc   6840
actggcagca gccactggta acaggattag cagagcgagg tatgtaggcg gtgctacaga   6900
gttcttgaag tggtggccta actacggcta cactagaagg acagtatttg gtatctgcgc   6960
tctgctgaag ccagttacct tcggaaaaag agttggtagc tcttgatccg gcaaacaaac   7020
caccgctggt agcggtggtt tttttgtttg caagcagcag attacgcgca gaaaaaaagg   7080
atctcaagaa gatcctttga tcttttctac ggggtctgac gctcagtgga acgaaaactc   7140
acgttaaggg attttggtca tgagattatc aaaaaggatc ttcacctaga tccttttaaa   7200
ttaaaaatga agttttaaat caatctaaag tatatatgag taaacttggt ctgacagtta   7260
ccaatgctta atcagtgagg cacctatctc agcgatctgt ctatttcgtt catccatagt   7320
tgcctgactc cccgtcgtgt agataactac gatacgggag ggcttaccat ctggccccag   7380
tgctgcaatg ataccgcgag acccacgctc accggctcca gatttatcag caataaacca   7440
gccagccgga agggccgagc gcagaagtgg tcctgcaact ttatccgcct ccatccagtc   7500
```

```
tattaattgt tgccgggaag ctagagtaag tagttcgcca gttaatagtt tgcgcaacgt   7560

tgttgccatt gctacaggca tcgtggtgtc acgctcgtcg tttggtatgg cttcattcag   7620

ctccggttcc caacgatcaa ggcgagttac atgatccccc atgttgtgca aaaaagcggt   7680

tagctccttc ggtcctccga tcgttgtcag aagtaagttg gccgcagtgt tatcactcat   7740

ggttatggca gcactgcata attctcttac tgtcatgcca tccgtaagat gcttttctgt   7800

gactggtgag tactcaacca agtcattctg agaatagtgt atgcggcgac cgagttgctc   7860

ttgcccggcg tcaatacggg ataataccgc gccacatagc agaactttaa aagtgctcat   7920

cattggaaaa cgttcttcgg ggcgaaaact ctcaaggatc ttaccgctgt tgagatccag   7980

ttcgatgtaa cccactcgtg cacccaactg atcttcagca tcttttactt tcaccagcgt   8040

ttctgggtga gcaaaaacag gaaggcaaaa tgccgcaaaa aagggaataa gggcgacacg   8100

gaaatgttga atactcatac tcttcctttt tcaatattat tgaagcattt atcagggtta   8160

ttgtctcatg agcggataca tatttgaatg tatttagaaa aataaacaaa taggggttcc   8220

gcgcacattt ccccgaaaag tgccacctga cgtctaagaa accattatta tcatgacatt   8280

aacctataaa aataggcgta tcacgaggcc ctttcgtctc gcgcgtttcg gtgatgacgg   8340

tgaaaacctc tgacacatgc agctcccgga gacggtcaca gcttgtctgt aagcggatgc   8400

cgggagcaga caagcccgtc agggcgcgtc agcgggtgtt ggcgggtgtc ggggctggct   8460

taactatgcg gcatcagagc agattgtact gagagtgcac catatgcggt gtgaaatacc   8520

gcacagatgc gtaaggagaa aataccgcat caggcgccat tcgccattca ggctgcgcaa   8580

ctgttgggaa gggcgatcgg tgcgggcctc ttcgctatta cgccagctgg cgaaaggggg   8640

atgtgctgca aggcgattaa gttgggtaac gccagggttt tcccagtcac gacgttgtaa   8700

aacgacggcc agtgccaagc tg                                            8722
```

```
<210> SEQ ID NO 17
<211> LENGTH: 8827
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 17
```

```
acgcgtgtag tcttatgcaa tactcttgta gtcttgcaac atggtaacga tgagttagca     60

acatgcctta caaggagaga aaaagcaccg tgcatgccga ttggtggaag taaggtggta    120

cgatcgtgcc ttattaggaa ggcaacagac gggtctgaca tggattggac gaaccactga    180

attgccgcat tgcagagata ttgtatttaa gtgcctagct cgatacaata aacgggtctc    240

tctggttaga ccagatctga gcctgggagc tctctggcta actagggaac ccactgctta    300

agcctcaata aagcttgcct tgagtgcttc aagtagtgtg tgcccgtctg ttgtgtgact    360

ctggtaacta gagatccctc agaccctttt agtcagtgtg gaaaatctct agcagtggcg    420

cccgaacagg gacctgaaag cgaaagggaa accagagctc tctcgacgca ggactcggct    480

tgctgaagcg cgcacggcaa gaggcgaggg gcggcgactg gtgagtacgc caaaaatttt    540

gactagcgga ggctagaagg agagagatgg gtgcgagagc gtcagtatta agcgggggag    600

aattagatcg cgatgggaaa aaattcggtt aaggccaggg ggaaagaaaa aatataaatt    660

aaaacatata gtatgggcaa gcagggagct agaacgattc gcagttaatc ctggcctgtt    720

agaaacatca gaaggctgta gacaaatact gggacagcta caaccatccc ttcagacagg    780
```

```
atcagaagaa cttagatcat tatataatac agtagcaacc ctctattgtg tgcatcaaag    840
gatagagata aaagacacca aggaagcttt agacaagata gaggaagagc aaaacaaaag    900
taagaccacc gcacagcaag cggccactga tcttcagacc tggaggagga gatatgaggg    960
acaattggag aagtgaatta tataaatata aagtagtaaa aattgaacca ttaggagtag   1020
cacccaccaa ggcaaagaga agagtggtgc agagagaaaa aagagcagtg ggaataggag   1080
ctttgttcct tgggttcttg ggagcagcag gaagcactat gggcgcagcc tcaatgacgc   1140
tgacggtaca ggccagacaa ttattgtctg gtatagtgca gcagcagaac aatttgctga   1200
gggctattga ggcgcaacag catctgttgc aactcacagt ctggggcatc aagcagctcc   1260
aggcaagaat cctggctgtg gaaagatacc taaaggatca acagctcctg gggatttggg   1320
gttgctctgg aaaactcatt tgcaccactg ctgtgccttg gaatgctagt tggagtaata   1380
aatctctgga acagattgga atcacacgac ctggatggag tgggacagag aaattaacaa   1440
ttacacaagc ttaatacact ccttaattga agaatcgcaa aaccagcaag aaaagaatga   1500
acaagaatta ttggaattag ataaatgggc aagtttgtgg aattggttta acataacaaa   1560
ttggctgtgg tatataaaat tattcataat gatagtagga ggcttggtag gtttaagaat   1620
agtttttgct gtactttcta tagtgaatag agttaggcag ggatattcac cattatcgtt   1680
tcagacccac ctcccaaccc cgaggggacc cgacaggccc gaaggaatag aagaagaagg   1740
tggagagaga gacagagaca gatccattcg attagtgaac ggatctcgac ggtatcggtt   1800
aacttttaaa agaaaagggg ggattggggg gtacagtgca ggggaaagaa tagtagacat   1860
aatagcaaca gacatacaaa ctaaagaatt acaaaaacaa attacaaaat tcaaaatttt   1920
atcgatacta gtattatgcc cagtacatga ccttatggga ctttcctact tggcagtaca   1980
tctacgtatt agtcatcgct attaccatgg tgatgcggtt ttggcagtac atcaatgggc   2040
gtggatagcg gtttgactca cggggatttc caagtctcca ccccattgac gtcaatggga   2100
gtttgttttg gcaccaaaat caacgggact ttccaaaatg tcgtaacaac tccgccccat   2160
tgacgcaaat gggcggtagg cgtgtacggt gggaggttta tataagcaga gctcgtttag   2220
tgaaccgtca gatcgcctgg agacgccatc cacgctgttt tgacctccat agaagattct   2280
agagccgcca ccatgcttct cctggtgaca agccttctgc tctgtgagtt accacaccca   2340
gcattcctcc tgatcccaga catccagatg acacagacta catcctccct gtctgcctct   2400
ctgggagaca gagtcaccat cagttgcagg gcaagtcagg acattagtaa atatttaaat   2460
tggtatcagc agaaaccaga tggaactgtt aaactcctga tctaccatac atcaagatta   2520
cactcaggag tcccatcaag gttcagtggc agtgggtctg gaacagatta ttctctcacc   2580
attagcaacc tggagcaaga agatattgcc acttactttt gccaacaggg taatacgctt   2640
ccgtacacgt tcggaggggg gactaagttg gaaataacag gctccacctc tggatccggc   2700
aagcccggat ctggcgaggg atccaccaag ggcgaggtga aactgcagga gtcaggacct   2760
ggcctggtgg cgccctcaca gagcctgtcc gtcacatgca ctgtctcagg ggtctcatta   2820
cccgactatg gtgtaagctg gattcgccag cctccacgaa agggtctgga gtggctggga   2880
gtaatatggg gtagtgaaac cacatactat aattcagctc tcaaatccag actgaccatc   2940
atcaaggaca actccaagag ccaagttttc ttaaaaatga acagtctgca aactgatgac   3000
acagccattt actactgtgc caaacattat tactacggtg gtagctatgc tatggactac   3060
tggggtcaag gaacctcagt caccgtctcc tcagcggccg caattgaagt tatgtatcct   3120
cctccttacc taggtggcgg cggttctggt ggcggcggtt ctggtggcgg cggttctctc   3180
```

```
gaggatggta atgaagaaat gggtggtatt acacagacac catataaagt ctccatctct   3240

ggaaccacag taatattgac atgccctcag tatcctggat ctgaaatact atggcaacac   3300

aatgataaaa acataggcgg tgatgaggat gataaaaaca taggcagtga tgaggatcac   3360

ctgtcactga aggaattttc agaattggag caaagtggtt attatgtctg ctaccccaga   3420

ggaagcaaac cagaagatgc gaacttttat ctctacctga gggcaagagt gtgtgagaac   3480

tgcatggaga tggatgtgat gtcggtggcc acaattgtca tagtggacat ctgcatcact   3540

gggggcttgc tgctgctggt ttactactgg agcaagaata gaaaggccaa ggccaagcct   3600

gtgacacgag gagcgggtgc tggcggcagg caaaggggac aaaacaagga gaggccacca   3660

cctgttccca acccagacta tgagcccatc cggaaaggcc agcgggacct gtattctggc   3720

ctgaatcaga gacgcatctg ataagaattc gatccgcggc cgcgaaggat ctgcgatcgc   3780

tccggtgccc gtcagtgggc agagcgcaca tcgcccacag tccccgagaa gttgggggga   3840

ggggtcggca attgaacggg tgcctagaga aggtggcgcg gggtaaactg ggaaagtgat   3900

gtcgtgtact ggctccgcct ttttcccgag ggtgggggag aaccgtatat aagtgcagta   3960

gtcgccgtga acgttctttt tcgcaacggg tttgccgcca gaacacagct gaagcttcga   4020

ggggctcgca tctctccttc acgcgcccgc cgccctacct gaggccgcca tccacgccgg   4080

ttgagtcgcg ttctgccgcc tcccgcctgt ggtgcctcct gaactgcgtc cgccgtctag   4140

gtaagtttaa agctcaggtc gagaccgggc ctttgtccgg cgctcccttg gagcctacct   4200

agactcagcc ggctctccac gctttgcctg accctgcttg ctcaactcta cgtctttgtt   4260

tcgttttctg ttctgcgccg ttacagatcc aagctgtgac cggcgcctac gctagatgac   4320

cgagtacaag cccacggtgc gcctcgccac ccgcgacgac gtccccaggg ccgtacgcac   4380

cctcgccgcc gcgttcgccg actaccccgc cacgcgccac accgtcgatc cggaccgcca   4440

catcgagcgg gtcaccgagc tgcaagaact cttcctcacg cgcgtcgggc tcgacatcgg   4500

caaggtgtgg gtcgcggacg acggcgccgc ggtggcggtc tggaccacgc cggagagcgt   4560

cgaagcgggg gcggtgttcg ccgagatcgg cccgcgcatg gccgagttga gcggttcccg   4620

gctggccgcg cagcaacaga tggaaggcct cctggcgccg caccggccca aggagcccgc   4680

gtggttcctg gccaccgtcg gcgtctcgcc cgaccaccag ggcaagggtc tgggcagcgc   4740

cgtcgtgctc cccggagtgg aggcggccga gcgcgccggg gtgcccgcct tcctggagac   4800

ctccgcgccc cgcaacctcc ccttctacga gcggctcggc ttcaccgtca ccgccgacgt   4860

cgaggtgccc gaaggaccgc gcacctggtg catgacccgc aagcccggtg cctgagtcga   4920

caatcaacct ctggattaca aaatttgtga aagattgact ggtattctta actatgttgc   4980

tccttttacg ctatgtggat acgctgcttt aatgcctttg tatcatgcta ttgcttcccg   5040

tatggctttc attttctcct ccttgtataa atcctggttg ctgtctcttt atgaggagtt   5100

gtggcccgtt gtcaggcaac gtggcgtggt gtgcactgtg tttgctgacg caacccccac   5160

tggttggggc attgccacca cctgtcagct cctttccggg actttcgctt tccccctccc   5220

tattgccacg gcggaactca tcgccgcctg ccttgcccgc tgctggacag gggctcggct   5280

gttgggcact gacaattccg tggtgttgtc ggggaaatca tcgtcctttc cttggctgct   5340

cgcctgtgtt gccacctgga ttctgcgcgg gacgtccttc tgctacgtcc cttcggccct   5400

caatccagcg gaccttcctt cccgcggcct gctgccggct ctgcggcctc ttccgcgtct   5460

tcgccttcgc cctcagacga gtcggatctc cctttgggcc gcctccccgc ctggtacctt   5520
```

```
taagaccaat gacttacaag gcagctgtag atcttagcca ctttttaaaa gaaaaggggg   5580
gactggaagg gctaattcac tcccaacgaa aataagatct gctttttgct tgtactgggt   5640
ctctctggtt agaccagatc tgagcctggg agctctctgg ctaactaggg aacccactgc   5700
ttaagcctca ataaagcttg ccttgagtgc ttcaagtagt gtgtgcccgt ctgttgtgtg   5760
actctggtaa ctagagatcc ctcagaccct tttagtcagt gtggaaaatc tctagcagta   5820
gtagttcatg tcatcttatt attcagtatt tataacttgc aaagaaatga atatcagaga   5880
gtgagaggaa cttgtttatt gcagcttata atggttacaa ataaagcaat agcatcacaa   5940
atttcacaaa taaagcattt ttttcactgc attctagttg tggtttgtcc aaactcatca   6000
atgtatctta tcatgtctgg ctctagctat cccgccccta actccgccca gttccgccca   6060
ttctccgccc catggctgac taattttttt tatttatgca gaggccgagg ccgcctcggc   6120
ctctgagcta ttccagaagt agtgaggagg cttttttgga ggcctagact tttgcagaga   6180
cggcccaaat tcgtaatcat ggtcatagct gtttcctgtg tgaaattgtt atccgctcac   6240
aattccacac aacatacgag ccggaagcat aaagtgtaaa gcctggggtg cctaatgagt   6300
gagctaactc acattaattg cgttgcgctc actgcccgct ttccagtcgg gaaacctgtc   6360
gtgccagctg cattaatgaa tcggccaacg cgcggggaga ggcggtttgc gtattgggcg   6420
ctcttccgct tcctcgctca ctgactcgct gcgctcggtc gttcggctgc ggcgagcggt   6480
atcagctcac tcaaaggcgg taatacggtt atccacagaa tcaggggata acgcaggaaa   6540
gaacatgtga gcaaaaggcc agcaaaaggc caggaaccgt aaaaaggccg cgttgctggc   6600
gtttttccat aggctccgcc cccctgacga gcatcacaaa aatcgacgct caagtcagag   6660
gtggcgaaac ccgacaggac tataaagata ccaggcgttt ccccctggaa gctccctcgt   6720
gcgctctcct gttccgaccc tgccgcttac cggatacctg tccgcctttc tcccttcggg   6780
aagcgtggcg ctttctcata gctcacgctg taggtatctc agttcggtgt aggtcgttcg   6840
ctccaagctg ggctgtgtgc acgaaccccc cgttcagccc gaccgctgcg ccttatccgg   6900
taactatcgt cttgagtcca acccggtaag acacgactta tcgccactgg cagcagccac   6960
tggtaacagg attagcagag cgaggtatgt aggcggtgct acagagttct tgaagtggtg   7020
gcctaactac ggctacacta gaaggacagt atttggtatc tgcgctctgc tgaagccagt   7080
taccttcgga aaaagagttg gtagctcttg atccggcaaa caaaccaccg ctggtagcgg   7140
tggttttttt gtttgcaagc agcagattac gcgcagaaaa aaaggatctc aagaagatcc   7200
tttgatcttt tctacggggt ctgacgctca gtggaacgaa aactcacgtt aagggatttt   7260
ggtcatgaga ttatcaaaaa ggatcttcac ctagatcctt ttaaattaaa aatgaagttt   7320
taaatcaatc taaagtatat atgagtaaac ttggtctgac agttaccaat gcttaatcag   7380
tgaggcacct atctcagcga tctgtctatt tcgttcatcc atagttgcct gactccccgt   7440
cgtgtagata actacgatac gggagggctt accatctggc cccagtgctg caatgatacc   7500
gcgagaccca cgctcaccgg ctccagattt atcagcaata aaccagccag ccggaagggc   7560
cgagcgcaga agtggtcctg caactttatc cgcctccatc cagtctatta attgttgccg   7620
ggaagctaga gtaagtagtt cgccagttaa tagtttgcgc aacgttgttg ccattgctac   7680
aggcatcgtg gtgtcacgct cgtcgtttgg tatggcttca ttcagctccg gttcccaacg   7740
atcaaggcga gttacatgat cccccatgtt gtgcaaaaaa gcggttagct ccttcggtcc   7800
tccgatcgtt gtcagaagta agttggccgc agtgttatca ctcatggtta tggcagcact   7860
gcataattct cttactgtca tgccatccgt aagatgcttt tctgtgactg gtgagtactc   7920
```

```
aaccaagtca ttctgagaat agtgtatgcg gcgaccgagt tgctcttgcc cggcgtcaat   7980

acgggataat accgcgccac atagcagaac tttaaaagtg ctcatcattg gaaaacgttc   8040

ttcggggcga aaactctcaa ggatcttacc gctgttgaga tccagttcga tgtaacccac   8100

tcgtgcaccc aactgatctt cagcatcttt tactttcacc agcgtttctg ggtgagcaaa   8160

aacaggaagg caaaatgccg caaaaaaggg aataagggcg acacggaaat gttgaatact   8220

catactcttc ctttttcaat attattgaag catttatcag ggttattgtc tcatgagcgg   8280

atacatattt gaatgtattt agaaaaataa acaaataggg gttccgcgca catttccccg   8340

aaaagtgcca cctgacgtct aagaaaccat tattatcatg acattaacct ataaaaatag   8400

gcgtatcacg aggccctttc gtctcgcgcg tttcggtgat gacggtgaaa acctctgaca   8460

catgcagctc ccggagacgg tcacagcttg tctgtaagcg gatgccggga gcagacaagc   8520

ccgtcagggc gcgtcagcgg gtgttggcgg gtgtcggggc tggcttaact atgcggcatc   8580

agagcagatt gtactgagag tgcaccatat gcggtgtgaa ataccgcaca gatgcgtaag   8640

gagaaaatac cgcatcaggc gccattcgcc attcaggctg cgcaactgtt gggaagggcg   8700

atcggtgcgg gcctcttcgc tattacgcca gctggcgaaa gggggatgtg ctgcaaggcg   8760

attaagttgg gtaacgccag ggttttccca gtcacgacgt tgtaaaacga cggccagtgc   8820

caagctg                                                             8827
```

```
<210> SEQ ID NO 18
<211> LENGTH: 8797
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 18

acgcgtgtag tcttatgcaa tactcttgta gtcttgcaac atggtaacga tgagttagca     60

acatgcctta caaggagaga aaaagcaccg tgcatgccga ttggtggaag taaggtggta    120

cgatcgtgcc ttattaggaa ggcaacagac gggtctgaca tggattggac gaaccactga    180

attgccgcat tgcagagata ttgtatttaa gtgcctagct cgatacaata aacgggtctc    240

tctggttaga ccagatctga gcctgggagc tctctggcta actagggaac ccactgctta    300

agcctcaata aagcttgcct tgagtgcttc aagtagtgtg tgcccgtctg ttgtgtgact    360

ctggtaacta gagatccctc agaccctttt agtcagtgtg gaaaatctct agcagtggcg    420

cccgaacagg gacctgaaag cgaaagggaa accagagctc tctcgacgca ggactcggct    480

tgctgaagcg cgcacggcaa gaggcgaggg gcggcgactg gtgagtacgc caaaaatttt    540

gactagcgga ggctagaagg agagagatgg gtgcgagagc gtcagtatta agcgggggag    600

aattagatcg cgatgggaaa aaattcggtt aaggccaggg ggaaagaaaa aatataaatt    660

aaaacatata gtatgggcaa gcagggagct agaacgattc gcagttaatc ctggcctgtt    720

agaaacatca gaaggctgta gacaaatact gggacagcta caaccatccc ttcagacagg    780

atcagaagaa cttagatcat tatataatac agtagcaacc ctctattgtg tgcatcaaag    840

gatagagata aaagacacca aggaagcttt agacaagata gaggaagagc aaaacaaaag    900

taagaccacc gcacagcaag cggccactga tcttcagacc tggaggagga gatatgaggg    960

acaattggag aagtgaatta tataaatata aagtagtaaa aattgaacca ttaggagtag   1020

cacccaccaa ggcaaagaga agagtggtgc agagagaaaa aagagcagtg ggaataggag   1080
```

```
ctttgttcct tgggttcttg ggagcagcag gaagcactat gggcgcagcc tcaatgacgc   1140

tgacggtaca ggccagacaa ttattgtctg gtatagtgca gcagcagaac aatttgctga   1200

gggctattga ggcgcaacag catctgttgc aactcacagt ctggggcatc aagcagctcc   1260

aggcaagaat cctggctgtg gaaagatacc taaaggatca acagctcctg gggatttggg   1320

gttgctctgg aaaactcatt tgcaccactg ctgtgccttg gaatgctagt tggagtaata   1380

aatctctgga acagattgga atcacacgac ctggatggag tgggacagag aaattaacaa   1440

ttacacaagc ttaatacact ccttaattga agaatcgcaa aaccagcaag aaaagaatga   1500

acaagaatta ttggaattag ataaatgggc aagtttgtgg aattggttta acataacaaa   1560

ttggctgtgg tatataaaat tattcataat gatagtagga ggcttggtag gtttaagaat   1620

agtttttgct gtactttcta tagtgaatag agttaggcag ggatattcac cattatcgtt   1680

tcagacccac ctcccaaccc cgaggggacc cgacaggccc gaaggaatag aagaagaagg   1740

tggagagaga gacagagaca gatccattcg attagtgaac ggatctcgac ggtatcggtt   1800

aacttttaaa agaaaagggg ggattggggg gtacagtgca ggggaaagaa tagtagacat   1860

aatagcaaca gacatacaaa ctaaagaatt acaaaaacaa attacaaaat tcaaaatttt   1920

atcgatacta gtattatgcc cagtacatga ccttatggga ctttcctact tggcagtaca   1980

tctacgtatt agtcatcgct attaccatgg tgatgcggtt ttggcagtac atcaatgggc   2040

gtggatagcg gtttgactca cggggatttc caagtctcca ccccattgac gtcaatggga   2100

gtttgttttg gcaccaaaat caacgggact ttccaaaatg tcgtaacaac tccgccccat   2160

tgacgcaaat gggcggtagg cgtgtacggt gggaggttta tataagcaga gctcgtttag   2220

tgaaccgtca gatcgcctgg agacgccatc cacgctgttt tgacctccat agaagattct   2280

agagccgcca ccatgcttct cctggtgaca agccttctgc tctgtgagtt accacaccca   2340

gcattcctcc tgatcccaga catccagatg acacagacta catcctccct gtctgcctct   2400

ctgggagaca gagtcaccat cagttgcagg gcaagtcagg acattagtaa atatttaaat   2460

tggtatcagc agaaaccaga tggaactgtt aaactcctga tctaccatac atcaagatta   2520

cactcaggag tcccatcaag gttcagtggc agtgggtctg gaacagatta ttctctcacc   2580

attagcaacc tggagcaaga agatattgcc acttactttt gccaacaggg taatacgctt   2640

ccgtacacgt tcggaggggg gactaagttg gaaataacag gctccacctc tggatccggc   2700

aagcccggat ctggcgaggg atccaccaag ggcgaggtga aactgcagga gtcaggacct   2760

ggcctggtgg cgccctcaca gagcctgtcc gtcacatgca ctgtctcagg ggtctcatta   2820

cccgactatg gtgtaagctg gattcgccag cctccacgaa agggtctgga gtggctggga   2880

gtaatatggg gtagtgaaac cacatactat aattcagctc tcaaatccag actgaccatc   2940

atcaaggaca actccaagag ccaagttttc ttaaaaatga acagtctgca aactgatgac   3000

acagccattt actactgtgc caaacattat tactacggtg gtagctatgc tatggactac   3060

tggggtcaag gaacctcagt caccgtctcc tcagcggccg caggtggcgg cggttctggt   3120

ggcggcggtt ctggtggcgg cggttctctc gaggatggta atgaagaaat gggtggtatt   3180

acacagacac catataaagt ctccatctct ggaaccacag taatattgac atgccctcag   3240

tatcctggat ctgaaatact atggcaacac aatgataaaa acataggcgg tgatgaggat   3300

gataaaaaca taggcagtga tgaggatcac ctgtcactga aggaattttc agaattggag   3360

caaagtggtt attatgtctg ctaccccaga ggaagcaaac cagaagatgc gaacttttat   3420
```

```
ctctacctga gggcaagagt gtgtgagaac tgcatggaga tggatgtgat gtcggtggcc   3480
acaattgtca tagtggacat ctgcatcact gggggcttgc tgctgctggt ttactactgg   3540
agcaagaata gaaaggccaa ggccaagcct gtgacacgag gagcgggtgc tggcggcagg   3600
caaaggggac aaaacaagga gaggccacca cctgttccca acccagacta tgagcccatc   3660
cggaaaggcc agcgggacct gtattctggc ctgaatcaga gacgcatctg ataagaattc   3720
gatccgcggc cgcgaaggat ctgcgatcgc tccggtgccc gtcagtgggc agagcgcaca   3780
tcgcccacag tccccgagaa gttgggggga ggggtcggca attgaacggg tgcctagaga   3840
aggtggcgcg gggtaaactg ggaaagtgat gtcgtgtact ggctccgcct ttttcccgag   3900
ggtgggggag aaccgtatat aagtgcagta gtcgccgtga acgttctttt tcgcaacggg   3960
tttgccgcca gaacacagct gaagcttcga ggggctcgca tctctccttc acgcgcccgc   4020
cgccctacct gaggccgcca tccacgccgg ttgagtcgcg ttctgccgcc tcccgcctgt   4080
ggtgcctcct gaactgcgtc cgccgtctag gtaagtttaa agctcaggtc gagaccgggc   4140
ctttgtccgg cgctcccttg gagcctacct agactcagcc ggctctccac gctttgcctg   4200
accctgcttg ctcaactcta cgtctttgtt tcgttttctg ttctgcgccg ttacagatcc   4260
aagctgtgac cggcgcctac gctagatgac cgagtacaag cccacggtgc gcctcgccac   4320
ccgcgacgac gtccccaggg ccgtacgcac cctcgccgcc gcgttcgccg actaccccgc   4380
cacgcgccac accgtcgatc cggaccgcca catcgagcgg gtcaccgagc tgcaagaact   4440
cttcctcacg cgcgtcgggc tcgacatcgg caaggtgtgg gtcgcggacg acggcgccgc   4500
ggtggcggtc tggaccacgc cggagagcgt cgaagcgggg gcggtgttcg ccgagatcgg   4560
cccgcgcatg gccgagttga gcggttcccg gctggccgcg cagcaacaga tggaaggcct   4620
cctggcgccg caccggccca aggagcccgc gtggttcctg gccaccgtcg gcgtctcgcc   4680
cgaccaccag ggcaagggtc tgggcagcgc cgtcgtgctc cccggagtgg aggcggccga   4740
gcgcgccggg gtgcccgcct tcctggagac ctccgcgccc cgcaacctcc ccttctacga   4800
gcggctcggc ttcaccgtca ccgccgacgt cgaggtgccc gaaggaccgc gcacctggtg   4860
catgacccgc aagcccggtg cctgagtcga caatcaacct ctggattaca aaatttgtga   4920
aagattgact ggtattctta actatgttgc tccttttacg ctatgtggat acgctgcttt   4980
aatgcctttg tatcatgcta ttgcttcccg tatggctttc attttctcct ccttgtataa   5040
atcctggttg ctgtctcttt atgaggagtt gtggcccgtt gtcaggcaac gtggcgtggt   5100
gtgcactgtg tttgctgacg caacccccac tggttggggc attgccacca cctgtcagct   5160
cctttccggg actttcgctt tccccctccc tattgccacg gcggaactca tcgccgcctg   5220
ccttgcccgc tgctggacag gggctcggct gttgggcact gacaattccg tggtgttgtc   5280
ggggaaatca tcgtcctttc cttggctgct cgcctgtgtt gccacctgga ttctgcgcgg   5340
gacgtccttc tgctacgtcc cttcggccct caatccagcg gaccttcctt cccgcggcct   5400
gctgccggct ctgcggcctc ttccgcgtct tcgccttcgc cctcagacga gtcggatctc   5460
cctttgggcc gcctccccgc ctggtacctt taagaccaat gacttacaag gcagctgtag   5520
atcttagcca ctttttaaaa gaaaaggggg gactggaagg gctaattcac tcccaacgaa   5580
aataagatct gctttttgct tgtactgggt ctctctggtt agaccagatc tgagcctggg   5640
agctctctgg ctaactaggg aacccactgc ttaagcctca ataaagcttg ccttgagtgc   5700
ttcaagtagt gtgtgcccgt ctgttgtgtg actctggtaa ctagagatcc ctcagaccct   5760
tttagtcagt gtggaaaatc tctagcagta gtagttcatg tcatcttatt attcagtatt   5820
```

```
tataacttgc aaagaaatga atatcagaga gtgagaggaa cttgtttatt gcagcttata   5880
atggttacaa ataaagcaat agcatcacaa atttcacaaa taaagcattt ttttcactgc   5940
attctagttg tggtttgtcc aaactcatca atgtatctta tcatgtctgg ctctagctat   6000
cccgccccta actccgccca gttccgccca ttctccgccc catggctgac taattttttt   6060
tatttatgca gaggccgagg ccgcctcggc ctctgagcta ttccagaagt agtgaggagg   6120
cttttttgga ggcctagact tttgcagaga cggcccaaat tcgtaatcat ggtcatagct   6180
gtttcctgtg tgaaattgtt atccgctcac aattccacac aacatacgag ccggaagcat   6240
aaagtgtaaa gcctggggtg cctaatgagt gagctaactc acattaattg cgttgcgctc   6300
actgcccgct ttccagtcgg gaaacctgtc gtgccagctg cattaatgaa tcggccaacg   6360
cgcggggaga ggcggtttgc gtattgggcg ctcttccgct tcctcgctca ctgactcgct   6420
gcgctcggtc gttcggctgc ggcgagcggt atcagctcac tcaaaggcgg taatacggtt   6480
atccacagaa tcaggggata acgcaggaaa gaacatgtga gcaaaaggcc agcaaaaggc   6540
caggaaccgt aaaaaggccg cgttgctggc gtttttccat aggctccgcc cccctgacga   6600
gcatcacaaa aatcgacgct caagtcagag gtggcgaaac ccgacaggac tataaagata   6660
ccaggcgttt ccccctggaa gctccctcgt gcgctctcct gttccgaccc tgccgcttac   6720
cggatacctg tccgcctttc tcccttcggg aagcgtggcg ctttctcata gctcacgctg   6780
taggtatctc agttcggtgt aggtcgttcg ctccaagctg ggctgtgtgc acgaaccccc   6840
cgttcagccc gaccgctgcg ccttatccgg taactatcgt cttgagtcca acccggtaag   6900
acacgactta tcgccactgg cagcagccac tggtaacagg attagcagag cgaggtatgt   6960
aggcggtgct acagagttct tgaagtggtg gcctaactac ggctacacta gaaggacagt   7020
atttggtatc tgcgctctgc tgaagccagt taccttcgga aaaagagttg gtagctcttg   7080
atccggcaaa caaaccaccg ctggtagcgg tggttttttt gtttgcaagc agcagattac   7140
gcgcagaaaa aaaggatctc aagaagatcc tttgatcttt tctacggggt ctgacgctca   7200
gtggaacgaa aactcacgtt aagggatttt ggtcatgaga ttatcaaaaa ggatcttcac   7260
ctagatcctt ttaaattaaa aatgaagttt taaatcaatc taaagtatat atgagtaaac   7320
ttggtctgac agttaccaat gcttaatcag tgaggcacct atctcagcga tctgtctatt   7380
tcgttcatcc atagttgcct gactccccgt cgtgtagata actacgatac gggagggctt   7440
accatctggc cccagtgctg caatgatacc gcgagaccca cgctcaccgg ctccagattt   7500
atcagcaata aaccagccag ccggaagggc cgagcgcaga agtggtcctg caactttatc   7560
cgcctccatc cagtctatta attgttgccg ggaagctaga gtaagtagtt cgccagttaa   7620
tagtttgcgc aacgttgttg ccattgctac aggcatcgtg gtgtcacgct cgtcgtttgg   7680
tatggcttca ttcagctccg gttcccaacg atcaaggcga gttacatgat cccccatgtt   7740
gtgcaaaaaa gcggttagct ccttcggtcc tccgatcgtt gtcagaagta agttggccgc   7800
agtgttatca ctcatggtta tggcagcact gcataattct cttactgtca tgccatccgt   7860
aagatgcttt tctgtgactg gtgagtactc aaccaagtca ttctgagaat agtgtatgcg   7920
gcgaccgagt tgctcttgcc cggcgtcaat acgggataat accgcgccac atagcagaac   7980
tttaaaagtg ctcatcattg gaaaacgttc ttcggggcga aaactctcaa ggatcttacc   8040
gctgttgaga tccagttcga tgtaacccac tcgtgcaccc aactgatctt cagcatcttt   8100
tactttcacc agcgtttctg ggtgagcaaa aacaggaagg caaaatgccg caaaaaaggg   8160
```

```
aataagggcg acacggaaat gttgaatact catactcttc ctttttcaat attattgaag   8220

catttatcag ggttattgtc tcatgagcgg atacatattt gaatgtattt agaaaaataa   8280

acaaataggg gttccgcgca catttccccg aaaagtgcca cctgacgtct aagaaaccat   8340

tattatcatg acattaacct ataaaaatag gcgtatcacg aggccctttc gtctcgcgcg   8400

tttcggtgat gacggtgaaa acctctgaca catgcagctc ccggagacgg tcacagcttg   8460

tctgtaagcg gatgccggga gcagacaagc ccgtcagggc gcgtcagcgg gtgttggcgg   8520

gtgtcggggc tggcttaact atgcggcatc agagcagatt gtactgagag tgcaccatat   8580

gcggtgtgaa ataccgcaca gatgcgtaag gagaaaatac cgcatcaggc gccattcgcc   8640

attcaggctg cgcaactgtt gggaagggcg atcggtgcgg gcctcttcgc tattacgcca   8700

gctggcgaaa gggggatgtg ctgcaaggcg attaagttgg gtaacgccag ggttttccca   8760

gtcacgacgt tgtaaaacga cggccagtgc caagctg                           8797
```

```
<210> SEQ ID NO 19
<211> LENGTH: 8722
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 19

acgcgtgtag tcttatgcaa tactcttgta gtcttgcaac atggtaacga tgagttagca     60

acatgcctta caaggagaga aaaagcaccg tgcatgccga ttggtggaag taaggtggta    120

cgatcgtgcc ttattaggaa ggcaacagac gggtctgaca tggattggac gaaccactga    180

attgccgcat tgcagagata ttgtatttaa gtgcctagct cgatacaata aacgggtctc    240

tctggttaga ccagatctga gcctgggagc tctctggcta actagggaac ccactgctta    300

agcctcaata aagcttgcct tgagtgcttc aagtagtgtg tgcccgtctg ttgtgtgact    360

ctggtaacta gagatccctc agaccctttt agtcagtgtg gaaaatctct agcagtggcg    420

cccgaacagg gacctgaaag cgaaagggaa accagagctc tctcgacgca ggactcggct    480

tgctgaagcg cgcacggcaa gaggcgaggg gcggcgactg gtgagtacgc caaaaatttt    540

gactagcgga ggctagaagg agagagatgg gtgcgagagc gtcagtatta agcgggggag    600

aattagatcg cgatgggaaa aaattcggtt aaggccaggg ggaaagaaaa aatataaatt    660

aaaacatata gtatgggcaa gcagggagct agaacgattc gcagttaatc ctggcctgtt    720

agaaacatca gaaggctgta gacaaatact gggacagcta caaccatccc ttcagacagg    780

atcagaagaa cttagatcat tatataatac agtagcaacc ctctattgtg tgcatcaaag    840

gatagagata aaagacacca aggaagcttt agacaagata gaggaagagc aaaacaaaag    900

taagaccacc gcacagcaag cggccactga tcttcagacc tggaggagga gatatgaggg    960

acaattggag aagtgaatta tataaatata aagtagtaaa aattgaacca ttaggagtag   1020

cacccaccaa ggcaaagaga agagtggtgc agagagaaaa aagagcagtg ggaataggag   1080

ctttgttcct tgggttcttg ggagcagcag gaagcactat gggcgcagcc tcaatgacgc   1140

tgacggtaca ggccagacaa ttattgtctg gtatagtgca gcagcagaac aatttgctga   1200

gggctattga ggcgcaacag catctgttgc aactcacagt ctggggcatc aagcagctcc   1260

aggcaagaat cctggctgtg gaaagatacc taaaggatca acagctcctg gggatttggg   1320

gttgctctgg aaaactcatt tgcaccactg ctgtgccttg gaatgctagt tggagtaata   1380
```

```
aatctctgga acagattgga atcacacgac ctggatggag tgggacagag aaattaacaa   1440
ttacacaagc ttaatacact ccttaattga agaatcgcaa aaccagcaag aaaagaatga   1500
acaagaatta ttggaattag ataaatgggc aagtttgtgg aattggttta acataacaaa   1560
ttggctgtgg tatataaaat tattcataat gatagtagga ggcttggtag gtttaagaat   1620
agtttttgct gtactttcta tagtgaatag agttaggcag ggatattcac cattatcgtt   1680
tcagacccac ctcccaaccc cgaggggacc cgacaggccc gaaggaatag aagaagaagg   1740
tggagagaga gacagagaca gatccattcg attagtgaac ggatctcgac ggtatcggtt   1800
aacttttaaa agaaaagggg ggattggggg gtacagtgca ggggaaagaa tagtagacat   1860
aatagcaaca gacatacaaa ctaaagaatt acaaaaacaa attacaaaat tcaaaatttt   1920
atcgatacta gtattatgcc cagtacatga ccttatggga ctttcctact tggcagtaca   1980
tctacgtatt agtcatcgct attaccatgg tgatgcggtt ttggcagtac atcaatgggc   2040
gtggatagcg gtttgactca cggggatttc caagtctcca ccccattgac gtcaatggga   2100
gtttgttttg gcaccaaaat caacgggact ttccaaaatg tcgtaacaac tccgccccat   2160
tgacgcaaat gggcggtagg cgtgtacggt gggaggttta tataagcaga gctcgtttag   2220
tgaaccgtca gatcgcctgg agacgccatc cacgctgttt tgacctccat agaagattct   2280
agagccgcca ccatgcttct cctggtgaca agccttctgc tctgtgagtt accacaccca   2340
gcattcctcc tgatcccaga catccagatg acacagacta catcctccct gtctgcctct   2400
ctgggagaca gagtcaccat cagttgcagg gcaagtcagg acattagtaa atatttaaat   2460
tggtatcagc agaaaccaga tggaactgtt aaactcctga tctaccatac atcaagatta   2520
cactcaggag tcccatcaag gttcagtggc agtgggtctg gaacagatta ttctctcacc   2580
attagcaacc tggagcaaga agatattgcc acttactttt gccaacaggg taatacgctt   2640
ccgtacacgt tcggaggggg gactaagttg gaaataacag gctccacctc tggatccggc   2700
aagcccggat ctggcgaggg atccaccaag ggcgaggtga aactgcagga gtcaggacct   2760
ggcctggtgg cgccctcaca gagcctgtcc gtcacatgca ctgtctcagg ggtctcatta   2820
cccgactatg gtgtaagctg gattcgccag cctccacgaa agggtctgga gtggctggga   2880
gtaatatggg gtagtgaaac cacatactat aattcagctc tcaaatccag actgaccatc   2940
atcaaggaca actccaagag ccaagttttc ttaaaaatga acagtctgca aactgatgac   3000
acagccattt actactgtgc caaacattat tactacggtg gtagctatgc tatggactac   3060
tggggtcaag gaacctcagt caccgtctcc tcagcggccg caggtggcgg cggttctggt   3120
ggcggcggtt ctggtggcgg cggttctctc gagcagtcaa tcaaaggaaa ccacttggtt   3180
aaggtgtatg actatcaaga agatggttcg gtacttctga cttgtgatgc agaagccaaa   3240
aatatcacat ggtttaaaga tgggaagatg atcggcttcc taactgaaga taaaaaaaaa   3300
tggaatctgg gaagtaatgc caaggaccca cgagggatgt atcagtgtaa aggatcacag   3360
aacaagtcaa aaccactcca agtgtattac agaatgtgtc agaactgcat tgaactaaat   3420
gcagccacca tatctggctt tctctttgct gaaatcgtca gcattttcgt ccttgctgtt   3480
ggggtctact tcattgctgg acaggatgga gttcgccagt cgagagcttc agacaagcag   3540
actctgttgc ccaatgacca gctctaccag cccctcaagg atcgagaaga tgaccagtac   3600
agccaccttc aaggaaacca gttgaggagg aattgataag aattcgatcc gcggccgcga   3660
aggatctgcg atcgctccgg tgcccgtcag tgggcagagc gcacatcgcc cacagtcccc   3720
gagaagttgg ggggaggggt cggcaattga acgggtgcct agagaaggtg gcgcggggta   3780
```

```
aactgggaaa gtgatgtcgt gtactggctc cgcctttttc ccgagggtgg gggagaaccg   3840
tatataagtg cagtagtcgc cgtgaacgtt ctttttcgca acgggtttgc cgccagaaca   3900
cagctgaagc ttcgaggggc tcgcatctct ccttcacgcg cccgccgccc tacctgaggc   3960
cgccatccac gccggttgag tcgcgttctg ccgcctcccg cctgtggtgc ctcctgaact   4020
gcgtccgccg tctaggtaag tttaaagctc aggtcgagac cgggcctttg tccggcgctc   4080
ccttggagcc tacctagact cagccggctc tccacgcttt gcctgaccct gcttgctcaa   4140
ctctacgtct ttgtttcgtt ttctgttctg cgccgttaca gatccaagct gtgaccggcg   4200
cctacgctag atgaccgagt acaagcccac ggtgcgcctc gccacccgcg acgacgtccc   4260
cagggccgta cgcaccctcg ccgccgcgtt cgccgactac cccgccacgc gccacaccgt   4320
cgatccggac cgccacatcg agcgggtcac cgagctgcaa gaactcttcc tcacgcgcgt   4380
cgggctcgac atcggcaagg tgtgggtcgc ggacgacggc gccgcggtgg cggtctggac   4440
cacgccggag agcgtcgaag cgggggcggt gttcgccgag atcggcccgc gcatggccga   4500
gttgagcggt tcccggctgg ccgcgcagca acagatggaa ggcctcctgg cgccgcaccg   4560
gcccaaggag cccgcgtggt tcctggccac cgtcggcgtc tcgcccgacc accagggcaa   4620
gggtctgggc agcgccgtcg tgctccccgg agtggaggcg gccgagcgcg ccggggtgcc   4680
cgccttcctg gagacctccg cgccccgcaa cctccccttc tacgagcggc tcggcttcac   4740
cgtcaccgcc gacgtcgagg tgcccgaagg accgcgcacc tggtgcatga cccgcaagcc   4800
cggtgcctga gtcgacaatc aacctctgga ttacaaaatt tgtgaaagat tgactggtat   4860
tcttaactat gttgctcctt ttacgctatg tggatacgct gctttaatgc ctttgtatca   4920
tgctattgct tcccgtatgg ctttcatttt ctcctccttg tataaatcct ggttgctgtc   4980
tctttatgag gagttgtggc ccgttgtcag gcaacgtggc gtggtgtgca ctgtgtttgc   5040
tgacgcaacc cccactggtt ggggcattgc caccacctgt cagctccttt ccgggacttt   5100
cgctttcccc ctccctattg ccacggcgga actcatcgcc gcctgccttg cccgctgctg   5160
gacaggggct cggctgttgg gcactgacaa ttccgtggtg ttgtcgggga aatcatcgtc   5220
ctttccttgg ctgctcgcct gtgttgccac ctggattctg cgcgggacgt ccttctgcta   5280
cgtcccttcg gccctcaatc cagcggacct tccttcccgc ggcctgctgc cggctctgcg   5340
gcctcttccg cgtcttcgcc ttcgccctca gacgagtcgg atctcccttt gggccgcctc   5400
cccgcctggt acctttaaga ccaatgactt acaaggcagc tgtagatctt agccactttt   5460
taaaagaaaa ggggggactg gaagggctaa ttcactccca acgaaaataa gatctgcttt   5520
ttgcttgtac tgggtctctc tggttagacc agatctgagc ctgggagctc tctggctaac   5580
tagggaaccc actgcttaag cctcaataaa gcttgccttg agtgcttcaa gtagtgtgtg   5640
cccgtctgtt gtgtgactct ggtaactaga gatccctcag acccttttag tcagtgtgga   5700
aaatctctag cagtagtagt tcatgtcatc ttattattca gtatttataa cttgcaaaga   5760
aatgaatatc agagagtgag aggaacttgt ttattgcagc ttataatggt tacaaataaa   5820
gcaatagcat cacaaatttc acaaataaag cattttttc actgcattct agttgtggtt    5880
tgtccaaact catcaatgta tcttatcatg tctggctcta gctatcccgc ccctaactcc   5940
gcccagttcc gcccattctc cgccccatgg ctgactaatt ttttttattt atgcagaggc   6000
cgaggccgcc tcggcctctg agctattcca gaagtagtga ggaggctttt ttggaggcct   6060
agacttttgc agagacggcc caaattcgta atcatggtca tagctgtttc ctgtgtgaaa   6120
```

-continued

```
ttgttatccg ctcacaattc cacacaacat acgagccgga agcataaagt gtaaagcctg   6180
gggtgcctaa tgagtgagct aactcacatt aattgcgttg cgctcactgc ccgctttcca   6240
gtcgggaaac ctgtcgtgcc agctgcatta atgaatcggc caacgcgcgg ggagaggcgg   6300
tttgcgtatt gggcgctctt ccgcttcctc gctcactgac tcgctgcgct cggtcgttcg   6360
gctgcggcga gcggtatcag ctcactcaaa ggcggtaata cggttatcca cagaatcagg   6420
ggataacgca ggaaagaaca tgtgagcaaa aggccagcaa aaggccagga accgtaaaaa   6480
ggccgcgttg ctggcgtttt tccataggct ccgcccccct gacgagcatc acaaaaatcg   6540
acgctcaagt cagaggtggc gaaacccgac aggactataa agataccagg cgtttccccc   6600
tggaagctcc ctcgtgcgct ctcctgttcc gaccctgccg cttaccggat acctgtccgc   6660
ctttctccct tcgggaagcg tggcgctttc tcatagctca cgctgtaggt atctcagttc   6720
ggtgtaggtc gttcgctcca agctgggctg tgtgcacgaa ccccccgttc agcccgaccg   6780
ctgcgcctta tccggtaact atcgtcttga gtccaacccg gtaagacacg acttatcgcc   6840
actggcagca gccactggta acaggattag cagagcgagg tatgtaggcg gtgctacaga   6900
gttcttgaag tggtggccta actacggcta cactagaagg acagtatttg gtatctgcgc   6960
tctgctgaag ccagttacct tcggaaaaag agttggtagc tcttgatccg gcaaacaaac   7020
caccgctggt agcggtggtt tttttgtttg caagcagcag attacgcgca gaaaaaaagg   7080
atctcaagaa gatcctttga tcttttctac ggggtctgac gctcagtgga acgaaaactc   7140
acgttaaggg attttggtca tgagattatc aaaaaggatc ttcacctaga tccttttaaa   7200
ttaaaaatga agttttaaat caatctaaag tatatatgag taaacttggt ctgacagtta   7260
ccaatgctta atcagtgagg cacctatctc agcgatctgt ctatttcgtt catccatagt   7320
tgcctgactc cccgtcgtgt agataactac gatacgggag ggcttaccat ctggccccag   7380
tgctgcaatg ataccgcgag acccacgctc accggctcca gatttatcag caataaacca   7440
gccagccgga agggccgagc gcagaagtgg tcctgcaact ttatccgcct ccatccagtc   7500
tattaattgt tgccgggaag ctagagtaag tagttcgcca gttaatagtt tgcgcaacgt   7560
tgttgccatt gctacaggca tcgtggtgtc acgctcgtcg tttggtatgg cttcattcag   7620
ctccggttcc caacgatcaa ggcgagttac atgatccccc atgttgtgca aaaaagcggt   7680
tagctccttc ggtcctccga tcgttgtcag aagtaagttg gccgcagtgt tatcactcat   7740
ggttatggca gcactgcata attctcttac tgtcatgcca tccgtaagat gcttttctgt   7800
gactggtgag tactcaacca agtcattctg agaatagtgt atgcggcgac cgagttgctc   7860
ttgcccggcg tcaatacggg ataataccgc gccacatagc agaactttaa aagtgctcat   7920
cattggaaaa cgttcttcgg ggcgaaaact ctcaaggatc ttaccgctgt tgagatccag   7980
ttcgatgtaa cccactcgtg cacccaactg atcttcagca tcttttactt tcaccagcgt   8040
ttctgggtga gcaaaaacag gaaggcaaaa tgccgcaaaa aagggaataa gggcgacacg   8100
gaaatgttga atactcatac tcttcctttt tcaatattat tgaagcattt atcagggtta   8160
ttgtctcatg agcggataca tatttgaatg tatttagaaa aataaacaaa taggggttcc   8220
gcgcacattt ccccgaaaag tgccacctga cgtctaagaa accattatta tcatgacatt   8280
aacctataaa aataggcgta tcacgaggcc ctttcgtctc gcgcgtttcg gtgatgacgg   8340
tgaaaacctc tgacacatgc agctcccgga gacggtcaca gcttgtctgt aagcggatgc   8400
cgggagcaga caagcccgtc agggcgcgtc agcgggtgtt ggcgggtgtc ggggctggct   8460
taactatgcg gcatcagagc agattgtact gagagtgcac catatgcggt gtgaaatacc   8520
```

```
gcacagatgc gtaaggagaa aataccgcat caggcgccat tcgccattca ggctgcgcaa   8580
ctgttgggaa gggcgatcgg tgcgggcctc ttcgctatta cgccagctgg cgaaaggggg   8640
atgtgctgca aggcgattaa gttgggtaac gccagggttt tcccagtcac gacgttgtaa   8700
aacgacggcc agtgccaagc tg                                            8722
```

```
<210> SEQ ID NO 20
<211> LENGTH: 8692
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 20

acgcgtgtag tcttatgcaa tactcttgta gtcttgcaac atggtaacga tgagttagca     60
acatgcctta caaggagaga aaaagcaccg tgcatgccga ttggtggaag taaggtggta    120
cgatcgtgcc ttattaggaa ggcaacagac gggtctgaca tggattggac gaaccactga    180
attgccgcat tgcagagata ttgtatttaa gtgcctagct cgatacaata aacgggtctc    240
tctggttaga ccagatctga gcctgggagc tctctggcta actagggaac ccactgctta    300
agcctcaata aagcttgcct tgagtgcttc aagtagtgtg tgcccgtctg ttgtgtgact    360
ctggtaacta gagatccctc agaccctttt agtcagtgtg gaaaatctct agcagtggcg    420
cccgaacagg gacctgaaag cgaaagggaa accagagctc tctcgacgca ggactcggct    480
tgctgaagcg cgcacggcaa gaggcgaggg gcggcgactg gtgagtacgc caaaaatttt    540
gactagcgga ggctagaagg agagagatgg gtgcgagagc gtcagtatta agcgggggag    600
aattagatcg cgatgggaaa aaattcggtt aaggccaggg ggaaagaaaa aatataaatt    660
aaaacatata gtatgggcaa gcagggagct agaacgattc gcagttaatc ctggcctgtt    720
agaaacatca gaaggctgta gacaaatact gggacagcta caaccatccc ttcagacagg    780
atcagaagaa cttagatcat tatataatac agtagcaacc ctctattgtg tgcatcaaag    840
gatagagata aaagacacca aggaagcttt agacaagata gaggaagagc aaaacaaaag    900
taagaccacc gcacagcaag cggccactga tcttcagacc tggaggagga gatatgaggg    960
acaattggag aagtgaatta tataaatata aagtagtaaa aattgaacca ttaggagtag   1020
cacccaccaa ggcaaagaga agagtggtgc agagagaaaa aagagcagtg ggaataggag   1080
ctttgttcct tgggttcttg ggagcagcag gaagcactat gggcgcagcc tcaatgacgc   1140
tgacggtaca ggccagacaa ttattgtctg gtatagtgca gcagcagaac aatttgctga   1200
gggctattga ggcgcaacag catctgttgc aactcacagt ctggggcatc aagcagctcc   1260
aggcaagaat cctggctgtg gaaagatacc taaaggatca acagctcctg gggatttggg   1320
gttgctctgg aaaactcatt tgcaccactg ctgtgccttg gaatgctagt tggagtaata   1380
aatctctgga acagattgga atcacacgac ctggatggag tgggacagag aaattaacaa   1440
ttacacaagc ttaatacact ccttaattga agaatcgcaa aaccagcaag aaaagaatga   1500
acaagaatta ttggaattag ataaatgggc aagtttgtgg aattggttta acataacaaa   1560
ttggctgtgg tatataaaat tattcataat gatagtagga ggcttggtag gtttaagaat   1620
agtttttgct gtactttcta tagtgaatag agttaggcag ggatattcac cattatcgtt   1680
tcagacccac ctcccaaccc cgaggggacc cgacaggccc gaaggaatag aagaagaagg   1740
tggagagaga gacagagaca gatccattcg attagtgaac ggatctcgac ggtatcggtt   1800
```

```
aacttttaaa agaaaagggg ggattggggg gtacagtgca ggggaaagaa tagtagacat   1860
aatagcaaca gacatacaaa ctaaagaatt acaaaaacaa attacaaaat tcaaaatttt   1920
atcgatacta gtattatgcc cagtacatga ccttatggga ctttcctact tggcagtaca   1980
tctacgtatt agtcatcgct attaccatgg tgatgcggtt ttggcagtac atcaatgggc   2040
gtggatagcg gtttgactca cggggatttc caagtctcca ccccattgac gtcaatggga   2100
gtttgttttg gcaccaaaat caacgggact ttccaaaatg tcgtaacaac tccgccccat   2160
tgacgcaaat gggcggtagg cgtgtacggt gggaggttta tataagcaga gctcgtttag   2220
tgaaccgtca gatcgcctgg agacgccatc cacgctgttt tgacctccat agaagattct   2280
agagccgcca ccatgcttct cctggtgaca agccttctgc tctgtgagtt accacaccca   2340
gcattcctcc tgatcccaga catccagatg acacagacta catcctccct gtctgcctct   2400
ctgggagaca gagtcaccat cagttgcagg gcaagtcagg acattagtaa atatttaaat   2460
tggtatcagc agaaaccaga tggaactgtt aaactcctga tctaccatac atcaagatta   2520
cactcaggag tcccatcaag gttcagtggc agtgggtctg gaacagatta ttctctcacc   2580
attagcaacc tggagcaaga agatattgcc acttactttt gccaacaggg taatacgctt   2640
ccgtacacgt tcggaggggg gactaagttg gaaataacag gctccacctc tggatccggc   2700
aagcccggat ctggcgaggg atccaccaag ggcgaggtga aactgcagga gtcaggacct   2760
ggcctggtgg cgccctcaca gagcctgtcc gtcacatgca ctgtctcagg ggtctcatta   2820
cccgactatg gtgtaagctg gattcgccag cctccacgaa agggtctgga gtggctggga   2880
gtaatatggg gtagtgaaac cacatactat aattcagctc tcaaatccag actgaccatc   2940
atcaaggaca actccaagag ccaagttttc ttaaaaatga acagtctgca aactgatgac   3000
acagccattt actactgtgc caaacattat tactacggtg gtagctatgc tatggactac   3060
tggggtcaag gaacctcagt caccgtctcc tcagcggccg caggtggcgg cggttctggt   3120
ggcggcggtt ctggtggcgg cggttctctc gagttcaaga tacctataga ggaacttgag   3180
gacagagtgt ttgtgaattg caataccagc atcacatggg tagagggaac ggtgggaaca   3240
ctgctctcag acattacaag actggacctg ggaaaacgca tcctggaccc acgaggaata   3300
tataggtgta atgggacaga tatatacaag gacaaagaat ctaccgtgca agttcattat   3360
cgaatgtgcc agagctgtgt ggagctggat ccagccaccg tggctggcat cattgtcact   3420
gatgtcattg ccactctgct ccttgctttg ggagtcttct gctttgctgg acatgagact   3480
ggaaggctgt ctggggctgc cgacacacaa gctctgttga ggaatgacca ggtctatcag   3540
cccctccgag atcgagatga tgctcagtac agccaccttg gaggaaactg ggctcggaac   3600
aagtgataag aattcgatcc gcggccgcga aggatctgcg atcgctccgg tgcccgtcag   3660
tgggcagagc gcacatcgcc cacagtcccc gagaagttgg ggggaggggt cggcaattga   3720
acgggtgcct agagaaggtg gcgcggggta aactgggaaa gtgatgtcgt gtactggctc   3780
cgcctttttc ccgagggtgg gggagaaccg tatataagtg cagtagtcgc cgtgaacgtt   3840
ctttttcgca acgggtttgc cgccagaaca cagctgaagc ttcgaggggc tcgcatctct   3900
ccttcacgcg cccgccgccc tacctgaggc cgccatccac gccggttgag tcgcgttctg   3960
ccgcctcccg cctgtggtgc ctcctgaact gcgtccgccg tctaggtaag tttaaagctc   4020
aggtcgagac cgggcctttg tccggcgctc ccttggagcc tacctagact cagccggctc   4080
tccacgcttt gcctgaccct gcttgctcaa ctctacgtct ttgtttcgtt ttctgttctg   4140
```

-continued

```
cgccgttaca gatccaagct gtgaccggcg cctacgctag atgaccgagt acaagcccac   4200
ggtgcgcctc gccacccgcg acgacgtccc cagggccgta cgcaccctcg ccgccgcgtt   4260
cgccgactac cccgccacgc gccacaccgt cgatccggac cgccacatcg agcgggtcac   4320
cgagctgcaa gaactcttcc tcacgcgcgt cgggctcgac atcggcaagg tgtgggtcgc   4380
ggacgacggc gccgcggtgg cggtctggac cacgccggag agcgtcgaag cgggggcggt   4440
gttcgccgag atcggcccgc gcatggccga gttgagcggt tcccggctgg ccgcgcagca   4500
acagatggaa ggcctcctgg cgccgcaccg gcccaaggag cccgcgtggt tcctggccac   4560
cgtcggcgtc tcgcccgacc accagggcaa gggtctgggc agcgccgtcg tgctccccgg   4620
agtggaggcg gccgagcgcg ccggggtgcc cgccttcctg gagacctccg cgccccgcaa   4680
cctccccttc tacgagcggc tcggcttcac cgtcaccgcc gacgtcgagg tgcccgaagg   4740
accgcgcacc tggtgcatga cccgcaagcc cggtgcctga gtcgacaatc aacctctgga   4800
ttacaaaatt tgtgaaagat tgactggtat tcttaactat gttgctcctt ttacgctatg   4860
tggatacgct gctttaatgc ctttgtatca tgctattgct tcccgtatgg ctttcatttt   4920
ctcctccttg tataaatcct ggttgctgtc tctttatgag gagttgtggc ccgttgtcag   4980
gcaacgtggc gtggtgtgca ctgtgtttgc tgacgcaacc cccactggtt ggggcattgc   5040
caccacctgt cagctccttt ccgggacttt cgctttcccc ctccctattg ccacggcgga   5100
actcatcgcc gcctgccttg cccgctgctg gacaggggct cggctgttgg gcactgacaa   5160
ttccgtggtg ttgtcgggga aatcatcgtc ctttccttgg ctgctcgcct gtgttgccac   5220
ctggattctg cgcgggacgt ccttctgcta cgtcccttcg gccctcaatc cagcggacct   5280
tccttcccgc ggcctgctgc cggctctgcg gcctcttccg cgtcttcgcc ttcgccctca   5340
gacgagtcgg atctcccttt gggccgcctc cccgcctggt acctttaaga ccaatgactt   5400
acaaggcagc tgtagatctt agccactttt taaaagaaaa ggggggactg gaagggctaa   5460
ttcactccca acgaaaataa gatctgcttt ttgcttgtac tgggtctctc tggttagacc   5520
agatctgagc ctgggagctc tctggctaac tagggaaccc actgcttaag cctcaataaa   5580
gcttgccttg agtgcttcaa gtagtgtgtg cccgtctgtt gtgtgactct ggtaactaga   5640
gatccctcag acccttttag tcagtgtgga aaatctctag cagtagtagt tcatgtcatc   5700
ttattattca gtatttataa cttgcaaaga aatgaatatc agagagtgag aggaacttgt   5760
ttattgcagc ttataatggt tacaaataaa gcaatagcat cacaaatttc acaaataaag   5820
catttttttc actgcattct agttgtggtt tgtccaaact catcaatgta tcttatcatg   5880
tctggctcta gctatcccgc ccctaactcc gcccagttcc gcccattctc cgccccatgg   5940
ctgactaatt ttttttattt atgcagaggc cgaggccgcc tcggcctctg agctattcca   6000
gaagtagtga ggaggctttt ttggaggcct agacttttgc agagacggcc caaattcgta   6060
atcatggtca tagctgtttc ctgtgtgaaa ttgttatccg ctcacaattc cacacaacat   6120
acgagccgga agcataaagt gtaaagcctg gggtgcctaa tgagtgagct aactcacatt   6180
aattgcgttg cgctcactgc ccgctttcca gtcgggaaac ctgtcgtgcc agctgcatta   6240
atgaatcggc caacgcgcgg ggagaggcgg tttgcgtatt gggcgctctt ccgcttcctc   6300
gctcactgac tcgctgcgct cggtcgttcg gctgcggcga gcggtatcag ctcactcaaa   6360
ggcggtaata cggttatcca cagaatcagg ggataacgca ggaaagaaca tgtgagcaaa   6420
aggccagcaa aaggccagga accgtaaaaa ggccgcgttg ctggcgtttt tccataggct   6480
ccgcccccct gacgagcatc acaaaaatcg acgctcaagt cagaggtggc gaaacccgac   6540
```

```
aggactataa agataccagg cgtttccccc tggaagctcc ctcgtgcgct ctcctgttcc   6600
gaccctgccg cttaccggat acctgtccgc ctttctccct tcgggaagcg tggcgctttc   6660
tcatagctca cgctgtaggt atctcagttc ggtgtaggtc gttcgctcca agctgggctg   6720
tgtgcacgaa ccccccgttc agcccgaccg ctgcgcctta tccggtaact atcgtcttga   6780
gtccaacccg gtaagacacg acttatcgcc actggcagca gccactggta acaggattag   6840
cagagcgagg tatgtaggcg gtgctacaga gttcttgaag tggtggccta actacggcta   6900
cactagaagg acagtatttg gtatctgcgc tctgctgaag ccagttacct tcggaaaaag   6960
agttggtagc tcttgatccg gcaaacaaac caccgctggt agcggtggtt tttttgtttg   7020
caagcagcag attacgcgca gaaaaaaagg atctcaagaa gatcctttga tcttttctac   7080
ggggtctgac gctcagtgga acgaaaactc acgttaaggg attttggtca tgagattatc   7140
aaaaaggatc ttcacctaga tccttttaaa ttaaaaatga agttttaaat caatctaaag   7200
tatatatgag taaacttggt ctgacagtta ccaatgctta atcagtgagg cacctatctc   7260
agcgatctgt ctatttcgtt catccatagt tgcctgactc cccgtcgtgt agataactac   7320
gatacgggag ggcttaccat ctggccccag tgctgcaatg ataccgcgag acccacgctc   7380
accggctcca gatttatcag caataaacca gccagccgga agggccgagc gcagaagtgg   7440
tcctgcaact ttatccgcct ccatccagtc tattaattgt tgccgggaag ctagagtaag   7500
tagttcgcca gttaatagtt tgcgcaacgt tgttgccatt gctacaggca tcgtggtgtc   7560
acgctcgtcg tttggtatgg cttcattcag ctccggttcc caacgatcaa ggcgagttac   7620
atgatccccc atgttgtgca aaaaagcggt tagctccttc ggtcctccga tcgttgtcag   7680
aagtaagttg gccgcagtgt tatcactcat ggttatggca gcactgcata attctcttac   7740
tgtcatgcca tccgtaagat gcttttctgt gactggtgag tactcaacca agtcattctg   7800
agaatagtgt atgcggcgac cgagttgctc ttgcccggcg tcaatacggg ataataccgc   7860
gccacatagc agaactttaa aagtgctcat cattggaaaa cgttcttcgg ggcgaaaact   7920
ctcaaggatc ttaccgctgt tgagatccag ttcgatgtaa cccactcgtg cacccaactg   7980
atcttcagca tcttttactt tcaccagcgt ttctgggtga gcaaaaacag gaaggcaaaa   8040
tgccgcaaaa aagggaataa gggcgacacg gaaatgttga atactcatac tcttcctttt   8100
tcaatattat tgaagcattt atcagggtta ttgtctcatg agcggataca tatttgaatg   8160
tatttagaaa aataaacaaa taggggttcc gcgcacattt ccccgaaaag tgccacctga   8220
cgtctaagaa accattatta tcatgacatt aacctataaa aataggcgta tcacgaggcc   8280
ctttcgtctc gcgcgtttcg gtgatgacgg tgaaaacctc tgacacatgc agctcccgga   8340
gacggtcaca gcttgtctgt aagcggatgc cgggagcaga caagcccgtc agggcgcgtc   8400
agcgggtgtt ggcgggtgtc ggggctggct taactatgcg gcatcagagc agattgtact   8460
gagagtgcac catatgcggt gtgaaatacc gcacagatgc gtaaggagaa aataccgcat   8520
caggcgccat tcgccattca ggctgcgcaa ctgttgggaa gggcgatcgg tgcgggcctc   8580
ttcgctatta cgccagctgg cgaaaggggg atgtgctgca aggcgattaa gttgggtaac   8640
gccagggttt tcccagtcac gacgttgtaa aacgacggcc agtgccaagc tg           8692
```

<210> SEQ ID NO 21
<211> LENGTH: 9133
<212> TYPE: DNA
<213> ORGANISM: Artificial Sequence
<220> FEATURE:

<223> OTHER INFORMATION: Description of Artificial Sequence: Synthetic polynucleotide

<400> SEQUENCE: 21

```
acgcgtgtag tcttatgcaa tactcttgta gtcttgcaac atggtaacga tgagttagca     60
acatgcctta caaggagaga aaaagcaccg tgcatgccga ttggtggaag taaggtggta    120
cgatcgtgcc ttattaggaa ggcaacagac gggtctgaca tggattggac gaaccactga    180
attgccgcat tgcagagata ttgtatttaa gtgcctagct cgatacaata aacgggtctc    240
tctggttaga ccagatctga gcctgggagc tctctggcta actagggaac ccactgctta    300
agcctcaata aagcttgcct tgagtgcttc aagtagtgtg tgcccgtctg ttgtgtgact    360
ctggtaacta gagatccctc agaccctttt agtcagtgtg gaaaatctct agcagtggcg    420
cccgaacagg gacctgaaag cgaaagggaa accagagctc tctcgacgca ggactcggct    480
tgctgaagcg cgcacggcaa gaggcgaggg gcggcgactg gtgagtacgc caaaaatttt    540
gactagcgga ggctagaagg agagagatgg gtgcgagagc gtcagtatta agcgggggag    600
aattagatcg cgatgggaaa aaattcggtt aaggccaggg ggaaagaaaa aatataaatt    660
aaaacatata gtatgggcaa gcagggagct agaacgattc gcagttaatc ctggcctgtt    720
agaaacatca gaaggctgta gacaaatact gggacagcta caaccatccc ttcagacagg    780
atcagaagaa cttagatcat tatataatac agtagcaacc ctctattgtg tgcatcaaag    840
gatagagata aaagacacca aggaagcttt agacaagata gaggaagagc aaaacaaaag    900
taagaccacc gcacagcaag cggccactga tcttcagacc tggaggagga gatatgaggg    960
acaattggag aagtgaatta tataaatata aagtagtaaa aattgaacca ttaggagtag   1020
cacccaccaa ggcaaagaga agagtggtgc agagagaaaa aagagcagtg ggaataggag   1080
ctttgttcct tgggttcttg ggagcagcag gaagcactat gggcgcagcc tcaatgacgc   1140
tgacggtaca ggccagacaa ttattgtctg gtatagtgca gcagcagaac aatttgctga   1200
gggctattga ggcgcaacag catctgttgc aactcacagt ctggggcatc aagcagctcc   1260
aggcaagaat cctggctgtg gaaagatacc taaaggatca acagctcctg gggatttggg   1320
gttgctctgg aaaactcatt tgcaccactg ctgtgccttg gaatgctagt tggagtaata   1380
aatctctgga acagattgga atcacacgac ctggatggag tgggacagag aaattaacaa   1440
ttacacaagc ttaatacact ccttaattga agaatcgcaa aaccagcaag aaaagaatga   1500
acaagaatta ttggaattag ataaatgggc aagtttgtgg aattggttta acataacaaa   1560
ttggctgtgg tatataaaat tattcataat gatagtagga ggcttggtag gtttaagaat   1620
agtttttgct gtactttcta tagtgaatag agttaggcag ggatattcac cattatcgtt   1680
tcagacccac ctcccaaccc cgaggggacc cgacaggccc gaaggaatag aagaagaagg   1740
tggagagaga gacagagaca gatccattcg attagtgaac ggatctcgac ggtatcggtt   1800
aacttttaaa agaaaagggg ggattggggg gtacagtgca ggggaaagaa tagtagacat   1860
aatagcaaca gacatacaaa ctaaagaatt acaaaaacaa attacaaaat tcaaaatttt   1920
atcgatacta gtattatgcc cagtacatga ccttatggga ctttcctact tggcagtaca   1980
tctacgtatt agtcatcgct attaccatgg tgatgcggtt ttggcagtac atcaatgggc   2040
gtggatagcg gtttgactca cggggatttc caagtctcca ccccattgac gtcaatggga   2100
gtttgttttg gcaccaaaat caacgggact ttccaaaatg tcgtaacaac tccgccccat   2160
tgacgcaaat gggcggtagg cgtgtacggt gggaggttta tataagcaga gctcgtttag   2220
```

```
tgaaccgtca gatcgcctgg agacgccatc cacgctgttt tgacctccat agaagattct   2280
agagccgcca ccatgcttct cctggtgaca agccttctgc tctgtgagtt accacaccca   2340
gcattcctcc tgatcccaga catccagatg acacagacta catcctccct gtctgcctct   2400
ctgggagaca gagtcaccat cagttgcagg gcaagtcagg acattagtaa atatttaaat   2460
tggtatcagc agaaaccaga tggaactgtt aaactcctga tctaccatac atcaagatta   2520
cactcaggag tcccatcaag gttcagtggc agtgggtctg gaacagatta ttctctcacc   2580
attagcaacc tggagcaaga agatattgcc acttactttt gccaacaggg taatacgctt   2640
ccgtacacgt tcggaggggg gactaagttg gaaataacag gctccacctc tggatccggc   2700
aagcccggat ctggcgaggg atccaccaag ggcgaggtga aactgcagga gtcaggacct   2760
ggcctggtgg cgccctcaca gagcctgtcc gtcacatgca ctgtctcagg ggtctcatta   2820
cccgactatg gtgtaagctg gattcgccag cctccacgaa agggtctgga gtggctggga   2880
gtaatatggg gtagtgaaac cacatactat aattcagctc tcaaatccag actgaccatc   2940
atcaaggaca actccaagag ccaagttttc ttaaaaatga acagtctgca aactgatgac   3000
acagccattt actactgtgc caaacattat tactacggtg gtagctatgc tatggactac   3060
tggggtcaag gaacctcagt caccgtctcc tcagcggccg caggtggcgg cggttctggt   3120
ggcggcggtt ctggtggcgg cggttctctc gagctgggag caggcccagt ggattctgga   3180
gtcacacaaa ccccaaagca cctgatcaca gcaactggac agcgagtgac gctgagatgc   3240
tcccctaggt ctggagacct ctctgtgtca tggtaccaac agagcctgga ccagggcctc   3300
cagttcctca ttcagtatta taatggagaa gagagagcaa aaggaaacat tcttgaacga   3360
ttctccgcac aacagttccc tgacttgcac tctgaactaa acctgagctc tctggagctg   3420
ggggactcag ctttgtattt ctgtgccagc agcccccgga caggcctgaa cactgaagct   3480
ttctttggac aaggcaccag actcacagtt gtagaggacc tgaacaaggt gttcccaccc   3540
gaggtcgctg tgtttgagcc atcagaagca gagatctccc acacccaaaa ggccacactg   3600
gtgtgcctgg ccacaggctt cttccccgac cacgtggagc tgagctggtg ggtgaatggg   3660
aaggaggtgc acagtggggt cagcacggac ccgcagcccc tcaaggagca gcccgccctc   3720
aatgactcca gatactgcct gagcagccgc ctgagggtct cggccacctt ctggcagaac   3780
ccccgcaacc acttccgctg tcaagtccag ttctacgggc tctcggagaa tgacgagtgg   3840
acccaggata gggccaaacc cgtcacccag atcgtcagcg ccgaggcctg ggtagagca   3900
gactgtggct ttacctcggt gtcctaccag caaggggtcc tgtctgccac catcctctat   3960
gagatcctgc tagggaaggc caccctgtat gctgtgctgg tcagcgccct tgtgttgatg   4020
gccatggtca agagaaagga tttctgataa gaattcgatc cgcggccgcg aaggatctgc   4080
gatcgctccg gtgcccgtca gtgggcagag cgcacatcgc ccacagtccc cgagaagttg   4140
gggggagggg tcggcaattg aacgggtgcc tagagaaggt ggcgcggggt aaactgggaa   4200
agtgatgtcg tgtactggct ccgccttttt cccgagggtg ggggagaacc gtatataagt   4260
gcagtagtcg ccgtgaacgt tctttttcgc aacgggtttg ccgccagaac acagctgaag   4320
cttcgagggg ctcgcatctc tccttcacgc gcccgccgcc ctacctgagg ccgccatcca   4380
cgccggttga gtcgcgttct gccgcctccc gcctgtggtg cctcctgaac tgcgtccgcc   4440
gtctaggtaa gtttaaagct caggtcgaga ccgggccttt gtccggcgct cccttggagc   4500
ctacctagac tcagccggct ctccacgctt tgcctgaccc tgcttgctca actctacgtc   4560
tttgtttcgt tttctgttct gcgccgttac agatccaagc tgtgaccggc gcctacgcta   4620
```

```
gatgaccgag tacaagccca cggtgcgcct cgccacccgc gacgacgtcc ccagggccgt   4680
acgcaccctc gccgccgcgt tcgccgacta ccccgccacg cgccacaccg tcgatccgga   4740
ccgccacatc gagcgggtca ccgagctgca agaactcttc ctcacgcgcg tcgggctcga   4800
catcggcaag gtgtgggtcg cggacgacgg cgccgcggtg gcggtctgga ccacgccgga   4860
gagcgtcgaa gcgggggcgg tgttcgccga gatcggcccg cgcatggccg agttgagcgg   4920
ttcccggctg gccgcgcagc aacagatgga aggcctcctg gcgccgcacc ggcccaagga   4980
gcccgcgtgg ttcctggcca ccgtcggcgt ctcgcccgac caccagggca agggtctggg   5040
cagcgccgtc gtgctccccg gagtggaggc ggccgagcgc gccggggtgc ccgccttcct   5100
ggagacctcc gcgccccgca acctccccct ctacgagcgg ctcggcttca ccgtcaccgc   5160
cgacgtcgag gtgcccgaag gaccgcgcac ctggtgcatg acccgcaagc ccggtgcctg   5220
agtcgacaat caacctctgg attacaaaat ttgtgaaaga ttgactggta ttcttaacta   5280
tgttgctcct tttacgctat gtggatacgc tgctttaatg cctttgtatc atgctattgc   5340
ttcccgtatg gctttcattt tctcctcctt gtataaatcc tggttgctgt ctctttatga   5400
ggagttgtgg cccgttgtca ggcaacgtgg cgtggtgtgc actgtgtttg ctgacgcaac   5460
ccccactggt tggggcattg ccaccacctg tcagctcctt tccgggactt tcgctttccc   5520
cctccctatt gccacggcgg aactcatcgc cgcctgcctt gcccgctgct ggacaggggc   5580
tcggctgttg ggcactgaca attccgtggt gttgtcgggg aaatcatcgt cctttccttg   5640
gctgctcgcc tgtgttgcca cctggattct gcgcgggacg tccttctgct acgtcccttc   5700
ggccctcaat ccagcggacc ttccttcccg cggcctgctg ccggctctgc ggcctcttcc   5760
gcgtcttcgc cttcgccctc agacgagtcg gatctccctt tgggccgcct ccccgcctgg   5820
tacctttaag accaatgact tacaaggcag ctgtagatct tagccacttt ttaaaagaaa   5880
aggggggact ggaagggcta attcactccc aacgaaaata agatctgctt tttgcttgta   5940
ctgggtctct ctggttagac cagatctgag cctgggagct ctctggctaa ctagggaacc   6000
cactgcttaa gcctcaataa agcttgcctt gagtgcttca agtagtgtgt gcccgtctgt   6060
tgtgtgactc tggtaactag agatccctca gaccctttta gtcagtgtgg aaaatctcta   6120
gcagtagtag ttcatgtcat cttattattc agtatttata acttgcaaag aaatgaatat   6180
cagagagtga gaggaacttg tttattgcag cttataatgg ttacaaataa agcaatagca   6240
tcacaaattt cacaaataaa gcattttttt cactgcattc tagttgtggt ttgtccaaac   6300
tcatcaatgt atcttatcat gtctggctct agctatcccg cccctaactc cgcccagttc   6360
cgcccattct ccgccccatg gctgactaat tttttttatt tatgcagagg ccgaggccgc   6420
ctcggcctct gagctattcc agaagtagtg aggaggcttt tttggaggcc tagacttttg   6480
cagagacggc ccaaattcgt aatcatggtc atagctgttt cctgtgtgaa attgttatcc   6540
gctcacaatt ccacacaaca tacgagccgg aagcataaag tgtaaagcct ggggtgccta   6600
atgagtgagc taactcacat taattgcgtt gcgctcactg cccgctttcc agtcgggaaa   6660
cctgtcgtgc cagctgcatt aatgaatcgg ccaacgcgcg gggagaggcg gtttgcgtat   6720
tgggcgctct tccgcttcct cgctcactga ctcgctgcgc tcggtcgttc ggctgcggcg   6780
agcggtatca gctcactcaa aggcggtaat acggttatcc acagaatcag gggataacgc   6840
aggaaagaac atgtgagcaa aaggccagca aaaggccagg aaccgtaaaa aggccgcgtt   6900
gctggcgttt ttccataggc tccgcccccc tgacgagcat cacaaaaatc gacgctcaag   6960
```

```
tcagaggtgg cgaaacccga caggactata aagataccag gcgtttcccc ctggaagctc   7020

cctcgtgcgc tctcctgttc cgaccctgcc gcttaccgga tacctgtccg cctttctccc   7080

ttcgggaagc gtggcgcttt ctcatagctc acgctgtagg tatctcagtt cggtgtaggt   7140

cgttcgctcc aagctgggct gtgtgcacga accccccgtt cagcccgacc gctgcgcctt   7200

atccggtaac tatcgtcttg agtccaaccc ggtaagacac gacttatcgc cactggcagc   7260

agccactggt aacaggatta gcagagcgag gtatgtaggc ggtgctacag agttcttgaa   7320

gtggtggcct aactacggct acactagaag gacagtattt ggtatctgcg ctctgctgaa   7380

gccagttacc ttcggaaaaa gagttggtag ctcttgatcc ggcaaacaaa ccaccgctgg   7440

tagcggtggt ttttttgttt gcaagcagca gattacgcgc agaaaaaaag gatctcaaga   7500

agatcctttg atcttttcta cggggtctga cgctcagtgg aacgaaaact cacgttaagg   7560

gattttggtc atgagattat caaaaaggat cttcacctag atccttttaa attaaaaatg   7620

aagttttaaa tcaatctaaa gtatatatga gtaaacttgg tctgacagtt accaatgctt   7680

aatcagtgag gcacctatct cagcgatctg tctatttcgt tcatccatag ttgcctgact   7740

ccccgtcgtg tagataacta cgatacggga gggcttacca tctggcccca gtgctgcaat   7800

gataccgcga gacccacgct caccggctcc agatttatca gcaataaacc agccagccgg   7860

aagggccgag cgcagaagtg gtcctgcaac tttatccgcc tccatccagt ctattaattg   7920

ttgccgggaa gctagagtaa gtagttcgcc agttaatagt ttgcgcaacg ttgttgccat   7980

tgctacaggc atcgtggtgt cacgctcgtc gtttggtatg gcttcattca gctccggttc   8040

ccaacgatca aggcgagtta catgatcccc catgttgtgc aaaaaagcgg ttagctcctt   8100

cggtcctccg atcgttgtca gaagtaagtt ggccgcagtg ttatcactca tggttatggc   8160

agcactgcat aattctctta ctgtcatgcc atccgtaaga tgcttttctg tgactggtga   8220

gtactcaacc aagtcattct gagaatagtg tatgcggcga ccgagttgct cttgcccggc   8280

gtcaatacgg gataataccg cgccacatag cagaacttta aaagtgctca tcattggaaa   8340

acgttcttcg gggcgaaaac tctcaaggat cttaccgctg ttgagatcca gttcgatgta   8400

acccactcgt gcacccaact gatcttcagc atcttttact ttcaccagcg tttctgggtg   8460

agcaaaaaca ggaaggcaaa atgccgcaaa aaagggaata agggcgacac ggaaatgttg   8520

aatactcata ctcttccttt ttcaatatta ttgaagcatt tatcagggtt attgtctcat   8580

gagcggatac atatttgaat gtatttagaa aaataaacaa ataggggttc cgcgcacatt   8640

tccccgaaaa gtgccacctg acgtctaaga aaccattatt atcatgacat taacctataa   8700

aaataggcgt atcacgaggc cctttcgtct cgcgcgtttc ggtgatgacg gtgaaaacct   8760

ctgacacatg cagctcccgg agacggtcac agcttgtctg taagcggatg ccgggagcag   8820

acaagcccgt cagggcgcgt cagcgggtgt tggcgggtgt cggggctggc ttaactatgc   8880

ggcatcagag cagattgtac tgagagtgca ccatatgcgg tgtgaaatac cgcacagatg   8940

cgtaaggaga aaataccgca tcaggcgcca ttcgccattc aggctgcgca actgttggga   9000

agggcgatcg gtgcgggcct cttcgctatt acgccagctg gcgaaagggg gatgtgctgc   9060

aaggcgatta agttgggtaa cgccagggtt ttcccagtca cgacgttgta aaacgacggc   9120

cagtgccaag ctg                                                      9133
```

<210> SEQ ID NO 22
<211> LENGTH: 8795
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 22

```
acgcgtgtag tcttatgcaa tactcttgta gtcttgcaac atggtaacga tgagttagca     60
acatgcctta caaggagaga aaaagcaccg tgcatgccga ttggtggaag taaggtggta    120
cgatcgtgcc ttattaggaa ggcaacagac gggtctgaca tggattggac gaaccactga    180
attgccgcat tgcagagata ttgtatttaa gtgcctagct cgatacaata aacgggtctc    240
tctggttaga ccagatctga gcctgggagc tctctggcta actagggaac ccactgctta    300
agcctcaata aagcttgcct tgagtgcttc aagtagtgtg tgcccgtctg ttgtgtgact    360
ctggtaacta gagatccctc agaccctttt agtcagtgtg gaaaatctct agcagtggcg    420
cccgaacagg gacctgaaag cgaaagggaa accagagctc tctcgacgca ggactcggct    480
tgctgaagcg cgcacggcaa gaggcgaggg gcggcgactg gtgagtacgc caaaaatttt    540
gactagcgga ggctagaagg agagagatgg gtgcgagagc gtcagtatta agcgggggag    600
aattagatcg cgatgggaaa aaattcggtt aaggccaggg ggaaagaaaa aatataaatt    660
aaaacatata gtatgggcaa gcagggagct agaacgattc gcagttaatc ctggcctgtt    720
agaaacatca gaaggctgta gacaaatact gggacagcta caaccatccc ttcagacagg    780
atcagaagaa cttagatcat tatataatac agtagcaacc ctctattgtg tgcatcaaag    840
gatagagata aaagacacca aggaagcttt agacaagata gaggaagagc aaaacaaaag    900
taagaccacc gcacagcaag cggccactga tcttcagacc tggaggagga gatatgaggg    960
acaattggag aagtgaatta tataaatata aagtagtaaa aattgaacca ttaggagtag   1020
cacccaccaa ggcaaagaga agagtggtgc agagagaaaa aagagcagtg ggaataggag   1080
ctttgttcct tgggttcttg ggagcagcag gaagcactat gggcgcagcc tcaatgacgc   1140
tgacggtaca ggccagacaa ttattgtctg gtatagtgca gcagcagaac aatttgctga   1200
gggctattga ggcgcaacag catctgttgc aactcacagt ctggggcatc aagcagctcc   1260
aggcaagaat cctggctgtg gaaagatacc taaaggatca acagctcctg gggatttggg   1320
gttgctctgg aaaactcatt tgcaccactg ctgtgccttg gaatgctagt tggagtaata   1380
aatctctgga acagattgga atcacacgac ctggatggag tgggacagag aaattaacaa   1440
ttacacaagc ttaatacact ccttaattga agaatcgcaa aaccagcaag aaaagaatga   1500
acaagaatta ttggaattag ataaatgggc aagtttgtgg aattggttta acataacaaa   1560
ttggctgtgg tatataaaat tattcataat gatagtagga ggcttggtag gtttaagaat   1620
agtttttgct gtactttcta tagtgaatag agttaggcag ggatattcac cattatcgtt   1680
tcagacccac ctcccaaccc cgaggggacc cgacaggccc gaaggaatag aagaagaagg   1740
tggagagaga gacagagaca gatccattcg attagtgaac ggatctcgac ggtatcggtt   1800
aacttttaaa agaaaagggg ggattggggg gtacagtgca ggggaaagaa tagtagacat   1860
aatagcaaca gacatacaaa ctaaagaatt acaaaaacaa attacaaaat tcaaaatttt   1920
atcgatacta gtattatgcc cagtacatga ccttatggga ctttcctact tggcagtaca   1980
tctacgtatt agtcatcgct attaccatgg tgatgcggtt ttggcagtac atcaatgggc   2040
gtggatagcg gtttgactca cggggatttc caagtctcca ccccattgac gtcaatggga   2100
gtttgttttg gcaccaaaat caacgggact ttccaaaatg tcgtaacaac tccgccccat   2160
tgacgcaaat gggcggtagg cgtgtacggt gggaggttta tataagcaga gctcgtttag   2220
```

```
tgaaccgtca gatcgcctgg agacgccatc cacgctgttt tgacctccat agaagattct   2280
agagccgcca ccatgcttct cctggtgaca agccttctgc tctgtgagtt accacaccca   2340
gcattcctcc tgatcccaca ggtgcagctg gtgcagagcg gcgcggaagt gaaaaaaccg   2400
ggcgcgagcg tgaaagtgag ctgcaaagcg agcggctata gctttccgga ttattatatt   2460
aactgggtgc gccaggcgcc gggccagggc ctggaatgga tgggctggat ttattttgcg   2520
agcggcaaca gcgaatataa ccagaaattt accggccgcg tgaccatgac ccgcgatacc   2580
agcagcagca ccgcgtatat ggaactgagc agcctgcgca gcgaagatac cgcggtgtat   2640
tttgcgcgca gcctgtatga ttatgattgg tattttgatg tgtggggcca gggcaccatg   2700
gtgaccgtga gcagcggcgg cggcggcagc ggcggcggcg gcagcggcgg cggcggcagc   2760
gatattgtga tgacccagac cccgctgagc ctgagcgtga ccccgggcga accggcgagc   2820
attagctgca aaagcagcca gagcctggtg catagcaacg gcaacaccta tctgcattgg   2880
tatctgcaga aaccgggcca gagcccgcag ctgctgattt ataaagtgag caaccgcttt   2940
agcggcgtgc cggatcgctt tagcggcagc ggcagcggcg cggattttac cctgaaaatt   3000
agccgcgtgg aagcggaaga tgtgggcgtg tattattgcg cggaaaccag ccatgtgccg   3060
tggacctttg gccagggcac caaactggaa attaaaagcg gtggcggcgg ttctggtggc   3120
ggcggttctg gtggcggcgg ttctctcgag gatggtaatg aagaaatggg tggtattaca   3180
cagacaccat ataaagtctc catctctgga accacagtaa tattgacatg ccctcagtat   3240
cctggatctg aaatactatg gcaacacaat gataaaaaca taggcggtga tgaggatgat   3300
aaaaacatag gcagtgatga ggatcacctg tcactgaagg aattttcaga attggagcaa   3360
agtggttatt atgtctgcta ccccagagga agcaaaccag aagatgcgaa cttttatctc   3420
tacctgaggg caagagtgtg tgagaactgc atggagatgg atgtgatgtc ggtggccaca   3480
attgtcatag tggacatctg catcactggg ggcttgctgc tgctggttta ctactggagc   3540
aagaatagaa aggccaaggc caagcctgtg acacgaggag cgggtgctgg cggcaggcaa   3600
aggggacaaa acaaggagag gccaccacct gttcccaacc cagactatga gcccatccgg   3660
aaaggccagc gggacctgta ttctggcctg aatcagagac gcatctgata agaattcgga   3720
tccgcggccg cgaaggatct gcgatcgctc cggtgcccgt cagtgggcag agcgcacatc   3780
gcccacagtc cccgagaagt tggggggagg ggtcggcaat tgaacgggtg cctagagaag   3840
gtggcgcggg gtaaactggg aaagtgatgt cgtgtactgg ctccgccttt ttcccgaggg   3900
tgggggagaa ccgtatataa gtgcagtagt cgccgtgaac gttctttttc gcaacgggtt   3960
tgccgccaga acacagctga agcttcgagg ggctcgcatc tctccttcac gcgcccgccg   4020
ccctacctga ggccgccatc cacgccggtt gagtcgcgtt ctgccgcctc ccgcctgtgg   4080
tgcctcctga actgcgtccg ccgtctaggt aagtttaaag ctcaggtcga gaccgggcct   4140
ttgtccggcg ctcccttgga gcctacctag actcagccgg ctctccacgc tttgcctgac   4200
cctgcttgct caactctacg tctttgtttc gttttctgtt ctgcgccgtt acagatccaa   4260
gctgtgaccg gcgcctacgc tagatgaccg agtacaagcc cacggtgcgc ctcgccaccc   4320
gcgacgacgt ccccagggcc gtacgcaccc tcgccgccgc gttcgccgac taccccgcca   4380
cgcgccacac cgtcgatccg gaccgccaca tcgagcgggt caccgagctg caagaactct   4440
tcctcacgcg cgtcgggctc gacatcggca aggtgtgggt cgcggacgac ggcgccgcgg   4500
tggcggtctg gaccacgccg gagagcgtcg aagcgggggc ggtgttcgcc gagatcggcc   4560
```

```
cgcgcatggc cgagttgagc ggttcccggc tggccgcgca gcaacagatg gaaggcctcc   4620
tggcgccgca ccggcccaag gagcccgcgt ggttcctggc caccgtcggc gtctcgcccg   4680
accaccaggg caagggtctg ggcagcgccg tcgtgctccc cggagtggag gcggccgagc   4740
gcgccggggt gcccgccttc ctggagacct ccgcgccccg caacctcccc ttctacgagc   4800
ggctcggctt caccgtcacc gccgacgtcg aggtgcccga aggaccgcgc acctggtgca   4860
tgacccgcaa gcccggtgcc tgagtcgaca atcaacctct ggattacaaa atttgtgaaa   4920
gattgactgg tattcttaac tatgttgctc cttttacgct atgtggatac gctgctttaa   4980
tgcctttgta tcatgctatt gcttcccgta tggctttcat tttctcctcc ttgtataaat   5040
cctggttgct gtctctttat gaggagttgt ggcccgttgt caggcaacgt ggcgtggtgt   5100
gcactgtgtt tgctgacgca acccccactg gttggggcat tgccaccacc tgtcagctcc   5160
tttccgggac tttcgctttc cccctcccta ttgccacggc ggaactcatc gccgcctgcc   5220
ttgcccgctg ctggacaggg gctcggctgt tgggcactga caattccgtg gtgttgtcgg   5280
ggaaatcatc gtcctttcct tggctgctcg cctgtgttgc cacctggatt ctgcgcggga   5340
cgtccttctg ctacgtccct tcggccctca atccagcgga ccttccttcc cgcggcctgc   5400
tgccggctct gcggcctctt ccgcgtcttc gccttcgccc tcagacgagt cggatctccc   5460
tttgggccgc ctccccgcct ggtaccttta agaccaatga cttacaaggc agctgtagat   5520
cttagccact ttttaaaaga aaagggggga ctggaagggc taattcactc ccaacgaaaa   5580
taagatctgc tttttgcttg tactgggtct ctctggttag accagatctg agcctgggag   5640
ctctctggct aactagggaa cccactgctt aagcctcaat aaagcttgcc ttgagtgctt   5700
caagtagtgt gtgcccgtct gttgtgtgac tctggtaact agagatccct cagacccttt   5760
tagtcagtgt ggaaaatctc tagcagtagt agttcatgtc atcttattat tcagtattta   5820
taacttgcaa agaaatgaat atcagagagt gagaggaact tgtttattgc agcttataat   5880
ggttacaaat aaagcaatag catcacaaat ttcacaaata aagcattttt ttcactgcat   5940
tctagttgtg gtttgtccaa actcatcaat gtatcttatc atgtctggct ctagctatcc   6000
cgcccctaac tccgcccagt tccgcccatt ctccgcccca tggctgacta atttttttta   6060
tttatgcaga ggccgaggcc gcctcggcct ctgagctatt ccagaagtag tgaggaggct   6120
tttttggagg cctagacttt tgcagagacg gcccaaattc gtaatcatgg tcatagctgt   6180
ttcctgtgtg aaattgttat ccgctcacaa ttccacacaa catacgagcc ggaagcataa   6240
agtgtaaagc ctggggtgcc taatgagtga gctaactcac attaattgcg ttgcgctcac   6300
tgcccgcttt ccagtcggga aacctgtcgt gccagctgca ttaatgaatc ggccaacgcg   6360
cggggagagg cggtttgcgt attgggcgct cttccgcttc ctcgctcact gactcgctgc   6420
gctcggtcgt tcggctgcgg cgagcggtat cagctcactc aaaggcggta atacggttat   6480
ccacagaatc aggggataac gcaggaaaga acatgtgagc aaaaggccag caaaaggcca   6540
ggaaccgtaa aaaggccgcg ttgctggcgt ttttccatag gctccgcccc cctgacgagc   6600
atcacaaaaa tcgacgctca agtcagaggt ggcgaaaccc gacaggacta taaagatacc   6660
aggcgtttcc ccctggaagc tccctcgtgc gctctcctgt tccgaccctg ccgcttaccg   6720
gatacctgtc cgcctttctc ccttcgggaa gcgtggcgct ttctcatagc tcacgctgta   6780
ggtatctcag ttcggtgtag gtcgttcgct ccaagctggg ctgtgtgcac gaaccccccg   6840
ttcagcccga ccgctgcgcc ttatccggta actatcgtct tgagtccaac ccggtaagac   6900
acgacttatc gccactggca gcagccactg gtaacaggat tagcagagcg aggtatgtag   6960
```

gcggtgctac agagttcttg aagtggtggc ctaactacgg ctacactaga aggacagtat 7020
ttggtatctg cgctctgctg aagccagtta ccttcggaaa aagagttggt agctcttgat 7080
ccggcaaaca aaccaccgct ggtagcggtg gtttttttgt ttgcaagcag cagattacgc 7140
gcagaaaaaa aggatctcaa gaagatcctt tgatcttttc tacggggtct gacgctcagt 7200
ggaacgaaaa ctcacgttaa gggattttgg tcatgagatt atcaaaaagg atcttcacct 7260
agatcctttt aaattaaaaa tgaagtttta aatcaatcta aagtatatat gagtaaactt 7320
ggtctgacag ttaccaatgc ttaatcagtg aggcacctat ctcagcgatc tgtctatttc 7380
gttcatccat agttgcctga ctccccgtcg tgtagataac tacgatacgg gagggcttac 7440
catctggccc cagtgctgca atgataccgc gagacccacg ctcaccggct ccagatttat 7500
cagcaataaa ccagccagcc ggaagggccg agcgcagaag tggtcctgca actttatccg 7560
cctccatcca gtctattaat tgttgccggg aagctagagt aagtagttcg ccagttaata 7620
gtttgcgcaa cgttgttgcc attgctacag gcatcgtggt gtcacgctcg tcgtttggta 7680
tggcttcatt cagctccggt tcccaacgat caaggcgagt tacatgatcc cccatgttgt 7740
gcaaaaaagc ggttagctcc ttcggtcctc cgatcgttgt cagaagtaag ttggccgcag 7800
tgttatcact catggttatg gcagcactgc ataattctct tactgtcatg ccatccgtaa 7860
gatgcttttc tgtgactggt gagtactcaa ccaagtcatt ctgagaatag tgtatgcggc 7920
gaccgagttg ctcttgcccg gcgtcaatac gggataatac cgcgccacat agcagaactt 7980
taaaagtgct catcattgga aaacgttctt cggggcgaaa actctcaagg atcttaccgc 8040
tgttgagatc cagttcgatg taacccactc gtgcacccaa ctgatcttca gcatctttta 8100
ctttcaccag cgtttctggg tgagcaaaaa caggaaggca aaatgccgca aaaaagggaa 8160
taagggcgac acggaaatgt tgaatactca tactcttcct ttttcaatat tattgaagca 8220
tttatcaggg ttattgtctc atgagcggat acatatttga atgtatttag aaaaataaac 8280
aaataggggt tccgcgcaca tttccccgaa aagtgccacc tgacgtctaa gaaaccatta 8340
ttatcatgac attaacctat aaaaataggc gtatcacgag gccctttcgt ctcgcgcgtt 8400
tcggtgatga cggtgaaaac ctctgacaca tgcagctccc ggagacggtc acagcttgtc 8460
tgtaagcgga tgccgggagc agacaagccc gtcagggcgc gtcagcgggt gttggcgggt 8520
gtcggggctg gcttaactat gcggcatcag agcagattgt actgagagtg caccatatgc 8580
ggtgtgaaat accgcacaga tgcgtaagga gaaaataccg catcaggcgc cattcgccat 8640
tcaggctgcg caactgttgg gaagggcgat cggtgcgggc ctcttcgcta ttacgccagc 8700
tggcgaaagg gggatgtgct gcaaggcgat taagttgggt aacgccaggg ttttcccagt 8760
cacgacgttg taaaacgacg gccagtgcca agctg 8795

<210> SEQ ID NO 23
<211> LENGTH: 8720
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 23
acgcgtgtag tcttatgcaa tactcttgta gtcttgcaac atggtaacga tgagttagca 60
acatgcctta caaggagaga aaaagcaccg tgcatgccga ttggtggaag taaggtggta 120
cgatcgtgcc ttattaggaa ggcaacagac gggtctgaca tggattggac gaaccactga 180

```
attgccgcat tgcagagata ttgtatttaa gtgcctagct cgatacaata aacgggtctc    240

tctggttaga ccagatctga gcctgggagc tctctggcta actagggaac ccactgctta    300

agcctcaata aagcttgcct tgagtgcttc aagtagtgtg tgcccgtctg ttgtgtgact    360

ctggtaacta gagatccctc agaccctttt agtcagtgtg gaaaatctct agcagtggcg    420

cccgaacagg gacctgaaag cgaaagggaa accagagctc tctcgacgca ggactcggct    480

tgctgaagcg cgcacggcaa gaggcgaggg gcggcgactg gtgagtacgc caaaaatttt    540

gactagcgga ggctagaagg agagagatgg gtgcgagagc gtcagtatta agcgggggag    600

aattagatcg cgatgggaaa aaattcggtt aaggccaggg ggaaagaaaa aatataaatt    660

aaaacatata gtatgggcaa gcagggagct agaacgattc gcagttaatc ctggcctgtt    720

agaaacatca gaaggctgta gacaaatact gggacagcta caaccatccc ttcagacagg    780

atcagaagaa cttagatcat tatataatac agtagcaacc ctctattgtg tgcatcaaag    840

gatagagata aaagacacca aggaagcttt agacaagata gaggaagagc aaaacaaaag    900

taagaccacc gcacagcaag cggccactga tcttcagacc tggaggagga gatatgaggg    960

acaattggag aagtgaatta tataaatata aagtagtaaa aattgaacca ttaggagtag   1020

cacccaccaa ggcaaagaga agagtggtgc agagagaaaa aagagcagtg ggaataggag   1080

ctttgttcct tgggttcttg ggagcagcag gaagcactat gggcgcagcc tcaatgacgc   1140

tgacggtaca ggccagacaa ttattgtctg gtatagtgca gcagcagaac aatttgctga   1200

gggctattga ggcgcaacag catctgttgc aactcacagt ctggggcatc aagcagctcc   1260

aggcaagaat cctggctgtg gaaagatacc taaaggatca acagctcctg gggatttggg   1320

gttgctctgg aaaactcatt tgcaccactg ctgtgccttg gaatgctagt tggagtaata   1380

aatctctgga acagattgga atcacacgac ctggatggag tgggacagag aaattaacaa   1440

ttacacaagc ttaatacact ccttaattga agaatcgcaa aaccagcaag aaaagaatga   1500

acaagaatta ttggaattag ataaatgggc aagtttgtgg aattggttta acataacaaa   1560

ttggctgtgg tatataaaat tattcataat gatagtagga ggcttggtag gtttaagaat   1620

agtttttgct gtactttcta tagtgaatag agttaggcag ggatattcac cattatcgtt   1680

tcagacccac ctcccaaccc cgaggggacc cgacaggccc gaaggaatag aagaagaagg   1740

tggagagaga gacagagaca gatccattcg attagtgaac ggatctcgac ggtatcggtt   1800

aacttttaaa agaaaagggg ggattggggg gtacagtgca ggggaaagaa tagtagacat   1860

aatagcaaca gacatacaaa ctaaagaatt acaaaaacaa attacaaaat tcaaaatttt   1920

atcgatacta gtattatgcc cagtacatga ccttatggga ctttcctact tggcagtaca   1980

tctacgtatt agtcatcgct attaccatgg tgatgcggtt ttggcagtac atcaatgggc   2040

gtggatagcg gtttgactca cggggatttc caagtctcca ccccattgac gtcaatggga   2100

gtttgttttg gcaccaaaat caacgggact ttccaaaatg tcgtaacaac tccgccccat   2160

tgacgcaaat gggcggtagg cgtgtacggt gggaggttta tataagcaga gctcgtttag   2220

tgaaccgtca gatcgcctgg agacgccatc cacgctgttt tgacctccat agaagattct   2280

agagccgcca ccatgcttct cctggtgaca agccttctgc tctgtgagtt accacaccca   2340

gcattcctcc tgatcccaca ggtgcagctg gtgcagagcg gcgcggaagt gaaaaaaccg   2400

ggcgcgagcg tgaaagtgag ctgcaaagcg agcggctata gctttccgga ttattatatt   2460

aactgggtgc gccaggcgcc gggccagggc ctggaatgga tgggctggat ttattttgcg   2520
```

```
agcggcaaca gcgaatataa ccagaaattt accggccgcg tgaccatgac ccgcgatacc   2580
agcagcagca ccgcgtatat ggaactgagc agcctgcgca gcgaagatac cgcggtgtat   2640
ttttgcgcga gcctgtatga ttatgattgg tattttgatg tgtggggcca gggcaccatg   2700
gtgaccgtga gcagcggcgg cggcggcagc ggcggcggcg gcagcggcgg cggcggcagc   2760
gatattgtga tgacccagac cccgctgagc ctgagcgtga ccccgggcga accggcgagc   2820
attagctgca aaagcagcca gagcctggtg catagcaacg gcaacaccta tctgcattgg   2880
tatctgcaga aaccgggcca gagcccgcag ctgctgattt ataaagtgag caaccgcttt   2940
agcggcgtgc cggatcgctt tagcggcagc ggcagcggcg cggattttac cctgaaaatt   3000
agccgcgtgg aagcggaaga tgtgggcgtg tattattgcg cggaaaccag ccatgtgccg   3060
tggacctttg gccagggcac caaactggaa attaaaagcg gtggcggcgg ttctggtggc   3120
ggcggttctg gtggcggcgg ttctctcgag cagtcaatca aaggaaacca cttggttaag   3180
gtgtatgact atcaagaaga tggttcggta cttctgactt gtgatgcaga agccaaaaat   3240
atcacatggt ttaaagatgg gaagatgatc ggcttcctaa ctgaagataa aaaaaaatgg   3300
aatctgggaa gtaatgccaa ggacccacga gggatgtatc agtgtaaagg atcacagaac   3360
aagtcaaaac cactccaagt gtattacaga atgtgtcaga actgcattga actaaatgca   3420
gccaccatat ctggctttct ctttgctgaa atcgtcagca ttttcgtcct tgctgttggg   3480
gtctacttca ttgctggaca ggatggagtt cgccagtcga gagcttcaga caagcagact   3540
ctgttgccca atgaccagct ctaccagccc ctcaaggatc gagaagatga ccagtacagc   3600
caccttcaag gaaaccagtt gaggaggaat tgataagaat tcggatccgc ggccgcgaag   3660
gatctgcgat cgctccggtg cccgtcagtg ggcagagcgc acatcgccca cagtccccga   3720
gaagttgggg ggaggggtcg gcaattgaac gggtgcctag agaaggtggc gcggggtaaa   3780
ctgggaaagt gatgtcgtgt actggctccg cctttttccc gagggtgggg gagaaccgta   3840
tataagtgca gtagtcgccg tgaacgttct ttttcgcaac gggtttgccg ccagaacaca   3900
gctgaagctt cgaggggctc gcatctctcc ttcacgcgcc cgccgcccta cctgaggccg   3960
ccatccacgc cggttgagtc gcgttctgcc gcctcccgcc tgtggtgcct cctgaactgc   4020
gtccgccgtc taggtaagtt taaagctcag gtcgagaccg ggcctttgtc cggcgctccc   4080
ttggagccta cctagactca gccggctctc cacgctttgc ctgaccctgc ttgctcaact   4140
ctacgtcttt gtttcgtttt ctgttctgcg ccgttacaga tccaagctgt gaccggcgcc   4200
tacgctagat gaccgagtac aagcccacgg tgcgcctcgc cacccgcgac gacgtcccca   4260
gggccgtacg caccctcgcc gccgcgttcg ccgactaccc cgccacgcgc cacaccgtcg   4320
atccggaccg ccacatcgag cgggtcaccg agctgcaaga actcttcctc acgcgcgtcg   4380
ggctcgacat cggcaaggtg tgggtcgcgg acgacggcgc cgcggtggcg gtctggacca   4440
cgccggagag cgtcgaagcg gggcggtgt tcgccgagat cggcccgcgc atggccgagt   4500
tgagcggttc ccggctggcc gcgcagcaac agatggaagg cctcctggcg ccgcaccggc   4560
ccaaggagcc cgcgtggttc ctggccaccg tcggcgtctc gcccgaccac cagggcaagg   4620
gtctgggcag cgccgtcgtg ctccccggag tggaggcggc cgagcgcgcc ggggtgcccg   4680
ccttcctgga gacctccgcg ccccgcaacc tccccttcta cgagcggctc ggcttcaccg   4740
tcaccgccga cgtcgaggtg cccgaaggac cgcgcacctg gtgcatgacc cgcaagcccg   4800
gtgcctgagt cgacaatcaa cctctggatt acaaaatttg tgaaagattg actggtattc   4860
ttaactatgt tgctcctttt acgctatgtg gatacgctgc tttaatgcct ttgtatcatg   4920
```

```
ctattgcttc ccgtatggct ttcattttct cctccttgta taaatcctgg ttgctgtctc   4980
tttatgagga gttgtggccc gttgtcaggc aacgtggcgt ggtgtgcact gtgtttgctg   5040
acgcaacccc cactggttgg ggcattgcca ccacctgtca gctcctttcc gggactttcg   5100
ctttccccct ccctattgcc acggcggaac tcatcgccgc ctgccttgcc cgctgctgga   5160
caggggctcg gctgttgggc actgacaatt ccgtggtgtt gtcggggaaa tcatcgtcct   5220
ttccttggct gctcgcctgt gttgccacct ggattctgcg cgggacgtcc ttctgctacg   5280
tcccttcggc cctcaatcca gcggaccttc cttcccgcgg cctgctgccg gctctgcggc   5340
ctcttccgcg tcttcgcctt cgccctcaga cgagtcggat ctccctttgg gccgcctccc   5400
cgcctggtac ctttaagacc aatgacttac aaggcagctg tagatcttag ccacttttta   5460
aaagaaaagg ggggactgga agggctaatt cactcccaac gaaaataaga tctgcttttt   5520
gcttgtactg ggtctctctg gttagaccag atctgagcct gggagctctc tggctaacta   5580
gggaacccac tgcttaagcc tcaataaagc ttgccttgag tgcttcaagt agtgtgtgcc   5640
cgtctgttgt gtgactctgg taactagaga tccctcagac ccttttagtc agtgtggaaa   5700
atctctagca gtagtagttc atgtcatctt attattcagt atttataact tgcaaagaaa   5760
tgaatatcag agagtgagag gaacttgttt attgcagctt ataatggtta caaataaagc   5820
aatagcatca caaatttcac aaataaagca tttttttcac tgcattctag ttgtggtttg   5880
tccaaactca tcaatgtatc ttatcatgtc tggctctagc tatcccgccc ctaactccgc   5940
ccagttccgc ccattctccg ccccatggct gactaatttt ttttatttat gcagaggccg   6000
aggccgcctc ggcctctgag ctattccaga agtagtgagg aggctttttt ggaggcctag   6060
acttttgcag agacggccca aattcgtaat catggtcata gctgtttcct gtgtgaaatt   6120
gttatccgct cacaattcca cacaacatac gagccggaag cataaagtgt aaagcctggg   6180
gtgcctaatg agtgagctaa ctcacattaa ttgcgttgcg ctcactgccc gctttccagt   6240
cgggaaacct gtcgtgccag ctgcattaat gaatcggcca acgcgcgggg agaggcggtt   6300
tgcgtattgg gcgctcttcc gcttcctcgc tcactgactc gctgcgctcg gtcgttcggc   6360
tgcggcgagc ggtatcagct cactcaaagg cggtaatacg gttatccaca gaatcagggg   6420
ataacgcagg aaagaacatg tgagcaaaag gccagcaaaa ggccaggaac cgtaaaaagg   6480
ccgcgttgct ggcgtttttc cataggctcc gcccccctga cgagcatcac aaaaatcgac   6540
gctcaagtca gaggtggcga aacccgacag gactataaag ataccaggcg tttccccctg   6600
gaagctccct cgtgcgctct cctgttccga ccctgccgct taccggatac ctgtccgcct   6660
ttctcccttc gggaagcgtg gcgctttctc atagctcacg ctgtaggtat ctcagttcgg   6720
tgtaggtcgt tcgctccaag ctgggctgtg tgcacgaacc ccccgttcag cccgaccgct   6780
gcgccttatc cggtaactat cgtcttgagt ccaacccggt aagacacgac ttatcgccac   6840
tggcagcagc cactggtaac aggattagca gagcgaggta tgtaggcggt gctacagagt   6900
tcttgaagtg gtggcctaac tacggctaca ctagaaggac agtatttggt atctgcgctc   6960
tgctgaagcc agttaccttc ggaaaaagag ttggtagctc ttgatccggc aaacaaacca   7020
ccgctggtag cggtggtttt tttgtttgca agcagcagat tacgcgcaga aaaaaaggat   7080
ctcaagaaga tcctttgatc ttttctacgg ggtctgacgc tcagtggaac gaaaactcac   7140
gttaagggat tttggtcatg agattatcaa aaaggatctt cacctagatc cttttaaatt   7200
aaaaatgaag ttttaaatca atctaaagta tatatgagta aacttggtct gacagttacc   7260
```

```
aatgcttaat cagtgaggca cctatctcag cgatctgtct atttcgttca tccatagttg   7320
cctgactccc cgtcgtgtag ataactacga tacgggaggg cttaccatct ggccccagtg   7380
ctgcaatgat accgcgagac ccacgctcac cggctccaga tttatcagca ataaaccagc   7440
cagccggaag ggccgagcgc agaagtggtc ctgcaacttt atccgcctcc atccagtcta   7500
ttaattgttg ccgggaagct agagtaagta gttcgccagt taatagtttg cgcaacgttg   7560
ttgccattgc tacaggcatc gtggtgtcac gctcgtcgtt tggtatggct tcattcagct   7620
ccggttccca acgatcaagg cgagttacat gatcccccat gttgtgcaaa aaagcggtta   7680
gctccttcgg tcctccgatc gttgtcagaa gtaagttggc cgcagtgtta tcactcatgg   7740
ttatggcagc actgcataat tctcttactg tcatgccatc cgtaagatgc ttttctgtga   7800
ctggtgagta ctcaaccaag tcattctgag aatagtgtat gcggcgaccg agttgctctt   7860
gcccggcgtc aatacgggat aataccgcgc cacatagcag aactttaaaa gtgctcatca   7920
ttggaaaacg ttcttcgggg cgaaaactct caaggatctt accgctgttg agatccagtt   7980
cgatgtaacc cactcgtgca cccaactgat cttcagcatc ttttactttc accagcgttt   8040
ctgggtgagc aaaaacagga aggcaaaatg ccgcaaaaaa gggaataagg gcgacacgga   8100
aatgttgaat actcatactc ttcctttttc aatattattg aagcatttat cagggttatt   8160
gtctcatgag cggatacata tttgaatgta tttagaaaaa taaacaaata ggggttccgc   8220
gcacatttcc ccgaaaagtg ccacctgacg tctaagaaac cattattatc atgacattaa   8280
cctataaaaa taggcgtatc acgaggccct ttcgtctcgc gcgtttcggt gatgacggtg   8340
aaaacctctg acacatgcag ctcccggaga cggtcacagc ttgtctgtaa gcggatgccg   8400
ggagcagaca agcccgtcag ggcgcgtcag cgggtgttgg cgggtgtcgg ggctggctta   8460
actatgcggc atcagagcag attgtactga gagtgcacca tatgcggtgt gaaataccgc   8520
acagatgcgt aaggagaaaa taccgcatca ggcgccattc gccattcagg ctgcgcaact   8580
gttgggaagg gcgatcggtg cgggcctctt cgctattacg ccagctggcg aaagggggat   8640
gtgctgcaag gcgattaagt tgggtaacgc cagggttttc ccagtcacga cgttgtaaaa   8700
cgacggccag tgccaagctg                                               8720
```

```
<210> SEQ ID NO 24
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 24

agggcaagtc aggacattag taaa                                          24


<210> SEQ ID NO 25
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Arg Ala Ser Gln Asp Ile Ser Lys
1               5


<210> SEQ ID NO 26
```

```
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 26

atctaccata catcaagatt a                                              21


<210> SEQ ID NO 27
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Ile Tyr His Thr Ser Arg Leu
1               5


<210> SEQ ID NO 28
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 28

caacagggta atacgcttcc gtacacg                                        27


<210> SEQ ID NO 29
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Gln Gln Gly Asn Thr Leu Pro Tyr Thr
1               5


<210> SEQ ID NO 30
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 30

ggggtctcat tacccgacta tggtgtaagc                                     30


<210> SEQ ID NO 31
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Gly Val Ser Leu Pro Asp Tyr Gly Val Ser
1               5                   10
```

<210> SEQ ID NO 32
<211> LENGTH: 42
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 32
gtaatatggg gtagtgaaac cacatactat aattcagctc tc 42

<210> SEQ ID NO 33
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 33

Val Ile Trp Gly Ser Glu Thr Thr Tyr Tyr Asn Ser Ala Leu
1 5 10

<210> SEQ ID NO 34
<211> LENGTH: 36
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 34
cattattact acggtggtag ctatgctatg gactac 36

<210> SEQ ID NO 35
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 35

His Tyr Tyr Tyr Gly Gly Ser Tyr Ala Met Asp Tyr
1 5 10

<210> SEQ ID NO 36
<211> LENGTH: 48
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 36
aaaagcagcc agagcctggt gcatagcaac ggcaacacct atctgcat 48

<210> SEQ ID NO 37
<211> LENGTH: 16
<212> TYPE: PRT
<213> ORGANISM: Artificial Sequence
<220> FEATURE:
<223> OTHER INFORMATION: Description of Artificial Sequence: Synthetic peptide

<400> SEQUENCE: 37

Lys Ser Ser Gln Ser Leu Val His Ser Asn Gly Asn Thr Tyr Leu His 1 5 10 15

<210> SEQ ID NO 38
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 38
aaagtgagca accgctttag c 21

<210> SEQ ID NO 39
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 39

Lys Val Ser Asn Arg Phe Ser
1 5

<210> SEQ ID NO 40
<211> LENGTH: 27
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 40
gcggaaacca gccatgtgcc gtggacc 27

<210> SEQ ID NO 41
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 41

Ala Glu Thr Ser His Val Pro Trp Thr
1 5

<210> SEQ ID NO 42
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 42
aaagcgagcg gctatagctt tccggattat tatattaac 39

<210> SEQ ID NO 43
<211> LENGTH: 13
<212> TYPE: PRT
<213> ORGANISM: Artificial Sequence
<220> FEATURE:
<223> OTHER INFORMATION: Description of Artificial Sequence: Synthetic peptide

<400> SEQUENCE: 43

```
Lys Ala Ser Gly Tyr Ser Phe Pro Asp Tyr Tyr Ile Asn
1               5                   10


<210> SEQ ID NO 44
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 44

tggatttatt ttgcgagcgg caacagcgaa tataaccaga aatttaccgg c              51


<210> SEQ ID NO 45
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Trp Ile Tyr Phe Ala Ser Gly Asn Ser Glu Tyr Asn Gln Lys Phe Thr
1               5                   10                  15

Gly


<210> SEQ ID NO 46
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 46

ctgtatgatt atgattggta ttttgatgtg                                      30


<210> SEQ ID NO 47
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Leu Tyr Asp Tyr Asp Trp Tyr Phe Asp Val
1               5                   10


<210> SEQ ID NO 48
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 48

gacatccaga tgacacagac tacatcctcc ctgtctgcct ctctgggaga cagagtcacc     60

atcagttgca gggcaagtca ggacattagt aaatatttaa attggtatca gcagaaacca    120

gatggaactg ttaaactcct gatctaccat acatcaagat tacactcagg agtcccatca    180

aggttcagtg gcagtgggtc tggaacagat tattctctca ccattagcaa cctggagcaa    240
```

```
gaagatattg ccacttactt ttgccaacag ggtaatacgc ttccgtacac gttcggaggg    300

gggactaagt tggaaataac a                                              321


<210> SEQ ID NO 49
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 49

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Lys Tyr
            20                  25                  30

Leu Asn Trp Tyr Gln Gln Lys Pro Asp Gly Thr Val Lys Leu Leu Ile
        35                  40                  45

Tyr His Thr Ser Arg Leu His Ser Gly Val Pro Ser Arg Phe Ser Gly
    50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Asn Thr Leu Pro Tyr
                85                  90                  95

Thr Phe Gly Gly Gly Thr Lys Leu Glu Ile Thr
            100                 105


<210> SEQ ID NO 50
<211> LENGTH: 360
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 50

gaggtgaaac tgcaggagtc aggacctggc ctggtggcgc cctcacagag cctgtccgtc     60

acatgcactg tctcaggggt ctcattaccc gactatggtg taagctggat tcgccagcct    120

ccacgaaagg gtctggagtg gctgggagta atatggggta gtgaaaccac atactataat    180

tcagctctca aatccagact gaccatcatc aaggacaact ccaagagcca agttttctta    240

aaaatgaaca gtctgcaaac tgatgacaca gccatttact actgtgccaa acattattac    300

tacggtggta gctatgctat ggactactgg ggtcaaggaa cctcagtcac cgtctcctca    360


<210> SEQ ID NO 51
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 51

Glu Val Lys Leu Gln Glu Ser Gly Pro Gly Leu Val Ala Pro Ser Gln
1               5                   10                  15

Ser Leu Ser Val Thr Cys Thr Val Ser Gly Val Ser Leu Pro Asp Tyr
            20                  25                  30

Gly Val Ser Trp Ile Arg Gln Pro Pro Arg Lys Gly Leu Glu Trp Leu
        35                  40                  45
```

```
Gly Val Ile Trp Gly Ser Glu Thr Thr Tyr Tyr Asn Ser Ala Leu Lys
    50                  55                  60

Ser Arg Leu Thr Ile Ile Lys Asp Asn Ser Lys Ser Gln Val Phe Leu
65                  70                  75                  80

Lys Met Asn Ser Leu Gln Thr Asp Asp Thr Ala Ile Tyr Tyr Cys Ala
                85                  90                  95

Lys His Tyr Tyr Tyr Gly Gly Ser Tyr Ala Met Asp Tyr Trp Gly Gln
            100                 105                 110

Gly Thr Ser Val Thr Val Ser Ser
        115                 120
```

<210> SEQ ID NO 52
<211> LENGTH: 339
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 52

```
gatattgtga tgacccagac cccgctgagc ctgagcgtga ccccgggcga accggcgagc     60

attagctgca aaagcagcca gagcctggtg catagcaacg gcaacaccta tctgcattgg    120

tatctgcaga aaccgggcca gagcccgcag ctgctgattt ataaagtgag caaccgcttt    180

agcggcgtgc cggatcgctt tagcggcagc ggcagcggcg cggattttac cctgaaaatt    240

agccgcgtgg aagcggaaga tgtgggcgtg tattattgcg cggaaaccag ccatgtgccg    300

tggacctttg gccagggcac caaactggaa attaaaagc                           339
```

<210> SEQ ID NO 53
<211> LENGTH: 113
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 53

```
Asp Ile Val Met Thr Gln Thr Pro Leu Ser Leu Ser Val Thr Pro Gly
1               5                   10                  15

Glu Pro Ala Ser Ile Ser Cys Lys Ser Ser Gln Ser Leu Val His Ser
            20                  25                  30

Asn Gly Asn Thr Tyr Leu His Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Ala Asp Phe Thr Leu Lys Ile
65                  70                  75                  80

Ser Arg Val Glu Ala Glu Asp Val Gly Val Tyr Tyr Cys Ala Glu Thr
                85                  90                  95

Ser His Val Pro Trp Thr Phe Gly Gln Gly Thr Lys Leu Glu Ile Lys
            100                 105                 110

Ser
```

<210> SEQ ID NO 54
<211> LENGTH: 357
<212> TYPE: DNA
<213> ORGANISM: Artificial Sequence
<220> FEATURE:
<223> OTHER INFORMATION: Description of Artificial Sequence: Synthetic

```
      polynucleotide

<400> SEQUENCE: 54

caggtgcagc tggtgcagag cggcgcggaa gtgaaaaaac cgggcgcgag cgtgaaagtg     60

agctgcaaag cgagcggcta tagctttccg gattattata ttaactgggt gcgccaggcg    120

ccgggccagg gcctggaatg gatgggctgg atttattttg cgagcggcaa cagcgaatat    180

aaccagaaat ttaccggccg cgtgaccatg acccgcgata ccagcagcag caccgcgtat    240

atggaactga gcagcctgcg cagcgaagat accgcggtgt atttttgcgc gagcctgtat    300

gattatgatt ggtattttga tgtgtggggc cagggcacca tggtgaccgt gagcagc       357


<210> SEQ ID NO 55
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 55

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Pro Asp Tyr
            20                  25                  30

Tyr Ile Asn Trp Val Arg Gln Ala Pro Gly Gln Gly Leu Glu Trp Met
        35                  40                  45

Gly Trp Ile Tyr Phe Ala Ser Gly Asn Ser Glu Tyr Asn Gln Lys Phe
    50                  55                  60

Thr Gly Arg Val Thr Met Thr Arg Asp Thr Ser Ser Ser Thr Ala Tyr
65                  70                  75                  80

Met Glu Leu Ser Ser Leu Arg Ser Glu Asp Thr Ala Val Tyr Phe Cys
                85                  90                  95

Ala Ser Leu Tyr Asp Tyr Asp Trp Tyr Phe Asp Val Trp Gly Gln Gly
            100                 105                 110

Thr Met Val Thr Val Ser Ser
        115


<210> SEQ ID NO 56
<211> LENGTH: 207
<212> TYPE: PRT
<213> ORGANISM: Homo sapiens

<400> SEQUENCE: 56

Met Gln Ser Gly Thr His Trp Arg Val Leu Gly Leu Cys Leu Leu Ser
1               5                   10                  15

Val Gly Val Trp Gly Gln Asp Gly Asn Glu Glu Met Gly Gly Ile Thr
            20                  25                  30

Gln Thr Pro Tyr Lys Val Ser Ile Ser Gly Thr Thr Val Ile Leu Thr
        35                  40                  45

Cys Pro Gln Tyr Pro Gly Ser Glu Ile Leu Trp Gln His Asn Asp Lys
    50                  55                  60

Asn Ile Gly Gly Asp Glu Asp Asp Lys Asn Ile Gly Ser Asp Glu Asp
65                  70                  75                  80

His Leu Ser Leu Lys Glu Phe Ser Glu Leu Glu Gln Ser Gly Tyr Tyr
                85                  90                  95

Val Cys Tyr Pro Arg Gly Ser Lys Pro Glu Asp Ala Asn Phe Tyr Leu
            100                 105                 110
```

```
Tyr Leu Arg Ala Arg Val Cys Glu Asn Cys Met Glu Met Asp Val Met
        115                 120                 125

Ser Val Ala Thr Ile Val Ile Val Asp Ile Cys Ile Thr Gly Gly Leu
    130                 135                 140

Leu Leu Leu Val Tyr Tyr Trp Ser Lys Asn Arg Lys Ala Lys Ala Lys
145                 150                 155                 160

Pro Val Thr Arg Gly Ala Gly Ala Gly Gly Arg Gln Arg Gly Gln Asn
                165                 170                 175

Lys Glu Arg Pro Pro Pro Val Pro Asn Pro Asp Tyr Glu Pro Ile Arg
            180                 185                 190

Lys Gly Gln Arg Asp Leu Tyr Ser Gly Leu Asn Gln Arg Arg Ile
        195                 200                 205


<210> SEQ ID NO 57
<211> LENGTH: 182
<212> TYPE: PRT
<213> ORGANISM: Homo sapiens

<400> SEQUENCE: 57

Met Glu Gln Gly Lys Gly Leu Ala Val Leu Ile Leu Ala Ile Ile Leu
1               5                   10                  15

Leu Gln Gly Thr Leu Ala Gln Ser Ile Lys Gly Asn His Leu Val Lys
            20                  25                  30

Val Tyr Asp Tyr Gln Glu Asp Gly Ser Val Leu Leu Thr Cys Asp Ala
        35                  40                  45

Glu Ala Lys Asn Ile Thr Trp Phe Lys Asp Gly Lys Met Ile Gly Phe
    50                  55                  60

Leu Thr Glu Asp Lys Lys Lys Trp Asn Leu Gly Ser Asn Ala Lys Asp
65                  70                  75                  80

Pro Arg Gly Met Tyr Gln Cys Lys Gly Ser Gln Asn Lys Ser Lys Pro
                85                  90                  95

Leu Gln Val Tyr Tyr Arg Met Cys Gln Asn Cys Ile Glu Leu Asn Ala
            100                 105                 110

Ala Thr Ile Ser Gly Phe Leu Phe Ala Glu Ile Val Ser Ile Phe Val
        115                 120                 125

Leu Ala Val Gly Val Tyr Phe Ile Ala Gly Gln Asp Gly Val Arg Gln
    130                 135                 140

Ser Arg Ala Ser Asp Lys Gln Thr Leu Leu Pro Asn Asp Gln Leu Tyr
145                 150                 155                 160

Gln Pro Leu Lys Asp Arg Glu Asp Asp Gln Tyr Ser His Leu Gln Gly
                165                 170                 175

Asn Gln Leu Arg Arg Asn
            180


<210> SEQ ID NO 58
<211> LENGTH: 171
<212> TYPE: PRT
<213> ORGANISM: Homo sapiens

<400> SEQUENCE: 58

Met Glu His Ser Thr Phe Leu Ser Gly Leu Val Leu Ala Thr Leu Leu
1               5                   10                  15

Ser Gln Val Ser Pro Phe Lys Ile Pro Ile Glu Glu Leu Glu Asp Arg
            20                  25                  30

Val Phe Val Asn Cys Asn Thr Ser Ile Thr Trp Val Glu Gly Thr Val
        35                  40                  45
```

```
Gly Thr Leu Leu Ser Asp Ile Thr Arg Leu Asp Leu Gly Lys Arg Ile
    50                  55                  60

Leu Asp Pro Arg Gly Ile Tyr Arg Cys Asn Gly Thr Asp Ile Tyr Lys
65                  70                  75                  80

Asp Lys Glu Ser Thr Val Gln Val His Tyr Arg Met Cys Gln Ser Cys
                85                  90                  95

Val Glu Leu Asp Pro Ala Thr Val Ala Gly Ile Ile Val Thr Asp Val
            100                 105                 110

Ile Ala Thr Leu Leu Leu Ala Leu Gly Val Phe Cys Phe Ala Gly His
        115                 120                 125

Glu Thr Gly Arg Leu Ser Gly Ala Ala Asp Thr Gln Ala Leu Leu Arg
    130                 135                 140

Asn Asp Gln Val Tyr Gln Pro Leu Arg Asp Arg Asp Asp Ala Gln Tyr
145                 150                 155                 160

Ser His Leu Gly Gly Asn Trp Ala Arg Asn Lys
                165                 170


<210> SEQ ID NO 59
<211> LENGTH: 164
<212> TYPE: PRT
<213> ORGANISM: Homo sapiens

<400> SEQUENCE: 59

Met Lys Trp Lys Ala Leu Phe Thr Ala Ala Ile Leu Gln Ala Gln Leu
1               5                   10                  15

Pro Ile Thr Glu Ala Gln Ser Phe Gly Leu Leu Asp Pro Lys Leu Cys
            20                  25                  30

Tyr Leu Leu Asp Gly Ile Leu Phe Ile Tyr Gly Val Ile Leu Thr Ala
        35                  40                  45

Leu Phe Leu Arg Val Lys Phe Ser Arg Ser Ala Asp Ala Pro Ala Tyr
    50                  55                  60

Gln Gln Gly Gln Asn Gln Leu Tyr Asn Glu Leu Asn Leu Gly Arg Arg
65                  70                  75                  80

Glu Glu Tyr Asp Val Leu Asp Lys Arg Arg Gly Arg Asp Pro Glu Met
                85                  90                  95

Gly Gly Lys Pro Gln Arg Arg Lys Asn Pro Gln Glu Gly Leu Tyr Asn
            100                 105                 110

Glu Leu Gln Lys Asp Lys Met Ala Glu Ala Tyr Ser Glu Ile Gly Met
        115                 120                 125

Lys Gly Glu Arg Arg Arg Gly Lys Gly His Asp Gly Leu Tyr Gln Gly
    130                 135                 140

Leu Ser Thr Ala Thr Lys Asp Thr Tyr Asp Ala Leu His Met Gln Ala
145                 150                 155                 160

Leu Pro Pro Arg


<210> SEQ ID NO 60
<211> LENGTH: 281
<212> TYPE: PRT
<213> ORGANISM: Homo sapiens

<400> SEQUENCE: 60

Met Ala Gly Thr Trp Leu Leu Leu Leu Leu Ala Leu Gly Cys Pro Ala
1               5                   10                  15

Leu Pro Thr Gly Val Gly Gly Thr Pro Phe Pro Ser Leu Ala Pro Pro
            20                  25                  30
```

```
Ile Met Leu Leu Val Asp Gly Lys Gln Gln Met Val Val Val Cys Leu
        35                  40                  45

Val Leu Asp Val Ala Pro Pro Gly Leu Asp Ser Pro Ile Trp Phe Ser
    50                  55                  60

Ala Gly Asn Gly Ser Ala Leu Asp Ala Phe Thr Tyr Gly Pro Ser Pro
65                  70                  75                  80

Ala Thr Asp Gly Thr Trp Thr Asn Leu Ala His Leu Ser Leu Pro Ser
                85                  90                  95

Glu Glu Leu Ala Ser Trp Glu Pro Leu Val Cys His Thr Gly Pro Gly
            100                 105                 110

Ala Glu Gly His Ser Arg Ser Thr Gln Pro Met His Leu Ser Gly Glu
        115                 120                 125

Ala Ser Thr Ala Arg Thr Cys Pro Gln Glu Pro Leu Arg Gly Thr Pro
    130                 135                 140

Gly Gly Ala Leu Trp Leu Gly Val Leu Arg Leu Leu Leu Phe Lys Leu
145                 150                 155                 160

Leu Leu Phe Asp Leu Leu Leu Thr Cys Ser Cys Leu Cys Asp Pro Ala
                165                 170                 175

Gly Pro Leu Pro Ser Pro Ala Thr Thr Thr Arg Leu Arg Ala Leu Gly
            180                 185                 190

Ser His Arg Leu His Pro Ala Thr Glu Thr Gly Gly Arg Glu Ala Thr
        195                 200                 205

Ser Ser Pro Arg Pro Gln Pro Arg Asp Arg Arg Trp Gly Asp Thr Pro
    210                 215                 220

Pro Gly Arg Lys Pro Gly Ser Pro Val Trp Gly Glu Gly Ser Tyr Leu
225                 230                 235                 240

Ser Ser Tyr Pro Thr Cys Pro Ala Gln Ala Trp Cys Ser Arg Ser Ala
                245                 250                 255

Leu Arg Ala Pro Ser Ser Ser Leu Gly Ala Phe Phe Ala Gly Asp Leu
            260                 265                 270

Pro Pro Pro Leu Gln Ala Gly Ala Ala
        275                 280


<210> SEQ ID NO 61
<211> LENGTH: 142
<212> TYPE: PRT
<213> ORGANISM: Homo sapiens

<400> SEQUENCE: 61

Pro Asn Ile Gln Asn Pro Asp Pro Ala Val Tyr Gln Leu Arg Asp Ser
1               5                   10                  15

Lys Ser Ser Asp Lys Ser Val Cys Leu Phe Thr Asp Phe Asp Ser Gln
            20                  25                  30

Thr Asn Val Ser Gln Ser Lys Asp Ser Asp Val Tyr Ile Thr Asp Lys
        35                  40                  45

Thr Val Leu Asp Met Arg Ser Met Asp Phe Lys Ser Asn Ser Ala Val
    50                  55                  60

Ala Trp Ser Asn Lys Ser Asp Phe Ala Cys Ala Asn Ala Phe Asn Asn
65                  70                  75                  80

Ser Ile Ile Pro Glu Asp Thr Phe Phe Pro Ser Pro Glu Ser Ser Cys
                85                  90                  95

Asp Val Lys Leu Val Glu Lys Ser Phe Glu Thr Asp Thr Asn Leu Asn
            100                 105                 110

Phe Gln Asn Leu Ser Val Ile Gly Phe Arg Ile Leu Leu Leu Lys Val
        115                 120                 125
```

```
Ala Gly Phe Asn Leu Leu Met Thr Leu Arg Leu Trp Ser Ser
    130                 135                 140


<210> SEQ ID NO 62
<211> LENGTH: 139
<212> TYPE: PRT
<213> ORGANISM: Homo sapiens

<400> SEQUENCE: 62

Met Ala Met Leu Leu Gly Ala Ser Val Leu Ile Leu Trp Leu Gln Pro
1               5                   10                  15

Asp Trp Val Asn Ser Gln Gln Lys Asn Asp Asp Gln Gln Val Lys Gln
            20                  25                  30

Asn Ser Pro Ser Leu Ser Val Gln Glu Gly Arg Ile Ser Ile Leu Asn
        35                  40                  45

Cys Asp Tyr Thr Asn Ser Met Phe Asp Tyr Phe Leu Trp Tyr Lys Lys
    50                  55                  60

Tyr Pro Ala Glu Gly Pro Thr Phe Leu Ile Ser Ile Ser Ser Ile Lys
65                  70                  75                  80

Asp Lys Asn Glu Asp Gly Arg Phe Thr Val Phe Leu Asn Lys Ser Ala
                85                  90                  95

Lys His Leu Ser Leu His Ile Val Pro Ser Gln Pro Gly Asp Ser Ala
            100                 105                 110

Val Tyr Phe Cys Ala Ala Lys Gly Ala Gly Thr Ala Ser Lys Leu Thr
        115                 120                 125

Phe Gly Thr Gly Thr Arg Leu Gln Val Thr Leu
    130                 135


<210> SEQ ID NO 63
<211> LENGTH: 177
<212> TYPE: PRT
<213> ORGANISM: Homo sapiens

<400> SEQUENCE: 63

Glu Asp Leu Asn Lys Val Phe Pro Pro Glu Val Ala Val Phe Glu Pro
1               5                   10                  15

Ser Glu Ala Glu Ile Ser His Thr Gln Lys Ala Thr Leu Val Cys Leu
            20                  25                  30

Ala Thr Gly Phe Phe Pro Asp His Val Glu Leu Ser Trp Trp Val Asn
        35                  40                  45

Gly Lys Glu Val His Ser Gly Val Ser Thr Asp Pro Gln Pro Leu Lys
    50                  55                  60

Glu Gln Pro Ala Leu Asn Asp Ser Arg Tyr Cys Leu Ser Ser Arg Leu
65                  70                  75                  80

Arg Val Ser Ala Thr Phe Trp Gln Asn Pro Arg Asn His Phe Arg Cys
                85                  90                  95

Gln Val Gln Phe Tyr Gly Leu Ser Glu Asn Asp Glu Trp Thr Gln Asp
            100                 105                 110

Arg Ala Lys Pro Val Thr Gln Ile Val Ser Ala Glu Ala Trp Gly Arg
        115                 120                 125

Ala Asp Cys Gly Phe Thr Ser Val Ser Tyr Gln Gln Gly Val Leu Ser
    130                 135                 140

Ala Thr Ile Leu Tyr Glu Ile Leu Leu Gly Lys Ala Thr Leu Tyr Ala
145                 150                 155                 160

Val Leu Val Ser Ala Leu Val Leu Met Ala Met Val Lys Arg Lys Asp
                165                 170                 175
```

Phe

<210> SEQ ID NO 64
<211> LENGTH: 133
<212> TYPE: PRT
<213> ORGANISM: Homo sapiens

<400> SEQUENCE: 64

```
Met Gly Thr Ser Leu Leu Cys Trp Met Ala Leu Cys Leu Leu Gly Ala
1               5                   10                  15

Asp His Ala Asp Thr Gly Val Ser Gln Asn Pro Arg His Asn Ile Thr
            20                  25                  30

Lys Arg Gly Gln Asn Val Thr Phe Arg Cys Asp Pro Ile Ser Glu His
        35                  40                  45

Asn Arg Leu Tyr Trp Tyr Arg Gln Thr Leu Gly Gln Gly Pro Glu Phe
    50                  55                  60

Leu Thr Tyr Phe Gln Asn Glu Ala Gln Leu Glu Lys Ser Arg Leu Leu
65                  70                  75                  80

Ser Asp Arg Phe Ser Ala Glu Arg Pro Lys Gly Ser Phe Ser Thr Leu
                85                  90                  95

Glu Ile Gln Arg Thr Glu Gln Gly Asp Ser Ala Met Tyr Leu Cys Ala
            100                 105                 110

Ser Ser Leu Ala Gly Leu Asn Gln Pro Gln His Phe Gly Asp Gly Thr
        115                 120                 125

Arg Leu Ser Ile Leu
    130
```

<210> SEQ ID NO 65
<211> LENGTH: 135
<212> TYPE: PRT
<213> ORGANISM: Homo sapiens

<400> SEQUENCE: 65

```
Met Asp Ser Trp Thr Phe Cys Cys Val Ser Leu Cys Ile Leu Val Ala
1               5                   10                  15

Lys His Thr Asp Ala Gly Val Ile Gln Ser Pro Arg His Glu Val Thr
            20                  25                  30

Glu Met Gly Gln Glu Val Thr Leu Arg Cys Lys Pro Ile Ser Gly His
        35                  40                  45

Asn Ser Leu Phe Trp Tyr Arg Gln Thr Met Met Arg Gly Leu Glu Leu
    50                  55                  60

Leu Ile Tyr Phe Asn Asn Asn Val Pro Ile Asp Asp Ser Gly Met Pro
65                  70                  75                  80

Glu Asp Arg Phe Ser Ala Lys Met Pro Asn Ala Ser Phe Ser Thr Leu
                85                  90                  95

Lys Ile Gln Pro Ser Glu Pro Arg Asp Ser Ala Val Tyr Phe Cys Ala
            100                 105                 110

Ser Ser Phe Ser Thr Cys Ser Ala Asn Tyr Gly Tyr Thr Phe Gly Ser
        115                 120                 125

Gly Thr Arg Leu Thr Val Val
    130                 135
```

<210> SEQ ID NO 66
<211> LENGTH: 20
<212> TYPE: PRT
<213> ORGANISM: Artificial Sequence
<220> FEATURE:

```
<223> OTHER INFORMATION: Description of Artificial Sequence: Synthetic
      peptide
<220> FEATURE:
<221> NAME/KEY: MISC_FEATURE
<222> LOCATION: (1)..(20)
<223> OTHER INFORMATION: This sequence may encompass 1-4 "Gly Gly Gly
      Gly Ser" repeating units

<400> SEQUENCE: 66

Gly Gly Gly Gly Ser Gly Gly Gly Gly Ser Gly Gly Gly Gly Ser Gly
1               5                   10                  15

Gly Gly Gly Ser
            20


<210> SEQ ID NO 67
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(20)
<223> OTHER INFORMATION: This sequence may encompass 2-4 "Gly Gly Gly
      Gly Ser" repeating units

<400> SEQUENCE: 67

Gly Gly Gly Gly Ser Gly Gly Gly Gly Ser Gly Gly Gly Gly Ser Gly
1               5                   10                  15

Gly Gly Gly Ser
            20


<210> SEQ ID NO 68
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(15)
<223> OTHER INFORMATION: This sequence may encompass 1-3 "Gly Gly Gly
      Gly Ser" repeating units

<400> SEQUENCE: 68

Gly Gly Gly Gly Ser Gly Gly Gly Gly Ser Gly Gly Gly Gly Ser
1               5                   10                  15


<210> SEQ ID NO 69
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (1)..(40)
<223> OTHER INFORMATION: This sequence may encompass 1-10 "Gly Gly Gly
      Ser" repeating units

<400> SEQUENCE: 69

Gly Gly Gly Ser Gly Gly Gly Ser Gly Gly Gly Ser Gly Gly Gly Ser
1               5                   10                  15

Gly Gly Gly Ser Gly Gly Gly Ser Gly Gly Gly Ser Gly Gly Gly Ser
            20                  25                  30
```

```
Gly Gly Gly Ser Gly Gly Gly Ser
        35                  40


<210> SEQ ID NO 70
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Gly Gly Gly Gly Ser Gly Gly Gly Gly Ser Gly Gly Gly Gly Ser Gly
1               5                   10                  15

Gly Gly Gly Ser
            20


<210> SEQ ID NO 71
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

Gly Gly Gly Gly Ser Gly Gly Gly Gly Ser Gly Gly Gly Gly Ser
1               5                   10                  15


<210> SEQ ID NO 72
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

Gly Gly Gly Ser
1


<210> SEQ ID NO 73
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (1)..(30)
<223> OTHER INFORMATION: This sequence may encompass 1-6 "Gly Gly Gly
      Gly Ser" repeating units

<400> SEQUENCE: 73

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser
            20                  25                  30


<210> SEQ ID NO 74
<211> LENGTH: 5
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 74

Gly Gly Gly Gly Ser
1               5
```

COMPOSITIONS AND METHODS FOR TCR REPROGRAMMING USING FUSION PROTEINS

CROSS-REFERENCE

This application is a continuation of Ser. No. 15/419,398, filed Jan. 30, 2017, which is a continuation of International Application No. PCT/US2016/033146, filed May 18, 2016, which claims the benefit of U.S. Provisional Application No. 62/163,342, filed May 18, 2015, each of which is incorporated herein by reference in its entirety.

SEQUENCE LISTING

The instant application contains a Sequence Listing which has been submitted electronically in ASCII format and is hereby incorporated by reference in its entirety. Said ASCII copy, created on Apr. 27, 2018, is named 48538-701.303_SL-from_601.txt and is 225,742 bytes in size.

BACKGROUND OF THE INVENTION

Most patients with hematological malignancies or with late-stage solid tumors are incurable with standard therapy. In addition, traditional treatment options often have serious side effects. Numerous attempts have been made to engage a patient's immune system for rejecting cancerous cells, an approach collectively referred to as cancer immunotherapy. However, several obstacles make it rather difficult to achieve clinical effectiveness. Although hundreds of so-called tumor antigens have been identified, these are often derived from self and thus can direct the cancer immunotherapy against healthy tissue, or are poorly immunogenic. Furthermore, cancer cells use multiple mechanisms to render themselves invisible or hostile to the initiation and propagation of an immune attack by cancer immunotherapies.

Recent developments using chimeric antigen receptor (CAR) modified autologous T-cell therapy, which relies on redirecting genetically engineered T-cells to a suitable cell-surface molecule on cancer cells, show promising results in harnessing the power of the immune system to treat B cell malignancies (see, e.g., Sadelain et al., Cancer Discovery 3:388-398 (2013)). The clinical results with CD19-specific CAR T-cells (called CTL019) have shown complete remissions in patients suffering from chronic lymphocytic leukemia (CLL) as well as in childhood acute lymphoblastic leukemia (ALL) (see, e.g., Kalos et al., Sci Transl Med 3:95ra73 (2011), Porter et al., NEJM 365:725-733 (2011), Grupp et al., NEJM 368:1509-1518 (2013)). An alternative approach is the use of T-cell receptor (TCR) alpha and beta chains selected for a tumor-associated peptide antigen for genetically engineering autologous T-cells. These TCR chains will form complete TCR complexes and provide the T-cells with a TCR for a second defined specificity. Encouraging results were obtained with engineered autologous T-cells expressing NY-ESO-1-specific TCR alpha and beta chains in patients with synovial carcinoma.

Besides the ability for genetically modified T-cells expressing a CAR or a second TCR to recognize and destroy respective target cells in vitro/ex vivo, successful patient therapy with engineered T-cells requires the T-cells to be capable of strong activation, expansion, persistence over time, and, in case of relapsing disease, to enable a 'memory' response. High and manageable clinical efficacy of CAR T-cells is currently limited to CD19-positive B cell malignancies and to NY-ESO-1-peptide expressing synovial sarcoma patients expressing HLA-A2. There is a clear need to improve genetically engineered T-cells to more broadly act against various human malignancies. Described herein are novel fusion proteins of TCR subunits, including CD3 epsilon, CD3 gamma and CD3 delta, and of TCR alpha and TCR beta chains with binding domains specific for cell surface antigens that have the potential to overcome limitations of existing approaches. Described herein are novel fusion proteins that more efficiently kill target cells than CARs, but release comparable or lower levels of pro-inflammatory cytokines. These fusion proteins and methods of their use represent an advantage for TFPs relative to CARs because elevated levels of these cytokines have been associated with dose-limiting toxicities for adoptive CAR-T therapies.

SUMMARY OF THE INVENTION

Provided herein are T-cell receptor (TCR) fusion proteins (TFPs), T-cells engineered to express one or more TFPs, and methods of use thereof for the treatment of diseases.

In one aspect, provided herein is an isolated recombinant nucleic acid molecule encoding a T-cell receptor (TCR) fusion protein (TFP) comprising a TCR subunit comprising at least a portion of a TCR extracellular domain, and a TCR intracellular domain comprising a stimulatory domain from an intracellular signaling domain of CD3 epsilon; and a human or humanized antibody domain comprising an antigen binding domain wherein the TCR subunit and the antibody domain are operatively linked, and wherein the TFP incorporates into a TCR when expressed in a T-cell.

In one aspect, provided herein is an isolated recombinant nucleic acid molecule encoding a T-cell receptor (TCR) fusion protein (TFP) comprising a TCR subunit comprising at least a portion of a TCR extracellular domain, and a TCR intracellular domain comprising a stimulatory domain from an intracellular signaling domain of CD3 gamma; and a human or humanized antibody domain comprising an antigen binding domain wherein the TCR subunit and the antibody domain are operatively linked, and wherein the TFP incorporates into a TCR when expressed in a T-cell.

In one aspect, provided herein is an isolated recombinant nucleic acid molecule encoding a T-cell receptor (TCR) fusion protein (TFP) comprising a TCR subunit comprising at least a portion of a TCR extracellular domain, and a TCR intracellular domain comprising a stimulatory domain from an intracellular signaling domain of CD3 delta; and a human or humanized antibody domain comprising an antigen binding domain wherein the TCR subunit and the antibody domain are operatively linked, and wherein the TFP incorporates into a TCR when expressed in a T-cell.

In one aspect, provided herein is an isolated recombinant nucleic acid molecule encoding a T-cell receptor (TCR) fusion protein (TFP) comprising a TCR subunit comprising at least a portion of a TCR extracellular domain, and a TCR intracellular domain comprising a stimulatory domain from an intracellular signaling domain of TCR alpha; and a human or humanized antibody domain comprising an antigen binding domain wherein the TCR subunit and the antibody domain are operatively linked, and wherein the TFP incorporates into a TCR when expressed in a T-cell.

In one aspect, provided herein is an isolated recombinant nucleic acid molecule encoding a T-cell receptor (TCR) fusion protein (TFP) comprising a TCR subunit comprising at least a portion of a TCR extracellular domain, and a TCR intracellular domain comprising a stimulatory domain from an intracellular signaling domain of TCR beta; and a human or humanized antibody domain comprising an antigen binding domain wherein the TCR subunit and the antibody domain are operatively linked, and wherein the TFP incorporates into a TCR when expressed in a T-cell.

In one aspect, provided herein is an isolated recombinant nucleic acid molecule encoding a T-cell receptor (TCR) fusion protein (TFP) comprising a TCR subunit and a human or humanized antibody domain comprising an antigen binding domain that is an anti-CD19 binding domain.

In one aspect, provided herein is an isolated recombinant nucleic acid molecule encoding a T-cell receptor (TCR) fusion protein (TFP) comprising a TCR subunit and a human or humanized antibody domain comprising an antigen binding domain that is an anti-B-cell maturation antigen (BCMA) binding domain.

In some instances, the TCR subunit and the antibody domain are operatively linked. In some instances, the TFP incorporates into a TCR when expressed in a T-cell. In some instances, the encoded antigen binding domain is connected to the TCR extracellular domain by a linker sequence. In some instances, the encoded linker sequence comprises $(G_4S)_n$, wherein n=1 to 4 (SEQ ID NO: 66). In some instances, the TCR subunit comprises a TCR extracellular domain. In some instances, the TCR subunit comprises a TCR transmembrane domain. In some instances, the TCR subunit comprises a TCR intracellular domain. In some instances, the TCR subunit comprises (i) a TCR extracellular domain, (ii) a TCR transmembrane domain, and (iii) a TCR intracellular domain, wherein at least two of (i), (ii), and (iii) are from the same TCR subunit. In some instances, the TCR subunit comprises a TCR intracellular domain comprising a stimulatory domain selected from an intracellular signaling domain of CD3 epsilon, CD3 gamma or CD3 delta, or an amino acid sequence having at least one, two or three modifications thereto. In some instances, the TCR subunit comprises an intracellular domain comprising a stimulatory domain selected from a functional signaling domain of 4-1BB and/or a functional signaling domain of CD3 zeta, or an amino acid sequence having at least one modification thereto. In some instances, the human or humanized antibody domain comprises an antibody fragment. In some instances, the human or humanized antibody domain comprises a scFv or a $V_H$ domain. In some instances, the isolated nucleic acid molecule encodes (i) a light chain (LC) CDR1, LC CDR2 and LC CDR3 of an anti-CD19 light chain binding domain amino acid sequence with 70-100% sequence identity to SEQ ID NO: 25, SEQ ID NO: 27 and SEQ ID NO: 29, respectively, and/or (ii) a heavy chain (HC) CDR1, HC CDR2 and HC CDR3 of an anti-CD19 heavy chain binding domain amino acid sequence with 70-100% sequence identity to SEQ ID NO: 31, SEQ ID NO: 33 and SEQ ID NO: 35, respectively. In some instances, the isolated nucleic acid molecule encodes a light chain variable region, wherein the light chain variable region comprises an amino acid sequence having at least one but not more than 30 modifications of a light chain variable region amino acid sequence of SEQ ID NO: 49, or a sequence with 95-99% identity to a light chain variable region amino acid sequence of SEQ ID NO: 49. In some instances, the isolated nucleic acid molecule encodes a heavy chain variable region, wherein the heavy chain variable region comprises an amino acid sequence having at least one but not more than 30 modifications of a heavy chain variable region amino acid sequence of SEQ ID NO: 51, or a sequence with 95-99% identity to a heavy chain variable region amino acid sequence of SEQ ID NO: 51. In some instances, the isolated nucleic acid molecule encodes (i) a light chain (LC) CDR1, LC CDR2 and LC CDR3 of an anti-BCMA light chain binding domain amino acid sequence with 70-100% sequence identity to SEQ ID NO: 37, SEQ ID NO: 39 and SEQ ID NO: 41, respectively, and/or (ii) a heavy chain (HC) CDR1, HC CDR2 and HC CDR3 of an anti-BCMA heavy chain binding domain amino acid sequence with 70-100% sequence identity to SEQ ID NO: 43, SEQ ID NO: 45 and SEQ ID NO: 47, respectively. In some instances, the isolated nucleic acid molecule encodes a light chain variable region, wherein the light chain variable region comprises an amino acid sequence having at least one but not more than 30 modifications of a light chain variable region amino acid sequence of SEQ ID NO: 53, or a sequence with 95-99% identity to a light chain variable region amino acid sequence of SEQ ID NO: 53. In some instances, the isolated nucleic acid molecule encodes a heavy chain variable region, wherein the heavy chain variable region comprises an amino acid sequence having at least one but not more than 30 modifications of a heavy chain variable region amino acid sequence of SEQ ID NO: 55, or a sequence with 95-99% identity to a heavy chain variable region amino acid sequence of SEQ ID NO: 55. In some instances, the TFP includes an extracellular domain of a TCR subunit that comprises an extracellular domain or portion thereof of a protein selected from the group consisting of a TCR alpha chain, a TCR beta chain, a CD3 epsilon TCR subunit, a CD3 gamma TCR subunit, a CD3 delta TCR subunit, functional fragments thereof, and amino acid sequences thereof having at least one but not more than 20 modifications. In some instances, the encoded TFP includes a transmembrane domain that comprises a transmembrane domain of a protein selected from the group consisting of a TCR alpha chain, a TCR beta chain, a CD3 epsilon TCR subunit, a CD3 gamma TCR subunit, a CD3 delta TCR subunit, functional fragments thereof, and amino acid sequences thereof having at least one but not more than 20 modifications. In some instances, the encoded TFP includes a transmembrane domain that comprises a transmembrane domain of a protein selected from the group consisting of a TCR alpha chain, a TCR beta chain, a TCR zeta chain, a CD3 epsilon TCR subunit, a CD3 gamma TCR subunit, a CD3 delta TCR subunit, CD45, CD4, CD5, CD8, CD9, CD16, CD22, CD33, CD28, CD37, CD64, CD80, CD86, CD134, CD137, CD154, functional fragments thereof, and amino acid sequences thereof having at least one but not more than 20 modifications. In some instances, the isolated nucleic acid molecule further comprises a sequence encoding a costimulatory domain. In some instances, the costimulatory domain is a functional signaling domain obtained from a protein selected from the group consisting of OX40, CD2, CD27, CD28, CDS, ICAM-1, LFA-1 (CD11a/CD18), ICOS (CD278), and 4-1BB (CD137), and amino acid sequences thereof having at least one but not more than 20 modifications thereto. In some instances, the isolated nucleic acid molecule further comprises a leader sequence. In some instances, the isolated nucleic acid molecule is mRNA.

In some instances, the TFP includes an immunoreceptor tyrosine-based activation motif (ITAM) of a TCR subunit that comprises an ITAM or portion thereof of a protein selected from the group consisting of CD3 zeta TCR subunit, CD3 epsilon TCR subunit, CD3 gamma TCR subunit, CD3 delta TCR subunit, TCR zeta chain, Fc epsilon receptor 1 chain, Fc epsilon receptor 2 chain, Fc gamma receptor 1 chain, Fc gamma receptor 2a chain, Fc gamma receptor 2b1 chain, Fc gamma receptor 2b2 chain, Fc gamma receptor 3a chain, Fc gamma receptor 3b chain, Fc beta receptor 1 chain, TYROBP (DAP12), CD5, CD16a, CD16b, CD22, CD23, CD32, CD64, CD79a, CD79b, CD89, CD278, CD66d, functional fragments thereof, and amino acid sequences thereof having at least one but not more than 20 modifications thereto. In some instances, the ITAM replaces an ITAM of CD3 gamma, CD3 delta, or CD3 epsilon. In some instances, the ITAM is selected from the group consisting of CD3 zeta TCR subunit, CD3 epsilon TCR subunit, CD3 gamma TCR subunit, and CD3 delta TCR subunit and replaces a difference ITAM selected from the group consisting of CD3 zeta TCR subunit, CD3 epsilon TCR subunit, CD3 gamma TCR subunit, and CD3 delta TCR subunit.

In some instances, the nucleic acid comprises a nucleotide analog. In some instances, the nucleotide analog is selected from the group consisting of 2'-O-methyl, 2'-O-methoxyethyl (2'-0-MOE), 2'-O-aminopropyl, 2'-deoxy, T-deoxy-2'-fluoro, 2'-O-aminopropyl (2'-O-AP), 2'-O-dimethylaminoethyl (2'-O-DMAOE), 2'-O-dimethylaminopropyl (2'-O-DMAP), T-O-dimethylaminoethyloxyethyl (2'-O-DMAEOE), 2'-O—N-methylacetamido (2'-O-NMA) modified, a locked nucleic acid (LNA), an ethylene nucleic acid (ENA), a peptide nucleic acid (PNA), a 1',5'-anhydrohexitol nucleic acid (HNA), a morpholino, a methylphosphonate nucleotide, a thiolphosphonate nucleotide, and a 2'-fluoro N3-P5'-phosphoramidite In one aspect, provided herein is an isolated polypeptide molecule encoded by a nucleic acid molecule provided herein.

In one aspect, provided herein is an isolated TFP molecule comprising a human or humanized anti-CD19 binding domain, a TCR extracellular domain, a transmembrane domain, and an intracellular domain.

In one aspect, provided herein is an isolated TFP molecule comprising a human or humanized anti-CD19 binding domain, a TCR extracellular domain, a transmembrane domain, and an intracellular signaling domain, wherein the TFP molecule is capable of functionally interacting with an endogenous TCR complex and/or at least one endogenous TCR polypeptide.

In one aspect, provided herein is an isolated TFP molecule comprising a human or humanized anti-CD19 binding domain, a TCR extracellular domain, a transmembrane domain, and an intracellular signaling domain, wherein the TFP molecule is capable of functionally integrating into an endogenous TCR complex In some instances, the isolated TFP molecule comprises an antibody or antibody fragment comprising a human or humanized anti-CD19 binding domain, a TCR extracellular domain, a transmembrane domain, and an intracellular domain. In some instances, the anti-CD19 binding domain is a scFv or a $V_H$ domain. In some instances, the anti-CD19 binding domain comprises a heavy chain with 95-100% identity to an amino acid sequence of SEQ ID NO: 51, a functional fragment thereof, or an amino acid sequence thereof having at least one but not more than 30 modifications. In some instances, the anti-CD19 binding domain comprises a light chain with 95-100% identity to an amino acid sequence of SEQ ID NO: 49, a functional fragment thereof, or an amino acid sequence thereof having at least one but not more than 30 modifications. In some instances, the isolated TFP molecule comprises a TCR extracellular domain that comprises an extracellular domain or portion thereof of a protein selected from the group consisting of a TCR alpha chain, a TCR beta chain, a CD3 epsilon TCR subunit, a CD3 gamma TCR subunit, a CD3 delta TCR subunit, functional fragments thereof, and amino acid sequences thereof having at least one but not more than 20 modifications. In some instances, the anti-CD19 binding domain is connected to the TCR extracellular domain by a linker sequence. In some instances, the linker region comprises $(G_4S)_n$, wherein n=1 to 4 (SEQ ID NO: 66).

In one aspect, provided herein is an isolated TFP molecule comprising a human or humanized anti-BCMA binding domain, a TCR extracellular domain, a transmembrane domain, and an intracellular domain.

In one aspect, provided herein is an isolated TFP molecule comprising a human or humanized anti-BCMA binding domain, a TCR extracellular domain, a transmembrane domain, and an intracellular signaling domain, wherein the TFP molecule is capable of functionally interacting with an endogenous TCR complex and/or at least one endogenous TCR polypeptide.

In one aspect, provided herein is an isolated TFP molecule comprising a human or humanized anti-BCMA binding domain, a TCR extracellular domain, a transmembrane domain, and an intracellular signaling domain, wherein the TFP molecule is capable of functionally integrating into an endogenous TCR complex.

In some instances, the isolated TFP molecule comprises an antibody or antibody fragment comprising a human or humanized anti-BCMA binding domain, a TCR extracellular domain, a transmembrane domain, and an intracellular domain. In some instances, the anti-BCMA binding domain is a scFv or a $V_H$ domain. In some instances, the anti-BCMA binding domain comprises a heavy chain with 95-100% identity to an amino acid sequence of SEQ ID NO: 55, a functional fragment thereof, or an amino acid sequence thereof having at least one but not more than 30 modifications. In some instances, the anti-BCMA binding domain comprises a light chain with 95-100% identity to an amino acid sequence of SEQ ID NO: 53, a functional fragment thereof, or an amino acid sequence thereof having at least one but not more than 30 modifications. In some instances, the isolated TFP molecule comprises a TCR extracellular domain that comprises an extracellular domain or portion thereof of a protein selected from the group consisting of a TCR alpha chain, a TCR beta chain, a CD3 epsilon TCR subunit, a CD3 gamma TCR subunit, a CD3 delta TCR subunit, functional fragments thereof, and amino acid sequences thereof having at least one but not more than 20 modifications. In some instances, the anti-BCMA binding domain is connected to the TCR extracellular domain by a linker sequence. In some instances, the linker region comprises $(G_4S)_n$, wherein n=1 to 4 (SEQ ID NO: 66). In some instances, the isolated TFP molecule further comprises a sequence encoding a costimulatory domain. In some instances, the isolated TFP molecule further comprises a sequence encoding an intracellular signaling domain. In some instances, the isolated TFP molecule further comprises a leader sequence.

In one aspect, provided herein is a vector comprising a nucleic acid molecule encoding a TFP provided herein. In some instances, the vector is selected from the group consisting of a DNA, a RNA, a plasmid, a lentivirus vector, adenoviral vector, a Rous sarcoma viral (RSV) vector, or a retrovirus vector. In some instances, the vector further comprises a promoter. In some instances, the vector is an in vitro transcribed vector. In some instances, a nucleic acid sequence in the vector further comprises a poly(A) tail. In some instances, a nucleic acid sequence in the vector further comprises a 3'UTR.

In one aspect, provided herein is a cell comprising a vector provided herein. In some instances, the cell is a human T-cell. In some instances, the T-cell is a CD8+ or CD4+ T-cell. In some instances, the cell further comprises a nucleic acid encoding an inhibitory molecule that comprises a first polypeptide that comprises at least a portion of an inhibitory molecule, associated with a second polypeptide that comprises a positive signal from an intracellular signaling domain. In some instances, the inhibitory molecule comprise first polypeptide that comprises at least a portion of PD1 and a second polypeptide comprising a costimulatory domain and primary signaling domain.

In one aspect, provided herein is a human CD8+ or CD4+ T-cell comprising at least two TFP molecules, the TFP molecules comprising a human or humanized anti-CD19 binding domain, a TCR extracellular domain, a transmembrane domain, and an intracellular domain, wherein the TFP molecule is capable of functionally interacting with an endogenous TCR complex and/or at least one endogenous TCR polypeptide in, at and/or on the surface of the human CD8+ or CD4+ T-cell.

In one aspect, provided herein is a protein complex comprising: a TFP molecule comprising a human or humanized anti-CD19 binding domain, a TCR extracellular domain, a transmembrane domain, and an intracellular domain; and at least one endogenous TCR complex.

In some instances, the TCR comprises an extracellular domain or portion thereof of a protein selected from the group consisting of TCR alpha chain, a TCR beta chain, a CD3 epsilon TCR subunit, a CD3 gamma TCR subunit, and a CD3 delta TCR subunit. In some instances, the anti-CD19 binding domain is connected to the TCR extracellular domain by a linker sequence. In some instances, the linker region comprises $(G_4S)_n$, wherein n=1 to 4 (SEQ ID NO: 66).

In one aspect, provided herein is a protein complex comprising: a TFP molecule comprising a human or humanized anti-BCMA binding domain, a TCR extracellular domain, a transmembrane domain, and an intracellular domain; and at least one endogenous TCR complex.

In some instances, the TCR comprises an extracellular domain or portion thereof of a protein selected from the group consisting of TCR alpha chain, a TCR beta chain, a CD3 epsilon TCR subunit, a CD3 gamma TCR subunit, and a CD3 delta TCR subunit. In some instances, the anti-BCMA binding domain is connected to the TCR extracellular domain by a linker sequence. In some instances, the linker region comprises $(G_4S)_n$, wherein n=1 to 4 (SEQ ID NO: 66).

In one aspect, provided herein is a human CD8+ or CD4+ T-cell comprising at least two different TFP proteins per a protein complex provided herein.

In one aspect, provided herein is a method of making a cell comprising transducing a T-cell with a vector provided herein.

In one aspect, provided herein is a method of generating a population of RNA-engineered cells comprising introducing an in vitro transcribed RNA or synthetic RNA into a cell, where the RNA comprises a nucleic acid encoding a TFP molecule provided herein.

In one aspect, provided herein is a method of providing an anti-tumor immunity in a mammal comprising administering to the mammal an effective amount of a cell expressing a TFP molecule provided herein, or expressing a polypeptide molecule provided herein.

In some instances, the cell is an autologous T-cell. In some instances, the cell is an allogeneic T-cell. In some instances, the mammal is a human.

In one aspect, provided herein is a method of treating a mammal having a disease associated with expression of CD19 or BCMA comprising administering to the mammal an effective amount of a TFP molecule provided herein, a cell provided herein, or a polypeptide molecule provided herein.

In some instances, the disease associated with CD19 or BCMA expression is selected from the group consisting of a proliferative disease, a cancer, a malignancy, myelodysplasia, a myelodysplastic syndrome, a preleukemia, a non-cancer related indication associated with expression of CD19. In some instances, the disease is a hematologic cancer selected from the group consisting of B-cell acute lymphoid leukemia (B-ALL), T-cell acute lymphoid leukemia (T-ALL), acute lymphoblastic leukemia (ALL); chronic myelogenous leukemia (CML), chronic lymphocytic leukemia (CLL), B cell prolymphocytic leukemia, blastic plasmacytoid dendritic cell neoplasm, Burkitt's lymphoma, diffuse large B cell lymphoma, follicular lymphoma, hairy cell leukemia, small cell-follicular lymphoma, large cell-follicular lymphoma, malignant lymphoproliferative conditions, MALT lymphoma, mantle cell lymphoma, Marginal zone lymphoma, multiple myeloma, myelodysplasia, myelodysplastic syndrome, non-Hodgkin's lymphoma, plasmablastic lymphoma, plasmacytoid dendritic cell neoplasm, Waldenstrom macroglobulinemia, preleukemia, a disease associated with CD19 or BCMA expression, and combinations thereof. In some instances, the cells expressing a TFP molecule are administered in combination with an agent that increases the efficacy of a cell expressing a TFP molecule. In some instances, less cytokines are released in the mammal compared a mammal administered an effective amount of a T-cell expressing an anti-CD19 chimeric antigen receptor (CAR) or an anti-BCMA CAR. In some instances, the cells expressing a TFP molecule are administered in combination with an agent that ameliorates one or more side effects associated with administration of a cell expressing a TFP molecule. In some instances, the cells expressing a TFP molecule are administered in combination with an agent that treats the disease associated with CD19 or BCMA.

In one aspect, an isolated nucleic acid molecule provided herein, an isolated polypeptide molecule provided herein, an isolated TFP provided herein, a complex provided herein, a vector provided herein, or a cell provided herein, is for use as a medicament.

In one aspect, provided herein is a method of treating a mammal having a disease associated with expression of CD19 or BCMA comprising administering to the mammal an effective amount of a TFP molecule provided herein, a cell provided herein, or a polypeptide molecule provided herein, wherein less cytokines are released in the mammal compared a mammal administered an effective amount of a T-cell expressing an anti-CD19 chimeric antigen receptor (CAR) or an anti-BCMA CAR.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

Figure 1:
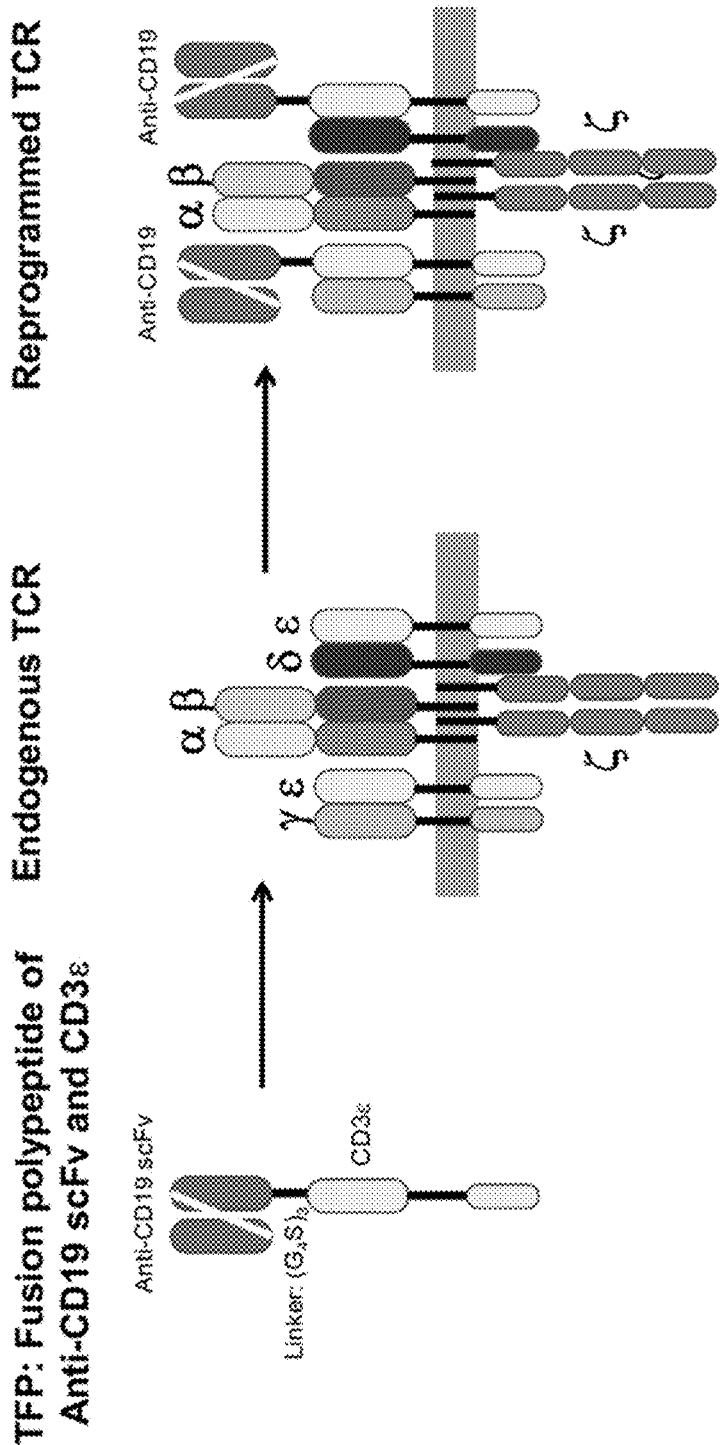
FIG. 1 is a schematic illustration demonstrating the use of T-cell receptor fusion polypeptides (TFPs) of the invention. An exemplary TFP contains an anti-CD19 scFv and a full-length CD3 epsilon polypeptide fused via a $(G_4S)_3$ (SEQ ID NO: 71) linker sequence. When produced by or introduced into a T-cell, the TFP associates with other polypeptides of the endogenous T-cell receptor (TCR) (shown to include two CD3 epsilon polypeptides, one CD3 gamma polypeptide, one CD3 delta polypeptide, two CD3 zeta polypeptides, one TCR alpha subunit and one TCR beta subunit, where the horizontal grey segment represents the plasma membrane) to form a reprogrammed TCR in which one or both of the endogenous CD3 epsilon polypeptides are substituted by the TFP.
Figures 2A, 2B, 2C, 2D:
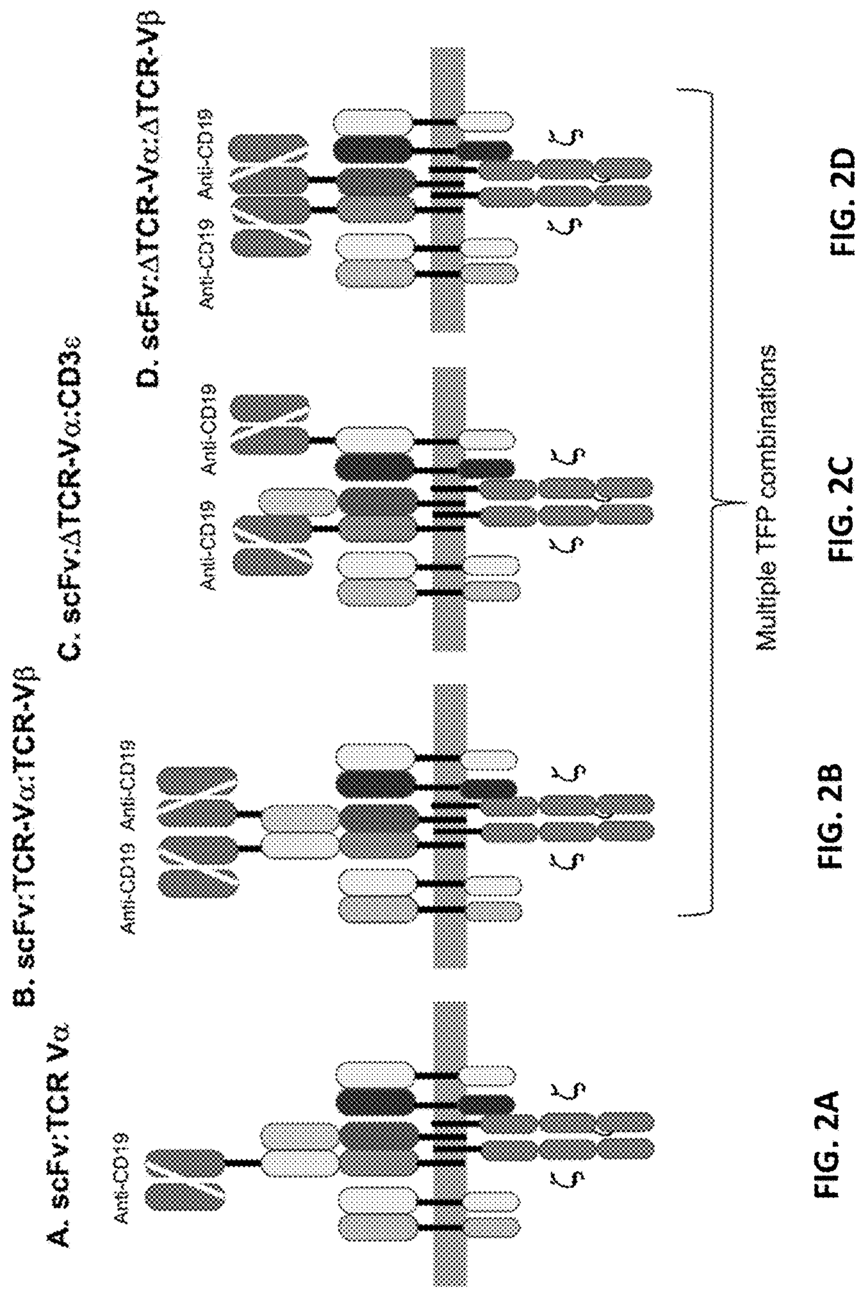
FIG. 2A represents schematic illustrations demonstrating exemplary variations of reprogrammed T-cell receptor fusion polypeptides (TFPs) of the invention. An exemplary reprogrammed TCR containing a TFP that contains an anti-CD19 scFv and a full-length TCR Vα polypeptide fused via a $(G_4S)_3$ (SEQ ID NO: 71) linker sequence is illustrated.
FIG. 2B illustrates a series of exemplary reprogrammed TCRs that contain multiple TFPs including i) an anti-CD19 scFv and a full-length TCR Vα polypeptide fused via a $(G_4S)_3$ (SEQ ID NO: 71) linker sequence and ii) an anti-CD19 scFv and a full-length TCR polypeptide fused via a $(G_4S)_3$ (SEQ ID NO: 71) linker sequence.
FIG. 2C illustrates an exemplary reprogrammed TCR that contains multiple TFPs including i) an anti-CD19 scFv and a truncated (A) TCR polypeptide fused via a $(G_4S)_3$ (SEQ ID NO: 71) linker sequence and ii) an anti-CD19 scFv and a full-length CD3 epsilon polypeptide fused via a $(G_4S)_3$ (SEQ ID NO: 71) linker sequence. The truncated (A) TCR polypeptide is truncated by the deletion of the Vα.
FIG. 2D illustrates an exemplary reprogrammed TCR that contains multiple TFPs including i) an anti-CD19 scFv and a truncated (Δ) TCR Vα polypeptide fused via a $(G_4S)_3$ (SEQ ID NO: 71) linker sequence and ii) an anti-CD19 scFv and a truncated (Δ) TCR polypeptide fused via a $(G_4S)_3$ (SEQ ID NO: 71) linker sequence. The truncated (Δ) TCR polypeptide is truncated by the deletion of the VP.
Figure 3:
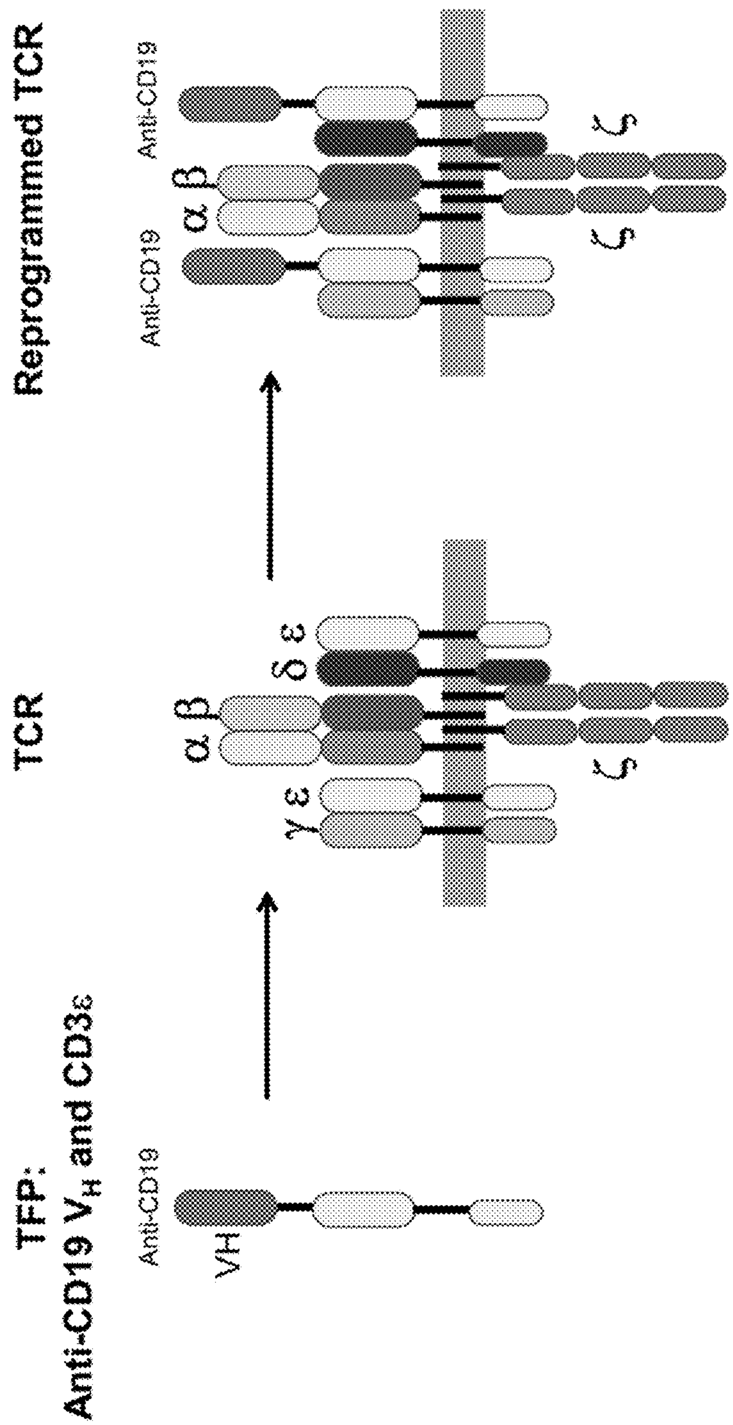
FIG. 3 is a schematic illustration demonstrating the use of T-cell receptor fusion polypeptides (TFPs) of the invention. An exemplary TFP contains an anti-CD19 $V_H$ domain and a full-length CD3 epsilon polypeptide fused via a $(G_4S)_3$ (SEQ ID NO: 71) linker sequence. When produced by a T-cell or introduced into a T-cell, the TFP associates with other polypeptides of the endogenous T-cell receptor (TCR) (shown to include two CD3 epsilon polypeptides, one CD3 gamma polypeptide, one CD3 delta polypeptide, two CD3 zeta polypeptides, one TCR alpha subunit and one TCR beta subunit, where the horizontal grey segment represents the plasma membrane) to form a reprogrammed TCR in which one or both of the endogenous CD3 epsilon polypeptides are substituted by the TFP.
Figure 4:
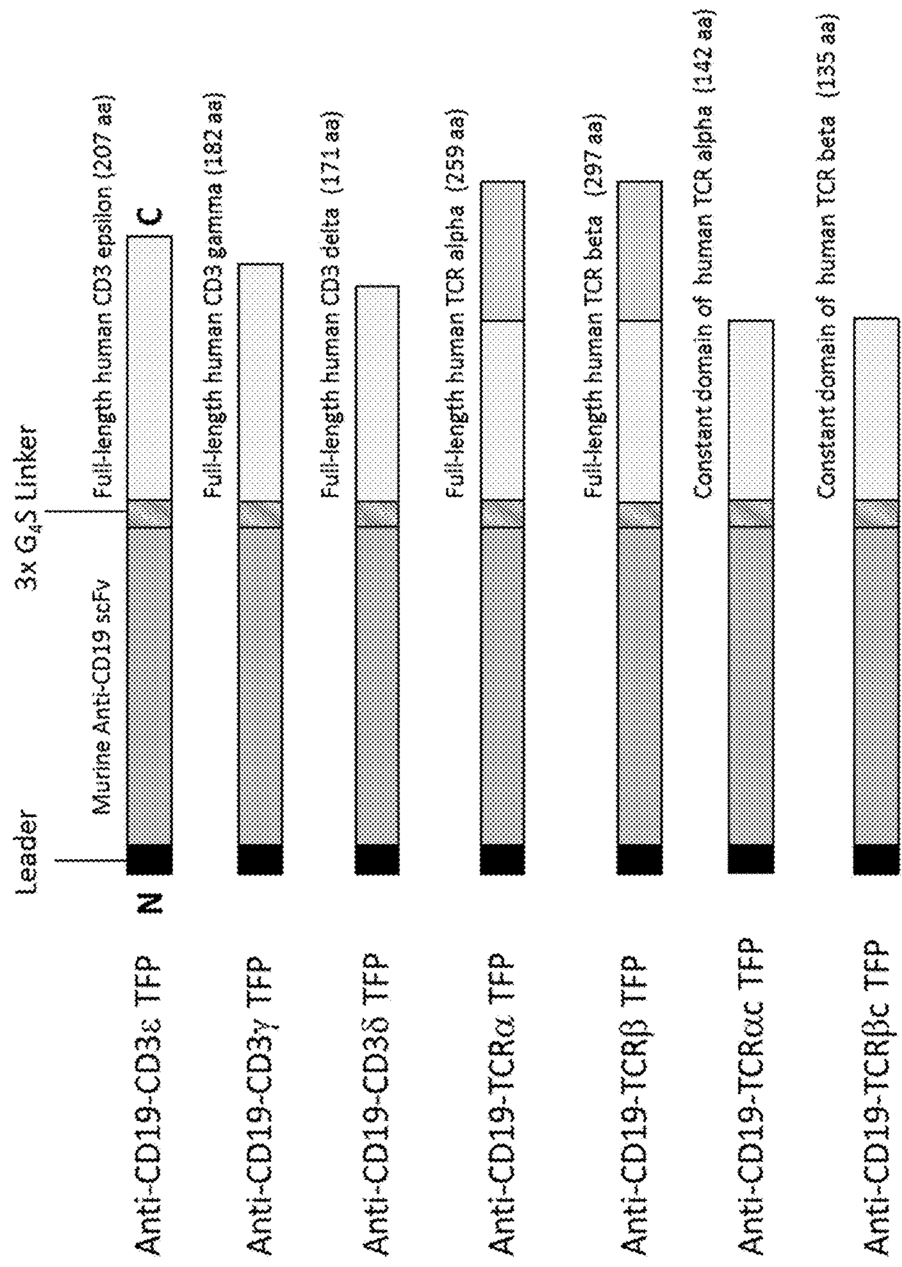
FIG. 4 is a series of schematic illustrations demonstrating DNA constructs encoding various TFPs ("$3\times G_4S$" disclosed as SEQ ID NO: 71).

In one aspect, described herein are isolated nucleic acid molecules encoding a T-cell Receptor (TCR) fusion protein (TFP) that comprise a TCR subunit and a human or humanized antibody domain comprising an anti-CD19 binding domain. In some embodiments, the TCR subunit comprises a TCR extracellular domain. In other embodiments, the TCR subunit comprises a TCR transmembrane domain. In yet other embodiments, the TCR subunit comprises a TCR intracellular domain. In further embodiments, the TCR subunit comprises (i) a TCR extracellular domain, (ii) a TCR transmembrane domain, and (iii) a TCR intracellular domain, wherein at least two of (i), (ii), and (iii) are from the same TCR subunit. In yet further embodiments, the TCR subunit comprises a TCR intracellular domain comprising a stimulatory domain selected from an intracellular signaling domain of CD3 epsilon, CD3 gamma or CD3 delta, or an amino acid sequence having at least one, two or three modifications thereto. In yet further embodiments, the TCR subunit comprises an intracellular domain comprising a stimulatory domain selected from a functional signaling domain of 4-1BB and/or a functional signaling domain of CD3 zeta, or an amino acid sequence having at least one, two or three modifications thereto.

In some embodiments, the human or humanized antibody domain comprises an antibody fragment. In some embodiments, the human or humanized antibody domain comprises a scFv or a $V_H$ domain.

In some embodiments, the isolated nucleic acid molecules comprise (i) a light chain (LC) CDR1, LC CDR2 and LC CDR3 of any anti-CD19 light chain binding domain amino acid sequence provided herein, and/or (ii) a heavy chain (HC) CDR1, HC CDR2 and HC CDR3 of any anti-CD19 heavy chain binding domain amino acid sequence provided herein.

In some embodiments, the light chain variable region comprises an amino acid sequence having at least one, two or three modifications but not more than 30, 20 or 10 modifications of an amino acid sequence of a light chain variable region provided herein, or a sequence with 95-99% identity to an amino acid sequence provided herein. In other embodiments, the heavy chain variable region comprises an amino acid sequence having at least one, two or three modifications but not more than 30, 20 or 10 modifications of an amino acid sequence of a heavy chain variable region provided herein, or a sequence with 95-99% identity to an amino acid sequence provided herein.

In some embodiments, the TFP includes an extracellular domain of a TCR subunit that comprises an extracellular domain or portion thereof of a protein selected from the group consisting of the alpha or beta chain of the T-cell receptor, CD3 delta, CD3 epsilon, or CD3 gamma, or a functional fragment thereof, or an amino acid sequence having at least one, two or three modifications but not more than 20, 10 or 5 modifications thereto. In other embodiments, the encoded TFP includes a transmembrane domain that comprises a transmembrane domain of a protein selected from the group consisting of the alpha, beta chain of the TCR or TCR subunits CD3 epsilon, CD3 gamma and CD3 delta, or a functional fragment thereof, or an amino acid sequence having at least one, two or three modifications but not more than 20, 10 or 5 modifications thereto.

In some embodiments, the encoded TFP includes a transmembrane domain that comprises a transmembrane domain of a protein selected from the group consisting of the alpha, beta or zeta chain of the TCR or CD3 epsilon, CD3 gamma and CD3 delta CD45, CD4, CD5, CD8, CD9, CD16, CD22, CD33, CD28, CD37, CD64, CD80, CD86, CD134, CD137 and CD154, or a functional fragment thereof, or an amino acid sequence having at least one, two or three modifications but not more than 20, 10 or 5 modifications thereto.

In some embodiments, the encoded anti-CD19 binding domain is connected to the TCR extracellular domain by a linker sequence. In some instances, the encoded linker sequence comprises $(G_4S)_n$, wherein n=1 to 4 (SEQ ID NO: 66). In some instances, the encoded linker sequence comprises a long linker (LL) sequence. In some instances, the encoded long linker sequence comprises $(G_4S)_n$, wherein n=2 to 4 (SEQ ID NO: 67). In some instances, the encoded linker sequence comprises a short linker (SL) sequence. In some instances, the encoded short linker sequence comprises $(G_4S)_n$, wherein n=1 to 3 (SEQ ID NO: 68).

In some embodiments, the isolated nucleic acid molecules further comprise a sequence encoding a costimulatory domain. In some instances, the costimulatory domain is a functional signaling domain obtained from a protein selected from the group consisting of OX40, CD2, CD27, CD28, CDS, ICAM-1, LFA-1 (CD11a/CD18), ICOS (CD278), and 4-1BB (CD137), or an amino acid sequence having at least one, two or three modifications but not more than 20, 10 or 5 modifications thereto.

In some embodiments, the isolated nucleic acid molecules further comprise a leader sequence.

Also provided herein are isolated polypeptide molecules encoded by any of the previously described nucleic acid molecules.

Also provided herein in another aspect, are isolated T-cell receptor fusion protein (TFP) molecules that comprise a human or humanized anti-CD19 binding domain, a TCR extracellular domain, a transmembrane domain, and an intracellular domain. In some embodiments, the isolated TFP molecules comprises an antibody or antibody fragment comprising a human or humanized anti-CD19 binding domain, a TCR extracellular domain, a transmembrane domain, and an intracellular domain.

In some embodiments, the anti-CD19 binding domain is a scFv or a $V_H$ domain. In other embodiments, the anti-CD19 binding domain comprises a light chain and a heavy chain of an amino acid sequence provided herein, or a functional fragment thereof, or an amino acid sequence having at least one, two or three modifications but not more than 30, 20 or 10 modifications of an amino acid sequence of a light chain variable region provided herein, or a sequence with 95-99% identity with an amino acid sequence provided herein.

In some embodiments, the isolated TFP molecules comprise a TCR extracellular domain that comprises an extracellular domain or portion thereof of a protein selected from the group consisting of the alpha or beta chain of the T-cell receptor, CD3 delta, CD3 epsilon, or CD3 gamma, or an amino acid sequence having at least one, two or three modifications but not more than 20, 10 or 5 modifications thereto.

In some embodiments, the anti-CD19 binding domain is connected to the TCR extracellular domain by a linker sequence. In some instances, the linker region comprises $(G_4S)_n$, wherein n=1 to 4 (SEQ ID NO: 66). In some instances, the linker sequence comprises a long linker (LL) sequence. In some instances, the long linker sequence comprises $(G_4S)_n$, wherein n=2 to 4 (SEQ ID NO: 67). In some instances, the linker sequence comprises a short linker (SL)

sequence. In some instances, the short linker sequence comprises $(G_4S)_n$, wherein n=1 to 3 (SEQ ID NO: 68).

In some embodiments, the isolated TFP molecules further comprise a sequence encoding a costimulatory domain. In other embodiments, the isolated TFP molecules further comprise a sequence encoding an intracellular signaling domain. In yet other embodiments, the isolated TFP molecules further comprise a leader sequence.

Also provided herein are vectors that comprise a nucleic acid molecule encoding any of the previously described TFP molecules. In some embodiments, the vector is selected from the group consisting of a DNA, a RNA, a plasmid, a lentivirus vector, adenoviral vector, or a retrovirus vector. In some embodiments, the vector further comprises a promoter. In some embodiments, the vector is an in vitro transcribed vector. In some embodiments, a nucleic acid sequence in the vector further comprises a poly(A) tail. In some embodiments, a nucleic acid sequence in the vector further comprises a 3'UTR.

Also provided herein are cells that comprise any of the described vectors. In some embodiments, the cell is a human T-cell. In some embodiments, the cell is a CD8+ or CD4+ T-cell. In other embodiments, the cells further comprise a nucleic acid encoding an inhibitory molecule that comprises a first polypeptide that comprises at least a portion of an inhibitory molecule, associated with a second polypeptide that comprises a positive signal from an intracellular signaling domain. In some instances, the inhibitory molecule comprise first polypeptide that comprises at least a portion of PD1 and a second polypeptide comprising a costimulatory domain and primary signaling domain.

In another aspect, provided herein are isolated TFP molecules that comprise a human or humanized anti-CD19 binding domain, a TCR extracellular domain, a transmembrane domain, and an intracellular signaling domain, wherein the TFP molecule is capable of functionally interacting with an endogenous TCR complex and/or at least one endogenous TCR polypeptide.

In another aspect, provided herein are isolated TFP molecules that comprise a human or humanized anti-CD19 binding domain, a TCR extracellular domain, a transmembrane domain, and an intracellular signaling domain, wherein the TFP molecule is capable of functionally integrating into an endogenous TCR complex.

In another aspect, provided herein are human CD8+ or CD4+ T-cells that comprise at least two TFP molecules, the TFP molecules comprising a human or humanized anti-CD19 binding domain, a TCR extracellular domain, a transmembrane domain, and an intracellular domain, wherein the TFP molecule is capable of functionally interacting with an endogenous TCR complex and/or at least one endogenous TCR polypeptide in, at and/or on the surface of the human CD8+ or CD4+ T-cell.

In another aspect, provided herein are protein complexes that comprise i) a TFP molecule comprising a human or humanized anti-CD19 binding domain, a TCR extracellular domain, a transmembrane domain, and an intracellular domain; and ii) at least one endogenous TCR complex.

In some embodiments, the TCR comprises an extracellular domain or portion thereof of a protein selected from the group consisting of the alpha or beta chain of the T-cell receptor, CD3 delta, CD3 epsilon, or CD3 gamma. In some embodiments, the anti-CD19 binding domain is connected to the TCR extracellular domain by a linker sequence. In some instances, the linker region comprises $(G_4S)_n$, wherein n=1 to 4 (SEQ ID NO: 66). In some instances, the linker sequence comprises a long linker (LL) sequence. In some instances, the long linker sequence comprises $(G_4S)_n$, wherein n=2 to 4 (SEQ ID NO: 67). In some instances, the linker sequence comprises a short linker (SL) sequence. In some instances, the short linker sequence comprises $(G_4S)_n$, wherein n=1 to 3 (SEQ ID NO: 68).

Also provided herein are human CD8+ or CD4+ T-cells that comprise at least two different TFP proteins per any of the described protein complexes.

In another aspect, provided herein is a population of human CD8+ or CD4+ T-cells, wherein the T-cells of the population individually or collectively comprise at least two TFP molecules, the TFP molecules comprising a human or humanized anti-CD19 or anti-BCMA binding domain, a TCR extracellular domain, a transmembrane domain, and an intracellular domain, wherein the TFP molecule is capable of functionally interacting with an endogenous TCR complex and/or at least one endogenous TCR polypeptide in, at and/or on the surface of the human CD8+ or CD4+ T-cell.

In another aspect, provided herein is a population of human CD8+ or CD4+ T-cells, wherein the T-cells of the population individually or collectively comprise at least two TFP molecules encoded by an isolated nucleic acid molecule provided herein.

In another aspect, provided herein are methods of making a cell that comprise transducing a T-cell with any of the described vectors.

In another aspect, provided herein are methods of generating a population of RNA-engineered cells that comprise introducing an in vitro transcribed RNA or synthetic RNA into a cell, where the RNA comprises a nucleic acid encoding any of the described TFP molecules.

In another aspect, provided herein are methods of providing an anti-tumor immunity in a mammal that comprise administering to the mammal an effective amount of a cell expressing any of the described TFP molecules. In some embodiments, the cell is an autologous T-cell. In some embodiments, the cell is an allogeneic T-cell. In some embodiments, the mammal is a human.

In another aspect, provided herein are methods of treating a mammal having a disease associated with expression of CD19 that comprise administering to the mammal an effective amount of the cell of comprising any of the described TFP molecules. In some embodiments, the disease associated with CD19 expression is selected from a proliferative disease such as a cancer or malignancy or a precancerous condition such as a myelodysplasia, a myelodysplastic syndrome or a preleukemia, or is a non-cancer related indication associated with expression of CD19. In some embodiments, the disease is a hematologic cancer selected from the group consisting of one or more acute leukemias including but not limited to B-cell acute lymphoid leukemia ("B-ALL"), T-cell acute lymphoid leukemia ("T-ALL"), acute lymphoblastic leukemia (ALL); one or more chronic leukemias including but not limited to chronic myelogenous leukemia (CML), chronic lymphocytic leukemia (CLL); additional hematologic cancers or hematologic conditions including, but not limited to B cell prolymphocytic leukemia, blastic plasmacytoid dendritic cell neoplasm, Burkitt's lymphoma, diffuse large B cell lymphoma, follicular lymphoma, hairy cell leukemia, small cell- or a large cell-follicular lymphoma, malignant lymphoproliferative conditions, MALT lymphoma, mantle cell lymphoma, Marginal zone lymphoma, multiple myeloma, myelodysplasia and myelodysplastic syndrome, non-Hodgkin's lymphoma, plasmablastic lymphoma, plasmacytoid dendritic cell neoplasm, Waldenstrom macroglobulinemia, and "preleukemia" which are a diverse collection of hematological conditions united by ineffective production (or dysplasia) of myeloid blood cells, and to disease associated with CD19 expression include, but not limited to atypical and/or non-classical cancers, malignancies, precancerous conditions or proliferative diseases expressing CD19; and combinations thereof.

In some embodiments, the cells expressing any of the described TFP molecules are administered in combination with an agent that ameliorates one or more side effects associated with administration of a cell expressing a TFP molecule. In some embodiments, the cells expressing any of the described TFP molecules are administered in combination with an agent that treats the disease associated with CD19.

Also provided herein are any of the described isolated nucleic acid molecules, any of the described isolated polypeptide molecules, any of the described isolated TFPs, any of the described protein complexes, any of the described vectors or any of the described cells for use as a medicament

Definitions

Unless defined otherwise, all technical and scientific terms used herein have the same meaning as commonly understood by one of ordinary skill in the art to which the invention pertains.

The term "a" and "an" refers to one or to more than one (i.e., to at least one) of the grammatical object of the article. By way of example, "an element" means one element or more than one element.

As used herein, "about" can mean plus or minus less than 1 or 1, 2, 3, 4, 5, 6, 7, 8, 9, 10, 11, 12, 13, 14, 15, 16, 17, 18, 19, 20, 25, 30, or greater than 30 percent, depending upon the situation and known or knowable by one skilled in the art.

As used herein the specification, "subject" or "subjects" or "individuals" may include, but are not limited to, mammals such as humans or non-human mammals, e.g., domesticated, agricultural or wild, animals, as well as birds, and aquatic animals. "Patients" are subjects suffering from or at risk of developing a disease, disorder or condition or otherwise in need of the compositions and methods provided herein.

As used herein, "treating" or "treatment" refers to any indicia of success in the treatment or amelioration of the disease or condition. Treating can include, for example, reducing, delaying or alleviating the severity of one or more symptoms of the disease or condition, or it can include reducing the frequency with which symptoms of a disease, defect, disorder, or adverse condition, and the like, are experienced by a patient. As used herein, "treat or prevent" is sometimes used herein to refer to a method that results in some level of treatment or amelioration of the disease or condition, and contemplates a range of results directed to that end, including but not restricted to prevention of the condition entirely.

As used herein, "preventing" refers to the prevention of the disease or condition, e.g., tumor formation, in the patient. For example, if an individual at risk of developing a tumor or other form of cancer is treated with the methods of the present invention and does not later develop the tumor or other form of cancer, then the disease has been prevented, at least over a period of time, in that individual.

As used herein, a "therapeutically effective amount" is the amount of a composition or an active component thereof sufficient to provide a beneficial effect or to otherwise reduce a detrimental non-beneficial event to the individual to whom the composition is administered. By "therapeutically effective dose" herein is meant a dose that produces one or more desired or desirable (e.g., beneficial) effects for which it is administered, such administration occurring one or more times over a given period of time. The exact dose will depend on the purpose of the treatment, and will be ascertainable by one skilled in the art using known techniques (see, e.g. Lieberman, Pharmaceutical Dosage Forms (vols. 1-3, 1992); Lloyd, *The Art, Science and Technology of Pharmaceutical Compounding* (1999); and Pickar, *Dosage Calculations* (1999))

As used herein, a "T-cell receptor (TCR) fusion protein" or "TFP" includes a recombinant polypeptide derived from the various polypeptides comprising the TCR that is generally capable of i) binding to a surface antigen on target cells and ii) interacting with other polypeptide components of the intact TCR complex, typically when co-located in or on the surface of a T-cell.

As used herein, the term "CD19" refers to the Cluster of Differentiation 19 protein, which is an antigenic determinant detectable on B cell leukemia precursor cells, other malignant B cells and most cells of the normal B cell lineage. The human and murine amino acid and nucleic acid sequences can be found in a public database, such as GenBank, UniProt and Swiss-Prot. For example, the amino acid sequence of human CD19 can be found as UniProt/Swiss-Prot Accession No. P15391. The human CD19 polypeptide canonical sequence is UniProt Accession No. P15391 (or P15391-1):

```
                                          (SEQ ID NO: 1)
MPPPRLLFFLLFLTPMEVRPEEPLVVKVEEGDNAVLQCLKGTSDGPTQQL

TWSRESPLKPFLKLSLGLPGLGIHMRPLAIWLFIFNVSQQMGGFYLCQPG

PPSEKAWQPGWTVNVEGSGELFRWNVSDLGGLGCGLKNRSSEGPSSPSGK

LMSPKLYVWAKDRPEIWEGEPPCLPPRDSLNQSLSQDLTMAPGSTLWLSC

GVPPDSVSRGPLSWTHVHPKGPKSLLSLELKDDRPARDMWVMETGLLLPR

ATAQDAGKYYCHRGNLTMSFHLEITARPVLWHWLLRTGGWKVSAVTLAYL

IFCLCSLVGILHLQRALVLRRKRKRMTDPTRRFFKVTPPPGSGPQNQYGN

VLSLPTPTSGLGRAQRWAAGLGGTAPSYGNPSSDVQADGALGSRSPPGVG

PEEEEGEGYEEPDSEEDSEFYENDSNLGQDQLSQDGSGYENPEDEPLGPE

DEDSFSNAESYENEDEELTQPVARTMDFLSPHGSAWDPSREATSLGSQSY

EDMRGILYAAPQLRSIRGQPGPNHEEDADSYENMDNPDGPDPAWGGGGRM

GTWSTR.
```

The nucleotide sequence encoding of the human CD19 can be found at Accession No. NM001178098. CD19 is expressed on most B lineage cancers, including, e.g., ALL, CLL and non-Hodgkin's lymphoma (NHL). Other cells that express CD19 are provided below in the definition of "disease associated with expression of CD19." It is also an early marker of normal B cell progenitors. See, e.g., Nicholson et al. Mol. Immun 34 (16-17): 1157-1165 (1997). In one example, the antigen-binding portion of TFPs recognizes and binds an epitope within the extracellular domain of the CD19 protein as expressed on a malignant and normal B cell.

As used herein, the term "BCMA" refers to the B-cell maturation antigen also known as tumor necrosis factor receptor superfamily member 17 (TNFRSF17) and Cluster of Differentiation 269 protein (CD269) is a protein that in humans is encoded by the TNFRSF17 gene. TNFRSF17 is a cell surface receptor of the TNF receptor superfamily which recognizes B-cell activating factor (BAFF) (see, e.g., Laabi et al., EMBO 11 (11): 3897-904 (1992). This receptor is expressed in mature B lymphocytes, and may be important for B-cell development and autoimmune response. The human and murine amino acid and nucleic acid sequences can be found in a public database, such as GenBank, UniProt and Swiss-Prot. For example, the amino acid sequence of human BCMA can be found as UniProt/Swiss-Prot Accession No. Q02223. The human BCMA polypeptide canonical sequence is UniProt Accession No. Q02223 (or Q02223-1):

```
                                         (SEQ ID NO: 2)
MLQMAGQCSQNEYFDSLLHACIPCQLRCSSNTPPLTCQRYCNASVTNSVK

GTNAILWTCLGLSLIISLAVFVLMFLLRKINSEPLKDEFKNTGSGLLGMA

NIDLEKSRTGDEIILPRGLEYTVEECTCEDCIKSKPKVDSDHCFPLPAME

EGATILVTTKTNDYCKSLPAALSATEIEKSISAR.
```

The nucleotide sequence encoding of the human BCMA-can be found at Accession No. NM001192. BCMA is expressed on most B-lineage cancers, including, e.g., leukemia, lymphomas, and multiple myeloma. Other cells that express BCMA are provided below in the definition of "disease associated with expression of BCMA." This receptor has been shown to specifically bind to the tumor necrosis factor (ligand) superfamily, member 13b (TNFSF13B/TALL-1/BAFF), and to lead to NF-kappaB and MAPK8/JNK activation. This receptor also binds to various TRAF family members, and thus may transduce signals for cell survival and proliferation (see, e.g., Laabi et al., Nucleic Acids Research 22 (7): 1147-54 (1994). In one example, the antigen-binding portion of TFPs recognizes and binds an epitope within the extracellular domain of the BCMA protein as expressed on a malignant and normal B cell.

The term "antibody," as used herein, refers to a protein, or polypeptide sequences derived from an immunoglobulin molecule, which specifically binds to an antigen. Antibodies can be intact immunoglobulins of polyclonal or monoclonal origin, or fragments thereof and can be derived from natural or from recombinant sources.

The terms "antibody fragment" or "antibody binding domain" refer to at least one portion of an antibody, or recombinant variants thereof, that contains the antigen binding domain, i.e., an antigenic determining variable region of an intact antibody, that is sufficient to confer recognition and specific binding of the antibody fragment to a target, such as an antigen and its defined epitope. Examples of antibody fragments include, but are not limited to, Fab, Fab', $F(ab')_2$, and Fv fragments, single-chain (sc)Fv ("scFv") antibody fragments, linear antibodies, single domain antibodies such as sdAb (either $V_L$ or $V_H$), camelid $V_{HH}$ domains, and multi-specific antibodies formed from antibody fragments.

The term "scFv" refers to a fusion protein comprising at least one antibody fragment comprising a variable region of a light chain and at least one antibody fragment comprising a variable region of a heavy chain, wherein the light and heavy chain variable regions are contiguously linked via a short flexible polypeptide linker, and capable of being expressed as a single polypeptide chain, and wherein the scFv retains the specificity of the intact antibody from which it is derived.

"Heavy chain variable region" or "$V_H$" with regard to an antibody refers to the fragment of the heavy chain that contains three CDRs interposed between flanking stretches known as framework regions, these framework regions are generally more highly conserved than the CDRs and form a scaffold to support the CDRs.

Unless specified, as used herein a scFv may have the $V_L$ and $V_H$ variable regions in either order, e.g., with respect to the N-terminal and C-terminal ends of the polypeptide, the scFv may comprise $V_L$-linker-$V_H$ or may comprise $V_H$-linker-$V_L$.

The portion of the TFP composition of the invention comprising an antibody or antibody fragment thereof may exist in a variety of forms where the antigen binding domain is expressed as part of a contiguous polypeptide chain including, for example, a single domain antibody fragment (sdAb), a single chain antibody (scFv) derived from a murine, humanized or human antibody (Harlow et al., 1999, In: Using Antibodies: A Laboratory Manual, Cold Spring Harbor Laboratory Press, N.Y.; Harlow et al., 1989, In: Antibodies: A Laboratory Manual, Cold Spring Harbor, N.Y.; Houston et al., 1988, Proc. Natl. Acad. Sci. USA 85:5879-5883; Bird et al., 1988, Science 242:423-426). In one aspect, the antigen binding domain of a TFP composition of the invention comprises an antibody fragment. In a further aspect, the TFP comprises an antibody fragment that comprises a scFv or a sdAb.

The term "antibody heavy chain," refers to the larger of the two types of polypeptide chains present in antibody molecules in their naturally occurring conformations, and which normally determines the class to which the antibody belongs.

The term "antibody light chain," refers to the smaller of the two types of polypeptide chains present in antibody molecules in their naturally occurring conformations. Kappa ("κ") and lambda ("λ") light chains refer to the two major antibody light chain isotypes.

The term "recombinant antibody" refers to an antibody that is generated using recombinant DNA technology, such as, for example, an antibody expressed by a bacteriophage or yeast expression system. The term should also be construed to mean an antibody which has been generated by the synthesis of a DNA molecule encoding the antibody and which DNA molecule expresses an antibody protein, or an amino acid sequence specifying the antibody, wherein the DNA or amino acid sequence has been obtained using recombinant DNA or amino acid sequence technology which is available and well known in the art.

The term "antigen" or "Ag" refers to a molecule that is capable of being bound specifically by an antibody, or otherwise provokes an immune response. This immune response may involve either antibody production, or the activation of specific immunologically-competent cells, or both.

The skilled artisan will understand that any macromolecule, including virtually all proteins or peptides, can serve as an antigen. Furthermore, antigens can be derived from recombinant or genomic DNA. A skilled artisan will understand that any DNA, which comprises a nucleotide sequences or a partial nucleotide sequence encoding a protein that elicits an immune response therefore encodes an "antigen" as that term is used herein. Furthermore, one skilled in the art will understand that an antigen need not be encoded solely by a full length nucleotide sequence of a gene. It is readily apparent that the present invention includes, but is not limited to, the use of partial nucleotide sequences of more than one gene and that these nucleotide sequences are arranged in various combinations to encode polypeptides that elicit the desired immune response. Moreover, a skilled artisan will understand that an antigen need not be encoded by a "gene" at all. It is readily apparent that an antigen can be generated synthesized or can be derived from a biological sample, or might be macromolecule besides a polypeptide. Such a biological sample can include, but is not limited to a tissue sample, a tumor sample, a cell or a fluid with other biological components.

The term "anti-tumor effect" refers to a biological effect which can be manifested by various means, including but not limited to, e.g., a decrease in tumor volume, a decrease in the number of tumor cells, a decrease in the number of metastases, an increase in life expectancy, decrease in tumor cell proliferation, decrease in tumor cell survival, or amelioration of various physiological symptoms associated with the cancerous condition. An "anti-tumor effect" can also be manifested by the ability of the peptides, polynucleotides, cells and antibodies of the invention in prevention of the occurrence of tumor in the first place.

The term "autologous" refers to any material derived from the same individual to whom it is later to be re-introduced into the individual.

The term "allogeneic" refers to any material derived from a different animal of the same species or different patient as the individual to whom the material is introduced. Two or more individuals are said to be allogeneic to one another when the genes at one or more loci are not identical. In some aspects, allogeneic material from individuals of the same species may be sufficiently unlike genetically to interact antigenically.

The term "xenogeneic" refers to a graft derived from an animal of a different species.

The term "cancer" refers to a disease characterized by the rapid and uncontrolled growth of aberrant cells. Cancer cells can spread locally or through the bloodstream and lymphatic system to other parts of the body. Examples of various cancers are described herein and include but are not limited to, breast cancer, prostate cancer, ovarian cancer, cervical cancer, skin cancer, pancreatic cancer, colorectal cancer, renal cancer, liver cancer, brain cancer, lymphoma, leukemia, lung cancer and the like.

The phrase "disease associated with expression of CD19" and "disease associated with expression of BCMA" includes, but is not limited to, a disease associated with expression of CD19 or BCMA or condition associated with cells which express CD19 or BCMA including, e.g., proliferative diseases such as a cancer or malignancy or a precancerous condition such as a myelodysplasia, a myelodysplastic syndrome or a preleukemia; or a noncancer related indication associated with cells which express CD19 or BCMA. In one aspect, a cancer associated with expression of CD19 or BCMA is a hematological cancer. In one aspect, the hematological cancer is a leukemia or a lymphoma. In one aspect, a cancer associated with expression of CD19 or BCMA includes cancers and malignancies including, but not limited to, e.g., one or more acute leukemias including but not limited to, e.g., B cell ALL, T-cell acute lymphoid leukemia (TALL), one or more chronic leukemias including but not limited to, e.g., CLL or chronic myelogenous leukemia (CML). Additional cancers or hematologic conditions associated with expression of CD19 comprise, but are not limited to, e.g., B cell prolymphocytic leukemia, blastic plasmacytoid dendritic cell neoplasm, Burkitt's lymphoma, diffuse large B cell lymphoma, Follicular lymphoma, Hairy cell leukemia, small cell- or a large cell-follicular lymphoma, malignant lymphoproliferative conditions, MALT lymphoma, mantle cell lymphoma, Marginal zone lymphoma, multiple myeloma, myelodysplasia and myelodysplastic syndrome, non-Hodgkin's lymphoma, plasmablastic lymphoma, plasmacytoid dendritic cell neoplasm, Waldenstrom macroglobulinemia, and "preleukemia" which are a diverse collection of hematological conditions united by ineffective production (or dysplasia) of myeloid blood cells, and the like. Further diseases associated with expression of CD19 or BCMA expression include, but are not limited to, e.g., atypical and/or non-classical cancers, malignancies, precancerous conditions or proliferative diseases associated with expression of CD19 or BCMA. Non-cancer related indications associated with expression of CD19 or BCMA include, but are not limited to, e.g., autoimmune disease, (e.g., lupus, rheumatoid arthritis, colitis), inflammatory disorders (allergy and asthma), and transplantation.

The term "conservative sequence modifications" refers to amino acid modifications that do not significantly affect or alter the binding characteristics of the antibody or antibody fragment containing the amino acid sequence. Such conservative modifications include amino acid substitutions, additions and deletions. Modifications can be introduced into an antibody or antibody fragment of the invention by standard techniques known in the art, such as site-directed mutagenesis and PCR-mediated mutagenesis. Conservative amino acid substitutions are ones in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). Thus, one or more amino acid residues within a TFP of the invention can be replaced with other amino acid residues from the same side chain family and the altered TFP can be tested using the functional assays described herein.

The term "stimulation" refers to a primary response induced by binding of a stimulatory domain or stimulatory molecule (e.g., a TCR/CD3 complex) with its cognate ligand thereby mediating a signal transduction event, such as, but not limited to, signal transduction via the TCR/CD3 complex. Stimulation can mediate altered expression of certain molecules, and/or reorganization of cytoskeletal structures, and the like.

The term "stimulatory molecule" or "stimulatory domain" refers to a molecule or portion thereof expressed by a T-cell that provides the primary cytoplasmic signaling sequence(s) that regulate primary activation of the TCR complex in a stimulatory way for at least some aspect of the T-cell signaling pathway. In one aspect, the primary signal is initiated by, for instance, binding of a TCR/CD3 complex with an MHC molecule loaded with peptide, and which leads to mediation of a T-cell response, including, but not limited to, proliferation, activation, differentiation, and the like. A primary cytoplasmic signaling sequence (also referred to as a "primary signaling domain") that acts in a stimulatory manner may contain a signaling motif which is known as immunoreceptor tyrosine-based activation motif or "ITAM". Examples of an ITAM containing primary cytoplasmic signaling sequence that is of particular use in the invention includes, but is not limited to, those derived from TCR zeta, FcR gamma, FcR beta, CD3 gamma, CD3 delta, CD3 epsilon, CD5, CD22, CD79a, CD79b, CD278 (also known as "ICOS") and CD66d.

The term "antigen presenting cell" or "APC" refers to an immune system cell such as an accessory cell (e.g., a B-cell, a dendritic cell, and the like) that displays a foreign antigen complexed with major histocompatibility complexes (MHC's) on its surface. T-cells may recognize these complexes using their T-cell receptors (TCRs). APCs process antigens and present them to T-cells.

An "intracellular signaling domain," as the term is used herein, refers to an intracellular portion of a molecule. The intracellular signaling domain generates a signal that promotes an immune effector function of the TFP containing cell, e.g., a TFP-expressing T-cell. Examples of immune effector function, e.g., in a TFP-expressing T-cell, include cytolytic activity and T helper cell activity, including the secretion of cytokines. In an embodiment, the intracellular signaling domain can comprise a primary intracellular signaling domain. Exemplary primary intracellular signaling domains include those derived from the molecules responsible for primary stimulation, or antigen dependent simulation. In an embodiment, the intracellular signaling domain can comprise a costimulatory intracellular domain. Exemplary costimulatory intracellular signaling domains include those derived from molecules responsible for costimulatory signals, or antigen independent stimulation.

A primary intracellular signaling domain can comprise an ITAM ("immunoreceptor tyrosine-based activation motif"). Examples of ITAM containing primary cytoplasmic signaling sequences include, but are not limited to, those derived from CD3 zeta, FcR gamma, FcR beta, CD3 gamma, CD3 delta, CD3 epsilon, CD5, CD22, CD79a, CD79b, and CD66d DAP10 and DAP12.

The term "costimulatory molecule" refers to the cognate binding partner on a T-cell that specifically binds with a costimulatory ligand, thereby mediating a costimulatory response by the T-cell, such as, but not limited to, proliferation. Costimulatory molecules are cell surface molecules other than antigen receptors or their ligands that are required for an efficient immune response. Costimulatory molecules include, but are not limited to an MHC class 1 molecule, BTLA and a Toll ligand receptor, as well as OX40, CD2, CD27, CD28, CDS, ICAM-1, LFA-1 (CD11a/CD18) and 4-1BB (CD137). A costimulatory intracellular signaling domain can be the intracellular portion of a costimulatory molecule. A costimulatory molecule can be represented in the following protein families: TNF receptor proteins, Immunoglobulin-like proteins, cytokine receptors, integrins, signaling lymphocytic activation molecules (SLAM proteins), and activating NK cell receptors. Examples of such molecules include CD27, CD28, 4-1BB (CD137), OX40, GITR, CD30, CD40, ICOS, BAFFR, HVEM, lymphocyte function-associated antigen-1 (LFA-1), CD2, CD7, LIGHT, NKG2C, SLAMF7, NKp80, CD160, B7-H3, and a ligand that specifically binds with CD83, and the like. The intracellular signaling domain can comprise the entire intracellular portion, or the entire native intracellular signaling domain, of the molecule from which it is derived, or a functional fragment thereof. The term "4-1BB" refers to a member of the TNFR superfamily with an amino acid sequence provided as GenBank Acc. No. AAA62478.2, or the equivalent residues from a non-human species, e.g., mouse, rodent, monkey, ape and the like; and a "4-1BB costimulatory domain" is defined as amino acid residues 214-255 of GenBank Acc. No. AAA62478.2, or the equivalent residues from a non-human species, e.g., mouse, rodent, monkey, ape and the like.

The term "encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (e.g., rRNA, tRNA and mRNA) or a defined sequence of amino acids and the biological properties resulting therefrom. Thus, a gene, cDNA, or RNA, encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

Unless otherwise specified, a "nucleotide sequence encoding an amino acid sequence" includes all nucleotide sequences that are degenerate versions of each other and that encode the same amino acid sequence. The phrase nucleotide sequence that encodes a protein or an RNA may also include introns to the extent that the nucleotide sequence encoding the protein may in some version contain one or more introns.

The term "effective amount" or "therapeutically effective amount" are used interchangeably herein, and refer to an amount of a compound, formulation, material, or composition, as described herein effective to achieve a particular biological or therapeutic result.

The term "endogenous" refers to any material from or produced inside an organism, cell, tissue or system.

The term "exogenous" refers to any material introduced from or produced outside an organism, cell, tissue or system.

The term "expression" refers to the transcription and/or translation of a particular nucleotide sequence driven by a promoter.

The term "transfer vector" refers to a composition of matter which comprises an isolated nucleic acid and which can be used to deliver the isolated nucleic acid to the interior of a cell. Numerous vectors are known in the art including, but not limited to, linear polynucleotides, polynucleotides associated with ionic or amphiphilic compounds, plasmids, and viruses. Thus, the term "transfer vector" includes an autonomously replicating plasmid or a virus. The term should also be construed to further include non-plasmid and non-viral compounds which facilitate transfer of nucleic acid into cells, such as, for example, a polylysine compound, liposome, and the like. Examples of viral transfer vectors include, but are not limited to, adenoviral vectors, adeno-associated virus vectors, retroviral vectors, lentiviral vectors, and the like.

The term "expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, including cosmids, plasmids (e.g., naked or contained in liposomes) and viruses (e.g., lentiviruses, retroviruses, adenoviruses, and adeno-associated viruses) that incorporate the recombinant polynucleotide.

The term "lentivirus" refers to a genus of the Retroviridae family Lentiviruses are unique among the retroviruses in being able to infect non-dividing cells; they can deliver a significant amount of genetic information into the DNA of the host cell, so they are one of the most efficient methods of a gene delivery vector. HIV, SIV, and FIV are all examples of lentiviruses.

The term "lentiviral vector" refers to a vector derived from at least a portion of a lentivirus genome, including especially a self-inactivating lentiviral vector as provided in Milone et al., Mol. Ther. 17(8): 1453-1464 (2009). Other examples of lentivirus vectors that may be used in the clinic, include but are not limited to, e.g., the LENTIVECTOR™ gene delivery technology from Oxford BioMedica, the LENTIMAX™ vector system from Lentigen, and the like. Nonclinical types of lentiviral vectors are also available and would be known to one skilled in the art.

The term "homologous" or "identity" refers to the subunit sequence identity between two polymeric molecules, e.g., between two nucleic acid molecules, such as, two DNA molecules or two RNA molecules, or between two polypeptide molecules. When a subunit position in both of the two molecules is occupied by the same monomeric subunit; e.g., if a position in each of two DNA molecules is occupied by adenine, then they are homologous or identical at that position. The homology between two sequences is a direct function of the number of matching or homologous positions; e.g., if half (e.g., five positions in a polymer ten subunits in length) of the positions in two sequences are homologous, the two sequences are 50% homologous; if 90% of the positions (e.g., 9 of 10), are matched or homologous, the two sequences are 90% homologous.

"Humanized" forms of non-human (e g, murine) antibodies are chimeric immunoglobulins, immunoglobulin chains or fragments thereof (such as Fv, Fab, Fab', $F(ab')_2$ or other antigen-binding subsequences of antibodies) which contain minimal sequence derived from non-human immunoglobulin. For the most part, humanized antibodies and antibody fragments thereof are human immunoglobulins (recipient antibody or antibody fragment) in which residues from a complementary-determining region (CDR) of the recipient are replaced by residues from a CDR of a non-human species (donor antibody) such as mouse, rat or rabbit having the desired specificity, affinity, and capacity. In some instances, Fv framework region (FR) residues of the human immunoglobulin are replaced by corresponding non-human residues. Furthermore, a humanized antibody/antibody fragment can comprise residues which are found neither in the recipient antibody nor in the imported CDR or framework sequences. These modifications can further refine and optimize antibody or antibody fragment performance. In general, the humanized antibody or antibody fragment thereof will comprise substantially all of at least one, and typically two, variable domains, in which all or substantially all of the CDR regions correspond to those of a non-human immunoglobulin and all or a significant portion of the FR regions are those of a human immunoglobulin sequence. The humanized antibody or antibody fragment can also comprise at least a portion of an immunoglobulin constant region (Fc), typically that of a human immunoglobulin. For further details, see Jones et al., Nature, 321: 522-525, 1986; Reichmann et al., Nature, 332: 323-329, 1988; Presta, Curr. Op. Struct. Biol., 2: 593-596, 1992.

"Human" or "fully human" refers to an immunoglobulin, such as an antibody or antibody fragment, where the whole molecule is of human origin or consists of an amino acid sequence identical to a human form of the antibody or immunoglobulin.

The term "isolated" means altered or removed from the natural state. For example, a nucleic acid or a peptide naturally present in a living animal is not "isolated," but the same nucleic acid or peptide partially or completely separated from the coexisting materials of its natural state is "isolated." An isolated nucleic acid or protein can exist in substantially purified form, or can exist in a non-native environment such as, for example, a host cell.

In the context of the present invention, the following abbreviations for the commonly occurring nucleic acid bases are used. "A" refers to adenosine, "C" refers to cytosine, "G" refers to guanosine, "T" refers to thymidine, and "U" refers to uridine.

The term "operably linked" or "transcriptional control" refers to functional linkage between a regulatory sequence and a heterologous nucleic acid sequence resulting in expression of the latter. For example, a first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Operably linked DNA sequences can be contiguous with each other and, e.g., where necessary to join two protein coding regions, are in the same reading frame.

The term "parenteral" administration of an immunogenic composition includes, e.g., subcutaneous (s.c.), intravenous (i.v.), intramuscular (i.m.), or intrasternal injection, intratumoral, or infusion techniques.

The term "nucleic acid" or "polynucleotide" refers to deoxyribonucleic acids (DNA) or ribonucleic acids (RNA) and polymers thereof in either single- or double-stranded form. Unless specifically limited, the term encompasses nucleic acids containing known analogues of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions), alleles, orthologs, SNPs, and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., Nucleic Acid Res. 19:5081 (1991); Ohtsuka et al., J. Biol. Chem. 260:2605-2608 (1985); and Rossolini et al., Mol. Cell. Probes 8:91-98 (1994)).

The terms "peptide," "polypeptide," and "protein" are used interchangeably, and refer to a compound comprised of amino acid residues covalently linked by peptide bonds. A protein or peptide must contain at least two amino acids, and no limitation is placed on the maximum number of amino acids that can comprise a protein's or peptide's sequence. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others. A polypeptide includes a natural peptide, a recombinant peptide, or a combination thereof.

The term "promoter" refers to a DNA sequence recognized by the transcription machinery of the cell, or introduced synthetic machinery, required to initiate the specific transcription of a polynucleotide sequence.

The term "promoter/regulatory sequence" refers to a nucleic acid sequence which is required for expression of a gene product operably linked to the promoter/regulatory sequence. In some instances, this sequence may be the core promoter sequence and in other instances, this sequence may also include an enhancer sequence and other regulatory elements which are required for expression of the gene product. The promoter/regulatory sequence may, for example, be one which expresses the gene product in a tissue specific manner.

The term "constitutive" promoter refers to a nucleotide sequence which, when operably linked with a polynucleotide which encodes or specifies a gene product, causes the gene product to be produced in a cell under most or all physiological conditions of the cell.

The term "inducible" promoter refers to a nucleotide sequence which, when operably linked with a polynucleotide which encodes or specifies a gene product, causes the gene product to be produced in a cell substantially only when an inducer which corresponds to the promoter is present in the cell.

The term "tissue-specific" promoter refers to a nucleotide sequence which, when operably linked with a polynucleotide encodes or specified by a gene, causes the gene product to be produced in a cell substantially only if the cell is a cell of the tissue type corresponding to the promoter.

The terms "linker" and "flexible polypeptide linker" as used in the context of a scFv refers to a peptide linker that consists of amino acids such as glycine and/or serine residues used alone or in combination, to link variable heavy and variable light chain regions together. In one embodiment, the flexible polypeptide linker is a Gly/Ser linker and comprises the amino acid sequence $(\text{Gly-Gly-Gly-Ser})_n$, where n is a positive integer equal to or greater than 1. For example, n=1, n=2, n=3, n=4, n=5, n=6, n=7, n=8, n=9 and n=10 (SEQ ID NO: 69). In one embodiment, the flexible polypeptide linkers include, but are not limited to, $(Gly_4Ser)_4$ (SEQ ID NO: 70) or $(Gly_4Ser)_3$ (SEQ ID NO: 71). In another embodiment, the linkers include multiple repeats of $(Gly_2Ser)$, (GlySer) or $(Gly_3Ser)$ (SEQ ID NO: 72). Also included within the scope of the invention are linkers described in WO2012/138475 (incorporated herein by reference). In some instances, the linker sequence comprises a long linker (LL) sequence. In some instances, the long linker sequence comprises $(G_4S)_n$, wherein n=2 to 4 (SEQ ID NO: 67). In some instances, the linker sequence comprises a short linker (SL) sequence. In some instances, the short linker sequence comprises $(G_4S)_n$, wherein n=1 to 3 (SEQ ID NO: 68).

As used herein, a 5' cap (also termed an RNA cap, an RNA 7-methylguanosine cap or an RNA m7G cap) is a modified guanine nucleotide that has been added to the "front" or 5' end of a eukaryotic messenger RNA shortly after the start of transcription. The 5' cap consists of a terminal group which is linked to the first transcribed nucleotide. Its presence is critical for recognition by the ribosome and protection from RNases. Cap addition is coupled to transcription, and occurs co-transcriptionally, such that each influences the other. Shortly after the start of transcription, the 5' end of the mRNA being synthesized is bound by a cap-synthesizing complex associated with RNA polymerase. This enzymatic complex catalyzes the chemical reactions that are required for mRNA capping. Synthesis proceeds as a multi-step biochemical reaction. The capping moiety can be modified to modulate functionality of mRNA such as its stability or efficiency of translation.

As used herein, "in vitro transcribed RNA" refers to RNA, preferably mRNA, which has been synthesized in vitro. Generally, the in vitro transcribed RNA is generated from an in vitro transcription vector. The in vitro transcription vector comprises a template that is used to generate the in vitro transcribed RNA.

As used herein, a "poly(A)" is a series of adenosines attached by polyadenylation to the mRNA. In the preferred embodiment of a construct for transient expression, the polyA is between 50 and 5000, preferably greater than 64, more preferably greater than 100, most preferably greater than 300 or 400. Poly(A) sequences can be modified chemically or enzymatically to modulate mRNA functionality such as localization, stability or efficiency of translation.

As used herein, "polyadenylation" refers to the covalent linkage of a polyadenylyl moiety, or its modified variant, to a messenger RNA molecule. In eukaryotic organisms, most messenger RNA (mRNA) molecules are polyadenylated at the 3' end. The 3' poly(A) tail is a long sequence of adenine nucleotides (often several hundred) added to the pre-mRNA through the action of an enzyme, polyadenylate polymerase. In higher eukaryotes, the poly(A) tail is added onto transcripts that contain a specific sequence, the polyadenylation signal. The poly(A) tail and the protein bound to it aid in protecting mRNA from degradation by exonucleases. Polyadenylation is also important for transcription termination, export of the mRNA from the nucleus, and translation. Polyadenylation occurs in the nucleus immediately after transcription of DNA into RNA, but additionally can also occur later in the cytoplasm. After transcription has been terminated, the mRNA chain is cleaved through the action of an endonuclease complex associated with RNA polymerase. The cleavage site is usually characterized by the presence of the base sequence AAUAAA near the cleavage site. After the mRNA has been cleaved, adenosine residues are added to the free 3' end at the cleavage site.

As used herein, "transient" refers to expression of a non-integrated transgene for a period of hours, days or weeks, wherein the period of time of expression is less than the period of time for expression of the gene if integrated into the genome or contained within a stable plasmid replicon in the host cell.

The term "signal transduction pathway" refers to the biochemical relationship between a variety of signal transduction molecules that play a role in the transmission of a signal from one portion of a cell to another portion of a cell. The phrase "cell surface receptor" includes molecules and complexes of molecules capable of receiving a signal and transmitting signal across the membrane of a cell.

The term "subject" is intended to include living organisms in which an immune response can be elicited (e.g., mammals, human).

The term, a "substantially purified" cell refers to a cell that is essentially free of other cell types. A substantially purified cell also refers to a cell which has been separated from other cell types with which it is normally associated in its naturally occurring state. In some instances, a population of substantially purified cells refers to a homogenous population of cells. In other instances, this term refers simply to cell that have been separated from the cells with which they are naturally associated in their natural state. In some aspects, the cells are cultured in vitro. In other aspects, the cells are not cultured in vitro.

The term "therapeutic" as used herein means a treatment. A therapeutic effect is obtained by reduction, suppression, remission, or eradication of a disease state.

The term "prophylaxis" as used herein means the prevention of or protective treatment for a disease or disease state.

In the context of the present invention, "tumor antigen" or "hyperproliferative disorder antigen" or "antigen associated with a hyperproliferative disorder" refers to antigens that are common to specific hyperproliferative disorders. In certain aspects, the hyperproliferative disorder antigens of the present invention are derived from, cancers including but not limited to primary or metastatic melanoma, thymoma, lymphoma, sarcoma, lung cancer, liver cancer, NHL, leukemias, uterine cancer, cervical cancer, bladder cancer, kidney cancer and adenocarcinomas such as breast cancer, prostate cancer, ovarian cancer, pancreatic cancer, and the like.

The term "transfected" or "transformed" or "transduced" refers to a process by which exogenous nucleic acid is transferred or introduced into the host cell. A "transfected" or "transformed" or "transduced" cell is one which has been transfected, transformed or transduced with exogenous nucleic acid. The cell includes the primary subject cell and its progeny.

The term "specifically binds," refers to an antibody, an antibody fragment or a specific ligand, which recognizes and binds a cognate binding partner (e.g., CD19) present in a sample, but which does not necessarily and substantially recognize or bind other molecules in the sample.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. As another example, a range such as 95-99% identity, includes something with 95%, 96%, 97%, 98% or 99% identity, and includes subranges such as 96-99%, 96-98%, 96-97%, 97-99%, 97-98% and 98-99% identity. This applies regardless of the breadth of the range.

DESCRIPTION

Provided herein are compositions of matter and methods of use for the treatment of a disease such as cancer, using T-cell receptor (TCR) fusion proteins. As used herein, a "T-cell receptor (TCR) fusion protein" or "TFP" includes a recombinant polypeptide derived from the various polypeptides comprising the TCR that is generally capable of i) binding to a surface antigen on target cells and ii) interacting with other polypeptide components of the intact TCR complex, typically when co-located in or on the surface of a T-cell. As provided herein, TFPs provide substantial benefits as compared to Chimeric Antigen Receptors. The term "Chimeric Antigen Receptor" or alternatively a "CAR" refers to a recombinant polypeptide comprising an extracellular antigen binding domain in the form of a scFv, a transmembrane domain, and cytoplasmic signaling domains (also referred to herein as "an intracellular signaling domains") comprising a functional signaling domain derived from a stimulatory molecule as defined below. Generally, the central intracellular signaling domain of a CAR is derived from the CD3 zeta chain that is normally found associated with the TCR complex. The CD3 zeta signaling domain can be fused with one or more functional signaling domains derived from at least one costimulatory molecule such as 4-1BB (i.e., CD137), CD27 and/or CD28.

T-Cell Receptor (TCR) Fusion Proteins (TFP)

The present invention encompasses recombinant DNA constructs encoding TFPs, wherein the TFP comprises an antibody fragment that binds specifically to CD19, e.g., human CD19, wherein the sequence of the antibody fragment is contiguous with and in the same reading frame as a nucleic acid sequence encoding a TCR subunit or portion thereof. The present invention encompasses recombinant DNA constructs encoding TFPs, wherein the TFP comprises an antibody fragment that binds specifically to BCMA, e.g., human BCMA, wherein the sequence of the antibody fragment is contiguous with and in the same reading frame as a nucleic acid sequence encoding a TCR subunit or portion thereof. The TFPs provided herein are able to associate with one or more endogenous (or alternatively, one or more exogenous, or a combination of endogenous and exogenous) TCR subunits in order to form a functional TCR complex.

In one aspect, the TFP of the invention comprises a target-specific binding element otherwise referred to as an antigen binding domain. The choice of moiety depends upon the type and number of target antigen that define the surface of a target cell. For example, the antigen binding domain may be chosen to recognize a target antigen that acts as a cell surface marker on target cells associated with a particular disease state. Thus examples of cell surface markers that may act as target antigens for the antigen binding domain in a TFP of the invention include those associated with viral, bacterial and parasitic infections; autoimmune diseases; and cancerous diseases (e.g., malignant diseases).

In one aspect, the TFP-mediated T-cell response can be directed to an antigen of interest by way of engineering an antigen-binding domain into the TFP that specifically binds a desired antigen.

In one aspect, the portion of the TFP comprising the antigen binding domain comprises an antigen binding domain that targets CD19. In one aspect, the antigen binding domain targets human CD19. In one aspect, the portion of the TFP comprising the antigen binding domain comprises an antigen binding domain that targets BCMA. In one aspect, the antigen binding domain targets human BCMA.

The antigen binding domain can be any domain that binds to the antigen including but not limited to a monoclonal antibody, a polyclonal antibody, a recombinant antibody, a human antibody, a humanized antibody, and a functional fragment thereof, including but not limited to a single-domain antibody such as a heavy chain variable domain ($V_H$), a light chain variable domain ($V_L$) and a variable domain ($V_{HH}$) of a camelid derived nanobody, and to an alternative scaffold known in the art to function as antigen binding domain, such as a recombinant fibronectin domain, anticalin, DARPIN and the like. Likewise a natural or synthetic ligand specifically recognizing and binding the target antigen can be used as antigen binding domain for the TFP. In some instances, it is beneficial for the antigen binding domain to be derived from the same species in which the TFP will ultimately be used in. For example, for use in humans, it may be beneficial for the antigen binding domain of the TFP to comprise human or humanized residues for the antigen binding domain of an antibody or antibody fragment.

Thus, in one aspect, the antigen-binding domain comprises a humanized or human antibody or an antibody fragment, or a murine antibody or antibody fragment. In one embodiment, the humanized or human anti-CD19 or anti-BCMA binding domain comprises one or more (e.g., all three) light chain complementary determining region 1 (LC CDR1), light chain complementary determining region 2

(LC CDR2), and light chain complementary determining region 3 (LC CDR3) of a humanized or human anti-CD19 or anti-BCMA binding domain described herein, and/or one or more (e.g., all three) heavy chain complementary determining region 1 (HC CDR1), heavy chain complementary determining region 2 (HC CDR2), and heavy chain complementary determining region 3 (HC CDR3) of a humanized or human anti-CD19 binding domain described herein, e.g., a humanized or human anti-CD19 or anti-BCMA binding domain comprising one or more, e.g., all three, LC CDRs and one or more, e.g., all three, HC CDRs. In one embodiment, the humanized or human anti-CD19 binding domain comprises one or more (e.g., all three) heavy chain complementary determining region 1 (HC CDR1), heavy chain complementary determining region 2 (HC CDR2), and heavy chain complementary determining region 3 (HC CDR3) of a humanized or human anti-CD19 or anti-BCMA binding domain described herein, e.g., the humanized or human anti-CD19 or anti-BCMA binding domain has two variable heavy chain regions, each comprising a HC CDR1, a HC CDR2 and a HC CDR3 described herein. In one embodiment, the humanized or human anti-CD19 or anti-BCMA binding domain comprises a humanized or human light chain variable region described herein and/or a humanized or human heavy chain variable region described herein. In one embodiment, the humanized or human anti-CD19 or anti-BCMA binding domain comprises a humanized heavy chain variable region described herein, e.g., at least two humanized or human heavy chain variable regions described herein. In one embodiment, the anti-CD19 or anti-BCMA binding domain is a scFv comprising a light chain and a heavy chain of an amino acid sequence provided herein. In an embodiment, the anti-CD19 or anti-BCMA binding domain (e g, a scFv) comprises: a light chain variable region comprising an amino acid sequence having at least one, two or three modifications (e.g., substitutions) but not more than 30, 20 or 10 modifications (e.g., substitutions) of an amino acid sequence of a light chain variable region provided herein, or a sequence with 95-99% identity with an amino acid sequence provided herein; and/or a heavy chain variable region comprising an amino acid sequence having at least one, two or three modifications (e.g., substitutions) but not more than 30, 20 or 10 modifications (e.g., substitutions) of an amino acid sequence of a heavy chain variable region provided herein, or a sequence with 95-99% identity to an amino acid sequence provided herein. In one embodiment, the humanized or human anti-CD19 or anti-BCMA binding domain is a scFv, and a light chain variable region comprising an amino acid sequence described herein, is attached to a heavy chain variable region comprising an amino acid sequence described herein, via a linker, e.g., a linker described herein. In one embodiment, the humanized anti-CD19 or anti-BCMA binding domain includes a $(Gly_4\text{-}Ser)_n$ linker, wherein n is 1, 2, 3, 4, 5, or 6 (SEQ ID NO: 73), preferably 3 or 4. The light chain variable region and heavy chain variable region of a scFv can be, e.g., in any of the following orientations: light chain variable region-linker-heavy chain variable region or heavy chain variable region-linker-light chain variable region. In some instances, the linker sequence comprises a long linker (LL) sequence. In some instances, the long linker sequence comprises $(G_4S)_n$, wherein n=2 to 4 (SEQ ID NO: 67). In some instances, the linker sequence comprises a short linker (SL) sequence. In some instances, the short linker sequence comprises $(G_4S)_n$, wherein n=1 to 3 (SEQ ID NO: 68).

In some aspects, a non-human antibody is humanized, where specific sequences or regions of the antibody are modified to increase similarity to an antibody naturally produced in a human or fragment thereof. In one aspect, the antigen binding domain is humanized.

A humanized antibody can be produced using a variety of techniques known in the art, including but not limited to, CDR-grafting (see, e.g., European Patent No. EP 239,400; International Publication No. WO 91/09967; and U.S. Pat. Nos. 5,225,539, 5,530,101, and 5,585,089, each of which is incorporated herein in its entirety by reference), veneering or resurfacing (see, e.g., European Patent Nos. EP 592,106 and EP 519,596; Padlan, 1991, Molecular Immunology, 28(4/5):489-498; Studnicka et al., 1994, Protein Engineering, 7(6):805-814; and Roguska et al., 1994, PNAS, 91:969-973, each of which is incorporated herein by its entirety by reference), chain shuffling (see, e.g., U.S. Pat. No. 5,565,332, which is incorporated herein in its entirety by reference), and techniques disclosed in, e.g., U.S. Patent Application Publication No. US2005/0042664, U.S. Patent Application Publication No. US2005/0048617, U.S. Pat. Nos. 6,407,213, 5,766,886, International Publication No. WO 9317105, Tan et al., J. Immunol., 169:1119-25 (2002), Caldas et al., Protein Eng., 13(5):353-60 (2000), Morea et al., Methods, 20(3):267-79 (2000), Baca et al., J. Biol. Chem., 272(16):10678-84 (1997), Roguska et al., Protein Eng., 9(10):895-904 (1996), Couto et al., Cancer Res., 55 (23 Supp):5973s-5977s (1995), Couto et al., Cancer Res., 55(8):1717-22 (1995), Sandhu J S, Gene, 150(2):409-10 (1994), and Pedersen et al., J. Mol. Biol., 235(3):959-73 (1994), each of which is incorporated herein in its entirety by reference. Often, framework residues in the framework regions will be substituted with the corresponding residue from the CDR donor antibody to alter, for example improve, antigen binding. These framework substitutions are identified by methods well-known in the art, e.g., by modeling of the interactions of the CDR and framework residues to identify framework residues important for antigen binding and sequence comparison to identify unusual framework residues at particular positions (see, e.g., Queen et al., U.S. Pat. No. 5,585,089; and Riechmann et al., 1988, Nature, 332:323, which are incorporated herein by reference in their entireties.)

A humanized antibody or antibody fragment has one or more amino acid residues remaining in it from a source which is nonhuman. These nonhuman amino acid residues are often referred to as "import" residues, which are typically taken from an "import" variable domain. As provided herein, humanized antibodies or antibody fragments comprise one or more CDRs from nonhuman immunoglobulin molecules and framework regions wherein the amino acid residues comprising the framework are derived completely or mostly from human germline. Multiple techniques for humanization of antibodies or antibody fragments are well-known in the art and can essentially be performed following the method of Winter and co-workers (Jones et al., Nature, 321:522-525 (1986); Riechmann et al., Nature, 332:323-327 (1988); Verhoeyen et al., Science, 239:1534-1536 (1988)), by substituting rodent CDRs or CDR sequences for the corresponding sequences of a human antibody, i.e., CDR-grafting (EP 239,400; PCT Publication No. WO 91/09967; and U.S. Pat. Nos. 4,816,567; 6,331,415; 5,225,539; 5,530,101; 5,585,089; 6,548,640, the contents of which are incorporated herein by reference in their entirety). In such humanized antibodies and antibody fragments, substantially less than an intact human variable domain has been substituted by the corresponding sequence from a nonhuman species. Humanized antibodies are often human antibodies in which some CDR residues and possibly some framework (FR)

residues are substituted by residues from analogous sites in rodent antibodies. Humanization of antibodies and antibody fragments can also be achieved by veneering or resurfacing (EP 592,106; EP 519,596; Padlan, 1991, Molecular Immunology, 28(4/5):489-498; Studnicka et al., Protein Engineering, 7(6):805-814 (1994); and Roguska et al., PNAS, 91:969-973 (1994)) or chain shuffling (U.S. Pat. No. 5,565,332), the contents of which are incorporated herein by reference in their entirety.

The choice of human variable domains, both light and heavy, to be used in making the humanized antibodies is to reduce antigenicity. According to the so-called "best-fit" method, the sequence of the variable domain of a rodent antibody is screened against the entire library of known human variable-domain sequences. The human sequence which is closest to that of the rodent is then accepted as the human framework (FR) for the humanized antibody (Sims et al., J. Immunol., 151:2296 (1993); Chothia et al., J. Mol. Biol., 196:901 (1987), the contents of which are incorporated herein by reference herein in their entirety). Another method uses a particular framework derived from the consensus sequence of all human antibodies of a particular subgroup of light or heavy chains. The same framework may be used for several different humanized antibodies (see, e.g., Nicholson et al. Mol. Immun 34 (16-17): 1157-1165 (1997); Carter et al., Proc. Natl. Acad. Sci. USA, 89:4285 (1992); Presta et al., J. Immunol., 151:2623 (1993), the contents of which are incorporated herein by reference herein in their entirety). In some embodiments, the framework region, e.g., all four framework regions, of the heavy chain variable region are derived from a $V_H$4-4-59 germline sequence. In one embodiment, the framework region can comprise, one, two, three, four or five modifications, e.g., substitutions, e.g., from the amino acid at the corresponding murine sequence. In one embodiment, the framework region, e.g., all four framework regions of the light chain variable region are derived from a VK3-1.25 germline sequence. In one embodiment, the framework region can comprise, one, two, three, four or five modifications, e.g., substitutions, e.g., from the amino acid at the corresponding murine sequence.

In some aspects, the portion of a TFP composition of the invention that comprises an antibody fragment is humanized with retention of high affinity for the target antigen and other favorable biological properties. According to one aspect of the invention, humanized antibodies and antibody fragments are prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, e.g., the analysis of residues that influence the ability of the candidate immunoglobulin to bind the target antigen. In this way, FR residues can be selected and combined from the recipient and import sequences so that the desired antibody or antibody fragment characteristic, such as increased affinity for the target antigen, is achieved. In general, the CDR residues are directly and most substantially involved in influencing antigen binding.

A humanized antibody or antibody fragment may retain a similar antigenic specificity as the original antibody, e.g., in the present invention, the ability to bind human CD19. In some embodiments, a humanized antibody or antibody fragment may have improved affinity and/or specificity of binding to human CD19 or human BCMA.

In one aspect, the anti-CD19 or anti-BCMA binding domain is characterized by particular functional features or properties of an antibody or antibody fragment. For example, in one aspect, the portion of a TFP composition of the invention that comprises an antigen binding domain specifically binds human CD19 pr human BCMA. In one aspect, the antigen binding domain has the same or a similar binding specificity to human CD19 as the FMC63 scFv described in Nicholson et al. Mol. Immun. 34 (16-17): 1157-1165 (1997). In one aspect, the invention relates to an antigen binding domain comprising an antibody or antibody fragment, wherein the antibody binding domain specifically binds to a CD19 or BCMA protein or fragment thereof, wherein the antibody or antibody fragment comprises a variable light chain and/or a variable heavy chain that includes an amino acid sequence provided herein. In certain aspects, the scFv is contiguous with and in the same reading frame as a leader sequence.

In one aspect, the anti-CD19 or anti-BCMA binding domain is a fragment, e.g., a single chain variable fragment (scFv). In one aspect, the anti-CD19 binding domain is a Fv, a Fab, a $(Fab')_2$, or a bi-functional (e.g. bi-specific) hybrid antibody (e.g., Lanzavecchia et al., Eur. J. Immunol. 17, 105 (1987)). In one aspect, the antibodies and fragments thereof of the invention binds a CD19 protein with wild-type or enhanced affinity.

Also provided herein are methods for obtaining an antibody antigen binding domain specific for a target antigen (e.g., CD19, BCMA or any target antigen described elsewhere herein for targets of fusion moiety binding domains), the method comprising providing by way of addition, deletion, substitution or insertion of one or more amino acids in the amino acid sequence of a $V_H$ domain set out herein a $V_H$ domain which is an amino acid sequence variant of the $V_H$ domain, optionally combining the $V_H$ domain thus provided with one or more $V_L$ domains, and testing the $V_H$ domain or $V_H/V_L$ combination or combinations to identify a specific binding member or an antibody antigen binding domain specific for a target antigen of interest (e.g., CD19 or BCMA) and optionally with one or more desired properties.

In some instances, $V_H$ domains and scFvs can be prepared according to method known in the art (see, for example, Bird et al., (1988) Science 242:423-426 and Huston et al., (1988) Proc. Natl. Acad. Sci. USA 85:5879-5883). scFv molecules can be produced by linking $V_H$ and $V_L$ regions together using flexible polypeptide linkers. The scFv molecules comprise a linker (e.g., a Ser-Gly linker) with an optimized length and/or amino acid composition. The linker length can greatly affect how the variable regions of a scFv fold and interact. In fact, if a short polypeptide linker is employed (e.g., between 5-10 amino acids) intra-chain folding is prevented. Inter-chain folding is also required to bring the two variable regions together to form a functional epitope binding site. In some instances, the linker sequence comprises a long linker (LL) sequence. In some instances, the long linker sequence comprises $(G_4S)_n$, wherein n=2 to 4 (SEQ ID NO: 67). In some instances, the linker sequence comprises a short linker (SL) sequence. In some instances, the short linker sequence comprises $(G_4S)_n$, wherein n=1 to 3 (SEQ ID NO: 68). For examples of linker orientation and size see, e.g., Hollinger et al. 1993 Proc Natl Acad. Sci. U.S.A. 90:6444-6448, U.S. Patent Application Publication Nos. 2005/0100543, 2005/0175606, 2007/0014794, and PCT publication Nos. WO2006/020258 and WO2007/024715, is incorporated herein by reference.

A scFv can comprise a linker of about 10, 11, 12, 13, 14, 15 or greater than 15 residues between its $V_L$ and $V_H$ regions. The linker sequence may comprise any naturally occurring amino acid. In some embodiments, the linker sequence comprises amino acids glycine and serine. In another embodiment, the linker sequence comprises sets of glycine and serine repeats such as $(Gly_4Ser)_n$ (SEQ ID NO: 74), where n is a positive integer equal to or greater than 1. In one embodiment, the linker can be $(Gly_4Ser)_4$ (SEQ ID NO: 70) or $(Gly_4Ser)_3$ (SEQ ID NO: 71). Variation in the linker length may retain or enhance activity, giving rise to superior efficacy in activity studies. In some instances, the linker sequence comprises a long linker (LL) sequence. In some instances, the long linker sequence comprises $(G_4S)_n$, wherein n=2 to 4 (SEQ ID NO: 67). In some instances, the linker sequence comprises a short linker (SL) sequence. In some instances, the short linker sequence comprises $(G_4S)_n$, wherein n=1 to 3 (SEQ ID NO: 68).

Stability and Mutations

The stability of an anti-CD19 or anti-BCMA binding domain, e.g., scFv molecules (e.g., soluble scFv) can be evaluated in reference to the biophysical properties (e.g., thermal stability) of a conventional control scFv molecule or a full length antibody. In one embodiment, the humanized or human scFv has a thermal stability that is greater than about 0.1, about 0.25, about 0.5, about 0.75, about 1, about 1.25, about 1.5, about 1.75, about 2, about 2.5, about 3, about 3.5, about 4, about 4.5, about 5, about 5.5, about 6, about 6.5, about 7, about 7.5, about 8, about 8.5, about 9, about 9.5, about 10 degrees, about 11 degrees, about 12 degrees, about 13 degrees, about 14 degrees, or about 15 degrees Celsius than a parent scFv in the described assays.

The improved thermal stability of the anti-CD19 or anti-BCMA binding domain, e.g., scFv is subsequently conferred to the entire CD19-TFP construct, leading to improved therapeutic properties of the anti-CD19 or anti-BCMA TFP construct. The thermal stability of the anti-CD19 or anti-BCMA binding domain, e.g., scFv can be improved by at least about 2° C. or 3° C. as compared to a conventional antibody. In one embodiment, the anti-CD19 or anti-BCMA binding domain, e.g., scFv has a 1° C. improved thermal stability as compared to a conventional antibody. In another embodiment, the anti-CD19 binding domain, e.g., scFv has a 2° C. improved thermal stability as compared to a conventional antibody. In another embodiment, the scFv has a 4° C., 5° C., 6° C., 7° C., 8° C., 9° C., 10° C., 11° C., 12° C., 13° C., 14° C., or 15° C. improved thermal stability as compared to a conventional antibody. Comparisons can be made, for example, between the scFv molecules disclosed herein and scFv molecules or Fab fragments of an antibody from which the scFv $V_H$ and $V_L$ were derived. Thermal stability can be measured using methods known in the art. For example, in one embodiment, $T_M$ can be measured. Methods for measuring $T_M$ and other methods of determining protein stability are described in more detail below.

Mutations in scFv (arising through humanization or direct mutagenesis of the soluble scFv) alter the stability of the scFv and improve the overall stability of the scFv and the anti-CD19 or anti-BCMA TFP construct. Stability of the humanized scFv is compared against the murine scFv using measurements such as $T_M$, temperature denaturation and temperature aggregation. In one embodiment, the anti-CD19 or anti-BCMA binding domain, e.g., a scFv, comprises at least one mutation arising from the humanization process such that the mutated scFv confers improved stability to the Anti-CD19 TFP construct. In another embodiment, the anti-CD19 binding domain, e.g., scFv comprises at least 1, 2, 3, 4, 5, 6, 7, 8, 9, 10 mutations arising from the humanization process such that the mutated scFv confers improved stability to the CD19-TFP or BCMA-TFP construct.

In one aspect, the antigen binding domain of the TFP comprises an amino acid sequence that is homologous to an antigen binding domain amino acid sequence described herein, and the antigen binding domain retains the desired functional properties of the anti-CD19 or anti-BCMA antibody fragments described herein. In one specific aspect, the TFP composition of the invention comprises an antibody fragment. In a further aspect, that antibody fragment comprises a scFv.

In various aspects, the antigen binding domain of the TFP is engineered by modifying one or more amino acids within one or both variable regions (e.g., $V_H$ and/or $V_L$), for example within one or more CDR regions and/or within one or more framework regions. In one specific aspect, the TFP composition of the invention comprises an antibody fragment. In a further aspect, that antibody fragment comprises a scFv.

It will be understood by one of ordinary skill in the art that the antibody or antibody fragment of the invention may further be modified such that they vary in amino acid sequence (e.g., from wild-type), but not in desired activity. For example, additional nucleotide substitutions leading to amino acid substitutions at "non-essential" amino acid residues may be made to the protein. For example, a nonessential amino acid residue in a molecule may be replaced with another amino acid residue from the same side chain family. In another embodiment, a string of amino acids can be replaced with a structurally similar string that differs in order and/or composition of side chain family members, e.g., a conservative substitution, in which an amino acid residue is replaced with an amino acid residue having a similar side chain, may be made.

Families of amino acid residues having similar side chains have been defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

Percent identity in the context of two or more nucleic acids or polypeptide sequences refers to two or more sequences that are the same. Two sequences are "substantially identical" if two sequences have a specified percentage of amino acid residues or nucleotides that are the same (e.g., 60% identity, optionally 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identity over a specified region, or, when not specified, over the entire sequence), when compared and aligned for maximum correspondence over a comparison window, or designated region as measured using one of the following sequence comparison algorithms or by manual alignment and visual inspection. Optionally, the identity exists over a region that is at least about 50 nucleotides (or 10 amino acids) in length, or more preferably over a region that is 100 to 500 or 1000 or more nucleotides (or 20, 50, 200 or more amino acids) in length.

For sequence comparison, typically one sequence acts as a reference sequence, to which test sequences are compared.

When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters. Methods of alignment of sequences for comparison are well known in the art. Optimal alignment of sequences for comparison can be conducted, e.g., by the local homology algorithm of Smith and Waterman, (1970) Adv. Appl. Math. 2:482c, by the homology alignment algorithm of Needleman and Wunsch, (1970) J. Mol. Biol. 48:443, by the search for similarity method of Pearson and Lipman, (1988) Proc. Nat'l. Acad. Sci. USA 85:2444, by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., Brent et al., (2003) Current Protocols in Molecular Biology). Two examples of algorithms that are suitable for determining percent sequence identity and sequence similarity are the BLAST and BLAST 2.0 algorithms, which are described in Altschul et al., (1977) Nuc. Acids Res. 25:3389-3402; and Altschul et al., (1990) J. Mol. Biol. 215:403-410, respectively. Software for performing BLAST analyses is publicly available through the National Center for Biotechnology Information.

In one aspect, the present invention contemplates modifications of the starting antibody or fragment (e.g., scFv) amino acid sequence that generate functionally equivalent molecules. For example, the $V_H$ or $V_L$ of an anti-CD19 or anti-BCMA binding domain, e.g., scFv, comprised in the TFP can be modified to retain at least about 70%, 71%. 72%. 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% identity of the starting $V_H$ or $V_L$ framework region of the anti-CD19 binding domain, e.g., scFv. The present invention contemplates modifications of the entire TFP construct, e.g., modifications in one or more amino acid sequences of the various domains of the TFP construct in order to generate functionally equivalent molecules. The TFP construct can be modified to retain at least about 70%, 71%. 72%. 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% identity of the starting TFP construct.

Extracellular Domain

The extracellular domain may be derived either from a natural or from a recombinant source. Where the source is natural, the domain may be derived from any protein, but in particular a membrane-bound or transmembrane protein. In one aspect the extracellular domain is capable of associating with the transmembrane domain. An extracellular domain of particular use in this invention may include at least the extracellular region(s) of e.g., the alpha, beta or zeta chain of the T-cell receptor, or CD3 epsilon, CD3 gamma, or CD3 delta, or in alternative embodiments, CD28, CD45, CD4, CD5, CD8, CD9, CD16, CD22, CD33, CD37, CD64, CD80, CD86, CD134, CD137, CD154.

Transmembrane Domain

In general, a TFP sequence contains an extracellular domain and a transmembrane domain encoded by a single genomic sequence. In alternative embodiments, a TFP can be designed to comprise a transmembrane domain that is heterologous to the extracellular domain of the TFP. A transmembrane domain can include one or more additional amino acids adjacent to the transmembrane region, e.g., one or more amino acid associated with the extracellular region of the protein from which the transmembrane was derived (e.g., 1, 2, 3, 4, 5, 6, 7, 8, 9, 10 or up to 15 amino acids of the extracellular region) and/or one or more additional amino acids associated with the intracellular region of the protein from which the transmembrane protein is derived (e.g., 1, 2, 3, 4, 5, 6, 7, 8, 9, 10 or up to 15 amino acids of the intracellular region). In one aspect, the transmembrane domain is one that is associated with one of the other domains of the TFP is used. In some instances, the transmembrane domain can be selected or modified by amino acid substitution to avoid binding of such domains to the transmembrane domains of the same or different surface membrane proteins, e.g., to minimize interactions with other members of the receptor complex. In one aspect, the transmembrane domain is capable of homodimerization with another TFP on the TFP-T-cell surface. In a different aspect the amino acid sequence of the transmembrane domain may be modified or substituted so as to minimize interactions with the binding domains of the native binding partner present in the same TFP.

The transmembrane domain may be derived either from a natural or from a recombinant source. Where the source is natural, the domain may be derived from any membrane-bound or transmembrane protein. In one aspect the transmembrane domain is capable of signaling to the intracellular domain(s) whenever the TFP has bound to a target. A transmembrane domain of particular use in this invention may include at least the transmembrane region(s) of e.g., the alpha, beta or zeta chain of the T-cell receptor, CD28, CD3 epsilon, CD45, CD4, CD5, CD8, CD9, CD16, CD22, CD33, CD37, CD64, CD80, CD86, CD134, CD137, CD154.

In some instances, the transmembrane domain can be attached to the extracellular region of the TFP, e.g., the antigen binding domain of the TFP, via a hinge, e.g., a hinge from a human protein. For example, in one embodiment, the hinge can be a human immunoglobulin (Ig) hinge, e.g., an IgG4 hinge, or a CD8a hinge.

Linkers

Optionally, a short oligo- or polypeptide linker, between 2 and 10 amino acids in length may form the linkage between the transmembrane domain and the cytoplasmic region of the TFP. A glycine-serine doublet provides a particularly suitable linker. For example, in one aspect, the linker comprises the amino acid sequence of GGGGSGGGGS (SEQ ID NO: 3). In some embodiments, the linker is encoded by a nucleotide sequence of GGTGGCGGAGGTTCTGGAGGTGGAGGTTCC (SEQ ID NO: 4).

Cytoplasmic Domain

The cytoplasmic domain of the TFP can include an intracellular signaling domain, if the TFP contains CD3 gamma, delta or epsilon polypeptides; TCR alpha and TCR beta subunits are generally lacking in a signaling domain. An intracellular signaling domain is generally responsible for activation of at least one of the normal effector functions of the immune cell in which the TFP has been introduced. The term "effector function" refers to a specialized function of a cell. Effector function of a T-cell, for example, may be cytolytic activity or helper activity including the secretion of cytokines. Thus the term "intracellular signaling domain" refers to the portion of a protein which transduces the effector function signal and directs the cell to perform a specialized function. While usually the entire intracellular signaling domain can be employed, in many cases it is not necessary to use the entire chain. To the extent that a truncated portion of the intracellular signaling domain is used, such truncated portion may be used in place of the intact chain as long as it transduces the effector function signal. The term intracellular signaling domain is thus meant to include any truncated portion of the intracellular signaling domain sufficient to transduce the effector function signal.

Examples of intracellular signaling domains for use in the TFP of the invention include the cytoplasmic sequences of the T-cell receptor (TCR) and co-receptors that act in concert to initiate signal transduction following antigen receptor engagement, as well as any derivative or variant of these sequences and any recombinant sequence that has the same functional capability.

It is known that signals generated through the TCR alone are insufficient for full activation of naive T-cells and that a secondary and/or costimulatory signal is required. Thus, naïve T-cell activation can be said to be mediated by two distinct classes of cytoplasmic signaling sequences: those that initiate antigen-dependent primary activation through the TCR (primary intracellular signaling domains) and those that act in an antigen-independent manner to provide a secondary or costimulatory signal (secondary cytoplasmic domain, e.g., a costimulatory domain).

A primary signaling domain regulates primary activation of the TCR complex either in a stimulatory way, or in an inhibitory way. Primary intracellular signaling domains that act in a stimulatory manner may contain signaling motifs which are known as immunoreceptor tyrosine-based activation motifs (ITAMs).

Examples of ITAMs containing primary intracellular signaling domains that are of particular use in the invention include those of CD3 zeta, FcR gamma, FcR beta, CD3 gamma, CD3 delta, CD3 epsilon, CD5, CD22, CD79a, CD79b, and CD66d. In one embodiment, a TFP of the invention comprises an intracellular signaling domain, e.g., a primary signaling domain of CD3-epsilon. In one embodiment, a primary signaling domain comprises a modified ITAM domain, e.g., a mutated ITAM domain which has altered (e.g., increased or decreased) activity as compared to the native ITAM domain. In one embodiment, a primary signaling domain comprises a modified ITAM-containing primary intracellular signaling domain, e.g., an optimized and/or truncated ITAM-containing primary intracellular signaling domain. In an embodiment, a primary signaling domain comprises one, two, three, four or more ITAM motifs.

The intracellular signaling domain of the TFP can comprise the CD3 zeta signaling domain by itself or it can be combined with any other desired intracellular signaling domain(s) useful in the context of a TFP of the invention. For example, the intracellular signaling domain of the TFP can comprise a CD3 epsilon chain portion and a costimulatory signaling domain. The costimulatory signaling domain refers to a portion of the TFP comprising the intracellular domain of a costimulatory molecule. A costimulatory molecule is a cell surface molecule other than an antigen receptor or its ligands that is required for an efficient response of lymphocytes to an antigen. Examples of such molecules include CD27, CD28, 4-1BB (CD137), OX40, CD30, CD40, PD1, ICOS, lymphocyte function-associated antigen-1 (LFA-1), CD2, CD7, LIGHT, NKG2C, B7-H3, and a ligand that specifically binds with CD83, and the like. For example, CD27 costimulation has been demonstrated to enhance expansion, effector function, and survival of human TFP-T-cells in vitro and augments human T-cell persistence and antitumor activity in vivo (Song et al. Blood. 2012; 119(3):696-706).

The intracellular signaling sequences within the cytoplasmic portion of the TFP of the invention may be linked to each other in a random or specified order. Optionally, a short oligo- or polypeptide linker, for example, between 2 and 10 amino acids (e.g., 2, 3, 4, 5, 6, 7, 8, 9, or 10 amino acids) in length may form the linkage between intracellular signaling sequences.

In one embodiment, a glycine-serine doublet can be used as a suitable linker. In one embodiment, a single amino acid, e.g., an alanine, a glycine, can be used as a suitable linker.

In one aspect, the TFP-expressing cell described herein can further comprise a second TFP, e.g., a second TFP that includes a different antigen binding domain, e.g., to the same target (CD19 or BCMA) or a different target (e.g., CD123). In one embodiment, when the TFP-expressing cell comprises two or more different TFPs, the antigen binding domains of the different TFPs can be such that the antigen binding domains do not interact with one another. For example, a cell expressing a first and second TFP can have an antigen binding domain of the first TFP, e.g., as a fragment, e.g., a scFv, that does not form an association with the antigen binding domain of the second TFP, e.g., the antigen binding domain of the second TFP is a $V_{HH}$.

In another aspect, the TFP-expressing cell described herein can further express another agent, e.g., an agent which enhances the activity of a TFP-expressing cell. For example, in one embodiment, the agent can be an agent which inhibits an inhibitory molecule. Inhibitory molecules, e.g., PD1, can, in some embodiments, decrease the ability of a TFP-expressing cell to mount an immune effector response. Examples of inhibitory molecules include PD1, PD-L1, CTLA4, TIM3, LAG3, VISTA, BTLA, TIGIT, LAIR1, CD160, 2B4 and TGFR beta. In one embodiment, the agent which inhibits an inhibitory molecule comprises a first polypeptide, e.g., an inhibitory molecule, associated with a second polypeptide that provides a positive signal to the cell, e.g., an intracellular signaling domain described herein. In one embodiment, the agent comprises a first polypeptide, e.g., of an inhibitory molecule such as PD1, LAG3, CTLA4, CD160, BTLA, LAIR1, TIM3, 2B4 and TIGIT, or a fragment of any of these (e.g., at least a portion of an extracellular domain of any of these), and a second polypeptide which is an intracellular signaling domain described herein (e.g., comprising a costimulatory domain (e.g., 4-1BB, CD27 or CD28, e.g., as described herein) and/or a primary signaling domain (e g, a CD3 zeta signaling domain described herein). In one embodiment, the agent comprises a first polypeptide of PD1 or a fragment thereof (e.g., at least a portion of an extracellular domain of PD1), and a second polypeptide of an intracellular signaling domain described herein (e.g., a CD28 signaling domain described herein and/or a CD3 zeta signaling domain described herein). PD1 is an inhibitory member of the CD28 family of receptors that also includes CD28, CTLA-4, ICOS, and BTLA. PD-1 is expressed on activated B cells, T-cells and myeloid cells (Agata et al. 1996 Int. Immunol 8:765-75). Two ligands for PD1, PD-L1 and PD-L2 have been shown to downregulate T-cell activation upon binding to PD1 (Freeman et al. 2000 J Exp Med 192:1027-34; Latchman et al. 2001 Nat Immunol 2:261-8; Carter et al. 2002 Eur J Immunol 32:634-43). PD-L1 is abundant in human cancers (Dong et al. 2003 J Mol Med 81:281-7; Blank et al. 2005 Cancer Immunol. Immunother 54:307-

314; Konishi et al. 2004 Clin Cancer Res 10:5094). Immune suppression can be reversed by inhibiting the local interaction of PD1 with PD-L1.

In one embodiment, the agent comprises the extracellular domain (ECD) of an inhibitory molecule, e.g., Programmed Death 1 (PD1) can be fused to a transmembrane domain and optionally an intracellular signaling domain such as 41BB and CD3 zeta (also referred to herein as a PD1 TFP). In one embodiment, the PD1 TFP, when used in combinations with an anti-CD19 TFP described herein, improves the persistence of the T-cell. In one embodiment, the TFP is a PD1 TFP comprising the extracellular domain of PD 1. Alternatively, provided are TFPs containing an antibody or antibody fragment such as a scFv that specifically binds to the Programmed Death-Ligand 1 (PD-L1) or Programmed Death-Ligand 2 (PD-L2).

In another aspect, the present invention provides a population of TFP-expressing T-cells, e.g., TFP-T-cells. In some embodiments, the population of TFP-expressing T-cells comprises a mixture of cells expressing different TFPs. For example, in one embodiment, the population of TFP-T-cells can include a first cell expressing a TFP having an anti-CD19 or anti-BCMA binding domain described herein, and a second cell expressing a TFP having a different anti-CD19 or anti-BCMA binding domain, e.g., an anti-CD19 or anti-BCMA binding domain described herein that differs from the anti-CD19 binding domain in the TFP expressed by the first cell. As another example, the population of TFP-expressing cells can include a first cell expressing a TFP that includes an anti-CD19 or anti-BCMA binding domain, e.g., as described herein, and a second cell expressing a TFP that includes an antigen binding domain to a target other than CD19 or BCMA (e.g., another tumor-associated antigen).

In another aspect, the present invention provides a population of cells wherein at least one cell in the population expresses a TFP having an anti-CD19 or anti-BCMA domain described herein, and a second cell expressing another agent, e.g., an agent which enhances the activity of a TFP-expressing cell. For example, in one embodiment, the agent can be an agent which inhibits an inhibitory molecule. Inhibitory molecules, e.g., can, in some embodiments, decrease the ability of a TFP-expressing cell to mount an immune effector response. Examples of inhibitory molecules include PD1, PD-L1, PD-L2, CTLA4, TIM3, LAG3, VISTA, BTLA, TIGIT, LAIR1, CD160, 2B4 and TGFR beta. In one embodiment, the agent that inhibits an inhibitory molecule comprises a first polypeptide, e.g., an inhibitory molecule, associated with a second polypeptide that provides a positive signal to the cell, e.g., an intracellular signaling domain described herein.

Disclosed herein are methods for producing in vitro transcribed RNA encoding TFPs. The present invention also includes a TFP encoding RNA construct that can be directly transfected into a cell. A method for generating mRNA for use in transfection can involve in vitro transcription (IVT) of a template with specially designed primers, followed by polyA addition, to produce a construct containing 3' and 5' untranslated sequence ("UTR"), a 5' cap and/or Internal Ribosome Entry Site (IRES), the nucleic acid to be expressed, and a polyA tail, typically 50-2000 bases in length. RNA so produced can efficiently transfect different kinds of cells. In one aspect, the template includes sequences for the TFP.

In one aspect the anti-CD19 or anti-BCMA TFP is encoded by a messenger RNA (mRNA). In one aspect the mRNA encoding the anti-CD19 or anti-BCMA TFP is introduced into a T-cell for production of a TFP-T-cell. In one embodiment, the in vitro transcribed RNA TFP can be introduced to a cell as a form of transient transfection. The RNA is produced by in vitro transcription using a polymerase chain reaction (PCR)-generated template. DNA of interest from any source can be directly converted by PCR into a template for in vitro mRNA synthesis using appropriate primers and RNA polymerase. The source of the DNA can be, for example, genomic DNA, plasmid DNA, phage DNA, cDNA, synthetic DNA sequence or any other appropriate source of DNA. The desired template for in vitro transcription is a TFP of the present invention. In one embodiment, the DNA to be used for PCR contains an open reading frame. The DNA can be from a naturally occurring DNA sequence from the genome of an organism. In one embodiment, the nucleic acid can include some or all of the 5' and/or 3' untranslated regions (UTRs). The nucleic acid can include exons and introns. In one embodiment, the DNA to be used for PCR is a human nucleic acid sequence. In another embodiment, the DNA to be used for PCR is a human nucleic acid sequence including the 5' and 3' UTRs. The DNA can alternatively be an artificial DNA sequence that is not normally expressed in a naturally occurring organism. An exemplary artificial DNA sequence is one that contains portions of genes that are ligated together to form an open reading frame that encodes a fusion protein. The portions of DNA that are ligated together can be from a single organism or from more than one organism.

PCR is used to generate a template for in vitro transcription of mRNA which is used for transfection. Methods for performing PCR are well known in the art. Primers for use in PCR are designed to have regions that are substantially complementary to regions of the DNA to be used as a template for the PCR. "Substantially complementary," as used herein, refers to sequences of nucleotides where a majority or all of the bases in the primer sequence are complementary, or one or more bases are non-complementary, or mismatched. Substantially complementary sequences are able to anneal or hybridize with the intended DNA target under annealing conditions used for PCR. The primers can be designed to be substantially complementary to any portion of the DNA template. For example, the primers can be designed to amplify the portion of a nucleic acid that is normally transcribed in cells (the open reading frame), including 5' and 3' UTRs. The primers can also be designed to amplify a portion of a nucleic acid that encodes a particular domain of interest. In one embodiment, the primers are designed to amplify the coding region of a human cDNA, including all or portions of the 5' and 3' UTRs. Primers useful for PCR can be generated by synthetic methods that are well known in the art. "Forward primers" are primers that contain a region of nucleotides that are substantially complementary to nucleotides on the DNA template that are upstream of the DNA sequence that is to be amplified. "Upstream" is used herein to refer to a location 5, to the DNA sequence to be amplified relative to the coding strand. "Reverse primers" are primers that contain a region of nucleotides that are substantially complementary to a double-stranded DNA template that are downstream of the DNA sequence that is to be amplified. "Downstream" is used herein to refer to a location 3' to the DNA sequence to be amplified relative to the coding strand.

Any DNA polymerase useful for PCR can be used in the methods disclosed herein. The reagents and polymerase are commercially available from a number of sources.

Chemical structures with the ability to promote stability and/or translation efficiency may also be used. The RNA preferably has 5' and 3' UTRs. In one embodiment, the 5'

UTR is between one and 3000 nucleotides in length. The length of 5' and 3' UTR sequences to be added to the coding region can be altered by different methods, including, but not limited to, designing primers for PCR that anneal to different regions of the UTRs. Using this approach, one of ordinary skill in the art can modify the 5' and 3' UTR lengths required to achieve optimal translation efficiency following transfection of the transcribed RNA.

The 5' and 3' UTRs can be the naturally occurring, endogenous 5' and 3' UTRs for the nucleic acid of interest. Alternatively, UTR sequences that are not endogenous to the nucleic acid of interest can be added by incorporating the UTR sequences into the forward and reverse primers or by any other modifications of the template. The use of UTR sequences that are not endogenous to the nucleic acid of interest can be useful for modifying the stability and/or translation efficiency of the RNA. For example, it is known that AU-rich elements in 3'UTR sequences can decrease the stability of mRNA. Therefore, 3' UTRs can be selected or designed to increase the stability of the transcribed RNA based on properties of UTRs that are well known in the art.

In one embodiment, the 5' UTR can contain the Kozak sequence of the endogenous nucleic acid. Alternatively, when a 5' UTR that is not endogenous to the nucleic acid of interest is being added by PCR as described above, a consensus Kozak sequence can be redesigned by adding the 5' UTR sequence. Kozak sequences can increase the efficiency of translation of some RNA transcripts, but does not appear to be required for all RNAs to enable efficient translation. The requirement for Kozak sequences for many mRNAs is known in the art. In other embodiments the 5' UTR can be 5'UTR of an RNA virus whose RNA genome is stable in cells. In other embodiments various nucleotide analogues can be used in the 3' or 5' UTR to impede exonuclease degradation of the mRNA.

To enable synthesis of RNA from a DNA template without the need for gene cloning, a promoter of transcription should be attached to the DNA template upstream of the sequence to be transcribed. When a sequence that functions as a promoter for an RNA polymerase is added to the 5' end of the forward primer, the RNA polymerase promoter becomes incorporated into the PCR product upstream of the open reading frame that is to be transcribed. In one preferred embodiment, the promoter is a T7 polymerase promoter, as described elsewhere herein. Other useful promoters include, but are not limited to, T3 and SP6 RNA polymerase promoters. Consensus nucleotide sequences for T7, T3 and SP6 promoters are known in the art.

In a preferred embodiment, the mRNA has both a cap on the 5' end and a 3' poly(A) tail which determine ribosome binding, initiation of translation and stability mRNA in the cell. On a circular DNA template, for instance, plasmid DNA, RNA polymerase produces a long concatameric product which is not suitable for expression in eukaryotic cells. The transcription of plasmid DNA linearized at the end of the 3' UTR results in normal sized mRNA which is not effective in eukaryotic transfection even if it is polyadenylated after transcription.

On a linear DNA template, phage T7 RNA polymerase can extend the 3' end of the transcript beyond the last base of the template (Schenborn and Mierendorf, Nuc Acids Res., 13:6223-36 (1985); Nacheva and Berzal-Herranz, Eur. J. Biochem., 270:1485-65 (2003).

The conventional method of integration of polyA/T stretches into a DNA template is molecular cloning. However polyA/T sequence integrated into plasmid DNA can cause plasmid instability, which is why plasmid DNA templates obtained from bacterial cells are often highly contaminated with deletions and other aberrations. This makes cloning procedures not only laborious and time consuming but often not reliable. That is why a method which allows construction of DNA templates with polyA/T 3' stretch without cloning highly desirable.

The polyA/T segment of the transcriptional DNA template can be produced during PCR by using a reverse primer containing a polyT tail, such as 100 T tail (size can be 50-5000 T), or after PCR by any other method, including, but not limited to, DNA ligation or in vitro recombination. Poly(A) tails also provide stability to RNAs and reduce their degradation. Generally, the length of a poly(A) tail positively correlates with the stability of the transcribed RNA. In one embodiment, the poly(A) tail is between 100 and 5000 adenosines.

Poly(A) tails of RNAs can be further extended following in vitro transcription with the use of a poly(A) polymerase, such as *E. coli* polyA polymerase (E-PAP). In one embodiment, increasing the length of a poly(A) tail from 100 nucleotides to between 300 and 400 nucleotides results in about a two-fold increase in the translation efficiency of the RNA. Additionally, the attachment of different chemical groups to the 3' end can increase mRNA stability. Such attachment can contain modified/artificial nucleotides, aptamers and other compounds. For example, ATP analogs can be incorporated into the poly(A) tail using poly(A) polymerase. ATP analogs can further increase the stability of the RNA.

5' caps on also provide stability to RNA molecules. In a preferred embodiment, RNAs produced by the methods disclosed herein include a 5' cap. The 5' cap is provided using techniques known in the art and described herein (Cougot, et al., Trends in Biochem. Sci., 29:436-444 (2001); Stepinski, et al., RNA, 7:1468-95 (2001); Elango, et al., Biochim Biophys. Res. Commun., 330:958-966 (2005)).

The RNAs produced by the methods disclosed herein can also contain an internal ribosome entry site (IRES) sequence. The IRES sequence may be any viral, chromosomal or artificially designed sequence which initiates cap-independent ribosome binding to mRNA and facilitates the initiation of translation. Any solutes suitable for cell electroporation, which can contain factors facilitating cellular permeability and viability such as sugars, peptides, lipids, proteins, antioxidants, and surfactants can be included.

RNA can be introduced into target cells using any of a number of different methods, for instance, commercially available methods which include, but are not limited to, electroporation (Amaxa Nucleofector-II (Amaxa Biosystems, Cologne, Germany)), (ECM 830 (BTX) (Harvard Instruments, Boston, Mass.) or the Gene Pulser II (BioRad, Denver, Colo.), Multiporator (Eppendort, Hamburg Germany), cationic liposome mediated transfection using lipofection, polymer encapsulation, peptide mediated transfection, or biolistic particle delivery systems such as "gene guns" (see, for example, Nishikawa, et al. Hum Gene Ther., 12(8):861-70 (2001).

Nucleic Acid Constructs Encoding a TFP

The present invention also provides nucleic acid molecules encoding one or more TFP constructs described herein. In one aspect, the nucleic acid molecule is provided as a messenger RNA transcript. In one aspect, the nucleic acid molecule is provided as a DNA construct.

The nucleic acid sequences coding for the desired molecules can be obtained using recombinant methods known in the art, such as, for example by screening libraries from cells expressing the gene, by deriving the gene from a vector known to include the same, or by isolating directly from cells and tissues containing the same, using standard techniques. Alternatively, the gene of interest can be produced synthetically, rather than cloned.

The present invention also provides vectors in which a DNA of the present invention is inserted. Vectors derived from retroviruses such as the lentivirus are suitable tools to achieve long-term gene transfer since they allow long-term, stable integration of a transgene and its propagation in daughter cells. Lentiviral vectors have the added advantage over vectors derived from onco-retroviruses such as murine leukemia viruses in that they can transduce non-proliferating cells, such as hepatocytes. They also have the added advantage of low immunogenicity.

In another embodiment, the vector comprising the nucleic acid encoding the desired TFP of the invention is an adenoviral vector (A5/35). In another embodiment, the expression of nucleic acids encoding TFPs can be accomplished using of transposons such as sleeping beauty, crisper, CAS9, and zinc finger nucleases. See below June et al. 2009 Nature Reviews Immunology 9.10: 704-716, is incorporated herein by reference.

The expression constructs of the present invention may also be used for nucleic acid immunization and gene therapy, using standard gene delivery protocols. Methods for gene delivery are known in the art (see, e.g., U.S. Pat. Nos. 5,399,346, 5,580,859, 5,589,466, incorporated by reference herein in their entireties). In another embodiment, the invention provides a gene therapy vector.

The nucleic acid can be cloned into a number of types of vectors. For example, the nucleic acid can be cloned into a vector including, but not limited to a plasmid, a phagemid, a phage derivative, an animal virus, and a cosmid. Vectors of particular interest include expression vectors, replication vectors, probe generation vectors, and sequencing vectors.

Further, the expression vector may be provided to a cell in the form of a viral vector. Viral vector technology is well known in the art and is described, for example, in Sambrook et al., 2012, Molecular Cloning: A Laboratory Manual, volumes 1-4, Cold Spring Harbor Press, NY), and in other virology and molecular biology manuals. Viruses, which are useful as vectors include, but are not limited to, retroviruses, adenoviruses, adeno-associated viruses, herpes viruses, and lentiviruses. In general, a suitable vector contains an origin of replication functional in at least one organism, a promoter sequence, convenient restriction endonuclease sites, and one or more selectable markers, (e.g., WO 01/96584; WO 01/29058; and U.S. Pat. No. 6,326,193).

A number of virally based systems have been developed for gene transfer into mammalian cells. For example, retroviruses provide a convenient platform for gene delivery systems. A selected gene can be inserted into a vector and packaged in retroviral particles using techniques known in the art. The recombinant virus can then be isolated and delivered to cells of the subject either in vivo or ex vivo. A number of retroviral systems are known in the art. In some embodiments, adenovirus vectors are used. A number of adenovirus vectors are known in the art. In one embodiment, lentivirus vectors are used.

Additional promoter elements, e.g., enhancers, regulate the frequency of transcriptional initiation. Typically, these are located in the region 30-110 bp upstream of the start site, although a number of promoters have been shown to contain functional elements downstream of the start site as well. The spacing between promoter elements frequently is flexible, so that promoter function is preserved when elements are inverted or moved relative to one another. In the thymidine kinase (tk) promoter, the spacing between promoter elements can be increased to 50 bp apart before activity begins to decline. Depending on the promoter, it appears that individual elements can function either cooperatively or independently to activate transcription.

An example of a promoter that is capable of expressing a TFP transgene in a mammalian T-cell is the EF1a promoter. The native EF1a promoter drives expression of the alpha subunit of the elongation factor-1 complex, which is responsible for the enzymatic delivery of aminoacyl tRNAs to the ribosome. The EF1a promoter has been extensively used in mammalian expression plasmids and has been shown to be effective in driving TFP expression from transgenes cloned into a lentiviral vector (see, e.g., Milone et al., Mol. Ther. 17(8): 1453-1464 (2009)). Another example of a promoter is the immediate early cytomegalovirus (CMV) promoter sequence. This promoter sequence is a strong constitutive promoter sequence capable of driving high levels of expression of any polynucleotide sequence operatively linked thereto. However, other constitutive promoter sequences may also be used, including, but not limited to the simian virus 40 (SV40) early promoter, mouse mammary tumor virus (MMTV), human immunodeficiency virus (HIV) long terminal repeat (LTR) promoter, MoMuLV promoter, an avian leukemia virus promoter, an Epstein-Barr virus immediate early promoter, a Rous sarcoma virus promoter, as well as human gene promoters such as, but not limited to, the actin promoter, the myosin promoter, the elongation factor-1a promoter, the hemoglobin promoter, and the creatine kinase promoter. Further, the invention should not be limited to the use of constitutive promoters. Inducible promoters are also contemplated as part of the invention. The use of an inducible promoter provides a molecular switch capable of turning on expression of the polynucleotide sequence which it is operatively linked when such expression is desired, or turning off the expression when expression is not desired. Examples of inducible promoters include, but are not limited to a metallothionine promoter, a glucocorticoid promoter, a progesterone promoter, and a tetracycline-regulated promoter.

In order to assess the expression of a TFP polypeptide or portions thereof, the expression vector to be introduced into a cell can also contain either a selectable marker gene or a reporter gene or both to facilitate identification and selection of expressing cells from the population of cells sought to be transfected or infected through viral vectors. In other aspects, the selectable marker may be carried on a separate piece of DNA and used in a co-transfection procedure. Both selectable markers and reporter genes may be flanked with appropriate regulatory sequences to enable expression in the host cells. Useful selectable markers include, for example, antibiotic-resistance genes, such as neo and the like.

Reporter genes are used for identifying potentially transfected cells and for evaluating the functionality of regulatory sequences. In general, a reporter gene is a gene that is not present in or expressed by the recipient organism or tissue and that encodes a polypeptide whose expression is manifested by some easily detectable property, e.g., enzymatic activity. Expression of the reporter gene is assayed at a suitable time after the DNA has been introduced into the recipient cells. Suitable reporter genes may include genes encoding luciferase, beta-galactosidase, chloramphenicol acetyl transferase, secreted alkaline phosphatase, or the green fluorescent protein gene (e.g., Ui-Tei et al., 2000 FEBS Letters 479: 79-82). Suitable expression systems are well known and may be prepared using known techniques or obtained commercially. In general, the construct with the minimal 5' flanking region showing the highest level of expression of reporter gene is identified as the promoter. Such promoter regions may be linked to a reporter gene and used to evaluate agents for the ability to modulate promoter-driven transcription.

Methods of introducing and expressing genes into a cell are known in the art. In the context of an expression vector, the vector can be readily introduced into a host cell, e.g., mammalian, bacterial, yeast, or insect cell by any method in the art. For example, the expression vector can be transferred into a host cell by physical, chemical, or biological means.

Physical methods for introducing a polynucleotide into a host cell include calcium phosphate precipitation, lipofection, particle bombardment, microinjection, electroporation, and the like. Methods for producing cells comprising vectors and/or exogenous nucleic acids are well-known in the art. See, for example, Sambrook et al., 2012, Molecular Cloning: A Laboratory Manual, volumes 1-4, Cold Spring Harbor Press, NY). A preferred method for the introduction of a polynucleotide into a host cell is calcium phosphate transfection Biological methods for introducing a polynucleotide of interest into a host cell include the use of DNA and RNA vectors. Viral vectors, and especially retroviral vectors, have become the most widely used method for inserting genes into mammalian, e.g., human cells. Other viral vectors can be derived from lentivirus, poxviruses, herpes simplex virus I, adenoviruses and adeno-associated viruses, and the like (see, e.g., U.S. Pat. Nos. 5,350,674 and 5,585,362.

Chemical means for introducing a polynucleotide into a host cell include colloidal dispersion systems, such as macromolecule complexes, nanocapsules, microspheres, beads, and lipid-based systems including oil-in-water emulsions, micelles, mixed micelles, and liposomes. An exemplary colloidal system for use as a delivery vehicle in vitro and in vivo is a liposome (e.g., an artificial membrane vesicle). Other methods of state-of-the-art targeted delivery of nucleic acids are available, such as delivery of polynucleotides with targeted nanoparticles or other suitable submicron sized delivery system.

In the case where a non-viral delivery system is utilized, an exemplary delivery vehicle is a liposome. The use of lipid formulations is contemplated for the introduction of the nucleic acids into a host cell (in vitro, ex vivo or in vivo). In another aspect, the nucleic acid may be associated with a lipid. The nucleic acid associated with a lipid may be encapsulated in the aqueous interior of a liposome, interspersed within the lipid bilayer of a liposome, attached to a liposome via a linking molecule that is associated with both the liposome and the oligonucleotide, entrapped in a liposome, complexed with a liposome, dispersed in a solution containing a lipid, mixed with a lipid, combined with a lipid, contained as a suspension in a lipid, contained or complexed with a micelle, or otherwise associated with a lipid. Lipid, lipid/DNA or lipid/expression vector associated compositions are not limited to any particular structure in solution. For example, they may be present in a bilayer structure, as micelles, or with a "collapsed" structure. They may also simply be interspersed in a solution, possibly forming aggregates that are not uniform in size or shape. Lipids are fatty substances which may be naturally occurring or synthetic lipids. For example, lipids include the fatty droplets that naturally occur in the cytoplasm as well as the class of compounds which contain long-chain aliphatic hydrocarbons and their derivatives, such as fatty acids, alcohols, amines, amino alcohols, and aldehydes.

Lipids suitable for use can be obtained from commercial sources. For example, dimyristyl phosphatidylcholine ("DMPC") can be obtained from Sigma, St. Louis, Mo.; dicetyl phosphate ("DCP") can be obtained from K & K Laboratories (Plainview, N.Y.); cholesterol ("Choi") can be obtained from Calbiochem-Behring; dimyristyl phosphatidylglycerol ("DMPG") and other lipids may be obtained from Avanti Polar Lipids, Inc. (Birmingham, Ala.). Stock solutions of lipids in chloroform or chloroform/methanol can be stored at about −20° C. Chloroform is used as the only solvent since it is more readily evaporated than methanol. "Liposome" is a generic term encompassing a variety of single and multilamellar lipid vehicles formed by the generation of enclosed lipid bilayers or aggregates. Liposomes can be characterized as having vesicular structures with a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh et al., 1991 Glycobiology 5: 505-10). However, compositions that have different structures in solution than the normal vesicular structure are also encompassed. For example, the lipids may assume a micellar structure or merely exist as nonuniform aggregates of lipid molecules. Also contemplated are lipofectamine-nucleic acid complexes.

Regardless of the method used to introduce exogenous nucleic acids into a host cell or otherwise expose a cell to the inhibitor of the present invention, in order to confirm the presence of the recombinant DNA sequence in the host cell, a variety of assays may be performed. Such assays include, for example, "molecular biological" assays well known to those of skill in the art, such as Southern and Northern blotting, RT-PCR and PCR; "biochemical" assays, such as detecting the presence or absence of a particular peptide, e.g., by immunological means (ELISAs and Western blots) or by assays described herein to identify agents falling within the scope of the invention.

The present invention further provides a vector comprising a TFP encoding nucleic acid molecule. In one aspect, a TFP vector can be directly transduced into a cell, e.g., a T-cell. In one aspect, the vector is a cloning or expression vector, e.g., a vector including, but not limited to, one or more plasmids (e.g., expression plasmids, cloning vectors, minicircles, minivectors, double minute chromosomes), retroviral and lentiviral vector constructs. In one aspect, the vector is capable of expressing the TFP construct in mammalian T-cells. In one aspect, the mammalian T-cell is a human T-cell.

Sources of T-Cells

Prior to expansion and genetic modification, a source of T-cells is obtained from a subject. The term "subject" is intended to include living organisms in which an immune response can be elicited (e.g., mammals) Examples of subjects include humans, dogs, cats, mice, rats, and transgenic species thereof. T-cells can be obtained from a number of sources, including peripheral blood mononuclear cells, bone marrow, lymph node tissue, cord blood, thymus tissue, tissue from a site of infection, ascites, pleural effusion, spleen tissue, and tumors. In certain aspects of the present invention, any number of T-cell lines available in the art, may be used. In certain aspects of the present invention, T-cells can be obtained from a unit of blood collected from a subject using any number of techniques known to the skilled artisan, such as Ficoll™ separation. In one preferred aspect, cells from the circulating blood of an individual are obtained by apheresis. The apheresis product typically contains lymphocytes, including T-cells, monocytes, granulocytes, B cells, other nucleated white blood cells, red blood cells, and platelets. In one aspect, the cells collected by apheresis may be washed to remove the plasma fraction and to place the cells in an appropriate buffer or media for subsequent processing steps. In one aspect of the invention, the cells are washed with phosphate buffered saline (PBS). In an alternative aspect, the wash solution lacks calcium and may lack magnesium or may lack many if not all divalent cations. Initial activation steps in the absence of calcium can lead to magnified activation. As those of ordinary skill in the art would readily appreciate a washing step may be accomplished by methods known to those in the art, such as by using a semi-automated "flow-through" centrifuge (for example, the Cobe 2991 cell processor, the Baxter CytoMate, or the Haemonetics Cell Saver 5) according to the manufacturer's instructions. After washing, the cells may be resuspended in a variety of biocompatible buffers, such as, for example, Ca-free, Mg-free PBS, PlasmaLyte A, or other saline solution with or without buffer. Alternatively, the undesirable components of the apheresis sample may be removed and the cells directly resuspended in culture media.

In one aspect, T-cells are isolated from peripheral blood lymphocytes by lysing the red blood cells and depleting the monocytes, for example, by centrifugation through a PERCOLL™ gradient or by counterflow centrifugal elutriation. A specific subpopulation of T-cells, such as CD3+, CD28+, CD4+, CD8+, CD45RA+, and CD45RO+ T-cells, can be further isolated by positive or negative selection techniques. For example, in one aspect, T-cells are isolated by incubation with anti-CD3/anti-CD28 (e.g., 3×28)-conjugated beads, such as DYNABEADS™ M-450 CD3/CD28 T, for a time period sufficient for positive selection of the desired T-cells. In one aspect, the time period is about 30 minutes. In a further aspect, the time period ranges from 30 minutes to 36 hours or longer and all integer values there between. In a further aspect, the time period is at least 1, 2, 3, 4, 5, or 6 hours. In yet another preferred aspect, the time period is 10 to 24 hours. In one aspect, the incubation time period is 24 hours. Longer incubation times may be used to isolate T-cells in any situation where there are few T-cells as compared to other cell types, such in isolating tumor infiltrating lymphocytes (TIL) from tumor tissue or from immunocompromised individuals. Further, use of longer incubation times can increase the efficiency of capture of CD8+ T-cells. Thus, by simply shortening or lengthening the time T-cells are allowed to bind to the CD3/CD28 beads and/or by increasing or decreasing the ratio of beads to T-cells (as described further herein), subpopulations of T-cells can be preferentially selected for or against at culture initiation or at other time points during the process. Additionally, by increasing or decreasing the ratio of anti-CD3 and/or anti-CD28 antibodies on the beads or other surface, subpopulations of T-cells can be preferentially selected for or against at culture initiation or at other desired time points. The skilled artisan would recognize that multiple rounds of selection can also be used in the context of this invention. In certain aspects, it may be desirable to perform the selection procedure and use the "unselected" cells in the activation and expansion process. "Unselected" cells can also be subjected to further rounds of selection.

Enrichment of a T-cell population by negative selection can be accomplished with a combination of antibodies directed to surface markers unique to the negatively selected cells. One method is cell sorting and/or selection via negative magnetic immunoadherence or flow cytometry that uses a cocktail of monoclonal antibodies directed to cell surface markers present on the cells negatively selected. For example, to enrich for CD4+ cells by negative selection, a monoclonal antibody cocktail typically includes antibodies to CD14, CD20, CD11b, CD16, HLA-DR, and CD8. In certain aspects, it may be desirable to enrich for or positively select for regulatory T-cells which typically express CD4+, CD25+, CD62Lhi, GITR+, and FoxP3+. Alternatively, in certain aspects, T regulatory cells are depleted by anti-C25 conjugated beads or other similar method of selection.

In one embodiment, a T-cell population can be selected that expresses one or more of IFN-γ, TNF-alpha, IL-17A, IL-2, IL-3, IL-4, GM-CSF, IL-10, IL-13, granzyme B, and perforin, or other appropriate molecules, e.g., other cytokines. Methods for screening for cell expression can be determined, e.g., by the methods described in PCT Publication No.: WO 2013/126712.

For isolation of a desired population of cells by positive or negative selection, the concentration of cells and surface (e.g., particles such as beads) can be varied. In certain aspects, it may be desirable to significantly decrease the volume in which beads and cells are mixed together (e.g., increase the concentration of cells), to ensure maximum contact of cells and beads. For example, in one aspect, a concentration of 2 billion cells/mL is used. In one aspect, a concentration of 1 billion cells/mL is used. In a further aspect, greater than 100 million cells/mL is used. In a further aspect, a concentration of cells of 10, 15, 20, 25, 30, 35, 40, 45, or 50 million cells/mL is used. In yet one aspect, a concentration of cells from 75, 80, 85, 90, 95, or 100 million cells/mL is used. In further aspects, concentrations of 125 or 150 million cells/mL can be used. Using high concentrations can result in increased cell yield, cell activation, and cell expansion. Further, use of high cell concentrations allows more efficient capture of cells that may weakly express target antigens of interest, such as CD28-negative T-cells, or from samples where there are many tumor cells present (e.g., leukemic blood, tumor tissue, etc.). Such populations of cells may have therapeutic value and would be desirable to obtain. For example, using high concentration of cells allows more efficient selection of CD8+ T-cells that normally have weaker CD28 expression.

In a related aspect, it may be desirable to use lower concentrations of cells. By significantly diluting the mixture of T-cells and surface (e.g., particles such as beads), interactions between the particles and cells is minimized. This selects for cells that express high amounts of desired antigens to be bound to the particles. For example, CD4+ T-cells express higher levels of CD28 and are more efficiently captured than CD8+ T-cells in dilute concentrations. In one aspect, the concentration of cells used is $5\times10^{6}$/mL. In other aspects, the concentration used can be from about $1\times10^{5}$/mL to $1\times10^{6}$/mL, and any integer value in between. In other aspects, the cells may be incubated on a rotator for varying lengths of time at varying speeds at either 2-10° C. or at room temperature.

T-cells for stimulation can also be frozen after a washing step. Wishing not to be bound by theory, the freeze and subsequent thaw step provides a more uniform product by removing granulocytes and to some extent monocytes in the cell population. After the washing step that removes plasma and platelets, the cells may be suspended in a freezing solution. While many freezing solutions and parameters are known in the art and will be useful in this context, one method involves using PBS containing 20% DMSO and 8% human serum albumin, or culture media containing 10%

Dextran 40 and 5% Dextrose, 20% Human Serum Albumin and 7.5% DMSO, or 31.25% Plasmalyte-A, 31.25% Dextrose 5%, 0.45% NaCl, 10% Dextran 40 and 5% Dextrose, 20% Human Serum Albumin, and 7.5% DMSO or other suitable cell freezing media containing for example, Hespan and PlasmaLyte A, the cells then are frozen to −80° C. at a rate of 1 per minute and stored in the vapor phase of a liquid nitrogen storage tank. Other methods of controlled freezing may be used as well as uncontrolled freezing immediately at −20° C. or in liquid nitrogen. In certain aspects, cryopreserved cells are thawed and washed as described herein and allowed to rest for one hour at room temperature prior to activation using the methods of the present invention.

Also contemplated in the context of the invention is the collection of blood samples or apheresis product from a subject at a time period prior to when the expanded cells as described herein might be needed. As such, the source of the cells to be expanded can be collected at any time point necessary, and desired cells, such as T-cells, isolated and frozen for later use in T-cell therapy for any number of diseases or conditions that would benefit from T-cell therapy, such as those described herein. In one aspect a blood sample or an apheresis is taken from a generally healthy subject. In certain aspects, a blood sample or an apheresis is taken from a generally healthy subject who is at risk of developing a disease, but who has not yet developed a disease, and the cells of interest are isolated and frozen for later use. In certain aspects, the T-cells may be expanded, frozen, and used at a later time. In certain aspects, samples are collected from a patient shortly after diagnosis of a particular disease as described herein but prior to any treatments. In a further aspect, the cells are isolated from a blood sample or an apheresis from a subject prior to any number of relevant treatment modalities, including but not limited to treatment with agents such as natalizumab, efalizumab, antiviral agents, chemotherapy, radiation, immunosuppressive agents, such as cyclosporin, azathioprine, methotrexate, mycophenolate, and FK506, antibodies, or other immunoablative agents such as CAMPATH, anti-CD3 antibodies, cytoxan, fludarabine, cyclosporin, FK506, rapamycin, mycophenolic acid, steroids, FR901228, and irradiation.

In a further aspect of the present invention, T-cells are obtained from a patient directly following treatment that leaves the subject with functional T-cells. In this regard, it has been observed that following certain cancer treatments, in particular treatments with drugs that damage the immune system, shortly after treatment during the period when patients would normally be recovering from the treatment, the quality of T-cells obtained may be optimal or improved for their ability to expand ex vivo. Likewise, following ex vivo manipulation using the methods described herein, these cells may be in a preferred state for enhanced engraftment and in vivo expansion. Thus, it is contemplated within the context of the present invention to collect blood cells, including T-cells, dendritic cells, or other cells of the hematopoietic lineage, during this recovery phase. Further, in certain aspects, mobilization (for example, mobilization with GM-CSF) and conditioning regimens can be used to create a condition in a subject wherein repopulation, recirculation, regeneration, and/or expansion of particular cell types is favored, especially during a defined window of time following therapy. Illustrative cell types include T-cells, B cells, dendritic cells, and other cells of the immune system.

Activation and Expansion of T Cells

T-cells may be activated and expanded generally using methods as described, for example, in U.S. Pat. Nos. 6,352,694; 6,534,055; 6,905,680; 6,692,964; 5,858,358; 6,887,466; 6,905,681; 7,144,575; 7,067,318; 7,172,869; 7,232,566; 7,175,843; 5,883,223; 6,905,874; 6,797,514; 6,867,041; and U.S. Patent Application Publication No. 20060121005.

Generally, the T-cells of the invention may be expanded by contact with a surface having attached thereto an agent that stimulates a CD3/TCR complex associated signal and a ligand that stimulates a costimulatory molecule on the surface of the T-cells. In particular, T-cell populations may be stimulated as described herein, such as by contact with an anti-CD3 antibody, or antigen-binding fragment thereof, or an anti-CD2 antibody immobilized on a surface, or by contact with a protein kinase C activator (e.g., bryostatin) in conjunction with a calcium ionophore. For costimulation of an accessory molecule on the surface of the T-cells, a ligand that binds the accessory molecule is used. For example, a population of T-cells can be contacted with an anti-CD3 antibody and an anti-CD28 antibody, under conditions appropriate for stimulating proliferation of the T-cells. To stimulate proliferation of either CD4+ T-cells or CD8+ T-cells, an anti-CD3 antibody and an anti-CD28 antibody. Examples of an anti-CD28 antibody include 9.3, B-T3, XR-CD28 (Diaclone, Besancon, France) can be used as can other methods commonly known in the art (Berg et al., Transplant Proc. 30(8):3975-3977, 1998; Haanen et al., J. Exp. Med. 190(9):13191328, 1999; Garland et al., J. Immunol. Meth. 227(1-2):53-63, 1999).

T-cells that have been exposed to varied stimulation times may exhibit different characteristics. For example, typical blood or apheresed peripheral blood mononuclear cell products have a helper T-cell population (TH, CD4+) that is greater than the cytotoxic or suppressor T-cell population (TC, CD8+). Ex vivo expansion of T-cells by stimulating CD3 and CD28 receptors produces a population of T-cells that prior to about days 8-9 consists predominately of TH cells, while after about days 8-9, the population of T-cells comprises an increasingly greater population of TC cells. Accordingly, depending on the purpose of treatment, infusing a subject with a T-cell population comprising predominately of TH cells may be advantageous. Similarly, if an antigen-specific subset of TC cells has been isolated it may be beneficial to expand this subset to a greater degree.

Further, in addition to CD4 and CD8 markers, other phenotypic markers vary significantly, but in large part, reproducibly during the course of the cell expansion process. Thus, such reproducibility enables the ability to tailor an activated T-cell product for specific purposes.

Once an anti-CD19 or anti-BCMA TFP is constructed, various assays can be used to evaluate the activity of the molecule, such as but not limited to, the ability to expand T-cells following antigen stimulation, sustain T-cell expansion in the absence of re-stimulation, and anti-cancer activities in appropriate in vitro and animal models. Assays to evaluate the effects of an anti-CD19 or anti-BCMA TFP are described in further detail below Western blot analysis of TFP expression in primary T-cells can be used to detect the presence of monomers and dimers (see, e.g., Milone et al., Molecular Therapy 17(8): 1453-1464 (2009)). Very briefly, T-cells (1:1 mixture of $CD4^+$ and $CD8^+$ T-cells) expressing the TFPs are expanded in vitro for more than 10 days followed by lysis and SDS-PAGE under reducing conditions. TFPs are detected by Western blotting using an antibody to a TCR chain. The same T-cell subsets are used for SDS-PAGE analysis under non-reducing conditions to permit evaluation of covalent dimer formation.

In vitro expansion of $TFP^+$ T-cells following antigen stimulation can be measured by flow cytometry. For example, a mixture of $CD4^+$ and $CD8^+$ T-cells are stimulated with alphaCD3/alphaCD28 and APCs followed by transduction with lentiviral vectors expressing GFP under the control of the promoters to be analyzed. Exemplary promoters include the CMV IE gene, EF-1alpha, ubiquitin C, or phosphoglycerokinase (PGK) promoters. GFP fluorescence is evaluated on day 6 of culture in the CD4+ and/or CD8+ T-cell subsets by flow cytometry (see, e.g., Milone et al., Molecular Therapy 17(8): 1453-1464 (2009)). Alternatively, a mixture of CD4+ and CD8+ T-cells are stimulated with alphaCD3/alphaCD28 coated magnetic beads on day 0, and transduced with TFP on day 1 using a bicistronic lentiviral vector expressing TFP along with eGFP using a 2A ribosomal skipping sequence. Cultures are re-stimulated with either CD19+K562 cells (K562-CD19), wild-type K562 cells (K562 wild type) or K562 cells expressing hCD32 and 4-1BBL in the presence of antiCD3 and anti-CD28 antibody (K562-BBL-3/28) following washing. Exogenous IL-2 is added to the cultures every other day at 100 IU/mL. GFP+ T-cells are enumerated by flow cytometry using bead-based counting (see, e.g., Milone et al., Molecular Therapy 17(8): 1453-1464 (2009)).

Sustained TFP+ T-cell expansion in the absence of re-stimulation can also be measured (see, e.g., Milone et al., Molecular Therapy 17(8): 1453-1464 (2009)). Briefly, mean T-cell volume (fl) is measured on day 8 of culture using a Coulter Multisizer III particle counter following stimulation with alphaCD3/alphaCD28 coated magnetic beads on day 0, and transduction with the indicated TFP on day 1.

Animal models can also be used to measure a TFP-T activity. For example, xenograft model using human CD19-specific TFP+ T-cells to treat a primary human pre-B ALL in immunodeficient mice can be used (see, e.g., Milone et al., Molecular Therapy 17(8): 1453-1464 (2009)). Very briefly, after establishment of ALL, mice are randomized as to treatment groups. Different numbers of engineered T-cells are coinjected at a 1:1 ratio into NOD/SCID/γ−/− mice bearing B-ALL. The number of copies of each vector in spleen DNA from mice is evaluated at various times following T-cell injection. Animals are assessed for leukemia at weekly intervals. Peripheral blood CD19+B-ALL blast cell counts are measured in mice that are injected with alphaCD19-zeta TFP+ T-cells or mock-transduced T-cells. Survival curves for the groups are compared using the log-rank test. In addition, absolute peripheral blood CD4+ and CD8+ T-cell counts 4 weeks following T-cell injection in NOD/SCID/γ−/− mice can also be analyzed. Mice are injected with leukemic cells and 3 weeks later are injected with T-cells engineered to express TFP by a bicistronic lentiviral vector that encodes the TFP linked to eGFP. T-cells are normalized to 45-50% input GFP+ T-cells by mixing with mock-transduced cells prior to injection, and confirmed by flow cytometry. Animals are assessed for leukemia at 1-week intervals. Survival curves for the TFP+ T-cell groups are compared using the log-rank test.

Dose dependent TFP treatment response can be evaluated (see, e.g., Milone et al., Molecular Therapy 17(8): 1453-1464 (2009)). For example, peripheral blood is obtained 35-70 days after establishing leukemia in mice injected on day 21 with TFP T-cells, an equivalent number of mock-transduced T-cells, or no T-cells. Mice from each group are randomly bled for determination of peripheral blood CD19+ ALL blast counts and then killed on days 35 and 49. The remaining animals are evaluated on days 57 and 70.

Assessment of cell proliferation and cytokine production has been previously described, e.g., at Milone et al., Molecular Therapy 17(8): 1453-1464 (2009). Briefly, assessment of TFP-mediated proliferation is performed in microtiter plates by mixing washed T-cells with K562 cells expressing CD19 (K19) or CD32 and CD137 (KT32-BBL) for a final T-cell: K562 ratio of 2:1. K562 cells are irradiated with gamma-radiation prior to use. Anti-CD3 (clone OKT3) and anti-CD28 (clone 9.3) monoclonal antibodies are added to cultures with KT32-BBL cells to serve as a positive control for stimulating T-cell proliferation since these signals support long-term CD8+ T-cell expansion ex vivo. T-cells are enumerated in cultures using CountBright™ fluorescent beads (Invitrogen) and flow cytometry as described by the manufacturer. TFP+ T-cells are identified by GFP expression using T-cells that are engineered with eGFP-2A linked TFP-expressing lentiviral vectors. For TFP+ T-cells not expressing GFP, the TFP+ T-cells are detected with biotinylated recombinant CD19 protein and a secondary avidin-PE conjugate. CD4+ and CD8+ expression on T-cells are also simultaneously detected with specific monoclonal antibodies (BD Biosciences). Cytokine measurements are performed on supernatants collected 24 hours following re-stimulation using the human TH1/TH2 cytokine cytometric bead array kit (BD Biosciences) according the manufacturer's instructions. Fluorescence is assessed using a FACScalibur flow cytometer, and data is analyzed according to the manufacturer's instructions.

Cytotoxicity can be assessed by a standard $^{51}Cr$-release assay (see, e.g., Milone et al., Molecular Therapy 17(8): 1453-1464 (2009)). Briefly, target cells (K562 lines and primary pro-B-ALL cells) are loaded with $^{51}Cr$ (as $NaCrO_4$, New England Nuclear) at 37° C. for 2 hours with frequent agitation, washed twice in complete RPMI and plated into microtiter plates. Effector T-cells are mixed with target cells in the wells in complete RPMI at varying ratios of effector cell:target cell (E:T). Additional wells containing media only (spontaneous release, SR) or a 1% solution of triton-X 100 detergent (total release, TR) are also prepared. After 4 hours of incubation at 37° C., supernatant from each well is harvested. Released $^{51}Cr$ is then measured using a gamma particle counter (Packard Instrument Co., Waltham, Mass.). Each condition is performed in at least triplicate, and the percentage of lysis is calculated using the formula: % Lysis=(ER-SR)/(TR-SR), where ER represents the average $^{51}Cr$ released for each experimental condition.

Imaging technologies can be used to evaluate specific trafficking and proliferation of TFPs in tumor-bearing animal models. Such assays have been described, e.g., in Barrett et al., Human Gene Therapy 22:1575-1586 (2011). Briefly, NOD/SCID/γc−/− (NSG) mice are injected IV with Nalm-6 cells followed 7 days later with T-cells 4 hour after electroporation with the TFP constructs. The T-cells are stably transfected with a lentiviral construct to express firefly luciferase, and mice are imaged for bioluminescence. Alternatively, therapeutic efficacy and specificity of a single injection of TFP+ T-cells in Nalm-6 xenograft model can be measured as the following: NSG mice are injected with Nalm-6 transduced to stably express firefly luciferase, followed by a single tail-vein injection of T-cells electroporated with CD19 TFP 7 days later. Animals are imaged at various time points post injection. For example, photon-density heat maps of firefly luciferase positive leukemia in representative mice at day 5 (2 days before treatment) and day 8 (24 hours post TFP+ PBLs) can be generated.

Other assays, including those described in the Example section herein as well as those that are known in the art can also be used to evaluate the anti-CD19 or anti-BCMA TFP constructs of the invention.

Therapeutic Applications

CD19 or BCMA Associated Diseases and/or Disorders

In one aspect, the invention provides methods for treating a disease associated with CD19 or BCMA expression. In one aspect, the invention provides methods for treating a disease wherein part of the tumor is negative for CD19 or BCMA and part of the tumor is positive for CD19 or BCMA. For example, the TFP of the invention is useful for treating subjects that have undergone treatment for a disease associated with elevated expression of CD19 or BCMA, wherein the subject that has undergone treatment for elevated levels of CD19 or BCMA exhibits a disease associated with elevated levels of CD19 or BCMA.

In one aspect, the invention pertains to a vector comprising anti-CD19 or BCMA TFP operably linked to promoter for expression in mammalian T-cells. In one aspect, the invention provides a recombinant T-cell expressing the CD19 or BCMA TFP for use in treating CD19- or BCMA-expressing tumors, wherein the recombinant T-cell expressing the CD19 or BCMA TFP is termed a CD19 or BCMA TFP-T. In one aspect, the CD19 or BCMA TFP-T of the invention is capable of contacting a tumor cell with at least one CD19 or BCMA TFP of the invention expressed on its surface such that the TFP-T targets the tumor cell and growth of the tumor is inhibited.

In one aspect, the invention pertains to a method of inhibiting growth of a CD19- or BCMA-expressing tumor cell, comprising contacting the tumor cell with a CD19 or BCMA TFP T-cell of the present invention such that the TFP-T is activated in response to the antigen and targets the cancer cell, wherein the growth of the tumor is inhibited.

In one aspect, the invention pertains to a method of treating cancer in a subject. The method comprises administering to the subject a CD19 or BCMA TFP T-cell of the present invention such that the cancer is treated in the subject. An example of a cancer that is treatable by the CD19 or BCMA TFP T-cell of the invention is a cancer associated with expression of CD19 or BCMA. In one aspect, the cancer associated with expression of CD19 or BCMA is a hematological cancer. In one aspect, the hematological cancer is leukemia or lymphoma. In one aspect, a cancer associated with expression of CD19 includes cancers and malignancies including, but not limited to, e.g., one or more acute leukemias including but not limited to, e.g., B-cell acute Lymphoid Leukemia ("BALL"), T-cell acute Lymphoid Leukemia ("TALL"), acute lymphoid leukemia (ALL); one or more chronic leukemias including but not limited to, e.g., chronic myelogenous leukemia (CML), Chronic Lymphoid Leukemia (CLL). Additional cancers or hematologic conditions associated with expression of CD19 or BCMA include, but are not limited to, e.g., B cell prolymphocytic leukemia, blastic plasmacytoid dendritic cell neoplasm, Burkitt's lymphoma, diffuse large B cell lymphoma, Follicular lymphoma, Hairy cell leukemia, small cell- or a large cell-follicular lymphoma, malignant lymphoproliferative conditions, MALT lymphoma, mantle cell lymphoma, Marginal zone lymphoma, multiple myeloma, myelodysplasia and myelodysplastic syndrome, non-Hodgkin's lymphoma, plasmablastic lymphoma, plasmacytoid dendritic cell neoplasm, Waldenstrom macroglobulinemia, and "preleukemia" which are a diverse collection of hematological conditions united by ineffective production (or dysplasia) of myeloid blood cells, and the like. Further a disease associated with CD19 or BCMA expression include, but not limited to, e.g., atypical and/or non-classical cancers, malignancies, precancerous conditions or proliferative diseases associated with expression of CD19 or BCMA.

In some embodiments, a cancer that can be treated with a CD19 or BCMA TFP, e.g., described herein, is multiple myeloma. Multiple myeloma is a cancer of the blood, characterized by accumulation of a plasma cell clone in the bone marrow. Current therapies for multiple myeloma include, but are not limited to, treatment with lenalidomide, which is an analog of thalidomide. Lenalidomide has activities which include anti-tumor activity, angiogenesis inhibition, and immunomodulation. Generally, myeloma cells are thought to be negative for CD19 or BCMA expression by flow cytometry. The present invention encompasses the recognition that a small percent of myeloma tumor cells express CD19 or BCMA. Thus, in some embodiments, a C19 or BCMA TFP, e.g., as described herein, may be used to target myeloma cells. In some embodiments, CD19 or BCMA TFP therapy can be used in combination with one or more additional therapies, e.g., lenalidomide treatment.

The invention includes a type of cellular therapy where T-cells are genetically modified to express a TFP and the TFP-expressing T-cell is infused to a recipient in need thereof. The infused cell is able to kill tumor cells in the recipient. Unlike antibody therapies, TFP-expressing T-cells are able to replicate in vivo resulting in long-term persistence that can lead to sustained tumor control. In various aspects, the T-cells administered to the patient, or their progeny, persist in the patient for at least four months, five months, six months, seven months, eight months, nine months, ten months, eleven months, twelve months, thirteen months, fourteen month, fifteen months, sixteen months, seventeen months, eighteen months, nineteen months, twenty months, twenty-one months, twenty-two months, twenty-three months, two years, three years, four years, or five years after administration of the T-cell to the patient.

The invention also includes a type of cellular therapy where T-cells are modified, e.g., by in vitro transcribed RNA, to transiently express a TFP and the TFP-expressing T-cell is infused to a recipient in need thereof. The infused cell is able to kill tumor cells in the recipient. Thus, in various aspects, the T-cells administered to the patient, is present for less than one month, e.g., three weeks, two weeks, or one week, after administration of the T-cell to the patient.

Without wishing to be bound by any particular theory, the anti-tumor immunity response elicited by the TFP-expressing T-cells may be an active or a passive immune response, or alternatively may be due to a direct vs indirect immune response. In one aspect, the TFP transduced T-cells exhibit specific proinflammatory cytokine secretion and potent cytolytic activity in response to human cancer cells expressing the CD19 or BCMA antigen, resist soluble CD19 or BCMA inhibition, mediate bystander killing and mediate regression of an established human tumor. For example, antigen-less tumor cells within a heterogeneous field of CD19-expressing or BCMA-expressing tumor may be susceptible to indirect destruction by CD19-redirected or BCMA-redirected T-cells that has previously reacted against adjacent antigen-positive cancer cells.

In one aspect, the human TFP-modified T-cells of the invention may be a type of vaccine for ex vivo immunization and/or in vivo therapy in a mammal. In one aspect, the mammal is a human.

With respect to ex vivo immunization, at least one of the following occurs in vitro prior to administering the cell into a mammal: i) expansion of the cells, ii) introducing a nucleic acid encoding a TFP to the cells or iii) cryopreservation of the cells.

Ex vivo procedures are well known in the art and are discussed more fully below. Briefly, cells are isolated from a mammal (e.g., a human) and genetically modified (i.e., transduced or transfected in vitro) with a vector expressing a TFP disclosed herein. The TFP-modified cell can be administered to a mammalian recipient to provide a therapeutic benefit. The mammalian recipient may be a human and the TFP-modified cell can be autologous with respect to the recipient. Alternatively, the cells can be allogeneic, syngeneic or xenogeneic with respect to the recipient.

The procedure for ex vivo expansion of hematopoietic stem and progenitor cells is described in U.S. Pat. No. 5,199,942, incorporated herein by reference, can be applied to the cells of the present invention. Other suitable methods are known in the art, therefore the present invention is not limited to any particular method of ex vivo expansion of the cells. Briefly, ex vivo culture and expansion of T-cells comprises: (1) collecting CD34+ hematopoietic stem and progenitor cells from a mammal from peripheral blood harvest or bone marrow explants; and (2) expanding such cells ex vivo. In addition to the cellular growth factors described in U.S. Pat. No. 5,199,942, other factors such as flt3-L, IL-1, IL-3 and c-kit ligand, can be used for culturing and expansion of the cells.

In addition to using a cell-based vaccine in terms of ex vivo immunization, the present invention also provides compositions and methods for in vivo immunization to elicit an immune response directed against an antigen in a patient.

Generally, the cells activated and expanded as described herein may be utilized in the treatment and prevention of diseases that arise in individuals who are immunocompromised. In particular, the TFP-modified T-cells of the invention are used in the treatment of diseases, disorders and conditions associated with expression of CD19 or BCMA. In certain aspects, the cells of the invention are used in the treatment of patients at risk for developing diseases, disorders and conditions associated with expression of CD19 or BCMA. Thus, the present invention provides methods for the treatment or prevention of diseases, disorders and conditions associated with expression of CD19 or BCMA comprising administering to a subject in need thereof, a therapeutically effective amount of the TFP-modified T-cells of the invention.

In one aspect the TFP-T-cells of the inventions may be used to treat a proliferative disease such as a cancer or malignancy or is a precancerous condition such as a myelodysplasia, a myelodysplastic syndrome or a preleukemia. In one aspect, the cancer is a hematological cancer. In one aspect, the hematological cancer is leukemia or lymphoma. In one aspect, the TFP-T-cells of the invention may be used to treat cancers and malignancies such as, but not limited to, e.g., acute leukemias including but not limited to, e.g., B-cell acute lymphoid leukemia ("BALL"), T-cell acute lymphoid leukemia ("TALL"), acute lymphoid leukemia (ALL); one or more chronic leukemias including but not limited to, e.g., chronic myelogenous leukemia (CML), chronic lymphocytic leukemia (CLL); additional hematologic cancers or hematologic conditions including, but not limited to, e.g., B cell prolymphocytic leukemia, blastic plasmacytoid dendritic cell neoplasm, Burkitt's lymphoma, diffuse large B cell lymphoma, Follicular lymphoma, Hairy cell leukemia, small cell- or a large cell-follicular lymphoma, malignant lymphoproliferative conditions, MALT lymphoma, mantle cell lymphoma, Marginal zone lymphoma, multiple myeloma, myelodysplasia and myelodysplastic syndrome, non-Hodgkin's lymphoma, plasmablastic lymphoma, plasmacytoid dendritic cell neoplasm, Waldenstrom macroglobulinemia, and "preleukemia" which are a diverse collection of hematological conditions united by ineffective production (or dysplasia) of myeloid blood cells, and the like. Further a disease associated with CD19 or BCMA expression include, but not limited to, e.g., atypical and/or non-classical cancers, malignancies, precancerous conditions or proliferative diseases expressing CD19 or BCMA. Non-cancer related indications associated with expression of CD19 or BCMA include, but are not limited to, e.g., autoimmune disease, (e.g., lupus), inflammatory disorders (allergy and asthma) and transplantation.

The TFP-modified T-cells of the present invention may be administered either alone, or as a pharmaceutical composition in combination with diluents and/or with other components such as IL-2 or other cytokines or cell populations.

Hematologic Cancer

Hematological cancer conditions are the types of cancer such as leukemia and malignant lymphoproliferative conditions that affect blood, bone marrow and the lymphatic system.

Leukemia can be classified as acute leukemia and chronic leukemia. Acute leukemia can be further classified as acute myelogenous leukemia (AML) and acute lymphoid leukemia (ALL). Chronic leukemia includes chronic myelogenous leukemia (CML) and chronic lymphoid leukemia (CLL). Other related conditions include myelodysplastic syndromes (MDS, formerly known as "preleukemia") which are a diverse collection of hematological conditions united by ineffective production (or dysplasia) of myeloid blood cells and risk of transformation to AML.

The present invention provides for compositions and methods for treating cancer. In one aspect, the cancer is a hematologic cancer including but is not limited to hematological cancer is a leukemia or a lymphoma. In one aspect, the TFP-T-cells of the invention may be used to treat cancers and malignancies such as, but not limited to, e.g., acute leukemias including but not limited to, e.g., B-cell acute lymphoid leukemia ("BALL"), T-cell acute lymphoid leukemia ("TALL"), acute lymphoid leukemia (ALL); one or more chronic leukemias including but not limited to, e.g., chronic myelogenous leukemia (CML), chronic lymphocytic leukemia (CLL); additional hematologic cancers or hematologic conditions including, but not limited to, e.g., B cell prolymphocytic leukemia, blastic plasmacytoid dendritic cell neoplasm, Burkitt's lymphoma, diffuse large B cell lymphoma, Follicular lymphoma, Hairy cell leukemia, small cell- or a large cell-follicular lymphoma, malignant lymphoproliferative conditions, MALT lymphoma, mantle cell lymphoma, Marginal zone lymphoma, multiple myeloma, myelodysplasia and myelodysplastic syndrome, non-Hodgkin's lymphoma, plasmablastic lymphoma, plasmacytoid dendritic cell neoplasm, Waldenstrom macroglobulinemia, and "preleukemia" which are a diverse collection of hematological conditions united by ineffective production (or dysplasia) of myeloid blood cells, and the like. Further a disease associated with CD19 or BCMA expression includes, but not limited to, e.g., atypical and/or non-classical cancers, malignancies, precancerous conditions or proliferative diseases expressing CD19 or BCMA.

The present invention also provides methods for inhibiting the proliferation or reducing a CD19- or BCMA-expressing cell population, the methods comprising contacting a population of cells comprising a CD19- or BCMA-expressing cell with an anti-CD19 or anti-BCMA TFP-T-cell of the invention that binds to the CD19- or BCMA-expressing cell. In a specific aspect, the present invention provides methods for inhibiting the proliferation or reducing the population of cancer cells expressing CD19 or BCMA, the methods comprising contacting the CD19- or BCMA-expressing cancer cell population with an anti-CD19 or anti-BCMA TFP-T-cell of the invention that binds to the CD19- or BCMA-expressing cell. In one aspect, the present invention provides methods for inhibiting the proliferation or reducing the population of cancer cells expressing CD19 or BCMA, the methods comprising contacting the CD19- or BCMA-expressing cancer cell population with an anti-CD19 or anti-BCMA TFP-T-cell of the invention that binds to the CD19- or BCMA-expressing cell. In certain aspects, the anti-CD19 or anti-BCMA TFP-T-cell of the invention reduces the quantity, number, amount or percentage of cells and/or cancer cells by at least 25%, at least 30%, at least 40%, at least 50%, at least 65%, at least 75%, at least 85%, at least 95%, or at least 99% in a subject with or animal model for myeloid leukemia or another cancer associated with CD19- or BCMA-expressing cells relative to a negative control. In one aspect, the subject is a human.

The present invention also provides methods for preventing, treating and/or managing a disease associated with CD19- or BCMA-expressing cells (e.g., a hematologic cancer or atypical cancer expressing CD19 or BCMA), the methods comprising administering to a subject in need an anti-CD19 or anti-BCMA TFP-T-cell of the invention that binds to the CD19- or BCMA-expressing cell. In one aspect, the subject is a human. Non-limiting examples of disorders associated with CD19- or BCMA-expressing cells include autoimmune disorders (such as lupus), inflammatory disorders (such as allergies and asthma) and cancers (such as hematological cancers or atypical cancers expressing CD19 or BCMA).

The present invention also provides methods for preventing, treating and/or managing a disease associated with CD19- or BCMA-expressing cells, the methods comprising administering to a subject in need an anti-CD19 or anti-BCMA TFP-T-cell of the invention that binds to the CD19- or BCMA-expressing cell. In one aspect, the subject is a human.

The present invention provides methods for preventing relapse of cancer associated with CD19- or BCMA-expressing cells, the methods comprising administering to a subject in need thereof an anti-CD19 or anti-BCMA TFP-T-cell of the invention that binds to the CD19- or BCMA-expressing cell. In one aspect, the methods comprise administering to the subject in need thereof an effective amount of an anti-CD19 or anti-BCMA TFP-T-cell described herein that binds to the CD19- or BCMA-expressing cell in combination with an effective amount of another therapy.

Combination Therapies

A TFP-expressing cell described herein may be used in combination with other known agents and therapies. Administered "in combination", as used herein, means that two (or more) different treatments are delivered to the subject during the course of the subject's affliction with the disorder, e.g., the two or more treatments are delivered after the subject has been diagnosed with the disorder and before the disorder has been cured or eliminated or treatment has ceased for other reasons. In some embodiments, the delivery of one treatment is still occurring when the delivery of the second begins, so that there is overlap in terms of administration. This is sometimes referred to herein as "simultaneous" or "concurrent delivery". In other embodiments, the delivery of one treatment ends before the delivery of the other treatment begins. In some embodiments of either case, the treatment is more effective because of combined administration. For example, the second treatment is more effective, e.g., an equivalent effect is seen with less of the second treatment, or the second treatment reduces symptoms to a greater extent, than would be seen if the second treatment were administered in the absence of the first treatment or the analogous situation is seen with the first treatment. In some embodiments, delivery is such that the reduction in a symptom, or other parameter related to the disorder is greater than what would be observed with one treatment delivered in the absence of the other. The effect of the two treatments can be partially additive, wholly additive, or greater than additive. The delivery can be such that an effect of the first treatment delivered is still detectable when the second is delivered.

In some embodiments, the "at least one additional therapeutic agent" includes a TFP-expressing cell. Also provided are T-cells that express multiple TFPs, which bind to the same or different target antigens, or same or different epitopes on the same target antigen. Also provided are populations of T-cells in which a first subset of T-cells express a first TFP and a second subset of T-cells express a second TFP.

A TFP-expressing cell described herein and the at least one additional therapeutic agent can be administered simultaneously, in the same or in separate compositions, or sequentially. For sequential administration, the TFP-expressing cell described herein can be administered first, and the additional agent can be administered second, or the order of administration can be reversed.

In further aspects, a TFP-expressing cell described herein may be used in a treatment regimen in combination with surgery, chemotherapy, radiation, immunosuppressive agents, such as cyclosporin, azathioprine, methotrexate, mycophenolate, and FK506, antibodies, or other immunoablative agents such as CAMPATH, anti-CD3 antibodies or other antibody therapies, cytoxin, fludarabine, cyclosporin, FK506, rapamycin, mycophenolic acid, steroids, FR901228, cytokines, and irradiation. peptide vaccine, such as that described in Izumoto et al. 2008 J Neurosurg 108:963-971.

In one embodiment, the subject can be administered an agent which reduces or ameliorates a side effect associated with the administration of a TFP-expressing cell. Side effects associated with the administration of a TFP-expressing cell include, but are not limited to cytokine release syndrome (CRS), and hemophagocytic lymphohistiocytosis (HLH), also termed Macrophage Activation Syndrome (MAS). Symptoms of CRS include high fevers, nausea, transient hypotension, hypoxia, and the like. Accordingly, the methods described herein can comprise administering a TFP-expressing cell described herein to a subject and further administering an agent to manage elevated levels of a soluble factor resulting from treatment with a TFP-expressing cell. In one embodiment, the soluble factor elevated in the subject is one or more of IFN-γ, TNFα, IL-2 and IL-6. Therefore, an agent administered to treat this side effect can be an agent that neutralizes one or more of these soluble factors. Such agents include, but are not limited to a steroid, an inhibitor of TNFα, and an inhibitor of IL-6. An example of a TNFα inhibitor is entanercept. An example of an IL-6 inhibitor is tocilizumab (toc).

In one embodiment, the subject can be administered an agent which enhances the activity of a TFP-expressing cell. For example, in one embodiment, the agent can be an agent which inhibits an inhibitory molecule. Inhibitory molecules, e.g., Programmed Death 1 (PD1), can, in some embodiments, decrease the ability of a TFP-expressing cell to mount an immune effector response. Examples of inhibitory molecules include PD1, PD-L1, CTLA4, TIM3, LAG3, VISTA, BTLA, TIGIT, LAIR1, CD160, 2B4 and TGFR beta. Inhibition of an inhibitory molecule, e.g., by inhibition at the DNA, RNA or protein level, can optimize a TFP-expressing cell performance. In embodiments, an inhibitory nucleic acid, e.g., an inhibitory nucleic acid, e.g., a dsRNA, e.g., an siRNA or shRNA, can be used to inhibit expression of an inhibitory molecule in the TFP-expressing cell. In an embodiment the inhibitor is a shRNA. In an embodiment, the inhibitory molecule is inhibited within a TFP-expressing cell. In these embodiments, a dsRNA molecule that inhibits expression of the inhibitory molecule is linked to the nucleic acid that encodes a component, e.g., all of the components, of the TFP. In one embodiment, the inhibitor of an inhibitory signal can be, e.g., an antibody or antibody fragment that binds to an inhibitory molecule. For example, the agent can be an antibody or antibody fragment that binds to PD1, PD-L1, PD-L2 or CTLA4 (e.g., ipilimumab (also referred to as MDX-010 and MDX-101, and marketed as Yervoy™; Bristol-Myers Squibb; Tremelimumab (IgG2 monoclonal antibody available from Pfizer, formerly known as ticilimumab, CP-675,206)). In an embodiment, the agent is an antibody or antibody fragment that binds to TIM3. In an embodiment, the agent is an antibody or antibody fragment that binds to LAGS.

In some embodiments, the agent which enhances the activity of a TFP-expressing cell can be, e.g., a fusion protein comprising a first domain and a second domain, wherein the first domain is an inhibitory molecule, or fragment thereof, and the second domain is a polypeptide that is associated with a positive signal, e.g., a polypeptide comprising an intracellular signaling domain as described herein. In some embodiments, the polypeptide that is associated with a positive signal can include a costimulatory domain of CD28, CD27, ICOS, e.g., an intracellular signaling domain of CD28, CD27 and/or ICOS, and/or a primary signaling domain, e.g., of CD3 zeta, e.g., described herein. In one embodiment, the fusion protein is expressed by the same cell that expressed the TFP. In another embodiment, the fusion protein is expressed by a cell, e.g., a T-cell that does not express an anti-CD19 TFP.

Pharmaceutical Compositions

Pharmaceutical compositions of the present invention may comprise a TFP-expressing cell, e.g., a plurality of TFP-expressing cells, as described herein, in combination with one or more pharmaceutically or physiologically acceptable carriers, diluents or excipients. Such compositions may comprise buffers such as neutral buffered saline, phosphate buffered saline and the like; carbohydrates such as glucose, mannose, sucrose or dextrans, mannitol; proteins; polypeptides or amino acids such as glycine; antioxidants; chelating agents such as EDTA or glutathione; adjuvants (e.g., aluminum hydroxide); and preservatives. Compositions of the present invention are in one aspect formulated for intravenous administration.

Pharmaceutical compositions of the present invention may be administered in a manner appropriate to the disease to be treated (or prevented). The quantity and frequency of administration will be determined by such factors as the condition of the patient, and the type and severity of the patient's disease, although appropriate dosages may be determined by clinical trials.

In one embodiment, the pharmaceutical composition is substantially free of, e.g., there are no detectable levels of a contaminant, e.g., selected from the group consisting of endotoxin, *mycoplasma*, replication competent lentivirus (RCL), p24, VSV-G nucleic acid, HIV gag, residual anti-CD3/anti-CD28 coated beads, mouse antibodies, pooled human serum, bovine serum albumin, bovine serum, culture media components, vector packaging cell or plasmid components, a bacterium and a fungus. In one embodiment, the bacterium is at least one selected from the group consisting of *Alcaligenes faecalis, Candida albicans, Escherichia coli, Haemophilus influenza, Neisseria meningitides, Pseudomonas aeruginosa, Staphylococcus aureus, Streptococcus pneumonia*, and *Streptococcus pyogenes* group A.

When "an immunologically effective amount," "an anti-tumor effective amount," "a tumor-inhibiting effective amount," or "therapeutic amount" is indicated, the precise amount of the compositions of the present invention to be administered can be determined by a physician with consideration of individual differences in age, weight, tumor size, extent of infection or metastasis, and condition of the patient (subject). It can generally be stated that a pharmaceutical composition comprising the T-cells described herein may be administered at a dosage of $10^4$ to $10^9$ cells/kg body weight, in some instances $10^5$ to $10^6$ cells/kg body weight, including all integer values within those ranges. T-cell compositions may also be administered multiple times at these dosages. The cells can be administered by using infusion techniques that are commonly known in immunotherapy (see, e.g., Rosenberg et al., New Eng. J. of Med. 319:1676, 1988).

In certain aspects, it may be desired to administer activated T-cells to a subject and then subsequently redraw blood (or have an apheresis performed), activate T-cells therefrom according to the present invention, and reinfuse the patient with these activated and expanded T-cells. This process can be carried out multiple times every few weeks. In certain aspects, T-cells can be activated from blood draws of from 10 cc to 400 cc. In certain aspects, T-cells are activated from blood draws of 20 cc, 30 cc, 40 cc, 50 cc, 60 cc, 70 cc, 80 cc, 90 cc, or 100 cc.

The administration of the subject compositions may be carried out in any convenient manner, including by aerosol inhalation, injection, ingestion, transfusion, implantation or transplantation. The compositions described herein may be administered to a patient trans arterially, subcutaneously, intradermally, intratumorally, intranodally, intramedullary, intramuscularly, by intravenous (i.v.) injection, or intraperitoneally. In one aspect, the T-cell compositions of the present invention are administered to a patient by intradermal or subcutaneous injection. In one aspect, the T-cell compositions of the present invention are administered by i.v. injection. The compositions of T-cells may be injected directly into a tumor, lymph node, or site of infection.

In a particular exemplary aspect, subjects may undergo leukapheresis, wherein leukocytes are collected, enriched, or depleted ex vivo to select and/or isolate the cells of interest, e.g., T-cells. These T-cell isolates may be expanded by methods known in the art and treated such that one or more TFP constructs of the invention may be introduced, thereby creating a TFP-expressing T-cell of the invention. Subjects in need thereof may subsequently undergo standard treatment with high dose chemotherapy followed by peripheral blood stem cell transplantation. In certain aspects, following or concurrent with the transplant, subjects receive an infusion of the expanded TFP T-cells of the present invention. In an additional aspect, expanded cells are administered before or following surgery.

The dosage of the above treatments to be administered to a patient will vary with the precise nature of the condition being treated and the recipient of the treatment. The scaling of dosages for human administration can be performed according to art-accepted practices. The dose for CAMPATH, for example, will generally be in the range 1 to about 100 mg for an adult patient, usually administered daily for a period between 1 and 30 days. The preferred daily dose is 1 to 10 mg per day although in some instances larger doses of up to 40 mg per day may be used (described in U.S. Pat. No. 6,120,766).

In one embodiment, the TFP is introduced into T-cells, e.g., using in vitro transcription, and the subject (e.g., human) receives an initial administration of TFP T-cells of the invention, and one or more subsequent administrations of the TFP T-cells of the invention, wherein the one or more subsequent administrations are administered less than 15 days, e.g., 14, 13, 12, 11, 10, 9, 8, 7, 6, 5, 4, 3, or 2 days after the previous administration. In one embodiment, more than one administration of the TFP T-cells of the invention are administered to the subject (e.g., human) per week, e.g., 2, 3, or 4 administrations of the TFP T-cells of the invention are administered per week. In one embodiment, the subject (e.g., human subject) receives more than one administration of the TFP T-cells per week (e.g., 2, 3 or 4 administrations per week) (also referred to herein as a cycle), followed by a week of no TFP T-cells administrations, and then one or more additional administration of the TFP T-cells (e.g., more than one administration of the TFP T-cells per week) is administered to the subject. In another embodiment, the subject (e.g., human subject) receives more than one cycle of TFP T-cells, and the time between each cycle is less than 10, 9, 8, 7, 6, 5, 4, or 3 days. In one embodiment, the TFP T-cells are administered every other day for 3 administrations per week. In one embodiment, the TFP T-cells of the invention are administered for at least two, three, four, five, six, seven, eight or more weeks.

In one aspect, CD19 TFP T-cells are generated using lentiviral viral vectors, such as lentivirus. TFP-T-cells generated that way will have stable TFP expression.

In one aspect, TFP T-cells transiently express TFP vectors for 4, 5, 6, 7, 8, 9, 10, 11, 12, 13, 14, 15 days after transduction. Transient expression of TFPs can be effected by RNA TFP vector delivery. In one aspect, the TFP RNA is transduced into the T-cell by electroporation.

A potential issue that can arise in patients being treated using transiently expressing TFP T-cells (particularly with murine scFv bearing TFP T-cells) is anaphylaxis after multiple treatments.

Without being bound by this theory, it is believed that such an anaphylactic response might be caused by a patient developing humoral anti-TFP response, i.e., anti-TFP antibodies having an anti-IgE isotype. It is thought that a patient's antibody producing cells undergo a class switch from IgG isotype (that does not cause anaphylaxis) to IgE isotype when there is a ten to fourteen day break in exposure to antigen.

If a patient is at high risk of generating an anti-TFP antibody response during the course of transient TFP therapy (such as those generated by RNA transductions), TFP T-cell infusion breaks should not last more than ten to fourteen days.

EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein. Without further description, it is believed that one of ordinary skill in the art can, using the preceding description and the following illustrative examples, make and utilize the compounds of the present invention and practice the claimed methods. The following working examples specifically point out various aspects of the present invention, and are not to be construed as limiting in any way the remainder of the disclosure.

Example 1: TFP Constructs

Anti-CD19 TFP constructs were engineered by cloning an anti-CD19 scFv DNA fragment linked to a CD3 or TCR DNA fragment by either a DNA sequence encoding a short linker (SL): AAAGGGGSGGGGSGGGGSLE (SEQ ID NO: 5) or a long linker (LL): AAAIEVMYPPPYLGGGGSGGGGSGGGGSLE (SEQ ID NO: 6) into p510 vector ((System Biosciences (SBI)) at XbaI and EcoR1 sites.

The anti-CD19 TRuC constructs generated were p510_antiCD19_LL_TCRα (anti-CD19 scFv—long linker-human full length T cell receptor α chain), p510_antiCD19_LL_TCR αC (anti-CD19 scFv—long linker-human T cell receptor α constant domain chain), p510_antiCD19_LL_TCRβ (anti-CD19 scFv—long linker-human full length T cell receptor β chain), p510_antiCD19_LL_TCRβC (anti-CD19 scFv—long linker-human T cell receptor β constant domain chain), p510_antiCD19_LL_CD3γ (anti-CD19 scFv—long linker-human CD3γ chain), p510_antiCD19_LL_CD3δ (anti-CD19 scFv—long linker-human CD3ε chain), p510_antiCD19_LL_CD3ε (anti-CD19 scFv—long linker-human CD3ε chain), p510_antiCD19_SL_TCRβ (anti-CD19 scFv—short linker-human full length T cell receptor β chain), p510_antiCD19_SL_CD3γ (anti-CD19 scFv—short linker-human CD3γ chain), p510_antiCD19_SL_CD3δ (anti-CD19 scFv—short linker-human CD3ε chain), p510_antiCD19_SL_CD3ε (anti-CD19 scFv—short linker-human CD3ε chain).

The anti-CD19 CAR construct, p510_antiCD19_28ζ was generated by cloning synthesized DNA encoding anti-CD19, partial CD28 extracellular domain, CD28 transmembrane domain, CD28 intracellular domain and CD3 zeta into p510 vector at XbaI and EcoR1 sites.

Anti-BCMA TFP constructs were engineered by cloning an anti-BCMA scFv DNA fragment linked to a CD3 DNA fragment by a DNA sequence encoding the linker: GGGGSGGGGSGGGGSLE (SEQ ID NO: 7) into p510 vector (SBI) at XbaI and EcoR1 sites.

The anti-BCMA TFP constructs generated were p510_antiBCMA_CD3γ (anti-BCMA scFv—linker-human CD3γ chain) and p510_antiBCMA_CD3ε (anti-BCMA scFv—linker-human CD3ε chain).

Full length BCMA was synthesized and cloned into p514 (SBI) at BamHI and NheI sites to generate the construct p514_BCMA, used to generate stable target cell lines.

Anti-Fibroblast activation protein (FAP) and anti-Carboanhydrase-9 (CAIX) TFP constructs are engineered by cloning an anti-FAP or anti-CAIX scFv DNA fragment linked to a CD3 DNA fragment by a DNA sequence encoding the linker: GGGGSGGGGSGGGGSLE (SEQ ID NO: 7) into p510 vector (SBI) at XbaI and EcoR1 sites. The anti-FAP or anti-CAIX TFP constructs that can be generated include p510_antiFAP_CD3γ (anti-FAP scFv—linker-human CD3γ chain) and p510_antiFAP_CD3ε (anti-FAP scFv—linker-human CD3ε chain) and p510_antiCAIX_CD3γ (anti-CAIX scFv—linker-human CD3γ chain) and p510_antiCAIX_CD3ε (anti-CAIX scFv—linker-human CD3ε chain).

Full length FAP and CAIX can be synthesized and cloned into p514 (SBI) at BamHI and NheI sites to generate the constructs p514_FAP and p514_CAIX, that can be used to generate stable target cell lines.

Exemplary construct sequences are shown below:

| CONSTRUCT SEQUENCES |
| --- |
| Target Construct |

P514_BCMA (SEQ ID NO: 8)

```
   1 acgcgtgtag tcttatgcaa tactcttgta gtcttgcaac atggtaacga tgagttagca
  61 acatgcctta caaggagaga aaaagcaccg tgcatgccga ttggtggaag taaggtggta
 121 cgatcgtgcc ttattaggaa ggcaacagac gggtctgaca tggattggac gaaccactga
 181 attgccgcat tgcagagata ttgtatttaa gtgcctagct cgatacataa acgggtctct
 241 ctggttagac cagatctgag cctgggagct ctctggctaa ctagggaacc cactgcttaa
 301 gcctcaataa agcttgcctt gagtgcttca agtagtgtgt gcccgtctgt tgtgtgactc
 361 tggtaactag agatccctca gaccctttta gtcagtgtgg aaaatctcta gcagtggcgc
 421 ccgaacaggg acctgaaagc gaaagggaaa ccagagctct ctcgacgcag gactcggctt
 481 gctgaagcgc gcacggcaag aggcgagggg cggcgactgg tgagtacgcc aaaaattttg
 541 actagcggag gctagaagga gagagatggg tgcgagagcg tcagtattaa gcgggggaga
 601 attagatcgc gatgggaaaa aattcggtta aggccagggg gaaagaaaaa atataaatta
 661 aaacatatag tatgggcaag cagggagcta gaacgattcg cagttaatcc tggcctgtta
 721 gaaacatcag aaggctgtag acaaatactg ggacagctac aaccatccct tcagacagga
 781 tcagaagaac ttagatcatt atataataca gtagcaaccc tctattgtgt gcatcaaagg
 841 atagagataa aagacaccaa ggaagcttta gacaagatag aggaagagca aaacaaaagt
 901 aagaccaccg cacagcaagc ggccactgat cttcagacct ggaggaggag atatgaggga
 961 caattggaga agtgaattat ataaatataa agtagtaaaa attgaaccat taggagtagc
1021 acccaccaag gcaaagagaa gagtggtgca gagagaaaaa agagcagtgg gaataggagc
1081 tttgttcctt gggttcttgg gagcagcagg aagcactatg ggcgcagcgt caatgacgct
1141 gacggtacag gccagacaat tattgtctgg tatagtgcag cagcagaaca atttgctgag
1201 ggctattgag gcgcaacagc atctgttgca actcacagtc tggggcatca agcagctcca
1261 ggcaagaatc ctggctgtgg aaagatacct aaaggatcaa cagctcctgg ggatttgggg
1321 ttgctctgga aaactcattt gcaccactgc tgtgccttgg aatgctagtt ggagtaataa
1381 atctctggaa cagatttgga atcacacgac ctggatggag tgggacagag aaattaacaa
1441 ttacacaagc ttaatacact ccttaattga agaatcgcaa aaccagcaag aaaagaatga
1501 acaagaatta ttggaattag ataaatgggc aagtttgtgg aattggttta acataacaaa
1561 ttggctgtgg tatataaaat tattcataat gatagtagga ggcttggtag gtttaagaat
1621 agtttttgct gtactttcta tagtgaatag agttaggcag ggatattcac cattatcgtt
1681 tcagacccac ctcccaaccc cgaggggacc cgacaggccc gaaggaatag aagaagaagg
1741 tggagagaga gacagagaca gatccattcg attagtgaac ggatctcgac ggtatcggtt
1801 aacttttaaa agaaaagggg ggattggggg gtacagtgca ggggaaagaa tagtagacat
1861 aatagcaaca gacatacaaa ctaaagaatt acaaaaacaa attacaaaat tcaaaatttt
1921 atcgatacta gtattatgcc cagtacatga ccttatggga ctttcctact tggcagtaca
1981 tctacgtatt agtcatcgct attaccatgg tgatgcggtt ttggcagtac atcaatgggc
2041 gtggatagcg gtttgactca cggggatttc caagtctcca ccccattgac gtcaatggga
2101 gtttgttttg gcaccaaaat caacgggact ttccaaaatg tcgtaacaac tccgccccat
2161 tgacgcaaat gggcggtagg cgtgtacggt gggaggttta tataagcaga gctcgtttag
2221 tgaaccgtca gatcgcctgg agacgccatc cacgctgttt tgacctccat agaagattct
2281 agagctagcg ccgccaccat gctccagatg gctggccagt gcagccagaa cgagtacttc
2341 gacagcctgc tgcacgcctg catcccttgc cagctgcggt gcagcagcaa caccccaccc
2401 ctgacctgcc agcggtactg caacgccagc gtgaccaaca gcgtgaaggg caccaacgcc
2461 atcctgtgga cctgcctggg cctgagcctg atcatcagcc tggccgtgtt cgtgctgatg
2521 ttcctgctgc ggaagatcaa cagcgagccc ctgaaggacg agttcaagaa caccggcagc
2581 ggcctgctgg gcatggccaa catcgacctg gaaaagagcc ggaccggcga cgagatcatc
2641 ctgcccagag gcctggagta caccgtggaa gagtgtacct gcgaggactg catcaagagc
2701 aagcccaagg tggacagcga ccactgcttc cctctgcccg ccatggaaga gggcgccacc
2761 atcctggtga caacaaagac caacgactac tgcaagagcc tgcctgccgc cctgagcgcc
2821 accgagatcg agaagtccat cagcgccaga tgaggatccg cggccgcaag gatctgcgat
2881 cgctccggtg cccgtcagtg ggcagagcgc acatcgccca cagtccccga gaagttgggg
2941 ggaggggtcg gcaattgaac gggtgcctag agaaggtggc gcggggtaaa ctgggaaagt
3001 gatgtcgtgt actggctccg cctttttccc gagggtgggg gagaaccgta tataagtgca
3061 gtagtcgccg tgaacgttct ttttcgcaac gggtttgccg ccagaacaca gctgaagctt
3121 cgaggggctc gcatctctcc ttcacgcgcc cgcccgccta cctgaggccg ccatccacgc
3181 cggttgagtc gcgttctgcc gcctcccgcc tgtggtgcct cctgaactgc gtccgccgtc
3241 taggtaagtt taaagctcag gtcgagaccg ggcctttgtc cggcgctccc ttggagccta
3301 cctagactca gccggctctc cacgctttgc ctgaccctgc ttgctcaact ctacgtcttt
3361 gtttcgtttt ctgttctgcg ccgttacaga tccaagctgt gaccggcgcc tacgtcgaga
3421 tgattgaaca agatggattg cacgcaggtt ctccggccgc ttgggtggag aggctattcg
3481 gctatgactg ggcacaacag acaatcggct gctctgatgc cgccgtgttc cggctgtcag
3541 cgcaggggcg cccggttctt tttgtcaaga ccgacctgtc cggtgccctg aatgaactgc
3601 aggacgaggc agcgcggcta tcgtggctgg ccgcgacggg cgttccttgc gcagctgtgc
3661 tcgacgttgt cactgaagcg ggaagggact ggctgctatt gggcgaagtg ccggggcagg
3721 atctcctgtc atctcacctt gctcctgccg agaaagtatc catcatggct gatgcaatgc
3781 ggcggctgca tacgcttgat ccggctacct gcccattcga ccaccaagcg aaacatcgca
3841 tcgagcgagc acgtactcgg atggaagccg gtcttgtcga tcaggatgat ctggacgaag
3901 agcatcaggg gctcgcgcca gccgaactgt tcgccaggct caaggcgcgc atgcccgacg
3961 gcgaggatct cgtcgtgacc catggcgatg cctgcttgcc gaatatcatg gtggaaaatg
4021 gccgcttttc tggattcatc gactgtggcc ggctgggtgt ggcggaccgc tatcaggaca
```

-continued

CONSTRUCT SEQUENCES

```
4081 tagcgttggc tacccgtgat attgctgaag agcttggcgg cgaatgggct gaccgcttcc
4141 tcgtgcttta cggtatcgcc gctcccgatt cgcagcgcat cgccttctat cgccttcttg
4201 acgagttctt ctgactcgac aatcaacctc tggattacaa aatttgtgaa agattgactg
4261 gtattcttaa ctatgttgct ccttttacgc tatgtggata cgctgcttta atgcctttgt
4321 atcatgctat tgcttcccgt atggctttca ttttctcctc cttgtataaa tcctggttgc
4381 tgtctcttta tgaggagttg tggcccgttg tcaggcaacg tggcgtggtg tgcactgtgt
4441 ttgctgacgc aacccccact ggttggggca ttgccaccac ctgtcagctc ctttccggga
4501 ctttcgcttt ccccctccct attgccacgg cggaactcat cgccgcctgc cttgcccgct
4561 gctggacagg ggctcggctg ttgggcactg acaattccgt ggtgttgtcg gggaaatcat
4621 cgtcctttcc ttggctgctc gcctgtgttg ccacctggat tctgcgcggg acgtccttct
4681 gctacgtccc ttcggccctc aatccagcgg accttccttc ccgcggcctg ctgccggctc
4741 tgcggcctct tccgcgtctt cgccttcgcc ctcagacgag tcggatctcc ctttgggccg
4801 cctccccgcc tggtaccttt aagaccaatg acttacaagg cagctgtaga tcttagccac
4861 tttttaaaag aaaagggggg actggaaggg ctaattcact cccaacgaag ataagatctg
4921 ctttttgctt gtactgggtc tctctggtta gaccagatct gagcctggga gctctctggc
4981 taactaggga acccactgct taagcctcaa taaagcttgc cttgagtgct tcaagtagtg
5041 tgtgcccgtc tgttgtgtga ctctggtaac tagagatccc tcagaccctt ttagtcagtg
5101 tggaaaatct ctagcagtag tagttcatgt catcttatta ttcagtattt ataacttgca
5161 aagaaatgaa tatcagagag tgagaggaac ttgtttattg cagcttataa tggttacaaa
5221 taaagcaata gcatcacaaa tttcacaaat aaagcatttt tttcactgca ttctagttgt
5281 ggtttgtcca aactcatcaa tgtatcttat catgtctggc tctagctatc ccgcccctaa
5341 ctccgcccat cccgccccta actccgccca gttccgccca ttctccgccc catggctgac
5401 taattttttt tatttatgca gaggccgagg ccgcctcggc ctctgagcta ttccagaagt
5461 agtgaggagg cttttttgga ggcctagact tttgcagaga cggcccaaat tcgtaatcat
5521 ggtcatagct gtttcctgtg tgaaattgtt atccgctcac aattccacac aacatacgag
5581 ccggaagcat aaagtgtaaa gcctggggtg cctaatgagt gagctaactc acattaattg
5641 cgttgcgctc actgcccgct ttccagtcgg gaaacctgtc gtgccagctg cattaatgaa
5701 tcggccaacg cgcggggaga ggcggtttgc gtattgggcg ctcttccgct tcctcgctca
5761 ctgactcgct gcgctcggtc gttcggctgc ggcgagcggt atcagctcac tcaaaggcgg
5821 taatacggtt atccacagaa tcaggggata acgcaggaaa gaacatgtga gcaaaaggcc
5881 agcaaaaggc caggaaccgt aaaaaggccg cgttgctggc gtttttccat aggctccgcc
5941 cccctgacga gcatcacaaa aatcgacgct caagtcagag gtggcgaaac ccgacaggac
6001 tataaagata ccaggcgttt ccccctggaa gctccctcgt gcgctctcct gttccgaccc
6061 tgccgcttac cggatacctg tccgcctttc tcccttcggg aagcgtggcg ctttctcata
6121 gctcacgctg taggtatctc agttcggtgt aggtcgttcg ctccaagctg ggctgtgtgc
6181 acgaaccccc cgttcagccc gaccgctgcg ccttatccgg taactatcgt cttgagtcca
6241 acccggtaag acacgactta tcgccactgg cagcagccac tggtaacagg attagcagag
6301 cgaggtatgt aggcggtgct acagagttct tgaagtggtg gcctaactac ggctacacta
6361 gaaggacagt atttggtatc tgcgctctgc tgaagccagt taccttcgga aaaagagttg
6421 gtagctcttg atccggcaaa caaaccaccg ctggtagcgg tggttttttt gtttgcaagc
6481 agcagattac gcgcagaaaa aaaggatctc aagaagatcc tttgatcttt tctacggggt
6541 ctgacgctca gtggaacgaa aactcacgtt aagggatttt ggtcatgaga ttatcaaaaa
6601 ggatcttcac ctagatcctt ttaaattaaa aatgaagttt taaatcaatc taaagtatat
6661 atgagtaaac ttggtctgac agttaccaat gcttaatcag tgaggcacct atctcagcga
6721 tctgtctatt tcgttcatcc atagttgcct gactccccgt cgtgtagata actacgatac
6781 gggagggctt accatctggc cccagtgctg caatgatacc gcgagaccca cgctcaccgg
6841 ctccagattt atcagcaata aaccagccag ccggaagggc cgagcgcaga agtggtcctg
6901 caactttatc cgcctccatc cagtctatta attgttgccg ggaagctaga gtaagtagtt
6961 cgccagttaa tagtttgcgc aacgttgttg ccattgctac aggcatcgtg gtgtcacgct
7021 cgtcgtttgg tatggcttca ttcagctccg gttcccaacg atcaaggcga gttacatgat
7081 cccccatgtt gtgcaaaaaa gcggttagct ccttcggtcc tccgatcgtt gtcagaagta
7141 agttggccgc agtgttatca ctcatggtta tggcagcact gcataattct cttactgtca
7201 tgccatccgt aagatgcttt tctgtgactg gtgagtactc aaccaagtca ttctgagaat
7261 agtgtatgcg gcgaccgagt tgctcttgcc cggcgtcaat acgggataat accgcgccac
7321 atagcagaac tttaaaagtg ctcatcattg gaaaacgttc ttcggggcga aaactctcaa
7381 ggatcttacc gctgttgaga tccagttcga tgtaacccac tcgtgcaccc aactgatctt
7441 cagcatcttt tactttcacc agcgtttctg ggtgagcaaa aacaggaagg caaaatgccg
7501 caaaaaaggg aataagggcg acacggaaat gttgaatact catactcttc ctttttcaat
7561 attattgaag catttatcag ggttattgtc tcatgagcgg atacatattt gaatgtattt
7621 agaaaaataa acaaataggg gttccgcgca catttccccg aaaagtgcca cctgacgtct
7681 aagaaaccat tattatcatg acattaacct ataaaaatag gcgtatcacg aggccctttc
7741 gtctcgcgcg tttcggtgat gacggtgaaa acctctgaca catgcagctc ccggagacgg
7801 tcacagcttg tctgtaagcg gatgccggga gcagacaagc ccgtcagggc gcgtcagcgg
7861 gtgttggcgg gtgtcggggc tggcttaact atgcggcatc agagcagatt gtactgagag
7921 tgcaccatat gcggtgtgaa ataccgcaca gatgcgtaag gagaaaatac cgcatcaggc
7981 gccattcgcc attcaggctg cgcaactgtt gggaagggcg atcggtgcgg gcctcttcgc
8041 tattacgcca gctggcgaaa gggggatgtg ctgcaaggcg attaagttgg gtaacgccag
8101 ggttttccca gtcacgacgt tgtaaaacga cggccagtgc caagctg.
```

CAR Constructs p510_antiCD19_28z (SEQ BD NO: 9)

```
   1 acgcgtgtag tcttatgcaa tactcttgta gtcttgcaac atggtaacga tgagttagca
  61 acatgcctta caaggagaga aaaagcaccg tgcatgccga ttggtggaag taaggtggta
 121 cgatcgtgcc ttattaggaa ggcaacagac gggtctgaca tggattggac gaaccactga
 181 attgccgcat tgcagagata ttgtatttaa gtgcctagct cgatacaata aacgggtctc
 241 tctggttaga ccagatctga gcctgggagc tctctggcta actagggaac ccactgctta
```

-continued

| CONSTRUCT SEQUENCES |
|---|
| 301 agcctcaata aagcttgcct tgagtgcttc aagtagtgtg tgcccgtctg ttgtgtgact |
| 361 ctggtaacta gagatccctc agaccctttt agtcagtgtg gaaaatctct agcagtggcg |
| 421 cccgaacagg gacctgaaag cgaaagggaa accagagctc tctcgacgca ggactcggct |
| 481 tgctgaagcg cgcacggcaa gaggcgaggg gcggcgactg gtgagtacgc caaaaatttt |
| 541 gactagcgga ggctagaagg agagagatgg gtgcgagagc gtcagtatta agcgggggag |
| 601 aattagatcg cgatgggaaa aaattcggtt aaggccaggg ggaaagaaaa aatataaatt |
| 661 aaaacatata gtatgggcaa gcagggagct agaacgattc gcagttaatc ctggcctgtt |
| 721 agaaacatca gaaggctgta gacaaatact gggacagcta caaccatccc ttcagacagg |
| 781 atcagaagaa cttagatcat tatataatac agtagcaacc ctctattgtg tgcatcaaag |
| 841 gatagagata aaagacacca aggaagcttt agacaagata gaggaagagc aaaacaaaag |
| 901 taagaccacc gcacagcaag cggccactga tcttcagacc tggaggagga gatatgaggg |
| 961 acaattggag aagtgaatta tataaatata aagtagtaaa aattgaacca ttaggagtag |
| 1021 cacccaccaa ggcaaagaga agagtggtgc agagagaaaa aagagcagtg ggaataggag |
| 1081 ctttgttcct tgggttcttg ggagcagcag gaagcactat gggcgcagcc tcaatgacgc |
| 1141 tgacggtaca ggccagacaa ttattgtctg gtatagtgca gcagcagaac aatttgctga |
| 1201 gggctattga ggcgcaacag catctgttgc aactcacagt ctggggcatc aagcagctcc |
| 1261 aggcaagaat cctggctgtg gaaagatacc taaaggatca acagctcctg gggatttggg |
| 1321 gttgctctgg aaaactcatt tgcaccactg ctgtgccttg gaatgctagt tggagtaata |
| 1381 aatctctgga acagattgga atcacacgac ctggatggag tgggacagag aaattaacaa |
| 1441 ttacacaagc ttaatacact ccttaattga agaatcgcaa aaccagcaag aaaagaatga |
| 1501 acaagaatta ttggaattag ataaatgggc aagtttgtgg aattggttta acataacaaa |
| 1561 ttggctgtgg tatataaaat tattcataat gatagtagga ggcttggtag gtttaagaat |
| 1621 agtttttgct gtactttcta tagtgaatag agttaggcag ggatattcac cattatcgtt |
| 1681 tcagacccac ctcccaaccc cgaggggacc cgacaggccc gaaggaatag aagaagaagg |
| 1741 tggagagaga gacagagaca gatccattcg attagtgaac ggatctcgac ggtatcggtt |
| 1801 aacttttaaa agaaaagggg ggattggggg gtacagtgca ggggaaagaa tagtagacat |
| 1861 aatagcaaca gacatacaaa ctaaagaatt acaaaaacaa attacaaaat tcaaaatttt |
| 1921 atcgatacta gtattatgcc cagtacatga ccttatggga ctttcctact tggcagtaca |
| 1981 tctacgtatt agtcatcgct attaccatgg tgatgcggtt ttggcagtac atcaatgggc |
| 2041 gtggatagcg gtttgactca cggggatttc caagtctcca ccccattgac gtcaatggga |
| 2101 gtttgttttg gcaccaaaat caacgggact ttccaaaatg tcgtaacaac tccgccccat |
| 2161 tgacgcaaat gggcggtagg cgtgtacggt gggaggttta tataagcaga gctcgtttag |
| 2221 tgaaccgtca gatcgcctgg agacgccatc cacgctgttt tgacctccat agaagattct |
| 2281 agagccgcca ccatgcttct cctggtgaca agccttctgc tctgtgagtt accacaccca |
| 2341 gcattcctcc tgatcccaga catccagatg acacagacta catcctccct gtctgcctct |
| 2401 ctgggagaca gagtcaccat cagttgcagg gcaagtcagg acattagtaa atatttaaat |
| 2461 tggtatcagc agaaaccaga tggaactgtt aaactcctga tctaccatac atcaagatta |
| 2521 cactcaggag tcccatcaag gttcagtggc agtgggtctg gaacagatta ttctctcacc |
| 2581 attagcaacc tggagcaaga agatattgcc acttactttt gccaacaggg taatacgctt |
| 2641 ccgtacacgt tcggaggggg gactaagttg gaaataacag gctccacctc tggatccggc |
| 2701 aagcccggat ctggcgaggg atccaccaag ggcgaggtga aactgcagga gtcaggacct |
| 2761 ggcctggtgg cgccctcaca gagcctgtcc gtcacatgca ctgtctcagg ggtctcatta |
| 2821 cccgactatg gtgtaagctg gattcgccag cctccacgaa agggtctgga gtggctggga |
| 2881 gtaatatggg gtagtgaaac cacatactat aattcagctc tcaaatccag actgaccatc |
| 2941 atcaaggaca actccaagag ccaagttttc ttaaaaatga acagtctgca aactgatgac |
| 3001 acagccattt actactgtgc caaacattat tactacggtg gtagctatgc tatggactac |
| 3061 tggggtcaag gaacctcagt caccgtctcc tcagcggccg caattgaagt tatgtatcct |
| 3121 cctccttacc tagacaatga gaagagcaat ggaaccatta tccatgtgaa agggaaacac |
| 3181 ctttgtccaa gtcccctatt tcccggacct tctaagccct tttgggtgct ggtggtggtt |
| 3241 gggggagtcc tggcttgcta tagcttgcta gtaacagtgg cctttattat tttctgggtg |
| 3301 aggagtaaga ggagcaggct cctgcacagt gactacatga acatgactcc ccgccgcccc |
| 3361 gggcccaccc gcaagcatta ccagccctat gccccaccac gcgacttcgc agcctatcgc |
| 3421 tccagagtga agttcagcag gagcgcagac gcccccgcgt accagcaggg ccagaaccag |
| 3481 ctctataacg agctcaatct aggacgaaga gaggagtacg atgttttgga caagagacgt |
| 3541 ggccgggacc ctgagatggg gggaaagccg agaaggaaga accctcagga aggcctgtac |
| 3601 aatgaactgc agaaagataa gatggcggag gcctacagtg agattgggat gaaaggcgag |
| 3661 cgccggaggg gcaaggggca cgatggcctt taccagggtc tcagtacagc caccaaggac |
| 3721 acctacgacg cccttcacat gcaggccctg ccccctcgct aagaattcgg atccgcggcc |
| 3781 gcgaaggatc tgcgatcgct ccggtgcccg tcagtgggca gagcgcacat cgcccacagt |
| 3841 ccccgagaag ttggggggag gggtcggcaa ttgaacgggt gcctagagaa ggtggcgcgg |
| 3901 ggtaaactgg gaaagtgatg tcgtgtactg gctccgcctt tttcccgagg gtgggggaga |
| 3961 accgtatata agtgcagtag tcgccgtgaa cgttcttttt cgcaacgggt ttgccgccag |
| 4021 aacacagctg aagcttcgag gggctcgcat ctctccttca cgcgcccgcc gccctacctg |
| 4081 aggccgccat ccacgccggt tgagtcgcgt tctgccgcct cccgcctgtg gtgcctcctg |
| 4141 aactgcgtcc gccgtctagg taagtttaaa gctcaggtcg agaccgggcc tttgtccggc |
| 4201 gctcccttgg agcctaccta gactcagccg gctctccacg ctttgcctga ccctgcttgc |
| 4261 tcaactctac gtctttgttt cgttttctgt tctgcgccgt tacagatcca agctgtgacc |
| 4321 ggcgcctacg ctagatgacc gagtacaagc ccacggtgcg cctcgccacc cgcgacgacg |
| 4381 tccccagggc cgtacgcacc ctcgccgccg cgttcgccga ctaccccgcc acgcgccaca |
| 4441 ccgtcgatcc ggaccgccac atcgagcggg tcaccgagct gcaagaactc ttcctcacgc |
| 4501 gcgtcgggct cgacatcggc aaggtgtggg tcgcggacga cggcgccgcg gtggcggtct |
| 4561 ggaccacgcc ggagagcgtc gaagcggggg cggtgttcgc cgagatcggc ccgcgcatgg |
| 4621 ccgagttgag cggttcccgg ctggccgcgc agcaacagat ggaaggcctc ctggcgccgc |
| 4681 accggcccaa ggagcccgcg tggttcctgg ccaccgtcgg cgtctcgccc gaccaccagg |
| 4741 gcaagggtct gggcagcgcc gtcgtgctcc ccggagtgga ggcggccgag cgcgccgggg |
| 4801 tgcccgcctt cctggagacc tccgcgcccc gcaacctccc cttctacgag cggctcggct |
| 4861 tcaccgtcac cgccgacgtc gaggtgcccg aaggaccgcg cacctggtgc atgacccgca |

-continued

CONSTRUCT SEQUENCES

```
4921 agcccggtgc ctgagtcgac aatcaacctc tggattacaa aatttgtgaa agattgactg
4981 gtattcttaa ctatgttgct ccttttacgc tatgtggata cgctgcttta atgcctttgt
5041 atcatgctat tgcttcccgt atggctttca ttttctcctc cttgtataaa tcctggttgc
5101 tgtctcttta tgaggagttg tggcccgttg tcaggcaacg tggcgtggtg tgcactgtgt
5161 ttgctgacgc aacccccact ggttggggca ttgccaccac ctgtcagctc ctttccggga
5221 ctttcgcttt ccccctccct attgccacgg cggaactcat cgccgcctgc cttgcccgct
5281 gctggacagg ggctcggctg ttgggcactg acaattccgt ggtgttgtcg gggaaatcat
5341 cgtcctttcc ttggctgctc gcctgtgttg ccacctggat tctgcgcggg acgtccttct
5401 gctacgtccc ttcggccctc aatccagcgg accttccttc ccgcggcctg ctgccggctc
5461 tgcggcctct tccgcgtctt cgccttcgcc ctcagacgag tcggatctcc ctttgggccg
5521 cctccccgcc tggtaccttt aagaccaatg acttacaagg cagctgtaga tcttagccac
5581 tttttaaaag aaaagggggg actggaaggg ctaattcact cccaacgaaa ataagatctg
5641 ctttttgctt gtactgggtc tctctggtta gaccagatct gagcctggga gctctctggc
5701 taactaggga acccactgct taagcctcaa taaagcttgc cttgagtgct tcaagtagtg
5761 tgtgcccgtc tgttgtgtga ctctggtaac tagagatccc tcagaccctt ttagtcagtg
5821 tggaaaatct ctagcagtag tagttcatgt catcttatta ttcagtattt ataacttgca
5881 aagaaatgaa tatcagagag tgagaggaac ttgtttattg cagcttataa tggttacaaa
5941 taaagcaata gcatcacaaa tttcacaaat aaagcatttt tttcactgca ttctagttgt
6001 ggtttgtcca aactcatcaa tgtatcttat catgtctggc tctagctatc ccgcccctaa
6061 ctccgcccag ttccgcccat tctccgcccc atggctgact aatttttttt atttatgcag
6121 aggccgaggc cgcctcggcc tctgagctat tccagaagta gtgaggaggc ttttttggag
6181 gcctagactt ttgcagagac ggcccaaatt cgtaatcatg gtcatagctg tttcctgtgt
6241 gaaattgtta tccgctcaca attccacaca acatacgagc cggaagcata aagtgtaaag
6301 cctggggtgc ctaatgagtg agctaactca cattaattgc gttgcgctca ctgcccgctt
6361 tccagtcggg aaacctgtcg tgccagctgc attaatgaat cggccaacgc gcggggagag
6421 gcggtttgcg tattgggcgc tcttccgctt cctcgctcac tgactcgctg cgctcggtcg
6481 ttcggctgcg gcgagcggta tcagctcact caaaggcggt aatacggtta tccacagaat
6541 caggggataa cgcaggaaag aacatgtgag caaaaggcca gcaaaaggcc aggaaccgta
6601 aaaaggccgc gttgctggcg tttttccata ggctccgccc ccctgacgag catcacaaaa
6661 atcgacgctc aagtcagagg tggcgaaacc cgacaggact ataaagatac caggcgtttc
6721 cccctggaag ctccctcgtg cgctctcctg ttccgaccct gccgcttacc ggatacctgt
6781 ccgcctttct cccttcggga agcgtggcgc tttctcatag ctcacgctgt aggtatctca
6841 gttcggtgta ggtcgttcgc tccaagctgg gctgtgtgca cgaacccccc gttcagcccg
6901 accgctgcgc cttatccggt aactatcgtc ttgagtccaa cccggtaaga cacgacttat
6961 cgccactggc agcagccact ggtaacagga ttagcagagc gaggtatgta ggcggtgcta
7021 cagagttctt gaagtggtgg cctaactacg gctacactag aaggacagta tttggtatct
7081 gcgctctgct gaagccagtt accttcggaa aaagagttgg tagctcttga tccggcaaac
7141 aaaccaccgc tggtagcggt ggtttttttg tttgcaagca gcagattacg cgcagaaaaa
7201 aaggatctca agaagatcct ttgatctttt ctacggggtc tgacgctcag tggaacgaaa
7261 actcacgtta agggattttg gtcatgagat tatcaaaaag gatcttcacc tagatccttt
7321 taaattaaaa atgaagtttt aaatcaatct aaagtatata tgagtaaact tggtctgaca
7381 gttaccaatg cttaatcagt gaggcaccta tctcagcgat ctgtctattt cgttcatcca
7441 tagttgcctg actccccgtc gtgtagataa ctacgatacg ggagggctta ccatctggcc
7501 ccagtgctgc aatgataccg cgagacccac gctcaccggc tccagattta tcagcaataa
7561 accagccagc cggaagggcc gagcgcagaa gtggtcctgc aactttatcc gcctccatcc
7621 agtctattaa ttgttgccgg gaagctagag taagtagttc gccagttaat agtttgcgca
7681 acgttgttgc cattgctaca ggcatcgtgg tgtcacgctc gtcgtttggt atggcttcat
7741 tcagctccgg ttcccaacga tcaaggcgag ttacatgatc ccccatgttg tgcaaaaaag
7801 cggttagctc cttcggtcct ccgatcgttg tcagaagtaa gttggccgca gtgttatcac
7861 tcatggttat ggcagcactg cataattctc ttactgtcat gccatccgta agatgctttt
7921 ctgtgactgg tgagtactca accaagtcat tctgagaata gtgtatgcgg cgaccgagtt
7981 gctcttgccc ggcgtcaata cgggataata ccgcgccaca tagcagaact ttaaaagtgc
8041 tcatcattgg aaaacgttct tcggggcgaa aactctcaag gatcttaccg ctgttgagat
8101 ccagttcgat gtaacccact cgtgcaccca actgatcttc agcatctttt actttcacca
8161 gcgtttctgg gtgagcaaaa acaggaaggc aaaatgccgc aaaaaaggga ataagggcga
8221 cacggaaatg ttgaatactc atactcttcc tttttcaata ttattgaagc atttatcagg
8281 gttattgtct catgagcgga tacatatttg aatgtattta gaaaaataaa caaatagggg
8341 ttccgcgcac atttccccga aaagtgccac ctgacgtcta agaaaccatt attatcatga
8401 cattaaccta taaaaatagg cgtatcacga ggccctttcg tctcgcgcgt ttcggtgatg
8461 acggtgaaaa cctctgacac atgcagctcc cggagacggt cacagcttgt ctgtaagcgg
8521 atgccgggag cagacaagcc cgtcagggcg cgtcagcggg tgttggcggg tgtcggggct
8581 ggcttaacta tgcggcatca gagcagattg tactgagagt gcaccatatg cggtgtgaaa
8641 taccgcacag atgcgtaagg agaaaatacc gcatcaggcg ccattcgcca ttcaggctgc
8701 gcaactgttg ggaagggcga tcggtgcggg cctcttcgct attacgccag ctggcgaaag
8761 ggggatgtgc tgcaaggcga ttaagttggg taacgccagg gttttcccag tcacgacgtt
8821 gtaaaacgac ggccagtgcc aagctg.
```

p526A_19BBZ (SEQ ID NO: 10)

```
   1 acgcgtgtag tcttatgcaa tactcttgta gtcttgcaac atggtaacga tgagttagca
  61 acatgcctta caaggagaga aaaagcaccg tgcatgccga ttggtggaag taaggtggta
 121 cgatcgtgcc ttattaggaa ggcaacagac gggtctgaca tggattggac gaaccactga
 181 attgccgcat tgcagagata ttgtatttaa gtgcctagct cgatacaata aacgggtctc
 241 tctggttaga ccagatctga gcctgggagc tctctggcta actagggaac ccactgctta
 301 agcctcaata aagcttgcct tgagtgcttc aagtagtgtg tgcccgtctg ttgtgtgact
 361 ctggtaacta gagatccctc agaccctttt agtcagtgtg gaaaatctct agcagtggcg
 421 cccgaacagg gacctgaaag cgaaagggaa accagagctc tctcgacgca ggactcggct
 481 tgctgaagcg cgcacggcaa gaggcgaggg gcggcgactg gtgagtacgc caaaaatttt
```

-continued

CONSTRUCT SEQUENCES

```
 541 gactagcgga ggctagaagg agagagatgg gtgcgagagc gtcagtatta agcgggggag
 601 aattagatcg cgatgggaaa aaattcggtt aaggccaggg ggaaagaaaa aatataaatt
 661 aaaacatata gtatgggcaa gcagggagct agaacgattc gcagttaatc ctggcctgtt
 721 agaaacatca gaaggctgta gacaaatact gggacagcta caaccatccc ttcagacagg
 781 atcagaagaa cttagatcat tatataatac agtagcaacc ctctattgtg tgcatcaaag
 841 gatagagata aaagacacca aggaagcttt agacaagata gaggaagagc aaaacaaaag
 901 taagaccacc gcacagcaag cggccactga tcttcagacc tggaggagga gatatgaggg
 961 acaattggag aagtgaatta tataaatata aagtagtaaa aattgaacca ttaggagtag
1021 cacccaccaa ggcaaagaga agagtggtgc agagagaaaa aagagcagtg ggaataggag
1081 ctttgttcct tgggttcttg ggagcagcag gaagcactat gggcgcagcg tcaatgacgc
1141 tgacggtaca ggccagacaa ttattgtctg gtatagtgca gcagcagaac aatttgctga
1201 gggctattga ggcgcaacag catctgttgc aactcacagt ctggggcatc aagcagctcc
1261 aggcaagaat cctggctgtg gaaagatacc taaaggatca acagctcctg gggatttggg
1321 gttgctctgg aaaactcatt tgcaccactg ctgtgccttg gaatgctagt tggagtaata
1381 aatctctgga acagatttgg aatcacacga cctggatgga gtgggacaga gaaattaaca
1441 attacacaag cttaatacac tccttaattg aagaatcgca aaaccagcaa gaaaagaatg
1501 aacaagaatt attggaatta gataaatggg caagtttgtg gaattggttt aacataacaa
1561 attggctgtg gtatataaaa ttattcataa tgatagtagg aggcttggta ggtttaagaa
1621 tagtttttgc tgtactttct atagtgaata gagttaggca gggatattca ccattatcgt
1681 ttcagaccca cctcccaacc ccgaggggac ccgacaggcc cgaaggaata gaagaagaag
1741 gtggagagag agacagagac agatccattc gattagtgaa cggatctcga cggtatcggt
1801 taacttttaa aagaaaaggg gggattgggg ggtacagtgc aggggaaaga atagtagaca
1861 taatagcaac agacatacaa actaaagaat tacaaaaaca aattacaaaa ttcaaaattt
1921 tatcgatact agtggatctg cgatcgctcc ggtgcccgtc agtgggcaga gcgcacatcg
1981 cccacagtcc ccgagaagtt ggggggaggg gtcggcaatt gaacgggtgc ctagagaagg
2041 tggcgcgggg taaactggga aagtgatgtc gtgtactggc tccgcctttt tcccgagggt
2101 gggggagaac cgtatataag tgcagtagtc gccgtgaacg ttcttttttcg caacgggttt
2161 gccgccagaa cacagctgaa gcttcgaggg gctcgcatct ctccttcacg cgcccgccgc
2221 cctacctgag gccgccatcc acgccggttg agtcgcgttc tgccgcctcc cgcctgtggt
2281 gcctcctgaa ctgcgtccgc cgtctaggta agtttaaagc tcaggtcgag accgggcctt
2341 tgtccggcgc tcccttggag cctacctaga ctcagccggc tctccacgct ttgcctgacc
2401 ctgcttgctc aactctacgt ctttgtttcg ttttctgttc tgcgccgtta cagatccaag
2461 ctgtgaccgg cgcctactct agagccgcca ccatggccct gcctgtgaca gctctgctgc
2521 tgcctctggc cctgctgctc catgccgcca gacccgatat ccagatgacc cagaccacca
2581 gcagcctgag cgccagcctg ggcgatagag tgaccatcag ctgccgggcc agccaggaca
2641 tcagcaagta cctgaactgg tatcagcaga aacccgacgg caccgtgaag ctgctgatct
2701 accacaccag cagactgcac agcggcgtgc ccagcagatt ttctggcagc ggctccggca
2761 ccgactacag cctgaccatc tccaacctgg aacaggaaga tatcgctacc tacttctgtc
2821 agcaaggcaa caccctgccc tacaccttcg gcggaggcac caagctggaa atcacaggcg
2881 gcggaggatc tggcggaggt ggaagtggcg gaggcggcag cgaagtgaaa ctgcaggaaa
2941 gcggccctgg cctggtggcc ccttctcagt ctctgtccgt gacctgtacc gtgtccggcg
3001 tgtccctgcc cgattatggc gtgtcctgga tccggcagcc tcccagaaag ggcctggaat
3061 ggctgggcgt gatctggggc agcgagacaa cctactacaa cagcgccctg aagtcccggc
3121 tgaccatcat caaggacaac tccaagagcc aggtgttcct gaagatgaac agcctgcaga
3181 ccgacgacac cgccatctac tactgcgcca agcactacta ctacggcggc agctacgcca
3241 tggactactg gggccagggc accagcgtga ccgtgtctag cacaaccacc cctgccccta
3301 gacctcccac cccagcccca acaattgcca gccagcctct gtctctgcgg cccgaagctt
3361 gtagacctgc tgccggcgga gccgtgcaca ccagaggact ggatttcgcc tgcgacatct
3421 acatctgggc ccctctggcc ggcacatgtg gcgtgctgct cctcagcctg gtcatcaccc
3481 tgtactgcaa gcggggcaga aagaaactgc tctacatctt caagcagccc ttcatgcggc
3541 ccgtgcagac cacacaggaa gaggacggct gctcctgcag attccccgag gaagaagaag
3601 gcggctgcga gctgagagtg aagttcagca gatccgccga cgcccctgcc taccagcagg
3661 gacagaacca gctgtacaac gagctgaacc tgggcagacg ggaagagtac gacgtgctgg
3721 acaagcggag aggcagagat cccgagatgg gcggcaagcc cagacggaag aatccccagg
3781 aaggcctgta taacgaactg cagaaagaca agatggccga ggcctacagc gagatcggaa
3841 tgaagggcga gcggagaaga ggcaagggcc acgatggcct gtaccagggc ctgagcaccg
3901 ccaccaagga cacctacgat gccctgcaca tgcaggccct gccacccaga gaattcgaag
3961 gatccgcggc cgctgagggc agaggaagtc ttctaacatg cggtgacgtg gaggagaatc
4021 ccggcccttc cggaatggag agcgacgaga gcggcctgcc cgccatggag atcgagtgcc
4081 gcatcaccgg caccctgaac ggcgtggagt tcgagctggt gggcggcgga gagggcaccc
4141 ccaagcaggg ccgcatgacc aacaagatga agagcaccaa aggcgccctg accttcagcc
4201 cctacctgct gagccacgtg atgggctacg gcttctacca cttcggcacc taccccagcg
4261 gctacgagaa ccccttcctg cacgccatca acaacggcgg ctacaccaac acccgcatcg
4321 agaagtacga ggacggcggc gtgctgcacg tgagcttcag ctaccgctac gaggccggcc
4381 gcgtgatcgg cgacttcaag gtggtgggca ccggcttccc cgaggacagc gtgatcttca
4441 ccgacaagat catccgcagc aacgccaccg tggagcacct gcaccccatg ggcgataacg
4501 tgctggtggg cagcttcgcc cgcaccttca gcctgcgcga cggcggctac tacagcttcg
4561 tggtggacag ccacatgcac ttcaagagcg ccatccaccc cagcatcctg cagaacgggg
4621 gccccatgtt cgccttccgc cgcgtggagg agctgcacag caacaccgag ctgggcatcg
4681 tggagtacca gcacgccttc aagaccccca tcgccttcgc cagatcccgc gctcagtcgt
4741 ccaattctgc cgtggacggc accgccggac ccggctccac cggatctcgc tagagctgaa
4801 tctaagtcga caatcaacct ctggattaca aaatttgtga aagattgact ggtattctta
4861 actatgttgc tccttttacg ctatgtggat acgctgcttt aatgcctttg tatcatgcta
4921 ttgcttcccg tatggctttc attttctcct ccttgtataa atcctggttg ctgtctcttt
4981 atgaggagtt gtggcccgtt gtcaggcaac gtggcgtggt gtgcactgtg tttgctgacg
5041 caacccccac tggttggggc attgccacca cctgtcagct cctttccggg actttcgctt
5101 tccccctccc tattgccacg gcggaactca tcgccgcctg ccttgcccgc tgctggacag
```

-continued

CONSTRUCT SEQUENCES 5161 gggctcggct gttgggcact gacaattccg tggtgttgtc ggggaaatca tcgtcctttc
5221 cttggctgct cgcctgtgtt gccacctgga ttctgcgcgg gacgtccttc tgctacgtcc
5281 cttcggccct caatccagcg gaccttcctt cccgcggcct gctgccggct ctgcggcctc
5341 ttccgcgtct tcgccttcgc cctcagacga gtcggatctc cctttgggcc gcctccccgc
5401 ctggtacctt taagaccaat gacttacaag gcagctgtag atcttagcca ctttttaaaa
5461 gaaaaggggg gactggaagg gctaattcac tcccaacgaa aataagatct gctttttgct
5521 tgtactgggt ctctctggtt agaccagatc tgagcctggg agctctctgg ctaactaggg
5581 aacccactgc ttaagcctca ataaagcttg ccttgagtgc ttcaagtagt gtgtgcccgt
5641 ctgttgtgtg actctggtaa ctagagatcc ctcagaccct tttagtcagt gtggaaaatc
5701 tctagcagta gtagttcatg tcatcttatt attcagtatt tataacttgc aaagaaatga
5761 atatcagaga gtgagaggaa cttgtttatt gcagcttata atggttacaa ataaagcaat
5821 agcatcacaa atttcacaaa taaagcattt ttttcactgc attctagttg tggtttgtcc
5881 aaactcatca atgtatctta tcatgtctgg ctctagctat cccgccccta actccgccca
5941 gttccgccca ttctccgccc catggctgac taattttttt tatttatgca gaggccgagg
6001 ccgcctcggc ctctgagcta ttccagaagt agtgaggagg cttttttgga ggcctagact
6061 tttgcagaga cggcccaaat tcgtaatcat ggtcatagct gtttcctgtg tgaaattgtt
6121 atccgctcac aattccacac aacatacgag ccggaagcat aaagtgtaaa gcctggggtg
6181 cctaatgagt gagctaactc acattaattg cgttgcgctc actgcccgct ttccagtcgg
6241 gaaacctgtc gtgccagctg cattaatgaa tcggccaacg cgcggggaga ggcggtttgc
6301 gtattgggcg ctcttccgct tcctcgctca ctgactcgct gcgctcggtc gttcggctgc
6361 ggcgagcggt atcagctcac tcaaaggcgg taatacggtt atccacagaa tcaggggata
6421 acgcaggaaa gaacatgtga gcaaaaggcc agcaaaaggc caggaaccgt aaaaaggccg
6481 cgttgctggc gtttttccat aggctccgcc cccctgacga gcatcacaaa aatcgacgct
6541 caagtcagag gtggcgaaac ccgacaggac tataaagata ccaggcgttt ccccctggaa
6601 gctccctcgt gcgctctcct gttccgaccc tgccgcttac cggatacctg tccgcctttc
6661 tcccttcggg aagcgtggcg ctttctcata gctcacgctg taggtatctc agttcggtgt
6721 aggtcgttcg ctccaagctg ggctgtgtgc acgaaccccc cgttcagccc gaccgctgcg
6781 ccttatccgg taactatcgt cttgagtcca acccggtaag acacgactta tcgccactgg
6841 cagcagccac tggtaacagg attagcagag cgaggtatgt aggcggtgct acagagttct
6901 tgaagtggtg gcctaactac ggctacacta gaaggacagt atttggtatc tgcgctctgc
6961 tgaagccagt taccttcgga aaaagagttg gtagctcttg atccggcaaa caaaccaccg
7021 ctggtagcgg tggttttttt gtttgcaagc agcagattac gcgcagaaaa aaaggatctc
7081 aagaagatcc tttgatcttt tctacggggt ctgacgctca gtggaacgaa aactcacgtt
7141 aagggatttt ggtcatgaga ttatcaaaaa ggatcttcac ctagatcctt ttaaattaaa
7201 aatgaagttt taaatcaatc taaagtatat atgagtaaac ttggtctgac agttaccaat
7261 gcttaatcag tgaggcacct atctcagcga tctgtctatt tcgttcatcc atagttgcct
7321 gactccccgt cgtgtagata actacgatac gggagggctt accatctggc cccagtgctg
7381 caatgatacc gcgagaccca cgctcaccgg ctccagattt atcagcaata aaccagccag
7441 ccggaagggc cgagcgcaga agtggtcctg caactttatc cgcctccatc cagtctatta
7501 attgttgccg ggaagctaga gtaagtagtt cgccagttaa tagtttgcgc aacgttgttg
7561 ccattgctac aggcatcgtg gtgtcacgct cgtcgtttgg tatggcttca ttcagctccg
7621 gttcccaacg atcaaggcga gttacatgat cccccatgtt gtgcaaaaaa gcggttagct
7681 ccttcggtcc tccgatcgtt gtcagaagta agttggccgc agtgttatca ctcatggtta
7741 tggcagcact gcataattct cttactgtca tgccatccgt aagatgcttt tctgtgactg
7801 gtgagtactc aaccaagtca ttctgagaat agtgtatgcg gcgaccgagt tgctcttgcc
7861 cggcgtcaat acgggataat accgcgccac atagcagaac tttaaaagtg ctcatcattg
7921 gaaaacgttc ttcggggcga aaactctcaa ggatcttacc gctgttgaga tccagttcga
7981 tgtaacccac tcgtgcaccc aactgatctt cagcatcttt tactttcacc agcgtttctg
8041 ggtgagcaaa aacaggaagg caaaatgccg caaaaaaggg aataagggcg acacggaaat
8101 gttgaatact catactcttc ctttttcaat attattgaag catttatcag ggttattgtc
8161 tcatgagcgg atacatattt gaatgtattt agaaaaataa acaaataggg gttccgcgca
8221 catttccccg aaaagtgcca cctgacgtct aagaaaccat tattatcatg acattaacct
8281 ataaaaatag gcgtatcacg aggccctttc gtctcgcgcg tttcggtgat gacggtgaaa
8341 acctctgaca catgcagctc ccggagacgg tcacagcttg tctgtaagcg gatgccggga
8401 gcagacaagc ccgtcagggc gcgtcagcgg gtgttggcgg gtgtcggggc tggcttaact
8461 atgcggcatc agagcagatt gtactgagag tgcaccatat gcggtgtgaa ataccgcaca
8521 gatgcgtaag gagaaaatac cgcatcaggc gccattcgcc attcaggctg cgcaactgtt
8581 gggaagggcg atcggtgcgg gcctcttcgc tattacgcca gctggcgaaa gggggatgtg
8641 ctgcaaggcg attaagttgg gtaacgccag ggttttccca gtcacgacgt tgtaaaacga
8701 cggccagtgc caagctg.

TFP (TRuC) constructs p510_antiCD19_LL_TCRalpha (SEQ ID NO: 11)

1 acgcgtgtag tcttatgcaa tactcttgta gtcttgcaac atggtaacga tgagttagca
61 acatgcctta caaggagaga aaaagcaccg tgcatgccga ttggtggaag taaggtggta
121 cgatcgtgcc ttattaggaa ggcaacagac gggtctgaca tggattggac gaaccactga
181 attgccgcat tgcagagata ttgtatttaa gtgcctagct cgatacaata aacgggtctc
241 tctggttaga ccagatctga gcctgggagc tctctggcta actagggaac ccactgctta
301 agcctcaata aagcttgcct tgagtgcttc aagtagtgtg tgcccgtctg ttgtgtgact
361 ctggtaacta gagatccctc agaccctttt agtcagtgtg gaaaatctct agcagtggcg
421 cccgaacagg gacctgaaag cgaaagggaa accagagctc tctcgacgca ggactcggct
481 tgctgaagcg cgcacggcaa gaggcgaggg gcggcgactg gtgagtacgc caaaaatttt
541 gactagcgga ggctagaagg agagagatgg gtgcgagagc gtcagtatta agcgggggag
601 aattagatcg cgatgggaaa aaattcggtt aaggccaggg ggaaagaaaa aatataaatt
661 aaaacatata gtatgggcaa gcagggagct agaacgattc gcagttaatc ctggcctgtt
721 agaaacatca gaaggctgta gacaaatact gggacagcta caaccatccc ttcagacagg -continued

| CONSTRUCT SEQUENCES |
|---|
| 781 atcagaagaa cttagatcat tatataatac agtagcaacc ctctattgtg tgcatcaaag<br>841 gatagagata aaagacacca aggaagcttt agacaagata gaggaagagc aaaacaaaag<br>901 taagaccacc gcacagcaag cggccactga tcttcagacc tggaggagga gatatgaggg<br>961 acaattggag aagtgaatta tataaatata aagtagtaaa aattgaacca ttaggagtag<br>1021 cacccaccaa ggcaaagaga agagtggtgc agagagaaaa aagagcagtg ggaataggag<br>1081 ctttgttcct tgggttcttg ggagcagcag gaagcactat gggcgcagcc tcaatgacgc<br>1141 tgacggtaca ggccagacaa ttattgtctg gtatagtgca gcagcagaac aatttgctga<br>1201 gggctattga ggcgcaacag catctgttgc aactcacagt ctggggcatc aagcagctcc<br>1261 aggcaagaat cctggctgtg gaaagatacc taaaggatca acagctcctg gggatttggg<br>1321 gttgctctgg aaaactcatt tgcaccactg ctgtgccttg gaatgctagt tggagtaata<br>1381 aatctctgga acagattgga atcacacgac ctggatggag tgggacagag aaattaacaa<br>1441 ttacacaagc ttaatacact ccttaattga agaatcgcaa aaccagcaag aaaagaatga<br>1501 acaagaatta ttggaattag ataaatgggc aagtttgtgg aattggttta acataacaaa<br>1561 ttggctgtgg tatataaaat tattcataat gatagtagga ggcttggtag gtttaagaat<br>1621 agtttttgct gtactttcta tagtgaatag agttaggcag ggatattcac cattatcgtt<br>1681 tcagacccac ctcccaaccc cgaggggacc cgacaggccc gaaggaatag aagaagaagg<br>1741 tggagagaga gacagagaca gatccattcg attagtgaac ggatctcgac ggtatcggtt<br>1801 aacttttaaa agaaaagggg ggattggggg gtacagtgca ggggaaagaa tagtagacat<br>1861 aatagcaaca gacatacaaa ctaaagaatt acaaaaacaa attacaaaat tcaaaatttt<br>1921 atcgatacta gtattatgcc cagtacatga ccttatggga ctttcctact tggcagtaca<br>1981 tctacgtatt agtcatcgct attaccatgg tgatgcggtt ttggcagtac atcaatgggc<br>2041 gtggatagcg gtttgactca cggggatttc caagtctcca ccccattgac gtcaatggga<br>2101 gtttgttttg gcaccaaaat caacgggact ttccaaaatg tcgtaacaac tccgccccat<br>2161 tgacgcaaat gggcggtagg cgtgtacggt gggaggttta tataagcaga gctcgtttag<br>2221 tgaaccgtca gatcgcctgg agacgccatc cacgctgttt tgacctccat agaagattct<br>2281 agagccgcca ccatgcttct cctggtgaca agccttctgc tctgtgagtt accacaccca<br>2341 gcattcctcc tgatcccaga catccagatg acacagacta catcctccct gtctgcctct<br>2401 ctgggagaca gagtcaccat cagttgcagg gcaagtcagg acattagtaa atatttaaat<br>2461 tggtatcagc agaaaccaga tggaactgtt aaactcctga tctaccatac atcaagatta<br>2521 cactcaggag tcccatcaag gttcagtggc agtgggtctg gaacagatta ttctctcacc<br>2581 attagcaacc tggagcaaga agatattgcc acttactttt gccaacaggg taatacgctt<br>2641 ccgtacacgt tcggaggggg gactaagttg gaaataacag gctccacctc tggatccggc<br>2701 aagcccggat ctggcgaggg atccaccaag ggcgaggtga aactgcagga gtcaggacct<br>2761 ggcctggtgg cgccctcaca gagcctgtcc gtcacatgca ctgtctcagg ggtctcatta<br>2821 cccgactatg gtgtaagctg gattcgccag cctccacgaa agggtctgga gtggctggga<br>2881 gtaatatggg gtagtgaaac cacatactat aattcagctc tcaaatccag actgaccatc<br>2941 atcaaggaca actccaagag ccaagttttc ttaaaaatga acagtctgca aactgatgac<br>3001 acagccattt actactgtgc caaacattat tactacggtg gtagctatgc tatggactac<br>3061 tggggtcaag gaacctcagt caccgtctcc tcagcggccg caattgaagt tatgtatcct<br>3121 cctccttacc taggtggcgg cggttctggt ggcggcggtt ctggtggcgg cggttctctc<br>3181 gaggtgaatg gagagaatgt ggagcagcat ccttcaaccc tgagtgtcca ggagggagac<br>3241 agcgctgtta tcaagtgtac ttattcagac agtgcctcaa actacttccc ttggtataag<br>3301 caagaacttg gaaaaagacc tcagcttatt atagacattc gttcaaatgt gggcgaaaag<br>3361 aaagaccaac gaattgctgt tacattgaac aagacagcca aacatttctc cctgcacatc<br>3421 acagagaccc aacctgaaga ctcggctgtc tacttctgtg cagcaagtag gaaggactct<br>3481 gggggttacc agaaagttac ctttggaact ggaacaaagc tccaagtcat cccaaatatc<br>3541 cagaaccctg accctgccgt gtaccagctg agagactcta aatccagtga caagtctgtc<br>3601 tgcctattca ccgattttga ttctcaaaca aatgtgtcac aaagtaagga ttctgatgtg<br>3661 tatatcacag acaaaactgt gctagacatg aggtctatgg acttcaagag caacagtgct<br>3721 gtggcctgga gcaacaaatc tgactttgca tgtgcaaacg ccttcaacaa cagcattatt<br>3781 ccagaagaca ccttcttccc cagcccagaa agttcctgtg atgtcaagct ggtcgagaaa<br>3841 agctttgaaa cagatacgaa cctaaacttt caaaacctgt cagtgattgg gttccgaatc<br>3901 ctcctcctga aagtggccgg gtttaatctg ctcatgacgc tgcggctgtg gtccagctga<br>3961 taagaattcg atccgcggcc gcgaaggatc tgcgatcgct ccggtgcccg tcagtgggca<br>4021 gagcgcacat cgcccacagt ccccgagaag ttggggggag gggtcggcaa ttgaacgggt<br>4081 gcctagagaa ggtggcgcgg ggtaaactgg gaaagtgatg tcgtgtactg gctccgcctt<br>4141 tttcccgagg gtgggggaga accgtatata agtgcagtag tcgccgtgaa cgttcttttt<br>4201 cgcaacgggt ttgccgccag aacacagctg aagcttcgag gggctcgcat ctctccttca<br>4261 cgcgcccgcc gccctacctg aggccgccat ccacgccggt tgagtcgcgt tctgccgcct<br>4321 cccgcctgtg gtgcctcctg aactgcgtcc gccgtctagg taagtttaaa gctcaggtcg<br>4381 agaccgggcc tttgtccggc gctcccttgg agcctaccta gactcagccg gctctccacg<br>4441 ctttgcctga ccctgcttgc tcaactctac gtctttgttt cgttttctgt tctgcgccgt<br>4501 tacagatcca agctgtgacc ggcgcctacg ctagatgacc gagtacaagc ccacggtgcg<br>4561 cctcgccacc cgcgacgacg tccccagggc cgtacgcacc ctcgccgccg cgttcgccga<br>4621 ctaccccgcc acgcgccaca ccgtcgatcc ggaccgccac atcgagcggg tcaccgagct<br>4681 gcaagaactc ttcctcacgc gcgtcgggct cgacatcggc aaggtgtggg tcgcggacga<br>4741 cggcgccgcg gtggcggtct ggaccacgcc ggagagcgtc gaagcggggg cggtgttcgc<br>4801 cgagatcggc ccgcgcatgg ccgagttgag cggttcccgg ctggccgcgc agcaacagat<br>4861 ggaaggcctc ctggcgccgc accggcccaa ggagcccgcg tggttcctgg ccaccgtcgg<br>4921 cgtctcgccc gaccaccagg gcaagggtct gggcagcgcc gtcgtgctcc ccggagtgga<br>4981 ggcggccgag cgcgccgggg tgcccgcctt cctggagacc tccgcgcccc gcaacctccc<br>5041 cttctacgag cggctcggct tcaccgtcac cgccgacgtc gaggtgcccg aaggaccgcg<br>5101 cacctggtgc atgacccgca agcccggtgc ctgagtcgac aatcaacctc tggattacaa<br>5161 aatttgtgaa agattgactg gtattcttaa ctatgttgct ccttttacgc tatgtggata<br>5221 cgctgcttta atgcctttgt atcatgctat tgcttcccgt atggctttca ttttctcctc<br>5281 cttgtataaa tcctggttgc tgtctcttta tgaggagttg tggcccgttg tcaggcaacg<br>5341 tggcgtggtg tgcactgtgt ttgctgacgc aacccccact ggttggggca ttgccaccac |

-continued

CONSTRUCT SEQUENCES

```
5401 ctgtcagctc ctttccggga ctttcgcttt ccccctccct attgccacgg cggaactcat
5461 cgccgcctgc cttgcccgct gctggacagg ggctcggctg ttgggcactg acaattccgt
5521 ggtgttgtcg gggaaatcat cgtcctttcc ttggctgctc gcctgtgttg ccacctggat
5581 tctgcgcggg acgtccttct gctacgtccc ttcggccctc aatccagcgg accttccttc
5641 ccgcggcctg ctgccggctc tgcggcctct tccgcgtctt cgccttcgcc ctcagacgag
5701 tcggatctcc ctttgggccg cctccccgcc tggtaccttt aagaccaatg acttacaagg
5761 cagctgtaga tcttagccac tttttaaaag aaaagggggg actggaaggg ctaattcact
5821 cccaacgaaa ataagatctg ctttttgctt gtactgggtc tctctggtta gaccagatct
5881 gagcctggga gctctctggc taactaggga acccactgct taagcctcaa taaagcttgc
5941 cttgagtgct tcaagtagtg tgtgcccgtc tgttgtgtga ctctggtaac tagagatccc
6001 tcagaccctt ttagtcagtg tggaaaatct ctagcagtag tagttcatgt catcttatta
6061 ttcagtattt ataacttgca aagaaatgaa tatcagagag tgagaggaac ttgtttattg
6121 cagcttataa tggttacaaa taaagcaata gcatcacaaa tttcacaaat aaagcatttt
6181 tttcactgca ttctagttgt ggtttgtcca aactcatcaa tgtatcttat catgtctggc
6241 tctagctatc ccgcccctaa ctccgcccag ttccgcccat tctccgcccc atggctgact
6301 aattttttt atttatgcag aggccgaggc cgcctcggcc tctgagctat tccagaagta
6361 gtgaggaggc ttttttggag gcctagactt ttgcagagac ggcccaaatt cgtaatcatg
6421 gtcatagctg tttcctgtgt gaaattgtta tccgctcaca attccacaca acatacgagc
6481 cggaagcata aagtgtaaag cctggggtgc ctaatgagtg agctaactca cattaattgc
6541 gttgcgctca ctgcccgctt tccagtcggg aaacctgtcg tgccagctgc attaatgaat
6601 cggccaacgc gcggggagag gcggtttgcg tattgggcgc tcttccgctt cctcgctcac
6661 tgactcgctg cgctcggtcg ttcggctgcg gcgagcggta tcagctcact caaaggcggt
6721 aatacggtta tccacagaat caggggataa cgcaggaaag aacatgtgag caaaaggcca
6781 gcaaaaggcc aggaaccgta aaaaggccgc gttgctggcg tttttccata ggctccgccc
6841 ccctgacgag catcacaaaa atcgacgctc aagtcagagg tggcgaaacc cgacaggact
6901 ataaagatac caggcgtttc cccctggaag ctccctcgtg cgctctcctg ttccgaccct
6961 gccgcttacc ggatacctgt ccgcctttct cccttcggga agcgtggcgc tttctcatag
7021 ctcacgctgt aggtatctca gttcggtgta ggtcgttcgc tccaagctgg gctgtgtgca
7081 cgaacccccc gttcagcccg accgctgcgc cttatccggt aactatcgtc ttgagtccaa
7141 cccggtaaga cacgacttat cgccactggc agcagccact ggtaacagga ttagcagagc
7201 gaggtatgta ggcggtgcta cagagttctt gaagtggtgg cctaactacg gctacactag
7261 aaggacagta tttggtatct gcgctctgct gaagccagtt accttcggaa aaagagttgg
7321 tagctcttga tccggcaaac aaaccaccgc tggtagcggt ggtttttttg tttgcaagca
7381 gcagattacg cgcagaaaaa aaggatctca agaagatcct ttgatctttt ctacggggtc
7441 tgacgctcag tggaacgaaa actcacgtta agggattttg gtcatgagat tatcaaaaag
7501 gatcttcacc tagatccttt taaattaaaa atgaagtttt aaatcaatct aaagtatata
7561 tgagtaaact tggtctgaca gttaccaatg cttaatcagt gaggcaccta tctcagcgat
7621 ctgtctattt cgttcatcca tagttgcctg actccccgtc gtgtagataa ctacgatacg
7681 ggagggctta ccatctggcc ccagtgctgc aatgataccg cgagacccac gctcaccggc
7741 tccagattta tcagcaataa accagccagc cggaagggcc gagcgcagaa gtggtcctgc
7801 aactttatcc gcctccatcc agtctattaa ttgttgccgg gaagctagag taagtagttc
7861 gccagttaat agtttgcgca acgttgttgc cattgctaca ggcatcgtgg tgtcacgctc
7921 gtcgtttggt atggcttcat tcagctccgg ttcccaacga tcaaggcgag ttacatgatc
7981 ccccatgttg tgcaaaaaag cggttagctc cttcggtcct ccgatcgttg tcagaagtaa
8041 gttggccgca gtgttatcac tcatggttat ggcagcactg cataattctc ttactgtcat
8101 gccatccgta agatgctttt ctgtgactgg tgagtactca accaagtcat tctgagaata
8161 gtgtatgcgg cgaccgagtt gctcttgccc ggcgtcaata cgggataata ccgcgccaca
8221 tagcagaact ttaaaagtgc tcatcattgg aaaacgttct tcggggcgaa aactctcaag
8281 gatcttaccg ctgttgagat ccagttcgat gtaacccact cgtgcaccca actgatcttc
8341 agcatctttt actttcacca gcgtttctgg gtgagcaaaa acaggaaggc aaaatgccgc
8401 aaaaaaggga ataagggcga cacggaaatg ttgaatactc atactcttcc tttttcaata
8461 ttattgaagc atttatcagg gttattgtct catgagcgga tacatatttg aatgtattta
8521 gaaaaataaa caaatagggg ttccgcgcac atttccccga aaagtgccac ctgacgtcta
8581 agaaaccatt attatcatga cattaaccta taaaaatagg cgtatcacga ggccctttcg
8641 tctcgcgcgt ttcggtgatg acggtgaaaa cctctgacac atgcagctcc cggagacggt
8701 cacagcttgt ctgtaagcgg atgccgggag cagacaagcc cgtcagggcg cgtcagcggg
8761 tgttggcggg tgtcggggct ggcttaacta tgcggcatca gagcagattg tactgagagt
8821 gcaccatatg cggtgtgaaa taccgcacag atgcgtaagg agaaaatacc gcatcaggcg
8881 ccattcgcca ttcaggctgc gcaactgttg ggaagggcga tcggtgcggg cctcttcgct
8941 attacgccag ctggcgaaag ggggatgtgc tgcaaggcga ttaagttggg taacgccagg
9001 gttttcccag tcacgacgtt gtaaaacgac ggccagtgcc aagctg.
```

p510_antiCD19_LL_TCRalphaC (SEQ ID NO: 12)

```
  1 acgcgtgtag tcttatgcaa tactcttgta gtcttgcaac atggtaacga tgagttagca
 61 acatgcctta caaggagaga aaaagcaccg tgcatgccga ttggtggaag taaggtggta
121 cgatcgtgcc ttattaggaa ggcaacagac gggtctgaca tggattggac gaaccactga
181 attgccgcat tgcagagata ttgtatttaa gtgcctagct cgatacaata aacgggtctc
241 tctggttaga ccagatctga gcctgggagc tctctggcta actagggaac ccactgctta
301 agcctcaata aagcttgcct tgagtgcttc aagtagtgtg tgcccgtctg ttgtgtgact
361 ctggtaacta gagatccctc agaccctttt agtcagtgtg gaaaatctct agcagtggcg
421 cccgaacagg gacctgaaag cgaaagggaa accagagctc tctcgacgca ggactcggct
481 tgctgaagcg cgcacggcaa gaggcgaggg gcggcgactg gtgagtacgc caaaaatttt
541 gactagcgga ggctagaagg agagagatgg gtgcgagagc gtcagtatta agcgggggag
601 aattagatcg cgatgggaaa aaattcggtt aaggccaggg ggaaagaaaa aatataaatt
661 aaaacatata gtatgggcaa gcagggagct agaacgattc gcagttaatc ctggcctgtt
721 agaaacatca gaaggctgta gacaaatact gggacagcta caaccatccc ttcagacagg
781 atcagaagaa cttagatcat tatataatac agtagcaacc ctctattgtg tgcatcaaag
```

-continued

CONSTRUCT SEQUENCES

```
 841 gatagagata aaagacacca aggaagcttt agacaagata gaggaagagc aaaacaaaag
 901 taagaccacc gcacagcaag cggccactga tcttcagacc tggaggagga gatatgaggg
 961 acaattggag aagtgaatta tataaatata aagtagtaaa aattgaacca ttaggagtag
1021 cacccaccaa ggcaaagaga agagtggtgc agagagaaaa aagagcagtg ggaataggag
1081 ctttgttcct tgggttcttg ggagcagcag gaagcactat gggcgcagcc tcaatgacgc
1141 tgacggtaca ggccagacaa ttattgtctg gtatagtgca gcagcagaac aatttgctga
1201 gggctattga ggcgcaacag catctgttgc aactcacagt ctggggcatc aagcagctcc
1261 aggcaagaat cctggctgtg gaaagatacc taaaggatca acagctcctg gggatttggg
1321 gttgctctgg aaaactcatt tgcaccactg ctgtgccttg gaatgctagt tggagtaata
1381 aatctctgga acagattgga atcacacgac ctggatggag tgggacagag aaattaacaa
1441 ttacacaagc ttaatacact ccttaattga agaatcgcaa aaccagcaag aaaagaatga
1501 acaagaatta ttggaattag ataaatgggc aagtttgtgg aattggttta acataacaaa
1561 ttggctgtgg tatataaaat tattcataat gatagtagga ggcttggtag gtttaagaat
1621 agtttttgct gtactttcta tagtgaatag agttaggcag ggatattcac cattatcgtt
1681 tcagacccac ctcccaaccc cgaggggacc cgacaggccc gaaggaatag aagaagaagg
1741 tggagagaga gacagagaca gatccattcg attagtgaac ggatctcgac ggtatcggtt
1801 aacttttaaa agaaaagggg ggattggggg gtacagtgca ggggaaagaa tagtagacat
1861 aatagcaaca gacatacaaa ctaaagaatt acaaaaacaa attacaaaat tcaaaatttt
1921 atcgatacta gtattatgcc cagtacatga ccttatggga ctttcctact tggcagtaca
1981 tctacgtatt agtcatcgct attaccatgg tgatgcggtt ttggcagtac atcaatgggc
2041 gtggatagcg gtttgactca cggggatttc caagtctcca ccccattgac gtcaatggga
2101 gtttgttttg gcaccaaaat caacgggact ttccaaaatg tcgtaacaac tccgccccat
2161 tgacgcaaat gggcggtagg cgtgtacggt gggaggttta tataagcaga gctcgtttag
2221 tgaaccgtca gatcgcctgg agacgccatc cacgctgttt tgacctccat agaagattct
2281 agagccgcca ccatgcttct cctggtgaca agccttctgc tctgtgagtt accacaccca
2341 gcattcctcc tgatcccaga catccagatg acacagacta catcctccct gtctgcctct
2401 ctgggagaca gagtcaccat cagttgcagg gcaagtcagg acattagtaa atatttaaat
2461 tggtatcagc agaaaccaga tggaactgtt aaactcctga tctaccatac atcaagatta
2521 cactcaggag tcccatcaag gttcagtggc agtgggtctg gaacagatta ttctctcacc
2581 attagcaacc tggagcaaga agatattgcc acttactttt gccaacaggg taatacgctt
2641 ccgtacacgt tcggaggggg gactaagttg gaaataacag gctccacctc tggatccggc
2701 aagcccggat ctggcgaggg atccaccaag ggcgaggtga aactgcagga gtcaggacct
2761 ggcctggtgg cgccctcaca gagcctgtcc gtcacatgca ctgtctcagg ggtctcatta
2821 cccgactatg gtgtaagctg gattcgccag cctccacgaa agggtctgga gtggctggga
2881 gtaatatggg gtagtgaaac cacatactat aattcagctc tcaaatccag actgaccatc
2941 atcaaggaca actccaagag ccaagttttc ttaaaaatga acagtctgca aactgatgac
3001 acagccattt actactgtgc caaacattat tactacggtg gtagctatgc tatggactac
3061 tggggtcaag gaacctcagt caccgtctcc tcagcggccg caattgaagt tatgtatcct
3121 cctccttacc taggtggcgg cggttctggt ggcggcggtt ctggtggcgg cggttctctc
3181 gagccaaata tccagaaccc tgaccctgcc gtgtaccagc tgagagactc taaatccagt
3241 gacaagtctg tctgcctatt caccgatttt gattctcaaa caaatgtgtc acaaagtaag
3301 gattctgatg tgtatatcac agacaaaact gtgctagaca tgaggtctat ggacttcaag
3361 agcaacagtg ctgtggcctg gagcaacaaa tctgactttg catgtgcaaa cgccttcaac
3421 aacagcatta ttccagaaga caccttcttc cccagcccag aaagttcctg tgatgtcaag
3481 ctggtcgaga aaagctttga aacagatacg aacctaaact ttcaaaacct gtcagtgatt
3541 gggttccgaa tcctcctcct gaaagtggcc gggtttaatc tgctcatgac gctgcggctg
3601 tggtccagct gataagaatt cgatccgcgg ccgcgaagga tctgcgatcg ctccggtgcc
3661 cgtcagtggg cagagcgcac atcgcccaca gtccccgaga agttgggggg aggggtcggc
3721 aattgaacgg gtgcctagag aaggtggcgc ggggtaaact gggaaagtga tgtcgtgtac
3781 tggctccgcc tttttcccga gggtggggga gaaccgtata taagtgcagt agtcgccgtg
3841 aacgttcttt ttcgcaacgg gtttgccgcc agaacacagc tgaagcttcg aggggctcgc
3901 atctctcctt cacgcgcccg ccgccctacc tgaggccgcc atccacgccg gttgagtcgc
3961 gttctgccgc ctcccgcctg tggtgcctcc tgaactgcgt ccgccgtcta ggtaagttta
4021 aagctcaggt cgagaccggg cctttgtccg gcgctccctt ggagcctacc tagactcagc
4081 cggctctcca cgctttgcct gaccctgctt gctcaactct acgtctttgt ttcgttttct
4141 gttctgcgcc gttacagatc caagctgtga ccggcgccta cgctagatga ccgagtacaa
4201 gcccacggtg cgcctcgcca cccgcgacga cgtccccagg gccgtacgca ccctcgccgc
4261 cgcgttcgcc gactaccccg ccacgcgcca caccgtcgat ccggaccgcc acatcgagcg
4321 ggtcaccgag ctgcaagaac tcttcctcac gcgcgtcggg ctcgacatcg gcaaggtgtg
4381 ggtcgcggac gacggcgccg cggtggcggt ctggaccacg ccggagagcg tcgaagcggg
4441 ggcggtgttc gccgagatcg gcccgcgcat ggccgagttg agcggttccc ggctggccgc
4501 gcagcaacag atggaaggcc tcctggcgcc gcaccggccc aaggagcccg cgtggttcct
4561 ggccaccgtc ggcgtctcgc ccgaccacca gggcaagggt ctgggcagcg ccgtcgtgct
4621 ccccggagtg gaggcggccg agcgcgccgg ggtgcccgcc ttcctggaga cctccgcgcc
4681 ccgcaacctc cccttctacg agcggctcgg cttcaccgtc accgccgacg tcgaggtgcc
4741 cgaaggaccg cgcacctggt gcatgacccg caagcccggt gcctgagtcg acaatcaacc
4801 tctggattac aaaatttgtg aaagattgac tggtattctt aactatgttg ctccttttac
4861 gctatgtgga tacgctgctt taatgccttt gtatcatgct attgcttccc gtatggcttt
4921 cattttctcc tccttgtata aatcctggtt gctgtctctt tatgaggagt tgtggcccgt
4981 tgtcaggcaa cgtggcgtgg tgtgcactgt gtttgctgac gcaaccccca ctggttgggg
5041 cattgccacc acctgtcagc tcctttccgg gactttcgct ttccccctcc ctattgccac
5101 ggcggaactc atcgccgcct gccttgcccg ctgctggaca ggggctcggc tgttgggcac
5161 tgacaattcc gtggtgttgt cggggaaatc atcgtccttt ccttggctgc tcgcctgtgt
5221 tgccacctgg attctgcgcg ggacgtcctt ctgctacgtc ccttcggccc tcaatccagc
5281 ggaccttcct tcccgcggcc tgctgccggc tctgcggcct cttccgcgtc ttcgccttcg
5341 ccctcagacg agtcggatct ccctttgggc cgcctccccg cctggtacct ttaagaccaa
5401 tgacttacaa ggcagctgta gatcttagcc actttttaaa agaaaagggg ggactggaag
```

-continued

CONSTRUCT SEQUENCES

```
5461 ggctaattca ctcccaacga aaataagatc tgctttttgc ttgtactggg tctctctggt
5521 tagaccagat ctgagcctgg gagctctctg gctaactagg gaacccactg cttaagcctc
5581 aataaagctt gccttgagtg cttcaagtag tgtgtgcccg tctgttgtgt gactctggta
5641 actagagatc cctcagaccc ttttagtcag tgtggaaaat ctctagcagt agtagttcat
5701 gtcatcttat tattcagtat ttataacttg caaagaaatg aatatcagag agtgagagga
5761 acttgtttat tgcagcttat aatggttaca aataaagcaa tagcatcaca aatttcacaa
5821 ataaagcatt tttttcactg cattctagtt gtggtttgtc caaactcatc aatgtatctt
5881 atcatgtctg gctctagcta tcccgcccct aactccgccc agttccgccc attctccgcc
5941 ccatggctga ctaatttttt ttatttatgc agaggccgag gccgcctcgg cctctgagct
6001 attccagaag tagtgaggag gcttttttgg aggcctagac ttttgcagag acggcccaaa
6061 ttcgtaatca tggtcatagc tgtttcctgt gtgaaattgt tatccgctca caattccaca
6121 caacatacga gccggaagca taaagtgtaa agcctggggt gcctaatgag tgagctaact
6181 cacattaatt gcgttgcgct cactgcccgc tttccagtcg ggaaacctgt cgtgccagct
6241 gcattaatga atcggccaac gcgcggggag aggcggtttg cgtattgggc gctcttccgc
6301 ttcctcgctc actgactcgc tgcgctcggt cgttcggctg cggcgagcgg tatcagctca
6361 ctcaaaggcg gtaatacggt tatccacaga atcaggggat aacgcaggaa agaacatgtg
6421 agcaaaaggc cagcaaaagg ccaggaaccg taaaaaggcc gcgttgctgg cgtttttcca
6481 taggctccgc ccccctgacg agcatcacaa aaatcgacgc tcaagtcaga ggtggcgaaa
6541 cccgacagga ctataaagat accaggcgtt tccccctgga agctccctcg tgcgctctcc
6601 tgttccgacc ctgccgctta ccggatacct gtccgccttt ctcccttcgg gaagcgtggc
6661 gctttctcat agctcacgct gtaggtatct cagttcggtg taggtcgttc gctccaagct
6721 gggctgtgtg cacgaacccc ccgttcagcc cgaccgctgc gccttatccg gtaactatcg
6781 tcttgagtcc aacccggtaa gacacgactt atcgccactg gcagcagcca ctggtaacag
6841 gattagcaga gcgaggtatg taggcggtgc tacagagttc ttgaagtggt ggcctaacta
6901 cggctacact agaaggacag tatttggtat ctgcgctctg ctgaagccag ttaccttcgg
6961 aaaaagagtt ggtagctctt gatccggcaa acaaaccacc gctggtagcg gtggtttttt
7021 tgtttgcaag cagcagatta cgcgcagaaa aaaaggatct caagaagatc ctttgatctt
7081 ttctacgggg tctgacgctc agtggaacga aaactcacgt taagggattt tggtcatgag
7141 attatcaaaa aggatcttca cctagatcct tttaaattaa aaatgaagtt ttaaatcaat
7201 ctaaagtata tatgagtaaa cttggtctga cagttaccaa tgcttaatca gtgaggcacc
7261 tatctcagcg atctgtctat ttcgttcatc catagttgcc tgactccccg tcgtgtagat
7321 aactacgata cgggagggct taccatctgg ccccagtgct gcaatgatac cgcgagaccc
7381 acgctcaccg gctccagatt tatcagcaat aaaccagcca gccggaaggg ccgagcgcag
7441 aagtggtcct gcaactttat ccgcctccat ccagtctatt aattgttgcc gggaagctag
7501 agtaagtagt tcgccagtta atagtttgcg caacgttgtt gccattgcta caggcatcgt
7561 ggtgtcacgc tcgtcgtttg gtatggcttc attcagctcc ggttcccaac gatcaaggcg
7621 agttacatga tcccccatgt tgtgcaaaaa agcggttagc tccttcggtc ctccgatcgt
7681 tgtcagaagt aagttggccg cagtgttatc actcatggtt atggcagcac tgcataattc
7741 tcttactgtc atgccatccg taagatgctt ttctgtgact ggtgagtact caaccaagtc
7801 attctgagaa tagtgtatgc ggcgaccgag ttgctcttgc ccggcgtcaa tacgggataa
7861 taccgcgcca catagcagaa ctttaaaagt gctcatcatt ggaaaacgtt cttcggggcg
7921 aaaactctca aggatcttac cgctgttgag atccagttcg atgtaaccca ctcgtgcacc
7981 caactgatct tcagcatctt ttactttcac cagcgtttct gggtgagcaa aaacaggaag
8041 gcaaaatgcc gcaaaaaagg gaataagggc gacacggaaa tgttgaatac tcatactctt
8101 cctttttcaa tattattgaa gcatttatca gggttattgt ctcatgagcg gatacatatt
8161 tgaatgtatt tagaaaaata aacaaatagg ggttccgcgc acatttcccc gaaaagtgcc
8221 acctgacgtc taagaaacca ttattatcat gacattaacc tataaaaata ggcgtatcac
8281 gaggcccttt cgtctcgcgc gtttcggtga tgacggtgaa aacctctgac acatgcagct
8341 cccggagacg gtcacagctt gtctgtaagc ggatgccggg agcagacaag cccgtcaggg
8401 cgcgtcagcg ggtgttggcg ggtgtcgggg ctggcttaac tatgcggcat cagagcagat
8461 tgtactgaga gtgcaccata tgcggtgtga aataccgcac agatgcgtaa ggagaaaata
8521 ccgcatcagg cgccattcgc cattcaggct gcgcaactgt tgggaagggc gatcggtgcg
8581 ggcctcttcg ctattacgcc agctggcgaa agggggatgt gctgcaaggc gattaagttg
8641 ggtaacgcca gggttttccc agtcacgacg ttgtaaaacg acggccagtg ccaagctg.
```

p510_antiCD19_LL_TCRbeta (SEQ ID NO: 13)

```
   1 acgcgtgtag tcttatgcaa tactcttgta gtcttgcaac atggtaacga tgagttagca
  61 acatgcctta caaggagaga aaaagcaccg tgcatgccga ttggtggaag taaggtggta
 121 cgatcgtgcc ttattaggaa ggcaacagac gggtctgaca tggattggac gaaccactga
 181 attgccgcat tgcagagata ttgtatttaa gtgcctagct cgatacaata aacgggtctc
 241 tctggttaga ccagatctga gcctgggagc tctctggcta actagggaac ccactgctta
 301 agcctcaata aagcttgcct tgagtgcttc aagtagtgtg tgcccgtctg ttgtgtgact
 361 ctggtaacta gagatccctc agaccctttt agtcagtgtg gaaaatctct agcagtggcg
 421 cccgaacagg gacctgaaag cgaaagggaa accagagctc tctcgacgca ggactcggct
 481 tgctgaagcg cgcacggcaa gaggcgaggg gcggcgactg gtgagtacgc caaaaatttt
 541 gactagcgga ggctagaagg agagagatgg gtgcgagagc gtcagtatta agcgggggag
 601 aattagatcg cgatgggaaa aaattcggtt aaggccaggg ggaaagaaaa aatataaatt
 661 aaaacatata gtatgggcaa gcagggagct agaacgattc gcagttaatc ctggcctgtt
 721 agaaacatca gaaggctgta gacaaatact gggacagcta caaccatccc ttcagacagg
 781 atcagaagaa cttagatcat tatataatac agtagcaacc ctctattgtg tgcatcaaag
 841 gatagagata aaagacacca aggaagcttt agacaagata gaggaagagc aaaacaaaag
 901 taagaccacc gcacagcaag cggccactga tcttcagacc tggaggagga gatatgaggg
 961 acaattggag aagtgaatta tataaatata aagtagtaaa aattgaacca ttaggagtag
1021 cacccaccaa ggcaaagaga agagtggtgc agagagaaaa aagagcagtg ggaataggag
1081 ctttgttcct tgggttcttg ggagcagcag gaagcactat gggcgcagcc tcaatgacgc
1141 tgacggtaca ggccagacaa ttattgtctg gtatagtgca gcagcagaac aatttgctga
1201 gggctattga ggcgcaacag catctgttgc aactcacagt ctggggcatc aagcagctcc
```

-continued

| CONSTRUCT SEQUENCES |
|---|
| 1261 aggcaagaat cctggctgtg gaaagatacc taaaggatca acagctcctg ggatttggg |
| 1321 gttgctctgg aaaactcatt tgcaccactg ctgtgccttg gaatgctagt tggagtaata |
| 1381 aatctctgga acagattgga atcacacgac ctggatggag tgggacagag aaattaacaa |
| 1441 ttacacaagc ttaatacact ccttaattga agaatcgcaa aaccagcaag aaaagaatga |
| 1501 acaagaatta ttggaattag ataaatgggc aagtttgtgg aattggttta acataacaaa |
| 1561 ttggctgtgg tatataaaat tattcataat gatagtagga ggcttggtag gtttaagaat |
| 1621 agtttttgct gtactttcta tagtgaatag agttaggcag ggatattcac cattatcgtt |
| 1681 tcagacccac ctcccaaccc cgaggggacc cgacaggccc gaaggaatag aagaagaagg |
| 1741 tggagagaga gacagagaca gatccattcg attagtgaac ggatctcgac ggtatcggtt |
| 1801 aacttttaaa agaaaagggg ggattggggg gtacagtgca ggggaaagaa tagtagacat |
| 1861 aatagcaaca gacatacaaa ctaaagaatt acaaaaacaa attacaaaat tcaaaatttt |
| 1921 atcgatacta gtattatgcc cagtacatga ccttatggga ctttcctact tggcagtaca |
| 1981 tctacgtatt agtcatcgct attaccatgg tgatgcggtt ttggcagtac atcaatgggc |
| 2041 gtggatagcg gtttgactca cggggatttc caagtctcca ccccattgac gtcaatggga |
| 2101 gtttgttttg gcaccaaaat caacgggact ttccaaaatg tcgtaacaac tccgccccat |
| 2161 tgacgcaaat gggcggtagg cgtgtacggt gggaggttta tataagcaga gctcgtttag |
| 2221 tgaaccgtca gatcgcctgg agacgccatc cacgctgttt tgacctccat agaagattct |
| 2281 agagccgcca ccatgcttct cctggtgaca agccttctgc tctgtgagtt accacaccca |
| 2341 gcattcctcc tgatcccaga catccagatg acacagacta catcctccct gtctgcctct |
| 2401 ctgggagaca gagtcaccat cagttgcagg gcaagtcagg acattagtaa atatttaaat |
| 2461 tggtatcagc agaaaccaga tggaactgtt aaactcctga tctaccatac atcaagatta |
| 2521 cactcaggag tcccatcaag gttcagtggc agtgggtctg gaacagatta ttctctcacc |
| 2581 attagcaacc tggagcaaga agatattgcc acttactttt gccaacaggg taatacgctt |
| 2641 ccgtacacgt tcggaggggg gactaagttg gaaataacag gctccacctc tggatccggc |
| 2701 aagcccggat ctggcgaggg atccaccaag ggcgaggtga aactgcagga gtcaggacct |
| 2761 ggcctggtgg cgccctcaca gagcctgtcc gtcacatgca ctgtctcagg ggtctcatta |
| 2821 cccgactatg gtgtaagctg gattcgccag cctccacgaa agggtctgga gtggctggga |
| 2881 gtaatatggg gtagtgaaac cacatactat aattcagctc tcaaatccag actgaccatc |
| 2941 atcaaggaca actccaagag ccaagttttc ttaaaaatga acagtctgca aactgatgac |
| 3001 acagccattt actactgtgc caaacattat tactacggtg gtagctatgc tatggactac |
| 3061 tggggtcaag gaacctcagt caccgtctcc tcagcggccg caattgaagt tatgtatcct |
| 3121 cctccttacc taggtggcgg cggttctggt ggcggcggtt ctggtggcgg cggttctctc |
| 3181 gagctgggag caggcccagt ggattctgga gtcacacaaa ccccaaagca cctgatcaca |
| 3241 gcaactggac agcgagtgac gctgagatgc tcccctaggt ctggagacct ctctgtgtca |
| 3301 tggtaccaac agagcctgga ccagggcctc cagttcctca ttcagtatta taatggagaa |
| 3361 gagagagcaa aaggaaacat tcttgaacga ttctccgcac aacagttccc tgacttgcac |
| 3421 tctgaactaa acctgagctc tctggagctg ggggactcag ctttgtattt ctgtgccagc |
| 3481 agcccccgga caggcctgaa cactgaagct ttctttggac aaggcaccag actcacagtt |
| 3541 gtagaggacc tgaacaaggt gttcccaccc gaggtcgctg tgtttgagcc atcagaagca |
| 3601 gagatctccc acacccaaaa ggccacactg gtgtgcctgg ccacaggctt cttccccgac |
| 3661 cacgtggagc tgagctggtg ggtgaatggg aaggaggtgc acagtggggt cagcacggac |
| 3721 ccgcagcccc tcaaggagca gcccgccctc aatgactcca gatactgcct gagcagccgc |
| 3781 ctgagggtct cggccacctt ctggcagaac ccccgcaacc acttccgctg tcaagtccag |
| 3841 ttctacgggc tctcggagaa tgacgagtgg acccaggata gggccaaacc cgtcacccag |
| 3901 atcgtcagcg ccgaggcctg ggtagagca gactgtggct ttacctcggt gtcctaccag |
| 3961 caaggggtcc tgtctgccac catcctctat gagatcctgc tagggaaggc caccctgtat |
| 4021 gctgtgctgg tcagcgccct tgtgttgatg gccatggtca agagaaagga tttctgataa |
| 4081 gaattcgatc cgcggccgcg aaggatctgc gatcgctccg gtgcccgtca gtgggcagag |
| 4141 cgcacatcgc ccacagtccc cgagaagttg gggggagggg tcggcaattg aacgggtgcc |
| 4201 tagagaaggt ggcgcggggt aaactgggaa agtgatgtcg tgtactggct ccgccttttt |
| 4261 cccgagggtg ggggagaacc gtatataagt gcagtagtcg ccgtgaacgt tctttttcgc |
| 4321 aacgggtttg ccgccagaac acagctgaag cttcgagggg ctcgcatctc tccttcacgc |
| 4381 gcccgccgcc ctacctgagg ccgccatcca cgccggttga gtcgcgttct gccgcctccc |
| 4441 gcctgtggtg cctcctgaac tgcgtccgcc gtctaggtaa gtttaaagct caggtcgaga |
| 4501 ccgggccttt gtccggcgct cccttggagc ctacctagac tcagccggct ctccacgctt |
| 4561 tgcctgaccc tgcttgctca actctacgtc tttgtttcgt tttctgttct gcgccgttac |
| 4621 agatccaagc tgtgaccggc gcctacgcta gatgaccgag tacaagccca cggtgcgcct |
| 4681 cgccacccgc gacgacgtcc ccagggccgt acgcaccctc gccgccgcgt tcgccgacta |
| 4741 ccccgccacg cgccacaccg tcgatccgga ccgccacatc gagcgggtca ccgagctgca |
| 4801 agaactcttc ctcacgcgcg tcgggctcga catcggcaag gtgtgggtcg cggacgacgg |
| 4861 cgccgcggtg gcggtctgga ccacgccgga gagcgtcgaa gcgggggcgg tgttcgccga |
| 4921 gatcggcccg cgcatggccg agttgagcgg ttcccggctg gccgcgcagc aacagatgga |
| 4981 aggcctcctg gcgccgcacc ggcccaagga gcccgcgtgg ttcctggcca ccgtcggcgt |
| 5041 ctcgcccgac caccaggcca agggtctggg cagcgccgtc gtgctccccg gagtggaggc |
| 5101 ggccgagcgc gccggggtgc ccgccttcct ggagacctcc gcgccccgca acctcccctt |
| 5161 ctacgagcgg ctcggcttca ccgtcaccgc cgacgtcgag gtgcccgaag gaccgcgcac |
| 5221 ctggtgcatg acccgcaagc ccggtgcctg agtcgacaat caacctctgg attacaaaat |
| 5281 ttgtgaaaga ttgactggta ttcttaacta tgttgctcct tttacgctat gtggatacgc |
| 5341 tgctttaatg cctttgtatc atgctattgc ttcccgtatg gctttcattt tctcctcctt |
| 5401 gtataaatcc tggttgctgt ctctttatga ggagttgtgg cccgttgtca ggcaacgtgg |
| 5461 cgtggtgtgc actgtgtttg ctgacgcaac ccccactggt tggggcattg ccaccacctg |
| 5521 tcagctcctt tccgggactt tcgctttccc cctccctatt gccacggcgg aactcatcgc |
| 5581 cgcctgcctt gcccgctgct ggacaggggc tcggctgttg ggcactgaca attccgtggt |
| 5641 gttgtcgggg aaatcatcgt cctttccttg gctgctcgcc tgtgttgcca cctggattct |
| 5701 gcgcgggacg tccttctgct acgtcccttc ggccctcaat ccagcggacc ttccttcccg |
| 5761 cggcctgctg ccggctctgc ggcctcttcc gcgtcttcgc cttcgccctc agacgagtcg |
| 5821 gatctccctt tgggccgcct ccccgcctgg tacctttaag accaatgact tacaaggcag |

-continued

CONSTRUCT SEQUENCES

```
5881 ctgtagatct tagccacttt ttaaaagaaa agggggact ggaagggcta attcactccc
5941 aacgaaaata agatctgctt tttgcttgta ctgggtctct ctggttagac cagatctgag
6001 cctgggagct ctctggctaa ctagggaacc cactgcttaa gcctcaataa agcttgcctt
6061 gagtgcttca agtagtgtgt gcccgtctgt tgtgtgactc tggtaactag agatccctca
6121 gacccttta gtcagtgtgg aaaatctcta gcagtagtag ttcatgtcat cttattattc
6181 agtatttata acttgcaaag aaatgaatat cagagagtga gaggaacttg tttattgcag
6241 cttataatgg ttacaaataa agcaatagca tcacaaattt cacaaataaa gcattttttt
6301 cactgcattc tagttgtggt ttgtccaaac tcatcaatgt atcttatcat gtctggctct
6361 agctatcccg cccctaactc cgcccagttc cgcccattct ccgccccatg gctgactaat
6421 tttttttatt tatgcagagg ccgaggccgc ctcggcctct gagctattcc agaagtagtg
6481 aggaggcttt tttggaggcc tagacttttg cagagacggc ccaaattcgt aatcatggtc
6541 atagctgttt cctgtgtgaa attgttatcc gctcacaatt ccacacaaca tacgagccgg
6601 aagcataaag tgtaaagcct ggggtgccta atgagtgagc taactcacat taattgcgtt
6661 gcgctcactg cccgctttcc agtcgggaaa cctgtcgtgc cagctgcatt aatgaatcgg
6721 ccaacgcgcg gggagaggcg gtttgcgtat tgggcgctct tccgcttcct cgctcactga
6781 ctcgctgcgc tcggtcgttc ggctgcggcg agcggtatca gctcactcaa aggcggtaat
6841 acggttatcc acagaatcag gggataacgc aggaaagaac atgtgagcaa aaggccagca
6901 aaaggccagg aaccgtaaaa aggccgcgtt gctggcgttt ttccataggc tccgcccccc
6961 tgacgagcat cacaaaaatc gacgctcaag tcagaggtgg cgaaacccga caggactata
7021 aagataccag gcgtttcccc ctggaagctc cctcgtgcgc tctcctgttc cgaccctgcc
7081 gcttaccgga tacctgtccg cctttctccc ttcgggaagc gtggcgcttt ctcatagctc
7141 acgctgtagg tatctcagtt cggtgtaggt cgttcgctcc aagctgggct gtgtgcacga
7201 accccccgtt cagcccgacc gctgcgcctt atccggtaac tatcgtcttg agtccaaccc
7261 ggtaagacac gacttatcgc cactggcagc agccactggt aacaggatta gcagagcgag
7321 gtatgtaggc ggtgctacag agttcttgaa gtggtggcct aactacggct acactagaag
7381 gacagtattt ggtatctgcg ctctgctgaa gccagttacc ttcggaaaaa gagttggtag
7441 ctcttgatcc ggcaaacaaa ccaccgctgg tagcggtggt ttttttgttt gcaagcagca
7501 gattacgcgc agaaaaaaag gatctcaaga agatcctttg atcttttcta cggggtctga
7561 cgctcagtgg aacgaaaact cacgttaagg gattttggtc atgagattat caaaaaggat
7621 cttcacctag atccttttaa attaaaaatg aagttttaaa tcaatctaaa gtatatatga
7681 gtaaacttgg tctgacagtt accaatgctt aatcagtgag gcacctatct cagcgatctg
7741 tctatttcgt tcatccatag ttgcctgact ccccgtcgtg tagataacta cgatacggga
7801 gggcttacca tctggcccca gtgctgcaat gataccgcga gacccacgct caccggctcc
7861 agatttatca gcaataaacc agccagccgg aagggccgag cgcagaagtg gtcctgcaac
7921 tttatccgcc tccatccagt ctattaattg ttgccgggaa gctagagtaa gtagttcgcc
7981 agttaatagt ttgcgcaacg ttgttgccat tgctacaggc atcgtggtgt cacgctcgtc
8041 gtttggtatg gcttcattca gctccggttc ccaacgatca aggcgagtta catgatcccc
8101 catgttgtgc aaaaaagcgg ttagctcctt cggtcctccg atcgttgtca gaagtaagtt
8161 ggccgcagtg ttatcactca tggttatggc agcactgcat aattctctta ctgtcatgcc
8221 atccgtaaga tgcttttctg tgactggtga gtactcaacc aagtcattct gagaatagtg
8281 tatgcggcga ccgagttgct cttgcccggc gtcaatacgg gataataccg cgccacatag
8341 cagaacttta aaagtgctca tcattggaaa acgttcttcg gggcgaaaac tctcaaggat
8401 cttaccgctg ttgagatcca gttcgatgta acccactcgt gcacccaact gatcttcagc
8461 atcttttact ttcaccagcg tttctgggtg agcaaaaaca ggaaggcaaa atgccgcaaa
8521 aaagggaata agggcgacac ggaaatgttg aatactcata ctcttccttt ttcaatatta
8581 ttgaagcatt tatcagggtt attgtctcat gagcggatac atatttgaat gtatttagaa
8641 aaataaacaa ataggggttc cgcgcacatt tccccgaaaa gtgccacctg acgtctaaga
8701 aaccattatt atcatgacat taacctataa aaataggcgt atcacgaggc cctttcgtct
8761 cgcgcgtttc ggtgatgacg gtgaaaacct ctgacacatg cagctcccgg agacggtcac
8821 agcttgtctg taagcggatg ccgggagcag acaagcccgt cagggcgcgt cagcgggtgt
8881 tggcgggtgt cggggctggc ttaactatgc ggcatcagag cagattgtac tgagagtgca
8941 ccatatgcgg tgtgaaatac cgcacagatg cgtaaggaga aaataccgca tcaggcgcca
9001 ttcgccattc aggctgcgca actgttggga agggcgatcg gtgcgggcct cttcgctatt
9061 acgccagctg gcgaaagggg gatgtgctgc aaggcgatta agttgggtaa cgccagggtt
9121 ttcccagtca cgacgttgta aaacgacggc cagtgccaag ctg
```

p510_antiCD19_LL_TCRbetaC (SEQ ID NO: 14)

```
   1 acgcgtgtag tcttatgcaa tactcttgta gtcttgcaac atggtaacga tgagttagca
  61 acatgcctta caaggagaga aaaagcaccg tgcatgccga ttggtggaag taaggtggta
 121 cgatcgtgcc ttattaggaa ggcaacagac gggtctgaca tggattggac gaaccactga
 181 attgccgcat tgcagagata ttgtatttaa gtgcctagct cgatacaata aacgggtctc
 241 tctggttaga ccagatctga gcctgggagc tctctggcta actagggaac ccactgctta
 301 agcctcaata aagcttgcct tgagtgcttc aagtagtgtg tgcccgtctg ttgtgtgact
 361 ctggtaacta gagatccctc agaccctttt agtcagtgtg gaaaatctct agcagtggcg
 421 cccgaacagg gacctgaaag cgaaagggaa accagagctc tctcgacgca ggactcggct
 481 tgctgaagcg cgcacggcaa gaggcgaggg gcggcgactg gtgagtacgc caaaaatttt
 541 gactagcgga ggctagaagg agagagatgg gtgcgagagc gtcagtatta agcgggggag
 601 aattagatcg cgatgggaaa aaattcggtt aaggccaggg ggaaagaaaa aatataaatt
 661 aaaacatata gtatgggcaa gcagggagct agaacgattc gcagttaatc ctggcctgtt
 721 agaaacatca gaaggctgta gacaaatact gggacagcta caaccatccc ttcagacagg
 781 atcagaagaa cttagatcat tatataatac agtagcaacc ctctattgtg tgcatcaaag
 841 gatagagata aaagacacca aggaagcttt agacaagata gaggaagagc aaaacaaaag
 901 taagaccacc gcacagcaag cggccactga tcttcagacc tggaggagga gatatgaggg
 961 acaattggag aagtgaatta tataaatata aagtagtaaa aattgaacca ttaggagtag
1021 cacccaccaa ggcaaagaga agagtggtgc agagagaaaa aagagcagtg ggaataggag
1081 ctttgttcct tgggttcttg ggagcagcag gaagcactat gggcgcagcc tcaatgacgc
1141 tgacggtaca ggccagacaa ttattgtctg gtatagtgca gcagcagaac aatttgctga
```

-continued

| CONSTRUCT SEQUENCES |
|---|
| 1201 gggctattga ggcgcaacag catctgttgc aactcacagt ctggggcatc aagcagctcc |
| 1261 aggcaagaat cctggctgtg gaaagatacc taaaggatca acagctcctg ggatttgggg |
| 1321 gttgctctgg aaaactcatt tgcaccactg ctgtgccttg gaatgctagt tggagtaata |
| 1381 aatctctgga acagattgga atcacacgac ctggatggag tgggacagag aaattaacaa |
| 1441 ttacacaagc ttaatacact ccttaattga agaatcgcaa aaccagcaag aaaagaatga |
| 1501 acaagaatta ttggaattag ataaatgggc aagtttgtgg aattggttta acataacaaa |
| 1561 ttggctgtgg tatataaaat tattcataat gatagtagga ggcttggtag gtttaagaat |
| 1621 agtttttgct gtactttcta tagtgaatag agttaggcag ggatattcac cattatcgtt |
| 1681 tcagacccac ctcccaaccc cgaggggacc cgacaggccc gaaggaatag aagaagaagg |
| 1741 tggagagaga gacagagaca gatccattcg attagtgaac ggatctcgac ggtatcggtt |
| 1801 aacttttaaa agaaaagggg ggattggggg gtacagtgca ggggaaagaa tagtagacat |
| 1861 aatagcaaca gacatacaaa ctaaagaatt acaaaaacaa attacaaaat tcaaaatttt |
| 1921 atcgatacta gtattatgcc cagtacatga ccttatggga ctttcctact tggcagtaca |
| 1981 tctacgtatt agtcatcgct attaccatgg tgatgcggtt ttggcagtac atcaatgggc |
| 2041 gtggatagcg gtttgactca cggggatttc caagtctcca ccccattgac gtcaatggga |
| 2101 gtttgttttg gcaccaaaat caacgggact ttccaaaatg tcgtaacaac tccgccccat |
| 2161 tgacgcaaat gggcggtagg cgtgtacggt gggaggttta tataagcaga gctcgtttag |
| 2221 tgaaccgtca gatcgcctgg agacgccatc cacgctgttt tgacctccat agaagattct |
| 2281 agagccgcca ccatgcttct cctggtgaca agccttctgc tctgtgagtt accacaccca |
| 2341 gcattcctcc tgatcccaga catccagatg acacagacta catcctccct gtctgcctct |
| 2401 ctgggagaca gagtcaccat cagttgcagg gcaagtcagg acattagtaa atatttaaat |
| 2461 tggtatcagc agaaaccaga tggaactgtt aaactcctga tctaccatac atcaagatta |
| 2521 cactcaggag tcccatcaag gttcagtggc agtgggtctg gaacagatta ttctctcacc |
| 2581 attagcaacc tggagcaaga agatattgcc acttactttt gccaacaggg taatacgctt |
| 2641 ccgtacacgt tcggaggggg gactaagttg gaaataacag gctccacctc tggatccggc |
| 2701 aagcccggat ctggcgaggg atccaccaag ggcgaggtga aactgcagga gtcaggacct |
| 2761 ggcctggtgg cgccctcaca gagcctgtcc gtcacatgca ctgtctcagg ggtctcatta |
| 2821 cccgactatg gtgtaagctg gattcgccag cctccacgaa agggtctgga gtggctggga |
| 2881 gtaatatggg gtagtgaaac cacatactat aattcagctc tcaaatccag actgaccatc |
| 2941 atcaaggaca actccaagag ccaagttttc ttaaaaatga acagtctgca aactgatgac |
| 3001 acagccattt actactgtgc caaacattat tactacggtg gtagctatgc tatggactac |
| 3061 tggggtcaag gaacctcagt caccgtctcc tcagcggccg caattgaagt tatgtatcct |
| 3121 cctccttacc taggtggcgg cggttctggt ggcggcggtt ctggtggcgg cggttctctc |
| 3181 gaggaggacc tgaacaaggt gttcccaccc gaggtcgctg tgtttgagcc atcagaagca |
| 3241 gagatctccc acacccaaaa ggccacactg gtgtgcctgg ccacaggctt cttccccgac |
| 3301 cacgtggagc tgagctggtg ggtgaatggg aaggaggtgc acagtggggt cagcacagac |
| 3361 ccgcagcccc tcaaggagca gcccgccctc aatgactcca gatactgcct gagcagccgc |
| 3421 ctgagggtct cggccacctt ctggcagaac ccccgcaacc acttccgctg tcaagtccag |
| 3481 ttctacgggc tctcggagaa tgacgagtgg acccaggata gggccaaacc cgtcacccag |
| 3541 atcgtcagcg ccgaggcctg gggtagagca gactgtggct ttacctcggt gtcctaccag |
| 3601 caaggggtcc tgtctgccac catcctctat gagatcctgc tagggaaggc caccctgtat |
| 3661 gctgtgctgg tcagcgccct tgtgttgatg gccatggtca agagaaagga tttctgataa |
| 3721 gaattcgatc cgcggccgcg aaggatctgc gatcgctccg gtgcccgtca gtgggcagag |
| 3781 cgcacatcgc ccacagtccc cgagaagttg gggggagggg tcggcaattg aacgggtgcc |
| 3841 tagagaaggt ggcgcggggt aaactgggaa agtgatgtcg tgtactggct ccgccttttt |
| 3901 cccgagggtg ggggagaacc gtatataagt gcagtagtcg ccgtgaacgt tctttttcgc |
| 3961 aacgggtttg ccgccagaac acagctgaag cttcgagggg ctcgcatctc tccttcacgc |
| 4021 gcccgccgcc ctacctgagg ccgccatcca cgccggttga gtcgcgttct gccgcctccc |
| 4081 gcctgtggtg cctcctgaac tgcgtccgcc gtctaggtaa gtttaaagct caggtcgaga |
| 4141 ccgggccttt gtccggcgct ccccttggag cctacctagac tcagccggct ctccacgctt |
| 4201 tgcctgaccc tgcttgctca actctacgtc tttgtttcgt tttctgttct gcgccgttac |
| 4261 agatccaagc tgtgaccggc gcctacgcta gatgaccgag tacaagccca cggtgcgcct |
| 4321 cgccacccgc gacgacgtcc ccagggccgt acgcaccctc gccgccgcgt tcgccgacta |
| 4381 ccccgccacg cgccacaccg tcgatccgga ccgccacatc gagcgggtca ccgagctgca |
| 4441 agaactcttc ctcacgcgcg tcgggctcga catcggcaag gtgtgggtcg cggacgacgg |
| 4501 cgccgcggtg gcggtctgga ccacgccgga gagcgtcgaa gcgggggcgg tgttcgccga |
| 4561 gatcggcccg cgcatggccg agttgagcgg ttcccggctg gccgcgcagc aacagatgga |
| 4621 aggcctcctg gcgccgcacc ggcccaagga gcccgcgtgg ttcctggcca ccgtcggcgt |
| 4681 ctcgcccgac caccagggca agggtctggg cagcgccgtc gtgctccccg gagtggaggc |
| 4741 ggccgagcgc gccggggtgc ccgccttcct ggagacctcc gcgccccgca acctcccctt |
| 4801 ctacgagcgg ctcggcttca ccgtcaccgc cgacgtcgag gtgcccgaag gaccgcgcac |
| 4861 ctggtgcatg acccgcaagc ccggtgcctg agtcgacaat caacctctgg attacaaaat |
| 4921 ttgtgaaaga ttgactggta ttcttaacta tgttgctcct tttacgctat gtggatacgc |
| 4981 tgctttaatg cctttgtatc atgctattgc ttcccgtatg gctttcattt tctcctcctt |
| 5041 gtataaatcc tggttgctgt ctctttatga ggagttgtgg cccgttgtca ggcaacgtgg |
| 5101 cgtggtgtgc actgtgtttg ctgacgcaac ccccactggt tggggcattg ccaccacctg |
| 5161 tcagctcctt tccgggactt tcgctttccc cctccctatt gccacggcgg aactcatcgc |
| 5221 cgcctgcctt gcccgctgct ggacaggggc tcggctgttg ggcactgaca attccgtggt |
| 5281 gttgtcgggg aaatcatcgt cctttccttg gctgctcgcc tgtgttgcca cctggattct |
| 5341 gcgcgggacg tccttctgct acgtcccttc ggccctcaat ccagcggacc ttccttcccg |
| 5401 cggcctgctg ccggctctgc ggcctcttcc gcgtcttcgc cttcgccctc agacgagtcg |
| 5461 gatctccctt tgggccgcct ccccgcctgg tacctttaag accaatgact tacaaggcag |
| 5521 ctgtagatct tagccacttt ttaaaagaaa aggggggact ggaagggcta attcactccc |
| 5581 aacgaaaata agatctgctt tttgcttgta ctgggtctct ctggttagac cagatctgag |
| 5641 cctgggagct ctctggctaa ctagggaacc cactgcttaa gcctcaataa agcttgcctt |
| 5701 gagtgcttca agtagtgtgt gcccgtctgt tgtgtgactc tggtaactag agatccctca |
| 5761 gacccttta gtcagtgtgg aaaatctcta gcagtagtag ttcatgtcat cttattattc |

-continued

CONSTRUCT SEQUENCES

```
5821 agtatttata acttgcaaag aaatgaatat cagagagtga gaggaacttg tttattgcag
5881 cttataatgg ttacaaataa agcaatagca tcacaaattt cacaaataaa gcattttttt
5941 cactgcattc tagttgtggt ttgtccaaac tcatcaatgt atcttatcat gtctggctct
6001 agctatcccg cccctaactc cgcccagttc cgcccattct ccgccccatg gctgactaat
6061 ttttttattt tatgcagagg ccgaggccgc ctcggcctct gagctattcc agaagtagtg
6121 aggaggcttt tttggaggcc tagacttttg cagagacggc ccaaattcgt aatcatggtc
6181 atagctgttt cctgtgtgaa attgttatcc gctcacaatt ccacacaaca tacgagccgg
6241 aagcataaag tgtaaagcct ggggtgccta atgagtgagc taactcacat taattgcgtt
6301 gcgctcactg cccgctttcc agtcgggaaa cctgtcgtgc cagctgcatt aatgaatcgg
6361 ccaacgcgcg gggagaggcg gtttgcgtat tgggcgctct tccgcttcct cgctcactga
6421 ctcgctgcgc tcggtcgttc ggctgcggcg agcggtatca gctcactcaa aggcggtaat
6481 acggttatcc acagaatcag gggataacgc aggaaagaac atgtgagcaa aaggccagca
6541 aaaggccagg aaccgtaaaa aggccgcgtt gctggcgttt ttccataggc tccgcccccc
6601 tgacgagcat cacaaaaatc gacgctcaag tcagaggtgg cgaaacccga caggactata
6661 aagataccag gcgtttcccc ctggaagctc cctcgtgcgc tctcctgttc cgaccctgcc
6721 gcttaccgga tacctgtccg cctttctccc ttcgggaagc gtggcgcttt ctcatagctc
6781 acgctgtagg tatctcagtt cggtgtaggt cgttcgctcc aagctgggct gtgtgcacga
6841 accccccgtt cagcccgacc gctgcgcctt atccggtaac tatcgtcttg agtccaaccc
6901 ggtaagacac gacttatcgc cactggcagc agccactggt aacaggatta gcagagcgag
6961 gtatgtaggc ggtgctacag agttcttgaa gtggtggcct aactacggct acactagaag
7021 gacagtattt ggtatctgcg ctctgctgaa gccagttacc ttcggaaaaa gagttggtag
7081 ctcttgatcc ggcaaacaaa ccaccgctgg tagcggtggt ttttttgttt gcaagcagca
7141 gattacgcgc agaaaaaaag gatctcaaga agatcctttg atcttttcta cggggtctga
7201 cgctcagtgg aacgaaaact cacgttaagg gattttggtc atgagattat caaaaaggat
7261 cttcacctag atccttttaa attaaaaatg aagttttaaa tcaatctaaa gtatatatga
7321 gtaaacttgg tctgacagtt accaatgctt aatcagtgag gcacctatct cagcgatctg
7381 tctatttcgt tcatccatag ttgcctgact ccccgtcgtg tagataacta cgatacggga
7441 gggcttacca tctggcccca gtgctgcaat gataccgcga gacccacgct caccggctcc
7501 agatttatca gcaataaacc agccagccgg aagggccgag cgcagaagtg gtcctgcaac
7561 tttatccgcc tccatccagt ctattaattg ttgccgggaa gctagagtaa gtagttcgcc
7621 agttaatagt ttgcgcaacg ttgttgccat tgctacaggc atcgtggtgt cacgctcgtc
7681 gtttggtatg gcttcattca gctccggttc ccaacgatca aggcgagtta catgatcccc
7741 catgttgtgc aaaaaagcgg ttagctcctt cggtcctccg atcgttgtca gaagtaagtt
7801 ggccgcagtg ttatcactca tggttatggc agcactgcat aattctctta ctgtcatgcc
7861 atccgtaaga tgcttttctg tgactggtga gtactcaacc aagtcattct gagaatagtg
7921 tatgcggcga ccgagttgct cttgcccggc gtcaatacgg gataataccg cgccacatag
7981 cagaacttta aaagtgctca tcattggaaa acgttcttcg gggcgaaaac tctcaaggat
8041 cttaccgctg ttgagatcca gttcgatgta acccactcgt gcacccaact gatcttcagc
8101 atcttttact ttcaccagcg tttctgggtg agcaaaaaca ggaaggcaaa atgccgcaaa
8161 aaagggaata agggcgacac ggaaatgttg aatactcata ctcttccttt ttcaatatta
8221 ttgaagcatt tatcagggtt attgtctcat gagcggatac atatttgaat gtatttagaa
8281 aaataaacaa ataggggttc cgcgcacatt tccccgaaaa gtgccacctg acgtctaaga
8341 aaccattatt atcatgacat taacctataa aaataggcgt atcacgaggc cctttcgtct
8401 cgcgcgtttc ggtgatgacg gtgaaaacct ctgacacatg cagctcccgg agacggtcac
8461 agcttgtctg taagcggatg ccgggagcag acaagcccgt cagggcgcgt cagcgggtgt
8521 tggcgggtgt cggggctggc ttaactatgc ggcatcagag cagattgtac tgagagtgca
8581 ccatatgcgg tgtgaaatac cgcacagatg cgtaaggaga aaataccgca tcaggcgcca
8641 ttcgccattc aggctgcgca actgttggga agggcgatcg gtgcgggcct cttcgctatt
8701 acgccagctg gcgaaagggg gatgtgctgc aaggcgatta agttgggtaa cgccagggtt
8761 ttcccagtca cgacgttgta aaacgacggc cagtgccaag ctg.
```

p510_antiCD19_LL_CD3gamma (SEQ ID NO: 15)

```
   1 acgcgtgtag tcttatgcaa tactcttgta gtcttgcaac atggtaacga tgagttagca
  61 acatgcctta caaggagaga aaaagcaccg tgcatgccga ttggtggaag taaggtggta
 121 cgatcgtgcc ttattaggaa ggcaacagac gggtctgaca tggattggac gaaccactga
 181 attgccgcat tgcagagata ttgtatttaa gtgcctagct cgatacaata aacgggtctc
 241 tctggttaga ccagatctga gcctgggagc tctctggcta actagggaac ccactgctta
 301 agcctcaata aagcttgcct tgagtgcttc aagtagtgtg tgcccgtctg ttgtgtgact
 361 ctggtaacta gagatccctc agaccctttt agtcagtgtg gaaaatctct agcagtggcg
 421 cccgaacagg gacctgaaag cgaaagggaa accagagctc tctcgacgca ggactcggct
 481 tgctgaagcg cgcacggcaa gaggcgaggg gcggcgactg gtgagtacgc caaaaatttt
 541 gactagcgga ggctagaagg agagagatgg gtgcgagagc gtcagtatta agcgggggag
 601 aattagatcg cgatgggaaa aaattcggtt aaggccaggg ggaaagaaaa aatataaatt
 661 aaaacatata gtatgggcaa gcagggagct agaacgattc gcagttaatc ctggcctgtt
 721 agaaacatca gaaggctgta gacaaatact gggacagcta caaccatccc ttcagacagg
 781 atcagaagaa cttagatcat tatataatac agtagcaacc ctctattgtg tgcatcaaag
 841 gatagagata aaagacacca aggaagcttt agacaagata gaggaagagc aaaacaaaag
 901 taagaccacc gcacagcaag cggccactga tcttcagacc tggaggagga gatatgaggg
 961 acaattggag aagtgaatta tataaatata aagtagtaaa aattgaacca ttaggagtag
1021 cacccaccaa ggcaaagaga agagtggtgc agagagaaaa aagagcagtg ggaataggag
1081 ctttgttcct tgggttcttg ggagcagcag gaagcactat gggcgcagcc tcaatgacgc
1141 tgacggtaca ggccagacaa ttattgtctg gtatagtgca gcagcagaac aatttgctga
1201 gggctattga ggcgcaacag catctgttgc aactcacagt ctggggcatc aagcagctcc
1261 aggcaagaat cctggctgtg gaaagatacc taaaggatca acagctcctg gggatttggg
1321 gttgctctgg aaaactcatt tgcaccactg ctgtgccttg gaatgctagt tggagtaata
1381 aatctctgga acagattgga atcacacgac ctggatggag tgggacagag aaattaacaa
1441 ttacacaagc ttaatacact ccttaattga agaatcgcaa aaccagcaag aaaagaatga
```

-continued

| CONSTRUCT SEQUENCES |
|---|
| 1501 acaagaatta ttggaattag ataaatgggc aagtttgtgg aattggttta acataacaaa |
| 1561 ttggctgtgg tatataaaat tattcataat gatagtagga ggcttggtag gtttaagaat |
| 1621 agtttttgct gtactttcta tagtgaatag agttaggcag ggatattcac cattatcgtt |
| 1681 tcagacccac ctcccaaccc cgaggggacc cgacaggccc gaaggaatag aagaagaagg |
| 1741 tggagagaga gacagagaca gatccattcg attagtgaac ggatctcgac ggtatcggtt |
| 1801 aacttttaaa agaaaagggg ggattggggg gtacagtgca ggggaaagaa tagtagacat |
| 1861 aatagcaaca gacatacaaa ctaaagaatt acaaaaacaa attacaaaat tcaaaatttt |
| 1921 atcgatacta gtattatgcc cagtacatga ccttatggga ctttcctact tggcagtaca |
| 1981 tctacgtatt agtcatcgct attaccatgg tgatgcggtt ttggcagtac atcaatgggc |
| 2041 gtggatagcg gtttgactca cggggatttc caagtctcca ccccattgac gtcaatggga |
| 2101 gtttgttttg gcaccaaaat caacgggact ttccaaaatg tcgtaacaac tccgccccat |
| 2161 tgacgcaaat gggcggtagg cgtgtacggt gggaggttta tataagcaga gctcgtttag |
| 2221 tgaaccgtca gatcgcctgg agacgccatc cacgctgttt tgacctccat agaagattct |
| 2281 agagccgcca ccatgcttct cctggtgaca agccttctgc tctgtgagtt accacaccca |
| 2341 gcattcctcc tgatcccaga catccagatg acacagacta catcctccct gtctgcctct |
| 2401 ctgggagaca gagtcaccat cagttgcagg gcaagtcagg acattagtaa atatttaaat |
| 2461 tggtatcagc agaaaccaga tggaactgtt aaactcctga tctaccatac atcaagatta |
| 2521 cactcaggag tcccatcaag gttcagtggc agtgggtctg gaacagatta ttctctcacc |
| 2581 attagcaacc tggagcaaga agatattgcc acttactttt gccaacaggg taatacgctt |
| 2641 ccgtacacgt tcggaggggg gactaagttg gaaataacag gctccacctc tggatccggc |
| 2701 aagcccggat ctggcgaggg atccaccaag ggcgaggtga aactgcagga gtcaggacct |
| 2761 ggcctggtgg cgccctcaca gagcctgtcc gtcacatgca ctgtctcagg ggtctcatta |
| 2821 cccgactatg gtgtaagctg gattcgccag cctccacgaa agggtctgga gtggctggga |
| 2881 gtaatatggg gtagtgaaac cacatactat aattcagctc tcaaatccag actgaccatc |
| 2941 atcaaggaca actccaagag ccaagttttc ttaaaaatga acagtctgca aactgatgac |
| 3001 acagccattt actactgtgc caaacattat tactacggtg gtagctatgc tatggactac |
| 3061 tggggtcaag gaacctcagt caccgtctcc tcagcggccg caattgaagt tatgtatcct |
| 3121 cctccttacc taggtggcgg cggttctggt ggcggcggtt ctggtggcgg cggttctctc |
| 3181 gagcagtcaa tcaaaggaaa ccacttggtt aaggtgtatg actatcaaga agatggttcg |
| 3241 gtacttctga cttgtgatgc agaagccaaa aatatcacat ggtttaaaga tgggaagatg |
| 3301 atcggcttcc taactgaaga taaaaaaaaa tggaatctgg gaagtaatgc caaggaccca |
| 3361 cgagggatgt atcagtgtaa aggatcacag aacaagtcaa aaccactcca agtgtattac |
| 3421 agaatgtgtc agaactgcat tgaactaaat gcagccacca tatctggctt tctctttgct |
| 3481 gaaatcgtca gcattttcgt ccttgctgtt ggggtctact tcattgctgg acaggatgga |
| 3541 gttcgccagt cgagagcttc agacaagcag actctgttgc ccaatgacca gctctaccag |
| 3601 cccctcaagg atcgagaaga tgaccagtac agccaccttc aaggaaacca gttgaggagg |
| 3661 aattgataag aattcgatcc gcggccgcga aggatctgcg atcgctccgg tgcccgtcag |
| 3721 tgggcagagc gcacatcgcc cacagtcccc gagaagttgg ggggaggggt cggcaattga |
| 3781 acgggtgcct agagaaggtg gcgcggggta aactgggaaa gtgatgtcgt gtactggctc |
| 3841 cgcctttttc ccgagggtgg gggagaaccg tatataagtg cagtagtcgc cgtgaacgtt |
| 3901 ctttttcgca acgggtttgc cgccagaaca cagctgaagc ttcgaggggc tcgcatctct |
| 3961 ccttcacgcg cccgccgccc tacctgaggc cgccatccac gccggttgag tcgcgttctg |
| 4021 ccgcctcccg cctgtggtgc ctcctgaact gcgtccgccg tctaggtaag tttaaagctc |
| 4081 aggtcgagac cgggcctttg tccggcgctc ccttggagcc tacctagact cagccggctc |
| 4141 tccacgcttt gcctgaccct gcttgctcaa ctctacgtct ttgtttcgtt ttctgttctg |
| 4201 cgccgttaca gatccaagct gtgaccggcg cctacgctag atgaccgagt acaagcccac |
| 4261 ggtgcgcctc gccacccgcg acgacgtccc cagggccgta cgcaccctcg ccgccgcgtt |
| 4321 cgccgactac cccgccacgc gccacaccgt cgatccggac cgccacatcg agcgggtcac |
| 4381 cgagctgcaa gaactcttcc tcacgcgcgt cgggctcgac atcggcaagg tgtgggtcgc |
| 4441 ggacgacggc gccgcggtgg cggtctggac cacgccggag agcgtcgaag cgggggcggt |
| 4501 gttcgccgag atcggcccgc gcatggccga gttgagcggt tcccggctgg ccgcgcagca |
| 4561 acagatggaa ggcctcctgg cgccgcaccg gcccaaggag cccgcgtggt tcctggccac |
| 4621 cgtcggcgtc tcgcccgacc accagggcaa gggtctgggc agcgccgtcg tgctccccgg |
| 4681 agtggaggcg gccgagcgcg ccggggtgcc cgccttcctg gagacctccg cgccccgcaa |
| 4741 cctccccttc tacgagcggc tcggcttcac cgtcaccgcc gacgtcgagg tgcccgaagg |
| 4801 accgcgcacc tggtgcatga cccgcaagcc cggtgcctga gtcgacaatc aacctctgga |
| 4861 ttacaaaatt tgtgaaagat tgactggtat tcttaactat gttgctcctt ttacgctatg |
| 4921 tggatacgct gctttaatgc ctttgtatca tgctattgct tcccgtatgg ctttcatttt |
| 4981 ctcctccttg tataaatcct ggttgctgtc tctttatgag gagttgtggc ccgttgtcag |
| 5041 gcaacgtggc gtggtgtgca ctgtgtttgc tgacgcaacc cccactggtt ggggcattgc |
| 5101 caccacctgt cagctccttt ccgggacttt cgctttcccc ctccctattg ccacggcgga |
| 5161 actcatcgcc gcctgccttg cccgctgctg gacaggggct cggctgttgg gcactgacaa |
| 5221 ttccgtggtg ttgtcgggga aatcatcgtc ctttccttgg ctgctcgcct gtgttgccac |
| 5281 ctggattctg cgcgggacgt ccttctgcta cgtcccttcg gccctcaatc cagcggacct |
| 5341 tccttcccgc ggcctgctgc cggctctgcg gcctcttccg cgtcttcgcc ttcgccctca |
| 5401 gacgagtcgg atctcccttt gggccgcctc cccgcctggt acctttaaga ccaatgactt |
| 5461 acaaggcagc tgtagatctt agccactttt taaaagaaaa ggggggactg gaagggctaa |
| 5521 ttcactccca acgaaaataa gatctgcttt ttgcttgtac tgggtctctc tggttagacc |
| 5581 agatctgagc ctgggagctc tctggctaac tagggaaccc actgcttaag cctcaataaa |
| 5641 gcttgccttg agtgcttcaa gtagtgtgtg cccgtctgtt gtgtgactct ggtaactaga |
| 5701 gatccctcag acccttttag tcagtgtgga aaatctctag cagtagtagt tcatgtcatc |
| 5761 ttattattca gtatttataa cttgcaaaga aatgaatatc agagagtgag aggaacttgt |
| 5821 ttattgcagc ttataatggt tacaaataaa gcaatagcat cacaaatttc acaaataaag |
| 5881 catttttttc actgcattct agttgtggtt tgtccaaact catcaatgta tcttatcatg |
| 5941 tctggctcta gctatcccgc ccctaactcc gcccagttcc gcccattctc cgccccatgg |
| 6001 ctgactaatt ttttttattt atgcagaggc cgaggccgcc tcggcctctg agctattcca |
| 6061 gaagtagtga ggaggctttt ttggaggcct agacttttgc agagacggcc caaattcgta |

-continued

CONSTRUCT SEQUENCES

```
6121 atcatggtca tagctgtttc ctgtgtgaaa ttgttatccg ctcacaattc cacacaacat
6181 acgagccgga agcataaagt gtaaagcctg gggtgcctaa tgagtgagct aactcacatt
6241 aattgcgttg cgctcactgc ccgctttcca gtcgggaaac ctgtcgtgcc agctgcatta
6301 atgaatcggc caacgcgcgg ggagaggcgg tttgcgtatt gggcgctctt ccgcttcctc
6361 gctcactgac tcgctgcgct cggtcgttcg gctgcggcga gcggtatcag ctcactcaaa
6421 ggcggtaata cggttatcca cagaatcagg ggataacgca ggaaagaaca tgtgagcaaa
6481 aggccagcaa aaggccagga accgtaaaaa ggccgcgttg ctggcgtttt tccataggct
6541 ccgcccccct gacgagcatc acaaaaatcg acgctcaagt cagaggtggc gaaacccgac
6601 aggactataa agataccagg cgtttccccc tggaagctcc ctcgtgcgct ctcctgttcc
6661 gaccctgccg cttaccggat acctgtccgc ctttctccct tcgggaagcg tggcgctttc
6721 tcatagctca cgctgtaggt atctcagttc ggtgtaggtc gttcgctcca agctgggctg
6781 tgtgcacgaa ccccccgttc agcccgaccg ctgcgcctta tccggtaact atcgtcttga
6841 gtccaacccg gtaagacacg acttatcgcc actggcagca gccactggta acaggattag
6901 cagagcgagg tatgtaggcg gtgctacaga gttcttgaag tggtggccta actacggcta
6961 cactagaagg acagtatttg gtatctgcgc tctgctgaag ccagttacct tcggaaaaag
7021 agttggtagc tcttgatccg gcaaacaaac caccgctggt agcggtggtt tttttgtttg
7081 caagcagcag attacgcgca gaaaaaaagg atctcaagaa gatcctttga tcttttctac
7141 ggggtctgac gctcagtgga acgaaaactc acgttaaggg attttggtca tgagattatc
7201 aaaaaggatc ttcacctaga tccttttaaa ttaaaaatga agttttaaat caatctaaag
7261 tatatatgag taaacttggt ctgacagtta ccaatgctta atcagtgagg cacctatctc
7321 agcgatctgt ctatttcgtt catccatagt tgcctgactc cccgtcgtgt agataactac
7381 gatacgggag ggcttaccat ctggccccag tgctgcaatg ataccgcgag acccacgctc
7441 accggctcca gatttatcag caataaacca gccagccgga agggccgagc gcagaagtgg
7501 tcctgcaact ttatccgcct ccatccagtc tattaattgt tgccgggaag ctagagtaag
7561 tagttcgcca gttaatagtt tgcgcaacgt tgttgccatt gctacaggca tcgtggtgtc
7621 acgctcgtcg tttggtatgg cttcattcag ctccggttcc caacgatcaa ggcgagttac
7681 atgatccccc atgttgtgca aaaaagcggt tagctccttc ggtcctccga tcgttgtcag
7741 aagtaagttg gccgcagtgt tatcactcat ggttatggca gcactgcata attctcttac
7801 tgtcatgcca tccgtaagat gcttttctgt gactggtgag tactcaacca agtcattctg
7861 agaatagtgt atgcggcgac cgagttgctc ttgcccggcg tcaatacggg ataataccgc
7921 gccacatagc agaactttaa aagtgctcat cattggaaaa cgttcttcgg ggcgaaaact
7981 ctcaaggatc ttaccgctgt tgagatccag ttcgatgtaa cccactcgtg cacccaactg
8041 atcttcagca tcttttactt tcaccagcgt ttctgggtga gcaaaaacag gaaggcaaaa
8101 tgccgcaaaa aagggaataa gggcgacacg gaaatgttga atactcatac tcttcctttt
8161 tcaatattat tgaagcattt atcagggtta ttgtctcatg agcggataca tatttgaatg
8221 tatttagaaa aataaacaaa taggggttcc gcgcacattt ccccgaaaag tgccacctga
8281 cgtctaagaa accattatta tcatgacatt aacctataaa aataggcgta tcacgaggcc
8341 ctttcgtctc gcgcgtttcg gtgatgacgg tgaaaacctc tgacacatgc agctcccgga
8401 gacggtcaca gcttgtctgt aagcggatgc cgggagcaga caagcccgtc agggcgcgtc
8461 agcgggtgtt ggcgggtgtc ggggctggct taactatgcg gcatcagagc agattgtact
8521 gagagtgcac catatgcggt gtgaaatacc gcacagatgc gtaaggagaa aataccgcat
8581 caggcgccat tcgccattca ggctgcgcaa ctgttgggaa gggcgatcgg tgcgggcctc
8641 ttcgctatta cgccagctgg cgaaaggggg atgtgctgca aggcgattaa gttgggtaac
8701 gccagggttt tcccagtcac gacgttgtaa aacgacggcc agtgccaagc tg.
```

p510_antiCD19_LL_CD3delta (SEQ ID NO: 16)

```
   1 acgcgtgtag tcttatgcaa tactcttgta gtcttgcaac atggtaacga tgagttagca
  61 acatgcctta caaggagaga aaaagcaccg tgcatgccga ttggtggaag taaggtggta
 121 cgatcgtgcc ttattaggaa ggcaacagac gggtctgaca tggattggac gaaccactga
 181 attgccgcat tgcagagata ttgtatttaa gtgcctagct cgatacaata aacgggtctc
 241 tctggttaga ccagatctga gcctgggagc tctctggcta actagggaac ccactgctta
 301 agcctcaata aagcttgcct tgagtgcttc aagtagtgtg tgcccgtctg ttgtgtgact
 361 ctggtaacta gagatccctc agaccctttt agtcagtgtg gaaaatctct agcagtggcg
 421 cccgaacagg gacctgaaag cgaaagggaa accagagctc tctcgacgca ggactcggct
 481 tgctgaagcg cgcacggcaa gaggcgaggg gcggcgactg gtgagtacgc caaaaatttt
 541 gactagcgga ggctagaagg agagagatgg gtgcgagagc gtcagtatta agcgggggag
 601 aattagatcg cgatgggaaa aaattcggtt aaggccaggg ggaaagaaaa aatataaatt
 661 aaaacatata gtatgggcaa gcagggagct agaacgattc gcagttaatc ctggcctgtt
 721 agaaacatca gaaggctgta gacaaatact gggacagcta caaccatccc ttcagacagg
 781 atcagaagaa cttagatcat tatataatac agtagcaacc ctctattgtg tgcatcaaag
 841 gatagagata aaagacacca aggaagcttt agacaagata gaggaagagc aaaacaaaag
 901 taagaccacc gcacagcaag cggccactga tcttcagacc tggaggagga gatatgaggg
 961 acaattggag aagtgaatta tataaatata aagtagtaaa aattgaacca ttaggagtag
1021 cacccaccaa ggcaaagaga agagtggtgc agagagaaaa aagagcagtg ggaataggag
1081 ctttgttcct tgggttcttg ggagcagcag gaagcactat gggcgcagcc tcaatgacgc
1141 tgacggtaca ggccagacaa ttattgtctg gtatagtgca gcagcagaac aatttgctga
1201 gggctattga ggcgcaacag catctgttgc aactcacagt ctggggcatc aagcagctcc
1261 aggcaagaat cctggctgtg gaaagatacc taaaggatca acagctcctg gggatttggg
1321 gttgctctgg aaaactcatt tgcaccactg ctgtgccttg gaatgctagt tggagtaata
1381 aatctctgga acagattgga atcacacgac ctggatggag tgggacagag aaattaacaa
1441 ttacacaagc ttaatacact ccttaattga agaatcgcaa aaccagcaag aaaagaatga
1501 acaagaatta ttggaattag ataaatgggc aagtttgtgg aattggttta acataacaaa
1561 ttggctgtgg tatataaaat tattcataat gatagtagga ggcttggtag gtttaagaat
1621 agtttttgct gtactttcta tagtgaatag agttaggcag ggatattcac cattatcgtt
1681 tcagacccac ctcccaaccc cgaggggacc cgacaggccc gaaggaatag aagaagaagg
1741 tggagagaga gacagagaca gatccattcg attagtgaac ggatctcgac ggtatcggtt
1801 aacttttaaa agaaaagggg ggattggggg gtacagtgca ggggaaagaa tagtagacat
```

-continued

CONSTRUCT SEQUENCES

```
1861 aatagcaaca gacatacaaa ctaaagaatt acaaaaacaa attacaaaat tcaaaatttt
1921 atcgatacta gtattatgcc cagtacatga ccttatggga ctttcctact tggcagtaca
1981 tctacgtatt agtcatcgct attaccatgg tgatgcggtt ttggcagtac atcaatgggc
2041 gtggatagcg gtttgactca cggggatttc caagtctcca ccccattgac gtcaatggga
2101 gtttgttttg gcaccaaaat caacgggact ttccaaaatg tcgtaacaac tccgccccat
2161 tgacgcaaat gggcggtagg cgtgtacggt gggaggttta tataagcaga gctcgtttag
2221 tgaaccgtca gatcgcctgg agacgccatc cacgctgttt tgacctccat agaagattct
2281 agagccgcca ccatgcttct cctggtgaca agccttctgc tctgtgagtt accacaccca
2341 gcattcctcc tgatcccaga catccagatg acacagacta catcctccct gtctgcctct
2401 ctgggagaca gagtcaccat cagttgcagg gcaagtcagg acattagtaa atatttaaat
2461 tggtatcagc agaaaccaga tggaactgtt aaactcctga tctaccatac atcaagatta
2521 cactcaggag tcccatcaag gttcagtggc agtgggtctg gaacagatta ttctctcacc
2581 attagcaacc tggagcaaga agatattgcc acttactttt gccaacaggg taatacgctt
2641 ccgtacacgt tcggaggggg gactaagttg gaaataacag gctccacctc tggatccggc
2701 aagcccggat ctggcgaggg atccaccaag ggcgaggtga aactgcagga gtcaggacct
2761 ggcctggtgg cgccctcaca gagcctgtcc gtcacatgca ctgtctcagg ggtctcatta
2821 cccgactatg gtgtaagctg gattcgccag cctccacgaa agggtctgga gtggctggga
2881 gtaatatggg gtagtgaaac cacatactat aattcagctc tcaaatccag actgaccatc
2941 atcaaggaca actccaagag ccaagttttc ttaaaaatga acagtctgca aactgatgac
3001 acagccattt actactgtgc caaacattat tactacggtg gtagctatgc tatggactac
3061 tggggtcaag gaacctcagt caccgtctcc tcagcggccg caattgaagt tatgtatcct
3121 cctccttacc taggtggcgg cggttctggt ggcggcggtt ctggtggcgg cggttctctc
3181 gagttcaaga tacctataga ggaacttgag gacagagtgt ttgtgaattg caataccagc
3241 atcacatggg tagagggaac ggtgggaaca ctgctctcag acattacaag actggacctg
3301 ggaaaacgca tcctggaccc acgaggaata tataggtgta atgggacaga tatatacaag
3361 gacaaagaat ctaccgtgca agttcattat cgaatgtgcc agagctgtgt ggagctggat
3421 ccagccaccg tggctggcat cattgtcact gatgtcattg ccactctgct ccttgctttg
3481 ggagtcttct gctttgctgg acatgagact ggaaggctgt ctggggctgc cgacacacaa
3541 gctctgttga ggaatgacca ggtctatcag cccctccgag atcgagatga tgctcagtac
3601 agccaccttg gaggaaactg ggctcggaac aagtgataag aattcgatcc gcggccgcga
3661 aggatctgcg atcgctccgg tgcccgtcag tgggcagagc gcacatcgcc cacagtcccc
3721 gagaagttgg ggggaggggt cggcaattga acgggtgcct agagaaggtg gcgcggggta
3781 aactgggaaa gtgatgtcgt gtactggctc cgcctttttc ccgagggtgg gggagaaccg
3841 tatataagtg cagtagtcgc cgtgaacgtt ctttttcgca acgggtttgc cgccagaaca
3901 cagctgaagc ttcgaggggc tcgcatctct ccttcacgcg cccgccgccc tacctgaggc
3961 cgccatccac gccggttgag tcgcgttctg ccgcctcccg cctgtggtgc ctcctgaact
4021 gcgtccgccg tctaggtaag tttaaagctc aggtcgagac cgggcctttg tccggcgctc
4081 ccttggagcc tacctagact cagccggctc tccacgcttt gcctgaccct gcttgctcaa
4141 ctctacgtct ttgtttcgtt ttctgttctg cgccgttaca gatccaagct gtgaccggcg
4201 cctacgctag atgaccgagt acaagcccac ggtgcgcctc gccacccgcg acgacgtccc
4261 cagggccgta cgcaccctcg ccgccgcgtt cgccgactac cccgccacgc gccacaccgt
4321 cgatccggac cgccacatcg agcgggtcac cgagctgcaa gaactcttcc tcacgcgcgt
4381 cgggctcgac atcggcaagg tgtgggtcgc ggacgacggc gccgcggtgg cggtctggac
4441 cacgccggag agcgtcgaag cgggggcggt gttcgccgag atcggcccgc gcatggccga
4501 gttgagcggt tcccggctgg ccgcgcagca acagatggaa ggcctcctgg cgccgcaccg
4561 gcccaaggag cccgcgtggt tcctggccac cgtcggcgtc tcgcccgacc accagggcaa
4621 gggtctgggc agcgccgtcg tgctccccgg agtggaggcg gccgagcgcg ccggggtgcc
4681 cgccttcctg gagacctccg cgccccgcaa cctccccttc tacgagcggc tcggcttcac
4741 cgtcaccgcc gacgtcgagg tgcccgaagg accgcgcacc tggtgcatga cccgcaagcc
4801 cggtgcctga gtcgacaatc aacctctgga ttacaaaatt tgtgaaagat tgactggtat
4861 tcttaactat gttgctcctt ttacgctatg tggatacgct gctttaatgc ctttgtatca
4921 tgctattgct tcccgtatgg ctttcatttt ctcctccttg tataaatcct ggttgctgtc
4981 tctttatgag gagttgtggc ccgttgtcag gcaacgtggc gtggtgtgca ctgtgtttgc
5041 tgacgcaacc cccactggtt ggggcattgc caccacctgt cagctccttt ccgggacttt
5101 cgctttcccc ctccctattg ccacggcgga actcatcgcc gcctgccttg cccgctgctg
5161 gacaggggct cggctgttgg gcactgacaa ttccgtggtg ttgtcgggga aatcatcgtc
5221 ctttccttgg ctgctcgcct gtgttgccac ctggattctg cgcgggacgt ccttctgcta
5281 cgtcccttcg gccctcaatc cagcggacct tccttcccgc ggcctgctgc cggctctgcg
5341 gcctcttccg cgtcttcgcc ttcgccctca gacgagtcgg atctcccttt gggccgcctc
5401 cccgcctggt acctttaaga ccaatgactt acaaggcagc tgtagatctt agccactttt
5461 taaaagaaaa ggggggactg gaagggctaa ttcactccca acgaaaataa gatctgcttt
5521 ttgcttgtac tgggtctctc tggttagacc agatctgagc ctgggagctc tctggctaac
5581 tagggaaccc actgcttaag cctcaataaa gcttgccttg agtgcttcaa gtagtgtgtg
5641 cccgtctgtt gtgtgactct ggtaactaga gatccctcag acccttttag tcagtgtgga
5701 aaatctctag cagtagtagt tcatgtcatc ttattattca gtatttataa cttgcaaaga
5761 aatgaatatc agagagtgag aggaacttgt ttattgcagc ttataatggt tacaaataaa
5821 gcaatagcat cacaaatttc acaaataaag cattttttc actgcattct agttgtggtt
5881 tgtccaaact catcaatgta tcttatcatg tctggctcta gctatcccgc ccctaactcc
5941 gcccagttcc gcccattctc cgccccatgg ctgactaatt ttttttattt atgcagaggc
6001 cgaggccgcc tcggcctctg agctattcca gaagtagtga ggaggctttt ttggaggcct
6061 agacttttgc agagacggcc caaattcgta atcatggtca tagctgtttc ctgtgtgaaa
6121 ttgttatccg ctcacaattc cacacaacat acgagccgga agcataaagt gtaaagcctg
6181 gggtgcctaa tgagtgagct aactcacatt aattgcgttg cgctcactgc ccgctttcca
6241 gtcgggaaac ctgtcgtgcc agctgcatta atgaatcggc caacgcgcgg ggagaggcgg
6301 tttgcgtatt gggcgctctt ccgcttcctc gctcactgac tcgctgcgct cggtcgttcg
6361 gctgcggcga gcggtatcag ctcactcaaa ggcggtaata cggttatcca cagaatcagg
6421 ggataacgca ggaaagaaca tgtgagcaaa aggccagcaa aaggccagga accgtaaaaa
```

CONSTRUCT SEQUENCES

```
6481 ggccgcgttg ctggcgtttt tccataggct ccgcccccct gacgagcatc acaaaaatcg
6541 acgctcaagt cagaggtggc gaaacccgac aggactataa agataccagg cgtttccccc
6601 tggaagctcc ctcgtgcgct ctcctgttcc gaccctgccg cttaccggat acctgtccgc
6661 ctttctccct tcgggaagcg tggcgctttc tcatagctca cgctgtaggt atctcagttc
6721 ggtgtaggtc gttcgctcca agctgggctg tgtgcacgaa ccccccgttc agcccgaccg
6781 ctgcgcctta tccggtaact atcgtcttga gtccaacccg gtaagacacg acttatcgcc
6841 actggcagca gccactggta acaggattag cagagcgagg tatgtaggcg gtgctacaga
6901 gttcttgaag tggtggccta actacggcta cactagaagg acagtatttg gtatctgcgc
6961 tctgctgaag ccagttacct tcggaaaaag agttggtagc tcttgatccg gcaaacaaac
7021 caccgctggt agcggtggtt tttttgtttg caagcagcag attacgcgca gaaaaaaagg
7081 atctcaagaa gatcctttga tcttttctac ggggtctgac gctcagtgga acgaaaactc
7141 acgttaaggg attttggtca tgagattatc aaaaaggatc ttcacctaga tccttttaaa
7201 ttaaaaatga agttttaaat caatctaaag tatatatgag taaacttggt ctgacagtta
7261 ccaatgctta atcagtgagg cacctatctc agcgatctgt ctatttcgtt catccatagt
7321 tgcctgactc cccgtcgtgt agataactac gatacgggag ggcttaccat ctggccccag
7381 tgctgcaatg ataccgcgag acccacgctc accggctcca gatttatcag caataaacca
7441 gccagccgga agggccgagc gcagaagtgg tcctgcaact ttatccgcct ccatccagtc
7501 tattaattgt tgccgggaag ctagagtaag tagttcgcca gttaatagtt tgcgcaacgt
7561 tgttgccatt gctacaggca tcgtggtgtc acgctcgtcg tttggtatgg cttcattcag
7621 ctccggttcc caacgatcaa ggcgagttac atgatccccc atgttgtgca aaaaagcggt
7681 tagctccttc ggtcctccga tcgttgtcag aagtaagttg gccgcagtgt tatcactcat
7741 ggttatggca gcactgcata attctcttac tgtcatgcca tccgtaagat gcttttctgt
7801 gactggtgag tactcaacca agtcattctg agaatagtgt atgcggcgac cgagttgctc
7861 ttgcccggcg tcaatacggg ataataccgc gccacatagc agaactttaa aagtgctcat
7921 cattggaaaa cgttcttcgg ggcgaaaact ctcaaggatc ttaccgctgt tgagatccag
7981 ttcgatgtaa cccactcgtg cacccaactg atcttcagca tcttttactt tcaccagcgt
8041 ttctgggtga gcaaaaacag gaaggcaaaa tgccgcaaaa aagggaataa gggcgacacg
8101 gaaatgttga atactcatac tcttcctttt tcaatattat tgaagcattt atcagggtta
8161 ttgtctcatg agcggataca tatttgaatg tatttagaaa aataaacaaa taggggttcc
8221 gcgcacattt ccccgaaaag tgccacctga cgtctaagaa accattatta tcatgacatt
8281 aacctataaa aataggcgta tcacgaggcc ctttcgtctc gcgcgtttcg gtgatgacgg
8341 tgaaaacctc tgacacatgc agctcccgga gacggtcaca gcttgtctgt aagcggatgc
8401 cgggagcaga caagcccgtc agggcgcgtc agcgggtgtt ggcgggtgtc ggggctggct
8461 taactatgcg gcatcagagc agattgtact gagagtgcac catatgcggt gtgaaatacc
8521 gcacagatgc gtaaggagaa aataccgcat caggcgccat tcgccattca ggctgcgcaa
8581 ctgttgggaa gggcgatcgg tgcgggcctc ttcgctatta cgccagctgg cgaaaggggg
8641 atgtgctgca aggcgattaa gttgggtaac gccagggttt tcccagtcac gacgttgtaa
8701 aacgacggcc agtgccaagc tg.
```

p510_antiCD19_LL_CD3epsilon (SEQ ID NO: 17)

```
   1 acgcgtgtag tcttatgcaa tactcttgta gtcttgcaac atggtaacga tgagttagca
  61 acatgcctta caaggagaga aaaagcaccg tgcatgccga ttggtggaag taaggtggta
 121 cgatcgtgcc ttattaggaa ggcaacagac gggtctgaca tggattggac gaaccactga
 181 attgccgcat tgcagagata ttgtatttaa gtgcctagct cgatacaata aacgggtctc
 241 tctggttaga ccagatctga gcctgggagc tctctggcta actagggaac ccactgctta
 301 agcctcaata aagcttgcct tgagtgcttc aagtagtgtg tgcccgtctg ttgtgtgact
 361 ctggtaacta gagatccctc agaccctttt agtcagtgtg gaaaatctct agcagtggcg
 421 cccgaacagg gacctgaaag cgaaagggaa accagagctc tctcgacgca ggactcggct
 481 tgctgaagcg cgcacggcaa gaggcgaggg gcggcgactg gtgagtacgc caaaaatttt
 541 gactagcgga ggctagaagg agagagatgg gtgcgagagc gtcagtatta agcgggggag
 601 aattagatcg cgatgggaaa aaattcggtt aaggccaggg ggaaagaaaa aatataaatt
 661 aaaacatata gtatgggcaa gcagggagct agaacgattc gcagttaatc ctggcctgtt
 721 agaaacatca gaaggctgta gacaaatact gggacagcta caaccatccc ttcagacagg
 781 atcagaagaa cttagatcat tatataatac agtagcaacc ctctattgtg tgcatcaaag
 841 gatagagata aaagacacca aggaagcttt agacaagata gaggaagagc aaaacaaaag
 901 taagaccacc gcacagcaag cggccactga tcttcagacc tggaggagga gatatgaggg
 961 acaattggag aagtgaatta tataaatata aagtagtaaa aattgaacca ttaggagtag
1021 cacccaccaa ggcaaagaga agagtggtgc agagagaaaa aagagcagtg ggaataggag
1081 ctttgttcct tgggttcttg ggagcagcag gaagcactat gggcgcagcc tcaatgacgc
1141 tgacggtaca ggccagacaa ttattgtctg gtatagtgca gcagcagaac aatttgctga
1201 gggctattga ggcgcaacag catctgttgc aactcacagt ctggggcatc aagcagctcc
1261 aggcaagaat cctggctgtg gaaagatacc taaaggatca acagctcctg gggatttggg
1321 gttgctctgg aaaactcatt tgcaccactg ctgtgccttg gaatgctagt tggagtaata
1381 aatctctgga acagattgga atcacacgac ctggatggag tgggacagag aaattaacaa
1441 ttacacaagc ttaatacact ccttaattga agaatcgcaa aaccagcaag aaaagaatga
1501 acaagaatta ttggaattag ataaatgggc aagtttgtgg aattggttta acataacaaa
1561 ttggctgtgg tatataaaat tattcataat gatagtagga ggcttggtag gtttaagaat
1621 agtttttgct gtactttcta tagtgaatag agttaggcag ggatattcac cattatcgtt
1681 tcagacccac ctcccaaccc cgaggggacc cgacaggccc gaaggaatag aagaagaagg
1741 tggagagaga gacagagaca gatccattcg attagtgaac ggatctcgac ggtatcggtt
1801 aacttttaaa agaaaagggg ggattggggg gtacagtgca ggggaaagaa tagtagacat
1861 aatagcaaca gacatacaaa ctaaagaatt acaaaaacaa attacaaaat tcaaaatttt
1921 atcgatacta gtattatgcc cagtacatga ccttatggga ctttcctact tggcagtaca
1981 tctacgtatt agtcatcgct attaccatgg tgatgcggtt ttggcagtac atcaatgggc
2041 gtggatagcg gtttgactca cggggatttc caagtctcca ccccattgac gtcaatggga
2101 gtttgttttg gcaccaaaat caacgggact ttccaaaatg tcgtaacaac tccgccccat
2161 tgacgcaaat gggcggtagg cgtgtacggt gggaggttta tataagcaga gctcgtttag
```

-continued

| CONSTRUCT SEQUENCES |
| --- |
| 2221 tgaaccgtca gatcgcctgg agacgccatc cacgctgttt tgacctccat agaagattct<br>2281 agagccgcca ccatgcttct cctggtgaca agccttctgc tctgtgagtt accacaccca<br>2341 gcattcctcc tgatcccaga catccagatg acacagacta catcctccct gtctgcctct<br>2401 ctgggagaca gagtcaccat cagttgcagg gcaagtcagg acattagtaa atatttaaat<br>2461 tggtatcagc agaaaccaga tggaactgtt aaactcctga tctaccatac atcaagatta<br>2521 cactcaggag tcccatcaag gttcagtggc agtgggtctg gaacagatta ttctctcacc<br>2581 attagcaacc tggagcaaga agatattgcc acttactttt gccaacaggg taatacgctt<br>2641 ccgtacacgt tcggaggggg gactaagttg gaaataacag gctccacctc tggatccggc<br>2701 aagcccggat ctggcgaggg atccaccaag ggcgaggtga aactgcagga gtcaggacct<br>2761 ggcctggtgg cgccctcaca gagcctgtcc gtcacatgca ctgtctcagg ggtctcatta<br>2821 cccgactatg gtgtaagctg gattcgccag cctccacgaa agggtctgga gtggctggga<br>2881 gtaatatggg gtagtgaaac cacatactat aattcagctc tcaaatccag actgaccatc<br>2941 atcaaggaca actccaagag ccaagttttc ttaaaaatga acagtctgca aactgatgac<br>3001 acagccattt actactgtgc caaacattat tactacggtg gtagctatgc tatggactac<br>3061 tggggtcaag gaacctcagt caccgtctcc tcagcggccg caattgaagt tatgtatcct<br>3121 cctccttacc taggtggcgg cggttctggt ggcggcggtt ctggtggcgg cggttctctc<br>3181 gaggatggta atgaagaaat gggtggtatt acacagacac catataaagt ctccatctct<br>3241 ggaaccacag taatattgac atgccctcag tatcctggat ctgaaatact atggcaacac<br>3301 aatgataaaa acataggcgg tgatgaggat gataaaaaca taggcagtga tgaggatcac<br>3361 ctgtcactga aggaattttc agaattggag caaagtggtt attatgtctg ctaccccaga<br>3421 ggaagcaaac cagaagatgc gaacttttat ctctacctga gggcaagagt gtgtgagaac<br>3481 tgcatggaga tggatgtgat gtcggtggcc acaattgtca tagtggacat ctgcatcact<br>3541 gggggcttgc tgctgctggt ttactactgg agcaagaata gaaaggccaa ggccaagcct<br>3601 gtgacacgag gagcgggtgc tggcggcagg caaaggggac aaaacaagga gaggccacca<br>3661 cctgttccca acccagacta tgagcccatc cggaaaggcc agcgggacct gtattctggc<br>3721 ctgaatcaga gacgcatctg ataagaattc gatccgcggc cgcgaaggat ctgcgatcgc<br>3781 tccggtgccc gtcagtgggc agagcgcaca tcgcccacag tccccgagaa gttgggggga<br>3841 ggggtcggca attgaacggg tgcctagaga aggtggcgcg gggtaaactg ggaaagtgat<br>3901 gtcgtgtact ggctccgcct ttttcccgag ggtgggggag aaccgtatat aagtgcagta<br>3961 gtcgccgtga acgttctttt tcgcaacggg tttgccgcca gaacacagct gaagcttcga<br>4021 ggggctcgca tctctccttc acgcgcccgc cgccctacct gaggccgcca tccacgccgg<br>4081 ttgagtcgcg ttctgccgcc tcccgcctgt ggtgcctcct gaactgcgtc cgccgtctag<br>4141 gtaagtttaa agctcaggtc gagaccgggc ctttgtccgg cgctcccttg gagcctacct<br>4201 agactcagcc ggctctccac gctttgcctg accctgcttg ctcaactcta cgtctttgtt<br>4261 tcgttttctg ttctgcgccg ttacagatcc aagctgtgac cggcgcctac gctagatgac<br>4321 cgagtacaag cccacggtgc gcctcgccac ccgcgacgac gtccccaggg ccgtacgcac<br>4381 cctcgccgcc gcgttcgccg actaccccgc cacgcgccac accgtcgatc cggaccgcca<br>4441 catcgagcgg gtcaccgagc tgcaagaact cttcctcacg cgcgtcgggc tcgacatcgg<br>4501 caaggtgtgg gtcgcggacg acggcgccgc ggtggcggtc tggaccacgc cggagagcgt<br>4561 cgaagcgggg gcggtgttcg ccgagatcgg cccgcgcatg gccgagttga gcggttcccg<br>4621 gctggccgcg cagcaacaga tggaaggcct cctggcgccg caccggccca aggagcccgc<br>4681 gtggttcctg gccaccgtcg gcgtctcgcc cgaccaccag ggcaagggtc tgggcagcgc<br>4741 cgtcgtgctc cccggagtgg aggcggccga gcgcgccggg gtgcccgcct tcctggagac<br>4801 ctccgcgccc cgcaacctcc ccttctacga gcggctcggc ttcaccgtca ccgccgacgt<br>4861 cgaggtgccc gaaggaccgc gcacctggtg catgacccgc aagcccggtg cctgagtcga<br>4921 caatcaacct ctggattaca aaatttgtga aagattgact ggtattctta actatgttgc<br>4981 tccttttacg ctatgtggat acgctgcttt aatgcctttg tatcatgcta ttgcttcccg<br>5041 tatggctttc attttctcct ccttgtataa atcctggttg ctgtctcttt atgaggagtt<br>5101 gtggcccgtt gtcaggcaac gtggcgtggt gtgcactgtg tttgctgacg caacccccac<br>5161 tggttggggc attgccacca cctgtcagct cctttccggg actttcgctt tccccctccc<br>5221 tattgccacg gcggaactca tcgccgcctg ccttgcccgc tgctggacag gggctcggct<br>5281 gttgggcact gacaattccg tggtgttgtc ggggaaatca tcgtcctttc cttggctgct<br>5341 cgcctgtgtt gccacctgga ttctgcgcgg gacgtccttc tgctacgtcc cttcggccct<br>5401 caatccagcg gaccttcctt cccgcggcct gctgccggct ctgcggcctc ttccgcgtct<br>5461 tcgccttcgc cctcagacga gtcggatctc cctttgggcc gcctccccgc ctggtacctt<br>5521 taagaccaat gacttacaag gcagctgtag atcttagcca ctttttaaaa gaaaaggggg<br>5581 gactggaagg gctaattcac tcccaacgaa aataagatct gctttttgct tgtactgggt<br>5641 ctctctggtt agaccagatc tgagcctggg agctctctgg ctaactaggg aacccactgc<br>5701 ttaagcctca ataaagcttg ccttgagtgc ttcaagtagt gtgtgcccgt ctgttgtgtg<br>5761 actctggtaa ctagagatcc ctcagaccct tttagtcagt gtggaaaatc tctagcagta<br>5821 gtagttcatg tcatcttatt attcagtatt tataacttgc aaagaaatga atatcagaga<br>5881 gtgagaggaa cttgtttatt gcagcttata atggttacaa ataaagcaat agcatcacaa<br>5941 atttcacaaa taaagcattt ttttcactgc attctagttg tggtttgtcc aaactcatca<br>6001 atgtatctta tcatgtctgg ctctagctat cccgccccta actccgccca gttccgccca<br>6061 ttctccgccc catggctgac taattttttt tatttatgca gaggccgagg ccgcctcggc<br>6121 ctctgagcta ttccagaagt agtgaggagg cttttttgga ggcctagact tttgcagaga<br>6181 cggcccaaat tcgtaatcat ggtcatagct gtttcctgtg tgaaattgtt atccgctcac<br>6241 aattccacac aacatacgag ccggaagcat aaagtgtaaa gcctggggtg cctaatgagt<br>6301 gagctaactc acattaattg cgttgcgctc actgcccgct ttccagtcgg gaaacctgtc<br>6361 gtgccagctg cattaatgaa tcggccaacg cgcggggaga ggcggtttgc gtattgggcg<br>6421 ctcttccgct tcctcgctca ctgactcgct gcgctcggtc gttcggctgc ggcgagcggt<br>6481 atcagctcac tcaaaggcgg taatacggtt atccacagaa tcaggggata acgcaggaaa<br>6541 gaacatgtga gcaaaaggcc agcaaaaggc caggaaccgt aaaaaggccg cgttgctggc<br>6601 gtttttccat aggctccgcc cccctgacga gcatcacaaa aatcgacgct caagtcagag<br>6661 gtggcgaaac ccgacaggac tataaagata ccaggcgttt ccccctggaa gctccctcgt<br>6721 gcgctctcct gttccgaccc tgccgcttac cggatacctg tccgcctttc tcccttcggg<br>6781 aagcgtggcg ctttctcata gctcacgctg taggtatctc agttcggtgt aggtcgttcg |

-continued

CONSTRUCT SEQUENCES

```
6841 ctccaagctg ggctgtgtgc acgaaccccc cgttcagccc gaccgctgcg ccttatccgg
6901 taactatcgt cttgagtcca acccggtaag acacgactta tcgccactgg cagcagccac
6961 tggtaacagg attagcagag cgaggtatgt aggcggtgct acagagttct tgaagtggtg
7021 gcctaactac ggctacacta gaaggacagt atttggtatc tgcgctctgc tgaagccagt
7081 taccttcgga aaaagagttg gtagctcttg atccggcaaa caaaccaccg ctggtagcgg
7141 tggttttttt gtttgcaagc agcagattac gcgcagaaaa aaaggatctc aagaagatcc
7201 tttgatcttt tctacggggt ctgacgctca gtggaacgaa aactcacgtt aagggatttt
7261 ggtcatgaga ttatcaaaaa ggatcttcac ctagatcctt ttaaattaaa aatgaagttt
7321 taaatcaatc taaagtatat atgagtaaac ttggtctgac agttaccaat gcttaatcag
7381 tgaggcacct atctcagcga tctgtctatt tcgttcatcc atagttgcct gactccccgt
7441 cgtgtagata actacgatac gggagggctt accatctggc cccagtgctg caatgatacc
7501 gcgagaccca cgctcaccgg ctccagattt atcagcaata aaccagccag ccggaagggc
7561 cgagcgcaga agtggtcctg caactttatc cgcctccatc cagtctatta attgttgccg
7621 ggaagctaga gtaagtagtt cgccagttaa tagtttgcgc aacgttgttg ccattgctac
7681 aggcatcgtg gtgtcacgct cgtcgtttgg tatggcttca ttcagctccg gttcccaacg
7741 atcaaggcga gttacatgat cccccatgtt gtgcaaaaaa gcggttagct ccttcggtcc
7801 tccgatcgtt gtcagaagta agttggccgc agtgttatca ctcatggtta tggcagcact
7861 gcataattct cttactgtca tgccatccgt aagatgcttt tctgtgactg gtgagtactc
7921 aaccaagtca ttctgagaat agtgtatgcg gcgaccgagt tgctcttgcc cggcgtcaat
7981 acgggataat accgcgccac atagcagaac tttaaaagtg ctcatcattg gaaaacgttc
8041 ttcggggcga aaactctcaa ggatcttacc gctgttgaga tccagttcga tgtaacccac
8101 tcgtgcaccc aactgatctt cagcatcttt tactttcacc agcgtttctg ggtgagcaaa
8161 aacaggaagg caaaatgccg caaaaaaggg aataagggcg acacggaaat gttgaatact
8221 catactcttc ctttttcaat attattgaag catttatcag ggttattgtc tcatgagcgg
8281 atacatattt gaatgtattt agaaaaataa acaaataggg gttccgcgca catttccccg
8341 aaaagtgcca cctgacgtct aagaaaccat tattatcatg acattaacct ataaaaatag
8401 gcgtatcacg aggccctttc gtctcgcgcg tttcggtgat gacggtgaaa acctctgaca
8461 catgcagctc ccggagacgg tcacagcttg tctgtaagcg gatgccggga gcagacaagc
8521 ccgtcagggc gcgtcagcgg gtgttggcgg gtgtcggggc tggcttaact atgcggcatc
8581 agagcagatt gtactgagag tgcaccatat gcggtgtgaa ataccgcaca gatgcgtaag
8641 gagaaaatac cgcatcaggc gccattcgcc attcaggctg cgcaactgtt gggaagggcg
8701 atcggtgcgg gcctcttcgc tattacgcca gctggcgaaa gggggatgtg ctgcaaggcg
8761 attaagttgg gtaacgccag ggttttccca gtcacgacgt tgtaaaacga cggccagtgc
8821 caagctg.
```

p510_antiCD19_SL_CD3epsilon (SEQ ID NO: 18)

```
   1 acgcgtgtag tcttatgcaa tactcttgta gtcttgcaac atggtaacga tgagttagca
  61 acatgcctta caaggagaga aaaagcaccg tgcatgccga ttggtggaag taaggtggta
 121 cgatcgtgcc ttattaggaa ggcaacagac gggtctgaca tggattggac gaaccactga
 181 attgccgcat tgcagagata ttgtatttaa gtgcctagct cgatacaata aacgggtctc
 241 tctggttaga ccagatctga gcctgggagc tctctggcta actagggaac ccactgctta
 301 agcctcaata aagcttgcct tgagtgcttc aagtagtgtg tgcccgtctg ttgtgtgact
 361 ctggtaacta gagatccctc agaccctttt agtcagtgtg gaaaatctct agcagtggcg
 421 cccgaacagg gacctgaaag cgaaagggaa accagagctc tctcgacgca ggactcggct
 481 tgctgaagcg cgcacggcaa gaggcgaggg gcggcgactg gtgagtacgc caaaaatttt
 541 gactagcgga ggctagaagg agagagatgg gtgcgagagc gtcagtatta agcgggggag
 601 aattagatcg cgatgggaaa aaattcggtt aaggccaggg ggaaagaaaa aatataaatt
 661 aaaacatata gtatgggcaa gcagggagct agaacgattc gcagttaatc ctggcctgtt
 721 agaaacatca gaaggctgta gacaaatact gggacagcta caaccatccc ttcagacagg
 781 atcagaagaa cttagatcat tatataatac agtagcaacc ctctattgtg tgcatcaaag
 841 gatagagata aaagacacca aggaagcttt agacaagata gaggaagagc aaaacaaaag
 901 taagaccacc gcacagcaag cggccactga tcttcagacc tggaggagga gatatgaggg
 961 acaattggag aagtgaatta tataaatata aagtagtaaa aattgaacca ttaggagtag
1021 cacccaccaa ggcaaagaga agagtggtgc agagagaaaa aagagcagtg ggaataggag
1081 ctttgttcct tgggttcttg ggagcagcag gaagcactat gggcgcagcc tcaatgacgc
1141 tgacggtaca ggccagacaa ttattgtctg gtatagtgca gcagcagaac aatttgctga
1201 gggctattga ggcgcaacag catctgttgc aactcacagt ctggggcatc aagcagctcc
1261 aggcaagaat cctggctgtg gaaagatacc taaaggatca acagctcctg gggatttggg
1321 gttgctctgg aaaactcatt tgcaccactg ctgtgccttg gaatgctagt tggagtaata
1381 aatctctgga acagattgga atcacacgac ctggatggag tgggacagag aaattaacaa
1441 ttacacaagc ttaatacact ccttaattga agaatcgcaa aaccagcaag aaaagaatga
1501 acaagaatta ttggaattag ataaatgggc aagtttgtgg aattggttta acataacaaa
1561 ttggctgtgg tatataaaat tattcataat gatagtagga ggcttggtag gtttaagaat
1621 agtttttgct gtactttcta tagtgaatag agttaggcag ggatattcac cattatcgtt
1681 tcagacccac ctcccaaccc cgaggggacc cgacaggccc gaaggaatag aagaagaagg
1741 tggagagaga gacagagaca gatccattcg attagtgaac ggatctcgac ggtatcggtt
1801 aacttttaaa agaaaagggg ggattggggg gtacagtgca ggggaaagaa tagtagacat
1861 aatagcaaca gacatacaaa ctaaagaatt acaaaaacaa attacaaaat tcaaaatttt
1921 atcgatacta gtattatgcc cagtacatga ccttatggga ctttcctact tggcagtaca
1981 tctacgtatt agtcatcgct attaccatgg tgatgcggtt ttggcagtac atcaatgggc
2041 gtggatagcg gtttgactca cggggatttc caagtctcca ccccattgac gtcaatggga
2101 gtttgttttg gcaccaaaat caacgggact ttccaaaatg tcgtaacaac tccgccccat
2161 tgacgcaaat gggcggtagg cgtgtacggt gggaggttta tataagcaga gctcgtttag
2221 tgaaccgtca gatcgcctgg agacgccatc cacgctgttt tgacctccat agaagattct
2281 agagccgcca ccatgcttct cctggtgaca agccttctgc tctgtgagtt accacaccca
2341 gcattcctcc tgatcccaga catccagatg acacagacta catcctccct gtctgcctct
2401 ctgggagaca gagtcaccat cagttgcagg gcaagtcagg acattagtaa atatttaaat
```

-continued

CONSTRUCT SEQUENCES

```
2461 tggtatcagc agaaaccaga tggaactgtt aaactcctga tctaccatac atcaagatta
2521 cactcaggag tcccatcaag gttcagtggc agtgggtctg gaacagatta ttctctcacc
2581 attagcaacc tggagcaaga agatattgcc acttactttt gccaacaggg taatacgctt
2641 ccgtacacgt tcggaggggg gactaagttg gaaataacag gctccacctc tggatccggc
2701 aagcccggat ctggcgaggg atccaccaag ggcgaggtga aactgcagga gtcaggacct
2761 ggcctggtgg cgccctcaca gagcctgtcc gtcacatgca ctgtctcagg ggtctcatta
2821 cccgactatg gtgtaagctg gattcgccag cctccacgaa agggtctgga gtggctggga
2881 gtaatatggg gtagtgaaac cacatactat aattcagctc tcaaatccag actgaccatc
2941 atcaaggaca actccaagag ccaagttttc ttaaaaatga acagtctgca aactgatgac
3001 acagccattt actactgtgc caaacattat tactacggtg gtagctatgc tatggactac
3061 tggggtcaag gaacctcagt caccgtctcc tcagcggccg caggtggcgg cggttctggt
3121 ggcggcggtt ctggtggcgg cggttctctc gaggatggta atgaagaaat gggtggtatt
3181 acacagacac catataaagt ctccatctct ggaaccacag taatattgac atgccctcag
3241 tatcctggat ctgaaatact atggcaacac aatgataaaa acataggcgg tgatgaggat
3301 gataaaaaca taggcagtga tgaggatcac ctgtcactga aggaattttc agaattggag
3361 caaagtggtt attatgtctg ctaccccaga ggaagcaaac cagaagatgc gaacttttat
3421 ctctacctga gggcaagagt gtgtgagaac tgcatggaga tggatgtgat gtcggtggcc
3481 acaattgtca tagtggacat ctgcatcact gggggcttgc tgctgctggt ttactactgg
3541 agcaagaata gaaaggccaa ggccaagcct gtgacacgag gagcgggtgc tggcggcagg
3601 caaaggggac aaaacaagga gaggccacca cctgttccca acccagacta tgagcccatc
3661 cggaaaggcc agcgggacct gtattctggc ctgaatcaga gacgcatctg ataagaattc
3721 gatccgcggc cgcgaaggat ctgcgatcgc tccggtgccc gtcagtgggc agagcgcaca
3781 tcgcccacag tccccgagaa gttgggggga ggggtcggca attgaacggg tgcctagaga
3841 aggtggcgcg gggtaaactg ggaaagtgat gtcgtgtact ggctccgcct ttttcccgag
3901 ggtgggggag aaccgtatat aagtgcagta gtcgccgtga acgttctttt tcgcaacggg
3961 tttgccgcca gaacacagct gaagcttcga ggggctcgca tctctccttc acgcgcccgc
4021 cgccctacct gaggccgcca tccacgccgg ttgagtcgcg ttctgccgcc tcccgcctgt
4081 ggtgcctcct gaactgcgtc cgccgtctag gtaagtttaa agctcaggtc gagaccgggc
4141 ctttgtccgg cgctcccttg gagcctacct agactcagcc ggctctccac gctttgcctg
4201 accctgcttg ctcaactcta cgtctttgtt tcgttttctg ttctgcgccg ttacagatcc
4261 aagctgtgac cggcgcctac gctagatgac cgagtacaag cccacggtgc gcctcgccac
4321 ccgcgacgac gtccccaggg ccgtacgcac cctcgccgcc gcgttcgccg actaccccgc
4381 cacgcgccac accgtcgatc cggaccgcca catcgagcgg gtcaccgagc tgcaagaact
4441 cttcctcacg cgcgtcgggc tcgacatcgg caaggtgtgg gtcgcggacg acggcgccgc
4501 ggtggcggtc tggaccacgc cggagagcgt cgaagcgggg gcggtgttcg ccgagatcgg
4561 cccgcgcatg gccgagttga gcggttcccg gctggccgcg cagcaacaga tggaaggcct
4621 cctggcgccg caccggccca aggagcccgc gtggttcctg gccaccgtcg gcgtctcgcc
4681 cgaccaccag ggcaagggtc tgggcagcgc cgtcgtgctc cccggagtgg aggcggccga
4741 gcgcgccggg gtgcccgcct tcctggagac ctccgcgccc cgcaacctcc ccttctacga
4801 gcggctcggc ttcaccgtca ccgccgacgt cgaggtgccc gaaggaccgc gcacctggtg
4861 catgacccgc aagcccggtg cctgagtcga caatcaacct ctggattaca aaatttgtga
4921 aagattgact ggtattctta actatgttgc tccttttacg ctatgtggat acgctgcttt
4981 aatgcctttg tatcatgcta ttgcttcccg tatggctttc attttctcct ccttgtataa
5041 atcctggttg ctgtctcttt atgaggagtt gtggcccgtt gtcaggcaac gtggcgtggt
5101 gtgcactgtg tttgctgacg caacccccac tggttggggc attgccacca cctgtcagct
5161 cctttccggg actttcgctt tccccctccc tattgccacg gcggaactca tcgccgcctg
5221 ccttgcccgc tgctggacag gggctcggct gttgggcact gacaattccg tggtgttgtc
5281 ggggaaatca tcgtcctttc cttggctgct cgcctgtgtt gccacctgga ttctgcgcgg
5341 gacgtccttc tgctacgtcc cttcggccct caatccagcg gaccttcctt cccgcggcct
5401 gctgccggct ctgcggcctc ttccgcgtct tcgccttcgc cctcagacga gtcggatctc
5461 cctttgggcc gcctccccgc ctggtacctt taagaccaat gacttacaag gcagctgtag
5521 atcttagcca ctttttaaaa gaaaaggggg gactggaagg gctaattcac tcccaacgaa
5581 aataagatct gctttttgct tgtactgggt ctctctggtt agaccagatc tgagcctggg
5641 agctctctgg ctaactaggg aacccactgc ttaagcctca ataaagcttg ccttgagtgc
5701 ttcaagtagt gtgtgcccgt ctgttgtgtg actctggtaa ctagagatcc ctcagaccct
5761 tttagtcagt gtggaaaatc tctagcagta gtagttcatg tcatcttatt attcagtatt
5821 tataacttgc aaagaaatga atatcagaga gtgagaggaa cttgtttatt gcagcttata
5881 atggttacaa ataaagcaat agcatcacaa atttcacaaa taaagcattt ttttcactgc
5941 attctagttg tggtttgtcc aaactcatca atgtatctta tcatgtctgg ctctagctat
6001 cccgccccta actccgccca gttccgccca ttctccgccc catggctgac taattttttt
6061 tatttatgca gaggccgagg ccgcctcggc ctctgagcta ttccagaagt agtgaggagg
6121 cttttttgga ggcctagact tttgcagaga cggcccaaat tcgtaatcat ggtcatagct
6181 gtttcctgtg tgaaattgtt atccgctcac aattccacac aacatacgag ccggaagcat
6241 aaagtgtaaa gcctggggtg cctaatgagt gagctaactc acattaattg cgttgcgctc
6301 actgcccgct ttccagtcgg gaaacctgtc gtgccagctg cattaatgaa tcggccaacg
6361 cgcggggaga ggcggtttgc gtattgggcg ctcttccgct tcctcgctca ctgactcgct
6421 gcgctcggtc gttcggctgc ggcgagcggt atcagctcac tcaaaggcgg taatacggtt
6481 atccacagaa tcaggggata acgcaggaaa gaacatgtga gcaaaaggcc agcaaaaggc
6541 caggaaccgt aaaaaggccg cgttgctggc gtttttccat aggctccgcc cccctgacga
6601 gcatcacaaa aatcgacgct caagtcagag gtggcgaaac ccgacaggac tataaagata
6661 ccaggcgttt ccccctggaa gctccctcgt gcgctctcct gttccgaccc tgccgcttac
6721 cggatacctg tccgcctttc tcccttcggg aagcgtggcg ctttctcata gctcacgctg
6781 taggtatctc agttcggtgt aggtcgttcg ctccaagctg ggctgtgtgc acgaaccccc
6841 cgttcagccc gaccgctgcg ccttatccgg taactatcgt cttgagtcca acccggtaag
6901 acacgactta tcgccactgg cagcagccac tggtaacagg attagcagag cgaggtatgt
6961 aggcggtgct acagagttct tgaagtggtg gcctaactac ggctacacta gaaggacagt
7021 atttggtatc tgcgctctgc tgaagccagt taccttcgga aaaagagttg gtagctcttg
```

-continued

CONSTRUCT SEQUENCES

```
7081 atccggcaaa caaaccaccg ctggtagcgg tggttttttt gtttgcaagc agcagattac
7141 gcgcagaaaa aaaggatctc aagaagatcc tttgatcttt tctacggggt ctgacgctca
7201 gtggaacgaa aactcacgtt aagggatttt ggtcatgaga ttatcaaaaa ggatcttcac
7261 ctagatcctt ttaaattaaa aatgaagttt taaatcaatc taaagtatat atgagtaaac
7321 ttggtctgac agttaccaat gcttaatcag tgaggcacct atctcagcga tctgtctatt
7381 tcgttcatcc atagttgcct gactccccgt cgtgtagata actacgatac gggagggctt
7441 accatctggc cccagtgctg caatgatacc gcgagaccca cgctcaccgg ctccagattt
7501 atcagcaata aaccagccag ccggaagggc cgagcgcaga agtggtcctg caactttatc
7561 cgcctccatc cagtctatta attgttgccg ggaagctaga gtaagtagtt cgccagttaa
7621 tagtttgcgc aacgttgttg ccattgctac aggcatcgtg gtgtcacgct cgtcgtttgg
7681 tatggcttca ttcagctccg gttcccaacg atcaaggcga gttacatgat cccccatgtt
7741 gtgcaaaaaa gcggttagct ccttcggtcc tccgatcgtt gtcagaagta agttggccgc
7801 agtgttatca ctcatggtta tggcagcact gcataattct cttactgtca tgccatccgt
7861 aagatgcttt tctgtgactg gtgagtactc aaccaagtca ttctgagaat agtgtatgcg
7921 gcgaccgagt tgctcttgcc cggcgtcaat acgggataat accgcgccac atagcagaac
7981 tttaaaagtg ctcatcattg gaaaacgttc ttcggggcga aaactctcaa ggatcttacc
8041 gctgttgaga tccagttcga tgtaacccac tcgtgcaccc aactgatctt cagcatcttt
8101 tactttcacc agcgtttctg ggtgagcaaa aacaggaagg caaaatgccg caaaaaaggg
8161 aataagggcg acacggaaat gttgaatact catactcttc ctttttcaat attattgaag
8221 catttatcag ggttattgtc tcatgagcgg atacatattt gaatgtattt agaaaaataa
8281 acaaataggg gttccgcgca catttccccg aaaagtgcca cctgacgtct aagaaaccat
8341 tattatcatg acattaacct ataaaaatag gcgtatcacg aggccctttc gtctcgcgcg
8401 tttcggtgat gacggtgaaa acctctgaca catgcagctc ccggagacgg tcacagcttg
8461 tctgtaagcg gatgccggga gcagacaagc ccgtcagggc gcgtcagcgg gtgttggcgg
8521 gtgtcggggc tggcttaact atgcggcatc agagcagatt gtactgagag tgcaccatat
8581 gcggtgtgaa ataccgcaca gatgcgtaag gagaaaatac cgcatcaggc gccattcgcc
8641 attcaggctg cgcaactgtt gggaagggcg atcggtgcgg gcctcttcgc tattacgcca
8701 gctggcgaaa gggggatgtg ctgcaaggcg attaagttgg gtaacgccag ggttttccca
8761 gtcacgacgt tgtaaaacga cggccagtgc caagctg.
```

p510_antiCD19_SL_CD3gamma (SEQ ID NO: 19)

```
   1 acgcgtgtag tcttatgcaa tactcttgta gtcttgcaac atggtaacga tgagttagca
  61 acatgcctta caaggagaga aaaagcaccg tgcatgccga ttggtggaag taaggtggta
 121 cgatcgtgcc ttattaggaa ggcaacagac gggtctgaca tggattggac gaaccactga
 181 attgccgcat tgcagagata ttgtatttaa gtgcctagct cgatacaata aacgggtctc
 241 tctggttaga ccagatctga gcctgggagc tctctggcta actagggaac ccactgctta
 301 agcctcaata aagcctgcct tgagtgcttc aagtagtgtg tgcccgtctg ttgtgtgact
 361 ctggtaacta gagatccctc agaccctttt agtcagtgtg gaaaatctct agcagtggcg
 421 cccgaacagg gacctgaaag cgaaagggaa accagagctc tctcgacgca ggactcggct
 481 tgctgaagcg cgcacggcaa gaggcgaggg gcggcgactg gtgagtacgc caaaaatttt
 541 gactagcgga ggctagaagg agagagatgg gtgcgagagc gtcagtatta agcgggggag
 601 aattagatcg cgatgggaaa aaattcggtt aaggccaggg ggaaagaaaa aatataaatt
 661 aaaacatata gtatgggcaa gcagggagct agaacgattc gcagttaatc ctggcctgtt
 721 agaaacatca gaaggctgta gacaaatact gggacagcta caaccatccc ttcagacagg
 781 atcagaagaa cttagatcat tatataatac agtagcaacc ctctattgtg tgcatcaaag
 841 gatagagata aaagacacca aggaagcttt agacaagata gaggaagagc aaaacaaaag
 901 taagaccacc gcacagcaag cggccactga tcttcagacc tggaggagga gatatgaggg
 961 acaattggag aagtgaatta tataaatata aagtagtaaa aattgaacca ttaggagtag
1021 cacccaccaa ggcaaagaga agagtggtgc agagagaaaa aagagcagtg ggaataggag
1081 ctttgttcct tgggttcttg ggagcagcag gaagcactat gggcgcagcc tcaatgacgc
1141 tgacggtaca ggccagacaa ttattgtctg gtatagtgca gcagcagaac aatttgctga
1201 gggctattga ggcgcaacag catctgttgc aactcacagt ctggggcatc aagcagctcc
1261 aggcaagaat cctggctgtg gaaagatacc taaaggatca acagctcctg gggatttggg
1321 gttgctctgg aaaactcatt tgcaccactg ctgtgccttg gaatgctagt tggagtaata
1381 aatctctgga acagattgga atcacacgac ctggatggag tgggacagag aaattaacaa
1441 ttacacaagc ttaatacact ccttaattga agaatcgcaa aaccagcaag aaaagaatga
1501 acaagaatta ttggaattag ataaatgggc aagtttgtgg aattggttta acataacaaa
1561 ttggctgtgg tatataaaat tattcataat gatagtagga ggcttggtag gtttaagaat
1621 agtttttgct gtactttcta tagtgaatag agttaggcag ggatattcac cattatcgtt
1681 tcagacccac ctcccaaccc cgaggggacc cgacaggccc gaaggaatag aagaagaagg
1741 tggagagaga gacagagaca gatccattcg attagtgaac ggatctcgac ggtatcggtt
1801 aacttttaaa agaaaagggg ggattggggg gtacagtgca ggggaaagaa tagtagacat
1861 aatagcaaca gacatacaaa ctaaagaatt acaaaaacaa attacaaaat tcaaaatttt
1921 atcgatacta gtattatgcc cagtacatga ccttatggga ctttcctact tggcagtaca
1981 tctacgtatt agtcatcgct attaccatgg tgatgcggtt ttggcagtac atcaatgggc
2041 gtggatagcg gtttgactca cggggatttc caagtctcca ccccattgac gtcaatggga
2101 gtttgttttg gcaccaaaat caacgggact ttccaaaatg tcgtaacaac tccgccccat
2161 tgacgcaaat gggcggtagg cgtgtacggt gggaggttta tataagcaga gctcgtttag
2221 tgaaccgtca gatcgcctgg agacgccatc cacgctgttt tgacctccat agaagattct
2281 agagccgcca ccatgcttct cctggtgaca agccttctgc tctgtgagtt accacaccca
2341 gcattcctcc tgatcccaga catccagatg acacagacta catcctccct gtctgcctct
2401 ctgggagaca gagtcaccat cagttgcagg gcaagtcagg acattagtaa atatttaaat
2461 tggtatcagc agaaaccaga tggaactgtt aaactcctga tctaccatac atcaagatta
2521 cactcaggag tcccatcaag gttcagtggc agtgggtctg gaacagatta ttctctcacc
2581 attagcaacc tggagcaaga agatattgcc acttactttt gccaacaggg taatacgctt
2641 ccgtacacgt tcggaggggg gactaagttg gaaataacag gctccacctc tggatccggc
2701 aagcccggat ctggcgaggg atccaccaag ggcgaggtga aactgcagga gtcaggacct
```

-continued

| CONSTRUCT SEQUENCES |
|---|
| 2761 ggcctggtgg cgccctcaca gagcctgtcc gtcacatgca ctgtctcagg ggtctcatta |
| 2821 cccgactatg gtgtaagctg gattcgccag cctccacgaa agggtctgga gtggctggga |
| 2881 gtaatatggg gtagtgaaac cacatactat aattcagctc tcaaatccag actgaccatc |
| 2941 atcaaggaca actccaagag ccaagttttc ttaaaaatga acagtctgca aactgatgac |
| 3001 acagccattt actactgtgc caaacattat tactacggtg gtagctatgc tatggactac |
| 3061 tggggtcaag gaacctcagt caccgtctcc tcagcggccg caggtggcgg cggttctggt |
| 3121 ggcggcggtt ctggtggcgg cggttctctc gagcagtcaa tcaaaggaaa ccacttggtt |
| 3181 aaggtgtatg actatcaaga agatggttcg gtacttctga cttgtgatgc agaagccaaa |
| 3241 aatatcacat ggtttaaaga tgggaagatg atcggcttcc taactgaaga taaaaaaaaa |
| 3301 tggaatctgg gaagtaatgc caaggaccca cgagggatgt atcagtgtaa aggatcacag |
| 3361 aacaagtcaa aaccactcca agtgtattac agaatgtgtc agaactgcat tgaactaaat |
| 3421 gcagccacca tatctggctt tctctttgct gaaatcgtca gcattttcgt ccttgctgtt |
| 3481 ggggtctact tcattgctgg acaggatgga gttcgccagt cgagagcttc agacaagcag |
| 3541 actctgttgc ccaatgacca gctctaccag cccctcaagg atcgagaaga tgaccagtac |
| 3601 agccaccttc aaggaaacca gttgaggagg aattgataag aattcgatcc gcggccgcga |
| 3661 aggatctgcg atcgctccgg tgcccgtcag tgggcagagc gcacatcgcc cacagtcccc |
| 3721 gagaagttgg ggggaggggt cggcaattga acgggtgcct agagaaggtg gcgcggggta |
| 3781 aactgggaaa gtgatgtcgt gtactggctc cgcctttttc ccgagggtgg gggagaaccg |
| 3841 tatataagtg cagtagtcgc cgtgaacgtt ctttttcgca acgggtttgc cgccagaaca |
| 3901 cagctgaagc ttcgaggggc tcgcatctct ccttcacgcg cccgccgccc tacctgaggc |
| 3961 cgccatccac gccggttgag tcgcgttctg ccgcctcccg cctgtggtgc ctcctgaact |
| 4021 gcgtccgccg tctaggtaag tttaaagctc aggtcgagac cgggcctttg tccggcgctc |
| 4081 ccttggagcc tacctagact cagccggctc tccacgcttt gcctgaccct gcttgctcaa |
| 4141 ctctacgtct ttgtttcgtt ttctgttctg cgccgttaca gatccaagct gtgaccggcg |
| 4201 cctacgctag atgaccgagt acaagcccac ggtgcgcctc gccacccgcg acgacgtccc |
| 4261 cagggccgta cgcaccctcg ccgccgcgtt cgccgactac cccgccacgc gccacaccgt |
| 4321 cgatccggac cgccacatcg agcgggtcac cgagctgcaa gaactcttcc tcacgcgcgt |
| 4381 cgggctcgac atcggcaagg tgtgggtcgc ggacgacggc gccgcggtgg cggtctggac |
| 4441 cacgccggag agcgtcgaag cgggggcggt gttcgccgag atcggcccgc gcatggccga |
| 4501 gttgagcggt tcccggctgg ccgcgcagca acagatggaa ggcctcctgg cgccgcaccg |
| 4561 gcccaaggag cccgcgtggt tcctggccac cgtcggcgtc tcgcccgacc accagggcaa |
| 4621 gggtctgggc agcgccgtcg tgctccccgg agtggaggcg gccgagcgcg ccggggtgcc |
| 4681 cgccttcctg gagacctccg cgccccgcaa cctcccctc tacgagcggc tcggcttcac |
| 4741 cgtcaccgcc gacgtcgagg tgcccgaagg accgcgcacc tggtgcatga cccgcaagcc |
| 4801 cggtgcctga gtcgacaatc aacctctgga ttacaaaatt tgtgaaagat tgactggtat |
| 4861 tcttaactat gttgctcctt ttacgctatg tggatacgct gctttaatgc ctttgtatca |
| 4921 tgctattgct tcccgtatgg ctttcatttt ctcctccttg tataaatcct ggttgctgtc |
| 4981 tctttatgag gagttgtggc ccgttgtcag gcaacgtggc gtggtgtgca ctgtgtttgc |
| 5041 tgacgcaacc cccactggtt ggggcattgc caccacctgt cagctccttt ccgggacttt |
| 5101 cgctttcccc ctccctattg ccacggcgga actcatcgcc gcctgccttg cccgctgctg |
| 5161 gacaggggct cggctgttgg gcactgacaa ttccgtggtg ttgtcgggga aatcatcgtc |
| 5221 ctttccttgg ctgctcgcct gtgttgccac ctggattctg cgcgggacgt ccttctgcta |
| 5281 cgtcccttcg gccctcaatc cagcggacct tccttcccgc ggcctgctgc cggctctgcg |
| 5341 gcctcttccg cgtcttcgcc ttcgccctca gacgagtcgg atctcccttt gggccgcctc |
| 5401 cccgcctggt acctttaaga ccaatgactt acaaggcagc tgtagatctt agccactttt |
| 5461 taaaagaaaa ggggggactg gaagggctaa ttcactccca acgaaaataa gatctgcttt |
| 5521 ttgcttgtac tgggtctctc tggttagacc agatctgagc ctgggagctc tctggctaac |
| 5581 tagggaaccc actgcttaag cctcaataaa gcttgccttg agtgcttcaa gtagtgtgtg |
| 5641 cccgtctgtt gtgtgactct ggtaactaga gatccctcag acccttttag tcagtgtgga |
| 5701 aaatctctag cagtagtagt tcatgtcatc ttattattca gtatttataa cttgcaaaga |
| 5761 aatgaatatc agagagtgag aggaacttgt ttattgcagc ttataatggt tacaaataaa |
| 5821 gcaatagcat cacaaatttc acaaataaag catttttttc actgcattct agttgtggtt |
| 5881 tgtccaaact catcaatgta tcttatcatg tctggctcta gctatcccgc ccctaactcc |
| 5941 gcccagttcc gcccattctc cgccccatgg ctgactaatt ttttttattt atgcagaggc |
| 6001 cgaggccgcc tcggcctctg agctattcca gaagtagtga ggaggctttt ttggaggcct |
| 6061 agacttttgc agagacggcc caaattcgta atcatggtca tagctgtttc ctgtgtgaaa |
| 6121 ttgttatccg ctcacaattc cacacaacat acgagccgga agcataaagt gtaaagcctg |
| 6181 gggtgcctaa tgagtgagct aactcacatt aattgcgttg cgctcactgc ccgctttcca |
| 6241 gtcgggaaac ctgtcgtgcc agctgcatta atgaatcggc caacgcgcgg ggagaggcgg |
| 6301 tttgcgtatt gggcgctctt ccgcttcctc gctcactgac tcgctgcgct cggtcgttcg |
| 6361 gctgcggcga gcggtatcag ctcactcaaa ggcggtaata cggttatcca cagaatcagg |
| 6421 ggataacgca ggaaagaaca tgtgagcaaa aggccagcaa aaggccagga accgtaaaaa |
| 6481 ggccgcgttg ctggcgtttt tccataggct ccgcccccct gacgagcatc acaaaaatcg |
| 6541 acgctcaagt cagaggtggc gaaacccgac aggactataa agataccagg cgtttccccc |
| 6601 tggaagctcc ctcgtgcgct ctcctgttcc gaccctgccg cttaccggat acctgtccgc |
| 6661 ctttctccct tcgggaagcg tggcgctttc tcatagctca cgctgtaggt atctcagttc |
| 6721 ggtgtaggtc gttcgctcca agctgggctg tgtgcacgaa ccccccgttc agcccgaccg |
| 6781 ctgcgcctta tccggtaact atcgtcttga gtccaacccg gtaagacacg acttatcgcc |
| 6841 actggcagca gccactggta acaggattag cagagcgagg tatgtaggcg gtgctacaga |
| 6901 gttcttgaag tggtggccta actacggcta cactagaagg acagtatttg gtatctgcgc |
| 6961 tctgctgaag ccagttacct tcggaaaaag agttggtagc tcttgatccg gcaaacaaac |
| 7021 caccgctggt agcggtggtt tttttgtttg caagcagcag attacgcgca gaaaaaaagg |
| 7081 atctcaagaa gatcctttga tcttttctac ggggtctgac gctcagtgga acgaaaactc |
| 7141 acgttaaggg attttggtca tgagattatc aaaaaggatc ttcacctaga tccttttaaa |
| 7201 ttaaaaatga agttttaaat caatctaaag tatatatgag taaacttggt ctgacagtta |
| 7261 ccaatgctta atcagtgagg cacctatctc agcgatctgt ctatttcgtt catccatagt |
| 7321 tgcctgactc cccgtcgtgt agataactac gatacgggag ggcttaccat ctggccccag |

-continued

| CONSTRUCT SEQUENCES |
|---|

```
7381 tgctgcaatg ataccgcgag acccacgctc accggctcca gatttatcag caataaacca
7441 gccagccgga agggccgagc gcagaagtgg tcctgcaact ttatccgcct ccatccagtc
7501 tattaattgt tgccgggaag ctagagtaag tagttcgcca gttaatagtt tgcgcaacgt
7561 tgttgccatt gctacaggca tcgtggtgtc acgctcgtcg tttggtatgg cttcattcag
7621 ctccggttcc caacgatcaa ggcgagttac atgatccccc atgttgtgca aaaaagcggt
7681 tagctccttc ggtcctccga tcgttgtcag aagtaagttg gccgcagtgt tatcactcat
7741 ggttatggca gcactgcata attctcttac tgtcatgcca tccgtaagat gcttttctgt
7801 gactggtgag tactcaacca agtcattctg agaatagtgt atgcggcgac cgagttgctc
7861 ttgcccggcg tcaatacggg ataataccgc gccacatagc agaactttaa aagtgctcat
7921 cattggaaaa cgttcttcgg ggcgaaaact ctcaaggatc ttaccgctgt tgagatccag
7981 ttcgatgtaa cccactcgtg cacccaactg atcttcagca tcttttactt tcaccagcgt
8041 ttctgggtga gcaaaaacag gaaggcaaaa tgccgcaaaa aagggaataa gggcgacacg
8101 gaaatgttga atactcatac tcttcctttt tcaatattat tgaagcattt atcagggtta
8161 ttgtctcatg agcggataca tatttgaatg tatttagaaa aataaacaaa taggggttcc
8221 gcgcacattt ccccgaaaag tgccacctga cgtctaagaa accattatta tcatgacatt
8281 aacctataaa aataggcgta tcacgaggcc ctttcgtctc gcgcgtttcg gtgatgacgg
8341 tgaaaacctc tgacacatgc agctcccgga gacggtcaca gcttgtctgt aagcggatgc
8401 cgggagcaga caagcccgtc agggcgcgtc agcgggtgtt ggcgggtgtc ggggctggct
8461 taactatgcg gcatcagagc agattgtact gagagtgcac catatgcggt gtgaaatacc
8521 gcacagatgc gtaaggagaa aataccgcat caggcgccat tcgccattca ggctgcgcaa
8581 ctgttgggaa gggcgatcgg tgcgggcctc ttcgctatta cgccagctgg cgaaaggggg
8641 atgtgctgca aggcgattaa gttgggtaac gccagggttt tcccagtcac gacgttgtaa
8701 aacgacggcc agtgccaagc tg.
```

p510_antiCD19_SL_CD3delta (SEQ ID NO: 20)

```
   1 acgcgtgtag tcttatgcaa tactcttgta gtcttgcaac atggtaacga tgagttagca
  61 acatgcctta caaggagaga aaaagcaccg tgcatgccga ttggtggaag taaggtggta
 121 cgatcgtgcc ttattaggaa ggcaacagac gggtctgaca tggattggac gaaccactga
 181 attgccgcat tgcagagata ttgtatttaa gtgcctagct cgatacaata aacgggtctc
 241 tctggttaga ccagatctga gcctgggagc tctctggcta actagggaac ccactgctta
 301 agcctcaata aagcttgcct tgagtgcttc aagtagtgtg tgcccgtctg ttgtgtgact
 361 ctggtaacta gagatccctc agaccctttt agtcagtgtg gaaaatctct agcagtggcg
 421 cccgaacagg gacctgaaag cgaaagggaa accagagctc tctcgacgca ggactcggct
 481 tgctgaagcg cgcacggcaa gaggcgaggg gcggcgactg gtgagtacgc caaaaatttt
 541 gactagcgga ggctagaagg agagagatgg gtgcgagagc gtcagtatta agcgggggag
 601 aattagatcg cgatgggaaa aaattcggtt aaggccaggg ggaaagaaaa aatataaatt
 661 aaaacatata gtatgggcaa gcagggagct agaacgattc gcagttaatc ctggcctgtt
 721 agaaacatca gaaggctgta gacaaatact gggacagcta caaccatccc ttcagacagg
 781 atcagaagaa cttagatcat tatataatac agtagcaacc ctctattgtg tgcatcaaag
 841 gatagagata aaagacacca aggaagcttt agacaagata gaggaagagc aaaacaaaag
 901 taagaccacc gcacagcaag cggccactga tcttcagacc tggaggagga gatatgaggg
 961 acaattggag aagtgaatta tataaatata aagtagtaaa aattgaacca ttaggagtag
1021 cacccaccaa ggcaaagaga agagtggtgc agagagaaaa aagagcagtg ggaataggag
1081 ctttgttcct tgggttcttg ggagcagcag gaagcactat gggcgcagcc tcaatgacgc
1141 tgacggtaca ggccagacaa ttattgtctg gtatagtgca gcagcagaac aatttgctga
1201 gggctattga ggcgcaacag catctgttgc aactcacagt ctggggcatc aagcagctcc
1261 aggcaagaat cctggctgtg gaaagatacc taaaggatca acagctcctg gggatttggg
1321 gttgctctgg aaaactcatt tgcaccactg ctgtgccttg gaatgctagt tggagtaata
1381 aatctctgga acagattgga atcacacgac ctggatggag tgggacagag aaattaacaa
1441 ttacacaagc ttaatacact ccttaattga agaatcgcaa aaccagcaag aaaagaatga
1501 acaagaatta ttggaattag ataaatgggc aagtttgtgg aattggttta acataacaaa
1561 ttggctgtgg tatataaaat tattcataat gatagtagga ggcttggtag gtttaagaat
1621 agtttttgct gtactttcta tagtgaatag agttaggcag ggatattcac cattatcgtt
1681 tcagacccac ctcccaaccc cgaggggacc cgacaggccc gaaggaatag aagaagaagg
1741 tggagagaga gacagagaca gatccattcg attagtgaac ggatctcgac ggtatcggtt
1801 aacttttaaa agaaaagggg ggattggggg gtacagtgca ggggaaagaa tagtagacat
1861 aatagcaaca gacatacaaa ctaaagaatt acaaaaacaa attacaaaat tcaaaatttt
1921 atcgatacta gtattatgcc cagtacatga ccttatggga ctttcctact tggcagtaca
1981 tctacgtatt agtcatcgct attaccatgg tgatgcggtt ttggcagtac atcaatgggc
2041 gtggatagcg gtttgactca cggggatttc caagtctcca ccccattgac gtcaatggga
2101 gtttgttttg gcaccaaaat caacgggact ttccaaaatg tcgtaacaac tccgccccat
2161 tgacgcaaat gggcggtagg cgtgtacggt gggaggttta tataagcaga gctcgtttag
2221 tgaaccgtca gatcgcctgg agacgccatc cacgctgttt tgacctccat agaagattct
2281 agagccgcca ccatgcttct cctggtgaca agccttctgc tctgtgagtt accacaccca
2341 gcattcctcc tgatcccaga catccagatg acacagacta catcctccct gtctgcctct
2401 ctgggagaca gagtcaccat cagttgcagg gcaagtcagg acattagtaa atatttaaat
2461 tggtatcagc agaaaccaga tggaactgtt aaactcctga tctaccatac atcaagatta
2521 cactcaggag tcccatcaag gttcagtggc agtgggtctg gaacagatta ttctctcacc
2581 attagcaacc tggagcaaga agatattgcc acttactttt gccaacaggg taatacgctt
2641 ccgtacacgt tcggaggggg gactaagttg gaaataacag gctccacctc tggatccggc
2701 aagcccggat ctggcgaggg atccaccaag ggcgaggtga aactgcagga gtcaggacct
2761 ggcctggtgg cgccctcaca gagcctgtcc gtcacatgca ctgtctcagg ggtctcatta
2821 cccgactatg gtgtaagctg gattcgccag cctccacgaa agggtctgga gtggctggga
2881 gtaatatggg gtagtgaaac cacatactat aattcagctc tcaaatccag actgaccatc
2941 atcaaggaca actccaagag ccaagttttc ttaaaaatga acagtctgca aactgatgac
3001 acagccattt actactgtgc caaacattat tactacggtg gtagctatgc tatggactac
3061 tggggtcaag gaacctcagt caccgtctcc tcagcggccg caggtggcgg cggttctggt
```

-continued

CONSTRUCT SEQUENCES

```
3121 ggcggcggtt ctggtggcgg cggttctctc gagttcaaga tacctataga ggaacttgag
3181 gacagagtgt ttgtgaattg caataccagc atcacatggg tagagggaac ggtgggaaca
3241 ctgctctcag acattacaag actggacctg ggaaaacgca tcctggaccc acgaggaata
3301 tataggtgta atgggacaga tatatacaag gacaaagaat ctaccgtgca agttcattat
3361 cgaatgtgcc agagctgtgt ggagctggat ccagccaccg tggctggcat cattgtcact
3421 gatgtcattg ccactctgct ccttgctttg ggagtcttct gctttgctgg acatgagact
3481 ggaaggctgt ctggggctgc cgacacacaa gctctgttga ggaatgacca ggtctatcag
3541 cccctccgag atcgagatga tgctcagtac agccaccttg gaggaaactg ggctcggaac
3601 aagtgataag aattcgatcc gcggccgcga aggatctgcg atcgctccgg tgcccgtcag
3661 tgggcagagc gcacatcgcc cacagtcccc gagaagttgg ggggaggggt cggcaattga
3721 acgggtgcct agagaaggtg gcgcggggta aactgggaaa gtgatgtcgt gtactggctc
3781 cgcctttttc ccgagggtgg gggagaaccg tatataagtg cagtagtcgc cgtgaacgtt
3841 ctttttcgca acgggtttgc cgccagaaca cagctgaagc ttcgaggggc tcgcatctct
3901 ccttcacgcg cccgccgccc tacctgaggc cgccatccac gccggttgag tcgcgttctg
3961 ccgcctcccg cctgtggtgc ctcctgaact gcgtccgccg tctaggtaag tttaaagctc
4021 aggtcgagac cgggcctttg tccggcgctc ccttggagcc tacctagact cagccggctc
4081 tccacgcttt gcctgaccct gcttgctcaa ctctacgtct ttgtttcgtt ttctgttctg
4141 cgccgttaca gatccaagct gtgaccggcg cctacgctag atgaccgagt acaagcccac
4201 ggtgcgcctc gccacccgcg acgacgtccc cagggccgta cgcaccctcg ccgccgcgtt
4261 cgccgactac cccgccacgc gccacaccgt cgatccggac cgccacatcg agcgggtcac
4321 cgagctgcaa gaactcttcc tcacgcgcgt cgggctcgac atcggcaagg tgtgggtcgc
4381 ggacgacggc gccgcggtgg cggtctggac cacgccggag agcgtcgaag cgggggcggt
4441 gttcgccgag atcggcccgc gcatggccga gttgagcggt tcccggctgg ccgcgcagca
4501 acagatggaa ggcctcctgg cgccgcaccg gcccaaggag cccgcgtggt tcctggccac
4561 cgtcggcgtc tcgcccgacc accagggcaa gggtctgggc agcgccgtcg tgctccccgg
4621 agtggaggcg gccgagcgcg ccggggtgcc cgccttcctg gagacctccg cgccccgcaa
4681 cctccccttc tacgagcggc tcggcttcac cgtcaccgcc gacgtcgagg tgcccgaagg
4741 accgcgcacc tggtgcatga cccgcaagcc cggtgcctga gtcgacaatc aacctctgga
4801 ttacaaaatt tgtgaaagat tgactggtat tcttaactat gttgctcctt ttacgctatg
4861 tggatacgct gctttaatgc ctttgtatca tgctattgct tcccgtatgg ctttcatttt
4921 ctcctccttg tataaatcct ggttgctgtc tctttatgag gagttgtggc ccgttgtcag
4981 gcaacgtggc gtggtgtgca ctgtgtttgc tgacgcaacc cccactggtt ggggcattgc
5041 caccacctgt cagctccttt ccgggacttt cgctttcccc ctccctattg ccacggcgga
5101 actcatcgcc gcctgccttg cccgctgctg gacaggggct cggctgttgg gcactgacaa
5161 ttccgtggtg ttgtcgggga aatcatcgtc ctttccttgg ctgctcgcct gtgttgccac
5221 ctggattctg cgcgggacgt ccttctgcta cgtcccttcg gccctcaatc cagcggacct
5281 tccttcccgc ggcctgctgc cggctctgcg gcctcttccg cgtcttcgcc ttcgccctca
5341 gacgagtcgg atctcccttt gggccgcctc cccgcctggt acctttaaga ccaatgactt
5401 acaaggcagc tgtagatctt agccactttt taaaagaaaa ggggggactg gaagggctaa
5461 ttcactccca acgaaaataa gatctgcttt ttgcttgtac tgggtctctc tggttagacc
5521 agatctgagc ctgggagctc tctggctaac tagggaaccc actgcttaag cctcaataaa
5581 gcttgccttg agtgcttcaa gtagtgtgtg cccgtctgtt gtgtgactct ggtaactaga
5641 gatccctcag acccttttag tcagtgtgga aaatctctag cagtagtagt tcatgtcatc
5701 ttattattca gtatttataa cttgcaaaga aatgaatatc agagagtgag aggaacttgt
5761 ttattgcagc ttataatggt tacaaataaa gcaatagcat cacaaatttc acaaataaag
5821 catttttttc actgcattct agttgtggtt tgtccaaact catcaatgta tcttatcatg
5881 tctggctcta gctatcccgc ccctaactcc gcccagttcc gcccattctc cgccccatgg
5941 ctgactaatt ttttttattt atgcagaggc cgaggccgcc tcggcctctg agctattcca
6001 gaagtagtga ggaggctttt ttggaggcct agacttttgc agagacggcc caaattcgta
6061 atcatggtca tagctgtttc ctgtgtgaaa ttgttatccg ctcacaattc cacacaacat
6121 acgagccgga agcataaagt gtaaagcctg gggtgcctaa tgagtgagct aactcacatt
6181 aattgcgttg cgctcactgc ccgctttcca gtcgggaaac ctgtcgtgcc agctgcatta
6241 atgaatcggc caacgcgcgg ggagaggcgg tttgcgtatt gggcgctctt ccgcttcctc
6301 gctcactgac tcgctgcgct cggtcgttcg gctgcggcga gcggtatcag ctcactcaaa
6361 ggcggtaata cggttatcca cagaatcagg ggataacgca ggaaagaaca tgtgagcaaa
6421 aggccagcaa aaggccagga accgtaaaaa ggccgcgttg ctggcgtttt tccataggct
6481 ccgcccccct gacgagcatc acaaaaatcg acgctcaagt cagaggtggc gaaacccgac
6541 aggactataa agataccagg cgtttccccc tggaagctcc ctcgtgcgct ctcctgttcc
6601 gaccctgccg cttaccggat acctgtccgc ctttctccct tcgggaagcg tggcgctttc
6661 tcatagctca cgctgtaggt atctcagttc ggtgtaggtc gttcgctcca agctgggctg
6721 tgtgcacgaa ccccccgttc agcccgaccg ctgcgcctta tccggtaact atcgtcttga
6781 gtccaacccg gtaagacacg acttatcgcc actggcagca gccactggta acaggattag
6841 cagagcgagg tatgtaggcg gtgctacaga gttcttgaag tggtggccta actacggcta
6901 cactagaagg acagtatttg gtatctgcgc tctgctgaag ccagttacct tcggaaaaag
6961 agttggtagc tcttgatccg gcaaacaaac caccgctggt agcggtggtt tttttgtttg
7021 caagcagcag attacgcgca gaaaaaaagg atctcaagaa gatcctttga tcttttctac
7081 ggggtctgac gctcagtgga acgaaaactc acgttaaggg attttggtca tgagattatc
7141 aaaaaggatc ttcacctaga tccttttaaa ttaaaaatga agttttaaat caatctaaag
7201 tatatatgag taaacttggt ctgacagtta ccaatgctta atcagtgagg cacctatctc
7261 agcgatctgt ctatttcgtt catccatagt tgcctgactc cccgtcgtgt agataactac
7321 gatacgggag ggcttaccat ctggccccag tgctgcaatg ataccgcgag acccacgctc
7381 accggctcca gatttatcag caataaacca gccagccgga agggccgagc gcagaagtgg
7441 tcctgcaact ttatccgcct ccatccagtc tattaattgt tgccgggaag ctagagtaag
7501 tagttcgcca gttaatagtt tgcgcaacgt tgttgccatt gctacaggca tcgtggtgtc
7561 acgctcgtcg tttggtatgg cttcattcag ctccggttcc caacgatcaa ggcgagttac
7621 atgatccccc atgttgtgca aaaaagcggt tagctccttc ggtcctccga tcgttgtcag
7681 aagtaagttg gccgcagtgt tatcactcat ggttatggca gcactgcata attctcttac
```

-continued

CONSTRUCT SEQUENCES

```
7741 tgtcatgcca tccgtaagat gcttttctgt gactggtgag tactcaacca agtcattctg
7801 agaatagtgt atgcggcgac cgagttgctc ttgcccggcg tcaatacggg ataataccgc
7861 gccacatagc agaactttaa aagtgctcat cattggaaaa cgttcttcgg ggcgaaaact
7921 ctcaaggatc ttaccgctgt tgagatccag ttcgatgtaa cccactcgtg cacccaactg
7981 atcttcagca tcttttactt tcaccagcgt ttctgggtga gcaaaaacag gaaggcaaaa
8041 tgccgcaaaa aagggaataa gggcgacacg gaaatgttga atactcatac tcttcctttt
8101 tcaatattat tgaagcattt atcagggtta ttgtctcatg agcggataca tatttgaatg
8161 tatttagaaa aataaacaaa taggggttcc gcgcacattt ccccgaaaag tgccacctga
8221 cgtctaagaa accattatta tcatgacatt aacctataaa aataggcgta tcacgaggcc
8281 ctttcgtctc gcgcgtttcg gtgatgacgg tgaaaacctc tgacacatgc agctcccgga
8341 gacggtcaca gcttgtctgt aagcggatgc cgggagcaga caagcccgtc agggcgcgtc
8401 agcgggtgtt ggcgggtgtc ggggctggct taactatgcg gcatcagagc agattgtact
8461 gagagtgcac catatgcggt gtgaaatacc gcacagatgc gtaaggagaa aataccgcat
8521 caggcgccat tcgccattca ggctgcgcaa ctgttgggaa gggcgatcgg tgcgggcctc
8581 ttcgctatta cgccagctgg cgaaaggggg atgtgctgca aggcgattaa gttgggtaac
8641 gccagggttt tcccagtcac gacgttgtaa aacgacggcc agtgccaagc tg.
```

p510_antiCD19_SL_TCRbeta (SEQ ID NO: 21)

```
   1 acgcgtgtag tcttatgcaa tactcttgta gtcttgcaac atggtaacga tgagttagca
  61 acatgcctta caaggagaga aaaagcaccg tgcatgccga ttggtggaag taaggtggta
 121 cgatcgtgcc ttattaggaa ggcaacagac gggtctgaca tggattggac gaaccactga
 181 attgccgcat tgcagagata ttgtatttaa gtgcctagct cgatacaata aacgggtctc
 241 tctggttaga ccagatctga gcctgggagc tctctggcta actagggaac ccactgctta
 301 agcctcaata aagcttgcct tgagtgcttc aagtagtgtg tgcccgtctg ttgtgtgact
 361 ctggtaacta gagatccctc agaccctttt agtcagtgtg gaaaatctct agcagtggcg
 421 cccgaacagg gacctgaaag cgaaagggaa accagagctc tctcgacgca ggactcggct
 481 tgctgaagcg cgcacggcaa gaggcgaggg gcggcgactg gtgagtacgc caaaaatttt
 541 gactagcgga ggctagaagg agagagatgg gtgcgagagc gtcagtatta agcgggggag
 601 aattagatcg cgatgggaaa aaattcggtt aaggccaggg ggaaagaaaa aatataaatt
 661 aaaacatata gtatgggcaa gcagggagct agaacgattc gcagttaatc ctggcctgtt
 721 agaaacatca gaaggctgta gacaaatact gggacagcta caaccatccc ttcagacagg
 781 atcagaagaa cttagatcat tatataatac agtagcaacc ctctattgtg tgcatcaaag
 841 gatagagata aaagacacca aggaagcttt agacaagata gaggaagagc aaaacaaaag
 901 taagaccacc gcacagcaag cggccactga tcttcagacc tggaggagga gatatgaggg
 961 acaattggag aagtgaatta tataaatata aagtagtaaa aattgaacca ttaggagtag
1021 cacccaccaa ggcaaagaga agagtggtgc agagagaaaa aagagcagtg ggaataggag
1081 ctttgttcct tgggttcttg ggagcagcag gaagcactat gggcgcagcc tcaatgacgc
1141 tgacggtaca ggccagacaa ttattgtctg gtatagtgca gcagcagaac aatttgctga
1201 gggctattga ggcgcaacag catctgttgc aactcacagt ctggggcatc aagcagctcc
1261 aggcaagaat cctggctgtg gaaagatacc taaaggatca acagctcctg gggatttggg
1321 gttgctctgg aaaactcatt tgcaccactg ctgtgccttg gaatgctagt tggagtaata
1381 aatctctgga acagattgga atcacacgac ctggatggag tgggacagag aaattaacaa
1441 ttacacaagc ttaatacact ccttaattga agaatcgcaa aaccagcaag aaaagaatga
1501 acaagaatta ttggaattag ataaatgggc aagtttgtgg aattggttta acataacaaa
1561 ttggctgtgg tatataaaat tattcataat gatagtagga ggcttggtag gtttaagaat
1621 agtttttgct gtactttcta tagtgaatag agttaggcag ggatattcac cattatcgtt
1681 tcagacccac ctcccaaccc cgaggggacc cgacaggccc gaaggaatag aagaagaagg
1741 tggagagaga gacagagaca gatccattcg attagtgaac ggatctcgac ggtatcggtt
1801 aacttttaaa agaaaagggg ggattggggg gtacagtgca ggggaaagaa tagtagacat
1861 aatagcaaca gacatacaaa ctaaagaatt acaaaaacaa attacaaaat tcaaaatttt
1921 atcgatacta gtattatgcc cagtacatga ccttatggga ctttcctact tggcagtaca
1981 tctacgtatt agtcatcgct attaccatgg tgatgcggtt ttggcagtac atcaatgggc
2041 gtggatagcg gtttgactca cggggatttc caagtctcca ccccattgac gtcaatggga
2101 gtttgttttg gcaccaaaat caacgggact ttccaaaatg tcgtaacaac tccgccccat
2161 tgacgcaaat gggcggtagg cgtgtacggt gggaggttta tataagcaga gctcgtttag
2221 tgaaccgtca gatcgcctgg agacgccatc cacgctgttt tgacctccat agaagattct
2281 agagccgcca ccatgcttct cctggtgaca agccttctgc tctgtgagtt accacaccca
2341 gcattcctcc tgatcccaga catccagatg acacagacta catcctccct gtctgcctct
2401 ctgggagaca gagtcaccat cagttgcagg gcaagtcagg acattagtaa atatttaaat
2461 tggtatcagc agaaaccaga tggaactgtt aaactcctga tctaccatac atcaagatta
2521 cactcaggag tcccatcaag gttcagtggc agtgggtctg gaacagatta ttctctcacc
2581 attagcaacc tggagcaaga agatattgcc acttactttt gccaacaggg taatacgctt
2641 ccgtacacgt tcggaggggg gactaagttg gaaataacag gctccacctc tggatccggc
2701 aagcccggat ctggcgaggg atccaccaag ggcgaggtga aactgcagga gtcaggacct
2761 ggcctggtgg cgccctcaca gagcctgtcc gtcacatgca ctgtctcagg ggtctcatta
2821 cccgactatg gtgtaagctg gattcgccag cctccacgaa agggtctgga gtggctggga
2881 gtaatatggg gtagtgaaac cacatactat aattcagctc tcaaatccag actgaccatc
2941 atcaaggaca actccaagag ccaagttttc ttaaaaatga acagtctgca aactgatgac
3001 acagccattt actactgtgc caaacattat tactacggtg gtagctatgc tatggactac
3061 tggggtcaag gaacctcagt caccgtctcc tcagcggccg caggtggcgg cggttctggt
3121 ggcggcggtt ctggtggcgg cggttctctc gagctgggag caggcccagt ggattctgga
3181 gtcacacaaa ccccaaagca cctgatcaca gcaactggac agcgagtgac gctgagatgc
3241 tcccctaggt ctggagacct ctctgtgtca tggtaccaac agagcctgga ccagggcctc
3301 cagttcctca ttcagtatta taatggagaa gagagagcaa aaggaaacat tcttgaacga
3361 ttctccgcac aacagttccc tgacttgcac tctgaactaa acctgagctc tctggagctg
3421 ggggactcag ctttgtattt ctgtgccagc agcccccgga caggcctgaa cactgaagct
3481 ttctttggac aaggcaccag actcacagtt gtagaggacc tgaacaaggt gttcccaccc
```

-continued

CONSTRUCT SEQUENCES

```
3541 gaggtcgctg tgtttgagcc atcagaagca gagatctccc acacccaaaa ggccacactg
3601 gtgtgcctgg ccacaggctt cttccccgac cacgtggagc tgagctggtg ggtgaatggg
3661 aaggaggtgc acagtggggt cagcacggac ccgcagcccc tcaaggagca gcccgccctc
3721 aatgactcca gatactgcct gagcagccgc ctgagggtct cggccacctt ctggcagaac
3781 ccccgcaacc acttccgctg tcaagtccag ttctacgggc tctcggagaa tgacgagtgg
3841 acccaggata gggccaaacc cgtcacccag atcgtcagcg ccgaggcctg ggtagagca
3901 gactgtggct ttacctcggt gtcctaccag caaggggtcc tgtctgccac catcctctat
3961 gagatcctgc tagggaaggc caccctgtat gctgtgctgg tcagcgccct tgtgttgatg
4021 gccatggtca agagaaagga tttctgataa gaattcgatc cgcggccgcg aaggatctgc
4081 gatcgctccg gtgcccgtca gtgggcagag cgcacatcgc ccacagtccc cgagaagttg
4141 gggggagggg tcggcaattg aacgggtgcc tagagaaggt ggcgcggggt aaactgggaa
4201 agtgatgtcg tgtactggct ccgccttttt cccgagggtg ggggagaacc gtatataagt
4261 gcagtagtcg ccgtgaacgt tctttttcgc aacgggtttg ccgccagaac acagctgaag
4321 cttcgagggg ctcgcatctc tccttcacgc gcccgccgcc ctacctgagg ccgccatcca
4381 cgccggttga gtcgcgttct gccgcctccc gcctgtggtg cctcctgaac tgcgtccgcc
4441 gtctaggtaa gtttaaagct caggtcgaga ccgggccttt gtccggcgct cccttggagc
4501 ctacctagac tcagccggct ctccacgctt tgcctgaccc tgcttgctca actctacgtc
4561 tttgtttcgt tttctgttct gcgccgttac agatccaagc tgtgaccggc gcctacgcta
4621 gatgaccgag tacaagccca cggtgcgcct cgccacccgc gacgacgtcc ccagggccgt
4681 acgcaccctc gccgccgcgt tcgccgacta ccccgccacg cgccacaccg tcgatccgga
4741 ccgccacatc gagcgggtca ccgagctgca agaactcttc ctcacgcgcg tcgggctcga
4801 catcggcaag gtgtgggtcg cggacgacgg cgccgcggtg gcggtctgga ccacgccgga
4861 gagcgtcgaa gcgggggcgg tgttcgccga gatcggcccg cgcatggccg agttgagcgg
4921 ttcccggctg gccgcgcagc aacagatgga aggcctcctg gcgccgcacc ggcccaagga
4981 gcccgcgtgg ttcctggcca ccgtcggcgt ctcgcccgac caccagggca agggtctggg
5041 cagcgccgtc gtgctccccg gagtggaggc ggccgagcgc gccggggtgc ccgccttcct
5101 ggagacctcc gcgccccgca acctcccctt ctacgagcgg ctcggcttca ccgtcaccgc
5161 cgacgtcgag gtgcccgaag gaccgcgcac ctggtgcatg acccgcaagc ccggtgcctg
5221 agtcgacaat caacctctgg attacaaaat ttgtgaaaga ttgactggta ttcttaacta
5281 tgttgctcct tttacgctat gtggatacgc tgctttaatg cctttgtatc atgctattgc
5341 ttcccgtatg gctttcattt tctcctcctt gtataaatcc tggttgctgt ctctttatga
5401 ggagttgtgg cccgttgtca ggcaacgtgg cgtggtgtgc actgtgtttg ctgacgcaac
5461 ccccactggt tggggcattg ccaccacctg tcagctcctt tccgggactt tcgctttccc
5521 cctccctatt gccacggcgg aactcatcgc cgcctgcctt gcccgctgct ggacaggggc
5581 tcggctgttg ggcactgaca attccgtggt gttgtcgggg aaatcatcgt cctttccttg
5641 gctgctcgcc tgtgttgcca cctggattct gcgcgggacg tccttctgct acgtcccttc
5701 ggccctcaat ccagcggacc ttccttcccg cggcctgctg ccggctctgc ggcctcttcc
5761 gcgtcttcgc cttcgccctc agacgagtcg gatctccctt tgggccgcct ccccgcctgg
5821 tacctttaag accaatgact tacaaggcag ctgtagatct tagccacttt ttaaaagaaa
5881 aggggggact ggaagggcta attcactccc aacgaaaata agatctgctt tttgcttgta
5941 ctgggtctct ctggttagac cagatctgag cctgggagct ctctggctaa ctagggaacc
6001 cactgcttaa gcctcaataa agcttgcctt gagtgcttca agtagtgtgt gcccgtctgt
6061 tgtgtgactc tggtaactag agatccctca gacccttta gtcagtgtgg aaaatctcta
6121 gcagtagtag ttcatgtcat cttattattc agtatttata acttgcaaag aaatgaatat
6181 cagagagtga gaggaacttg tttattgcag cttataatgg ttacaaataa agcaatagca
6241 tcacaaattt cacaaataaa gcattttttt cactgcattc tagttgtggt ttgtccaaac
6301 tcatcaatgt atcttatcat gtctggctct agctatcccg cccctaactc cgcccagttc
6361 cgcccattct ccgccccatg gctgactaat tttttttatt tatgcagagg ccgaggccgc
6421 ctcggcctct gagctattcc agaagtagtg aggaggcttt tttggaggcc tagacttttg
6481 cagagacggc ccaaattcgt aatcatggtc atagctgttt cctgtgtgaa attgttatcc
6541 gctcacaatt ccacacaaca tacgagccgg aagcataaag tgtaaagcct ggggtgccta
6601 atgagtgagc taactcacat taattgcgtt gcgctcactg cccgctttcc agtcgggaaa
6661 cctgtcgtgc cagctgcatt aatgaatcgg ccaacgcgcg gggagaggcg gtttgcgtat
6721 tgggcgctct tccgcttcct cgctcactga ctcgctgcgc tcggtcgttc ggctgcggcg
6781 agcggtatca gctcactcaa aggcggtaat acggttatcc acagaatcag gggataacgc
6841 aggaaagaac atgtgagcaa aaggccagca aaaggccagg aaccgtaaaa aggccgcgtt
6901 gctggcgttt ttccataggc tccgcccccc tgacgagcat cacaaaaatc gacgctcaag
6961 tcagaggtgg cgaaacccga caggactata aagataccag gcgtttcccc ctggaagctc
7021 cctcgtgcgc tctcctgttc cgaccctgcc gcttaccgga tacctgtccg cctttctccc
7081 ttcgggaagc gtggcgcttt ctcatagctc acgctgtagg tatctcagtt cggtgtaggt
7141 cgttcgctcc aagctgggct gtgtgcacga accccccgtt cagcccgacc gctgcgcctt
7201 atccggtaac tatcgtcttg agtccaaccc ggtaagacac gacttatcgc cactggcagc
7261 agccactggt aacaggatta gcagagcgag gtatgtaggc ggtgctacag agttcttgaa
7321 gtggtggcct aactacggct acactagaag gacagtattt ggtatctgcg ctctgctgaa
7381 gccagttacc ttcggaaaaa gagttggtag ctcttgatcc ggcaaacaaa ccaccgctgg
7441 tagcggtggt ttttttgttt gcaagcagca gattacgcgc agaaaaaaag gatctcaaga
7501 agatcctttg atcttttcta cggggtctga cgctcagtgg aacgaaaact cacgttaagg
7561 gattttggtc atgagattat caaaaaggat cttcacctag atccttttaa attaaaaatg
7621 aagttttaaa tcaatctaaa gtatatatga gtaaacttgg tctgacagtt accaatgctt
7681 aatcagtgag gcacctatct cagcgatctg tctatttcgt tcatccatag ttgcctgact
7741 ccccgtcgtg tagataacta cgatacggga gggcttacca tctggcccca gtgctgcaat
7801 gataccgcga gacccacgct caccggctcc agatttatca gcaataaacc agccagccgg
7861 aagggccgag cgcagaagtg gtcctgcaac tttatccgcc tccatccagt ctattaattg
7921 ttgccgggaa gctagagtaa gtagttcgcc agttaatagt ttgcgcaacg ttgttgccat
7981 tgctacaggc atcgtggtgt cacgctcgtc gtttggtatg gcttcattca gctccggttc
8041 ccaacgatca aggcgagtta catgatcccc catgttgtgc aaaaaagcgg ttagctcctt
8101 cggtcctccg atcgttgtca gaagtaagtt ggccgcagtg ttatcactca tggttatggc
```

-continued

CONSTRUCT SEQUENCES

```
8161 agcactgcat aattctctta ctgtcatgcc atccgtaaga tgcttttctg tgactggtga
8221 gtactcaacc aagtcattct gagaatagtg tatgcggcga ccgagttgct cttgcccggc
8281 gtcaatacgg gataataccg cgccacatag cagaacttta aaagtgctca tcattggaaa
8341 acgttcttcg gggcgaaaac tctcaaggat cttaccgctg ttgagatcca gttcgatgta
8401 acccactcgt gcacccaact gatcttcagc atcttttact ttcaccagcg tttctgggtg
8461 agcaaaaaca ggaaggcaaa atgccgcaaa aaagggaata agggcgacac ggaaatgttg
8521 aatactcata ctcttccttt ttcaatatta ttgaagcatt tatcagggtt attgtctcat
8581 gagcggatac atatttgaat gtatttagaa aaataaacaa ataggggttc cgcgcacatt
8641 tccccgaaaa gtgccacctg acgtctaaga aaccattatt atcatgacat taacctataa
8701 aaataggcgt atcacgaggc cctttcgtct cgcgcgtttc ggtgatgacg gtgaaaacct
8761 ctgacacatg cagctcccgg agacggtcac agcttgtctg taagcggatg ccgggagcag
8821 acaagcccgt cagggcgcgt cagcgggtgt tggcgggtgt cggggctggc ttaactatgc
8881 ggcatcagag cagattgtac tgagagtgca ccatatgcgg tgtgaaatac cgcacagatg
8941 cgtaaggaga aaataccgca tcaggcgcca ttcgccattc aggctgcgca actgttggga
9001 agggcgatcg gtgcgggcct cttcgctatt acgccagctg gcgaaagggg gatgtgctgc
9061 aaggcgatta agttgggtaa cgccagggtt ttcccagtca cgacgttgta aaacgacggc
9121 cagtgccaag ctg.
```

p510_antiBCMA_CD3epsilon (SEQ ID NO: 22)

```
   1 acgcgtgtag tcttatgcaa tactcttgta gtcttgcaac atggtaacga tgagttagca
  61 acatgcctta caaggagaga aaaagcaccg tgcatgccga ttggtggaag taaggtggta
 121 cgatcgtgcc ttattaggaa ggcaacagac gggtctgaca tggattggac gaaccactga
 181 attgccgcat tgcagagata ttgtatttaa gtgcctagct cgatacaata aacgggtctc
 241 tctggttaga ccagatctga gcctgggagc tctctggcta actagggaac ccactgctta
 301 agcctcaata aagcttgcct tgagtgcttc aagtagtgtg tgcccgtctg ttgtgtgact
 361 ctggtaacta gagatccctc agaccctttt agtcagtgtg gaaaatctct agcagtggcg
 421 cccgaacagg gacctgaaag cgaaagggaa accagagctc tctcgacgca ggactcggct
 481 tgctgaagcg cgcacggcaa gaggcgaggg gcggcgactg gtgagtacgc caaaaatttt
 541 gactagcgga ggctagaagg agagagatgg gtgcgagagc gtcagtatta agcgggggag
 601 aattagatcg cgatgggaaa aaattcggtt aaggccaggg ggaaagaaaa aatataaatt
 661 aaaacatata gtatgggcaa gcagggagct agaacgattc gcagttaatc ctggcctgtt
 721 agaaacatca gaaggctgta gacaaatact gggacagcta caaccatccc ttcagacagg
 781 atcagaagaa cttagatcat tatataatac agtagcaacc ctctattgtg tgcatcaaag
 841 gatagagata aaagacacca aggaagcttt agacaagata gaggaagagc aaaacaaaag
 901 taagaccacc gcacagcaag cggccactga tcttcagacc tggaggagga gatatgaggg
 961 acaattggag aagtgaatta tataaatata aagtagtaaa aattgaacca ttaggagtag
1021 cacccaccaa ggcaaagaga agagtggtgc agagagaaaa aagagcagtg ggaataggag
1081 ctttgttcct tgggttcttg ggagcagcag gaagcactat gggcgcagcc tcaatgacgc
1141 tgacggtaca ggccagacaa ttattgtctg gtatagtgca gcagcagaac aatttgctga
1201 gggctattga ggcgcaacag catctgttgc aactcacagt ctggggcatc aagcagctcc
1261 aggcaagaat cctggctgtg gaaagatacc taaaggatca acagctcctg gggatttggg
1321 gttgctctgg aaaactcatt tgcaccactg ctgtgccttg gaatgctagt tggagtaata
1381 aatctctgga acagattgga atcacacgac ctggatggag tgggacagag aaattaacaa
1441 ttacacaagc ttaatacact ccttaattga agaatcgcaa aaccagcaag aaaagaatga
1501 acaagaatta ttggaattag ataaatgggc aagtttgtgg aattggttta acataacaaa
1561 ttggctgtgg tatataaaat tattcataat gatagtagga ggcttggtag gtttaagaat
1621 agtttttgct gtactttcta tagtgaatag agttaggcag ggatattcac cattatcgtt
1681 tcagacccac ctcccaaccc cgaggggacc cgacaggccc gaaggaatag aagaagaagg
1741 tggagagaga gacagagaca gatccattcg attagtgaac ggatctcgac ggtatcggtt
1801 aacttttaaa agaaaagggg ggattggggg gtacagtgca ggggaaagaa tagtagacat
1861 aatagcaaca gacatacaaa ctaaagaatt acaaaaacaa attacaaaat tcaaaatttt
1921 atcgatacta gtattatgcc cagtacatga ccttatggga ctttcctact tggcagtaca
1981 tctacgtatt agtcatcgct attaccatgg tgatgcggtt ttggcagtac atcaatgggc
2041 gtggatagcg gtttgactca cggggatttc caagtctcca ccccattgac gtcaatggga
2101 gtttgttttg gcaccaaaat caacgggact ttccaaaatg tcgtaacaac tccgccccat
2161 tgacgcaaat gggcggtagg cgtgtacggt gggaggttta tataagcaga gctcgtttag
2221 tgaaccgtca gatcgcctgg agacgccatc cacgctgttt tgacctccat agaagattct
2281 agagccgcca ccatgcttct cctggtgaca agccttctgc tctgtgagtt accacaccca
2341 gcattcctcc tgatcccaca ggtgcagctg gtgcagagcg gcgcggaagt gaaaaaaccg
2401 ggcgcgagcg tgaaagtgag ctgcaaagcg agcggctata gctttccgga ttattatatt
2461 aactgggtgc gccaggcgcc gggccagggc ctggaatgga tgggctggat ttattttgcg
2521 agcggcaaca gcgaatataa ccagaaattt accggccgcg tgaccatgac ccgcgatacc
2581 agcagcagca ccgcgtatat ggaactgagc agcctgcgca gcgaagatac cgcggtgtat
2641 ttttgcgcga gcctgtatga ttatgattgg tattttgatg tgtggggcca gggcaccatg
2701 gtgaccgtga gcagcggcgg cggcggcagc ggcggcggcg gcagcggcgg cggcggcagc
2761 gatattgtga tgacccagac cccgctgagc ctgagcgtga ccccgggcga accggcgagc
2821 attagctgca aaagcagcca gagcctggtg catagcaacg gcaacaccta tctgcattgg
2881 tatctgcaga aaccgggcca gagcccgcag ctgctgattt ataaagtgag caaccgcttt
2941 agcggcgtgc cggatcgctt tagcggcagc ggcagcggcg cggattttac cctgaaaatt
3001 agccgcgtgg aagcggaaga tgtgggcgtg tattattgcg cggaaaccag ccatgtgccg
3061 tggacctttg gccagggcac caaactggaa attaaaagcg gtggcggcgg ttctggtggc
3121 ggcggttctg gtggcggcgg ttctctcgag gatggtaatg aagaaatggg tggtattaca
3181 cagacaccat ataaagtctc catctctgga accacagtaa tattgacatg ccctcagtat
3241 cctggatctg aaatactatg gcaacacaat gataaaaaca taggcggtga tgaggatgat
3301 aaaaacatag gcagtgatga ggatcacctg tcactgaagg aattttcaga attggagcaa
3361 agtggttatt atgtctgcta ccccagagga agcaaaccag aagatgcgaa cttttatctc
3421 tacctgaggg caagagtgtg tgagaactgc atggagatgg atgtgatgtc ggtggccaca
```

-continued

| CONSTRUCT SEQUENCES |
|---|
| 3481 attgtcatag tggacatctg catcactggg ggcttgctgc tgctggttta ctactggagc |
| 3541 aagaatagaa aggccaaggc caagcctgtg acacgaggag cgggtgctgg cggcaggcaa |
| 3601 aggggacaaa acaaggagag gccaccacct gttcccaacc cagactatga gcccatccgg |
| 3661 aaaggccagc gggacctgta ttctggcctg aatcagagac gcatctgata agaattcgga |
| 3721 tccgcggccg cgaaggatct gcgatcgctc cggtgcccgt cagtgggcag agcgcacatc |
| 3781 gcccacagtc cccgagaagt tggggggagg ggtcggcaat tgaacgggtg cctagagaag |
| 3841 gtggcgcggg gtaaactggg aaagtgatgt cgtgtactgg ctccgccttt ttcccgaggg |
| 3901 tgggggagaa ccgtatataa gtgcagtagt cgccgtgaac gttctttttc gcaacgggtt |
| 3961 tgccgccaga acacagctga agcttcgagg ggctcgcatc tctccttcac gcgcccgccg |
| 4021 ccctacctga ggccgccatc cacgccggtt gagtcgcgtt ctgccgcctc ccgcctgtgg |
| 4081 tgcctcctga actgcgtccg ccgtctaggt aagtttaaag ctcaggtcga gaccgggcct |
| 4141 ttgtccggcg ctcccttgga gcctacctag actcagccgg ctctccacgc tttgcctgac |
| 4201 cctgcttgct caactctacg tctttgtttc gttttctgtt ctgcgccgtt acagatccaa |
| 4261 gctgtgaccg gcgcctacgc tagatgaccg agtacaagcc cacggtgcgc ctcgccaccc |
| 4321 gcgacgacgt ccccagggcc gtacgcaccc tcgccgccgc gttcgccgac taccccgcca |
| 4381 cgcgccacac cgtcgatccg gaccgccaca tcgagcgggt caccgagctg caagaactct |
| 4441 tcctcacgcg cgtcgggctc gacatcggca aggtgtgggt cgcggacgac ggcgccgcgg |
| 4501 tggcggtctg gaccacgccg gagagcgtcg aagcgggggc ggtgttcgcc gagatcggcc |
| 4561 cgcgcatggc cgagttgagc ggttcccggc tggccgcgca gcaacagatg gaaggcctcc |
| 4621 tggcgccgca ccggcccaag gagcccgcgt ggttcctggc caccgtcggc gtctcgcccg |
| 4681 accaccaggg caagggtctg ggcagcgccg tcgtgctccc cggagtggag gcggccgagc |
| 4741 gcgccggggt gcccgccttc ctggagacct ccgcgccccg caacctcccc ttctacgagc |
| 4801 ggctcggctt caccgtcacc gccgacgtcg aggtgcccga aggaccgcgc acctggtgca |
| 4861 tgacccgcaa gcccggtgcc tgagtcgaca atcaacctct ggattacaaa atttgtgaaa |
| 4921 gattgactgg tattcttaac tatgttgctc cttttacgct atgtggatac gctgctttaa |
| 4981 tgcctttgta tcatgctatt gcttcccgta tggctttcat tttctcctcc ttgtataaat |
| 5041 cctggttgct gtctctttat gaggagttgt ggcccgttgt caggcaacgt ggcgtggtgt |
| 5101 gcactgtgtt tgctgacgca acccccactg gttggggcat tgccaccacc tgtcagctcc |
| 5161 tttccgggac tttcgctttc cccctcccta ttgccacggc ggaactcatc gccgcctgcc |
| 5221 ttgcccgctg ctggacaggg gctcggctgt tgggcactga caattccgtg gtgttgtcgg |
| 5281 ggaaatcatc gtcctttcct tggctgctcg cctgtgttgc cacctggatt ctgcgcggga |
| 5341 cgtccttctg ctacgtccct tcggccctca atccagcgga ccttccttcc cgcggcctgc |
| 5401 tgccggctct gcggcctctt ccgcgtcttc gccttcgccc tcagacgagt cggatctccc |
| 5461 tttgggccgc ctccccgcct ggtaccttta agaccaatga cttacaaggc agctgtagat |
| 5521 cttagccact ttttaaaaga aaagggggga ctggaagggc taattcactc ccaacgaaaa |
| 5581 taagatctgc tttttgcttg tactgggtct ctctggttag accagatctg agcctgggag |
| 5641 ctctctggct aactagggaa cccactgctt aagcctcaat aaagcttgcc ttgagtgctt |
| 5701 caagtagtgt gtgcccgtct gttgtgtgac tctggtaact agagatccct cagacccttt |
| 5761 tagtcagtgt ggaaaatctc tagcagtagt agttcatgtc atcttattat tcagtattta |
| 5821 taacttgcaa agaaatgaat atcagagagt gagaggaact tgtttattgc agcttataat |
| 5881 ggttacaaat aaagcaatag catcacaaat ttcacaaata aagcattttt ttcactgcat |
| 5941 tctagttgtg gtttgtccaa actcatcaat gtatcttatc atgtctggct ctagctatcc |
| 6001 cgcccctaac tccgcccagt tccgcccatt ctccgcccca tggctgacta atttttttta |
| 6061 tttatgcaga ggccgaggcc gcctcggcct ctgagctatt ccagaagtag tgaggaggct |
| 6121 tttttggagg cctagacttt tgcagagacg gcccaaattc gtaatcatgg tcatagctgt |
| 6181 ttcctgtgtg aaattgttat ccgctcacaa ttccacacaa catacgagcc ggaagcataa |
| 6241 agtgtaaagc ctggggtgcc taatgagtga gctaactcac attaattgcg ttgcgctcac |
| 6301 tgcccgcttt ccagtcggga aacctgtcgt gccagctgca ttaatgaatc ggccaacgcg |
| 6361 cggggagagg cggtttgcgt attgggcgct cttccgcttc ctcgctcact gactcgctgc |
| 6421 gctcggtcgt tcggctgcgg cgagcggtat cagctcactc aaaggcggta atacggttat |
| 6481 ccacagaatc aggggataac gcaggaaaga acatgtgagc aaaaggccag caaaaggcca |
| 6541 ggaaccgtaa aaaggccgcg ttgctggcgt ttttccatag gctccgcccc cctgacgagc |
| 6601 atcacaaaaa tcgacgctca agtcagaggt ggcgaaaccc gacaggacta taaagatacc |
| 6661 aggcgtttcc ccctggaagc tccctcgtgc gctctcctgt tccgaccctg ccgcttaccg |
| 6721 gatacctgtc cgcctttctc ccttcgggaa gcgtggcgct ttctcatagc tcacgctgta |
| 6781 ggtatctcag ttcggtgtag gtcgttcgct ccaagctggg ctgtgtgcac gaaccccccg |
| 6841 ttcagcccga ccgctgcgcc ttatccggta actatcgtct tgagtccaac ccggtaagac |
| 6901 acgacttatc gccactggca gcagccactg gtaacaggat tagcagagcg aggtatgtag |
| 6961 gcggtgctac agagttcttg aagtggtggc ctaactacgg ctacactaga aggacagtat |
| 7021 ttggtatctg cgctctgctg aagccagtta ccttcggaaa aagagttggt agctcttgat |
| 7081 ccggcaaaca aaccaccgct ggtagcggtg gtttttttgt ttgcaagcag cagattacgc |
| 7141 gcagaaaaaa aggatctcaa gaagatcctt tgatcttttc tacggggtct gacgctcagt |
| 7201 ggaacgaaaa ctcacgttaa gggattttgg tcatgagatt atcaaaaagg atcttcacct |
| 7261 agatcctttt aaattaaaaa tgaagtttta aatcaatcta aagtatatat gagtaaactt |
| 7321 ggtctgacag ttaccaatgc ttaatcagtg aggcacctat ctcagcgatc tgtctatttc |
| 7381 gttcatccat agttgcctga ctccccgtcg tgtagataac tacgatacgg gagggcttac |
| 7441 catctggccc cagtgctgca atgataccgc gagacccacg ctcaccggct ccagatttat |
| 7501 cagcaataaa ccagccagcc ggaagggccg agcgcagaag tggtcctgca actttatccg |
| 7561 cctccatcca gtctattaat tgttgccggg aagctagagt aagtagttcg ccagttaata |
| 7621 gtttgcgcaa cgttgttgcc attgctacag gcatcgtggt gtcacgctcg tcgtttggta |
| 7681 tggcttcatt cagctccggt tcccaacgat caaggcgagt tacatgatcc cccatgttgt |
| 7741 gcaaaaaagc ggttagctcc ttcggtcctc cgatcgttgt cagaagtaag ttggccgcag |
| 7801 tgttatcact catggttatg gcagcactgc ataattctct tactgtcatg ccatccgtaa |
| 7861 gatgcttttc tgtgactggt gagtactcaa ccaagtcatt ctgagaatag tgtatgcggc |
| 7921 gaccgagttg ctcttgcccg gcgtcaatac gggataatac cgcgccacat agcagaactt |
| 7981 taaaagtgct catcattgga aaacgttctt cggggcgaaa actctcaagg atcttaccgc |
| 8041 tgttgagatc cagttcgatg taacccactc gtgcacccaa ctgatcttca gcatctttta |

-continued

CONSTRUCT SEQUENCES

```
8101 ctttcaccag cgtttctggg tgagcaaaaa caggaaggca aaatgccgca aaaaagggaa
8161 taagggcgac acggaaatgt tgaatactca tactcttcct ttttcaatat tattgaagca
8221 tttatcaggg ttattgtctc atgagcggat acatatttga atgtatttag aaaaataaac
8281 aaataggggt tccgcgcaca tttccccgaa aagtgccacc tgacgtctaa gaaaccatta
8341 ttatcatgac attaacctat aaaaataggc gtatcacgag gccctttcgt ctcgcgcgtt
8401 tcggtgatga cggtgaaaac ctctgacaca tgcagctccc ggagacggtc acagcttgtc
8461 tgtaagcgga tgccgggagc agacaagccc gtcagggcgc gtcagcgggt gttggcgggt
8521 gtcggggctg gcttaactat gcggcatcag agcagattgt actgagagtg caccatatgc
8581 ggtgtgaaat accgcacaga tgcgtaagga gaaaataccg catcaggcgc cattcgccat
8641 tcaggctgcg caactgttgg gaagggcgat cggtgcgggc ctcttcgcta ttacgccagc
8701 tggcgaaagg gggatgtgct gcaaggcgat taagttgggt aacgccaggg ttttcccagt
8761 cacgacgttg taaaacgacg gccagtgcca agctg
```

p510_antiBCMA_CD3gamma (SEQ ID NO: 23)

```
   1 acgcgtgtag tcttatgcaa tactcttgta gtcttgcaac atggtaacga tgagttagca
  61 acatgcctta caaggagaga aaaagcaccg tgcatgccga ttggtggaag taaggtggta
 121 cgatcgtgcc ttattaggaa ggcaacagac gggtctgaca tggattggac gaaccactga
 181 attgccgcat tgcagagata ttgtatttaa gtgcctagct cgatacaata aacgggtctc
 241 tctggttaga ccagatctga gcctgggagc tctctggcta actagggaac ccactgctta
 301 agcctcaata aagcttgcct tgagtgcttc aagtagtgtg tgcccgtctg ttgtgtgact
 361 ctggtaacta gagatccctc agaccctttt agtcagtgtg gaaaatctct agcagtggcg
 421 cccgaacagg gacctgaaag cgaaagggaa accagagctc tctcgacgca ggactcggct
 481 tgctgaagcg cgcacggcaa gaggcgaggg gcggcgactg gtgagtacgc caaaaatttt
 541 gactagcgga ggctagaagg agagagatgg gtgcgagagc gtcagtatta agcgggggag
 601 aattagatcg cgatgggaaa aaattcggtt aaggccaggg ggaaagaaaa aatataaatt
 661 aaaacatata gtatgggcaa gcagggagct agaacgattc gcagttaatc ctggcctgtt
 721 agaaacatca gaaggctgta gacaaatact gggacagcta caaccatccc ttcagacagg
 781 atcagaagaa cttagatcat tatataatac agtagcaacc ctctattgtg tgcatcaaag
 841 gatagagata aaagacacca aggaagcttt agacaagata gaggaagagc aaaacaaaag
 901 taagaccacc gcacagcaag cggccactga tcttcagacc tggaggagga gatatgaggg
 961 acaattggag aagtgaatta tataaatata aagtagtaaa aattgaacca ttaggagtag
1021 cacccaccaa ggcaaagaga agagtggtgc agagagaaaa aagagcagtg ggaataggag
1081 ctttgttcct tgggttcttg ggagcagcag gaagcactat gggcgcagcc tcaatgacgc
1141 tgacggtaca ggccagacaa ttattgtctg gtatagtgca gcagcagaac aatttgctga
1201 gggctattga ggcgcaacag catctgttgc aactcacagt ctggggcatc aagcagctcc
1261 aggcaagaat cctggctgtg gaaagatacc taaaggatca acagctcctg gggatttggg
1321 gttgctctgg aaaactcatt tgcaccactg ctgtgccttg gaatgctagt tggagtaata
1381 aatctctgga acagattgga atcacacgac ctggatggag tgggacagag aaattaacaa
1441 ttacacaagc ttaatacact ccttaattga agaatcgcaa aaccagcaag aaaagaatga
1501 acaagaatta ttggaattag ataaatgggc aagtttgtgg aattggttta acataacaaa
1561 ttggctgtgg tatataaaat tattcataat gatagtagga ggcttggtag gtttaagaat
1621 agtttttgct gtactttcta tagtgaatag agttaggcag ggatattcac cattatcgtt
1681 tcagacccac ctcccaaccc cgaggggacc cgacaggccc gaaggaatag aagaagaagg
1741 tggagagaga gacagagaca gatccattcg attagtgaac ggatctcgac ggtatcggtt
1801 aacttttaaa agaaaagggg ggattggggg gtacagtgca ggggaaagaa tagtagacat
1861 aatagcaaca gacatacaaa ctaaagaatt acaaaaacaa attacaaaat tcaaaatttt
1921 atcgatacta gtattatgcc cagtacatga ccttatggga ctttcctact tggcagtaca
1981 tctacgtatt agtcatcgct attaccatgg tgatgcggtt ttggcagtac atcaatgggc
2041 gtggatagcg gtttgactca cggggatttc caagtctcca ccccattgac gtcaatggga
2101 gtttgttttg gcaccaaaat caacgggact ttccaaaatg tcgtaacaac tccgccccat
2161 tgacgcaaat gggcggtagg cgtgtacggt gggaggttta tataagcaga gctcgtttag
2221 tgaaccgtca gatcgcctgg agacgccatc cacgctgttt tgacctccat agaagattct
2281 agagccgcca ccatgcttct cctggtgaca agccttctgc tctgtgagtt accacaccca
2341 gcattcctcc tgatcccaca ggtgcagctg gtgcagagcg gcgcggaagt gaaaaaaccg
2401 ggcgcgagcg tgaaagtgag ctgcaaagcg agcggctata gctttccgga ttattatatt
2461 aactgggtgc gccaggcgcc gggccagggc ctggaatgga tgggctggat ttattttgcg
2521 agcggcaaca gcgaatataa ccagaaattt accggccgcg tgaccatgac ccgcgatacc
2581 agcagcagca ccgcgtatat ggaactgagc agcctgcgca gcgaagatac cgcggtgtat
2641 ttttgcgcga gcctgtatga ttatgattgg tattttgatg tgtggggcca gggcaccatg
2701 gtgaccgtga gcagcggcgg cggcggcagc ggcggcggcg gcagcggcgg cggcggcagc
2761 gatattgtga tgacccagac cccgctgagc ctgagcgtga ccccgggcga accggcgagc
2821 attagctgca aaagcagcca gagcctggtg catagcaacg gcaacaccta tctgcattgg
2881 tatctgcaga aaccgggcca gagcccgcag ctgctgattt ataaagtgag caaccgcttt
2941 agcggcgtgc cggatcgctt tagcggcagc ggcagcggcg cggattttac cctgaaaatt
3001 agccgcgtgg aagcggaaga tgtgggcgtg tattattgcg cggaaaccag ccatgtgccg
3061 tggacctttg gccagggcac caaactggaa attaaaagcg gtggcggcgg ttctggtggc
3121 ggcggttctg gtggcggcgg ttctctcgag cagtcaatca aaggaaacca cttggttaag
3181 gtgtatgact atcaagaaga tggttcggta cttctgactt gtgatgcaga agccaaaaat
3241 atcacatggt ttaaagatgg gaagatgatc ggcttcctaa ctgaagataa aaaaaaatgg
3301 aatctgggaa gtaatgccaa ggacccacga gggatgtatc agtgtaaagg atcacagaac
3361 aagtcaaaac cactccaagt gtattacaga atgtgtcaga actgcattga actaaatgca
3421 gccaccatat ctggctttct ctttgctgaa atcgtcagca ttttcgtcct tgctgttggg
3481 gtctacttca ttgctggaca ggatggagtt cgccagtcga gagcttcaga caagcagact
3541 ctgttgccca atgaccagct ctaccagccc ctcaaggatc gagaagatga ccagtacagc
3601 caccttcaag gaaaccagtt gaggaggaat tgataagaat tcggatccgc ggccgcgaag
3661 gatctgcgat cgctccggtg cccgtcagtg ggcagagcgc acatcgccca cagtccccga
3721 gaagttgggg ggaggggtcg gcaattgaac gggtgcctag agaaggtggc gcggggtaaa
```

-continued

CONSTRUCT SEQUENCES

```
3781 ctgggaaagt gatgtcgtgt actggctccg cctttttccc gagggtgggg gagaaccgta
3841 tataagtgca gtagtcgccg tgaacgttct ttttcgcaac gggtttgccg ccagaacaca
3901 gctgaagctt cgaggggctc gcatctctcc ttcacgcgcc cgccgcccta cctgaggccg
3961 ccatccacgc cggttgagtc gcgttctgcc gcctcccgcc tgtggtgcct cctgaactgc
4021 gtccgccgtc taggtaagtt taaagctcag gtcgagaccg ggcctttgtc cggcgctccc
4081 ttggagccta cctagactca gccggctctc cacgctttgc ctgaccctgc ttgctcaact
4141 ctacgtcttt gtttcgtttt ctgttctgcg ccgttacaga tccaagctgt gaccggcgcc
4201 tacgctagat gaccgagtac aagcccacgg tgcgcctcgc cacccgcgac gacgtcccca
4261 gggccgtacg caccctcgcc gccgcgttcg ccgactaccc cgccacgcgc cacaccgtcg
4321 atccggaccg ccacatcgag cgggtcaccg agctgcaaga actcttcctc acgcgcgtcg
4381 ggctcgacat cggcaaggtg tgggtcgcgg acgacggcgc cgcggtggcg gtctggacca
4441 cgccggagag cgtcgaagcg gggggcggtgt tcgccgagat cggcccgcgc atggccgagt
4501 tgagcggttc ccggctggcc gcgcagcaac agatggaagg cctcctggcg ccgcaccggc
4561 ccaaggagcc cgcgtggttc ctggccaccg tcggcgtctc gcccgaccac cagggcaagg
4621 gtctgggcag cgccgtcgtg ctccccggag tggaggcggc cgagcgcgcc ggggtgcccg
4681 ccttcctgga gacctccgcg ccccgcaacc tccccttcta cgagcggctc ggcttcaccg
4741 tcaccgccga cgtcgaggtg cccgaaggac cgcgcacctg gtgcatgacc cgcaagcccg
4801 gtgcctgagt cgacaatcaa cctctggatt acaaaatttg tgaaagattg actggtattc
4861 ttaactatgt tgctcctttt acgctatgtg gatacgctgc tttaatgcct ttgtatcatg
4921 ctattgcttc ccgtatggct ttcattttct cctccttgta taaatcctgg ttgctgtctc
4981 tttatgagga gttgtggccc gttgtcaggc aacgtggcgt ggtgtgcact gtgtttgctg
5041 acgcaacccc cactggttgg ggcattgcca ccacctgtca gctcctttcc gggactttcg
5101 ctttccccct ccctattgcc acggcggaac tcatcgccgc ctgccttgcc cgctgctgga
5161 caggggctcg gctgttgggc actgacaatt ccgtggtgtt gtcggggaaa tcatcgtcct
5221 ttccttggct gctcgcctgt gttgccacct ggattctgcg cgggacgtcc ttctgctacg
5281 tcccttcggc cctcaatcca gcggaccttc cttcccgcgg cctgctgccg gctctgcggc
5341 ctcttccgcg tcttcgcctt cgccctcaga cgagtcggat ctccctttgg gccgcctccc
5401 cgcctggtac ctttaagacc aatgacttac aaggcagctg tagatcttag ccacttttta
5461 aaagaaaagg ggggactgga agggctaatt cactcccaac gaaaataaga tctgcttttt
5521 gcttgtactg ggtctctctg gttagaccag atctgagcct gggagctctc tggctaacta
5581 gggaacccac tgcttaagcc tcaataaagc ttgccttgag tgcttcaagt agtgtgtgcc
5641 cgtctgttgt gtgactctgg taactagaga tccctcagac ccttttagtc agtgtggaaa
5701 atctctagca gtagtagttc atgtcatctt attattcagt atttataact tgcaaagaaa
5761 tgaatatcag agagtgagag gaacttgttt attgcagctt ataatggtta caaataaagc
5821 aatagcatca caaatttcac aaataaagca tttttttcac tgcattctag ttgtggtttg
5881 tccaaactca tcaatgtatc ttatcatgtc tggctctagc tatcccgccc ctaactccgc
5941 ccagttccgc ccattctccg ccccatggct gactaatttt ttttatttat gcagaggccg
6001 aggccgcctc ggcctctgag ctattccaga agtagtgagg aggctttttt ggaggcctag
6061 acttttgcag agacggccca aattcgtaat catggtcata gctgtttcct gtgtgaaatt
6121 gttatccgct cacaattcca cacaacatac gagccggaag cataaagtgt aaagcctggg
6181 gtgcctaatg agtgagctaa ctcacattaa ttgcgttgcg ctcactgccc gctttccagt
6241 cgggaaacct gtcgtgccag ctgcattaat gaatcggcca acgcgcgggg agaggcggtt
6301 tgcgtattgg gcgctcttcc gcttcctcgc tcactgactc gctgcgctcg gtcgttcggc
6361 tgcggcgagc ggtatcagct cactcaaagg cggtaatacg gttatccaca gaatcagggg
6421 ataacgcagg aaagaacatg tgagcaaaag gccagcaaaa ggccaggaac cgtaaaaagg
6481 ccgcgttgct ggcgtttttc cataggctcc gcccccctga cgagcatcac aaaaatcgac
6541 gctcaagtca gaggtggcga aacccgacag gactataaag ataccaggcg tttccccctg
6601 gaagctccct cgtgcgctct cctgttccga ccctgccgct taccggatac ctgtccgcct
6661 ttctcccttc gggaagcgtg gcgctttctc atagctcacg ctgtaggtat ctcagttcgg
6721 tgtaggtcgt tcgctccaag ctgggctgtg tgcacgaacc ccccgttcag cccgaccgct
6781 gcgccttatc cggtaactat cgtcttgagt ccaacccggt aagacacgac ttatcgccac
6841 tggcagcagc cactggtaac aggattagca gagcgaggta tgtaggcggt gctacagagt
6901 tcttgaagtg gtggcctaac tacggctaca ctagaaggac agtatttggt atctgcgctc
6961 tgctgaagcc agttaccttc ggaaaaagag ttggtagctc ttgatccggc aaacaaacca
7021 ccgctggtag cggtggtttt tttgtttgca agcagcagat tacgcgcaga aaaaaaggat
7081 ctcaagaaga tcctttgatc ttttctacgg ggtctgacgc tcagtggaac gaaaactcac
7141 gttaagggat tttggtcatg agattatcaa aaaggatctt cacctagatc cttttaaatt
7201 aaaaatgaag ttttaaatca atctaaagta tatatgagta aacttggtct gacagttacc
7261 aatgcttaat cagtgaggca cctatctcag cgatctgtct atttcgttca tccatagttg
7321 cctgactccc cgtcgtgtag ataactacga tacgggaggg cttaccatct ggccccagtg
7381 ctgcaatgat accgcgagac ccacgctcac cggctccaga tttatcagca ataaaccagc
7441 cagccggaag ggccgagcgc agaagtggtc ctgcaacttt atccgcctcc atccagtcta
7501 ttaattgttg ccgggaagct agagtaagta gttcgccagt taatagtttg cgcaacgttg
7561 ttgccattgc tacaggcatc gtggtgtcac gctcgtcgtt tggtatggct tcattcagct
7621 ccggttccca acgatcaagg cgagttacat gatcccccat gttgtgcaaa aaagcggtta
7681 gctccttcgg tcctccgatc gttgtcagaa gtaagttggc cgcagtgtta tcactcatgg
7741 ttatggcagc actgcataat tctcttactg tcatgccatc cgtaagatgc ttttctgtga
7801 ctggtgagta ctcaaccaag tcattctgag aatagtgtat gcggcgaccg agttgctctt
7861 gcccggcgtc aatacgggat aataccgcgc cacatagcag aactttaaaa gtgctcatca
7921 ttggaaaacg ttcttcgggg cgaaaactct caaggatctt accgctgttg agatccagtt
7981 cgatgtaacc cactcgtgca cccaactgat cttcagcatc ttttactttc accagcgttt
8041 ctgggtgagc aaaaacagga aggcaaaatg ccgcaaaaaa gggaataagg gcgacacgga
```

-continued

| CONSTRUCT SEQUENCES |
|---|
| 8101 aatgttgaat actcatactc ttcctttttc aatattattg aagcatttat cagggttatt |
| 8161 gtctcatgag cggatacata tttgaatgta tttagaaaaa taaacaaata ggggttccgc |
| 8221 gcacatttcc ccgaaaagtg ccacctgacg tctaagaaac cattattatc atgacattaa |
| 8281 cctataaaaa taggcgtatc acgaggccct ttcgtctcgc gcgtttcggt gatgacggtg |
| 8341 aaaacctctg acacatgcag ctcccggaga cggtcacagc ttgtctgtaa gcggatgccg |
| 8401 ggagcagaca agcccgtcag ggcgcgtcag cgggtgttgg cgggtgtcgg ggctggctta |
| 8461 actatgcggc atcagagcag attgtactga gagtgcacca tatgcggtgt gaaataccgc |
| 8521 acagatgcgt aaggagaaaa taccgcatca ggcgccattc gccattcagg ctgcgcaact |
| 8581 gttgggaagg gcgatcggtg cgggcctctt cgctattacg ccagctggcg aaagggggat |
| 8641 gtgctgcaag gcgattaagt tgggtaacgc cagggttttc ccagtcacga cgttgtaaaa |
| 8701 cgacggccag tgccaagctg. |

Example 2: Antibody Sequences

Generation of Antibody Sequences

The human CD19 polypeptide canonical sequence is UniProt Accession No. P15391 (or P15391-1). The human BCMA polypeptide canonical sequence is UniProt Accession No. Q02223 (or Q02223-1). Provided are antibody polypeptides that are capable of specifically binding to the human CD19 polypeptide or human BCMA polypeptide or human FAP polypeptide or human BCMA polypeptide, and fragments or domains thereof. Anti-CD19, anti-FAP, anti-CAIX and anti-BCMA antibodies can be generated using diverse technologies (see, e.g., (Nicholson et al, 1997). Where murine anti-CD19, anti-FAP, anti-CAIX or anti-BCMA antibodies are used as a starting material, humanization of murine anti-CD19, anti-FAP, anti-CAIX or anti-BCMA antibodies is desired for the clinical setting, where the mouse-specific residues may induce a human-anti-mouse antigen (HAMA) response in subjects who receive T-cell receptor (TCR) fusion protein (TFP) treatment, i.e., treatment with T-cells transduced with the TFP.CD19, TFP-.FAP, TFP.CAIX, or TFP.BCMA construct. Humanization is accomplished by grafting CDR regions from murine anti-CD19, anti-FAP, anti-CAIX or anti-BCMA antibody onto appropriate human germline acceptor frameworks, optionally including other modifications to CDR and/or framework regions. As provided herein, antibody and antibody fragment residue numbering follows Kabat (Kabat E. A. et al, 1991; Chothia et al, 1987).

Generation of scFvs

Human or humanized anti-CD19, anti-FAP, anti-CAIX or anti-BMCA IgGs are used to generate scFv sequences for TFP constructs. DNA sequences coding for human or humanized $V_L$ and $V_H$ domains are obtained, and the codons for the constructs are, optionally, optimized for expression in cells from *Homo sapiens*. The order in which the $V_L$ and $V_H$ domains appear in the scFv is varied (i.e., $V_L$—$V_H$, or $V_H$—$V_L$ orientation), and three copies of the (SEQ ID NO: 74)" or "$G_4S$ (SEQ ID NO: 74)" subunit $(G_4S)_3$ (SEQ ID NO: 71) connect the variable domains to create the scFv domain. Anti-CD19, anti-FAP, anti-CAIX and anti-BCMA scFv plasmid constructs can have optional Flag, His or other affinity tags, and are electroporated into HEK293 or other suitable human or mammalian cell lines and purified. Validation assays include binding analysis by FACS, kinetic analysis using Proteon, and staining of CD19-expressing cells.

Exemplary anti-CD19 or anti-BMCA CDRs of $V_L$ and $V_H$ domains and the nucleotide sequences encoding them, respectively, are shown below:

Anti-CD19

Anti-CD19 light chain CDR1

Coding Sequence:

(SEQ ID NO: 24)
AGGGCAAGTCAGGACATTAGTAAA.

Amino acid sequence:

(SEQ ID NO: 25)
RASQDISK.

Anti-CD19 light chain CDR2

Coding Sequence:

(SEQ ID NO: 26)
ATCTACCATACATCAAGATTA.

Amino acid sequence:

(SEQ ID NO: 27)
IYHTSRL.

Anti-CD19 light chain CDR3

Coding Sequence:

(SEQ ID NO: 28)
CAACAGGGTAATACGCTTCCGTACACG.

Amino acid sequence:

(SEQ ID NO: 29)
QQGNTLPYT.

Anti-CD19 heavy chain CDR1

Coding Sequence:

(SEQ ID NO: 30)
GGGGTCTCATTACCCGACTATGGTGTAAGC.

Amino acid sequence:

(SEQ ID NO: 31)
GVSLPDYGVS.

Anti-CD19 heavy chain CDR2

Coding Sequence:

(SEQ ID NO: 32)
GTAATATGGGGTAGTGAAACCACATACTATAATTCAGCTCTC.

Amino acid sequence:

(SEQ ID NO: 33)
VIWGSETTYYNSAL.

Anti-CD19 heavy chain CDR3

Coding Sequence:
(SEQ ID NO: 34)
CATTATTACTACGGTGGTAGCTATGCTATGGACTAC.

Amino acid sequence:
(SEQ ID NO: 35)
HYYYGGSYAMDY.

Anti-BCMA

Anti-BCMA light chain CDR1

Coding Sequence:
(SEQ ID NO: 36)
AAAAGCAGCCAGAGCCTGGTGCATAGCAACGGCAACACCTATCTGCAT.

Amino acid sequence:
(SEQ ID NO: 37)
KSSQSLVHSNGNTYLH.

Anti-BCMA light chain CDR2

Coding Sequence:
(SEQ ID NO: 38)
AAAGTGAGCAACCGCTTTAGC.

Amino acid sequence:
(SEQ ID NO: 39)
KVSNRFS.

Anti-BCMA light chain CDR3

Coding Sequence:
(SEQ ID NO: 40)
GCGGAAACCAGCCATGTGCCGTGGACC

Amino acid sequence:
(SEQ ID NO: 41)
AETSHVPWT.

Anti-BCMA heavy chain CDR1

Coding Sequence:
(SEQ ID NO: 42)
AAAGCGAGCGGCTATAGCTTTCCGGATTATTATATTAAC.

Amino acid sequence:
(SEQ ID NO: 43)
KASGYSFPDYYIN.

Anti-BCMA heavy chain CDR2

Coding Sequence:
(SEQ ID NO: 44)
TGGATTTATTTTGCGAGCGGCAACAGCGAATATAACCAGAAATTTACCGG
C.

Amino acid sequence:
(SEQ ID NO: 45)
WIYFASGNSEYNQKFTG.

Anti-BCMA heavy chain CDR3

Coding Sequence:
(SEQ ID NO: 46)
CTGTATGATTATGATTGGTATTTTGATGTG.

-continued

Amino acid sequence:
(SEQ ID NO: 47)
LYDYDWYFDV.

Anti-CD19 light chain variable region

Coding Sequence:
(SEQ ID NO: 48)
GACATCCAGATGACACAGACTACATCCTCCCTGTCTGCCTCTCTGGGAGA
CAGAGTCACCATCAGTTGCAGGGCAAGTCAGGACATTAGTAAATATTTAA
ATTGGTATCAGCAGAAACCAGATGGAACTGTTAAACTCCTGATCTACCAT
ACATCAAGATTACACTCAGGAGTCCCATCAAGGTTCAGTGGCAGTGGGTC
TGGAACAGATTATTCTCTCACCATTAGCAACCTGGAGCAAGAAGATATTG
CCACTTACTTTTGCCAACAGGGTAATACGCTTCCGTACACGTTCGGAGGG
GGGACTAAGTTGGAAATAACA.

Amino acid sequence:
(SEQ ID NO: 49)
DIQMTQTTSSLSASLGDRVTISCRASQDISKYLNWYQQKPDGTVKLLIYH
TSRLHSGVPSRFSGSGSGTDYSLTISNLEQEDIATYFCQQGNTLPYTFGG
GTKLEIT.

Anti-CD19 heavy chain variable region

Coding Sequence:
(SEQ ID NO: 50)
GAGGTGAAACTGCAGGAGTCAGGACCTGGCCTGGTGGCGCCCTCACAGAG
CCTGTCCGTCACATGCACTGTCTCAGGGGTCTCATTACCCGACTATGGTG
TAAGCTGGATTCGCCAGCCTCCACGAAAGGGTCTGGAGTGGCTGGGAGTA
ATATGGGGTAGTGAAACCACATACTATAATTCAGCTCTCAAATCCAGACT
GACCATCATCAAGGACAACTCCAAGAGCCAAGTTTTCTTAAAAATGAACA
GTCTGCAAACTGATGACACAGCCATTTACTACTGTGCCAAACATTATTAC
TACGGTGGTAGCTATGCTATGGACTACTGGGGTCAAGGAACCTCAGTCAC
CGTCTCCTCA.

Amino acid sequence:
(SEQ ID NO: 51)
EVKLQESGPGLVAPSQSLSVTCTVSGVSLPDYGVSWIRQPPRKGLEWLGV
IWGSETTYYNSALKSRLTIIKDNSKSQVFLKMNSLQTDDTAIYYCAKHYY
YGGSYAMDYWGQGTSVTVSS.

Anti-BCMA light chain variable region

Coding Sequence:
(SEQ ID NO: 52)
GATATTGTGATGACCCAGACCCCGCTGAGCCTGAGCGTGACCCCGGGCGA
ACCGGCGAGCATTAGCTGCAAAAGCAGCCAGAGCCTGGTGCATAGCAACG
GCAACACCTATCTGCATTGGTATCTGCAGAAACCGGGCCAGAGCCCGCAG
CTGCTGATTTATAAAGTGAGCAACCGCTTTAGCGGCGTGCCGGATCGCTT
TAGCGGCAGCGGCAGCGGCGCGGATTTTACCCTGAAAATTAGCCGCGTGG
AAGCGGAAGATGTGGGCGTGTATTATTGCGCGGAAACCAGCCATGTGCCG
TGGACCTTTGGCCAGGGCACCAAACTGGAAATTAAAAGC.

-continued

Amino acid sequence:

(SEQ ID NO: 53)
DIVMTQTPLSLSVTPGEPASISCKSSQSLVHSNGNTYLHWYLQKPGQSPQ

LLIYKVSNRFSGVPDRFSGSGSGADFTLKISRVEAEDVGVYYCAETSHVP

WTFGQGTKLEIKS.

Anti-BCMA heavy chain variable region

Coding Sequence:

(SEQ ID NO: 54)
CAGGTGCAGCTGGTGCAGAGCGGCGCGGAAGTGAAAAAACCGGGCGCGAG

CGTGAAAGTGAGCTGCAAAGCGAGCGGCTATAGCTTTCCGGATTATTATA

TTAACTGGGTGCGCCAGGCGCCGGGCCAGGGCCTGGAATGGATGGGCTGG

ATTTATTTTGCGAGCGGCAACAGCGAATATAACCAGAAATTTACCGGCCG

CGTGACCATGACCCGCGATACCAGCAGCAGCACCGCGTATATGGAACTGA

GCAGCCTGCGCAGCGAAGATACCGCGGTGTATTTTTGCGCGAGCCTGTAT

GATTATGATTGGTATTTTGATGTGTGGGGCCAGGGCACCATGGTGACCGT

GAGCAGC.

Amino acid sequence:

(SEQ ID NO: 55)
QVQLVQSGAEVKKPGASVKVSCKASGYSFPDYYINVVVRQAPGQGLEWMG

WIYFASGNSEYNQKFTGRVTMTRDTSSSTAYMELSSLRSEDTAVYFCASL

YDYDWYFDVWGQGTMVTVSS.

Source of TCR Subunits

Subunits of the human T Cell Receptor (TCR) complex all contain an extracellular domain, a transmembrane domain, and an intracellular domain. A human TCR complex contains the CD3-epsilon polypeptide, the CD3-gamma polypeptide, the CD3-delta polypeptide, the CD3-zeta polypeptide, the TCR alpha chain polypeptide and the TCR beta chain polypeptide. The human CD3-epsilon polypeptide canonical sequence is Uniprot Accession No. P07766. The human CD3-gamma polypeptide canonical sequence is Uniprot Accession No. P09693. The human CD3-delta polypeptide canonical sequence is Uniprot Accession No. P043234. The human CD3-zeta polypeptide canonical sequence is Uniprot Accession No. P20963. The human TCR alpha chain canonical sequence is Uniprot Accession No. Q6ISU1. The human TCR beta chain C region canonical sequence is Uniprot Accession No. P01850, a human TCR beta chain V region sequence is P04435.

The human CD3-epsilon polypeptide canonical sequence is:

(SEQ ID NO: 56)
MQSGTHWRVLGLCLLSVGVWGQDGNEEMGGITQTPYKVSISGTTVILTCP

QYPGSEILWQHNDKNIGGDEDDKNIGSDEDHLSLKEFSELEQSGYYVCYP

RGSKPEDANFYLYLRARVCENCMEMDVMSVATIVIVDICITGGLLLLVYY

WSKNRKAKAKPVTRGAGAGGRQRGQNKERPPPVPNPDYEPIRKGQRDLYS

GLNQRRI.

The human CD3-gamma polypeptide canonical sequence is:

(SEQ ID NO: 57)
MEQGKGLAVLILAIILLQGTLAQSIKGNHLVKVYDYQEDGSVLLTCDAEA

KNITWFKDGKMIGFLTEDKKKWNLGSNAKDPRGMYQCKGSQNKSKPLQVY

YRMCQNCIELNAATISGFLFAEIVSIFVLAVGVYFIAGQDGVRQSRASDK

QTLLPNDQLYQPLKDREDDQYSHLQGNQLRRN.

The human CD3-delta polypeptide canonical sequence is:

(SEQ ID NO: 58)
MEHSTFLSGLVLATLLSQVSPFKIPIEELEDRVFVNCNTSITWVEGTVGT

LLSDITRLDLGKRILDPRGIYRCNGTDIYKDKESTVQVHYRMCQSCVELD

PATVAGIIVTDVIATLLLALGVFCFAGHETGRLSGAADTQALLRNDQVYQ

PLRDRDDAQYSHLGGNWARNK.

The human CD3-zeta polypeptide canonical sequence is:

(SEQ ID NO: 59)
MKWKALFTAAILQAQLPITEAQSFGLLDPKLCYLLDGILFIYGVILTALF

LRVKFSRSADAPAYQQGQNQLYNELNLGRREEYDVLDKRRGRDPEMGGKP

QRRKNPQEGLYNELQKDKMAEAYSEIGMKGERRRGKGHDGLYQGLSTATK

DTYDALHMQALPPR.

The human TCR alpha chain canonical sequence is:

(SEQ ID NO: 60)
MAGTWLLLLLALGCPALPTGVGGTPFPSLAPPIMLLVDGKQQMVVVCLVL

DVAPPGLDSPIWFSAGNGSALDAFTYGPSPATDGTWTNLAHLSLPSEELA

SWEPLVCHTGPGAEGHSRSTQPMHLSGEASTARTCPQEPLRGTPGGALWL

GVLRLLLFKLLLFDLLLTCSCLCDPAGPLPSPATTTRLRALGSHRLHPAT

ETGGREATSSPRPQPRDRRWGDTPPGRKPGSPVWGEGSYLSSYPTCPAQA

WCSRSALRAPSSSLGAFFAGDLPPPLQAGAA.

The human TCR alpha chain C region canonical sequence is:

(SEQ ID NO: 61)
PNIQNPDPAVYQLRDSKSSDKSVCLFTDFDSQTNVSQSKDSDVYITDKTV

LDMRSMDFKSNSAVAWSNKSDFACANAFNNSIIPEDTFFPSPESSCDVKL

VEKSFETDTNLNFQNLSVIGFRILLLKVAGFNLLMTLRLWSS.

The human TCR alpha chain V region CTL-L17 canonical sequence is:

(SEQ ID NO: 62)
MAMLLGASVLILWLQPDWVNSQQKNDDQQVKQNSPSLSVQEGRISILNCD

YTNSMFDYFLWYKKYPAEGPTFLISISSIKDKNEDGRFTVFLNKSAKHLS

LHIVPSQPGDSAVYFCAAKGAGTASKLTFGTGTRLQVTL.

The human TCR beta chain C region canonical sequence is:

(SEQ ID NO: 63)
EDLNKVFPPEVAVFEPSEAEISHTQKATLVCLATGFFPDHVELSWWVNGK

EVHSGVSTDPQPLKEQPALNDSRYCLSSRLRVSATFWQNPRNHFRCQVQF

YGLSENDEWTQDRAKPVTQIVSAEAWGRADCGFTSVSYQQGVLSATILYE

ILLGKATLYAVLVSALVLMAMVKRKDF.

The human TCR beta chain V region CTL-L17 canonical sequence is:

(SEQ ID NO: 64)
MGTSLLCWMALCLLGADHADTGVSQNPRHNITKRGQNVTFRCDPISEHNR

LYWYRQTLGQGPEFLTYFQNEAQLEKSRLLSDRFSAERPKGSFSTLEIQR

TEQGDSAMYLCASSLAGLNQPQHFGDGTRLSIL.

The human TCR beta chain V region YT35 canonical sequence is:

(SEQ ID NO: 65)
MDSWTFCCVSLCILVAKHTDAGVIQSPRHEVTEMGQEVTLRCKPISGHNS

LFWYRQTMMRGLELLIYFNNNVPIDDSGMPEDRFSAKMPNASFSTLKIQP

SEPRDSAVYFCASSFSTCSANYGYTFGSGTRLTVV.

An exemplary anti-BCMA heavy chain sequence is:

Generation of TFPs from TCR Domains and scFvs

The CD19 or BCMA scFvs are recombinantly linked to CD3-epsilon or other TCR subunits (see 1C) using a linker sequence, such as $G_4S$ (SEQ ID NO: 74), $(G_4S)_2$ (SEQ ID NO: 3), $(G_4S)_3$ (SEQ ID NO: 71) or $(G_4S)_4$ (SEQ ID NO: 70). Various linkers and scFv configurations are utilized. TCR alpha and TCR beta chains were used for generation of TFPs either as full length polypeptides or only their constant domains. Any variable sequence of TCR alpha and TCR beta chains is allowed for making TFPs.

TFP Expression Vectors

Expression vectors are provided that include: a promoter (Cytomegalovirus (CMV) enhancer-promoter), a signal sequence to enable secretion, a polyadenylation signal and transcription terminator (Bovine Growth Hormone (BGH) gene), an element allowing episomal replication and replication in prokaryotes (e.g., SV40 origin and ColE1 or others known in the art) and elements to allow selection (ampicillin resistance gene and zeocin marker).

Preferably, the TFP-encoding nucleic acid construct is cloned into a lentiviral expression vector and expression validated based on the quantity and quality of the effector T-cell response of TFP.CD19-transduced T-cells ("CD19.TFP" or "CD19.TFP T-cells" or "TFP.CD19" or "TFP.CD19 T-cells") in response to CD19+ target cells, TFP.FAP-transduced T-cells ("FAP.TFP" or "FAP.TFP T-cells" or "TFP.FAP" or "TFP.FAP T-cells") in response to FAP+ target cells, TFP.CAIX-transduced T-cells ("CAIX-.TFP" or "CAIX.TFP T-cells" or "TFP.CAIX" or "TFP-.CAIX T-cells") in response to CAIX+ target cells, or TFP.BCMA-transduced T-cells ("BCMA.TFP" or "BCMA.TFP T-cells" or "TFP.BCMA" or "TFP.BCMA T-cells") in response to BCMA+ target cells. Effector T-cell responses include, but are not limited to, cellular expansion, proliferation, doubling, cytokine production and target cell lysis or cytolytic activity (i.e., degranulation).

The TFP.CD19, TFP.FAP, TFP.CAIX or TFP.BCMA lentiviral transfer vectors are used to produce the genomic material packaged into the VSVg pseudotyped lentiviral particles. Lentiviral transfer vector DNA is mixed with the three packaging components of VSVg, gag/pol and rev in combination with Lipofectamine reagent to transfect them together into 293 cells. After 24 and 48 hours, the media is collected, filtered and concentrated by ultracentrifugation. The resulting viral preparation is stored at −80 C. The number of transducing units is determined by titration on SupT1 cells. Redirected TFP.CD19, TFP.FAP, TFP.CAIX or TFP.BCMA T-cells are produced by activating fresh naive T-cells with anti-CD3× anti-CD28 beads for 24 hrs and then adding the appropriate number of transducing units to obtain the desired percentage of transduced T-cells. These modified T-cells are allowed to expand until they become rested and come down in size at which point they are cryopreserved for later analysis. The cell numbers and sizes are measured using a coulter multisizer III. Before cryopreserving, percentage of cells transduced (expressing the TFP.CD19, TFP-.FAP, TFP.CAIX or TFP.BCMA on the cell surface) and their relative fluorescence intensity of that expression are determined by flow cytometric analysis. From the histogram plots, the relative expression levels of the TFPs are examined by comparing percentage transduced with their relative fluorescent intensity.

In some embodiments multiple TFPs are introduced by T-cell transduction with multiple viral vectors.

Evaluating Cytolytic Activity, Proliferation Capabilities and Cytokine Secretion of Humanized TFP Redirected T Cells The functional abilities of TFP.CD19, TFP.FAP, TFP-.CAIX or TFP.BCMA T-cells to produce cell-surface expressed TFPs, and to kill target tumor cells, proliferate and secrete cytokines are determined using assays known in the art.

Human PBMCs (e.g., blood from a normal apheresed donor whose naive T-cells are obtained by negative selection for T-cells, CD4+ and CD8+ lymphocytes) are treated with human interleukin-2 (IL-2) then activated with anti-CD3× anti-CD28 beads, e.g., in 10% RPMI at 37° C., 5% $CO_2$ prior to transduction with the TFP-encoding lentiviral vectors. Flow cytometry assays are utilized to confirm cell surface presence of a TFP, such as by an anti-FLAG antibody or an anti-murine variable domain antibody. Cytokine (e.g., IFN-γ) production is measured using ELISA or other assays.

Example 3: Human TFP T-cell Efficacy in a Human ALL Mouse Model

Primary human ALL cells can be grown in immune compromised mice (e.g., NSG or NOD) without having to culture them in vitro. Likewise, cultured human ALL cell lines can induce leukemia in such mice. ALL-bearing mice can be used to test the efficacy of human TFP.CD19, TFP.FAP, TFP.CAIX or TFP.BCMA T-cells, for instance, in the model HALLX5447. The readout in this model is the survival of mice after intravenous (i.v.) infusion of ALL cells in the absence and presence of i.v. administered human TFP.CD19, TFP.FAP, TFP.CAIX or TFP.BCMA T-cells.

Example 4: Human TFP T-Cell Treatment in an In Vivo Solid Tumor Xenograft Mouse Model The efficacy of human TFP.CD19 or TFP.BCMA T-cells can also be tested in immune compromised mouse models bearing subcutaneous solid tumors derived from human CD19- or BCMA-expressing ALL, CLL or NHL human cell lines. Tumor shrinkage in response to human TFP.CD19, TFP.FAP, TFP.CAIX or TFP.BCMA T-cell treatment can be either assessed by caliper measurement of tumor size, or by following the intensity of a GFP fluorescence signal emitted by GFP-expressing tumor cells.

Primary human solid tumor cells can be grown in immune compromised mice without having to culture them in vitro. Exemplary solid cancer cells include solid tumor cell lines, such as provided in The Cancer Genome Atlas (TCGA) and/or the Broad Cancer Cell Line Encyclopedia (CCLE, see Barretina et al., Nature 483:603 (2012)). Exemplary solid cancer cells include primary tumor cells isolated from renal cell carcinoma, breast cancer, lung cancer, ovarian cancer, prostate cancer, colon cancer, cervical cancer, brain cancer, liver cancer, pancreatic cancer, kidney or stomach cancer. These mice can be used to test the efficacy of TFP.CD19, TFP.FAP, TFP.CAIX or TFP.BCMA T-cells in the human tumor xenograft models (see, e.g., Morton et al., Nat. Procol. 2:247 (2007)). Following an implant or injection of $1\times10^6$-$1\times10^7$ primary cells (collagenase-treated bulk tumor suspensions in EC matrix material) or tumor fragments (primary tumor fragments in EC matrix material) subcutaneously, tumors are allowed to grow to 200-500 $mm^3$ prior to initiation of treatment.

Example 5: Demonstration of Multiplexed TFP Polypeptides, and Use of Multiplexed Humanized TFP Redirected T Cells The TFP polypeptides provided herein are capable of functionally associating with endogenous TCR subunit polypeptides to form functional TCR complexes. Here, multiple TFPs in lentiviral vectors are used to transduce T-cells in order to create a functional, multiplexed recombinant TCR complex. For example, provided is T-cell containing i) a first TFP having an extracellular domain, a transmembrane domain, and an intracellular domain from the CD3-dselta polypeptide and an CD19-, FAP-, CAIX-, or BCMA-specific scFv antibody fragment, and ii) a second TFP having an extracellular domain, a transmembrane domain, and an intracellular domain from the CD3-gamma polypeptide and a CD19-, FAP-, CAIX-, or BCMA-specific antibody fragment. The first TFP and second TFP are capable of interacting with each other and with endogenous TCR subunit polypeptides, thereby forming a functional TCR complex.

The use of these multiplexed humanized TFP.CD19, TFP.FAP, TFP.CAIX or TFP.BCMA T-cells is demonstrated in liquid and solid tumors as provided in Examples 2 and 3 above.

Example 6: Preparation of T-Cells Transduced with TFPs

Lentiviral Production

Lentivirus encoding the appropriate constructs were prepared as follows. $5\times10^6$ HEK293FT-cells were seeded into a 100 mm dish and allowed to reach 70-90% confluency overnight. 2.5 μg of the indicated DNA plasmids and 20 μL Lentivirus Packaging Mix (ALSTEM, cat# VP100; see Appendix B3) were diluted in 0.5 mL DMEM or Opti-MEM I Medium without serum and mixed gently. In a separate tube, 30 μL of NanoFect transfection reagent (ALSTEM, cat. no. NF100) was diluted in 0.5 mL DMEM or Opti-MEM I Medium without serum and mixed gently. The NanoFect/DMEM and DNA/DMEM solutions were then mixed together and votrexed for 10-15 seconds prior to incubation of the DMEM-plasmid-NanoFect mixture at room temperature for 15 minutes. The complete transfection complex from the previous step was added dropwise to the plate of cells and rocked to disperse the transfection complex evenly in the plate. The plate was then incubated overnight at 37° C. in a humidified 5% $CO_2$ incubator. The following day, the supernatant was replaced with 10 mL fresh media and supplemented with 20 μL of ViralBoost (500×, ALSTEM, cat. no. VB100). The plates were then incubated at 37° C. for an additional 24 hours. The lentivirus containing supernatant was then collected into a 50 mL sterile, capped conical centrifuge tube and put on ice. After centrifugation at 3000 rpm for 15 minutes at 4° C., the cleared supernatant was filtered with a low-protein binding 0.45 μm sterile filter and virus was subsequently isolated by ultracentrifugation at 25,000 rpm (Beckmann, L8-70M) for 1.5 hours, at 4° C. The pellet was removed and re-suspended in DMEM media and Lentivirus concentrations/titers were established by quantitative RT-PCR, using the *Lenti*-X qRT-PCR Titration kit (Clontech; catalog number 631235). Any residual plasmid DNA was removed by treatment with DNaseI. The virus stock preparation was either used for infection immediately or aliquoted and stored at −80° C. for future use.

Similar experiments can be carried out with FAP.TFP and CAIX.TFP constructs.

PBMC Isolation

Peripheral Blood Mononuclear Cells (PBMCs) were prepared from either whole blood or buffy coat. Whole blood was collected in 10 mL Heparin vacutainers and either processed immediately or stored overnight at 4° C. Approximately 10 mL of whole anti-coagulated blood was mixed with sterile phosphate buffered saline (PBS) buffer for a total volume of 20 mL in a 50 mL conical centrifuge tube (PBS, pH 7.4, without $Ca^{2\pm}/Mg^{2\pm}$). 20 mL of this blood/PBS mixture was then gently overlayed onto the surface of 15 mL of Ficoll-Paque PLUS (GE Healthcare, 17-1440-03) prior to centrifugation at 400 g for 30-40 min at room temperature with no brake application.

Buffy coat was purchased from Research Blood Components (Boston, Mass.). Leucosep tubes (Greiner bio-one) were prepared by adding 15 mL Ficoll-Paque (GE Health Care) and centrifuged at 1000 g for 1 minute. Buffy coat was diluted 1:3 in PBS (pH 7.4, without $Ca^{2+}$ or $Mg^{2\pm}$). The diluted buffy coat was transferred to Leucosep tube and centrifuged at 1000 g for 15 minutes with no brake application. The layer of cells containing peripheral blood mononuclear cells (PBMC), seen at the diluted plasma/Ficoll interface, was removed carefully to minimize contamination by Ficoll. Residual Ficoll, platelets, and plasma proteins were then removed by washing the PBMCs three times with 40 mL of PBS by centrifugation at 200 g for 10 minutes at room temperature. The cells were then counted with a hemocytometer. The washed PBMC were washed once with CAR-T media (AIM V-AlbuMAX (BSA) (Life Technologies), with 5% AB serum and 1.25 μg/mL amphotericin B (Gemini Bioproducts, Woodland, Calif.), 100 U/mL penicillin, and 100 μg/mL streptomycin). Alternatively, the washed PBMC's were transferred to insulated vials and frozen at −80° C. for 24 hours before storing in liquid nitrogen for later use.

Similar experiments can be carried out with FAP.TFP and CAIX.TFP constructs.

T-Cell Activation

Peripheral Blood Mononuclear Cells (PBMCs) prepared from either whole blood or buffy coat were stimulated with anti-human CD28 and CD3 antibody-conjugated magnetic beads for 24 hours prior to viral transduction. Freshly isolated PBMC were washed once in CAR-T media (AIM V-AlbuMAX(BSA)(Life Technologies), with 5% AB serum and 1.25 μg/mL amphotericin B (Gemini Bioproducts), 100

U/mL penicillin, and 100 μg/mL streptomycin) without huIL-2, before being re-suspended at a final concentration of $1\times10^6$ cells/mL in CAR-T medium with 300 IU/mL human IL-2 (from a 1000× stock; Invitrogen). If the PBMCs had previously been frozen they were thawed and re-suspended at $1\times10^7$ cells/mL in 9 mL of pre-warmed (37° C.) cDMEM media (Life Technologies), in the presence of 10% FBS, 100 U/mL penicillin, and 100 μg/mL streptomycin, at a concentration of $1\times10^6$ cells/mL prior to washing once in CART medium, re-suspension at $1\times10^6$ cells/mL in CAR-T medium, and addition of IL-2 as described above.

Prior to activation, anti-human CD28 and CD3 antibody-conjugated magnetic beads (Invitrogen) were washed three times with 1 mL of sterile 1×PBS (pH7.4), using a magnetic rack to isolate beads from the solution, before re-suspension in CAR-T medium, with 300 IU/mL human IL-2, to a final concentration of $4\times10^7$ beads/mL. PBMC and beads were then mixed at a 1:1 bead-to-cell ratio, by transferring 25 μL ($1\times10^6$ beads) of beads to 1 mL of PBMC. The desired number of aliquots were then dispensed to single wells of a 12-well low-attachment, or non-treated cell culture plate, and incubated at 37° C., with 5% $CO_2$, for 24 hours before viral transduction.

Similar experiments can be carried out with FAP.TFP and CAIX.TFP constructs.

T-Cell Transduction/Transfection and Expansion

Following activation of PBMC cells were incubated for 24 hours at 37° C., 5% $CO_2$. Lentivirus was thawed on ice and $5\times10^6$ lentivirus, along with 2 μL of Transplus (Alstem) per mL of media (a final dilution of 1:500) was added to each well of $1\times10^6$ cells. Cells were incubated for an additional 24 hours before repeating addition of virus. Alternatively, lentivirus was thawed on ice and the respective virus was added at 5 or 50 MOI in presence of 5 μg/mL Polybrene (Sigma). Cells were spinoculated at 100 g for 100 minutes at room temperature. Cells were then grown in the continued presence of 300 IU/mL of human IL-2 for a period of 6-14 days (total incubation time is dependent on the final number of CAR-T-cells required). Cell concentrations were analyzed every 2-3 days, with media being added at that time to maintain the cell suspension at $1\times10^6$ cells/mL.

Figure 14:
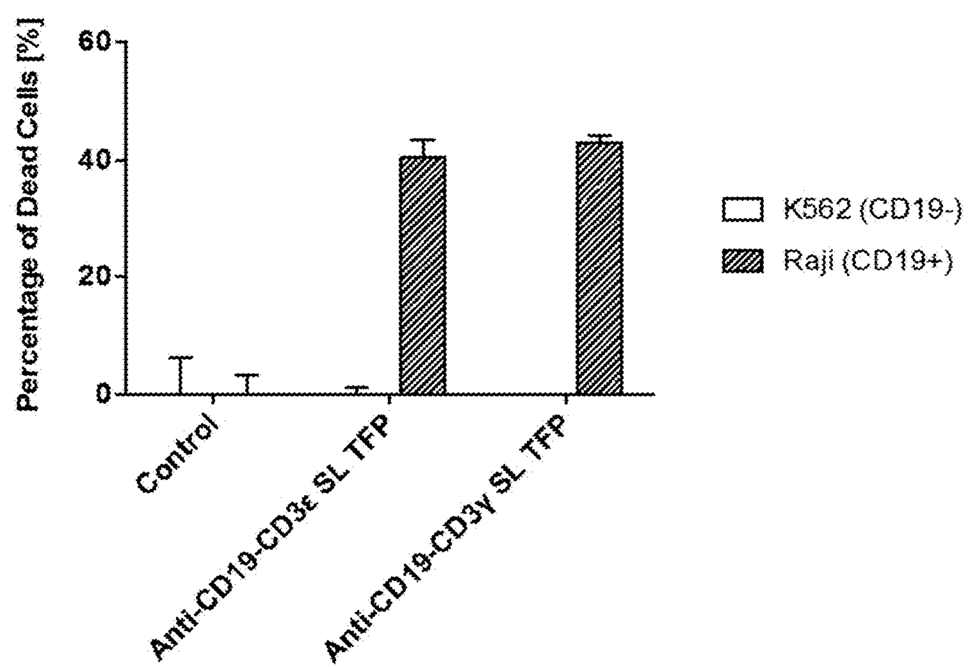
FIG. 14 is an exemplary graph depicting killing activity of T-cells transfected by electroporation with in vitro transcribed (IVT) mRNA encoding anti-CD19-CD3ε SL or anti-CD19-CD3γ SL TRuCs. Effector T cells were transfected by electroporation of activated PBMCs with in vitro transcribed (IVT) mRNAs encoding either GFP control, anti-CD19-CD3ε SL, or anti-CD19-CD3γ SL TRuCs. After expansion for 3 days the effectors were incubated for 4 hours with $1\times10^4$ Raji cells or K562 cells at E:T ratios of 10:1. The percentage cytotoxicity was determined in a flow-cytometric cytotoxicity assay.
Figure 15A:
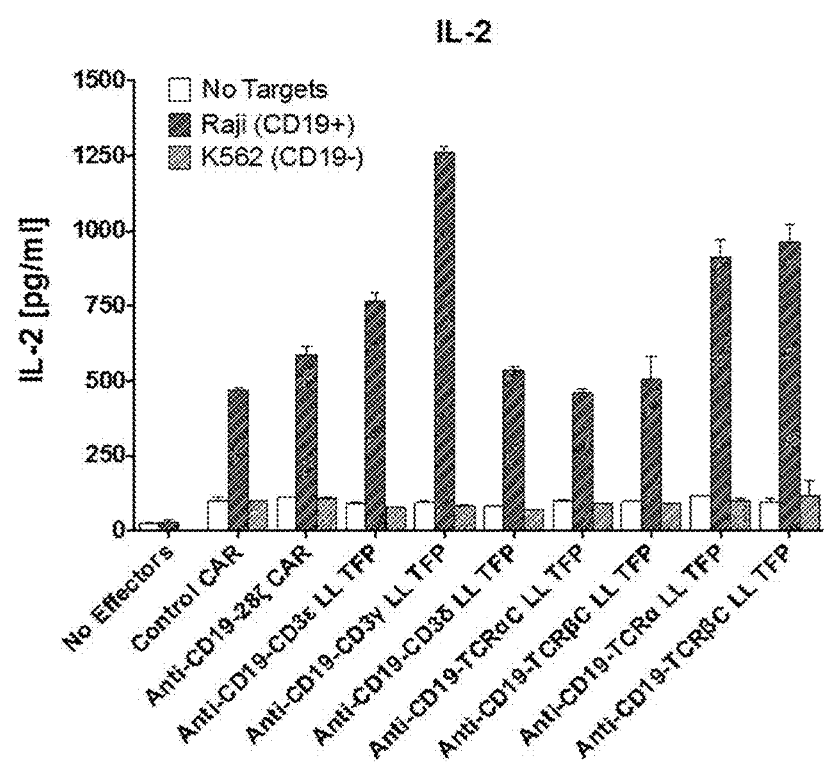
FIG. 15A is an exemplary graph depicting IL-2 release by T-cells transduced with anti-CD19 LL TFPs in response to CD19-bearing target cells. Effector T-cells that were either non-transduced, transduced with a control CAR, an anti-CD19-28ζ CAT or the indicated anti-CD19 LL TFP, were expanded for 14 days prior to incubation with either $1\times10^4$ Raji or K562 target cells. IL-2 levels were determined by ELISA.
Figure 15B:
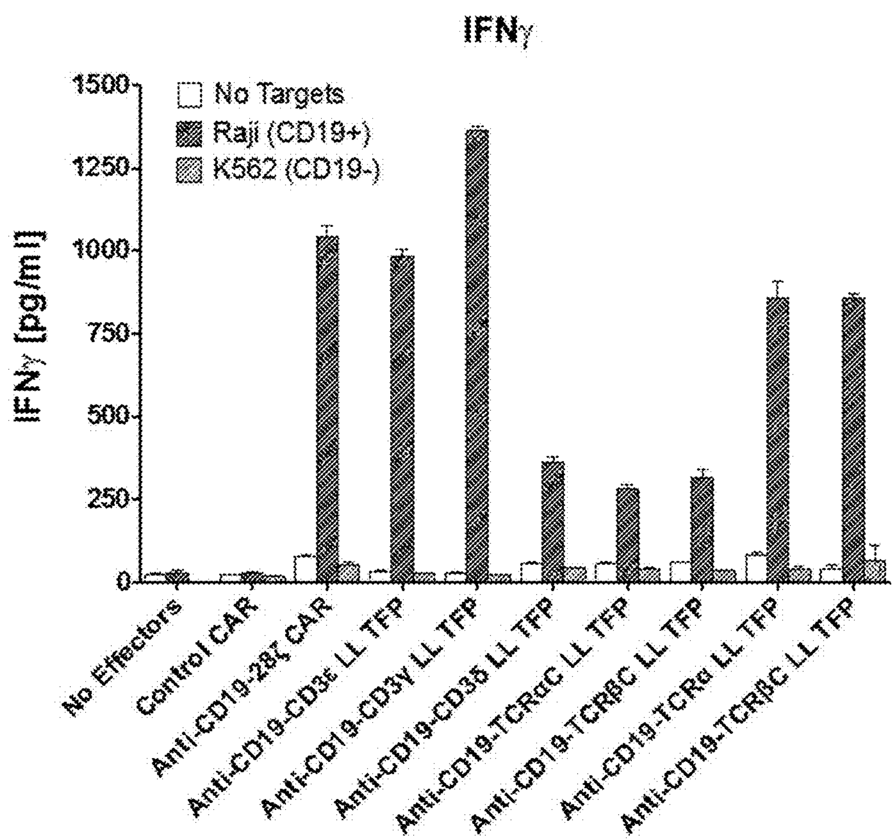
FIG. 15B is an exemplary graph depicting IFN-γ release by T-cells transduced with anti-CD19 LL TFPs in response to CD19-bearing target cells. Effector T-cells that were either non-transduced, transduced with a control CAR, an anti-CD19-28ζ CAT or the indicated anti-CD19 LL TFP, were expanded for 14 days prior to incubation with either $1\times10^4$ Raji or K562 target cells. IFN-γ levels were determined by ELISA.
Figure 15C:
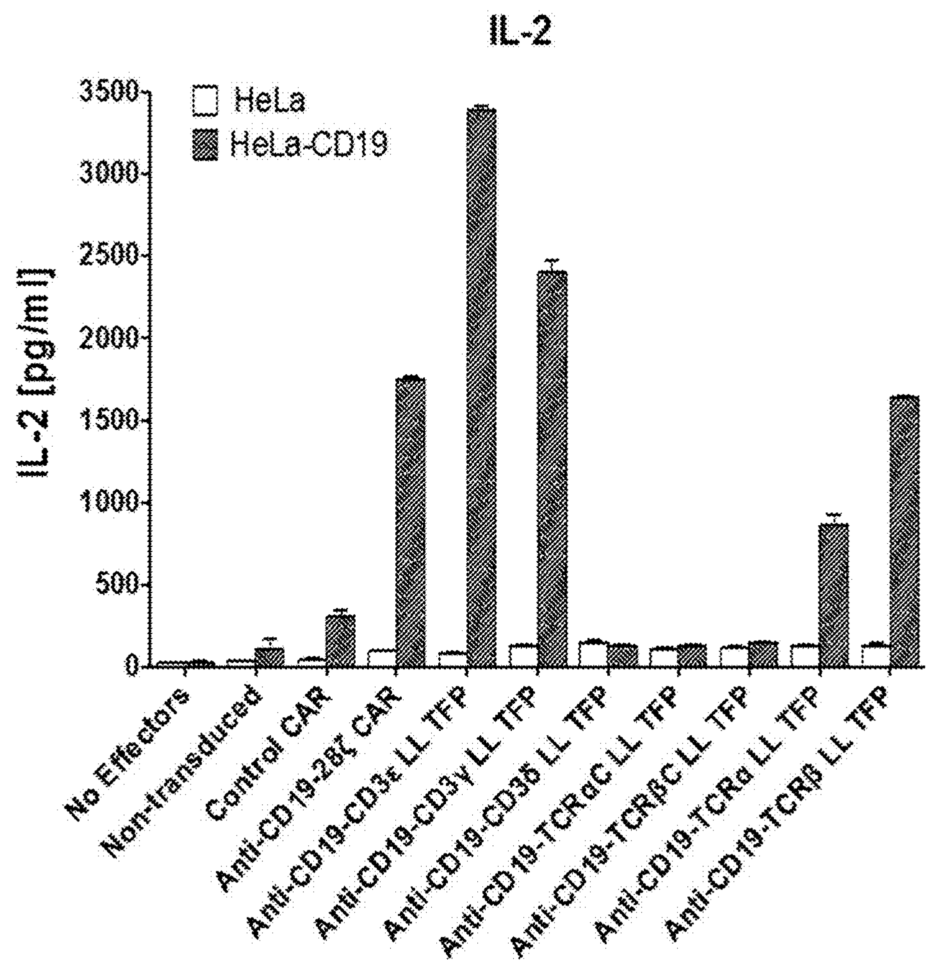
FIG. 15C is an exemplary graph depicting IL-2 release by T-cells transduced with anti-CD19 LL TFPs in response to CD19-bearing target cells. Effector T-cells that were either non-transduced, transduced with a control CAR, an anti-CD19-28ζ CAT or the indicated anti-CD19 LL TFP, were expanded for 14 days prior to incubation with either $1\times10^4$ HeLa or CD19-HeLa target cells. IL-2 levels were determined by ELISA.
Figure 15D:
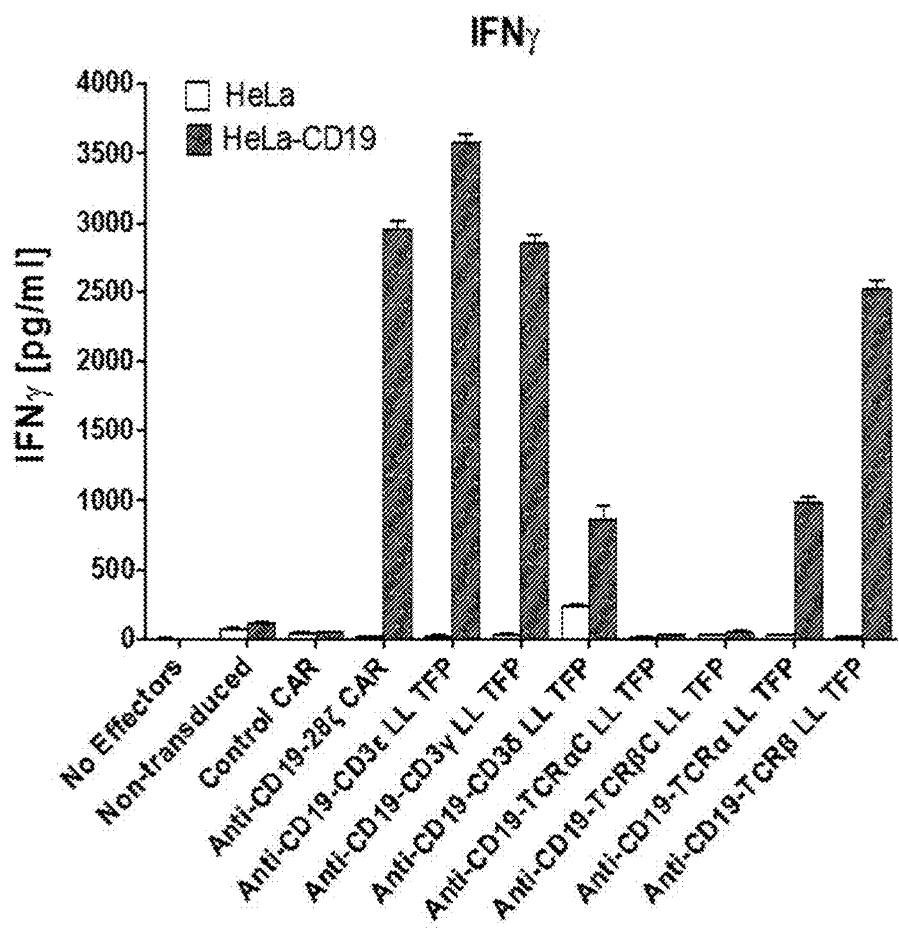
FIG. 15D is an exemplary graph depicting IFN-γ release by T-cells transduced with anti-CD19 LL TFPs in response to CD19-bearing target cells. Effector T-cells that were either non-transduced, transduced with a control CAR, an anti-CD19-28ζ CAT or the indicated anti-CD19 LL TFP, were expanded for 14 days prior to incubation with either $1\times10^4$ HeLa or CD19-HeLa target cells. IFN-γ levels were determined by ELISA.

In some instances, activated PBMCs were electroporated with in vitro transcribed (IVT) mRNA (FIG. 14). Human PBMCs were stimulated with Dyna beads (ThermoFisher) at 1-to-1 ratio for 3 days in the presence of 300 IU/ml recombinant human IL-2 (R&D System). The beads were removed before electroporation. The cells were washed and re-suspended in OPTI-MEM medium (ThermoFisher) at the concentration of $2.5\times10^7$ cells/mL. 200 μL of the cell suspension ($5\times10^6$ cells) were transferred to the 2 mm gap Electroporation Cuvettes Plus™ (Harvard Apparatus BTX) and pre-chilled on ice. 10 μg of IVT TFP mRNA was added to the cell suspension. The mRNA/cell mixture was then electroporated at 200 V for 20 milliseconds using ECM830 Electro Square Wave Porator (Harvard Apparatus BTX) Immediately after the electroporation, the cells were transferred to fresh cell culture medium (AIM V AlbuMAX (BSA) serum free medium+5% human AB serum+300 IU/ml IL-2) and incubated at 37° C.

Similar experiments can be carried out with FAP.TFP and CAIX.TFP constructs.

Verification of TFP Expression by Cell Staining

Figure 5:
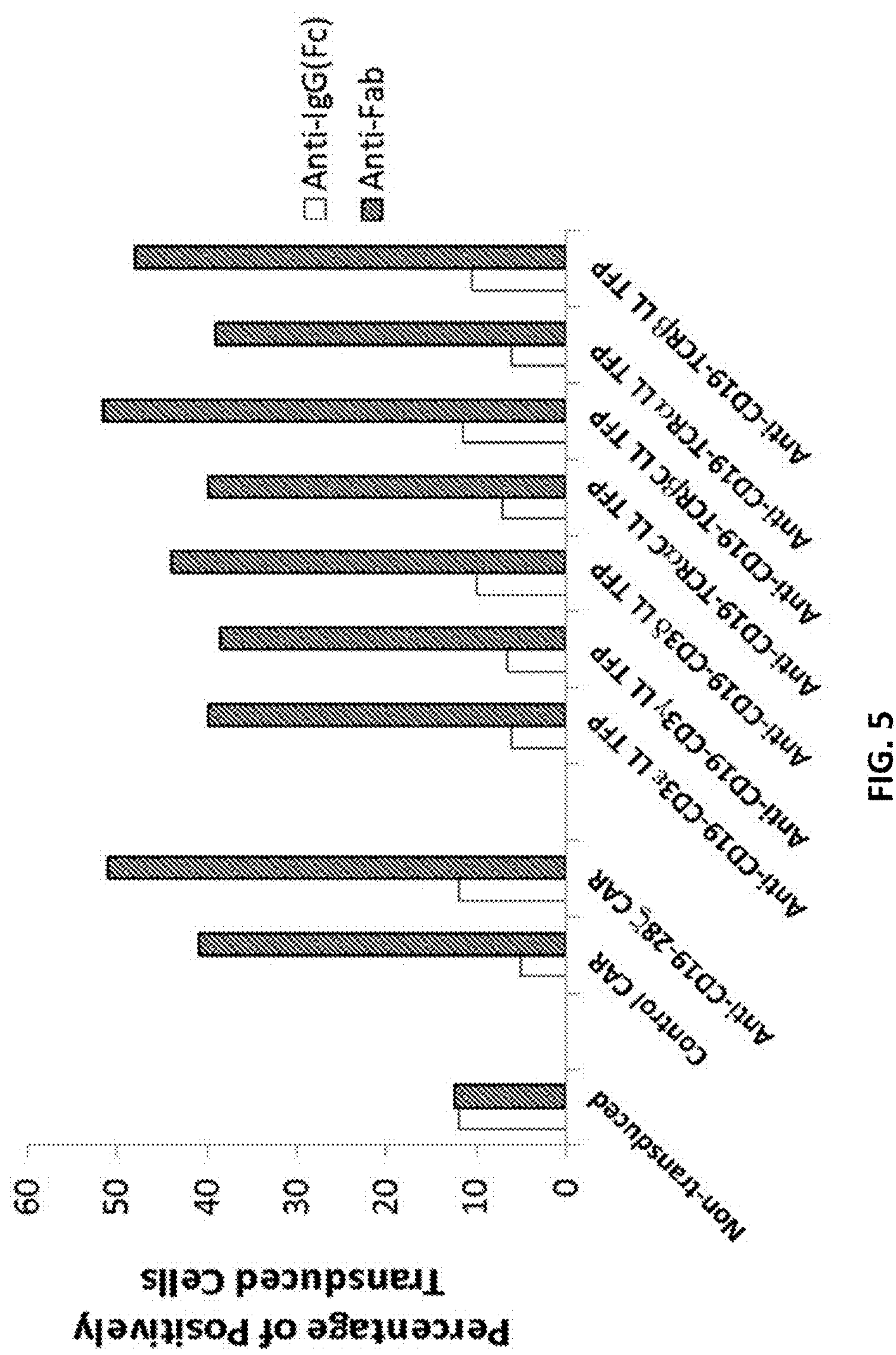
FIG. 5 is an exemplary bar graph depicting surface expression of anti-CD19 LL (long linker) TFPs on T-cells after lentiviral transduction. Effector T-cells were either un-transduced or transduced with either anti-CD19-28ζ CAR or the indicated anti-CD19 LL TFP constructs. After being expanded for 10 days in IL-2, their surface expression of the appropriate CAR or TFP construct was determined by flow cytometry.
Figure 6:
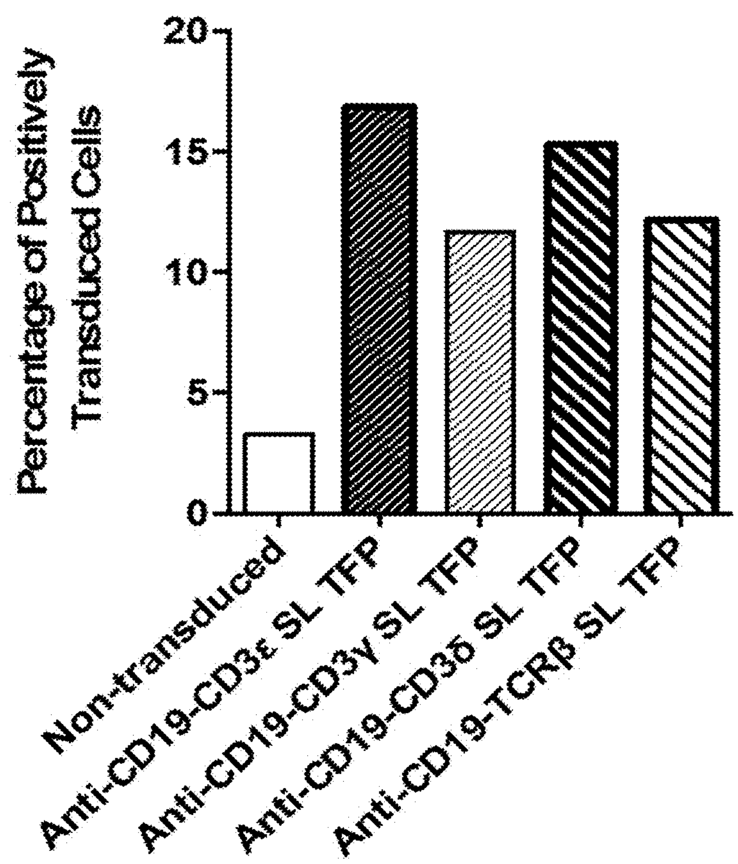
FIG. 6 is an exemplary bar graph depicting surface expression of anti-CD19 SL (short linker) TFPs on T-cells after lentiviral transduction. Effector T-cells were either un-transduced or transduced with either anti-CD19-28 CAR or the indicated anti-CD19 SL TFP constructs. After being expanded for 7 days in IL-2, their surface expression of the appropriate CAR or TFP construct was determined by flow cytometry.
Figure 7:
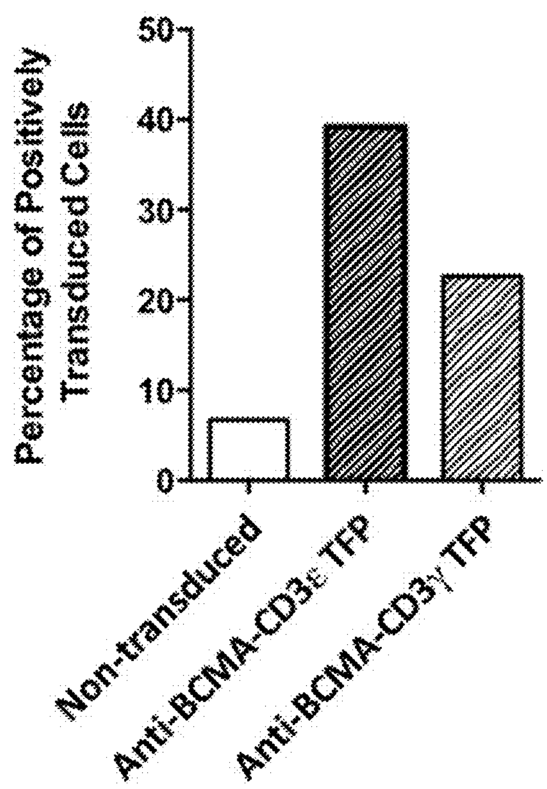
FIG. 7 is an exemplary bar graph depicting surface expression of anti-BCMA TFPs on T-cells after lentiviral transduction. Effector T-cells were either un-transduced or transduced with either anti-BCMA-CD3ε or anti-BCMA-CD3γ TFP constructs. After being expanded for 10 days in IL-2, their surface TFP expression was determined by flow cytometry.

Following lentiviral transduction or mRNA electroporation, expression of anti-CD19, anti-FAP, anti-CAIX and anti-BCMA CARs and TFPs was confirmed by flow cytometry, using an anti-mouse Fab antibody to detect the murine anti-CD19, anti-FAP, anti-CAIX or anti-BCMA scFv. T-cells were washed three times in 3 mL staining buffer (PBS, 4% BSA) and re-suspended in PBS at $1\times10^6$ cells per well. For dead cell exclusion, cells were incubated with Live dead aqua (Invitrogen) for 30 minutes on ice. Cells were washed twice with PBS and re-suspended in 50 μL staining buffer. To block Fc receptors, 1 μL of 1:100 diluted normal goat lgG (LifeTechnologies) was added to each tube and incubated in ice for 10 minutes. 1.0 mL FACS buffer was added to each tube, mixed well, and cells were pelleted by centrifugation at 300 g for 5 min Surface expression of scFv TFPs was detected by biotin-labeled polyclonal goat anti-mouse-F $(ab)_2$ antibodies (Life Technologies) with biotin-labeled normal polyclonal goat IgG antibodies (Life Technologies) serving as an isotype control. Both antibodies were added at 10 μg/mL in a reaction volume of 100 μL. Cells were then incubated at 4° C. for 45 minutes, washed once, re-suspended in FACS buffer, and blocked with normal mouse IgG (Invitrogen) by adding 100 μL 1:1000 diluted normal mouse lgG to each tube. The cells were then incubated on ice for 10 minutes, washed with stain buffer and re-suspended in 100 μL stain buffer. The cells were then stained by the addition of 1.0 μL phycoerythrin (PE)-labeled streptavidin (BD Biosciences) and APC anti-human CD3 antibody (Clone-UCHT1, BD Biosciences), PerCP/Cy5.5 anti-human CD8 antibody (Clone-SK1, BD Biosciences) and Pacific Blue anti-human CD4 antibody (Clone-RPA-T4, BD Biosciences) were added to each tube. Flow cytometry was performed using LSRFortessa™ X20 (BD Biosciences) and data was acquired using FACS diva software and was analyzed with FlowJo (Treestar, Inc. Ashland, Oreg.). Between 20% and 40% of the transduced T-cells expressed anti-CD19 CAR, anti-CD19 LL TFP, anti-CD19 SL TFP or anti-BCMA TFP, indicating comparable levels of transduction and surface expression of CAR and TFP constructs (FIGS. 5-7).

Similar experiments can be carried out with FAP.TFP and CAIX.TFP constructs.

Example 7: Cytotoxicity Assay by Flow Cytometry

Target cells that were either positive or negative for the respective CD19, FAP, CAIX or BCMA targets, were labelled with the fluorescent dye, carboxyfluorescein diacetate succinimidyl ester (CFSE). These target cells were mixed with effector T-cells that were either un-transduced, transduced with control CAR-T constructs, or transduced with TFPs. After the indicated incubation period, the percentage of dead to live CFSE-labeled target cells and negative control target cells was determined for each effector/target cell culture by flow cytometry. The percent survival of target cells in each T-cell+ target cell culture was calculated relative to wells containing target cells alone.

The cytotoxic activity of effector T-cells was measured by comparing the number of surviving target cells in target cells without or with effector T-cells, following co-incubation of effector and target cells, using flow cytometry. In experiments with CD19 TFPs or CAR-T-cells, the target cells were CD19-positive Raji Burkitt lymphoma cells (ATCC, CCL-86), while cells used as a negative control were CD19-negative K562 cells (ATCC, CCL-243). In experiments with BCMA TFP T-cells, the target cells were BCMA-positive RPMI-8226 plasmacytoma/myeloma cells (ATCC, CCL-155), while cells used as a negative control were BCMA-negative Raji Burkitt's lymphoma cells (ATCC, CCL-86).

Target cells were washed once, and re-suspended in PBS at $1\times10^6$ cells/mL. The fluorescent dye carboxyfluorescein diacetate succinimidyl ester (CFSE) (ThermoFisher) was added to the cell suspension at a concentration of 0.03 μM and the cells were incubated for 20 minutes at room temperature. The labeling reaction was stopped, by adding to the cell suspension with complete cell culture medium (RPMI-1640+10% HI-FBS) at the volume 5 times of the reaction volume, and the cells were incubated for an additional 2 minutes at room temperature. The cells were pelleted by centrifugation and re-suspended in cytotoxicity medium (Phenol red-free RPMI1640 (Invitrogen) plus 5% AB serum (Gemini Bioproducts) at $2\times10^5$ cells/mL. Fifty microliters of CFSE labelled-target cell suspension (equivalent to 10,000 cells) were added to each well of the 96-well U-bottom plate (Corning).

Effector T-cells transduced with BCMA TFP constructs, together with non-transduced T-cells as negative controls, were washed and suspended at $2\times10^6$ cells/mL, or $1\times10^6$ cells/mL in cytotoxicity medium. 50 μL of effector T-cell suspensions (equivalent to 100,000 or 50,000 cells) were added to the plated target cells to reach the effector-to-target ratio of 10-to-1 or 5-to-1, respectively, in a total volume of 100 μL. The cultures were then mixed, spin down, and incubated for 4 hours at 37° C., 5% $CO_2$ Immediately following this incubation, 7AAD (7-aminoactinomycin D) (BioLegend) was added to the cultured cells as recommended by the manufacturer, and flow cytometry was performed with a BD Fortessa X-20 (BD Biosciences). Analysis of flow cytometric data was performed using FlowJo software (TreeStar, Inc.).

The percentage of survival for RPMI-8226 target cells was calculated by dividing the number of alive RPMI-8226 target cells (CFSE+7-AAD-) in sample with effector T-cells and target cells, by the number of alive RPMI-8226 (CFSE+7-AAD-) cells in the sample with target cells alone. The Cytotoxicity for effector cells was calculated as the percentage of killing for RPMI-8226=100%-percentage of survival for RPMI-8226 cells.

Figure 8:
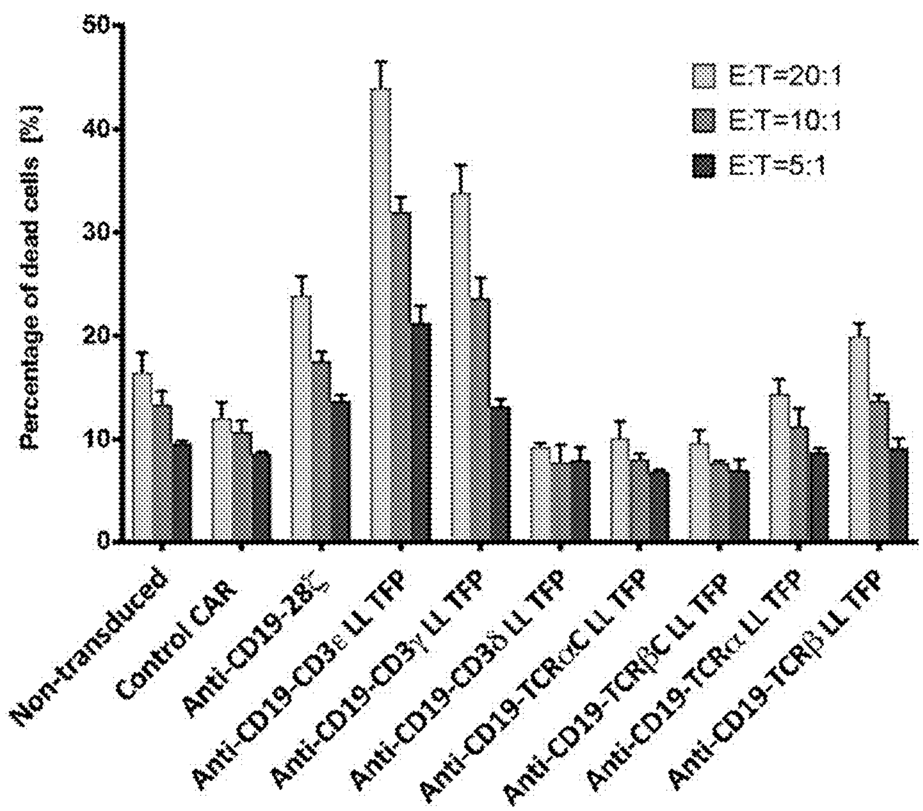
FIG. 8 is an exemplary bar graph depicting killing of CD19-expressing Raji target cells by anti-CD19 LL TFPs. Transduced effector T-cells were expanded for 14 days prior to incubation for 18 hours with $1\times10^4$ Raji target cells at E:T ratios of 20:1, 10:1, or 5:1. The percentage cytotoxicity was determined in a flow-cytometric cytotoxicity assay.

As previously described, T-cells transduced with an anti-CD19 28ζ CAR construct demonstrated cytotoxicity against CD19-expressing Raji B cells, when compared to T-cells that were either non-transduced or were transduced with a non-CD19-specific CAR control (FIG. 8). However, T-cells transduced with anti-CD19-CD3ε induced more efficient cytotoxicity against the Raji targets than the anti-CD19 CAR control at all effector:target ratios tested. Anti-CD19-CD3γ TFPs also mediated robust cytotoxicity that was greater than that observed with anti-CD19-CAR at effector:target ratios between 5 and 10:1 (FIG. 8). Some cytotoxicity was observed with anti-CD19-TCRα and anti-CD19-TCRβ TFPs Similar results were obtained with anti-CD19 TFPs constructed with an alternative hinge region. Once again, cytotoxicity against CD19-expressing Raji target cells was greater with anti-CD19-CD3ε or anti-CD19-CD3γ TFP-transduced T-cells than with anti-CD19-CAR-transduced T-cells.

T-cells electroporated with mRNA encoding TFPs specific for CD-19 also demonstrated robust cytotoxicity against CD19-expressing Raji cells While no significant killing of the CD19-negative K562 cells was seen with either control or anti-CD19 TRuC constructs, CD19-specific killing of Raji was observed by T cells transduced with either anti-CD19-CD3ε SL, or anti-CD19-CD3γ SL TRuCs (FIG. 14).

Figure 9:
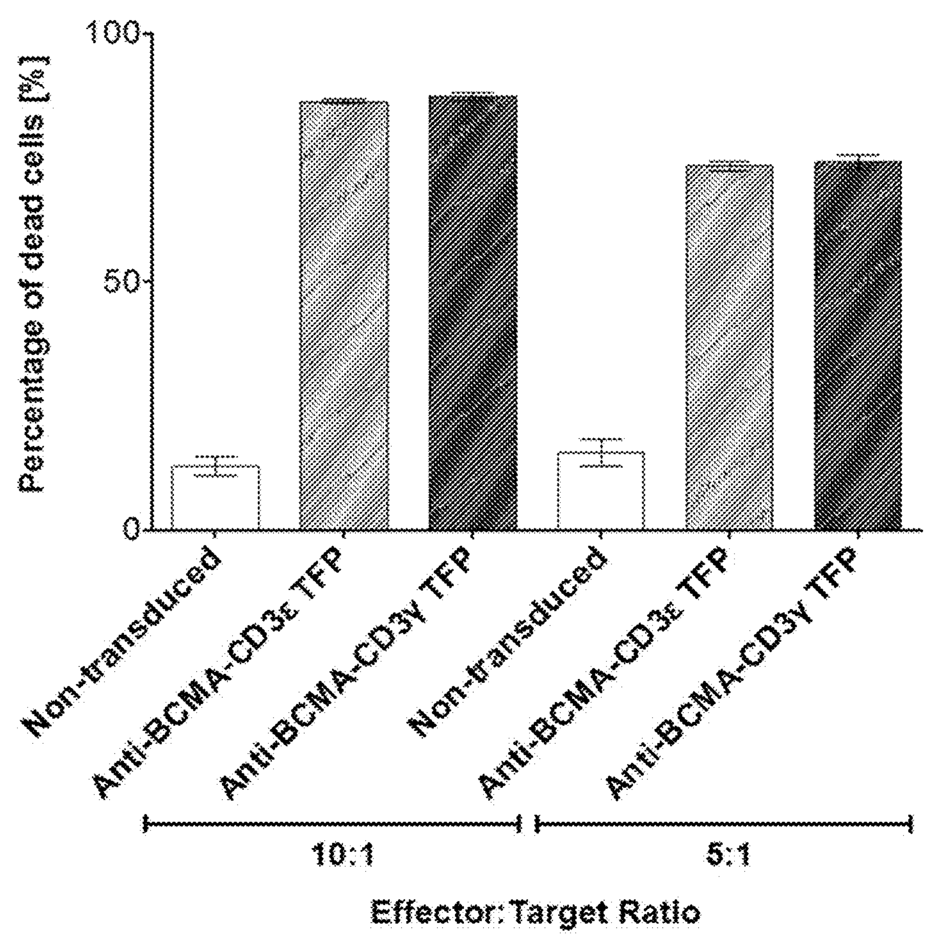
FIG. 9 is an exemplary bar graph depicting killing of BCMA-expressing RPMI8226 target cells by anti-BCMA TFPs. Transduced effector T-cells were expanded for 12 days prior to incubation for 4 hours with $1\times10^4$ RPMI8226 target cells at E:T ratios of 10:1, or 5:1. The percentage cytotoxicity was determined in a flow-cytometric cytotoxicity assay.
Figure 10A:
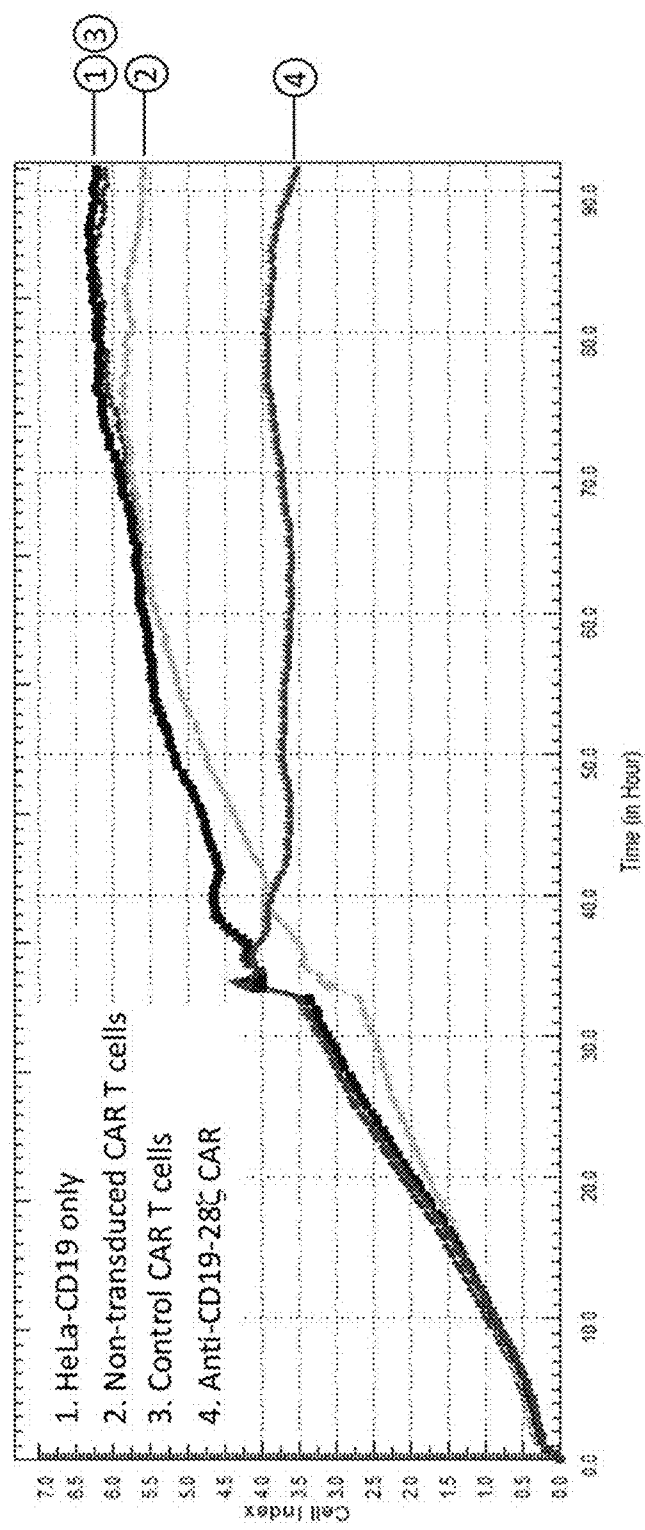
FIG. 10A is an exemplary graph depicting killing of CD19-transduced HeLa target cells by an anti-CD19-28ζ CAR construct over time. Transduced effector T-cells were expanded for 14 days prior to incubation with $1\times10^4$ CD19-transduced HeLa target cells. The cell index, indicative of cytotoxicity, was determined in a RTCA assay.
Figure 10B:
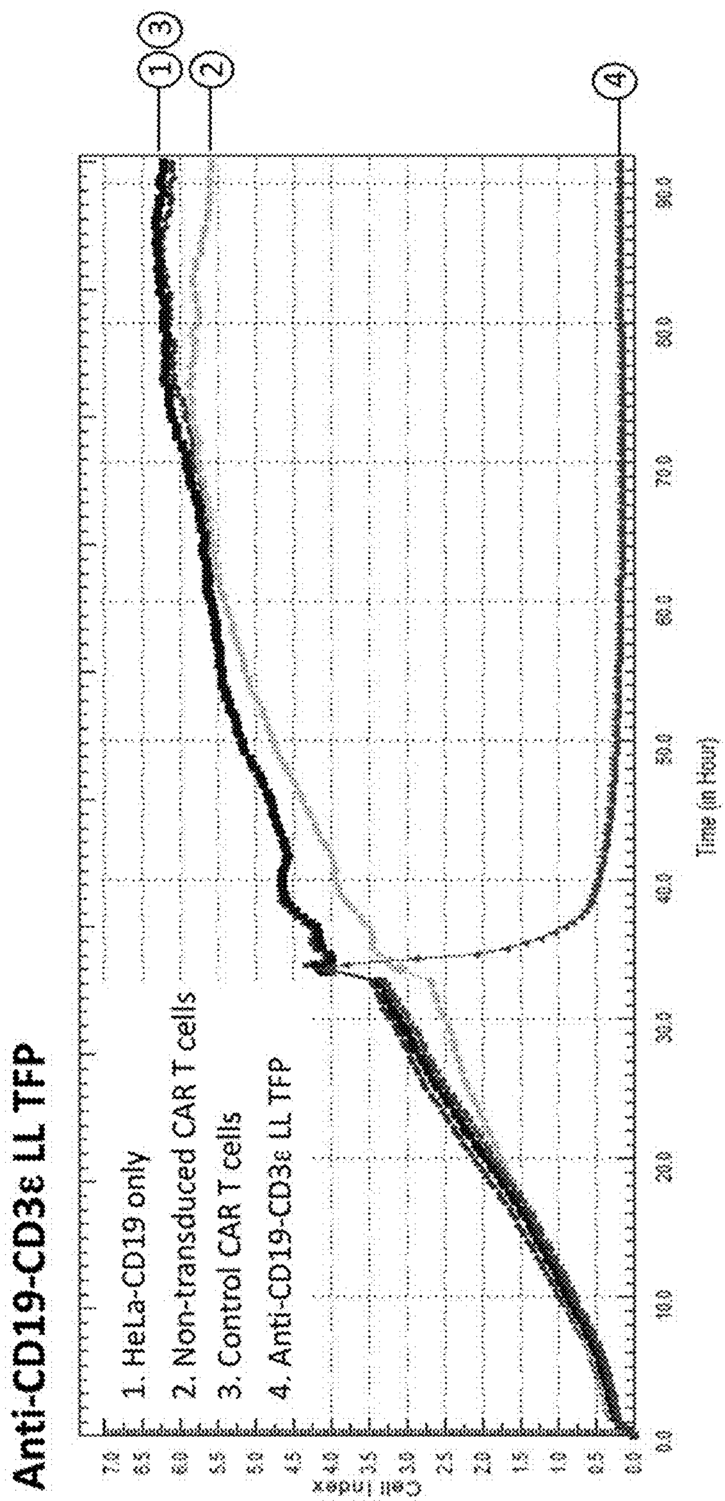
FIG. 10B is an exemplary graph depicting killing of CD19-transduced HeLa target cells by an anti-CD19-CD3ε LL TFP construct over time. Transduced effector T-cells were expanded for 14 days prior to incubation with $1\times10^4$ CD19-transduced HeLa target cells. The cell index, indicative of cytotoxicity, was determined in a RTCA assay.
Figure 10C:
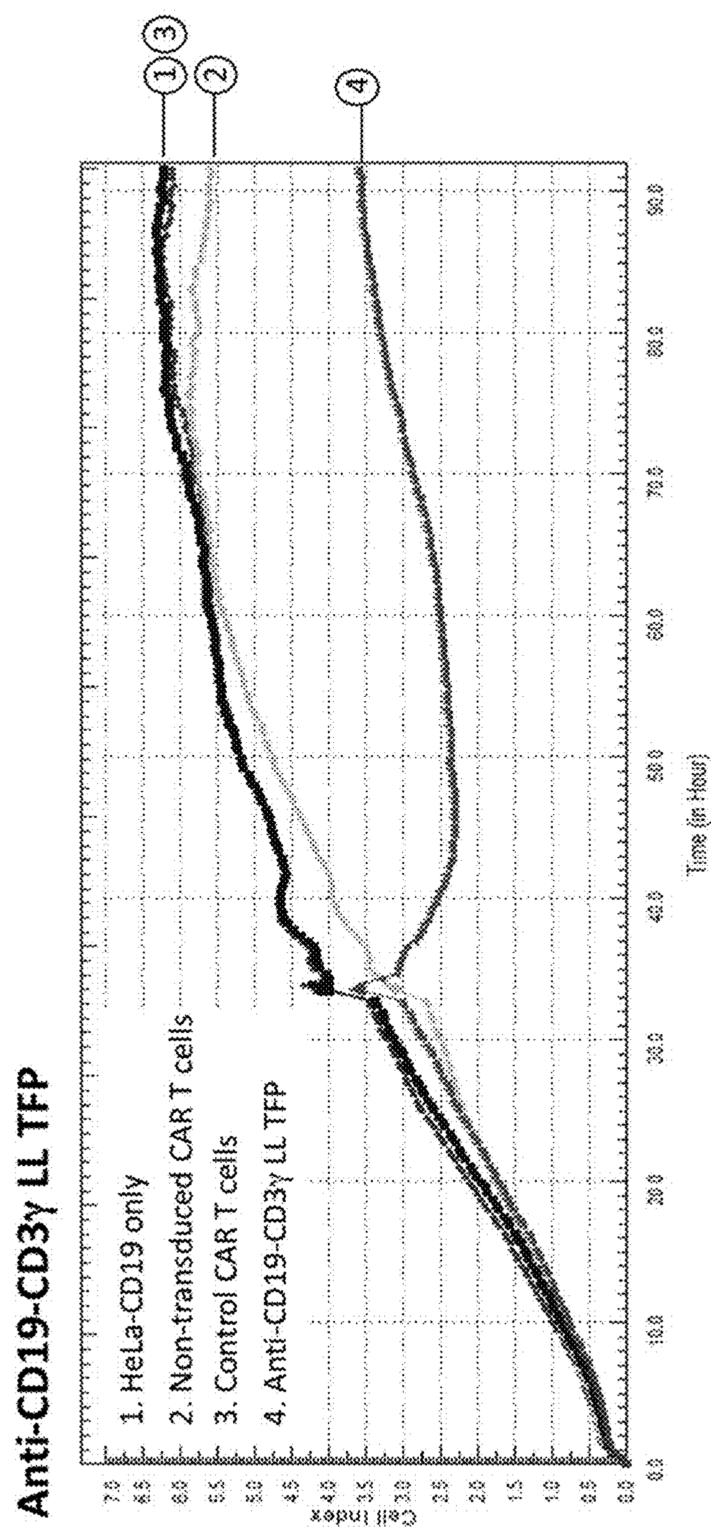
FIG. 10C is an exemplary graph depicting killing of CD19-transduced HeLa target cells by an anti-CD19-CD3γ LL TFP construct over time. Transduced effector T-cells were expanded for 14 days prior to incubation with $1\times10^4$ CD19-transduced HeLa target cells. The cell index, indicative of cytotoxicity, was determined in a RTCA assay.
Figure 10D:
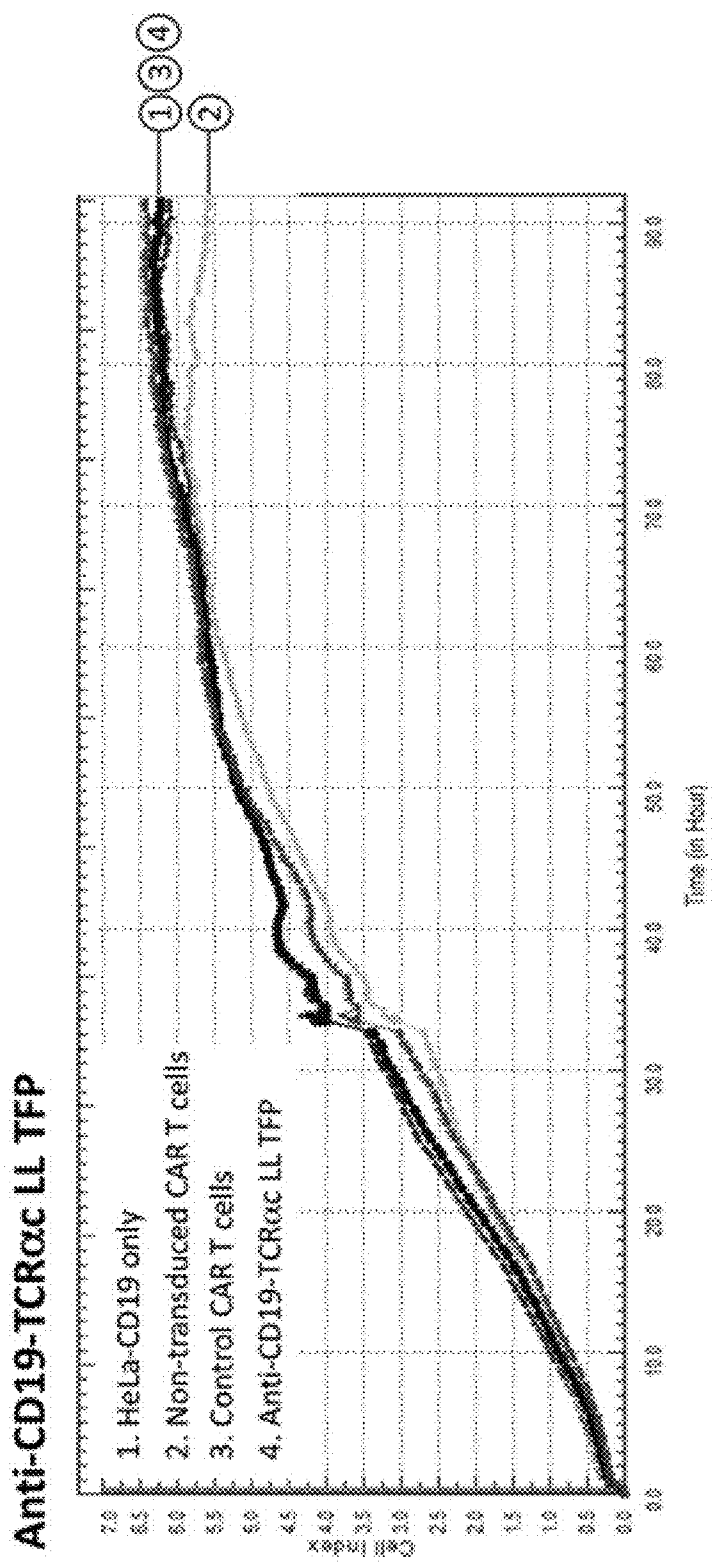
FIG. 10D is an exemplary graph depicting killing of CD19-transduced HeLa target cells by anti-CD19-TCRαc LL TFP construct over time. Transduced effector T-cells were expanded for 14 days prior to incubation with $1\times10^4$ CD19-transduced HeLa target cells. The cell index, indicative of cytotoxicity, was determined in a RTCA assay.
Figure 10E:
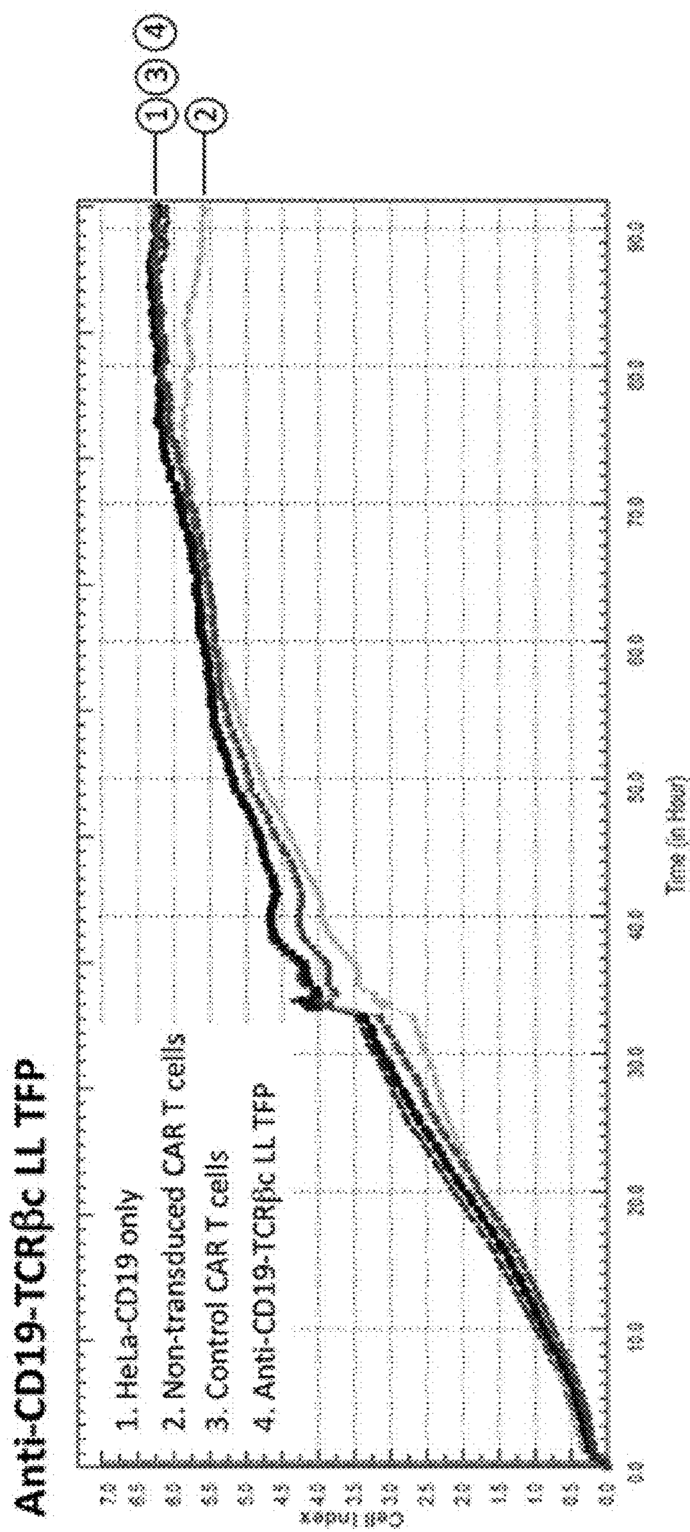
FIG. 10E is an exemplary graph depicting killing of CD19-transduced HeLa target cells by anti-CD19-TCRβc LL TFP construct over time. Transduced effector T-cells were expanded for 14 days prior to incubation with $1\times10^4$ CD19-transduced HeLa target cells. The cell index, indicative of cytotoxicity, was determined in a RTCA assay.
Figure 10F:
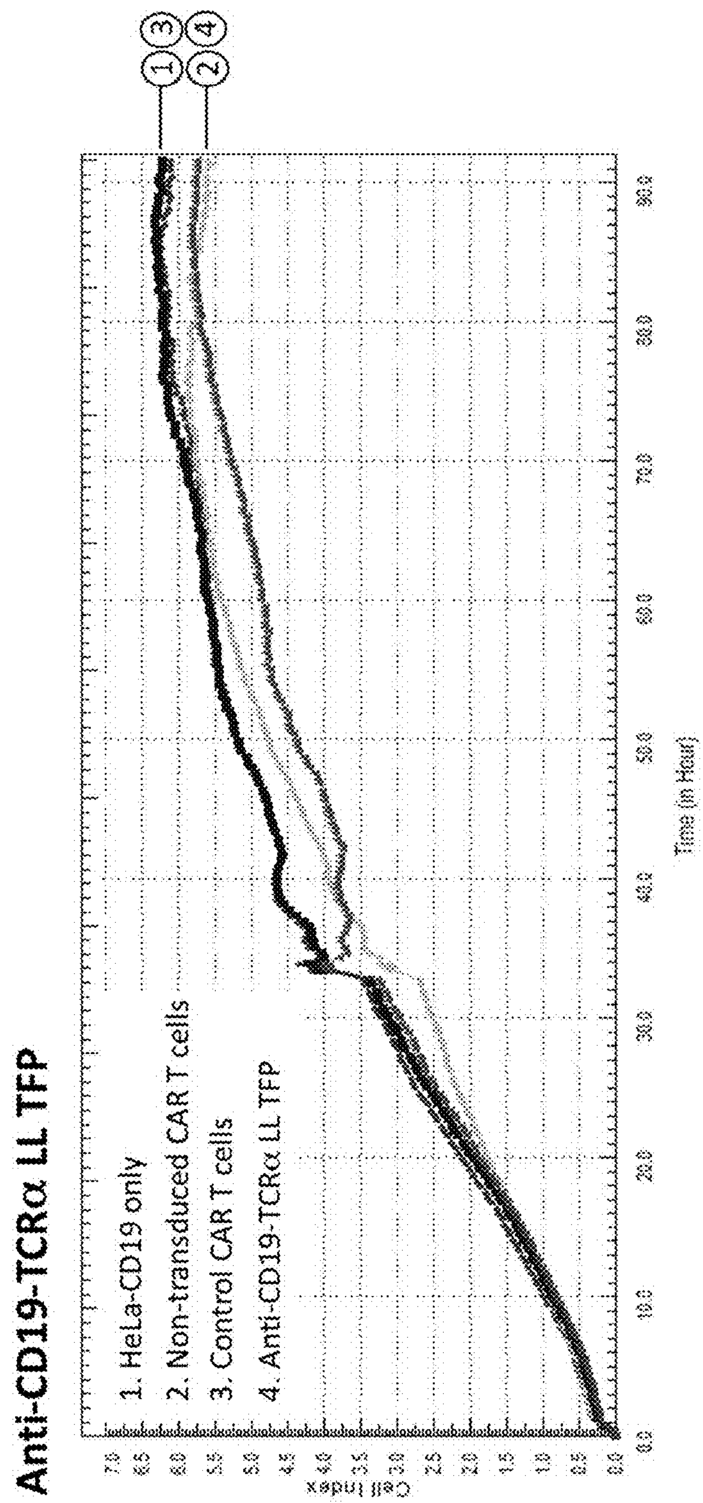
FIG. 10F is an exemplary graph depicting killing of CD19-transduced HeLa target cells by anti-CD19-TCRα LL TFP construct over time. Transduced effector T-cells were expanded for 14 days prior to incubation with $1\times10^4$ CD19-transduced HeLa target cells. The cell index, indicative of cytotoxicity, was determined in a RTCA assay.
Figure 10G:
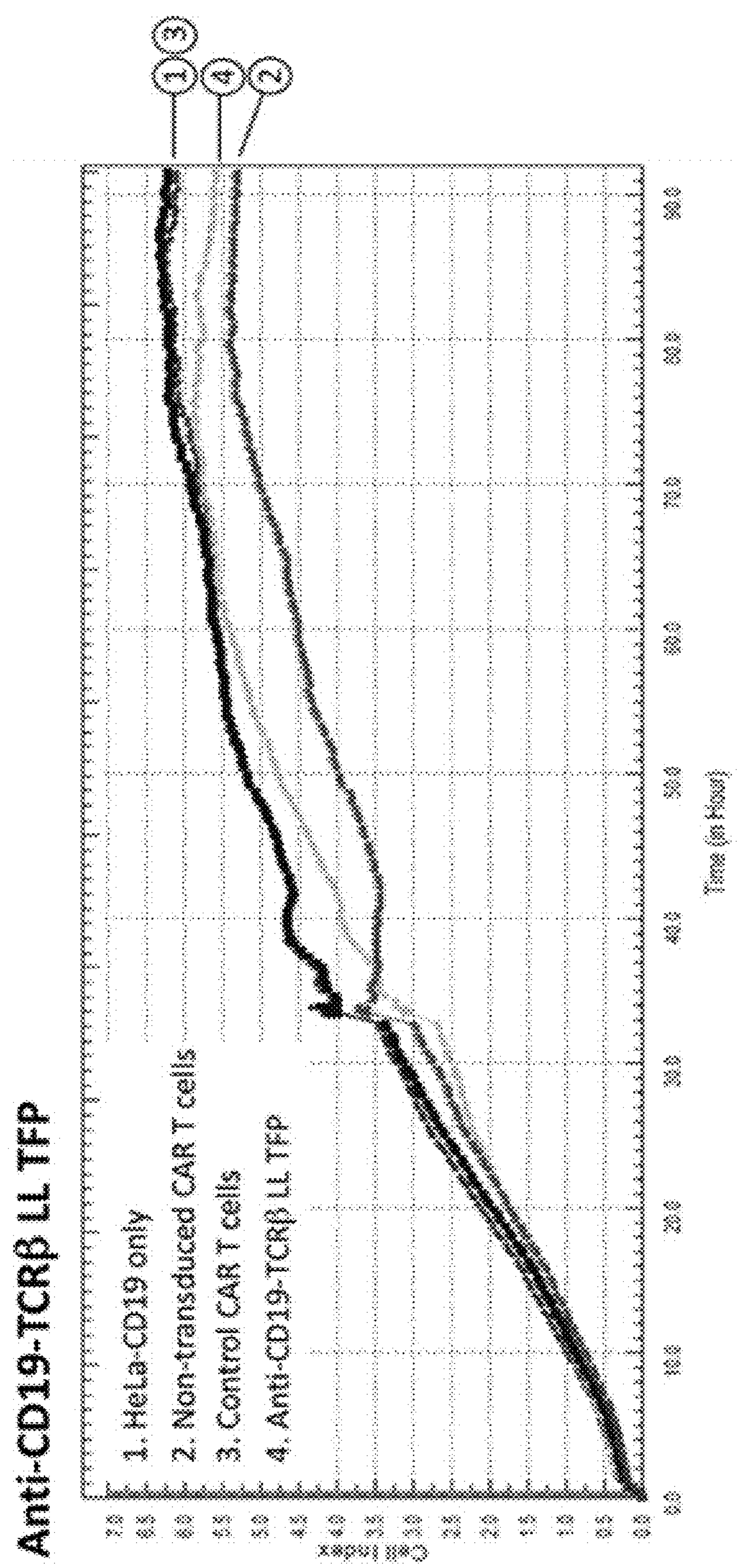
FIG. 10G is an exemplary graph depicting killing of CD19-transduced HeLa target cells by anti-CD19-TCRβ LL TFP construct over time. Transduced effector T-cells were expanded for 14 days prior to incubation with $1\times10^4$ CD19-transduced HeLa target cells. The cell index, indicative of cytotoxicity, was determined in a RTCA assay.

T-cells transduced with TFPs specific for B-cell maturation antigen (BCMA) also demonstrated robust cytotoxicity against BCMA-expressing RPMI8226 cells. T-cells transduced with anti-BCMA-CD3ε or anti-BCMA-CD3γ TFPs efficiently mediated cytotoxicity against the BCMA-expressing RPMI8226 target cells. At 10:1 ratio of effectors to target cells, almost 100% of the target cells were killed (FIG. 9).

Similar experiments can be carried out with FAP.TFP and CAIX.TFP constructs.

Example 8: Cytotoxicity by Real Time Cytotoxicity Assay

Anti-CD19 and anti-BCMA TFPs also demonstrated superior cytotoxicity to anti-CD19 CARs in the real-time cytotoxicity assay (RTCA) format. The RTCA assay measures the electrical impedance of an adherent target cell monolayer, in each well of a specialized 96-well plate, in real time and presents the final readout as a value called the cell index. Changes in cell index indicate disruption of the target cell monolayer as a result of killing of target cells by co-incubated T-cell effectors. Thus the cytotoxicity of the effector T-cells can be evaluated as the change in cell index of wells with both target cells and effector T-cells compared to that of wells with target cells alone.

Target cells for RTCA were HeLa cells expressing either CD19 (CD19-HeLa) or BCMA (BCMA-HeLa) with parental, non-transduced, HeLa cells as negative controls. The DNA encoding full-length human CD19 or BCMA was synthesized by GeneArt (ThermoFisher) and inserted into the multiple cloning site of dual-promoter lentiviral vector pCDH514B (System Bioscience) carrying neomycin as selection marker, under the control of EF1a promoter. Lentivirus carrying either the CD19 or BCMA encoding vector was then packaged. HeLa cells were transduced with either CD19- or BCMA-lentivirus for 24 hours and then selected with G418 (1 mg/mL). The expression of CD19 or BCMA by the transduced CD19-Hela or BCMA-HeLa was confirmed by FACS analysis with anti-human CD19 or BCMA antibodies (BioLegend, clone#19A2; Miltenyi, clone# REA315).

Adherent target cells were cultured in DMEM, 10% FBS, 1% Antibiotic-Antimycotic (Life Technologies). To prepare the RTCA, 50 μL of RPMI medium was added into the appropriate wells of an E-plate (ACEA Biosciences, Inc, Catalog#: JL-10-156010-1A). The plate was then placed into a RTCA MP instrument (ACEA Biosciences, Inc.) and the appropriate plate layout and assay schedule entered into the RTCA 2.0 software as described in the manufacturers manual. Baseline measurement was performed every 15 minutes for 100 measurements. $1\times10^4$ target cells in a 100 μL volume were then added to each assay well and the cells were allowed to settle for 15 minutes. The plate was returned to the reader and readings were resumed.

The next day, effector T-cells were washed and re-suspended in cytotoxicity media (Phenol red-free RPMI1640 (Invitrogen) plus 5% AB serum (Gemini Bioproducts; 100-318)). The plate was then removed from the instrument and the effector T-cells, suspended in cytotoxicity medium (Phenol red-free RPMI1640+5% AB serum), were added to each well at 100,000 cells or 50,000 cells to reach the effector-to-target ratio of 10-to-1 or 5-to-1, respectively. The plate was then placed back to the instrument. The measurement was carried out for every 2 minutes for 100 measurements, and then every 15 minutes for 1000 measurements.

Figure 11:
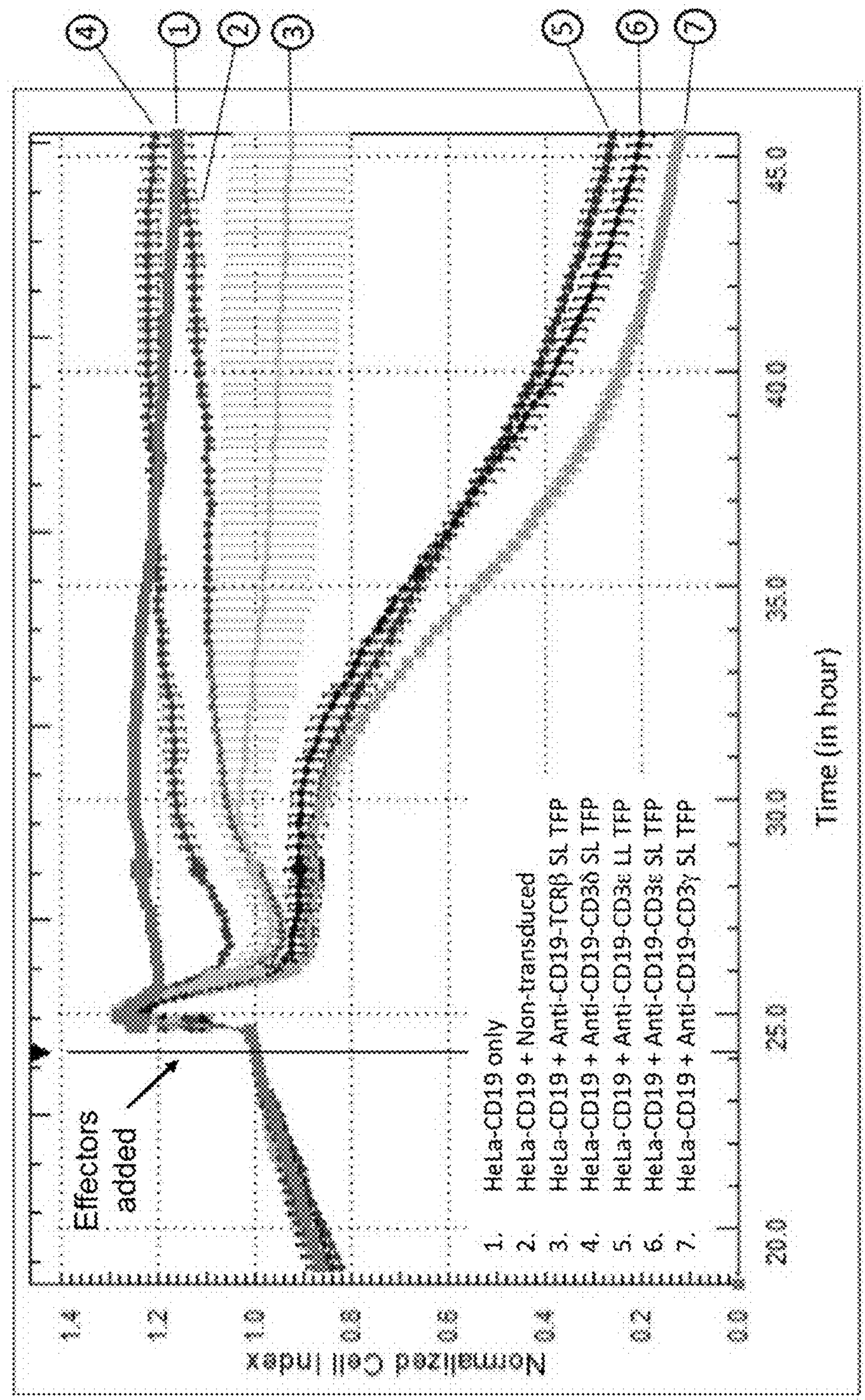
FIG. 11 is an exemplary graph depicting killing of CD19-transduced HeLa target cells by anti-CD19 TFPs. Transduced effector T-cells were expanded for 7 days prior to incubation with $1\times10^4$ CD19-transduced HeLa target cells. The cell index, indicative of cytotoxicity, was determined in a RTCA assay.

In the RTCA assay, killing of CD19-transduced HeLa was observed by T-cells transduced with anti-CD19-28ζ CAR-transduced T-cells, as demonstrated by a time-dependent decrease in the cell index following addition of the effector cells relative to HeLa alone or HeLa co-incubated with T-cells transduced with a control CAR construct (FIG. 11).

However, target cell killing by anti-CD19-CD3ε or anti-BCMA-CD3γ TFP-expressing T-cells was deeper and more rapid than that observed with the anti-CD19 CAR. For example, within 4 hours of addition of T-cells transduced with anti-CD19-CD3ε TFP, killing of the CD19-expressing target cells was essentially complete. Little or no killing was observed with T-cells transduced with a number of TFP constructs comprising other CD3 and TCR constructs. Similar results were obtained with anti-CD19 TFPs constructed with an alternative hinge region. Cytotoxicity against CD19-transduced HeLa target cells was again greater with anti-CD 19-CD3ε or anti-CD19-CD3γ TFP-transduced T-cells than with anti-CD19-CAR-transduced T-cells.

Figure 12:
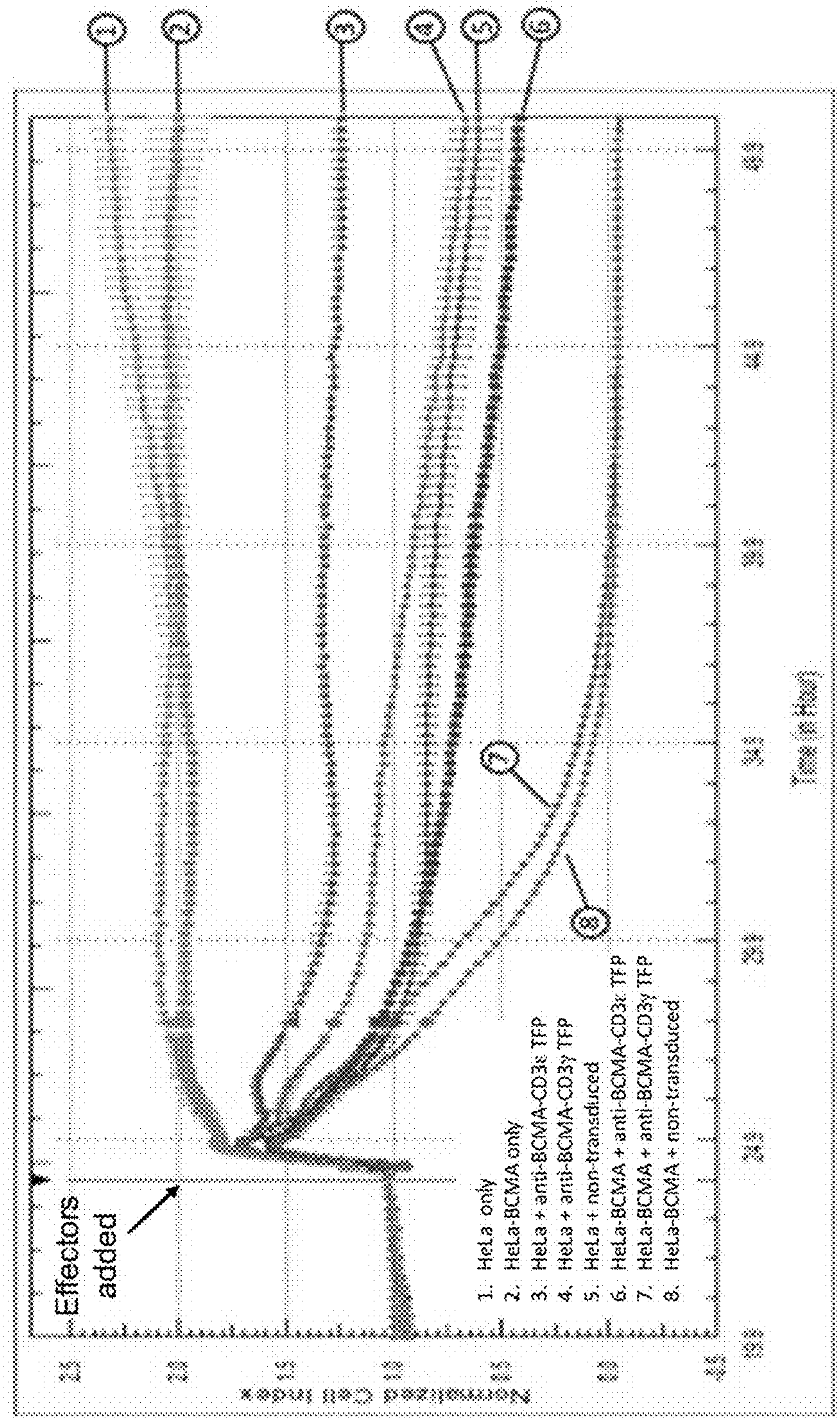
FIG. 12 is an exemplary graph depicting killing of BCMA-transduced HeLa target cells by anti-BCMA TFPs over time. Effector T-cells that were either non-transduced or transduced with either anti-BCMA-CD3ε or anti-BCMA-CD3γ TFPs were expanded for 7 days prior to incubation with either $1\times10^4$ HeLa or HeLa-BCMA target cells. The cell index, indicative of cytotoxicity, was determined in a RTCA assay.

T-cells transduced with anti-BCMA TFPs also demonstrated robust cytotoxicity against BCMA-expressing RPMI8226 cells. As shown in FIG. 9, T-cells transduced with anti-BCMA-CD3ε or anti-BCMA-CD3γ TFPs efficiently mediated cytotoxicity against the BCMA-expressing RPMI8226 target cells. At an effector to target ratio of 10:1, almost 100% of the target cells were killed (FIG. 12).

Figure 13:
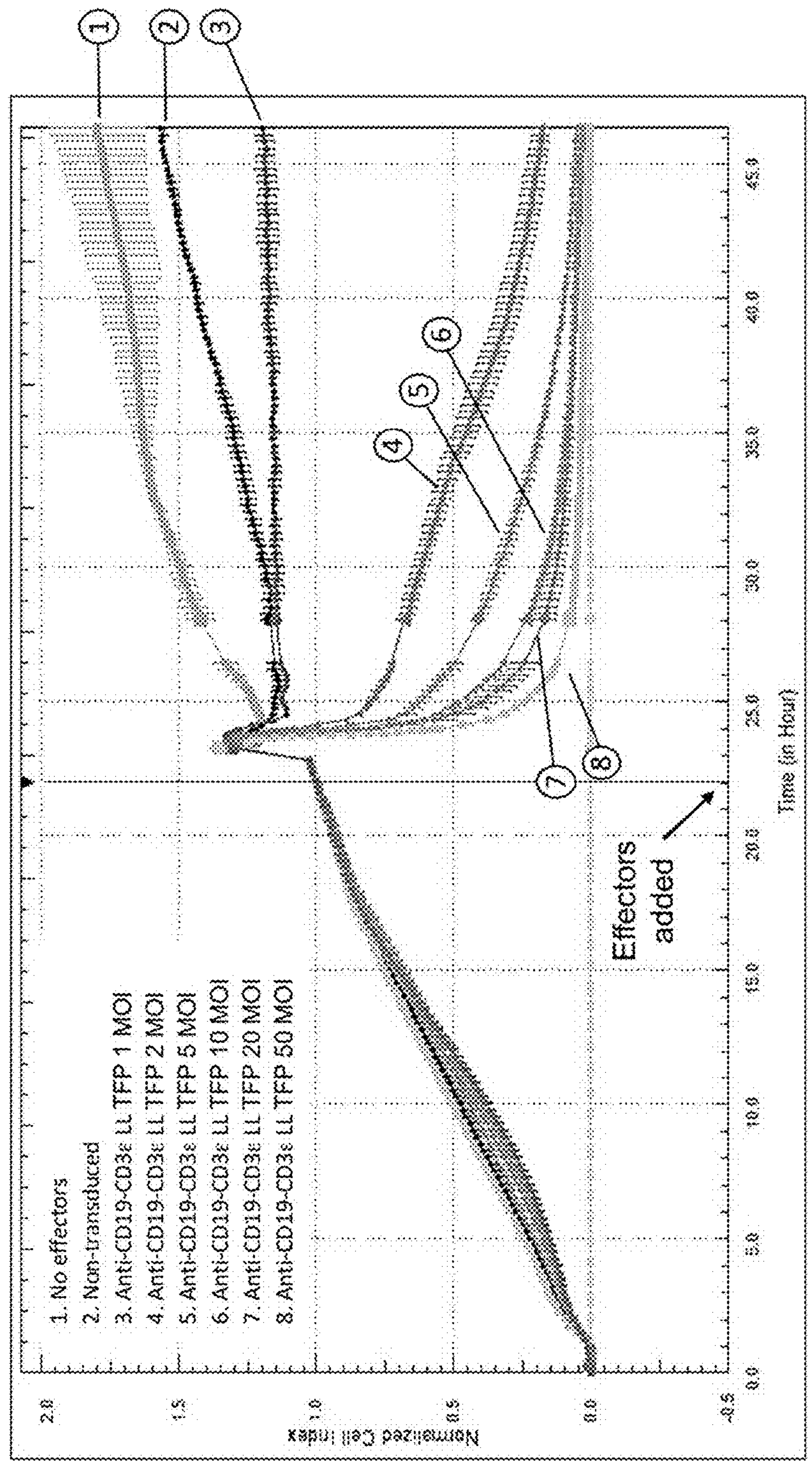
FIG. 13 is an exemplary graph depicting killing activity of T-cells transduced with various amounts of lentivirus encoding anti-CD19-CD3ε LL TFP over time. T-cells transduced with the indicated MOI of lentivirus encoding anti-CD19-CD3ε LL TFP were expanded for 14 days prior to incubation with $1\times10^4$ CD19-transduced HeLa target cells. The cell index, indicative of cytotoxicity, was determined.

The cytotoxic activity of TFP-transduced T-cells was dose-dependent with respect to the amount of virus (MOI) used for transduction. Increased killing of CD19-HeLa was observed with increasing MOI of anti-CD19-CD3ε TFP lentivirus, further reinforcing the relationship between TFP transduction and cytotoxic activity (FIG. 13).

Similar experiments can be carried out with FAP.TFP and CAIX.TFP constructs.

Example 9: IL-2 and IFN-γ Secretion by ELISA

Another measure of effector T-cell activation and proliferation associated with the recognition of cells bearing cognate antigen is the production of effector cytokines such as interleukin-2 (IL-2) and interferon-gamma (IFN-γ).

ELISA assays for Human IL-2 (catalog #EH2IL2, Thermo Scientific) and IFN-γ catalog #KHC4012, Invitrogen) were performed as described in the product inserts. Briefly, 50 μL of reconstituted standards or samples in duplicate were added to each well of a 96 well plate followed by 50 μL of Biotinylated Antibody Reagent. Samples were mixed by gently tapping the plate several times. 50 μL of Standard Diluent was then added to all wells that did not contain standards or samples and the plate was carefully sealed with an adhesive plate cover prior to incubation for 3 hours at room temperature (20-25° C.). The plate cover was then removed, plate contents were emptied, and each well was filled with Wash Buffer. This wash procedure was repeated a total of 3 times and the plate was blotted onto paper towels or other absorbent material. 100 μL of prepared Streptavidin-HRP Solution was added to each well and a new plate cover was attached prior to incubation for 30 minutes at room temperature. The plate cover was again removed, the plate contents were discarded, and 100 μL of TMB Substrate Solution was added into each well. The reaction was allowed to develop at room temperature in the dark for 30 minutes, after which 100 μL of Stop Solution was added to each well. Evaluate the plate. Absorbance was measured on an ELISA plate reader set at 450 nm and 550 nm within 30 minutes of stopping the reaction. 550 nm values were subtracted from 450 nm values and IL-2 amounts in unknown samples were calculated relative to values obtained from an IL-2 standard curve.

Alternatively, 2-Plex assays were performed using the Human Cytokine Magnetic Buffer Reagent Kit (Invitrogen, LHB0001M) with the Human IL-2 Magnetic Bead Kit (Invitrogen, LHC0021M) and the Human IFN-γ Magnetic Bead Kit (Invitrogen, LHC4031M). Briefly, 25 μL of Human IL-2 and IFN-γ antibody beads were added to each well of a 96 well plate and washed using the following guidelines: two washes of 200 μL 1× wash solution, placing the plate in contact with a Magnetic 96-well plate Separator (Invitrogen, A14179), letting the beads settle for 1 minute and decanting the liquid. Then, 50 μL of Incubation Buffer was added to each well of the plate with 100 μL of reconstituted standards in duplicates or 50 μL of samples (supernatants from cytotoxicity assays) and 50 μL of Assay Diluent, in triplicate, for a total volume of 150 μL. Samples were mixed in the dark at 600 rpm with an orbital shaker with a 3 mm orbital radius for 2 hours at room temperature. The plate was washed following the same washing guidelines and 100 μL of human IL-2 and IFN-γ biotinylated detector antibody was added to each well. Samples were mixed in the dark at 600 rpm with an orbital shaker with a 3 mm orbital radius for 1 hour at room temperature. The plate was washed following the same washing guidelines and 100 μL of Streptavidin-R-Phycoerythrin was added to each well. Samples were mixed in the dark at 600 rpm with an orbital shaker with a 3 mm orbital radius for 30 minutes at room temperature. The plate was washed 3 times using the same washing guidelines and after decanting the liquid the samples were re-suspended in 150 μL of 1× wash solution. The samples were mixed at 600 rpm with an orbital shaker with a 3 mm orbital radius for 3 minutes and stored over night at 4° C. Afterwards, the plate was washed following the same washing guidelines and the samples were re-suspended in 150 μL of 1× wash solution.

The plate was read using the MAGPIX System (Luminex) and xPONENT software. Analysis of the data was performed using MILLIPLEX Analyst software, which provides the standard curve and cytokine concentrations.

FIG. 15 shows that, relative to non-transduced or control CAR-transduced T-cells, T-cells transduced with anti-CD19 TFPs produce higher levels of both IL-2 and IFN-γ when co-cultured with either Raji cells that endogenously express CD19 or CD19-transduced HeLa cells. In contrast, co-culture with CD19 negative K562 cells or non-transduced HeLa cells, results in little or no cytokine release from TFP-transduced T-cells. Consistent with the previous cytotoxicity data, anti-CD19 TFPs constructed with an alternative hinge region generated similar results upon co-culture with CD19-bearing target cells (FIG. 16).

Figure 16:
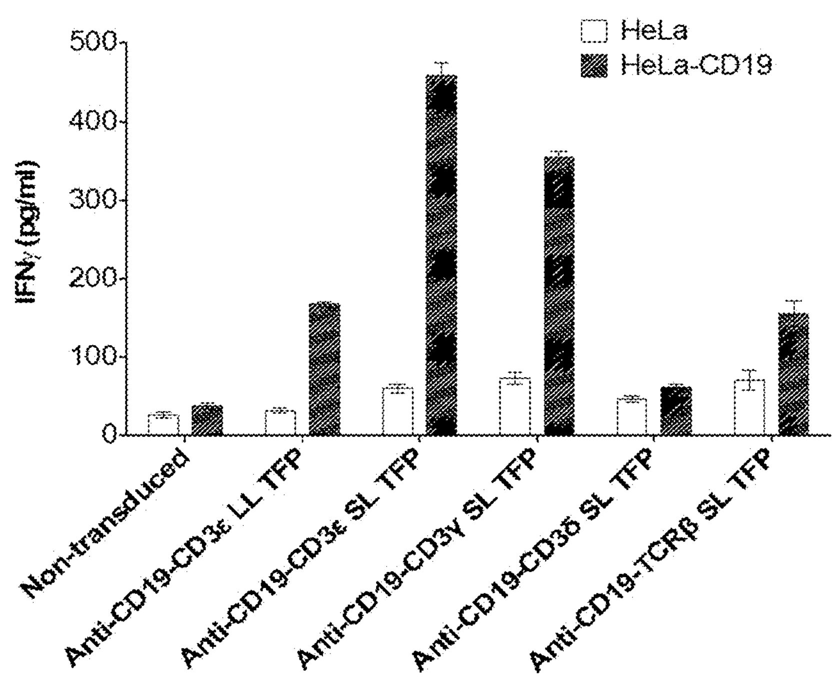
FIG. 16 is an exemplary graph depicting IFN-γ release by T-cells transduced with anti-CD19 TFPs in response to CD19-bearing target cells. Effector T-cells that were either non-transduced or transduced with the indicated anti-CD19 TFP were expanded for 7 days prior to incubation with either $1\times10^4$ HeLa or CD19-HeLa target cells. IFN-γ levels were determined by ELISA.

In agreement with the previous cytotoxicity data, anti-CD19-CD3ε and anti-CD19-CD3γ produced the highest IL-2 and IFN-γ levels of the TFP constructs (FIGS. 15 and 16). However, cytokine production by T-cells transduced with anti-CD19-CD3ε and anti-CD19-CD3γ TFPs was comparable to that of T-cells expressing anti-CD19-28ζ CAR, despite the TFPs demonstrating much higher levels of target cell killing (FIGS. 8 and 11). The possibility that TFPs may more efficiently kill target cells than CARs, but release comparable or lower levels of pro-inflammatory cytokines, represents a potential advantage for TFPs relative to CARs since elevated levels of these cytokines have been associated with dose-limiting toxicities for adoptive CAR-T therapies.

Figure 17A:
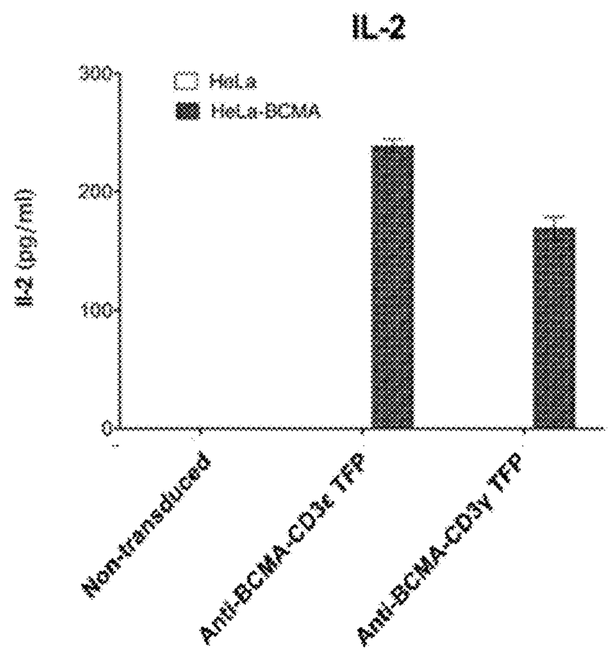
FIG. 17A is an exemplary graph depicting IL-2 release by T-cells transduced with anti-BCMA TFPs in response to BCMA-bearing target cells. Effector T-cells that were either non-transduced or transduced with either anti-BCMA-CD3ε or anti-BCMA-CD3γ TFPs were expanded for 7 days prior to incubation with either $1\times10^4$ HeLa or HeLa-BCMA target cells. IL-2 production was determined by 2-plex Luminex.
Figure 17B:
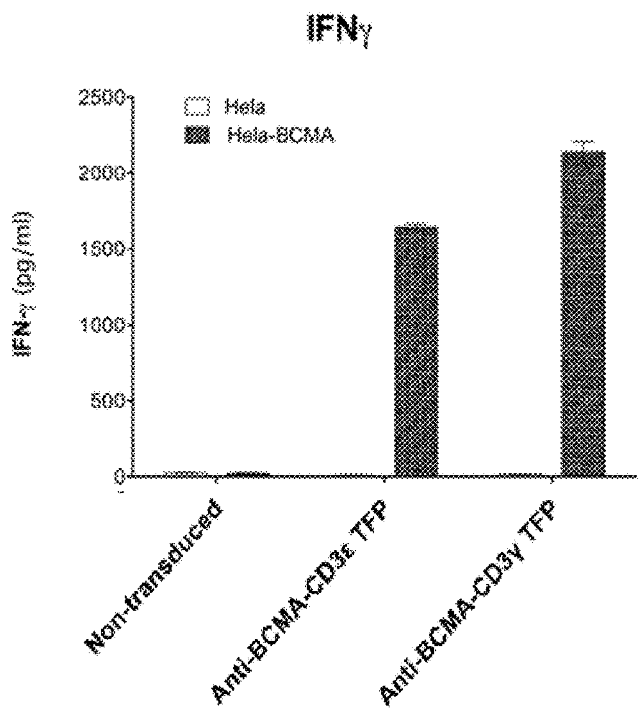
FIG. 17B is an exemplary graph depicting IFN-γ release by T-cells transduced with anti-BCMA TFPs in response to BCMA-bearing target cells. Effector T-cells that were either non-transduced or transduced with either anti-BCMA-CD3ε or anti-BCMA-CD3γ TFPs were expanded for 7 days prior to incubation with either $1\times10^4$ HeLa or HeLa-BCMA target cells. IFN-γ production was determined by 2-plex Luminex.

T-cells transduced with anti-BCMA-CD3ε or anti-BCMA-CD3γ TFPs also produced IL-2 and IFN-γ upon co-culture with BCMA-HeLa but not control HeLa cells that did not express BCMA (FIG. 17).

Similar experiments can be carried out with FAP.TFP and CAIX.TFP constructs.

Example 10: CD107a Exposure by Flow Cytometry

An additional assay for T-cell activation is surface expression of CD107a, a lysosomal associated membrane protein (LAMP-1) that is located in the membrane of cytoplasmic cytolytic granules in resting cells. Degranulation of effector T-cells, a prerequisite for cytolytic activity, results in mobilization of CD107a to the cell surface following activation-induced granule exocytosis. Thus, CD107a exposure provides an additional measure of T-cell activation, in addition to cytokine production, that correlates closely with cytotoxicity.

Target and effector cells were separately washed and re-suspended in cytotoxicity medium (RPMI+5% human AB serum+1% antibiotic antimycotic). The assay was performed by combining $2\times10^5$ effectors cells with $2\times10^5$ target cells in a 100 μL final volume in U-bottom 96-well plates (Corning), in the presence of 0.5 μL/well of PE/Cy7-labelled anti-human CD107a (LAMP-1) antibody (Clone-H4A3, BD Biosciences). The cultures were then incubated for an hour at 37° C., 5% $CO_2$. Immediately following this incubation, 10 μL of a 1:10 dilution of the secretion inhibitor monensin (1000× solution, BD GolgiStop™) was carefully added to each well without disturbing the cells. The plates were then incubated for a further 2.5 hours at 37° C., 5% $CO_2$. Following this incubation, the cells were stained with APC anti-human CD3 antibody (Clone-UCHT1, BD Biosciences), PerCP/Cy5.5 anti-human CD8 antibody (Clone-SK1, BD Biosciences) and Pacific Blue anti-human CD4 antibody (Clone-RPA-T4, BD Biosciences) and then incubated for 30 minutes at 37° C., 5% $CO_2$. The cells were then washed 2× with FACS buffer (and resuspended in 100 μL FACS buffer and 100 ul IC fix buffer prior to analysis.

Exposure of CD107a on the surface of T-cells was detected by flow cytometry. Flow cytometry was performed with a LSRFortessa™ X20 (BD Biosciences) and analysis of flow cytometric data was performed using FlowJo software (Treestar, Inc. Ashland, Oreg.). The percentage of CD8+ effector cells, within the CD3 gate, that were CD107+ve was determined for each effector/target cell culture.

Figure 18:
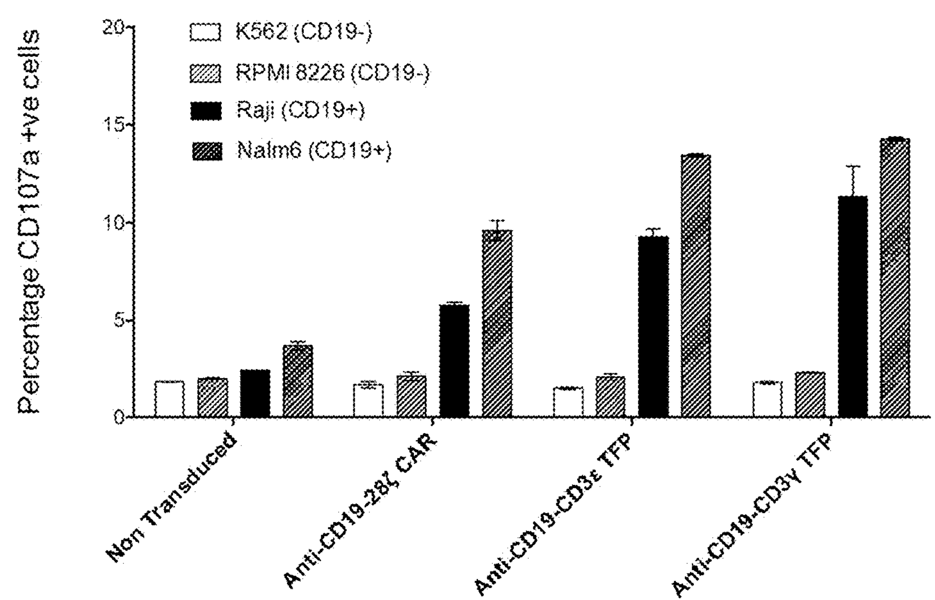
FIG. 18 is an exemplary graph depicting degranulation of T-cells transduced with anti-CD19 TFPs in response to CD19-bearing target cells. Effector T-cells that were either non-transduced or transduced with either anti-CD19-28ζ CAR, anti-BCMA-CD3ε LL TFP or anti-BCMA-CD3γ LL TFP were expanded for 14 days prior to incubation with $1\times10^4$ of the indicated CD19+ve or CD19−ve target cells. The percentage of CD107+ cells in the CD3+CD8+ gate was determined. Target and effector cells were co-cultured in the presence of a fluorescently-labelled anti-CD107a antibody. The percentage of T-cells within CD3 and CD4/CD8 gates that stained positively for cell surface CD107a was then determined by flow cytometry.

Consistent with the previous cytotoxicity and cytokine data, co-culture of CD19-expressing target cells, such as Raji or Nalm-6 cells, with effector T-cells transduced with anti-CD19-28ζ CAR induced a 3 to 5-fold increase in surface CD107a expression relative to effectors incubated with CD19−ve target cells (FIG. 18). In comparison, under the same conditions, anti-CD19-CD3ε LL or anti-CD19-CD3γ LL TFP-expressing effectors exhibited a 5 to 7-fold induction of CD107a expression. Anti-CD19 TFPs constructed with an alternative hinge region generated similar results upon co-culture with CD19-bearing target cells.

Figure 19:
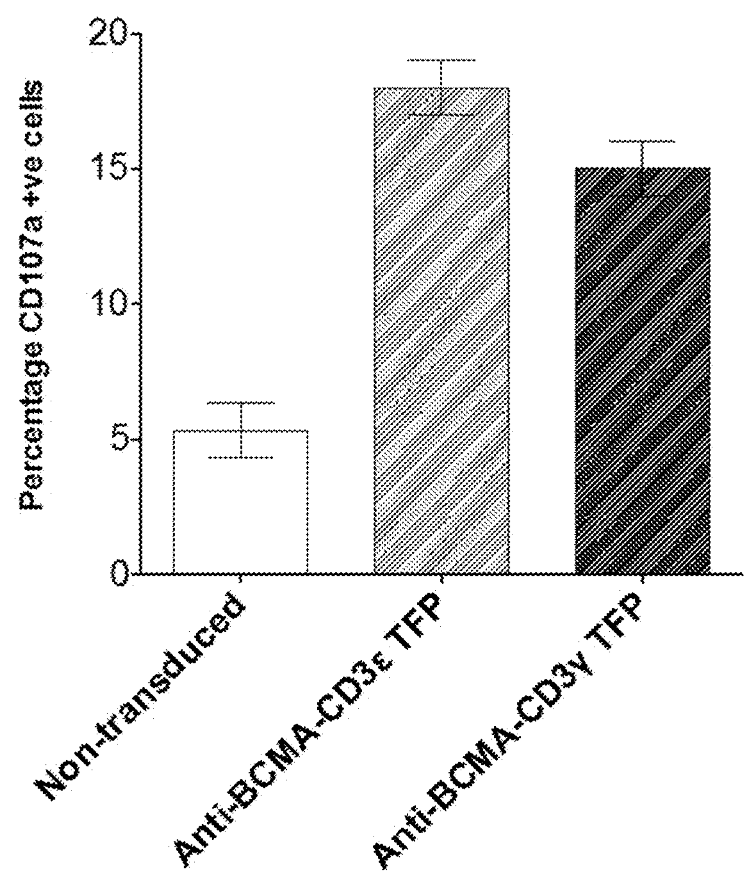
FIG. 19 is an exemplary graph depicting degranulation of T-cells transduced with anti-BCMA TFPs in response to BCMA-bearing target cells. Effector T-cells that were either non-transduced or transduced with 50 MOI of either anti-BCMA-CD3ε or anti-BCMA-CD3γ TFPs were expanded for 13 days prior to incubation with $1\times10^4$ of the indicated BCMA+ve RPMI8226 target cells. The percentage of CD107+ cells in the CD3+CD8+ gate was determined.

Relative to non-transduced T-cells, cells transduced with anti-BCMA-CD3ε or anti-BCMA-CD3γ TFPs also exhibited an increase in surface expression of CD107a upon co-culture with BCMA+ve RPMI8226 cells (FIG. 19). These results indicate that TFP-transduced effector T-cells become activated and degranulate upon exposure to target cells expressing their cognate antigen.

Similar experiments can be carried out with FAP.TFP and CAIX.TFP constructs.

Example 11: In Vivo Mouse Efficacy Studies

To assess the ability of effector T-cells transduced with anti-CD19 TFPs to achieve anti-tumor responses in vivo, effector T-cells transduced with either anti-CD19-28ζ CAR, anti-CD19-CD3ε LL TFP or anti-CD19-CD3γ LL TFP were adoptively transferred into NOD/SCID/IL-2Rγ−/− (NSG-JAX) mice that had previously been inoculated with CD19+ Raji or Nalm6 human leukemic cell lines.

Female NOD/SCID/IL-2Rγ−/− (NSG-JAX) mice, at least 6 weeks of age prior to the start of the study, were obtained from The Jackson Laboratory (stock number 005557) and acclimated for 3 days before experimental use. Raji and Nalm-6 human leukemic cell lines for inoculation were maintained in log-phase culture prior to harvesting and counting with trypan blue to determine a viable cell count. On the day of tumor challenge, the cells were centrifuged at 300 g for 5 minutes and re-suspended in pre-warmed sterile PBS at either $1\times10^6$ cells/100 μL (Nalm-6) or $5\times10^5$ cells/100 μL (Raji). T-cells for adoptive transfer, either non-transduced or transduced with anti-CD19-28ζ CAR, anti-CD19-CD3ε LL TFP or anti-CD3γ LL TFP constructs were prepared. On day 0 of the study, 10 animals per experimental group were challenged intravenously with either $5\times10^5$ Raji or $1\times10^6$ Nalm-6 cells. 3 days later, $5\times10^6$ of the indicated effector T-cell populations were intravenously transferred to each animal in 100 μL of sterile PBS. Detailed clinical observations on the animals were recorded daily until euthanasia. Body weight measurements were made on all animals weekly until death or euthanasia. All animals were euthanized 35 days after adoptive transfer of test and control articles. Any animals appearing moribund during the study were euthanized at the discretion of the study director in consultation with a veterinarian.

Figure 20A:
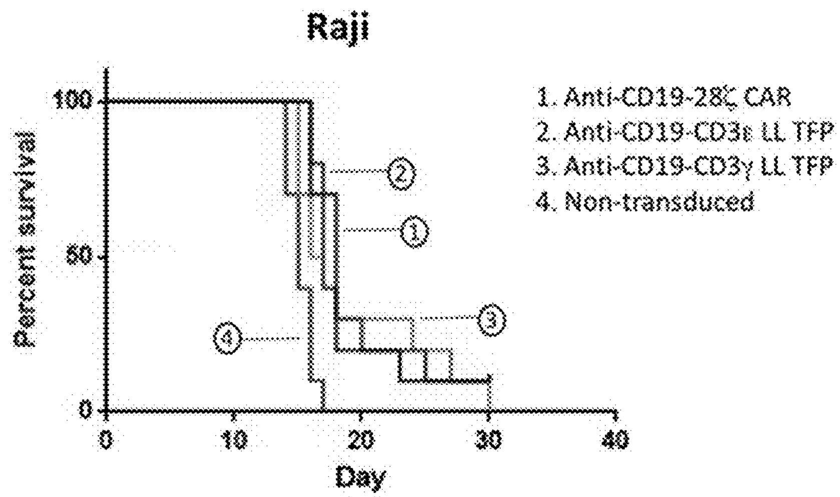
FIG. 20A depicts exemplary graphs of the in-vivo efficacy of T-cells transduced with anti-CD19 LL TFPs in disseminated human leukemic xenograft models. NSG mice were challenged intravenously with either $5\times10^5$ Raji cells three days prior to adoptive transfer of $5\times10^6$ T-cells that were either non-transduced or transduced with either anti-CD19-28ζ CAR, anti-CD19-CD3ε LL TFP or anti-CD19-CD3γ LL TFP.
Figure 20B:
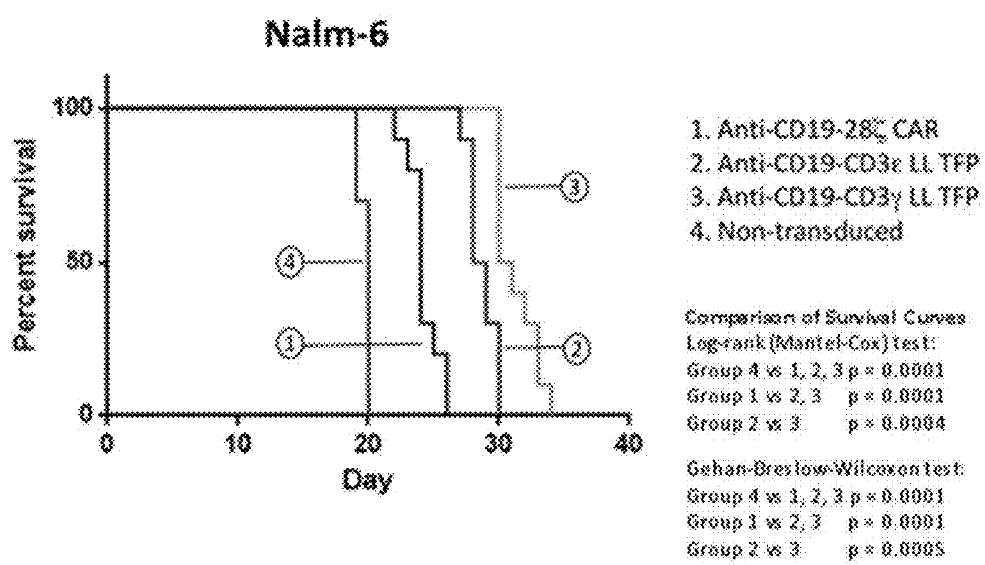
FIG. 20B depicts exemplary graphs of the in-vivo efficacy of T-cells transduced with anti-CD19 LL TFPs in disseminated human leukemic xenograft models. NS G mice were challenged intravenously with either $1\times10^6$ Nalm-6 cells (right) three days prior to adoptive transfer of $5\times10^6$ T-cells that were either non-transduced or transduced with either anti-CD19-28ζ CAR, anti-CD19-CD3ε LL TFP or anti-CD19-CD3γ LL TFP. Comparison of survival curves by the log-rank (Mantel-Cox) test showed a p=0.0001 (Group 4 vs 1, 2, 3), p=0.0001 (Group 1 vs 2, 3), and p=0.0004 (Group 2 vs 3). Comparison of survival curves by the Gehan-Breslow-Wilcoxon testshowed a p=0.0001 (Group 4 vs 1, 2, 3), p=0.0001 (Group 1 vs 2, 3), and p=0.0005 (Group 2 vs 3).

Relative to non-transduced T-cells, adoptive transfer of T-cell transduced with either anti-CD19-28ζ CAR, anti-CD19-CD3ε LL TFP or anti-CD19-CD3γ LL TFP prolonged survival of both Raji (FIG. 20A) and Nalm6 (FIG. 20B) tumor-bearing mice, indicating that both anti-CD19 CAR and TFP-transduced T-cells were capable of mediating target cell killing with corresponding increased survival in these mouse models. Collectively, these data indicate that TFPs represent an alternative platform for engineering chimeric receptors that demonstrate superior antigen-specific killing to first generation CARs both in vitro and in vivo.

Similar experiments can be carried out with FAP.TFP and CAIX.TFP constructs.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A pharmaceutical composition comprising (I) a T cell from a human subject, wherein the T cell comprises a recombinant nucleic acid molecule encoding a T cell receptor (TCR) fusion protein (TFP) comprising (a) a TCR subunit comprising a full-length CD3 epsilon sequence or a full-length CD3 gamma sequence; and (b) a mammalian scFv or single domain antibody comprising an anti-B-cell maturation antigen (BCMA) binding domain; and (II) a pharmaceutically acceptable carrier;

wherein the TCR subunit and the anti-BCMA binding domain are operatively linked;

wherein the TFP functionally interacts with an endogenous TCR when expressed in the T cell; and wherein the T cell exhibits increased cytotoxicity to a cell expressing an antigen that specifically interacts with the anti-BCMA binding domain compared to a T cell not containing the TFP.

2. The pharmaceutical composition of claim 1, wherein the anti-BCMA binding domain is connected to an extracellular domain of the TCR subunit by a linker.

3. The pharmaceutical composition of claim 2, wherein the linker comprises $(G_4S)_n$, wherein G is glycine, S is serine, and n is an integer from 1 to 4.

4. The pharmaceutical composition of claim 1, wherein the anti-BCMA binding domain comprises (i) a light chain (LC) CDR1, LC CDR2 and LC CDR3 sequence of SEQ ID NO: 37, SEQ ID NO: 39 and SEQ ID NO: 41, respectively;

(ii) a heavy chain (HC) CDR1, HC CDR2 and HC CDR3 sequence of SEQ ID NO: 43, SEQ ID NO: 45 and SEQ ID NO: 47, respectively; or (iii) a combination thereof.

5. The pharmaceutical composition of claim 1, wherein the pharmaceutical composition is substantially free of serum.

6. The pharmaceutical composition of claim 1, wherein the TFP comprises the scFv.

7. The pharmaceutical composition of claim 1, wherein the TFP comprises the single domain antibody.

8. The pharmaceutical composition of claim 7, wherein the single domain antibody is a $V_H$ domain.

9. The pharmaceutical composition of claim 1, wherein in the presence of a human cell expressing an antigen that specifically interacts with the anti-BCMA binding domain the T cell has greater than or more efficient cytotoxic activity than a T cell comprising a nucleic acid encoding a chimeric antigen receptor (CAR) comprising the anti-BCMA binding domain operatively linked to at a CD28 extracellular domain, a CD28 transmembrane domain, a CD28 intracellular domain, and a CD3 zeta intracellular domain.

10. The pharmaceutical composition of claim 1, wherein the TFP molecule functionally interacts with an endogenous TCR complex, at least one endogenous TCR polypeptide, or a combination thereof when expressed in the T cell.

11. The pharmaceutical composition of claim 1, wherein the T cell is a primary T cell.

12. The pharmaceutical composition of claim 4, wherein in the presence of a human cell expressing BCMA production of IL-2 by the T cell is lower than production of the IL-2 by a T cell comprising a nucleic acid encoding a chimeric antigen receptor (CAR) comprising the anti-BCMA binding domain operatively linked to a CD28 extracellular domain, a CD28 transmembrane domain, a CD28 intracellular domain, and a CD3 zeta intracellular domain.

13. The pharmaceutical composition of claim 1, wherein the T cell is a human CD8+ T cell or a human CD4+ T cell.

14. The pharmaceutical composition of claim 1, wherein the TCR subunit comprises a sequence as set forth in SEQ ID NO: 56.

15. The pharmaceutical composition of claim 1, wherein the TCR subunit comprises a sequence as set forth in SEQ ID NO: 57.

16. The pharmaceutical composition of claim 1, wherein production of IFNγ by the T cell is increased in the presence of a cell expressing compared to a T cell not containing the TFP.

17. The pharmaceutical composition of claim 1, wherein the T cell is a population of human CD8+ or CD4+ T cells, wherein an individual T cell of the population comprises at least two TFP molecules, or at least two T cells of the population collectively comprise at least two TFP molecules; wherein the at least two TFP molecules comprise a mammalian anti-BCMA binding domain, a TCR extracellular domain, a TCR transmembrane domain, and a TCR intracellular domain; and wherein at least one of the at least two TFP molecules functionally interacts with an endogenous TCR complex, at least one endogenous TCR polypeptide, or a combination thereof.

18. The pharmaceutical composition of claim 1, wherein the single TCR subunit comprises an intracellular domain derived only from CD3 gamma.

19. The pharmaceutical composition of claim 1, wherein the TCR subunit comprises an intracellular domain derived only from CD3 epsilon.

20. The pharmaceutical composition of claim 1, wherein the TFP lacks a heterologous stimulatory domain.

21. The pharmaceutical composition of claim 1, wherein the TFP lacks a costimulatory domain.

22. The pharmaceutical composition of claim 1, wherein in the presence of a human cell expressing BCMA production of a pro-inflammatory cytokine by the T cell is lower compared to production of the pro-inflammatory cytokine by a T cell comprising a nucleic acid encoding a CAR comprising the anti-BCMA binding domain operatively linked to a CD28 extracellular domain, a CD28 transmembrane domain, a CD28 intracellular domain, and a CD3 zeta intracellular domain.

23. The pharmaceutical composition of claim 21, wherein the pro-inflammatory cytokine is TNFα.

24. The pharmaceutical composition of claim 21, wherein the pro-inflammatory cytokine is IL-2.

25. The pharmaceutical composition of claim 21, wherein the pro-inflammatory cytokine is GM-CSF.

26. A pharmaceutical composition comprising (I) a T cell from a human subject, wherein the T cell comprises a recombinant nucleic acid molecule encoding a T cell receptor (TCR) fusion protein (TFP) comprising (a) a TCR subunit comprising a full-length CD3 epsilon sequence or a full-length CD3 gamma sequence; and (b) a mammalian scFv or single domain antibody comprising an anti-BCMA binding domain; and (II) a pharmaceutically acceptable carrier;

wherein the TCR subunit and the anti-BCMA binding domain are operatively linked;

wherein the TFP functionally interacts with an endogenous TCR when expressed in the T cell;

wherein the TFP lacks a costimulatory domain and lacks a heterologous stimulatory domain; and wherein the T cell exhibits increased cytotoxicity to a cell expressing an antigen that specifically interacts with the anti-BCMA binding domain compared to a T cell not containing the TFP.

27. The pharmaceutical composition of claim 26, wherein in the presence of a human cell expressing BCMA production of a pro-inflammatory cytokine by the T cell is lower compared to production of the pro-inflammatory cytokine by a T cell comprising a nucleic acid encoding a CAR comprising the anti-BCMA binding domain operatively linked to a CD28 extracellular domain, a CD28 transmembrane domain, a CD28 intracellular domain, and a CD3 zeta intracellular domain.

28. The pharmaceutical composition of claim 27, wherein the pro-inflammatory cytokine is selected from the group consisting of TNFα, GM-CSF, IL-2 and combinations thereof.

29. The pharmaceutical composition of claim 26, wherein the TCR subunit comprises a sequence as set forth in SEQ ID NO: 56.

30. The pharmaceutical composition of claim 26, wherein the TCR subunit comprises a sequence as set forth in SEQ ID NO: 57.

* * * * *